United States Patent
Reich et al.

(10) Patent No.: US 9,814,718 B2
(45) Date of Patent: Nov. 14, 2017

(54) MNK INHIBITORS AND METHODS RELATED THERETO

(71) Applicant: eFFECTOR Therapeutics, Inc., San Diego, CA (US)

(72) Inventors: Siegfried H. Reich, La Jolla, CA (US); Paul A. Sprengeler, Escondido, CA (US); Stephen E. Webber, San Diego, CA (US); Alan X. Xiang, Irvine, CA (US); Justin T. Ernst, San Diego, CA (US)

(73) Assignee: eFFECTOR THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/611,966

(22) Filed: Jun. 2, 2017

(65) Prior Publication Data
US 2017/0266185 A1   Sep. 21, 2017

Related U.S. Application Data

(60) Continuation of application No. 15/187,854, filed on Jun. 21, 2016, now Pat. No. 9,669,031, which is a (Continued)

(51) Int. Cl.
*C07D 471/04* (2006.01)
*A61K 31/506* (2006.01)
(Continued)

(52) U.S. Cl.
CPC .......... *A61K 31/506* (2013.01); *A61K 31/519* (2013.01); *A61K 31/52* (2013.01); (Continued)

(58) Field of Classification Search
None
See application file for complete search history.

(56) References Cited

U.S. PATENT DOCUMENTS 5,491,144 A   2/1996   Trinks et al.
8,637,525 B2   1/2014   Boy et al.
(Continued)

FOREIGN PATENT DOCUMENTS

JP   2009-173629 A1   8/2009
WO   2005082856 A2   9/2005
(Continued)

OTHER PUBLICATIONS

Aurora Fine Chemicals, Jan. 5, 2014 Chemical Catalog excerpt 1511646-58-4.
(Continued)

*Primary Examiner* — Karl J Puttlitz
(74) *Attorney, Agent, or Firm* — Mintz, Levin, Cohn, Ferris, Glovsky and Popeo, P.C.

(57) ABSTRACT

The present invention relates to compounds according to Formula (I):

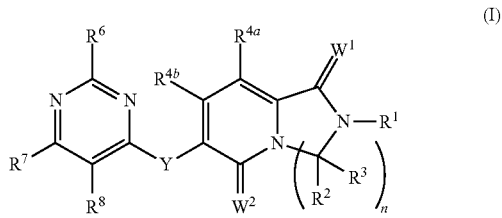

or a stereoisomer, tautomer or pharmaceutically acceptable salt thereof, wherein $R^1$, $R^2$, $R^3$, $R^{4a}$, $R^{4b}$, $R^5$, $R^6$, $R^7$, $R^8$, $W^1$, $W^2$, Y and n are as defined herein. Also described are pharmaceutically acceptable compositions of Formula I compounds as well as methods for utilizing the compounds of Formula I and the pharmaceutically acceptable compo-
(Continued)

sitions of Formula I compounds as inhibitors of Mnk as well as therapeutics for the treatment of diseases such as cancer.

20 Claims, 1 Drawing Sheet

Related U.S. Application Data division of application No. 14/748,990, filed on Jun. 24, 2015, now Pat. No. 9,382,248.

(60) Provisional application No. 62/017,112, filed on Jun. 25, 2014.

(51) Int. Cl.
| A61K 31/52 | (2006.01) |
| A61K 31/519 | (2006.01) |
| C07D 487/04 | (2006.01) |
| A61K 31/551 | (2006.01) |
| C07D 519/00 | (2006.01) |
| C07D 495/20 | (2006.01) |
| C07D 491/20 | (2006.01) |
| C07D 471/20 | (2006.01) |
| C07D 471/10 | (2006.01) |
| C07D 473/34 | (2006.01) |

(52) U.S. Cl.
CPC .......... *A61K 31/551* (2013.01); *C07D 471/04* (2013.01); *C07D 471/10* (2013.01); *C07D 471/20* (2013.01); *C07D 473/34* (2013.01); *C07D 487/04* (2013.01); *C07D 491/20* (2013.01); *C07D 495/20* (2013.01); *C07D 519/00* (2013.01)

(56) References Cited

U.S. PATENT DOCUMENTS

| 9,382,248 B2 | 7/2016 | Reich et al. |
| 9,669,031 B2 | 6/2017 | Reich et al. |
| 2007/0219218 A1 | 9/2007 | Yu et al. |
| 2010/0105708 A1 | 4/2010 | Jakel et al. |
| 2015/0038506 A1 | 2/2015 | Nacro et al. |
| 2017/0121339 A1 | 5/2017 | Sprengeler et al. |
| 2017/0121346 A1 | 5/2017 | Sprengeler et al. |
| 2017/0145009 A1 | 5/2017 | Sprengeler et al. |

FOREIGN PATENT DOCUMENTS

| WO | 2006020879 A1 | 2/2006 |
| WO | 2007021309 A1 | 2/2007 |
| WO | 2008115369 A2 | 9/2008 |
| WO | 2008117061 A2 | 10/2008 |
| WO | 2009112445 A1 | 9/2009 |
| WO | 2011106168 A1 | 1/2011 |
| WO | 2011014535 A1 | 2/2011 |
| WO | 2011017296 A1 | 2/2011 |
| WO | 2012041987 A1 | 4/2012 |
| WO | 2012075140 A1 | 6/2012 |
| WO | 2013000994 A1 | 1/2013 |
| WO | 2013043192 A1 | 3/2013 |
| WO | 2013100632 A1 | 4/2013 |
| WO | 2013147711 A1 | 10/2013 |
| WO | 2013148748 A1 | 10/2013 |
| WO | 2013151975 A1 | 10/2013 |
| WO | 2014044691 A1 | 3/2014 |
| WO | 2014088519 A1 | 6/2014 |
| WO | 2014099941 A1 | 6/2014 |
| WO | 2014128093 A1 | 8/2014 |
| WO | 2015074986 A1 | 5/2015 |
| WO | 2017085483 A1 | 5/2017 |
| WO | 2017085484 A1 | 5/2017 |

OTHER PUBLICATIONS

Aurora Fine Chemicals, Dec. 29, 2013 Chemical Catalog excerpt 1505663-52-4.
Aurora Fine Chemicals, Dec. 17, 2013 Chemical Catalog excerpt 1496979-81-7.
Aurora Fine Chemicals, Dec. 1, 2013 Chemical Catalog excerpt 1484631-21-1.
Aurora Fine Chemicals, Nov. 26, 2013 Chemical Catalog excerpt 1481116-61-3.
U.S. Appl. No. 15/337,237, filed Oct. 28, 2016 in the name of eFFECTOR Therapeutics, Inc.
U.S. Appl. No. 15/130,538, filed Apr. 15, 2016 in the name of eFFECTOR Therapeutics, Inc.
U.S. Appl. No. 15/337,184, filed Oct. 28, 2016 in the name of eFFECTOR Therapeutics, Inc.
Oyarzabal, Julen et al., "Discovery of Mitogen-Activated Protein Kinase-Interacting Kinase 1 Inhibitors by a Comprehensive Fragment-Oriented Virtual Screening Approach" Journa of Medicinal Chemistry, 2010, vol. 53, No. 18, 6618-6628.
International Search Report PCT/US2015/037416 dated, Sep. 17, 2015.
Yu et al., "Discovery of 4-(dihydropyridinon-3-yl)amino-5-methylthieno[2,3-d] pyrimidine derivatives as potent Mnk Inhibitors: synthesis, structure activity relationship analsysi and biological evaluation" European Journal of Medicinal Chemistry, May 5, 2015, vol. 95, 116-126.
Teo et al., "An integrated approach for discovery of highly potent and selective Mnk inhibitors: Screening, synthesis and SAR analsysis" European Journal of Medicinal Chemistry, Sep. 2015, vol. 103, 539-550.
U.S. Appl. No. 14/748,990, filed Jun. 24, 2015.

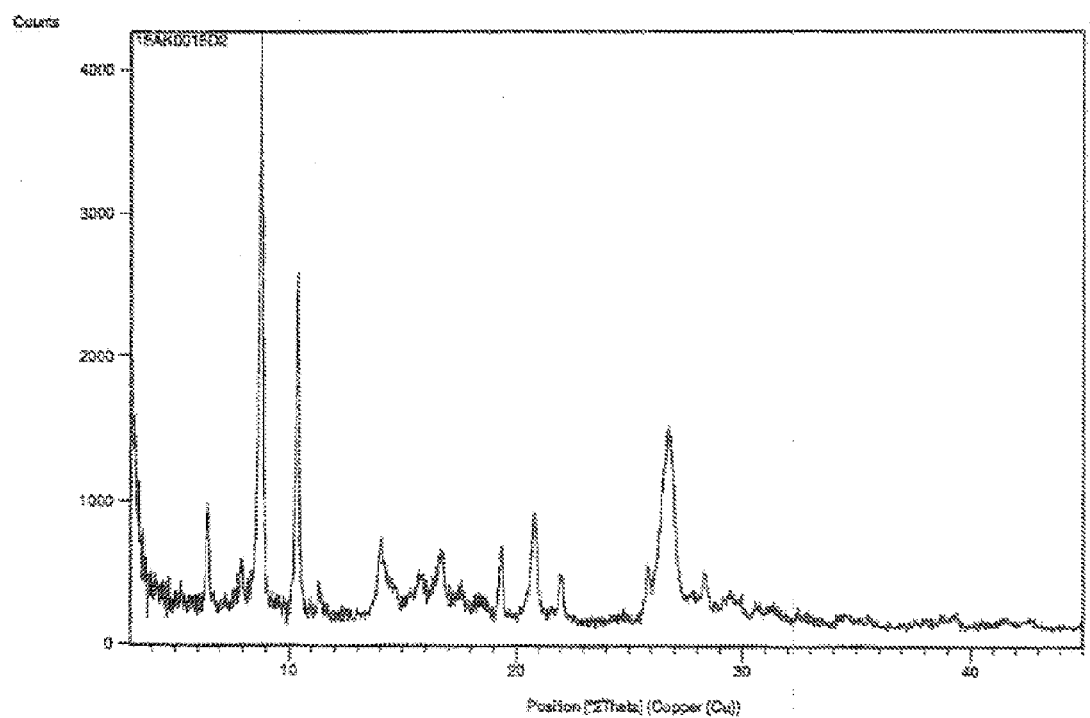

MNK INHIBITORS AND METHODS RELATED THERETO

CROSS-REFERENCE TO RELATED APPLICATIONS

The present application is a Continuation of U.S. patent application Ser. No. 15/187,854, filed Jun. 21, 2016, which is a Divisional of U.S. patent application Ser. No. 14/748,990, filed Jun. 24, 2015 which claims the benefit of U.S. provisional application No. 62/017,112, filed Jun. 25, 2014, which is herein incorporated by reference in its entirety.

FIELD

The present invention generally relates to compounds having activity as inhibitors of MAP kinase interacting kinase (Mnk), as well as to related compositions and methods containing or utilizing the same. Such compounds find utility in any number of therapeutic applications, including the treatment of cancer.

BACKGROUND

Eukaryotic initiation factor 4E (eIF4E) is a general translation factor, but it has the potential to enhance preferentially the translation of messenger RNAs (mRNAs) that lead to production of malignancy-associated proteins. This selectivity may relate to an increased requirement for eIF4E and its binding partners for the translation of mRNAs containing extensive secondary structure in their 5'-untranslated regions (5'-UTRs). These mRNAs include those encoding certain proteins that control cell cycle progression and tumorigenesis. Under normal cellular conditions the translation of these malignancy-associated mRNAs is suppressed as the availability of active eIF4E is limited; however, their levels can increase when eIF4E is over-expressed or hyperactivated. Elevated levels of eIF4E have been found in many types of tumors and cancer cell lines including cancers of the colon, breast, bladder, lung, prostate, gastrointestinal tract, head and neck, Hodgkin's lymphomas and neuroblastomas.

Initiation of cap-dependent translation is thought to depend on the assembly of eIF4F, an initiation factor complex including eIF4E, the scaffold protein eIF4G, and the RNA helicase eIF4A. Because eIF4E is the only one of these proteins that binds directly to the mRNA cap structure, it is the key factor for the assembly of eIF4F at the 5' cap. The scaffold protein, eJF4G, also recruits the 40S ribosomal subunit to the mRNA via its interaction with eIF3 and binds eIF4B, a protein that aids the RNA-helicase function of eIF4A, thus facilitating the translation of mRNAs that contain structured 5'-UTRs. The availability of eIF4E as part of the eIF4F complex is a limiting factor in controlling the rate of translation, and therefore eIF4E is an important regulator of mRNA translation.

Regulation of eIF4E activity forms a node of convergence of the PI3K/Akt/mTOR and Ras/Raf/MAPK signaling pathways. The PI3K (phosphoinositide 3-kinase)/PTEN (phosphatase and tensin homologue deleted on chromosome ten)/Akt/mTOR (mammalian target of rapamycin) pathway is often involved in tumorgenesis and in sensitivity and resistance to cancer therapy. Deregulated signaling through the PI3K/PTEN/Akt/mTOR pathway is often the result of genetic alterations in critical components of this pathway and/or mutations at upstream growth factor receptors or signaling components. PI3K initiates a cascade of events when activated by, for example, extracellular growth factors, mitogens, cytokines and/or receptors, PDK1 activates Akt, which in turn phosphorylates and inactivates the tumor suppressor complex comprising TSC1 and 2 (tuberous sclerosis complex 1/2), resulting in the activation of mTORC1 (target of rapamycin complex 1) by Rheb-GTP. Activation of PDK1 and Akt by PI3Ks is negatively regulated by PTEN.

PTEN is a critical tumor suppressor gene and is often mutated or silenced in human cancers. Its loss results in activation of Akt and increases downstream mTORC1 signaling. The involvement of mTOR complex 1 (mTORC1) in neoplastic transformation appears to depend on its regulatory role toward the eIF4F complex; overexpression of eIF4E can confer resistance to rapamycin. mTORC1 regulates the eIF4F complex assembly that is critical for the translation of mRNAs associated with cell growth, prevention of apoptosis and transformation. mTORC1 achieves this by phosphorylation and inactivation of 4E-BPs and the subsequent dissociation of 4E-BPs from eIF4E. This then enables eIF4E to interact with the scaffold protein eIF4G, permitting assembly of the eIF4F complex for the translation of structured mRNAs. mTORC1 also promotes activation of the translational activator, S6K, which phosphorylates the ribosomal protein S6 and other substrates, including eIF4B. mTORC1 signaling is inhibited by rapamycin and its analogues (rapalogs), although these compounds act allosterically, rather than directly inhibiting mTOR kinase activity.

Given the importance of the PI3K/Akt/mTOR pathway in regulating mRNA translation of genes that encode for pro-oncogenic proteins and activated mTORC1 signaling in a high proportion of cancers, these kinases have been actively pursued as oncology drug targets. A number of pharmacological inhibitors have been identified, some of which have reached advanced clinical stages. However, it has recently become clear that the mTOR pathway participates in a complicated feedback loop that can impair activation of Akt. It has been shown that prolonged treatment of cancer cells or patients with mTOR inhibitors causes elevated PI3K activity that leads to phosphorylation of Akt and eIF4E, and promotes cancer cell survival. eIF4E, acting downstream of Akt and mTOR, recapitulates Akt's action in tumorigenesis and drug resistance, and Akt signaling via eIF4E is an important mechanism of oncogenesis and drug resistance in vivo.

In addition to the PI3K/Akt/mTOR pathway, eIF4E is also the target of the Ras/Raf/MAP signaling cascade which is activated by growth factors and for the stress-activated p38 MAP kinase pathway. Erk1/2 and p38 then phosphorylate MAP kinase-interacting kinase 1 (Mnk1) and MAP kinase-interacting kinase 2 (Mnk2). The Erk pathway is also activated in many cancers, reflecting, for example, activating mutations in Ras (found in around 20% of tumors) or loss of function of the Ras GTPase-activator protein NF1. Mnk1 and Mnk2 are threonine/serine protein kinases and specifically phosphorylate serine 209 (Ser209) of eIF4E within the eIF4F complex, by virtue of the interaction between eIF4E and the Mnks, which serves to recruit Mnks to act on eIF4E. Mice with mutated eIF4E, in which Ser209 is replaced by alanine, show no eIF4E phosphorylation and significantly attenuated tumor growth. Significantly, while Mnk activity is necessary for eIF4E-mediated oncogenic transformation, it is dispensable for normal development. Pharmacologically inhibiting Mnks thus presents an attractive therapeutic strategy for cancer.

Despite increased understanding of Mnk structure and function, little progress has been made with regard to the discovery of pharmacological Mnk inhibitors and relatively few Mnk inhibitors have been reported: CGP052088

(Tschopp et al., *Mol Cell Biol Res Commun.* 3(4):205-211, 2000); CGP57380 (Rowlett et al., *Am J Physiol Gastrointest Liver Physiol.* 294(2):G452-459, 2008); and Cercosporamide (Konicek et al., *Cancer Res.* 71(5):1849-1857, 2011). These compounds, however, have mainly been used for the purpose of Mnk target validation. More recently, investigators have proposed further compounds for treating diseases influenced by the inhibition of kinase activity of Mnk1 and/or Mnk2, including, for example, the compounds disclosed in WO 2014/044691 and the various patent documents cited therein and the 4-(dihydropyridinon-3-yl) amino-5-methylthieno[2,3,-d]pyrimidines disclosed by Yu et al., *European Journal of Med. Chem.*, 95: 116-126, 2015.

Accordingly, while advances have been made in this field there remains a significant need in the art for compounds that specifically inhibit Mnk kinase activity, particularly with regard to Mnk's role in regulation of cancer pathways, as well as for associated composition and methods. The present invention fulfills this need and provides further related advantages.

SUMMARY

The present invention is directed to compounds that inhibit or modulate the activity of Mnk, as well as stereoisomers, tautomers and pharmaceutically acceptable salts of such compounds as candidate therapeutic agents. The present invention also is directed to compositions containing such compounds and associated methods for treating conditions that would benefit from Mnk inhibition, such as cancer.

In one embodiment, the invention is directed to compounds that conform to Formula I as well as to a stereoisomer, tautomer or pharmaceutically acceptable salt of such compounds.

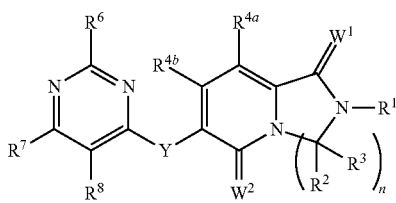

(I)

For Formula I compounds, $R^1$, $R^2$, $R^3$, $R^{4a}$, $R^{4b}$, $R^6$, $R^7$, $R^8$, $W^1$, $W^2$, Y and "n" are as defined below.

In another embodiment, compositions are disclosed comprising a compound of structure (I) in combination with a pharmaceutically acceptable carrier, diluent or excipient.

In a further embodiment, methods are provided for treating a Mnk dependent condition in a mammal in need thereof. Such methods comprise administering an effective amount of a compound of structure (I), or compositions comprising the same, to the mammal. Such conditions include, but are not limited to, various forms of cancer as discussed in more detail below.

These and other aspects of the invention will be apparent upon reference to the following detailed description. To this end, various references are set forth herein which describe in more detail certain background information, procedures, compounds and/or compositions, and are each hereby incorporated by reference in their entirety.

FIGURES

FIG. 1 illustrates XRPD data for the hydrogen chloride salt form of an exemplary Formula I compound.

DETAILED DESCRIPTION

In the following description, certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, and unless noted to the contrary, the following terms and phrases have the meaning noted below.

"Amino" refers to the —NH$_2$ substituent.

"Aminocarbonyl" refers to the —C(O)NH$_2$ substituent.

"Carboxyl" refers to the —CO$_2$H substituent.

"Carbonyl" refers to a —C(O)— or —C(=O)— group. Both notations are used interchangeably within the specification.

"Cyano" refers to the —C≡N substituent.

"Cyanoalkylene" refers to the -(alkylene)C≡N subsituent.

"Acetyl" refers to the —C(O)CH$_3$ substituent.

"Hydroxy" or "hydroxyl" refers to the —OH substituent.

"Hydroxyalkylene" refers to the -(alkylene)OH subsituent.

"Oxo" refers to an oxygen of —O— substituent.

"Thio" or "thiol" refer to a —SH substituent.

The phrase "MAP kinase interacting kinase" or the term "Mnk" refers to all isoforms of the MAP kinase interacting kinase protein including Mnk-1 and Mnk-2.

"Alkyl" refers to a saturated, straight or branched hydrocarbon chain radical consisting solely of carbon and hydrogen atoms, having from one to twelve carbon atoms (C$_1$-C$_{12}$ alkyl), from one to eight carbon atoms (C$_1$-C$_8$ alkyl) or from one to six carbon atoms (C$_1$-C$_6$ alkyl), and which is attached to the rest of the molecule by a single bond. Exemplary alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like.

"Lower alkyl" has the same meaning as alkyl defined above but having from one to four carbon atoms (C$_1$-C$_4$ alkyl).

"Alkenyl" refers to an unsaturated alkyl group having at least one double bond and from two to twelve carbon atoms (C$_2$-C$_{12}$ alkenyl), from two to eight carbon atoms (C$_2$-C$_8$ alkenyl) or from two to six carbon atoms (C$_2$-C$_6$ alkenyl), and which is attached to the rest of the molecule by a single bond, e.g., ethenyl, propenyl, butenyl, pentenyl, hexenyl, and the like.

"Alkynyl" refers to an unsaturated alkyl group having at least one triple bond and from two to twelve carbon atoms ($C_2$-$C_{12}$ alkynyl), from two to ten carbon atoms ($C_2$-$C_{10}$ alkynyl) from two to eight carbon atoms ($C_2$-$C_8$ alkynyl) or from two to six carbon atoms ($C_2$-$C_6$ alkynyl), and which is attached to the rest of the molecule by a single bond, e.g., ethynyl, propynyl, butynyl, pentynyl, hexynyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkynylene" refers to divalent alkyne. Examples of alkynylene include without limitation, ethynylene, propynylene. "Substituted alkynylene" refers to divalent substituted alkyne.

"Alkoxy" refers to a radical of the formula —$OR_a$ where $R_a$ is an alkyl having the indicated number of carbon atoms as defined above. Examples of alkoxy groups include without limitation —O-methyl (methoxy), —O-ethyl (ethoxy), —O-propyl (propoxy), —O— isopropyl (iso propoxy) and the like.

"Acyl" refers to a radical of the formula —$C(O)R_a$ where $R_a$ is an alkyl having the indicated number of carbon atoms.

"Alkylaminyl" refers to a radical of the formula —$NHR_a$ or —$NR_aR_a$ where each $R_a$ is, independently, an alkyl radical having the indicated number of carbon atoms as defined above.

"Cycloalkylaminyl" refers to a radical of the formula —$NHR_a$ where $R_a$ is a cycloalkyl radical as defined herein.

"Alkylcarbonylaminyl" refers to a radical of the formula —$NHC(O)R_a$, where $R_a$ is an alkyl radical having the indicated number of carbon atoms as defined herein.

"Cycloalkylcarbonylaminyl" refers to a radical of the formula —$NHC(O)R_a$, where $R_a$ is a cycloalkyl radical as defined herein.

"Alkylaminocarbonyl" refers to a radical of the formula —$C(O)NHR_a$ or —$C(O)NR_aR_a$, where each $R_a$ is independently, an alkyl radical having the indicated number of carbon atoms as defined herein.

"Cyclolkylaminocarbonyl" refers to a radical of the formula —$C(O)NHR_a$, where $R_a$ is a cycloalkyl radical as defined herein.

"Aryl" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted aryl" refers to an aryl group or a substituted aryl group.

"Arylene" denotes divalent aryl, and "substituted arylene" refers to divalent substituted aryl.

"Aralkyl" or "araalkylene" may be used interchangeably and refer to a radical of the formula —$R_b$-$R_c$ where $R_b$ is an alkylene chain as defined herein and $R_c$ is one or more aryl radicals as defined herein, for example, benzyl, diphenylmethyl and the like.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo [2.2.1]heptanyl, and the like.

"Cycloalkylalkylene" or "cycloalkylalkyl" may be used interchangeably and refer to a radical of the formula —$R_bR_e$ where $R_b$ is an alkylene chain as defined herein and $R_e$ is a cycloalkyl radical as defined herein. In certain embodiments, $R_b$ is further substituted with a cycloalkyl group, such that the cycloalkylalkylene comprises two cycloalkyl moieties. Cyclopropylalkylene and cyclobutylalkylene are exemplary cycloalkylalkylene groups, comprising at least one cyclopropyl or at least one cyclobutyl group, respectively.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different. Exemplary haloalkyls are trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl", heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

"Heterocyclylalkyl" or "heterocyclylalkylene" refers to a radical of the formula —$R_bR_f$ where $R_b$ is an alkylene chain as defined herein and $R_f$ is a heterocyclyl radical as defined above, and if the heterocyclyl is a nitrogen-containing heterocyclyl, the heterocyclyl may be attached to the alkyl radical at the nitrogen atom.

"Heteroaryl" or "heteroarylene" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

"Heteroarylalkyl" or "heteroarylalkylene" refers to a radical of the formula —$R_bR_g$ where $R_b$ is an alkylene chain as defined above and $R_g$ is a heteroaryl radical as defined above.

"Thioalkyl" refers to a radical of the formula —$SR_a$ where $R_a$ is an alkyl radical as defined above containing one to twelve carbon atoms, at least 1-10 carbon atoms, at least 1-8 carbon atoms, at least 1-6 carbon atoms, or at least 1-4 carbon atoms.

"Heterocyclylaminyl" refers to a radical of the formula —$NHR_f$ where $R_f$ is a heterocyclyl radical as defined above.

"Thione" refers to a =S group attached to a carbon atom of a saturated or unsaturated ($C_3$-$C_8$)cyclic or a ($C_1$-$C_8$) acyclic moiety.

"Sulfoxide" refers to a —S(O)— group in which the sulfur atom is covalently attached to two carbon atoms.

"Sulfone" refers to a —$S(O)_2$— group in which a hexavalent sulfur is attached to each of the two oxygen atoms through double bonds and is further attached to two carbon atoms through single covalent bonds.

The term "oxime" refers to a —C($R_a$)=N—$OR_a$ radical where $R_a$ is hydrogen, lower alkyl, an alkylene or arylene group as defined above.

The compound of the invention can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The term "effective amount" refers to an amount of a compound of the invention or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy or synergies with another therapeutic agent.

The terms "modulate", "modulation" and the like refer to the ability of a compound to increase or decrease the function, or activity of, for example, MAP kinase interacting kinase (Mnk). "Modulation", in its various forms, is intended to encompass inhibition, antagonism, partial antagonism, activation, agonism and/or partial agonism of the activity associated with Mnk. Mnk inhibitors are compounds that bind to, partially or totally block stimulation, decrease, prevent, delay activation, inactivate, desensitize, or down regulate signal transduction. The ability of a compound to modulate Mnk activity can be demonstrated in an enzymatic assay or a cell-based assay.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug that is a compound which upon administration to a patient must undergo chemical conversion by metabolic processes before becoming an active pharmacological agent. Exemplary prodrugs of compounds in accordance with Formula I are esters, acetamides, and amides.

Compounds of the Invention

The present invention is generally directed to compounds encompassed by the genus of Formula I

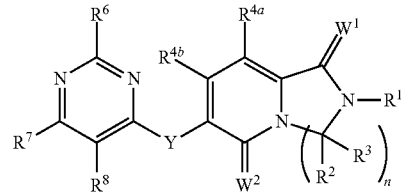

or a stereoisomer, tautomer or pharmaceutically acceptable salt thereof wherein:

$W^1$ and $W^2$ are independently O, S or N—OR', where R' is lower alkyl;

Y is —N($R^5$)—, —O—, —S—, —C(O)—, —S=O, —S(O)$_2$—, or —CH$R^9$—;

$R^1$ is hydrogen, lower alkyl, cycloalkyl or heterocyclyl wherein any lower alkyl, cycloalkyl or heterocyclyl is optionally substituted with 1, 2 or 3 J groups;

n is 1, 2 or 3;

$R^2$ and $R^3$ are each independently hydrogen, alkyl, alkenyl, alkynyl, aryl, araalkylene, heteroaryl, heteroarylalkylene, cycloalkyl, cycloalkylalkylene, heterocyclyl, or heterocyclylalkylene, wherein any alkyl, aryl, araalkylene, heteroaryl, heteroarylalkylene, cycloalkyl, cycloalkylalkylene, heterocyclyl, or heterocyclylalkylene, is optionally substituted with 1, 2 or 3 J groups;

or $R^2$ and $R^3$ taken together with the carbon atom to which they are attached form a cycloalkyl or heterocyclyl, wherein any cycloalkyl or heterocyclyl is optionally substituted with 1, 2 or 3 J groups;

$R^{4a}$ and $R^{4b}$ are each independently hydrogen, halogen, hydroxyl, thiol, hydroxyalkylene, cyano, alkyl, alkoxy, acyl, thioalkyl, alkenyl, alkynyl, cycloalkyl, aryl, or heterocyclyl;

$R^5$ is hydrogen, cyano, or lower alkyl;

or $R^5$ and $R^8$ taken together with the atoms to which they are attached form a fused heterocyclyl optionally substituted with 1, 2 or 3 J groups;

$R^6$, $R^7$ and $R^8$ are each independently hydrogen, hydroxy, halogen, cyano, amino, alkyl, alkenyl, alkynyl, alkoxy, cycloalkyl, cycloalkylalkylene, cycloalkylalkenylene, alkylaminyl, alkylcarbonylaminyl, cycloalkylcarbonylaminyl, cycloalkylaminyl, heterocyclylaminyl, heteroaryl, or heterocyclyl, and wherein any amino, alkyl, alkenyl, alkynyl, alkoxy, cycloalkyl, cycloalkylalkylene, cycloalkylalkenylene, amino, alkylaminyl, alkylcarbonylaminyl, cycloalkylcarbonylaminyl, cycloalkylaminyl, heterocyclylaminyl, heteroaryl, or heterocyclyl is optionally substituted with 1, 2 or 3 J groups;

or $R^7$ and $R^8$ taken together with the atoms to which they are attached form a fused heterocyclyl or heteroaryl optionally substituted with 1, 2 or 3 J groups;

J is —SH, —$SR^9$, —S(O)$R^9$, —S(O)$_2R^9$, —S(O)NH$_2$, —S(O)N$R^9R^9$, —NH$_2$, —N$R^9R^9$, —COOH, —C(O)O$R^9$, —C(O)$R^9$, —C(O)—NH$_2$, —C(O)—N$R^9R^9$, hydroxy, cyano, halogen, acetyl, alkyl, lower alkyl, alkenyl, alkynyl, alkoxy, haloalkyl, thioalkyl, cyanoalkylene, alkylaminyl, NH$_2$—C(O)-alkylene, N$R^9R^9$—C(O)-alkylene, —CH$R^9$—C(O)-lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —CH$R^9$—C(O)-cycloalkyl, —C(O)-cycloalkyl, —CH$R^9$—C(O)-aryl, —CH$R^9$-aryl, —C(O)-aryl, —CH$R^9$—C(O)-heterocycloalkyl, —C(O)-heterocycloalkyl, heterocyclylaminyl, or heterocyclyl; or any two J groups bound to the same carbon or hetero atom may be taken together to form oxo; and $R^9$ is hydrogen, lower alkyl or —OH.

In one embodiment of structure (I), the present disclosure provides a compound having the following structure (Ia), as well as stereoisomers, tautomers or pharmaceutically acceptable salts thereof.

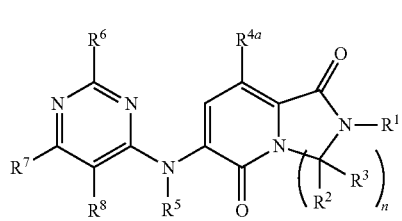
(Ia)

For Formula Ia compounds, substituent $R^1$ is hydrogen or lower alkyl and subscript n is 1, 2 or 3. Substituents $R^2$ and $R^3$ in Formula Ia are each independently hydrogen, alkyl, cycloalkyl, cycloalkylalkylene, heterocyclyl or heterocyclylalkyl, and any such alkyl, cycloalkyl, cycloalkylalkylene, heterocyclyl or heterocyclylalkyl can optionally be substituted with 1, 2 or 3 J groups.

Substitutents $R^2$ and $R^3$ in Formula Ia when taken together with the carbon atom to which they are attached can form a cycloalkyl or heterocyclyl, wherein any such cycloalkyl or heterocyclyl is optionally substituted with 1, 2 or 3 J groups. In Formula Ia, $R^{4a}$ is hydrogen, halogen, hydroxy, alkyl, alkoxy, thioalkyl, alkenyl or cycloalkyl and substituent $R^5$ is hydrogen or lower alkyl.

Alternatively, substituent groups $R^5$ and $R^8$ taken together with the atoms to which they are attached form a fused heterocyclyl that is optionally substituted with 1, 2 or 3 J groups.

In one embodiment, substituents $R^6$, $R^7$ and $R^8$ are independently and at each occurrence hydrogen, halogen, alkyl, alkenyl, cycloalkly, cycloalkylalkyl, cycloalkylalkenyl, amino, alkylaminyl, alklycarbonylaminyl, cycloalkylcarbonylaminyl, alkylaminyl or cycloalkylaminyl, and any such alkyl, alkenyl, cycloalkly, cycloalkylalkyl, cycloalkylalkenyl, amino, alkylaminyl, alklycarbonylaminyl, cycloalkylcarbonylaminyl, alkylaminyl or cycloalkylaminyl is optionally substituted with 1, 2 or 3 J groups. For some compounds in accordance with Formula Ia, $R^7$ and $R^8$ taken together with the atoms to which they are attached form a fused heterocyclyl unsubstituted or substituted with 1, 2 or 3 J groups.

Variable J in Formula Ia is —SH, —$SR^9$, —S(O) $R^9$, —S(O)$_2R^9$, —S(O)NH$_2$, —S(O)N$R^9R^9$, —NH$_2$, —N$R^9R^9$, —COOH, —C(O)O$R^9$, —C(O)$R^9$, —C(O)— NH$_2$, —C(O)—N$R^9R^9$, hydroxy, cyano, halogen, acetyl, alkyl, lower alkyl, alkenyl, alkynyl, alkoxy, haloalkyl, thioalkyl, cyanoalkylene, alkylaminyl, NH$_2$—C(O)-alkylene, N$R^9R^9$—C(O)-alkylene, —CH$R^9$—C(O)-lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —CH$R^9$—C(O)-cycloalkyl, —C(O)-cycloalkyl, —CH$R^9$—C(O)-aryl, —CH$R^9$-aryl, —C(O)-aryl, —CH$R^9$—C(O)-heterocycloalkyl, —C(O)-heterocycloalkyl, heterocyclylaminyl, or heterocyclyl. For some of the inventive compounds according to Formula Ia, any two J groups bound to the same carbon or hetero atom may be taken together to form an oxo group.

In some embodiments, variable J in Formula Ia is halogen, amino, alkyl, haloalkyl, alkylaminyl, cycloalkyl or heterocyclyl. Alternatively, for certain Formula Ia compounds, any two J groups when bound to the same carbon or hetero atom may be taken together to form oxo group.

The present invention is further directed to compounds according to Formula IIa, illustrated below, where variable Y is —N($R^5$)— and subscript "n" is 1.

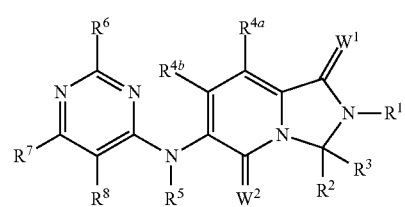
(IIa)

According to one embodiment, variable Y in Formula I is —O—, —S—, —C(O)—, sulfoxide, sulfone, —CH$R^9$— or —CH$_2$—, subscript "n" is 1 and the inventive compounds conform to Formula IIb. When "Y" is —CH$R^9$— in Formula IIb, substituent $R^9$ is hydrogen, lower alkyl or hydroxy.

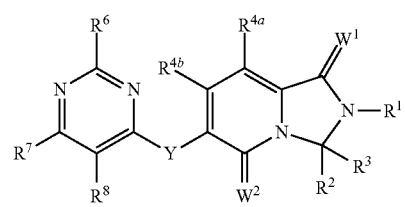
(IIb)

In another embodiment of the invention, variable "Y" in Formula I is —N($R^5$)—, subscript "n" is 2 or 3 and the inventive compounds conform to Formula IIIa or Formula IVa, respectively:

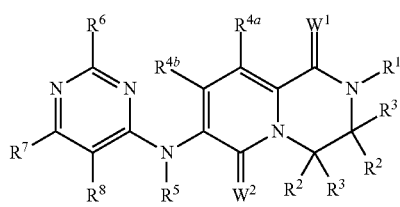
(IIIa)

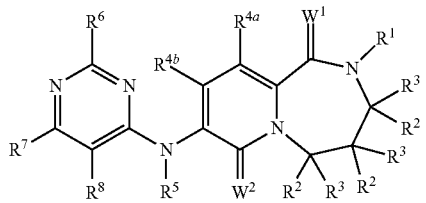

(IVa)

Alternatively, in certain embodiments variable "Y" in Formula I is —O—, —S—, —C(O)—, sulfoxide, sulfone, —CHR$^9$— or —CH$_2$—, "n" is 2 or 3 and the inventive compounds conform to Formula IIIb and Formula IVb, respectively: When "Y" is —CHR$^9$— in Formula IIIb or Formula IVb, substituent R$^9$ is either hydrogen, lower alkyl or hydroxy.

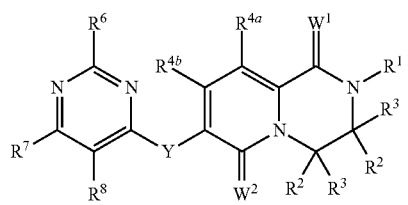

(IIIb)

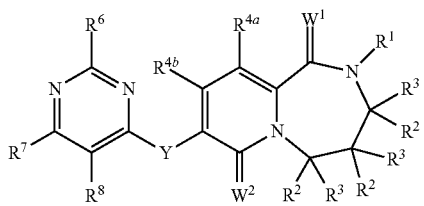

(IVb)

For compounds according to Formulae IIa, IIb, IIIa, IIIb, IVa and IVb, variables W$^1$ and W$^2$ are both oxo. In certain embodiments for compounds according to Formulae IIa, IIb, IIIa, IIIb, IVa and IVb, W$^1$ is oxo and W$^2$ is thione group. According to one embodiment, Formulae IIa, IIb, IIIa, IIIb, IVa and IVb compounds comprise an oxo at W$^1$ and a =N—OR' group at W$^2$. Also encompassed within the scope of the present invention are Formulae IIa, IIb, IIIa, IIIb, IVa and IVb compounds having a thione group at W$^1$ and an oxo group at W$^2$.

For Formulae IIa, IIb, IIIa, IIIb, IVa and IVb compounds, each of substituents R$^2$ and R$^3$ can be the same in which case the carbon atom which R$^2$ and R$^3$ are attached is not a chiral carbon. In certain embodiments, however, substituents R$^2$ and R$^3$ are different. Thus, the carbon atom which R$^2$ and R$^3$ are attached is chiral and the resulting compound will have stereoisomers.

In an embodiment of the invention, each R$^2$ and R$^3$ in Formulae IIa, IIb, IIIa, IIIb, IVa and IVb is hydrogen. Alternatively, one of R$^2$ or R$^3$ groups in Formulae IIa, IIb, IIIa, IIIb, IVa and IVb is hydrogen and the other group is alkyl optionally substituted with 1, 2 or 3 J groups. For certain compounds according to Formulae IIa, IIb, IIIa, IIIb, IVa and IVb, R$^2$ and R$^3$ are both alkyl groups that are optionally substituted with 1, 2 or 3 J groups.

For some compounds in accordance with Formula IIa or Formula IIb, R$^2$ is alkyl and R$^3$ is alkyl substituted with 1, 2 or 3 J groups. Exemplary of this category of Formula IIa and Formula IIb compounds are the following—compounds with substituent R$^2$ as alkyl and R$^3$ is haloalkyl; compounds with substituent compounds with substituent R$^2$ as alkyl and R$^3$ is cycloalkyl optionally substituted with 1, 2 or 3 J groups; compounds with substituent R$^2$ as alkyl and R$^3$ is cyclopentyl optionally substituted with 1, 2 or 3 J groups; compounds with substituent R$^2$ as alkyl and R$^3$ is aryl optionally substituted with 1, 2 or 3 J groups; compounds with substituent R$^2$ as alkyl and R$^3$ is phenyl optionally substituted with 1, 2 or 3 J groups; compounds with substituent R$^2$ as alkyl and R$^3$ is cycloalkylalkylene optionally substituted with 1, 2 or 3 J groups; compounds with substituent R$^2$ as alkyl and R$^3$ is aralkylene optionally substituted with 1, 2 or 3 J groups; compounds with substituent R$^2$ as alkyl and R$^3$ is benzyl optionally substituted with 1, 2 or 3 J groups; compounds with substituent R$^2$ as alkyl and R$^3$ is heterocyclyl optionally substituted with 1, 2 or 3 J groups; compounds with substituent R$^2$ as alkyl and R$^3$ is heteroaryl optionally substituted with 1, 2 or 3 J groups; compounds with substituent R$^2$ as alkyl and R$^3$ is thiophenyl, thiazolyl or pyridinyl; compounds with substituent R$^2$ as alkyl and R$^3$ is heterocyclylalkylene substituted or substituted with 1, 2 or 3 J groups; or compounds with substituent R$^2$ as alkyl and R$^3$ is heteroarylalkylene optionally substituted with 1, 2 or 3 J groups.

In one embodiment, for compounds according to Formulae IIa, IIb, IIIa, IIIb, IVa and IVb each R$^2$ and R$^3$ are independently hydrogen, alkyl, cycloalkyl, cycloalkylalkylene, heterocyclyl or heterocyclylalkylene, and any such alkyl, cycloalkyl, cycloalkylalkylene, heterocyclyl or heterocyclylalkylene can optionally be substituted with 1, 2 or 3 J groups, independently selected from the group consisting of halogen, amino, alkylaminyl and alkyl.

For certain Formulae IIIa, IIIb, IVa and IVb compounds, R$^2$ and R$^3$ together with the carbon atom to which they are attached form a cycloalkyl or heterocyclyl ring.

Also contemplated are Formula I compounds where Y is —N(R$^5$)—, subscript "n" is 1 and R$^2$ and R$^3$ together with the carbon atom to which they are attached form a cycloalkyl or heterocyclyl ring "A". Such compounds conform to Formula Va and the cycloalkyl or heterocyclyl ring "A" may optionally be substituted with 1, 2 or 3 J groups.

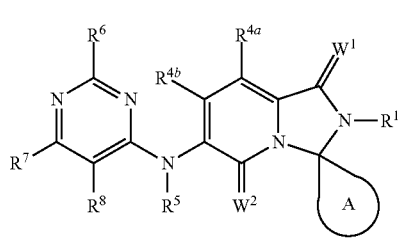

(Va)

Alternatively, in some embodiments Y in Formula I is —O—, —S—, —C(O)—, sulfoxide, sulfone, —CHR$^9$— or —CH$_2$—, "n" is 1 and R$^2$ and R$^3$ together with the carbon atom to which they are attached form a cycloalkyl or heterocyclyl ring A. Such compounds conform to Formula Vb and the cycloalkyl or heterocyclyl ring "A" may optionally be substituted with 1, 2 or 3 J groups. When "Y" is —CHR$^9$— in Formula Vb, substituent R$^9$ is either hydrogen, lower alkyl or hydroxy.

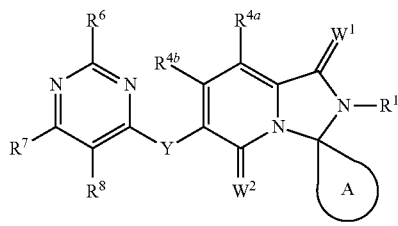

(Vb)

For Formula Va and Formula Vb compounds $W^1$ and $W^2$ are both oxo and ring A is a cycloalkyl optionally substituted with 1, 2 or 3 J groups. Also contemplated are Formula Va and Formula Vb compounds for which ring A is a fused cycloalkyl optionally substituted with 1, 2 or 3 J groups; ring A is a cycloalkyl optionally substituted with 1, 2 or 3 J groups; ring A is a cyclobutyl, cyclopentyl or cyclohexyl optionally substituted with 1, 2 or 3 J groups, for example, J groups selected from from the group consisting of halogen, amino, alkylaminyl and alkyl.

For some embodiments, ring A of a Formula Va or a Formula Vb is a heterocyclyl optionally substituted with 1, 2 or 3 J groups. Exemplary of such heterocyclyl groups are pyrrolidinyl, piperidinyl, tetrahydropyranyl, thietanyl or azetidinyl. In one embodiment, each of the above exemplified heterocyclyl may optionally be substituted with 1, 2 or 3 J groups. For certain Formula Va or a Formula Vb compounds ring A is a cycloalkyl substituted with at least 2J groups attached to the same carbon atom of the cycloalkyl, and the two J groups attached to the same carbon taken together form oxo group. In another embodiment, ring A of a Formula Va or a Formula Vb is a heterocyclyl substituted with at least 2J groups that are attached to the same hetero atom and wherein such 2 J groups taken together to form oxo. For some Formula Va or a Formula Vb compounds the cycloalkyl or heterocyclyl ring A is substituted with J groups selected from from the group consisting of halogen, cyano, hydroxy, trifluoromethyl, N-methyl amino, methyl, difluoroethylene, and methylenenitrile.

The present invention also provides compounds in accordance with Formula VI or its stereoisomers, tautomers or pharmaceutically acceptable salts. Formula VI is a subgenus of Formula I in which Y is —N($R^5$)— and substituent groups $R^5$ and $R^8$ together with the atoms to which they are attached form a heterocycle ring B which may optionally be substituted with 1, 2 or 3 J groups.

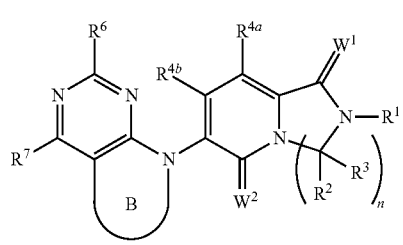

(VI)

Also encompassed within the scope of the present invention are Formula I compounds in which variable "Y" is —N($R^5$)—, and substituent groups $R^7$ and $R^8$ together with the atoms to which they are attached form a fused ring C. Such compounds or the stereoisomer, tautomer or pharmaceutically acceptable salt conform to Formula VIIa. For Formula VIIa compounds ring C may optionally be substituted with 1, 2 or 3 J groups.

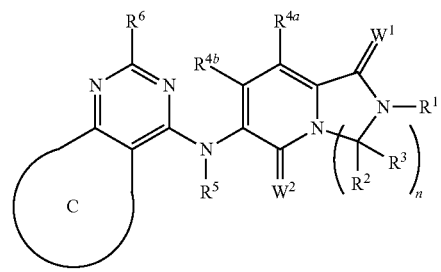

(VIIa)

According to one embodiment, variable "Y" in Formula I is —O—, —S—, —C(O)—, sulfoxide, sulfone, —CHR$^9$— or —CH$_2$—, and substituent groups $R^7$ and $R^8$ together with the atoms to which they are attached form a fused ring C. Such compounds and their stereoisomers, tautomers or pharmaceutically acceptable salts conform to Formula VIIb. For Formula VIIb compounds where "Y" is —CHR$^9$—, substituent $R^9$ can be hydrogen, lower alkyl or hydroxy.

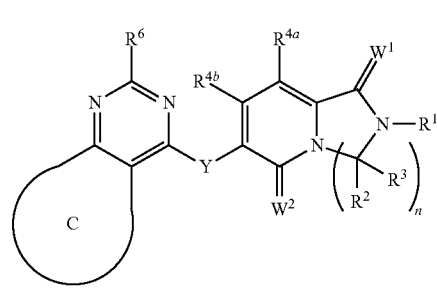

(VIIb)

For Formula VIIb compounds fused ring C may optionally be substituted with 1, 2 or 3 J groups. In one embodiment of the invention, $W^1$ and $W^2$ are both oxo for Formula VI, Formula VIIa and Formula VIIb compounds.

The present invention is further directed to Formulae I, Ia, IIa, IIb, IIIa, IIIb, IVa, IVb, Va, Vb, VI, VIIa and VIIb compounds where $R^1$ is hydrogen or a lower alkyl group selected from methyl, ethyl, propyl, butyl, iso-propyl, sec-butyl, or tert-butyl, for example, compounds with $R^1$ as methyl.

For certain Formulae I, Ia, IIa, IIb, IIIa, IIIb, IVa, IVb, Va, Vb, VI, VIIa and VIIb compounds, $R^{4a}$ is selected from from the group consisting of hydrogen, halogen, alkyl, alkoxy, thioalkyl, alkenyl, and cycloalkyl while substituent $R^{4b}$ is hydrogen or halogen. $R^5$ in Formulae I, Ia, IIa, IIb, IIIa, IIIb, IVa, IVb, Va, Vb, VI, VIIa and VIIb is hydrogen or lower alkyl, while substituents $R^6$, $R^7$ and $R^8$ are hydrogen.

In an embodiment of the invention, $R^6$ and $R^7$ in Formula VI are both hydrogen, while for certain Formula VIIa and Formula VIIb compounds $R^6$ is hydrogen.

The present invention is further directed to Formulae I, Ia, IIa, IIb, IIIa, IIIb, IVa, IVb, Va, and Vb compounds where substituent groups $R^6$ and $R^8$ are both hydrogen, and $R_7$ is selected from from the group consisting of hydroxy, halogen, cyano, alkyl, alkenyl, alkynyl, alkoxy, cycloalkyl cycloalkylalkylene, cycloalkylalkenylene, amino, alkylaminyl, alkylcarbonylaminyl, cycloalkylcarbonylaminyl, cycloalkylaminyl, heterocyclylaminyl, heteroaryl, and heterocyclyl. For these inventive compounds any alkyl, alkenyl, alkynyl, alkoxy, cycloalkyl, cycloalkylalkylene, cycloalkylalkenylene, amino, alkylaminyl, alkylcarbonylaminyl, cycloalkylcarbonylaminyl, cycloalkylaminyl, heterocyclylaminyl, heteroaryl, or heterocyclyl is optionally substituted with 1, 2 or 3 J groups. In one embodiment $R_7$ is selected from the group consisting of alkyl, cycloalkyl, cycloalkylalkylene, cycloalkylalkenylene, amino, alkylaminyl, alklycarbonylaminyl, cycloalkylcarbonylaminyl, heterocyclylaminyl, heteroaryl, heterocyclyl and cycloalkylaminyl. For such compounds any alkyl, alkenyl, cycloalkyl, cycloalkylalkylene, cycloalkylalkenylene, amino, alkylaminyl, alklycarbonylaminyl, cycloalkylcarbonylaminyl, heterocyclylaminyl, heteroaryl, heterocyclyl or cycloalkylaminyl may optionally be substituted with 1, 2 or 3 J groups. Thus, the invention provides Formulae I, Ia, IIa, IIb, IIIa, IIIb, IVa, IVb, Va, and Vb compounds where substituent groups $R^6$ and $R^8$ are both hydrogen, and $R_7$ is amino; substituent groups $R^6$ and $R^8$ are both hydrogen, and $R_7$ is alkylaminyl; substituent groups $R^6$ and $R^8$ are both hydrogen, and $R_7$ is —NHCH$_3$; substituent groups $R^6$ and $R^8$ are both hydrogen, and $R_7$ is cycloalkyl, for example cyclopropyl; substituent groups $R^6$ and $R^8$ are both hydrogen, and $R_7$ is cycloalkylaminyl substituted with 1 to 3 J groups, for instance halogens.

In one embodiment, for compounds in accordance with Formulae I, Ia, IIa, IIb, IIIa, IIIb, IVa, IVb, Va, and Vb, substituent groups $R^6$ and $R^8$ are both hydrogen, and $R_7$ is selected from from the group consisting of —NHCH(CF$_3$) cyclopropyl, cycloalkylcarbonylaminyl, —NHC(O)cyclopropyl, cycloalkylalkenylene, and —CH═CHcyclopropyl.

For any compound in accordance with Formulae I, Ia, IIa, IIb, IIIa, IIIb, IVa, IVb, Va, Vb, VI, VIIa, and VIIb, J is —SH, —SR$^9$, —S(O)R$^9$, —S(O)$_2$R$^9$, —S(O)NH$_2$, —S(O)NR$^9$R$^9$, —NH$_2$, —NR$^9$R$^9$, —COOH, —C(O)OR$^9$, —C(O)R$^9$, —C(O)—NH$_2$, —C(O)—NR$^9$R$^9$, hydroxy, cyano, halogen, acetyl, alkyl, lower alkyl, alkenyl, alkynyl, alkoxy, haloalkyl, thioalkyl, cyanoalkylene, alkylaminyl, NH$_2$—C(O)-alkylene, NR$^9$R$^9$—C(O)-alkylene, —CHR$^9$—C(O)-lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —CHR$^9$—C(O)-cycloalkyl, —C(O)-cycloalkyl, —CHR$^9$—C(O)-aryl, —CHR$^9$-aryl, —C(O)-aryl, —CHR$^9$—C(O)-heterocycloalkyl, —C(O)-heterocycloalkyl, heterocyclylaminyl, or heterocyclyl and R$^9$ is hydrogen, lower alkyl or —OH. Additionally, when two J groups bound to the same carbon or hetero atom they may be taken together to form oxo.

For certain compounds according to Formulae I, Ia, IIa, IIb, IIIa, IIb, IVa, IVb, Va, Vb, VI, VIIa, and VIIb, J is halogen, hydroxy, alkyl, alkenyl, alkynyl or cyanoalkylene. Illustrative alkyl or alkylene chains are those having $C_1$-$C_{10}$ carbon atoms, $C_1$-$C_8$ carbon atoms, $C_1$-$C_6$ carbon atoms, $C_1$-$C_4$ carbon atoms, $C_1$-$C_3$ carbon atoms as well as ethyl and methyl groups. Alternatively, when J is alkenyl, or alkynyl, the carbon chain has at least one double or triple bond respectively and $C_2$-$C_{10}$ carbon atoms, $C_2$-$C_8$ carbon atoms, $C_2$-$C_6$ carbon atoms, $C_2$-$C_4$ carbon atoms, or $C_2$-$C_3$ carbon atoms.

The inventive compounds according to Formula I, as well as Formulae Ia, IIa, IIb, IIIa, IIIb, IVa, IVb, Va, Vb VI, VIIa and VIIb may be isotopically-labelled by having one or more atoms replaced by an atom having a different atomic mass or mass number. Examples of isotopes that can be incorporated into compounds of according to Formula I include isotopes of hydrogen, carbon, nitrogen, oxygen, phosphorous, fluorine, chlorine, or iodine. Illustrative of such isotopes are $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds can be used to measure the biodistribution, tissue concentration and the kinetics of transport and excretion from biological tissues including a subject to which such a labelled compound is administered. Labeled compounds are also used to determine therapeutic effectiveness, the site or mode of action, and the binding affinity of a candidate therapeutic to a pharmacologically important target. Certain radioactive-labelled compounds according to Formula I, therefore, are useful in drug and/or tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron emitting isotopes, such as $^{11}$C, $^{18}$F, $^{15}$O and $^{13}$N, provides labeled analogs of the inventive compounds that are useful in Positron Emission Tomography (PET) studies, e.g., for examining substrate receptor occupancy. Isotopically-labeled compounds according to Formula I, as well as Formulae Ia, IIa, IIb, IIIa, IIIb, IVa, IVb, Va, Vb VI, VIIa and VIIb can generally be prepared by conventional techniques known to those skilled in the art or by processes analogous to those described in the Preparations and Examples section as set out below using an appropriate isotopic-labeling reagent.

Embodiments of the invention disclosed herein are also meant to encompass the in vivo metabolic products of compounds according to Formulae I, Ia, IIa, IIb, IIIa, IIIb, IVa, IVb, Va, Vb VI, VIIa and VIIb. Such products may result from, for example, the oxidation, reduction, hydrolysis, amidation, esterification, and like processes primarily due to enzymatic activity upon administration of a compound of the invention. Accordingly, the invention includes compounds that are produced as by-products of enzymatic or non-enzymatic activity on an inventive compound following the administration of such a compound to a mammal for a period of time sufficient to yield a metabolic product. Metabolic products, particularly pharmaceutically active metabolites are typically identified by administering a radiolabelled compound of the invention in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabelled compound.

The invention also provides pharmaceutically acceptable salt forms of Formulae I, Ia, IIa, IIb, IIIa, IIIb, IVa, IVb, Va, Vb VI, VIIa and VIIb compounds. Encompassed within the scope of the invention are both acid and base addition salts that are formed by contacting a pharmaceutically suitable acid or a pharmaceutically suitable base with a compound of the invention.

To this end, a "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

Similarly, a "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases, the compounds of the invention may merely retain adventitious water or be a mixture of water plus some adventitious solvent.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

Compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)-for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The term "tautomer" refers to a proton shift from one atom of a molecule to another atom of the same molecule. For example, when $W^1$ is oxo and $R^1$ is H, the present invention provides tautomers of a Formula I compound as illustrated below:

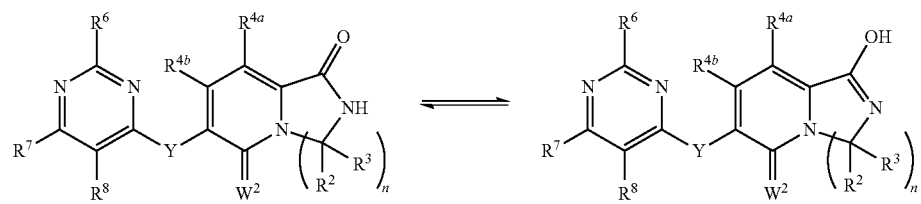

Similar tautomers exists for Formulae I, Ia, IIa, IIb, IIIa, IIIb, IVa, IVb, Va, Vb VI, VIIa and VIIb compounds. The inventive compounds are synthesized using conventional synthetic methods, and more specifically using the general methods noted below. Specific synthetic protocols for several compounds in accordance with the present invention are described in the Examples.

General Synthetic Methods
Method 1:

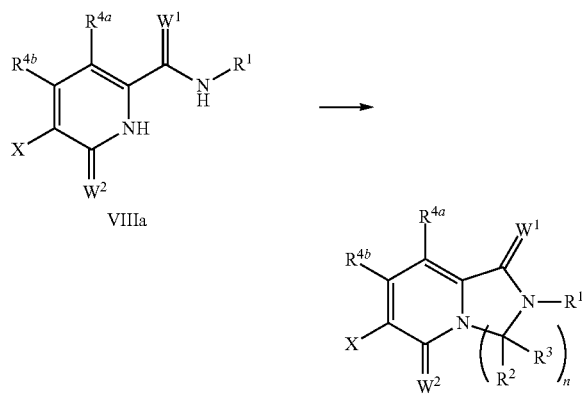

Formation of IXa, when n=1 and X=halogen or other leaving group, such as -OTf, -OTs or -OMs, was accomplished by exposing intermediate VIIIa to an aldehyde or ketone Xa, or an aldehyde or ketone equivalent Xb-d under acidic conditions where $R^2$-$R^3$ are as previously defined and $R^m$=H, $CH_3$, $CH_2CH_3$, or alkyl. More specifically, exposing VIIIa where X is Cl or Br to an aldehyde or ketone Xa in 1,4-dioxane and concentrated sulfuric acid with heating yields intermediated IXa (n=1).

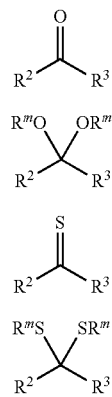

Pyrimidine-type compounds according to Formula XIIa or XIIb where Y is $N(R^5)$, O, or S and P is a protecting group can be purchased or prepared from XIa by various methods, for example, by displacing the leaving group X of compound XIa with an appropriate N, O, or S nucleophile. The resulting compound XIIb can be deprotected to give XIIa.

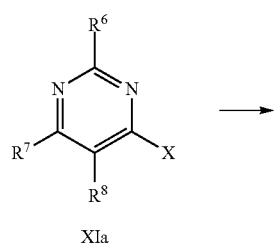

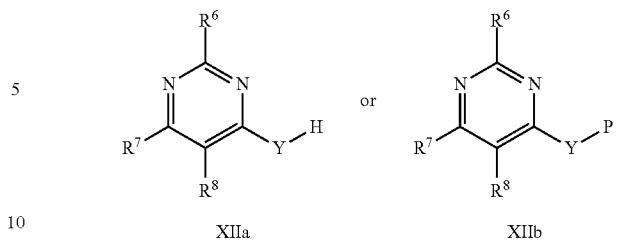

Inventive compounds according to Formula I when Y is $N(R^5)$, O, or S were synthesized by contacting intermediate IXa with a pyrimidine compound XIIa where $R^6$-$R^8$ are as previously defined, under appropriate reaction conditions as further described below.

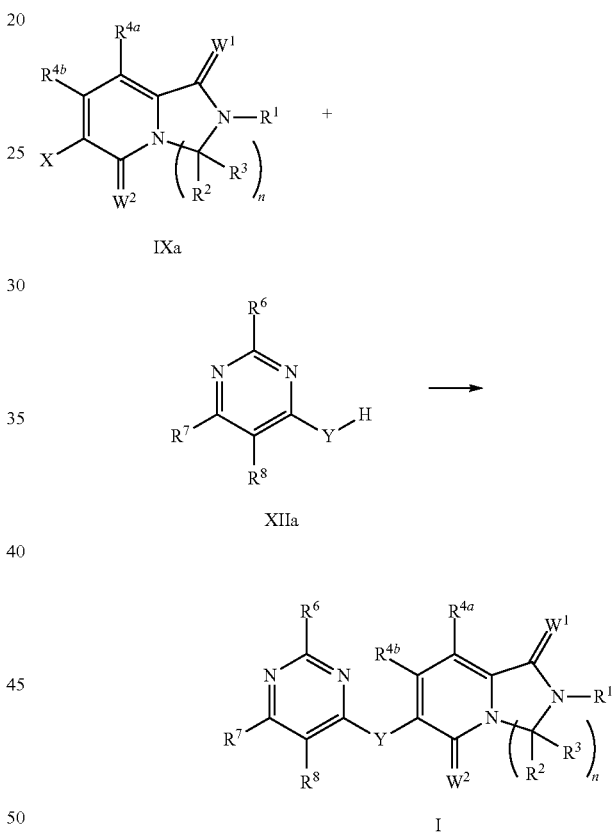

More specifically, Formula I compounds when Y is $N(R^5)$, O, or S were synthesized using Buchwald-Hartwig coupling, Ullmann-type coupling, or nucleophilic aromatic substitution. Thus, contacting intermediate IXa where X=Cl or Br and n=1 with a compound of Formula XIIa where Y is $N(R^5)$, O, or S under conditions suitable for coupling, or nucleophilic aromatic substitution gave Formula I compounds.

Alternatively, the leaving group X of intermediate IXa may be displaced with an appropriate N, O, or S nucleophile under conditions similar to those described above for synthesis of XIIa so as to afford intermediate XIIIa or protected intermediate XIIIb where Y is $N(R^5)$, O, or S. XIIIb may be deprotected to yield XIIIa.

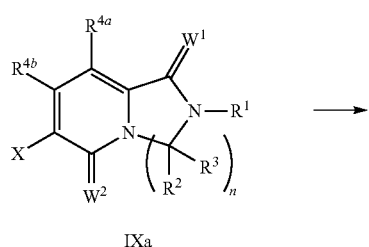

IXa

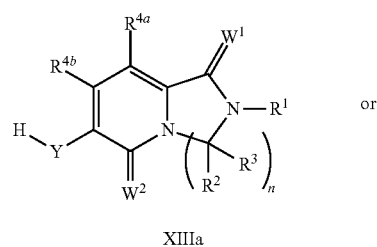

XIIIa

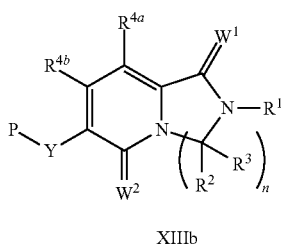

XIIIb

Formula I compounds when Y is N(R⁵), O, or S are readily synthesized by contacting intermediate XIIIa where Y is N(R⁵), O, or S with a pyrimidine compound XIa where X=halogen or other leaving group such as -OTf, -OTs or -OMs under the conditions of Buchwald-Hartwig coupling, Ullmann-type coupling, or nucleophilic aromatic substitution.

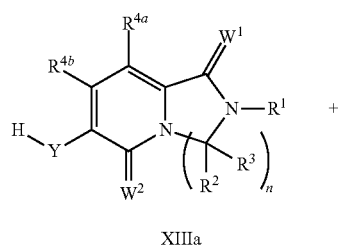

XIIIa       +

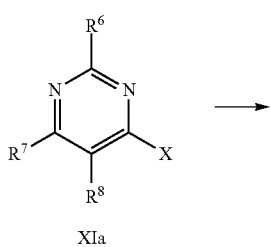

XIa

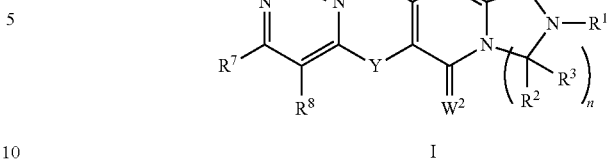

I

More specific synthetic methods for several Formula I compounds are set forth below. It is understood that if protecting groups are used during the synthesis of intermediates, or if a Formula I compound contains one or more protecting groups, then such protecting groups are removed by methods known in the chemical art. Other transformations, such as the displacement of a halogen, for example, the conversion of $R^{4a}$, or $R^{4b}$=Cl to $R^{4a}$, or $R^{4b}$=OMe, SMe, CH=CH₂ or Me, the conversion of $W^1$, or $W^2$ or both groups from O to S; the formation of an oxime by converting $W^1$, or $W^2$ or both groups from an oxo (=O) group to a =NHOR' group, the conversion of Y from S to S=O or S(=O)₂, and the conversion of an intermediate or a Formula I compound to a pharmaceutically acceptable salt are carried out using conventional methods known in the chemical art.

Method 2:

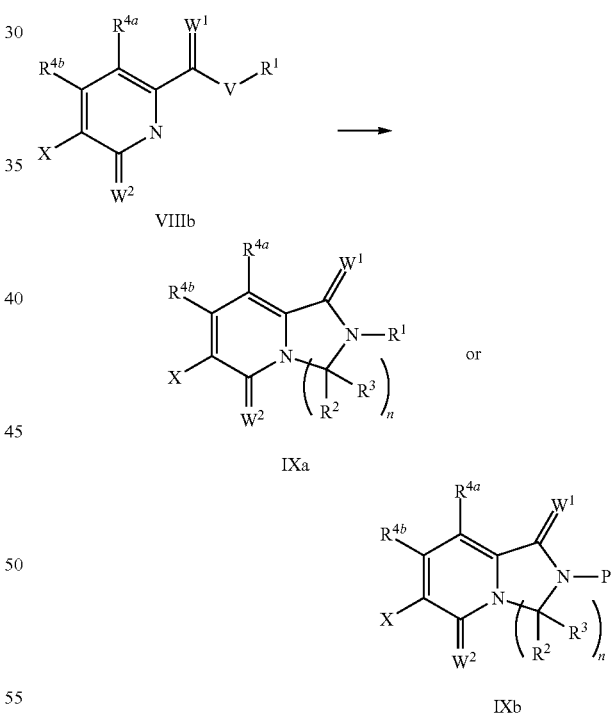

Formation of IXa or IXb, when n=2 or 3, variable "X" is a halogen or another leaving group such as -OTf, -OTs or -OMs, and variable "V" is O or N can be accomplished by contacting intermediate VIIIb to a 1,2-difunctionalized ethyl intermediate XIVa, or a 1,3-difunctionalized propyl intermediate XIVb under conditions suitable for the synthesis of compounds IXa and IXb respectively. Variables $Z^1$ and $Z^2$ in XIVa and XIVb can be a halogen or other leaving groups such as -OTf, -OTs or -OMs, or OH, NHR¹ or NHP, where P is an appropriate protecting group.

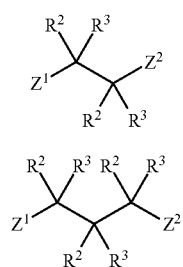

XIVa

XIVb

According to this synthetic strategy, intermediate VIIIb where variable "X" is Cl or Br and variable "V" is O is contacted with XIVa where $R^2$ and $R^3$ are H, $Z^1$ is OH and $Z^2$ is NH-(4-methoxybenzyl) in acetonitrile in the presence of an amide bond forming reagent such as HATU. The reaction mixture is heated to promote coupling and yields intermediated IXb where n=2 and P is 4-methoxybenzyl.

The inventive Formula I compounds when Y is $N(R^5)$, O, or S are synthesized by contacting intermediates IXa or IXb (n=2 or 3 and X=halogen or other leaving group such as -OTf, -OTs or -OMs), with pyrimidine XIIa where Y is $N(R^5)$, O, or S and $R^6$-$R^8$ are as previously defined, under appropriate conditions followed by deprotection of the resultant Formula I compound if required.

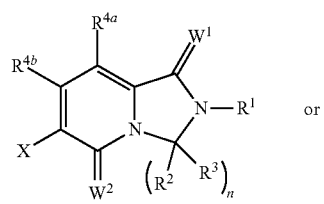

IXa

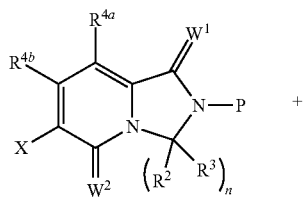

IXb

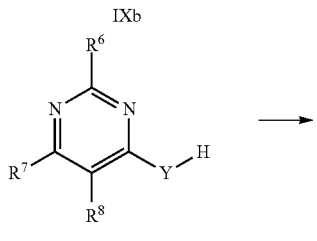

XIIa

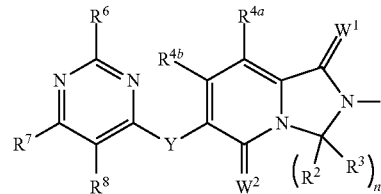

I

Thus, contacting intermediate IXb where n=2, X is Cl or Br and P is 4-methoxybenzyl with pyrimidine XIIa, where Y is $N(R^5)$, O, or S, under the conditions suitable for Buchwald-Hartwig coupling, Ullmann-type coupling, or nucleophilic aromatic substitution results in a 4-methoxybenzyl protected Formula I compound. The therapeutically active Formula I compound can readily be obtained by deprotection of the 4-methoxybenzyl group with trifluoroacetic acid.

Alternatively, certain Formula I compounds were synthesized by displacing the leaving group "X" of intermediate IXa with suitable N, O, or S nucleophiles under similar conditions similar to those described in Method 1 to give XIIIa or protected intermediate XIIIb which can be deprotected to yield XIIIa. The leaving group "X" of intermediate IXa can be halogen, -OTf, -OTs or -OMs and subscript n is either 2 or 3.

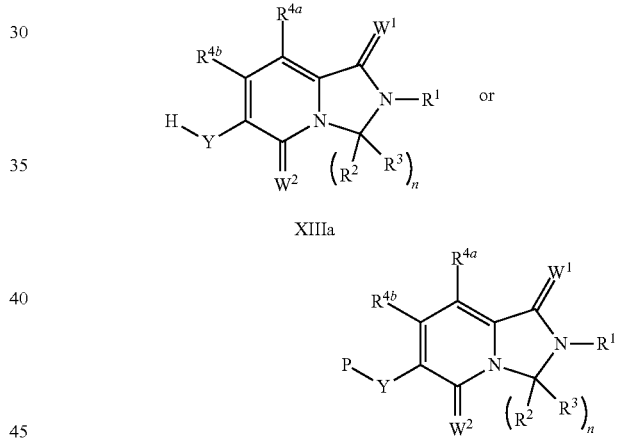

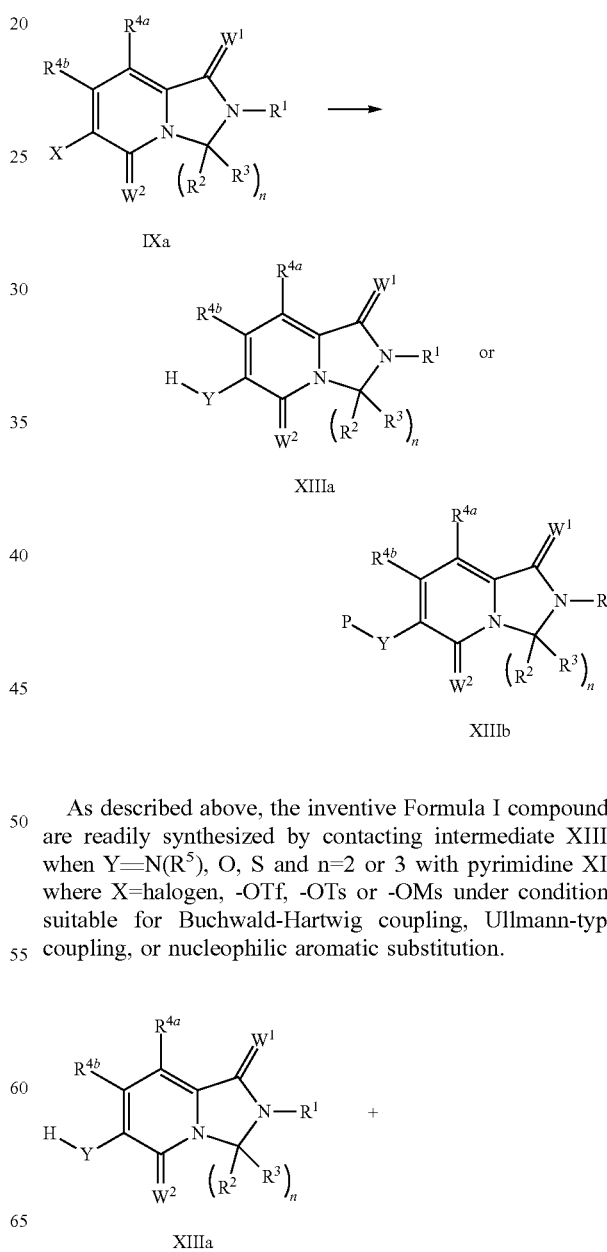

As described above, the inventive Formula I compounds are readily synthesized by contacting intermediate XIIIa when Y=$N(R^5)$, O, S and n=2 or 3 with pyrimidine XIa where X=halogen, -OTf, -OTs or -OMs under conditions suitable for Buchwald-Hartwig coupling, Ullmann-type coupling, or nucleophilic aromatic substitution.

-continued

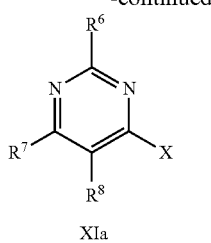
XIa

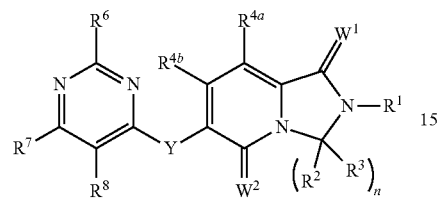
I

The synthesis of some Formula I compounds was carried out by contacting the protected intermediate IXb (n=2 or 3), with an appropriate N, O, or S nucleophile to give XIIIc under similar conditions described above with IXa.

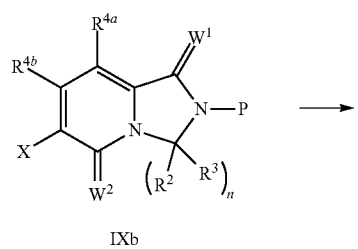
IXb

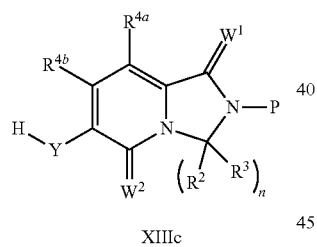
XIIIc

Intermediate XIIIc, thus obtained, was then contacted with pyrimidine XIa where X is either halogen or a leaving group selected from the group consisting of -OTf, -OTs and -OMs under conditions suitable for Buchwald-Hartwig coupling, Ullmann-type coupling, or nucleophilic aromatic substitution. Deprotection by methods known in the chemical art gave the candidate MnK inhibitor Formula I compounds.

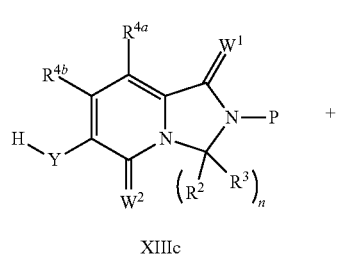
XIIIc

-continued

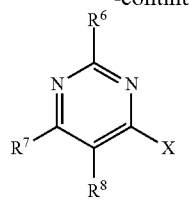
XIa

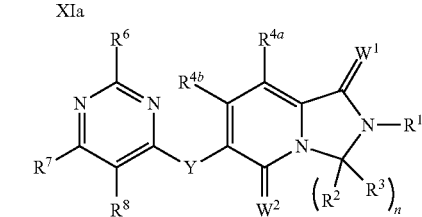
I

Method 3:

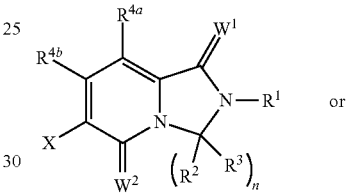
IXa or

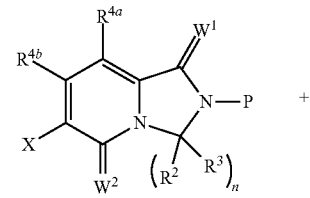
IXb

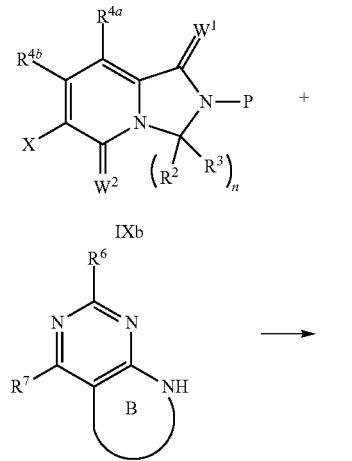
XV

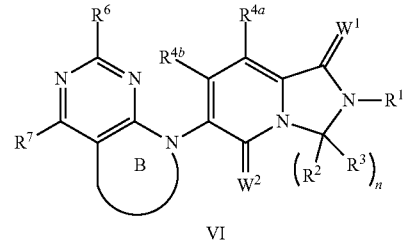
VI

Synthesis of Formula VI compounds, where n=1, 2, or 3 was accomplished by contacting intermediates IXa or IXb where variable "X" is a leaving group selected from the group consisting of halogen, -OTf, -OTs and -OMs, and P is a protecting group with a bicyclic intermediate XV in the presence of a homogeneous palladium-phosphine catalyst and a base such as cesium carbonate or sodium t-butoxide using 1,4-dioxane as a solvent. The reaction mixture was heated to promote coupling, followed by deprotection if needed. Illustrative of intermediate XV compounds without limitation are substituted or unsubstituted 6,7-dihydro-5H-pyrrolo[2,3-d]pyrimidine, 7H-pyrrolo[2,3-d]pyrimidine, 9H-purine, 1H-pyrazolo[3,4-d]pyrimidine, and 5,6,7,8-tetrahydropyrido[2,3-d]pyrimidine).

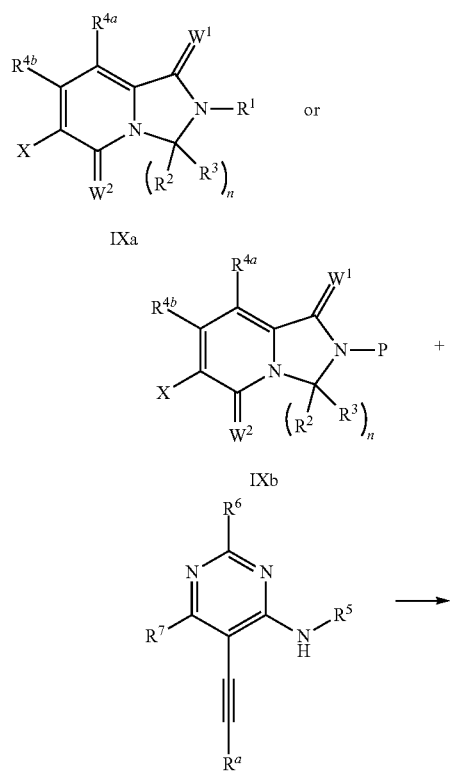

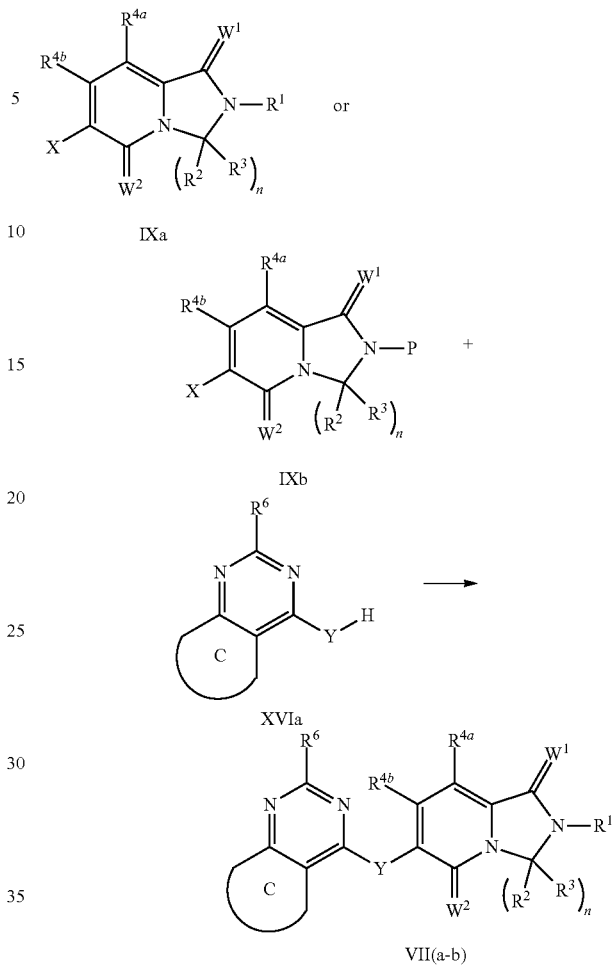

Method 4:

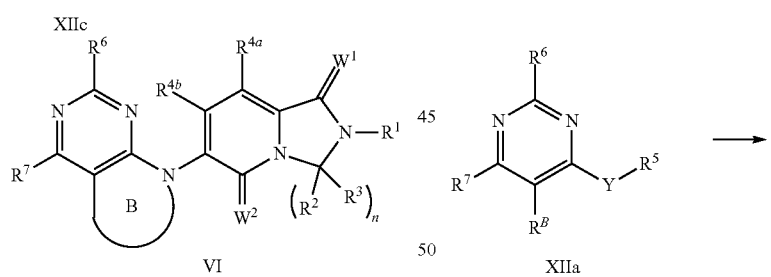

Alternatively, Formula VI compounds where B is an unsaturated 5-membered ring and n=1, 2 or 3 may be synthesized by contacting intermediates IXa or IXb with a 5-ethynyl-4-amino-pyrimidine intermediate XIIc (where $R^a$ is a J group as defined herein) in the presence of a homogeneous palladium-phosphine catalyst and a base such as cesium carbonate or sodium t-butoxide using 1,4-dioxane as solvent for the coupling reaction. The reaction mixture may be heated to promote coupling, followed by deprotection if required. The 5-Ethynyl-4-amino-pyrimidine intermediates XIIc synthesized by a cross-coupling reaction between XIIa where Y=N($R^5$) and $R^8$ is a leaving group such as halogen or -OTf and a suitable alkyne using copper and/or homogeneous palladium catalysts.

Compounds according to Formula VIIa or Formula VIIb, where Y=N($R^5$), O, or S and n is 1, 2 or 3 can be synthesized by contacting intermediates IXa or IXb where X is a leaving group such as halogen, -OTf, -OTs or -OMs, and P is a protecting group with the bicyclic intermediate XVIa under the conditions of Buchwald-Hartwig coupling, Ullmann-type coupling, or nucleophilic aromatic substitution. Ring C of bicyclic intermediate is as defined above and variable Y can be —N(R$^5$), O, or S. Representative examples of XVIa intermediates include without limitation substituted or unsubstituted 6-amino-purine, 4-amino-1H-pyrazolo[3,4-d]pyrimidine, 4-amino-7H-pyrrolo[2,3-d]pyrimidine, 4-amino-6,7-dihydro-5H-pyrrolo[2,3-d]pyrimidine, 7-amino-3H-[1,2,3]triazolo[4,5-d]pyrimidine, 4-aminoquinazoline, 4-amino-5,6,7,8-tetrahydropyrido[2,3-d]pyrimidine, various 4-amino-pyrido[d]pyrimidines, pyrimido[5,4-d]pyrimidin-4-amine, and 7,8-dihydro-6H-pyrimido[5,4-b][1,4]oxazin-4-amine).

Bicyclic pyrimidine-type intermediate compounds according to Formula XVIa where Y=N(R$^5$), O, or S can be purchased or prepared from XVI by displacing the leaving group X with an appropriate N, O, or S nucleophile using methods known in the chemical art. The protecting group "P" in an intermediate according to XVIb can be removed to give intermediate XVIa.

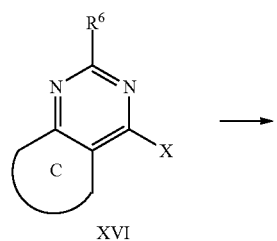

XVI

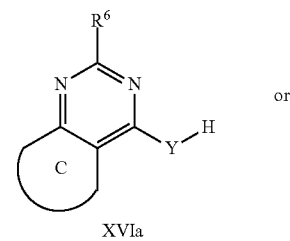

XVIa

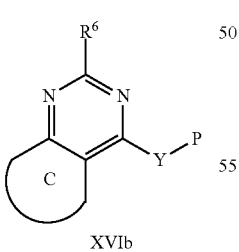

XVIb

Alternatively intermediates XIIIa or XIIIb may be contacted with the fused pyrimidine XVI where X=halogen or other leaving group such as -OTf, -OTs or -OMs under conditions suitable for Buchwald-Hartwig or Ullmann-type couplings, or conditions suitable for nucleophilic aromatic substitution followed by deprotection if necessary to give Formula VIIa or Formula VIIb compounds.

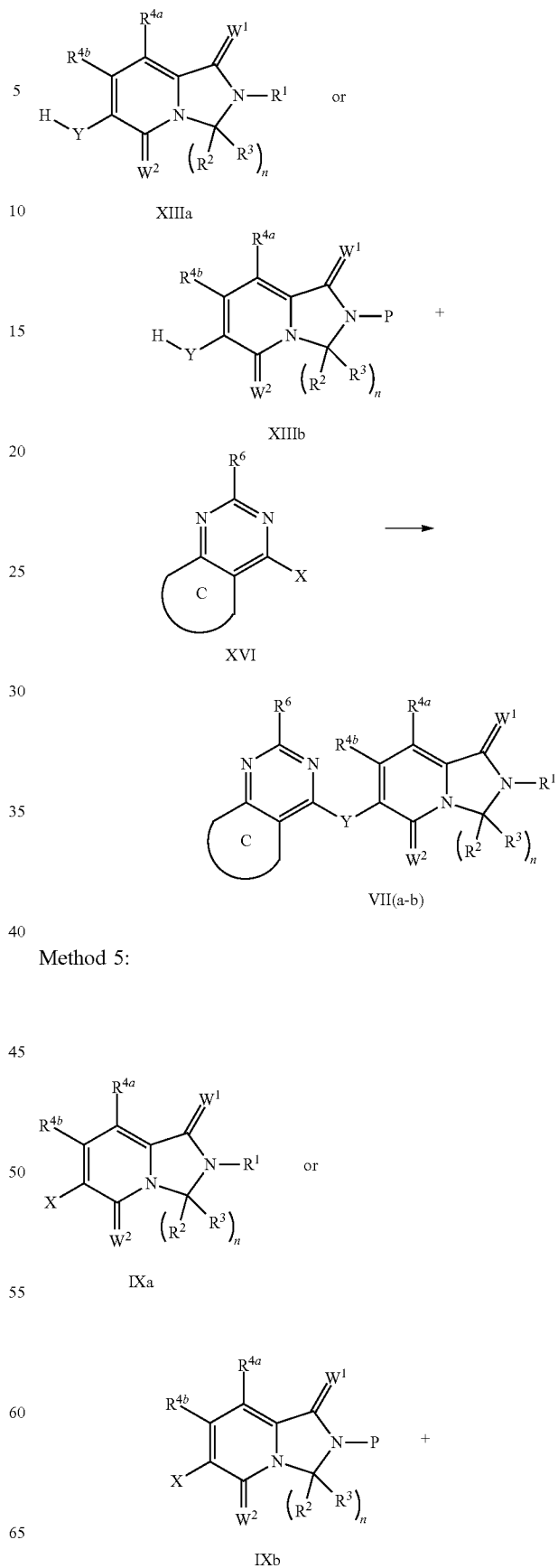

Method 5:

-continued

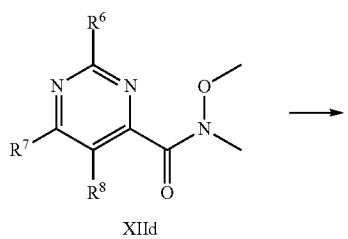

XIId

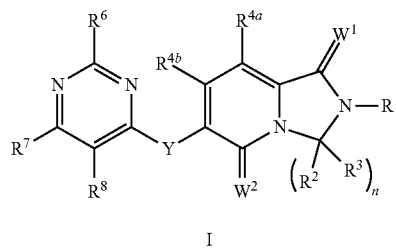

I

Methods for synthesizing a Formula I, when Y is —C(O) and n=1, 2 or 3 comprise contacting intermediate IXa or intermediate IXb (where X is a leaving group, such as halogen, -OTf, -OTs or -OMs, and P is a protecting group) with the intermediate XIId in the presence of a base such as n-butyllithium. The resultant product may be deprotected if required to provide Formula I compounds.

Formation of Formula I, where Y=CH and n=1, 2 or 3 may be carried out by reducing the carbonyl (—C(O)) at "Y" under Wolff-Kishner reduction conditions.

Method 6:

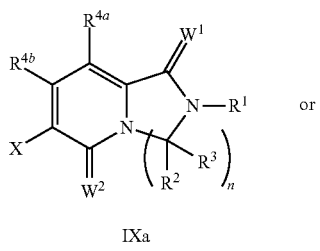

IXa or

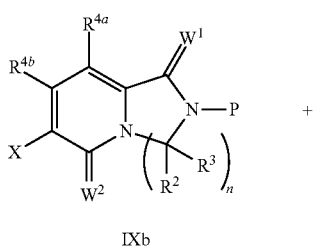

IXb

+

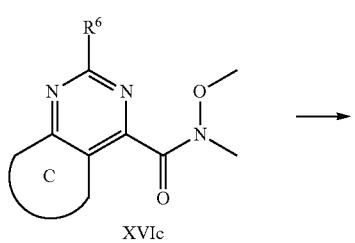

XVIc

-continued

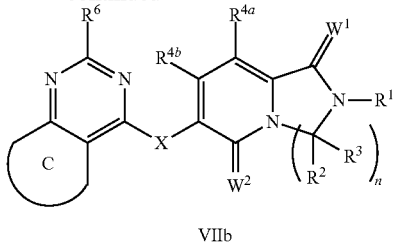

VIIb

Synthesis of Formula VIIb compounds, when Y=C(O), n=1, 2 or 3 and C is as defined previously is carried out by contacting intermediate IXa or intermediate IXb (where X is a leaving group, such as halogen, -OTf, -OTs or -OMs, and P is a protecting group) with the intermediate XVIc in the presence of a base such as n-butyllithium. The resultant product may be deprotected if required to provide Formula VIIb compounds.

Formation of VIIb, when Y=CH and n=1, 2 or 3 may be accomplished by reducing the carbonyl (—C(O)) at "Y" under Wolff-Kishner reduction conditions.

Pharmaceuticals Formulations

In one embodiment, a compounds according Formulae I through VII, are formulated as pharmaceutically acceptable compositions that contain a Formulae I-VII compound in an amount effective to treat a particular disease or condition of interest upon administration of the pharmaceutical composition to a mammal. Pharmaceutical compositions in accordance with the present invention can comprise a Formulae I-VII compound in combination with a pharmaceutically acceptable carrier, diluent or excipient.

In this regard, a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Further, a "mammal" includes humans and both domestic animals such as laboratory animals and household pets (e.g., cats, dogs, swine, cattle, sheep, goats, horses, rabbits), and non-domestic animals such as wildlife and the like.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by any methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

In certain embodiments a pharmaceutical composition comprising a compound of Formula I is administered to a mammal in an amount sufficient to inhibit Mnk activity upon administration, and preferably with acceptable toxicity to the same. Mnk activity of Formula I compounds can be determined by one skilled in the art, for example, as described in the Examples below. Appropriate concentrations and dosages can be readily determined by one skilled in the art.

Therapeutic Use

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

"Effective amount" or "therapeutically effective amount" refers to that amount of a compound of the invention which, when administered to a mammal, preferably a human, is sufficient to effect treatment, as defined below, of a Mnk related condition or disease in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

Compounds of the invention, or pharmaceutically acceptable salt thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In certain embodiments, the disclosed compounds are useful for inhibiting the activity of Mnk and/or can be useful in analyzing Mnk signaling activity in model systems and/or for preventing, treating, or ameliorating a symptom associated with a disease, disorder, or pathological condition involving Mnk, preferably one afflicting humans. A compound which inhibits the activity of Mnk will be useful in preventing, treating, ameliorating, or reducing the symptoms or progression of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mnk, such as, for example, haematological tumors, solid tumors, and/or metastases thereof, including leukaemias and myelodysplastic syndrome, malignant lymphomas, for example, B-cell lymphoma, T-cell lymphoma, hairy cell lymphoma, Hodgkins lymphoma, non-Hodgins lymphoma and Burkitts lymphoma, head and neck tumors including brain tumors and brain metastases, tumors of the thorax including non-small cell and small cell lung tumors, gastrointestinal tumors, endocrine tumors, mammary and other gynecological tumors, urological tumors including renal, bladder and prostate tumors, skin tumors, and sarcomas, and/or metastases thereof.

Furthermore, the inventive compounds and their pharmaceutical compositions are candidate theraputics for the prophylaxis and/or therapy of cytokine related diseases, such as inflammatory diseases, allergies, or other conditions associated with proinflammatory cytokines. Exemplary inflammatory diseases include without limitation, chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from the group consisting of granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis. oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Although inflammation is the unifying pathogenic process of these diseases, current therapies only treat the symptoms of the disease and not the underlying cause of inflammation. The compositions of the present invention are useful for the treatment and/or prophylaxis of inflammatory diseases and related complications and disorders.

Accordingly, certain embodiments are directed to a method for treating a Mnk dependent condition in a mammal in need thereof, the method comprising administering an effective amount of a pharmaceutical composition as described above (i.e., a pharmaceutical composition comprising any one or more compounds of Formula I) to a mammal.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As described above deregulation of protein synthesis is a common event in human cancers. A key regulator of translational control is eIF4E whose activity is a key determinant of tumorigenicity. Because activation of eIF4E involves phosphorylation of a key serine (Ser209) specifically by MAP kinase interacting kinases (Mnk), inhibitors of Mnk are suitable candidate therapeutics for treating cell proliferative disorders such as cancer. A wide variety of cancers, including solid tumors, lymphomas and leukemias, are amenable to the compositions and methods disclosed herein. Types of cancer that may be treated include, but are not limited to adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include histiocytic disorders; leukemia; histiocytosis malignant; Hodgkin's disease; immunoproliferative small; non-Hodgkin's lymphoma; diffuse large B cell lymphoma, T-cell lymphoma, B-cell lymphoma, hairy cell lymphoma, Burkitts lymphoma, plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor.

Other cancers that can be treated using the inventive compounds include without limitation adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin.

In one embodiment the inventive compounds are candidate therapeutic agents for the treatment of cancers such as angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In a particular embodiment, the present disclosure provides methods for treating solid tumor, colon cancer, rectal cancer, colorectalcancer, bladder cancer, gastric cancer, esophageal cancer, head and neck cancer, myelodysplastic syndrome, brain cancer, CNS cancer, malignant glioma, glioblastoma, hepatocellular cancers, hepatocellular carcinoma, thyroid cancer, lung cancer, non-small cell lung cancer, a hematological cancer, leukemia, B-cell lymphoma, T-cell lymphoma, hairy cell lymphoma, diffuse large B cell lymphoma, Hodgkins lymphoma, non-Hodgkins lymphoma, Burkitt lymphoma, pancreatic cancer, melanoma, myeloma, multiple myeloma, pancreatic carcinoma, renal cell carcinoma, renal cancer, cervical cancer, urothelial cancer, prostate cancer, castration-resistant prostate cancer, ovarian cancer, breast cancer or triple-negative breast cancer. According to such a method, a therapeutically effective amount of at least one compound according to Formula I or a stereoisomer, tautomer or pharmaceutically acceptable salt thereof can be administered to a subject who has been diagnosed with a cell proliferative disease, such as a cancer. Alternatively, a pharmaceutical composition comprising at least one compound according to Formula I or a stereoisomer, tautomer or pharmaceutically acceptable salt thereof can be administered to a subject who has been diagnosed with cancer.

In certain embodiments, the compounds in accordance with the invention are administered to a subject with cancer in conjunction with other conventional cancer therapies such as radiation treatment or surgery. Radiation therapy is well-known in the art and includes X-ray therapies, such as gamma-irradiation, and radiopharmaceutical therapies.

In certain embodiments, the inventive Mnk inhibitor compounds are used with at least one anti-cancer agent. Anti-cancer agents include chemotherapeutic drugs. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

In certain embodiments, an Mnk inhibitor in accordance with the present invention is used simultaneously, in the same formulation or in separate formulations, or sequentially with an additional agent(s) as part of a combination therapy regimen.

Mnk inhibitors according to Formula I, Ia, IIa, IIb, IIIa, IIIb, IVa, IVb, Va, Vb, VI, VIIa, and VIIb including their corresponding salts and pharmaceutical compositions of Formula I, Ia, IIa, IIb, IIIa, IIIb, IVa, IVb, Va, Vb, VI, VIIa, and VIIb compounds are also effective as therapeutic agents for treating or preventing cytokine mediated disorders, such as inflammation in a patient, preferably in a human. In one embodiment, a compound or composition in accordance with the invention is particularly useful for treating or preventing a disease selected from the group consisting of chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

In a further aspect of the invention, the inventive compounds or pharmaceutically acceptable formulations of the inventive compounds are provided as inhibitors of Mnk activity. Such inhibition is achieved by contacting a cell expressing Mnk with a compound or a pharmaceutically acceptable formulation, to lower or inhibit Mnk activity, to provide therapeutic efficacy for a Mnk dependent condition in a mammal in need thereof.

Therapeutically effective dosages of a compound according to Formula I or a composition of a Formula I compound will generally range from about 1 to 2000 mg/day, from about 10 to about 1000 mg/day, from about 10 to about 500 mg/day, from about 10 to about 250 mg/day, from about 10 to about 100 mg/day, or from about 10 to about 50 mg/day. The therapeutically effective dosages may be administered in one or multiple doses. It will be appreciated, however, that specific doses of the compounds of the invention for any particular patient will depend on a variety of factors such as age, sex, body weight, general health condition, diet, individual response of the patient to be treated, time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician. In any case the compound or composition will be administered at dosages and in a manner which allows a therapeutically effective amount to be delivered based upon patient's unique condition.

Synthesis

The following examples are provided for purpose of illustration and not limitation.

Example 1

Synthesis of 7-(pyrimidin-4-ylamino)-3,4-dihydro-1H-pyrido[1,2-a]pyrazine-1,6-(2H)-dione (Cpd. No. 1)

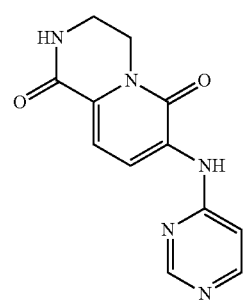 [SMILES: O=C1NCCn2c1ccc(Nc1ccncn1)c2=O]

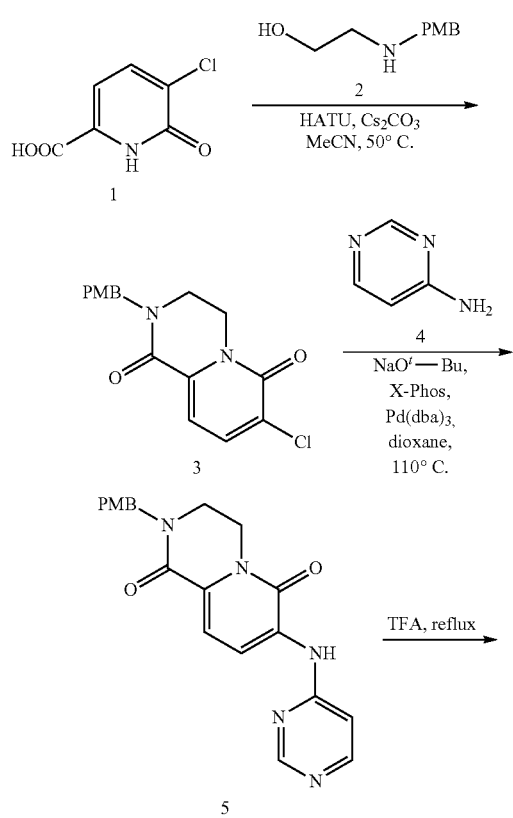

Synthesis of 7-chloro-2-(4-methoxybenzyl)-3,4-dihydro-1H-pyrido[1,2-a]pyrazine-1,6-(2H)-dione (3)

To a solution of 5-chloro-6-oxo-1,6-dihydropyridine-2-carboxylic acid (1, 0.25 g, 1.44 mmol) in acetonitrile (10 mL), 2-((4-methoxybenzyl)amino)ethanol (2, 0.31 g, 1.73 mmol) followed by cesium carbonate (1.18 g, 3.61 mmol) and HATU (1.26 g, 3.32 mmol) were added and the reaction mixture was stirred at 50° C. for 16 h. The reaction mixture was diluted with water and the compound was extracted in ethyl acetate. The organic layer was washed with brine, separated, dried over sodium sulphate and concentrated under reduced pressure. The residue obtained was purified via column chromatography (silica, ethyl acetate/hexanes=60%) to afford 7-chloro-2-(4-methoxybenzyl)-3,4-dihydro-1H-pyrido[1,2-a]pyrazine-1,6-(2H)-dione (3). Yield: 0.24 g, 52%; MS (ESI) m/z 319 [M+1]$^+$.

Synthesis of 2-(4-methoxybenzyl)-7-(pyrimidin-4-ylamino)-3,4-dihydro-1H-pyrido[1,2-a]pyrazine-1,6(2H)-dione (5)

To a solution of 7-chloro-2-(4-methoxybenzyl)-3,4-dihydro-1H-pyrido[1,2-a]pyrazine-1,6-(2H)-dione (3, 0.45 g, 1.41 mmol) in dioxane (10 mL), pyrimidin-4-amine (4, 0.13 g, 1.41 mmol), sodium tert-butoxide (0.41 g, 4.2 mmol) followed by X-Phos (0.14 g, 0.28 mmol) were added and the reaction mixture was degassed with argon for 5 min. Tris(dibenzylideneacetone)dipalladium(0) (0.13 g, 0.14 mmol) was added and the reaction mixture was degassed with argon for another 5 min and stirred at 110° C. for 16 h. The reaction mixture was diluted with water and the compound was extracted in ethyl acetate. The organic layer was washed with brine, separated, dried over sodium sulphate and concentrated under reduced pressure. The residue obtained was purified via column chromatography (silica, methanol/dichloromethane=5%) to afford 2-(4-methoxybenzyl)-7-(pyrimidin-4-ylamino)-3,4-dihydro-1H-pyrido[1,2-a]pyrazine-1,6(2H)-dione (5) as a yellow solid. Yield: 0.42 g, 79%; MS (ESI) m/z 378 [M+1]$^+$.

Synthesis of 7-(pyrimidin-4-ylamino)-3,4-dihydro-1H-pyrido[1,2-a]pyrazine-1,6(2H)-dione (Cpd. No. 1)

A solution of 2-(4-methoxybenzyl)-7-(pyrimidin-4-ylamino)-3,4-dihydro-1H-pyrido[1,2-a]pyrazine-1,6(2H)-dione (5, 0.3 g, 0.79 mmol) in trifluoroacetic acid (5 mL) was heated at 90° C. for 48 h. The reaction mixture was cooled to room temperature and concentrated under reduced pressure. The residue was neutralized with saturated solution of sodium bicarbonate and the compound was extracted in 10% methanol in ethyl acetate. The organic layer was separated, dried over sodium sulphate, concentrated under reduced pressure and the residue obtained was purified via column chromatography (silica, methanol/dichloromethane=10%) to afford 7-(pyrimidin-4-ylamino)-3,4-dihydro-1H-pyrido[1,2-a]pyrazine-1,6(2H)-dione (Cpd. No. 1) as a beige solid. Yield: 0.12 g, 59%; MS (ESI) m/z 258 [M+1]$^+$; $^1$H NMR (400 MHz, DMSO-d$_6$) δ 9.45 (s, 1H), 8.79-8.64 (m, 2H), 8.48 (s, 1H), 8.38 (d, J=5.9 Hz, 1H), 7.41 (dd, J=6.0, 1.3 Hz, 1H), 7.11 (d, J=7.9 Hz, 1H), 4.23-4.16 (m, 2H), 3.55-3.48 (m, 2H).

Example 2

Synthesis of 3,3-dimethyl-6-(pyrimidin-4-ylamino)-2,3-dihydroimidazo[1,5-a]pyridine-1,5-dione (Cpd. No. 2)

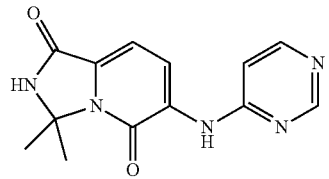 [SMILES: CC1(C)NC(=O)c2ccc(Nc3ccncn3)c(=O)n21]

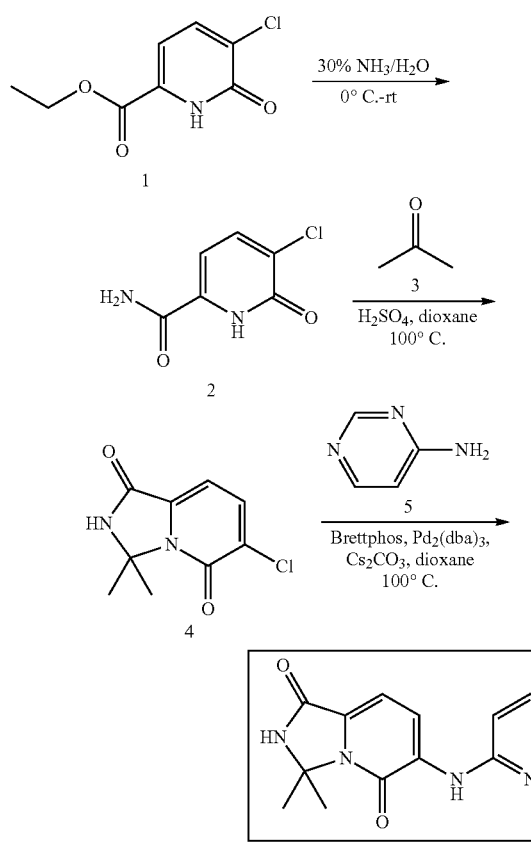

Synthesis of 5-chloro-6-oxo-1,6-dihydropyridine-2-carboxamide (2)

Aqueous ammonia (15 mL, 30% solution) was added to ethyl 5-chloro-6-oxo-1,6-dihydropyridine-2-carboxylate (1, 0.65 g, 3.2 mmol) at 0° C. and the reaction mixture was allowed to stir at room temperature for 16 h. The reaction mixture was concentrated under reduced pressure and the residue was triturated with diethyl ether, filtered and dried to afford 5-chloro-6-oxo-1,6-dihydropyridine-2-carboxamide (2). Yield: 0.43 g, 75%; MS (ESI) m/z 173[M+1]$^+$.

Synthesis of 6-chloro-3,3-dimethyl-2,3-dihydroimidazo[1,5-a]pyridine-1,5-dione (4)

Procedure A: To a solution of 5-chloro-6-oxo-1,6-dihydropyridine-2-carboxamide (2, 1.4 g, 7.9 mmol) in 1,4-dioxane (20 mL), acetone (3, 4.6 g, 79 mmol) and concentrated sulfuric acid (0.038 g, 0.39 mmol) were added at room temperature and the reaction mixture was allowed to heat at 100° C. for 8 h. The reaction mixture was concentrated under reduced pressure and the residue was triturated with diethyl ether and hexane, filtered and dried to afford 6-chloro-3,3-dimethyl-2,3-dihydroimidazo[1,5-a]pyridine-1,5-dione (4). Yield: 1.4 g, 83%; MS (ESI) m/z 213[M+1]$^+$.

Synthesis of 3,3-dimethyl-6-(pyrimidin-4-ylamino)-2,3-dihydroimidazo[1,5-a]pyridine-1,5-dione (Cpd. No. 2)

Procedure B: To a solution of 6-chloro-3,3-dimethyl-2,3-dihydroimidazo[1,5-a]pyridine-1,5-dione (4, 0.25 g, 1.18 mmol) in 1,4-dioxane (8 mL), pyrimidin-4-amine (5, 0.14 g, 1.41 mmol), Brettphos (0.19 g, 0.23 mmol) and cesium carbonate (0.76 g, 2.36 mmol) were added and the reaction mixture was degassed with argon for 5 min. Tris dibenzylideneacetone dipalladium (0) (0.11 g, 0.12 mmol) was added. The reaction was degassed with argon for another 5 min and then stirred at 100° C. for 10 h. The reaction mixture was cooled to room temperature, filtered through celite and the filtrate was concentrated under reduced pressure. The residue was purified by silica gel column chromatography using 5% methanol in dichloromethane to afford 3,3-dimethyl-6-(pyrimidin-4-ylamino)-2,3-dihydroimidazo[1,5-a]pyridine-1,5-dione (Cpd. No. 2) as a light yellow solid. Yield: 0.036 g, 11%; MS (ESI) m/z 272[M+1]$^+$; $^1$H NMR (400 MHz, DMSO-d$_6$) δ 9.70 (s, 1H), 9.42 (s, 1H), 8.81-8.73 (m, 2H), 8.37 (d, J=5.9 Hz, 1H), 7.40-7.34 (m, 1H), 6.87 (d, J=7.7 Hz, 1H), 1.82 (s, 6H).

Example 3

Synthesis of 3-(4-fluorobenzyl)-3-methyl-6-(pyrimidin-4-ylamino)-2,3-dihydroimidazo[1,5-a]pyridine-1,5-dione (Cpd. No. 3)

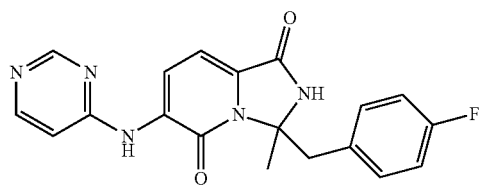 [SMILES: CC1(Cc2ccc(F)cc2)NC(=O)c2ccc(Nc3ccncn3)c(=O)n21]

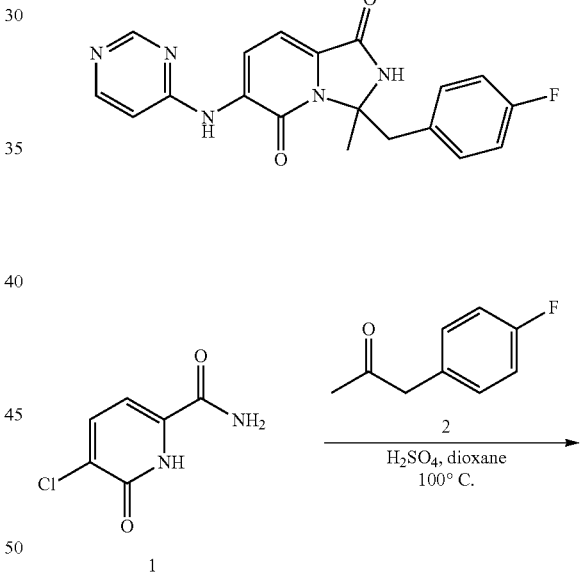

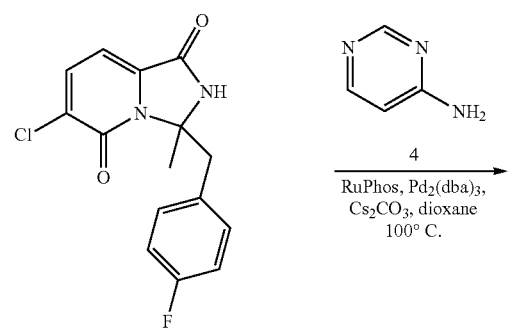

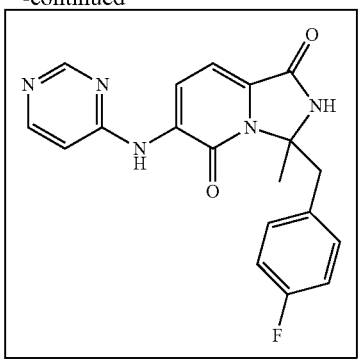

Synthesis of 6-chloro-3-(4-fluorobenzyl)-3-methyl-2,3-dihydroimidazo[1,5-a]pyridine-1,5-dione (3)

The synthesis of intermediate 3 was carried out as described above using the general protocol of Procedure A. Yield: 0.17 g, 49%; MS (ESI) m/z 307[M+1]⁺.

Synthesis of 3-(4-fluorobenzyl)-3-methyl-6-(pyrimidin-4-ylamino)-2,3-dihydroimidazo-[1,5-a]pyridine-1,5-dione (Cpd. No. 3)

The synthesis of compound 3 was carried out as described above using the general protocol of Procedure B. White solid; Yield: 0.012 g, 40%; MS (ESI) m/z 366[M+1]⁺; ¹H NMR (400 MHz, DMSO-d₆) δ 9.66 (s, 1H), 9.50 (s, 1H), 8.75 (s, 1H), 8.68 (d, J=7.6 Hz, 1H), 8.40 (d, J=5.9 Hz, 1H), 7.41 (d, J=5.9 Hz, 1H), 7.04-6.92 (m, 4H), 6.57 (d, J=7.7 Hz, 1H), 3.99 (d, J=13.9 Hz, 1H), 3.07 (d, J=13.9 Hz, 1H), 1.97 (s, 3H).

Example 4

Synthesis of 3-(4-chlorobenzyl)-3-methyl-6-(pyrimidin-4-ylamino)-2,3-dihydroimidazo[1,5-a]pyridine-1,5-dione (Cpd. No. 4)

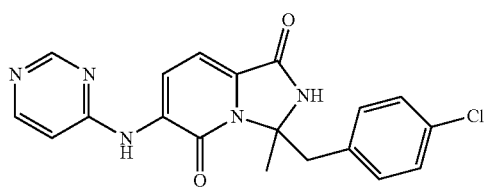 [SMILES: CC1(Cc2ccc(Cl)cc2)NC(=O)c2ccc(Nc3ccncn3)c(=O)n21]

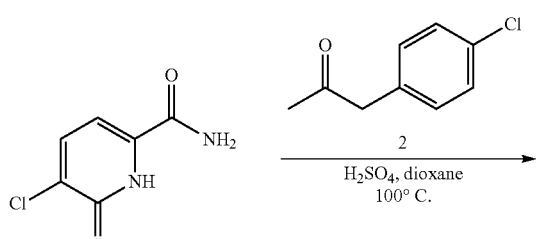

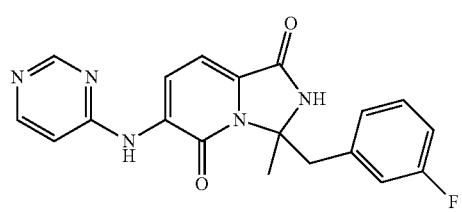 [SMILES: CC1(Cc2cccc(F)c2)NC(=O)c2ccc(Nc3ccncn3)c(=O)n21]

Synthesis of 6-chloro-3-(4-chlorobenzyl)-3-methyl-2,3-dihydroimidazo[1,5-a]pyridine-1,5-dione (3)

The synthesis of intermediate 3 was carried out as described above using the general protocol of Procedure A. Yield: 0.278 g, 59%; MS (ESI) m/z 323 [M+1]⁺.

Synthesis of 3-(4-chlorobenzyl)-3-methyl-6-(pyrimidin-4-ylamino)-2,3-dihydroimidazo-[1,5-a]pyridine-1,5-dione (Cpd. No. 4)

The synthesis of compound 4 was carried out as described above using the general protocol of Procedure B. Tan solid; Yield: 0.18 g, 59%; MS (ESI) m/z 382[M+1]⁺; ¹H NMR (400 MHz, DMSO-d₆) δ 9.68 (s, 1H), 9.51 (s, 1H), 8.75 (s, 1H), 8.68 (d, J=7.6 Hz, 1H), 8.40 (d, J=5.9 Hz, 1H), 7.41 (d, J=6.1 Hz, 1H), 7.20-7.01 (m, 1H), 6.99-6.92 (m, 2H), 6.77 (dd, J=8.6, 5.0 Hz, 1H), 6.58 (d, J=7.6 Hz, 1H), 4.02 (d, J=13.8 Hz, 1H), 3.12 (d, J=13.8 Hz, 1H), 1.98 (s, 3H).

Example 5

Synthesis of 3-(3-fluorobenzyl)-3-methyl-6-(pyrimidin-4-ylamino)-2,3-dihydroimidazo[1,5-a]pyridine-1,5-dione (Cpd. No. 5)

49

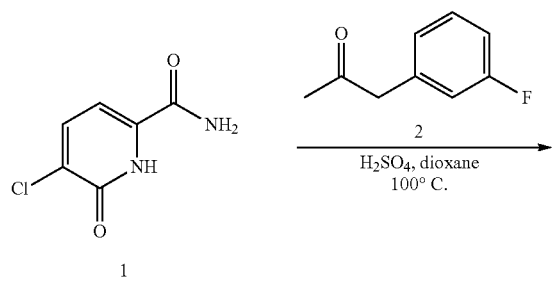

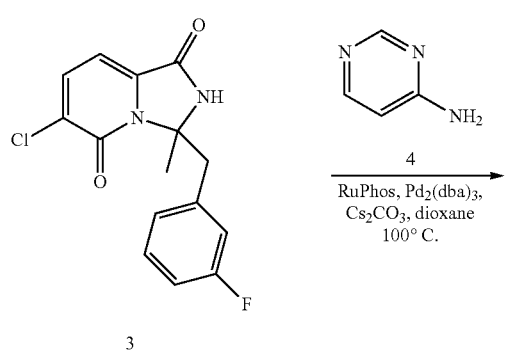

Synthesis of 6-chloro-3-(3-fluorobenzyl)-3-methyl-2,3-dihydroimidazo[1,5-a]pyridine-1,5-dione (3)

The synthesis of intermediate 3 was carried out as described above using the general protocol of Procedure A. Yield: 0.265 g, 59%; MS (ESI) m/z 307 [M+1]⁺.

Synthesis of 3-(3-fluorobenzyl)-3-methyl-6-(pyrimidin-4-ylamino)-2,3-dihydroimidazo-[1,5-a]pyridine-1,5-dione (Cpd. No. 5)

The synthesis of compound 5 was carried out as described above using the general protocol of Procedure B. Beige solid; Yield: 0.17 g, 56%; MS (ESI) m/z 366[M+1]⁺; $^1$H NMR (400 MHz, DMSO-$d_6$) δ 9.68 (s, 1H), 9.51 (s, 1H), 8.75 (s, 1H), 8.68 (d, J=7.6 Hz, 1H), 8.40 (d, J=5.9 Hz, 1H), 7.41 (d, J=6.1 Hz, 1H), 7.2-7.08 (m, 1H), 6.99-6.91 (m, 1H), 6.77 (dd, J=8.6, 5.0 Hz, 2H), 6.58 (d, J=7.6 Hz, 1H), 4.02 (d, J=13.8 Hz, 1H), 3.12 (d, J=13.8 Hz, 1H), 1.98 (s, 3H).

50

Example 6

Synthesis of 6'-(pyrimidin-4-ylamino)-1'H-spiro[cyclopentane-1,3'-imidazo[1,5-a]pyridine]-1',5'(2'H)-dione (Cpd. No. 6)

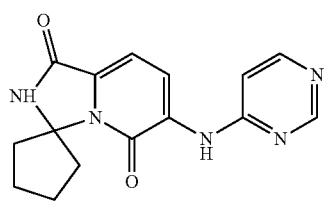 [SMILES: O=C1NC2(CCCC2)n2c1ccc(Nc1ccncn1)c2=O]

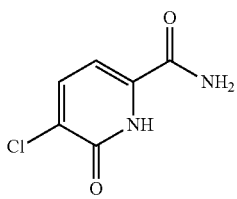 

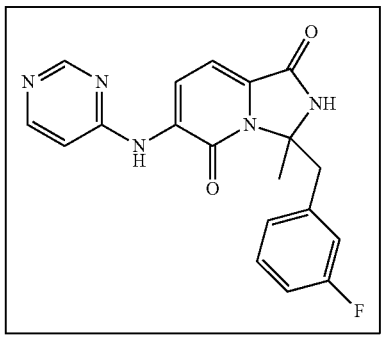

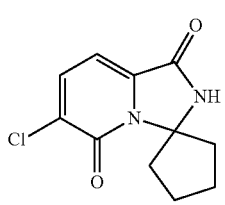

Synthesis of 6'-chloro-1'H-spiro[cyclopentane-1,3'-imidazo[1,5-a]pyridine]-1',5'(2'H)-dione (3)

The synthesis of intermediate 3 was carried out as described above using the general protocol of Procedure A. Yield: 0.18 g, 42%; MS (ESI) m/z 239[M+1]⁺.

Synthesis of 6'-(pyrimidin-4-ylamino)-1'H-spiro[cyclopentane-1,3'-imidazo[1,5-a]-pyridine]-1',5'(2'H)-dione (Cpd. No. 6)

The synthesis of compound 6 was carried out as described above using the general protocol of Procedure B. Light brown solid; Yield: 0.1 g, 45%; MS (ESI) m/z 298.10[M+1]⁺; $^1$H NMR (400 MHz, DMSO-$d_6$) δ 10.01 (s, 1H), 9.43

(s, 1H), 8.82-8.73 (m, 2H), 8.37 (d, J=5.9 Hz, 1H), 7.37 (d, J=5.9 Hz, 1H), 6.88 (d, J=7.6 Hz, 1H), 2.89-2.81 (m, 2H), 2.08-1.92 (m, 2H), 1.96-1.70 (m, 4H).

Example 7

Synthesis of 3-methyl-6-(pyrimidin-4-ylamino)-3-(2,2,2-trifluoroethyl)-2,3-dihydroimidazo[1,5-a]pyridine-1,5-dione (Cpd. No. 7)

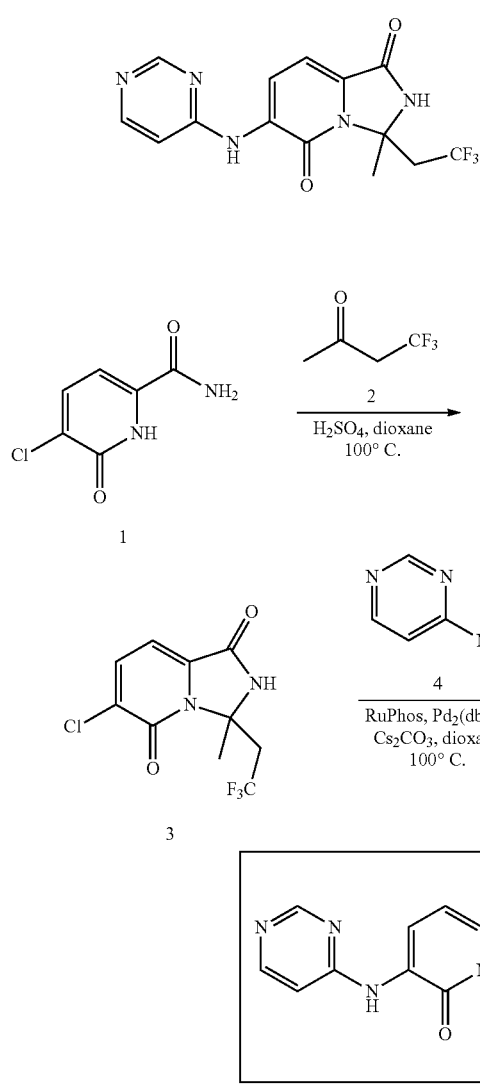

Synthesis of 6-chloro-3-methyl-3-(2,2,2-trifluoroethyl)-2,3-dihydroimidazo[1,5-a]pyridine-1,5-dione (3)

The synthesis of intermediate 3 was carried out as described above using the general protocol of Procedure A. Yield: 0.12 g, 22%.

Synthesis of 3-methyl-6-(pyrimidin-4-ylamino)-3-(2,2,2-trifluoroethyl)-2,3-dihydroimidazo[1,5-a]pyridine-1,5-dione (Cpd. No. 7)

The synthesis of compound 7 was carried out as described above using the general protocol of Procedure B. Green-yellow solid; Yield: 0.020 g, 15%; MS (ESI) m/z 340[M+1]$^+$; $^1$H NMR (400 MHz, DMSO-d$_6$) δ 10.69 (s, 1H), 9.42 (s, 1H), 8.70 (dd, J=4.5, 1.7 Hz, 1H), 8.79 (s, 1H), 8.30-8.20 (m, 1H), 7.73 (d, J=1.1 Hz, 1H), 7.32 (dd, J=9.2, 4.4 Hz, 1H), 3.38-3.75 (m, 1H), 3.19-3.08 (m, 1H), 1.81 (s, 3H).

Example 8

Synthesis of 3-isopropyl-3-methyl-6-(pyrimidin-4-ylamino)-2,3-dihydroimidazo[1,5-a]pyridine-1,5-dione (Cpd. No. 8)

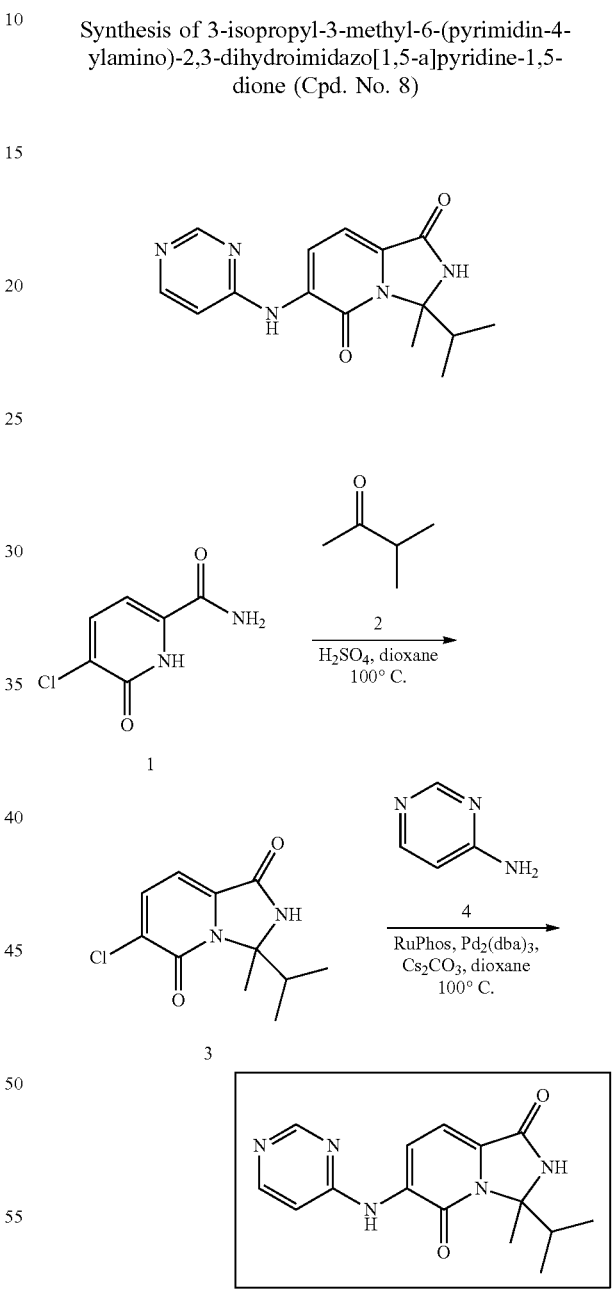

Synthesis of 6-chloro-3-isopropyl-3-methyl-2,3-dihydroimidazo[1,5-a]pyridine-1,5-dione (3)

The synthesis of intermediate 3 was carried out as described above using the general protocol of Procedure A. Yield: 0.32 g, 77%.

Synthesis of 3-isopropyl-3-methyl-6-(pyrimidin-4-ylamino)-2,3-dihydroimidazo[1,5-a]pyridine-1,5-dione (Cpd. No. 8)

The synthesis of compound 8 was carried out as described above using the general protocol of Procedure B. Off-white solid; Yield: 0.036 g, 19%; MS (ESI) m/z 300[M+1]⁺; ¹H NMR (400 MHz, DMSO-$d_6$) δ 9.67 (s, 1H), 9.41 (s, 1H), 8.83-8.73 (m, 2H), 8.37 (d, J=5.9 Hz, 1H), 7.37 (d, J=5.9 Hz, 1H), 6.87 (d, J=7.6 Hz, 1H), 3.1-2.90 (m, 1H), 1.83 (s, 3H), 1.05 (d, J=7.0 Hz, 3H), 0.46 (d, J=6.6 Hz, 3H).

Example 9

Synthesis of 3-cyclopentyl-3-methyl-6-(pyrimidin-4-ylamino)-2,3-dihydroimidazo[1,5-a]pyridine-1,5-dione (Cpd. No. 9)

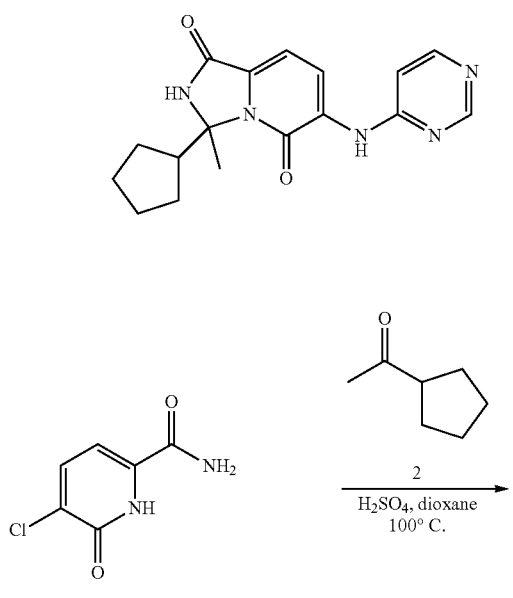

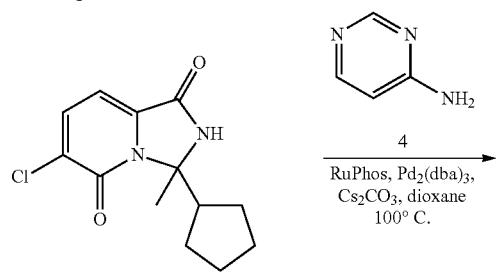

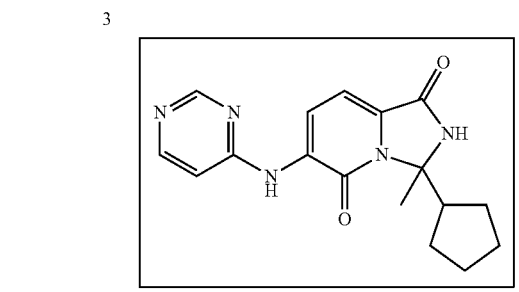

Synthesis of 6-chloro-3-cyclopentyl-3-methyl-2,3-dihydroimidazo[1,5-a]pyridine-1,5-dione (3)

The synthesis of intermediate 3 was carried out as described above using the general protocol of Procedure A. Yield: 0.2 g, 47%; MS (ESI) m/z 267[M+1]⁺.

Synthesis of 3-cyclopentyl-3-methyl-6-(pyrimidin-4-ylamino)-2,3-dihydroimidazo[1,5-a]pyridine-1,5-dione (Cpd. No. 9)

The synthesis of compound 9 was carried out as described above using the general protocol of Procedure B. Beige solid; Yield: 0.12 g, 47%; MS (ESI) m/z 326[M+1]⁺; ¹H NMR (400 MHz, DMSO-$d_6$) δ 9.72 (s, 1H), 9.39 (s, 1H), 8.81-8.73 (m, 2H), 8.37 (d, J=5.9 Hz, 1H), 7.39-7.32 (m, 1H), 6.86 (d, J=7.7 Hz, 1H), 3.45-3.40 (m, 1H), 1.84 (s, 3H), 1.68-1.35 (m, 4H), 1.18-1.1 (m, 1H), 0.85-0.80 (m, 1H).

Example 10

Synthesis of N-(6-((3,3-dimethyl-1,5-dioxo-1,2,3,5-tetrahydroimidazo[1,5-a]pyridin-6-yl)amino)pyrimidin-4-yl)cyclopropanecarboxamide (Cpd. No. 10)

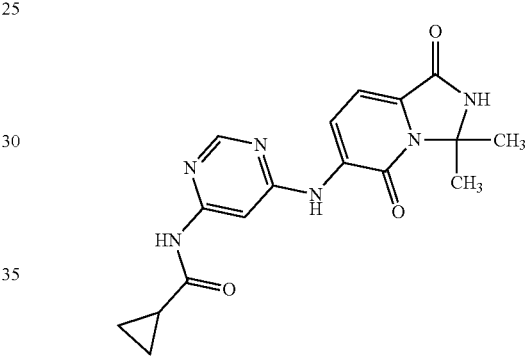

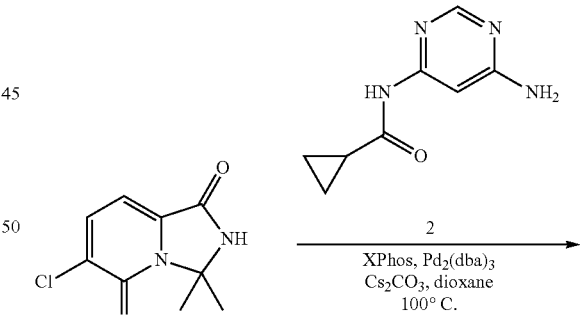

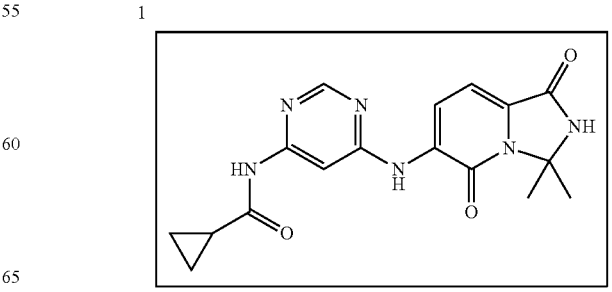

Synthesis of N-(6-((3,3-dimethyl-1,5-dioxo-1,2,3,5-tetrahydroimidazo[1,5-a]pyridin-6-yl)-amino)pyrimidin-4-yl)cyclopropanecarboxamide (Cpd. No. 10)

The synthesis of compound 10 was carried out as described above using the general protocol of Procedure B. Beige solid; Yield: 0.075 g, 15%; MS (ESI) m/z 355[M+1]+; 1H NMR (400 MHz, DMSO-$d_6$) δ 10.87 (s, 1H), 9.68 (s, 1H), 9.20 (s, 1H), 8.64 (d, J=7.7 Hz, 1H), 8.51 (s, 1H), 7.88 (d, J=1.0 Hz, 1H), 6.85 (d, J=7.6 Hz, 1H), 2.02 (m, J=6.2 Hz, 1H), 1.80 (s, 6H), 0.84 (d, J=6.1 Hz, 4H).

Example 11

Synthesis of 3-(4-fluorophenyl)-3-methyl-6-(pyrimidin-4-ylamino)-2,3-dihydroimidazo[1,5-a]pyridine-1,5-dione (Cpd. No. 11)

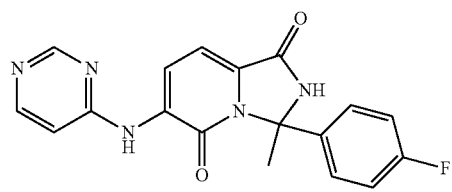 [SMILES: CC1(c2ccc(F)cc2)NC(=O)c2ccc(Nc3ccncn3)c(=O)n21]

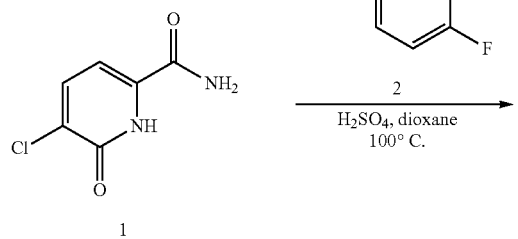

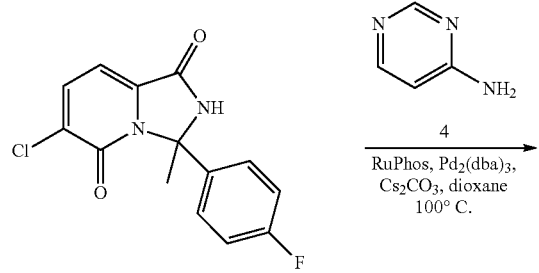

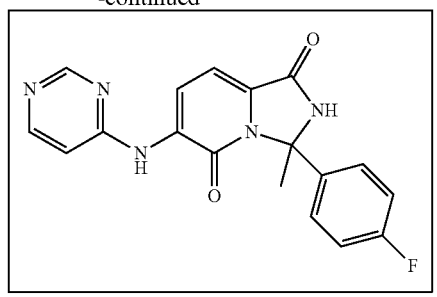

Synthesis of 6-chloro-3-(4-fluorophenyl)-3-methyl-2,3-dihydroimidazo[1,5-a]pyridine-1,5-dione (3)

The synthesis of intermediate 3 was carried out as described above using the general protocol of Procedure A. Yield: 0.216 g, 52%; MS (ESI) m/z 293 [M+1]+.

Synthesis of 3-(4-fluorophenyl)-3-methyl-6-(pyrimidin-4-ylamino)-2,3-dihydroimidazo-[1,5-a]pyridine-1,5-dione (Cpd. No. 11)

The synthesis of compound 11 was carried out as described above using the general protocol of Procedure B. Brown solid; Yield: 0.14 g, 41%; MS (ESI) m/z 252.15 [M+1]+; 1H NMR (400 MHz, DMSO-$d_6$) δ 10.05 (s, 1H), 9.35 (s, 1H), 8.83-8.73 (m, 2H), 8.35 (d, J=5.9 Hz, 1H), 7.44 (dd, J=8.5, 5.2 Hz, 2H), 7.31-7.16 (m, 3H), 6.99 (d, J=7.6 Hz, 1H), 2.26 (s, 3H).

Example 12

Synthesis of 3-(3-fluorophenyl)-3-methyl-6-(pyrimidin-4-ylamino)-2,3-dihydroimidazo[1,5-a]pyridine-1,5-dione (Cpd. No. 12)

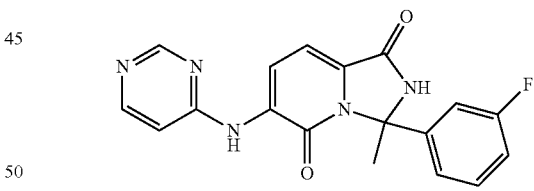

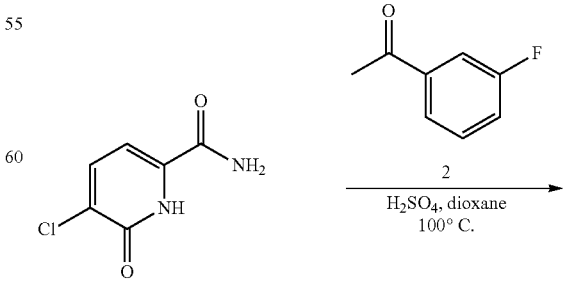

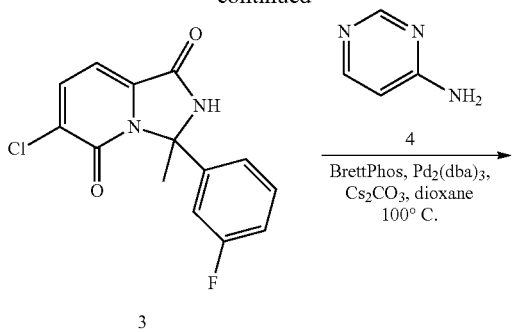

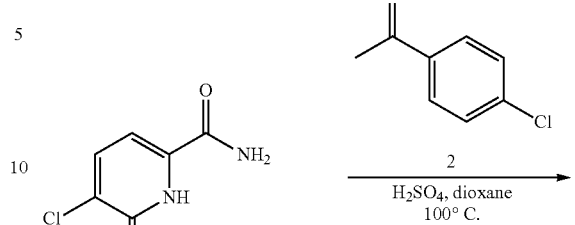

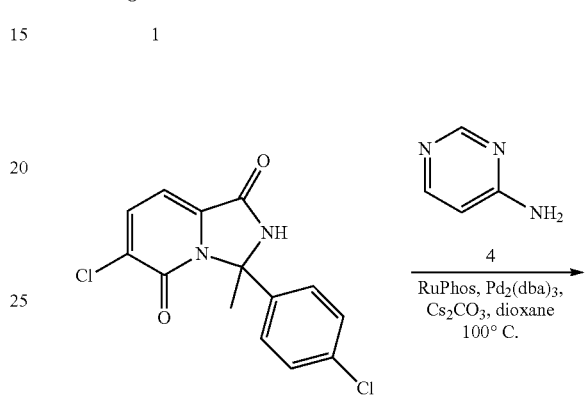

Synthesis of 6-chloro-3-(3-fluorophenyl)-3-methyl-2,3-dihydroimidazo[1,5-a]pyridine-1,5-dione (3)

The synthesis of intermediate 3 was carried out as described above using the general protocol of Procedure A. Yield: 0.208 g, 50%; MS (ESI) m/z 293 [M+1]⁺.

Synthesis of 3-(3-fluorophenyl)-3-methyl-6-(pyrimidin-4-ylamino)-2,3-dihydroimidazo-[1,5-a]pyridine-1,5-dione (Cpd. No. 12)

The synthesis of compound 12 was carried out as described above using the general protocol of Procedure B. Yellow solid; Yield: 0.08 g, 34%; MS (ESI) m/z 252.25 [M+1]⁺; ¹H NMR (400 MHz, DMSO-d₆) δ 10.07 (s, 1H), 9.34 (s, 1H), 8.84-8.73 (m, 2H), 8.35 (d, J=5.9 Hz, 1H), 7.43 (m, 1H), 7.32-7.12 (m, 4H), 7.00 (d, J=7.6 Hz, 1H), 2.26 (s, 3H).

Example 13

Synthesis of 3-(4-chlorophenyl)-3-methyl-6-(pyrimidin-4-ylamino)-2,3-dihydroimidazo[1,5-a]pyridine-1,5-dione (Cpd. No. 13)

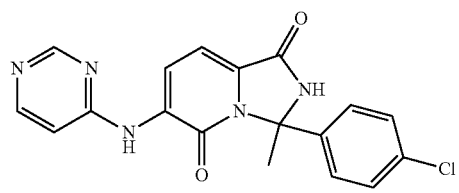 [SMILES: CC1(c2ccc(Cl)cc2)NC(=O)c2ccc(Nc3ccncn3)c(=O)n21]

Synthesis of 6-chloro-3-(4-chlorophenyl)-3-methyl-2,3-dihydroimidazo[1,5-a]pyridine-1,5-dione (3)

The synthesis of intermediate 3 was carried out as described above using the general protocol of Procedure A. Yield: 0.17 g, 31%; MS (ESI) m/z 309 [M+1]⁺.

Synthesis of 3-(4-chlorophenyl)-3-methyl-6-(pyrimidin-4-ylamino)-2,3-dihydroimidazo-[1,5-a]pyridine-1,5-dione (Cpd. No. 13)

The synthesis of compound 13 was carried out as described above using the general protocol of Procedure B. Yellow solid; Yield: 0.11 g, 55%; MS (ESI) m/z 368.15 [M+1]⁺; ¹H NMR (400 MHz, DMSO-d₆) δ 10.05 (s, 1H), 9.32 (s, 1H), 8.84-8.73 (m, 2H), 8.35 (d, J=5.9 Hz, 1H), 7.42 (m, 4H), 7.27 (dd, J=5.9, 1.3 Hz, 1H), 7.00 (d, J=7.7 Hz, 1H), 2.25 (s, 3H).

Example 14

Synthesis of 3-methyl-6-(pyrimidin-4-ylamino)-3-(trifluoromethyl)-2,3-dihydroimidazo[1,5-a]pyridine-1,5-dione (Cpd. No. 14)

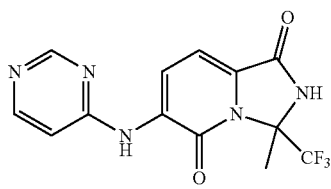 [SMILES: CC1(C(F)(F)F)NC(=O)c2ccc(Nc3ccncn3)c(=O)n21]

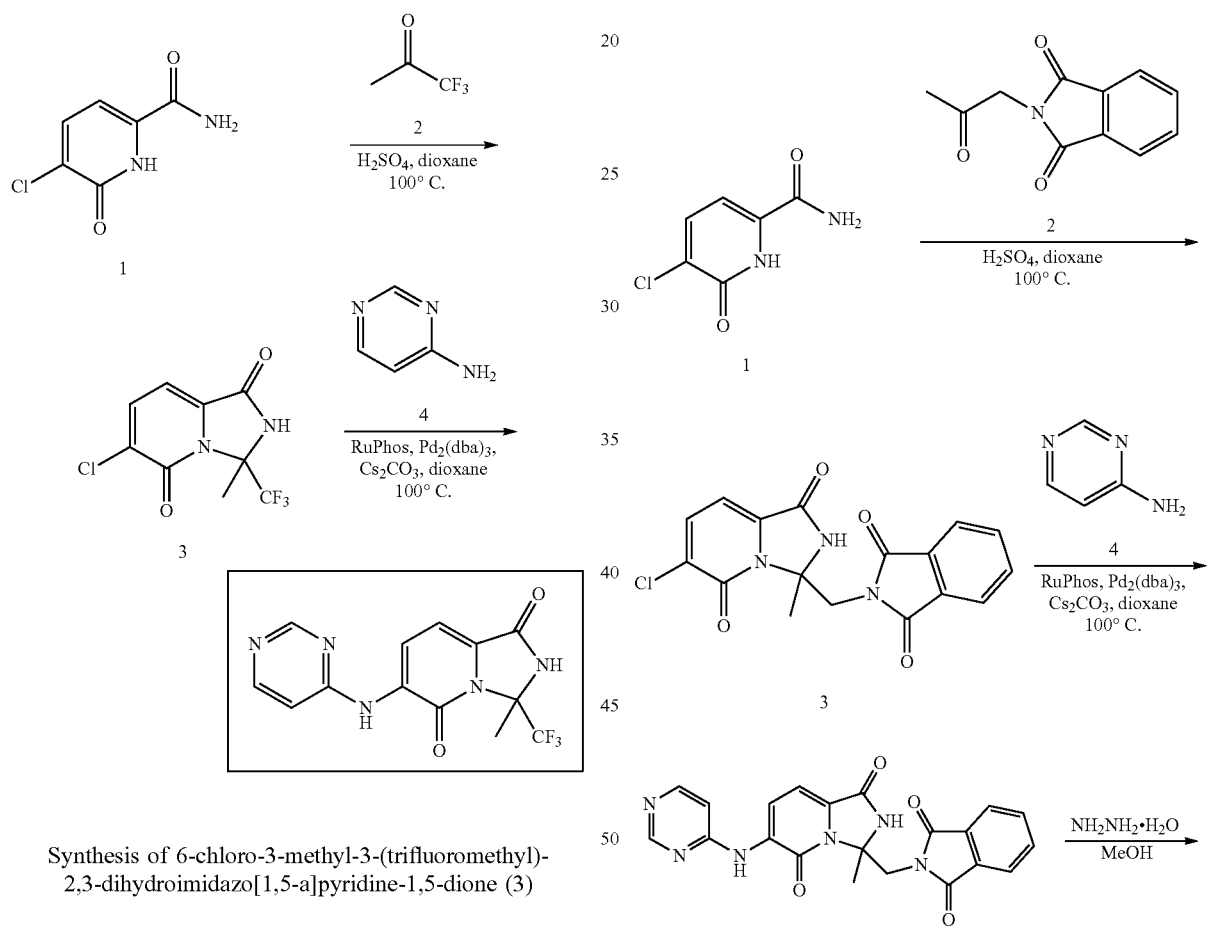

Synthesis of 6-chloro-3-methyl-3-(trifluoromethyl)-2,3-dihydroimidazo[1,5-a]pyridine-1,5-dione (3)

The synthesis of intermediate 3 was carried out as described above using the general protocol of Procedure A. Yield: 0.255 g, 66%; MS (ESI) m/z 267 [M+1]$^+$

Synthesis of 3-methyl-6-(pyrimidin-4-ylamino)-3-(trifluoromethyl)-2,3-dihydroimidazo-[1,5-a]pyridine-1,5-dione (Cpd. No. 14)

The synthesis of compound 14 was carried out as described above using the general protocol of Procedure B. Off-white solid; Yield: 0.06 g, 19%; MS (ESI) m/z 326 [M+1]$^+$; $^1$H NMR (400 MHz, DMSO-d$_6$) δ 10.50 (s, 1H), 9.58 (s, 1H), 8.84-8.76 (m, 2H), 8.41 (d, J=5.9 Hz, 1H), 7.40 (dd, J=5.9, 1.4 Hz, 1H), 7.02 (d, J=7.7 Hz, 1H), 2.14 (s, 3H).

Example 15

Synthesis of 3-(aminomethyl)-3-methyl-6-(pyrimidin-4-ylamino)-2,3-dihydroimidazo[1,5-a]pyridine-1,5-dione (Cpd. No. 15)

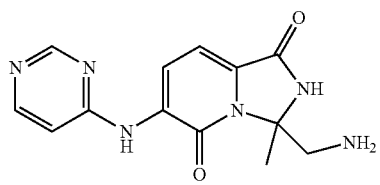 [SMILES: CC1(CN)NC(=O)c2ccc(Nc3ccncn3)c(=O)n21]

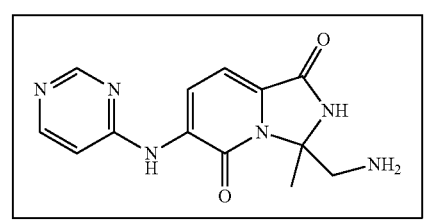

Synthesis of 6-chloro-3-((1,3-dioxoisoindolin-2-yl)methyl)-3-methyl-2,3-dihydroimidazo-[1,5-a]pyridine-1,5-dione (3)

The synthesis of intermediate 3 was carried out as described above using the general protocol of Procedure A. Yield: 0.5 g, 50%; MS (ESI) m/z 358 [M+1]$^+$.

Synthesis of 3-((1,3-dioxoisoindolin-2-yl)methyl)-3-methyl-6-(pyrimidin-4-ylamino)-2,3-dihydroimidazo[1,5-a]pyridine-1,5-dione (5)

The synthesis of intermediate 5 was carried out as described above using the general protocol of Procedure B. Yield: 0.09 g, 26%; MS (ESI) m/z 417[M+1]$^+$.

Synthesis of 3-(aminomethyl)-3-methyl-6-(pyrimidin-4-ylamino)-2,3-dihydroimidazo[1,5-a]pyridine-1,5-dione (Cpd. No. 15)

Procedure C: To a solution of 3-((1,3-dioxoisoindolin-2-yl)methyl)-3-methyl-6-(pyrimidin-4-ylamino)-2,3-dihydroimidazo[1,5-a]pyridine-1,5-dione (5, 0.085 g, 0.29 mmol) in methanol (20 mL), hydrazine hydrate (2 mL) was added and the reaction mixture was stirred at room temperature for 16 h. The reaction mixture was filtered and the filtrate was concentrated under reduced pressure. The residue was dissolved in dichloromethane and washed with water, separated, dried over sodium sulphate and concentrated under reduced pressure, which was purified by repeated washing with diethyl ether and hexane to obtain 3-(aminomethyl)-3-methyl-6-(pyrimidin-4-ylamino)-2,3-dihydroimidazo[1,5-a]pyridine-1,5-dione (Cpd. No. 15) as an off-white solid. Yield: 0.008 g, 9%; MS (ESI) m/z 287.05 [M+1]$^+$; $^1$H NMR (400 MHz, DMSO-d$_6$) δ 9.35 (s, 1H), 8.76 (d, J=7.8 Hz, 2H), 8.36 (d, J=5.9 Hz, 1H), 7.36 (d, J=6.0 Hz, 1H), 6.83 (d, J=7.6 Hz, 1H), 3.55 (d, J=13.6 Hz, 1H), 2.92 (d, J=13.7 Hz, 1H), 1.75 (s, 3H), 1.44 (s, 1H), 1.41-1.34 (m, 2H).

Example 16

Synthesis of 3-methyl-6-(pyrimidin-4-ylamino)-3-(thiophen-3-yl)-2,3-dihydroimidazo[1,5-a]pyridine-1,5-dione (Cpd. No. 16)

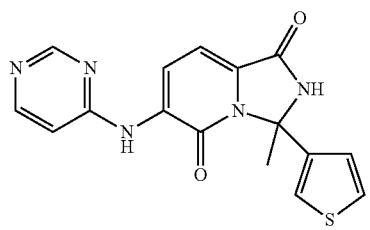 [SMILES: CC1(c2ccsc2)NC(=O)c2ccc(Nc3ccncn3)c(=O)n21]

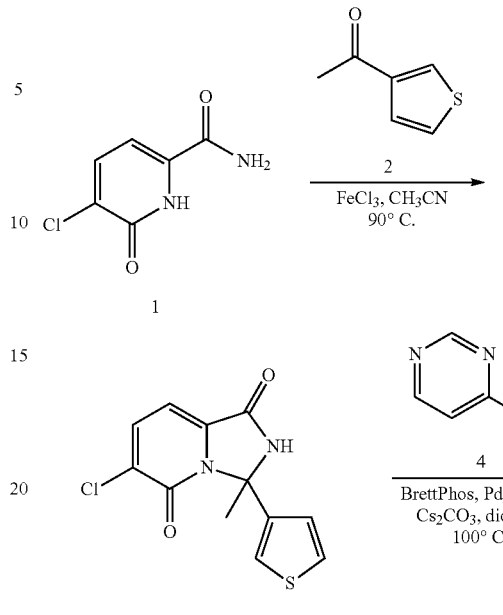

Synthesis of 6-chloro-3-methyl-3-(thiophen-3-yl)-2,3-dihydroimidazo[1,5-a]pyridine-1,5-dione (3)

To a solution of 5-chloro-6-oxo-1,6-dihydropyridine-2-carboxamide (1, 0.1 g, 0.58 mmol) in acetonitrile (4 mL), 1-(thiophen-3-yl)ethanone (2, 0.37 g, 2.9 mmol) and ferric chloride (0.094 g, 0.58 mmol) were added and the reaction mixture was allowed to heat at 90° C. for 18 h. The reaction mixture was filtered and the filtrate was concentrated under reduced pressure. The residue was purified by column chromatography (silica, ethyl acetate/hexanes=50%) to afford 6-chloro-3-methyl-3-(thiophen-3-yl)-2,3-dihydroimidazo[1,5-a]pyridine-1,5-dione (3). Yield: 0.021 g, 13%; MS (ESI) m/z 281[M+1]$^+$.

Synthesis of 3-methyl-6-(pyrimidin-4-ylamino)-3-(thiophen-3-yl)-2,3-dihydroimidazo[1,5-a]pyridine-1,5-dione (Cpd. No. 16)

The synthesis of compound 16 was carried out as described above using the general protocol of Procedure B. Beige solid; Yield: 0.008 g, 12%; MS (ESI) m/z 340[M+1]$^+$; $^1$H NMR (400 MHz, DMSO-d$_6$) δ 10.05 (s, 1H), 9.35 (s, 1H), 8.81-8.73 (m, 2H), 8.35 (d, J=5.9 Hz, 1H), 7.74-7.68 (m, 1H), 7.49 (dd, J=5.1, 2.9 Hz, 1H), 7.29 (d, J=5.9 Hz, 1H), 7.00-6.92 (m, 2H), 2.25 (s, 3H).

Example 17

Synthesis of 3-methyl-6-(pyrimidin-4-ylamino)-3-(thiazol-4-yl)-2,3-dihydroimidazo[1,5-a]pyridine-1,5-dione (Cpd. No. 17)

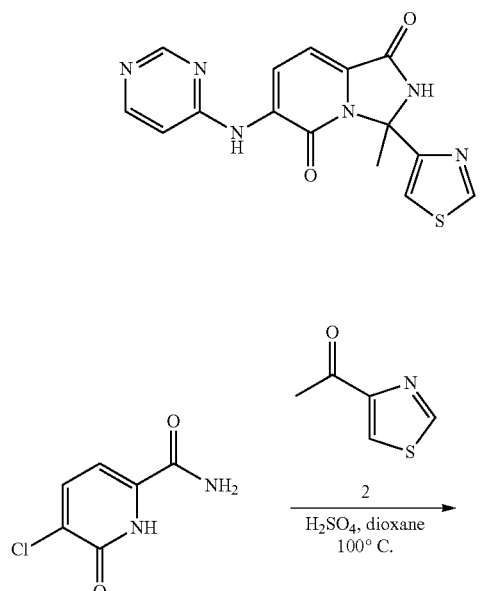

Synthesis of 6-chloro-3-methyl-3-(thiazol-4-yl)-2,3-dihydroimidazo[1,5-a]pyridine-1,5-dione (3)

The synthesis of intermediate 3 was carried out as described above using the general protocol of Procedure A. Yield: 0.2 g, 49%; MS (ESI) m/z 282[M+1]$^+$.

Synthesis of 3-methyl-6-(pyrimidin-4-ylamino)-3-(thiazol-4-yl)-2,3-dihydroimidazo[1,5-a]-pyridine-1,5-dione (Cpd. No. 17)

The synthesis of compound 17 was carried out as described above using the general protocol of Procedure B.

Yellow solid. Yield: 0.013 g, 21%; MS (ESI) m/z 341[M+1]$^+$; $^1$H NMR (400 MHz, DMSO-$d_6$) δ 9.97 (s, 1H), 9.43 (s, 1H), 8.99 (d, J=1.8 Hz, 1H), 8.83-8.71 (m, 2H), 8.35 (d, J=6.0 Hz, 1H), 8.07 (d, J=1.9 Hz, 1H), 7.27 (d, J=6.0 Hz, 1H), 6.94 (d, J=7.6 Hz, 1H), 2.30 (s, 3H).

Example 18

Synthesis of 3-(3-chlorophenyl)-3-methyl-6-(pyrimidin-4-ylamino)-2,3-dihydroimidazo[1,5-a]pyridine-1,5-dione (Cpd. No. 18)

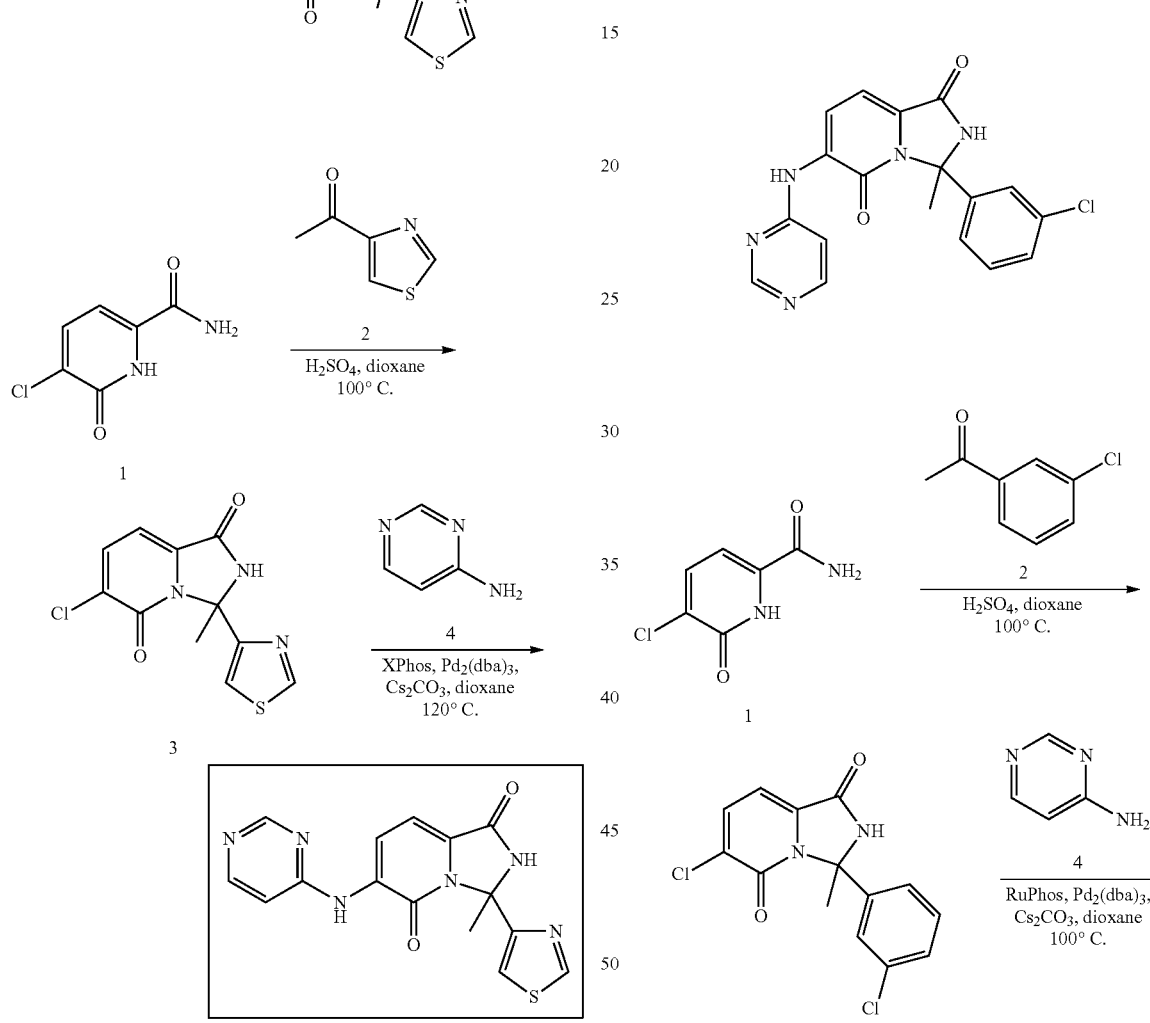

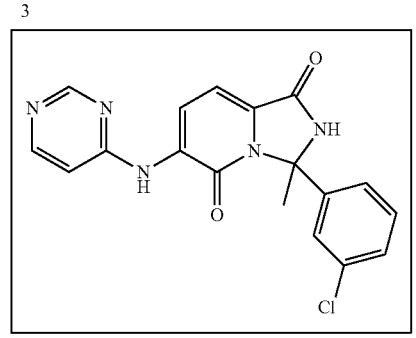

Synthesis of 6-chloro-3-(3-chlorophenyl)-3-methyl-2, 3-dihydroimidazo[1,5-a]pyridine-1,5-dione (3)

The synthesis of intermediate 3 was carried out as described above using the general protocol of Procedure A. Yield: 0.210 g, 39%; MS (ESI) m/z 309 [M+1]+.

Synthesis of 3-(3-chlorophenyl)-3-methyl-6-(pyrimidin-4-ylamino)-2,3-dihydroimidazo-[1,5-a]pyridine-1,5-dione (Cpd. No. 18)

The synthesis of compound 18 was carried out as described above using the general protocol of Procedure B. Light yellow solid; Yield: 0.053 g, 22%; MS (ESI) m/z 368 [M+1]+; $^1$H NMR (400 MHz, DMSO-$d_6$) δ 10.07 (s, 1H), 9.35 (s, 1H), 8.86-8.73 (m, 2H), 8.35 (d, J=5.9 Hz, 1H), 7.51-7.34 (m, 3H), 7.34-7.23 (m, 2H), 7.09 (s, 1H), 7.01 (d, J=7.6 Hz, 1H), 2.25 (s, 3H).

Example 19

Synthesis of 3-(3-chlorobenzyl)-3-methyl-6-(pyrimidin-4-ylamino)-2,3-dihydroimidazo[1,5-a]pyridine-1,5-dione (Cpd. No. 19)

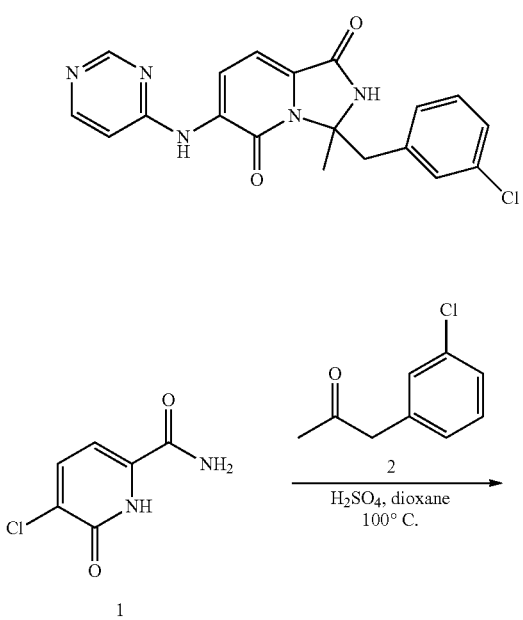

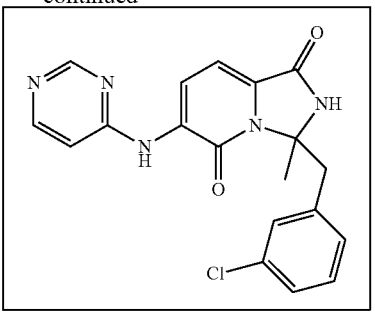

Synthesis of 6-chloro-3-(3-chlorobenzyl)-3-methyl-2,3-dihydroimidazo[1,5-a]pyridine-1,5-dione (3)

The synthesis of intermediate 3 was carried out as described above using the general protocol of Procedure A. Yield: 0.4 g, 70%; MS (ESI) m/z 324 [M+1]+

Synthesis of 3-(3-chlorobenzyl)-3-methyl-6-(pyrimidin-4-ylamino)-2,3-dihydroimidazo-[1,5-a]pyridine-1,5-dione (Cpd. No. 19)

The synthesis of compound 19 was carried out as described above using the general protocol of Procedure B. White solid; Yield: 0.2 g, 56%; MS (ESI) m/z 382 [M+1]+; $^1$H NMR (400 MHz, DMSO-$d_6$) δ 9.67 (s, 1H), 9.49 (s, 1H), 8.75 (s, 1H), 8.68 (d, J=7.7 Hz, 1H), 8.39 (d, J=5.9 Hz, 1H), 7.41 (d, J=5.9 Hz, 1H), 7.24-7.12 (m, 2H), 7.04 (d, J=2.3 Hz, 1H), 6.87 (dd, J=6.8, 2.1 Hz, 1H), 6.58 (d, J=7.7 Hz, 1H), 4.00 (d, J=13.8 Hz, 1H), 3.11 (d, J=13.8 Hz, 1H), 1.97 (s, 3H).

Example 20

Synthesis of 6-(pyrimidin-4-ylamino)-1H-spiro[imidazo[1,5-a]pyridine-3,3'-piperidine]-1,5(2H)-dione (Cpd. No. 20)

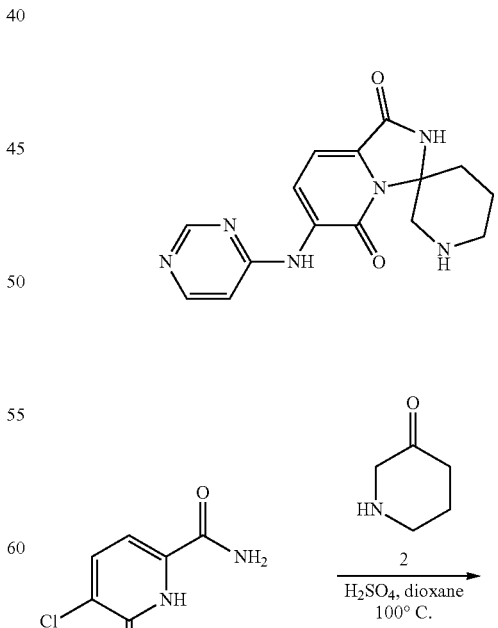

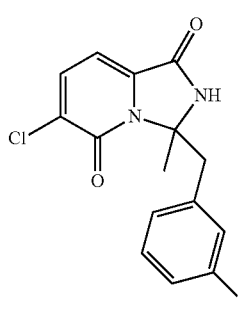

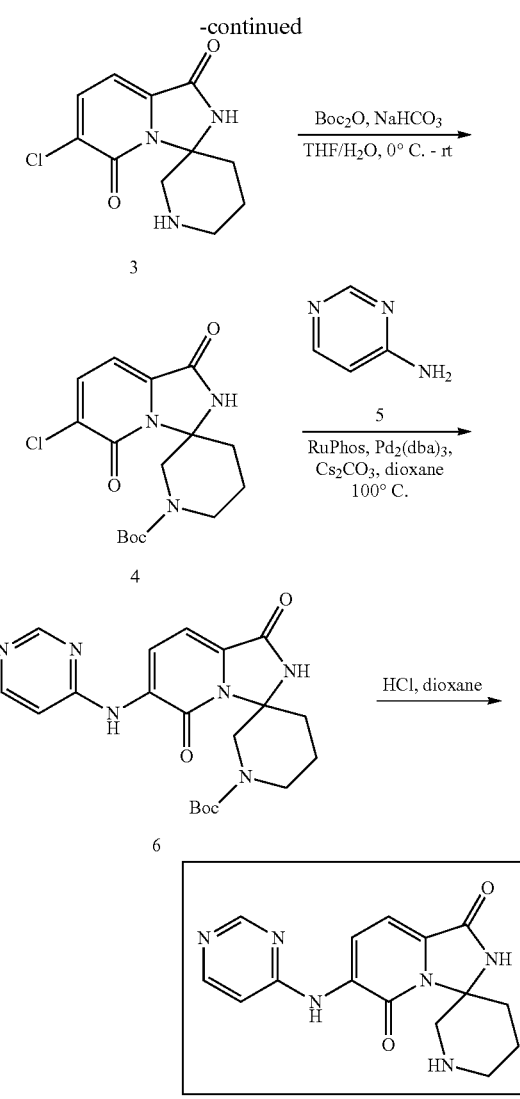

Synthesis of 6-chloro-2H-spiro[imidazo[1,5-a]pyridine-3,3'-piperidine]-1,5-dione (3)

The synthesis of intermediate 3 was carried out as described above using the general protocol of Procedure A. Yield: 0.504 g, crude; MS (ESI) m/z 254 [M+1]+.

Synthesis of tert-butyl 6-chloro-1,5-dioxo-2,5-dihydro-1H-spiro[imidazo[1,5-a]pyridine-3,3'-piperidine]-1'-carboxylate (4)

To a solution of 1'-benzyl-6-chloro-1H-spiro[imidazo[1,5-a]pyridine-3,3'-piperidine]-1,5(2H)-dione (3, 0.5 g, 1.9 mmol) in tetrahydrofuran (8 mL) and water (4 mL), sodium bicarbonate (0.66 g, 7.8 mmol) and di-tertiarybutyl dicarbonate (1.31 mL, 5.9 mmol) were added at 0° C. and the reaction mixture was allowed to stir at room temperature for 2 h. The reaction mixture was diluted with water and the compound was extracted in ethyl acetate. The organic layer was separated, dried over sodium sulphate and concentrated under reduced pressure. The residue was purified by column chromatography (silica, methanol/dichloromethane=2%) to afford tert-butyl 6-chloro-1,5-dioxo-2,5-dihydro-1H-spiro[imidazo[1,5-a]pyridine-3,3'-piperidine]-1'-carboxylate 4. Yield: 0.33 g, 47%; MS (ESI) m/z 354 [M+1]+.

Synthesis of tert-butyl 1,5-dioxo-6-(pyrimidin-4-ylamino)-1,5-dihydro-2H-spiro[imidazo[1,5-a]pyridine-3,3'-piperidine]-1'-carboxylate (6)

The synthesis of intermediate 6 was carried out as described above using the general protocol of Procedure B. Yield: 0.126 g, 31%; MS (ESI) m/z 413 [M+1]+.

Synthesis of 6-(pyrimidin-4-ylamino)-1H-spiro[imidazo[1,5-a]pyridine-3,3'-piperidine]-1,5(2H)-dione (Cpd. No. 20)

Procedure D: To a stirred solution of 1'-benzyl-6-(pyrimidin-4-ylamino)-1H-spiro[imidazo[1,5-a]pyridine-3,3'-piperidine]-1,5(2H)-dione (5, 0.12 g, 0.29 mmol) in dioxane (1 mL), 4 M hydrogenchloride in dioxane (2 mL) was added at 0° C. and the reaction mixture was stirred at room temperature for 3 h. The solvent was removed under reduced pressure and the residue was purified by repeated washing with pentane. Compound was dissolved in water and passed through strata column to obtain 6-(pyrimidin-4-ylamino)-1H-spiro[imidazo[1,5-a]pyridine-3,3'-piperidine]-1,5(2H)-dione (Cpd. No. 20) as a light brown solid. Yield: 0.062 g, 67%; MS (ESI) m/z 313.15 [M+1]+; 1H NMR (400 MHz, DMSO-$d_6$) δ 10.13 (s, 1H), 9.40 (s, 1H), 8.80-8.73 (m, 2H), 8.38 (d, J=5.9 Hz, 1H), 7.37 (dd, J=5.9, 1.3 Hz, 1H), 6.89 (d, J=7.7 Hz, 1H), 3.94 (d, J=12.5 Hz, 1H), 3.16-3.12 (m, 1H), 2.95 (d, J=13.1 Hz, 1H), 2.74-2.65 (m, 1H), 2.60 (s, 1H), 2.46 (d, J=11.7 Hz, 1H), 1.72 (d, J=8.2 Hz, 2H), 1.61 (d, J=13.0 Hz, 1H).

Example 21

Synthesis of N-[6-[(1,5-dioxospiro[2H-imidazo[1,5-a]pyridine-3,1'-cyclopentane]-6-yl)amino]pyrimidin-4-yl]cyclopropanecarboxamide (Cpd. No. 21)

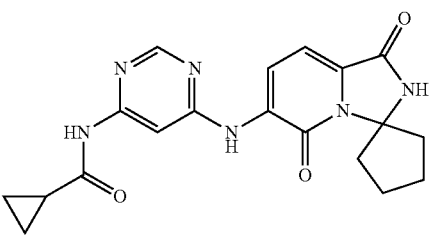 [SMILES: O=C1NC2(CCCC2)n2c1ccc(Nc1cc(NC(=O)C3CC3)ncn1)c2=O]

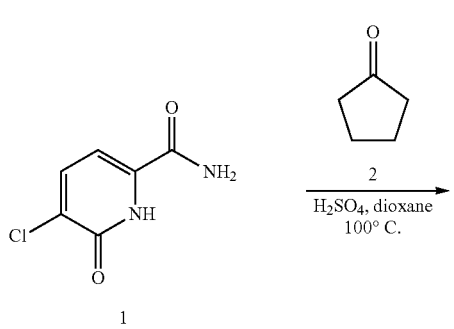

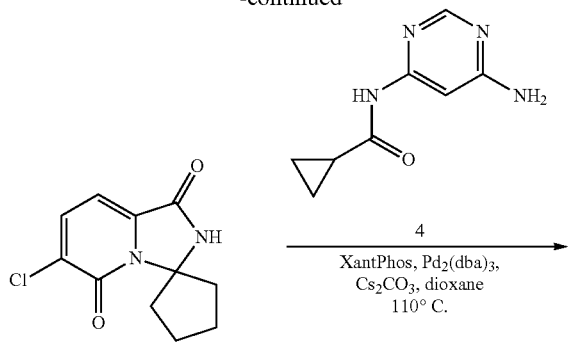
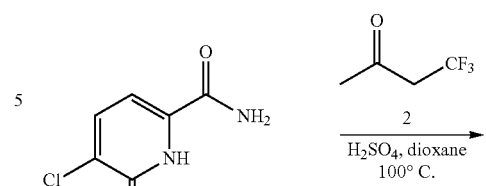
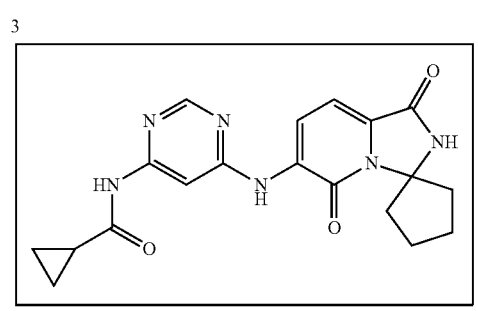
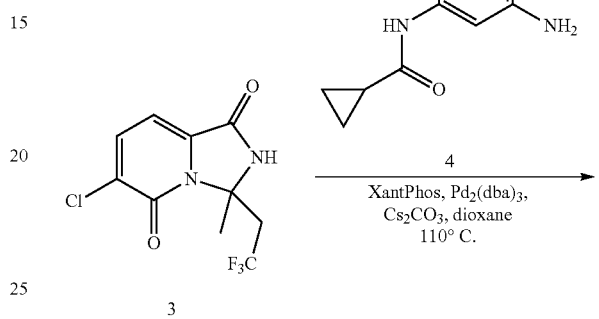

Synthesis of
6-chlorospiro[2H-imidazo[1,5-a]pyridine-3,
1'-cyclopentane]-1,5-dione (3)

The synthesis of intermediate 3 was carried out as described above using the general protocol of Procedure A. Off white solid; Yield: 0.8 g, 58%; MS (ESI) m/z 237 [M−1]⁻; ¹H NMR (400 MHz, DMSO-d₆) δ 10.33 (s, 1H), 7.94 (m, 1H), 6.72 (m, 1H), 2.76 (m, 2H), 1.95 (m, 2H), 1.82 (m, 2H), 1.70 (m, 2H).

Synthesis of N-[6-[(1,5-dioxospiro[2H-imidazo[1,5-a]pyridine-3,1'-cyclopentane]-6-yl)amino]pyrimidin-4-yl]cyclopropanecarboxamide (Cpd. No. 21)

The synthesis of compound 21 was carried out as described above using the general protocol of Procedure B. Off white solid; Yield: 0.12 g, 15%; MS (ESI) m/z 381.13 [M+1]⁺; ¹H NMR (400 MHz, DMSO-d₆) δ 10.87 (s, 1H), 10.01 (s, 1H), 9.24 (s, 1H), 8.65 (d, J=7.6 Hz, 1H), 8.50 (s, 1H), 7.87 (s, 1H), 6.85 (d, J=7.6 Hz, 1H), 2.80 (m, 2H), 2.01 (m, 3H), 1.86 (s, 2H), 1.72 (m, 2H), 0.83 (m, 4H).

Example 22

Synthesis of N-(6-((3-methyl-1,5-dioxo-3-(2,2,2-trifluoroethyl)-1,2,3,5-tetrahydroimidazo[1,5-a]pyridin-6-yl)amino)pyrimidin-4-yl)cyclopropanecarboxamide (Cpd. No. 22)

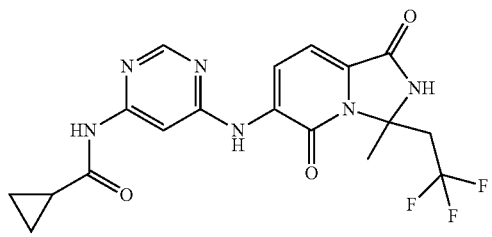 [SMILES: CC1(CC(F)(F)F)NC(=O)c2ccc(Nc3cc(NC(=O)C4CC4)ncn3)c(=O)n21]

Synthesis of 6-chloro-3-methyl-3-(2,2,2-trifluoroethyl)-2H-imidazo[1,5-a]pyridine-1,5-dione (3)

The synthesis of intermediate 3 was carried out as described above using the general protocol of Procedure A. Brown solid; Yield: 0.35 g, 43%; MS (ESI) m/z 279.1 [M−1]⁻; ¹H NMR (400 MHz, DMSO-d₆) δ 10.15 (bs, 1H), 7.99 (d, J=4 Hz, 1H), 6.79 (d, J=4 Hz, 1H), 3.74-3.65 (m, 1H), 3.17-3.01 (m, 1H), 1.84 (s, 3H).

Synthesis of N-[6-[[3-methyl-1,5-dioxo-3-(2,2,2-trifluoroethyl)-2H-imidazo[1,5-a]pyridin-6-yl]amino]pyrimidin-4-yl]cyclopropanecarboxamide (Cpd. No. 22)

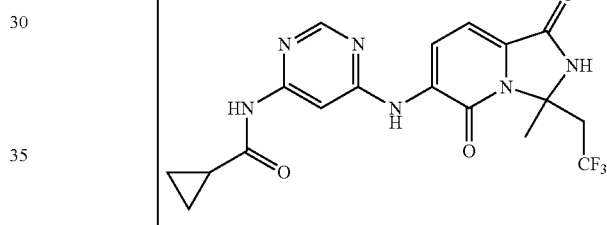

The synthesis of compound 22 was carried out as described above using the general protocol of Procedure B. Brown solid; Yield: 0.2 g, 28%; MS (ESI) m/z 423.1[M+1]⁺; ¹H NMR (400 MHz, DMSO-d₆) δ 10.88 (s, 1H), 9.80 (s, 1H), 9.29 (s, 1H), 8.69 (d, J=7.6 Hz, 1H), 8.51 (s, 1H), 7.90 (s, 1H), 6.93 (d, J=7.6 Hz, 1H), 3.82-3.70 (m, 1H), 3.16-3.04 (m, 1H), 2.07-1.99 (m, 1H), 1.80 (s, 3H), 0.84 (d, J=6.0 Hz, 4H).

Example 23

Synthesis of N-[6-[(3-cyclopentyl-3-methyl-1,5-dioxo-2H-imidazo[1,5-a]pyridin-6-yl)amino]pyrimidin-4-yl]cyclopropanecarboxamide (Cpd. No. 23)

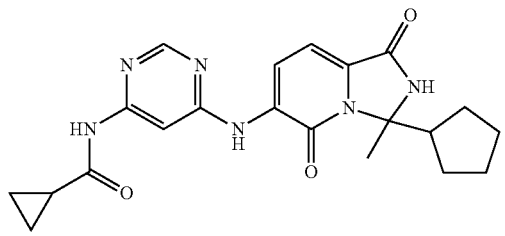 [SMILES: CC1(C2CCCC2)NC(=O)c2ccc(Nc3cc(NC(=O)C4CC4)ncn3)c(=O)n21]

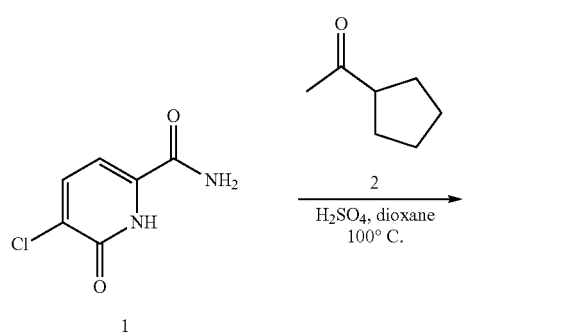

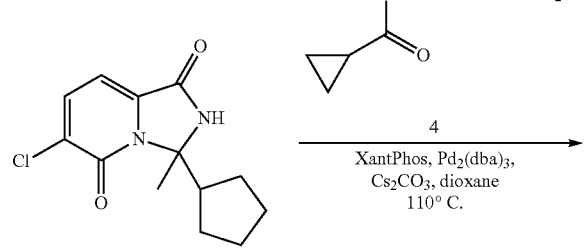

Synthesis of 6-chloro-3-cyclopentyl-3-methyl-2H-imidazo[1,5-a]pyridine-1,5-dione (3)

The synthesis of intermediate 3 was carried out as described above using the general protocol of Procedure A. Off-white solid; Yield: 1.61 g, 52%; MS (ESI) m/z 267.0 [M+1]+; 1H NMR (400 MHz, CDCl3) δ 8.61 (s, 1H), 7.71 (d, J=7.2 Hz, 1H), 6.77 (d, J=7.2 Hz, 1H), 3.54 (m, 1H), 2.01 (m, 1H), 1.98 (s, 3H), 1.68 (m, 2H), 1.55 (m, 2H), 1.34 (m, 2H), 0.91 (m, 1H).

Synthesis of N-[6-[(3-cyclopentyl-3-methyl-1,5-dioxo-2H-imidazo[1,5-a]pyridin-6-yl)-amino]pyrimidin-4-yl]cyclopropanecarboxamide (Cpd. No. 23)

The synthesis of compound 23 was carried out as described above using the general protocol of Procedure B. Off-white solid; Yield: 1.4 g, 57%; MS (ESI) m/z 409.36 [M+1]+; 1H NMR (400 MHz, DMSO-d6) δ 10.88 (s, 1H), 9.69 (s, 1H), 9.17 (s, 1H), 8.63 (d, J=7.6 Hz, 1H), 8.50 (s, 1H), 7.85 (s, 1H), 6.83 (d, J=7.6 Hz, 1H), 3.39 (m, 1H), 2.02 (m, 1H), 1.83 (s, 3H), 1.82 (m, 1H), 1.51 (m, 5H), 1.10 (m, 1H), 0.83 (d, J=6.0 Hz, 4H), 0.78 (m, 1H).

Example 24

Synthesis of N-[6-[[3-methyl-1,5-dioxo-3-(trifluoromethyl)-2H-imidazo[1,5-a]pyridin-6-yl]amino]pyrimidin-4-yl]cyclopropanecarboxamide (Cpd. No. 24)

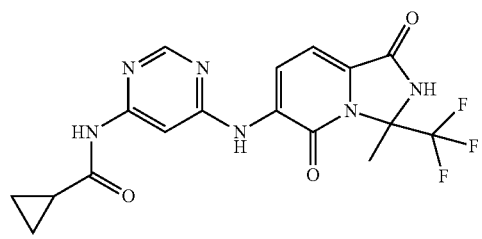 [SMILES: CC1(C(F)(F)F)NC(=O)c2ccc(Nc3cc(NC(=O)C4CC4)ncn3)c(=O)n21]

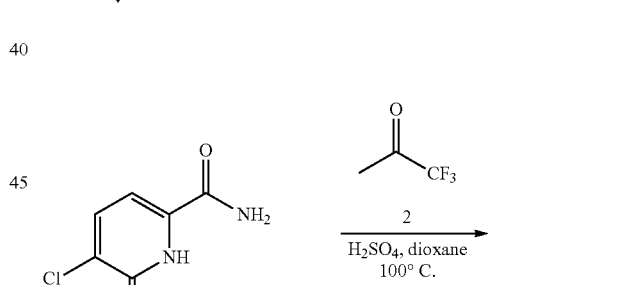

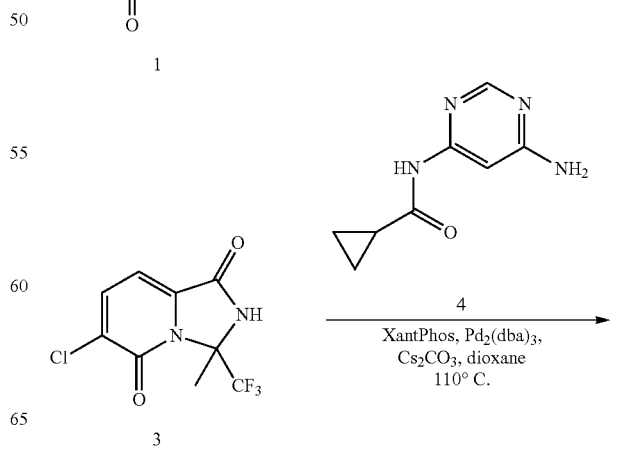

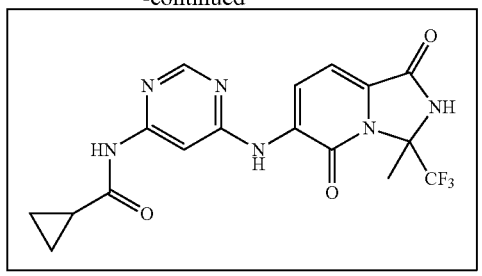

Synthesis of 6-chloro-3-methyl-3-(trifluoromethyl)-2H-imidazo[1,5-a]pyridine-1,5-dione (3)

The synthesis of intermediate 3 was carried out as described above using the general protocol of Procedure A. Off-white solid; Yield: 6.50 g, 84%; MS (ESI) m/z 267.11 [M+1]$^+$; $^1$H NMR (400 MHz, DMSO-d$_6$) δ 10.84 (s, 1H), 8.10 (d, J=7.2 Hz, 1H), 6.85 (d, J=7.2 Hz, 1H), 2.09 (s, 3H).

Synthesis of N-[6-[[3-methyl-1,5-dioxo-3-(trifluoromethyl)-2H-imidazo[1,5-a]pyridin-6-yl]amino]pyrimidin-4-yl]cyclopropanecarboxamide (Cpd. No. 24)

The synthesis of compound 24 was carried out as described above using the general protocol of Procedure B. Light yellow solid; Yield: 1.75 g, 64%; MS (ESI) m/z 409.29 [M+1]$^+$; $^1$H NMR (400 MHz, DMSO-d$_6$) δ 10.90 (s, 1H), 10.48 (s, 1H), 9.43 (s, 1H), 8.68 (d, J=7.6 Hz, 1H), 8.53 (s, 1H), 7.94 (s, 1H), 6.97 (d, J=8.0 Hz, 1H), 2.17 (s, 3H), 2.02 (m, 1H), 0.84 (d, J=6.0 Hz, 4H).

Example 25

Synthesis of 3-methyl-3-((methylamino)methyl)-6-(pyrimidin-4-ylamino)-2,3-dihydroimidazo[1,5-a]pyridine-1,5-dione (Cpd. No. 25)

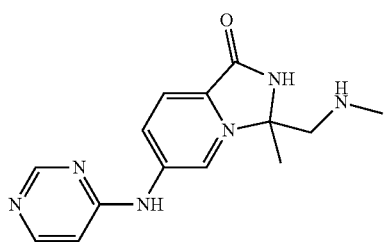

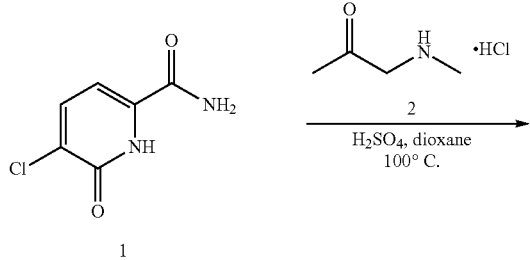

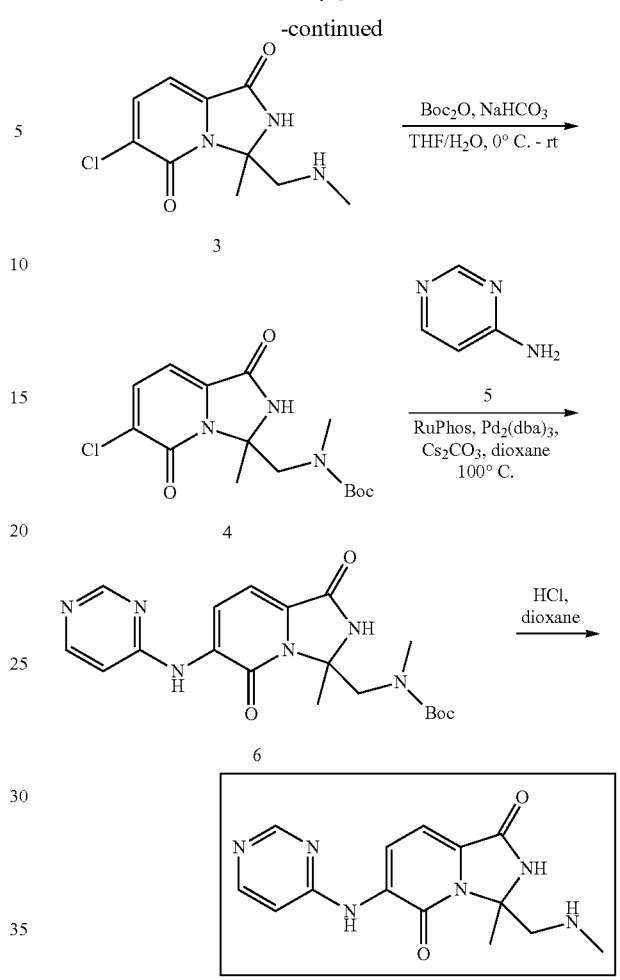

Synthesis of 6-chloro-3-methyl-3-((methylamino)methyl)-2,3-dihydroimidazo[1,5-a]pyridine-1,5-dione (3)

The synthesis of intermediate 3 was carried out as described above using the general protocol of Procedure A. Yield: 0.56 g, crude; MS (ESI) m/z 242 [M+1]$^+$.

Synthesis of tert-butyl ((6-chloro-3-methyl-1,5-dioxo-1,2,3,5-tetrahydroimidazo[1,5-a]pyridin-3-yl)methyl)(methyl)carbamate (4)

To a stirred solution of 6-chloro-3-methyl-3-((methylamino)methyl)-2,3-dihydroimidazo[1,5-a]pyridine-1,5-dione (3, 0.56 g, 2.3 mmol) in tetrahydrofuran (2 mL), sodium bicarbonate (2.91 g, 34.0 mmol) followed by di-tertiary butyl dicarbonate (2.58 mL, 11.0 mmol) were added and the reaction mixture was heated at 100° C. for 16 h. The reaction mixture was quenched with water and the compound was extracted in ethyl acetate. The organic layer was washed with 0.5 M hydrochloric acid and brine, separated, dried over sodium sulphate and concentrated under reduced pressure, and the residue was purified by repeated washing with pentane to obtain tert-butyl ((6-chloro-3-methyl-1,5-dioxo-1,2,3,5-tetrahydroimidazo[1,5-a]pyridin-3-yl)methyl)(methyl)carbamate (4). Yield: 0.67 g, crude; MS (ESI) m/z 343[M+1]$^+$.

Synthesis of tert-butyl methyl((3-methyl-1,5-dioxo-6-(pyrimidin-4-ylamino)-1,2,3,5-tetrahydroimidazo[1,5-a]pyridin-3-yl)methyl)carbamate (6)

The synthesis of intermediate 6 was carried out as described above using the general protocol of Procedure B. Yield: 0.340 g, 72%; MS (ESI) m/z 401 [M+1]+.

Synthesis of 3-methyl-3-((methylamino)methyl)-6-(pyrimidin-4-ylamino)-2,3-dihydroimidazo[1,5-a]pyridine-1,5-dione (Cpd. No. 25)

The synthesis of compound 25 was carried out as described above using the general protocol of Procedure D. Light yellow solid; Yield: 0.11 g, 44%; MS (ESI) m/z 301.20 [M+1]+; $^1$H NMR (400 MHz, DMSO-$d_6$) δ 9.37 (s, 2H), 8.75 (d, J=6.8 Hz, 2H), 8.36 (d, J=5.8 Hz, 1H), 7.36 (d, J=5.9 Hz, 1H), 6.82 (d, J=7.1 Hz, 1H), 3.58 (d, J=13.1 Hz, 1H), 2.82 (d, J=13.1 Hz, 1H), 2.16 (s, 3H), 1.76 (s, 3H).

Example 26

Synthesis of 6-(pyrimidin-4-ylamino)-1H-spiro[imidazo[1,5-a]pyridine-3,3'-pyrrolidine]-1,5(2H)-dione (Cpd. No. 26)

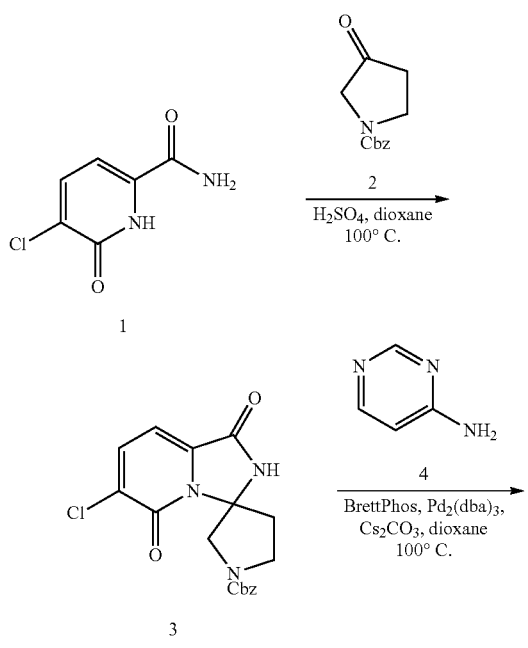

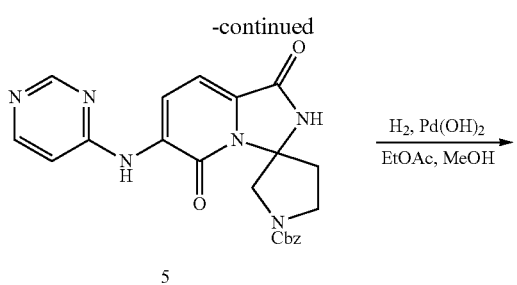

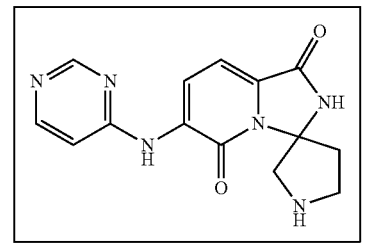

Synthesis of benzyl 6-chloro-1,5-dioxo-2,5-dihydro-1H-spiro[imidazo[1,5-a]pyridine-3,3'-pyrrolidine]-1'-carboxylate (3)

The synthesis of intermediate 3 was carried out as described above using the general protocol of Procedure A. Yield: 0.4 g, 37%; MS (ESI) m/z 374 [M+1]+.

Synthesis of benzyl 1,5-dioxo-6-(pyrimidin-4-ylamino)-2,5-dihydro-1H-spiro[imidazo[1,5-a]pyridine-3,3'-pyrrolidine]-1'-carboxylate (5)

The synthesis of intermediate 5 was carried out as described above using the general protocol of Procedure B. Yield: 0.1 g, 34%; MS (ESI) m/z 432 [M+1]+.

Synthesis of 6-(pyrimidin-4-ylamino)-1H-spiro[imidazo[1,5-a]pyridine-3,3'-pyrrolidine]-1,5(2H)-dione (Cpd. No. 26)

To a stirred solution of benzyl 1,5-dioxo-6-(pyrimidin-4-ylamino)-2,5-dihydro-1H-spiro[imidazo[1,5-a]pyridine-3,3'-pyrrolidine]-1'-carboxylate (5, 0.06 g, 0.138 mmol) in ethyl acetate: methanol (10:1, 33 mL), 20% palladium hydroxide (0.03 g) was added. The reaction mixture was hydrogenated under balloon pressure for 4 h. The progress of the reaction was monitored by TLC. After complete consumption of starting material, the reaction mixture was filtered through a pad of celite and the filtrate was concentrated under reduced pressure. The residue was purified by preparative TLC and repeated washing with ether to afford 6-(pyrimidin-4-ylamino)-1H-spiro[imidazo[1,5-a]pyridine-3,3'-pyrrolidine]-1,5(2H)-dione (Cpd. No. 26) as a white solid. Yield: 0.025 g, 60%; MS (ESI) m/z 299.20 [M+1]+; $^1$H NMR (400 MHz, DMSO-$d_6$) δ 9.47 (s, 1H), 8.83-8.74 (m, 2H), 8.38 (d, J=5.9 Hz, 1H), 7.37 (d, J=5.9 Hz, 1H), 6.92 (d, J=7.7 Hz, 1H), 3.67 (d, J=12.6 Hz, 1H), 3.19-3.03 (m, 2H), 2.95-2.75 (m, 2H), 2.05-1.88 (m, 1H).

Example 27

Synthesis of 3-(3,5-difluorophenyl)-3-methyl-6-(pyrimidin-4-ylamino)-2,3-dihydroimidazo[1,5-a]pyridine-1,5-dione (Cpd. No. 27)

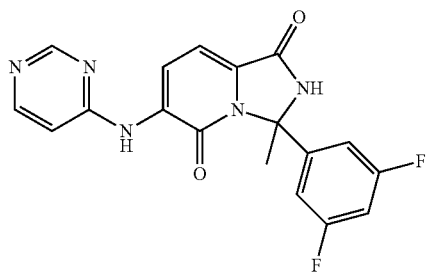 [SMILES: CC1(c2cc(F)cc(F)c2)NC(=O)c2ccc(Nc3ccncn3)c(=O)n21]

Synthesis of 6-chloro-3-(3,5-difluorophenyl)-3-methyl-2,3-dihydroimidazo[1,5-a]pyridine-1,5-dione (3)

The synthesis of intermediate 3 was carried out as described above using the general protocol of Procedure A. White solid; Yield: 0.21 g, 23%; MS (ESI) m/z 311 [M+1]$^+$.

Synthesis of 3-(3,5-difluorophenyl)-3-methyl-6-(pyrimidin-4-ylamino)-2,3-dihydroimidazo[1,5-a]pyridine-1,5-dione (Cpd. No. 27)

The synthesis of compound 27 was carried out as described above using the general protocol of Procedure B. Yellow solid; Yield: 0.12 g, 50%; MS (ESI) m/z 370 [M+1]$^+$; $^1$H NMR (400 MHz, DMSO-d$_6$) δ 10.09 (s, 1H), 9.37 (s, 1H), 8.85-8.74 (m, 2H), 8.36 (d, J=5.9 Hz, 1H), 7.33-7.23 (m, 2H), 7.13 (d, J=8.0 Hz, 2H), 7.01 (d, J=7.7 Hz, 1H), 2.23 (s, 3H).

Example 28

Synthesis of 3-(3-chloro-5-fluorophenyl)-3-methyl-6-(pyrimidin-4-ylamino)-2,3-dihydroimidazo[1,5-a]pyridine-1,5-dione (Cpd. No. 28)

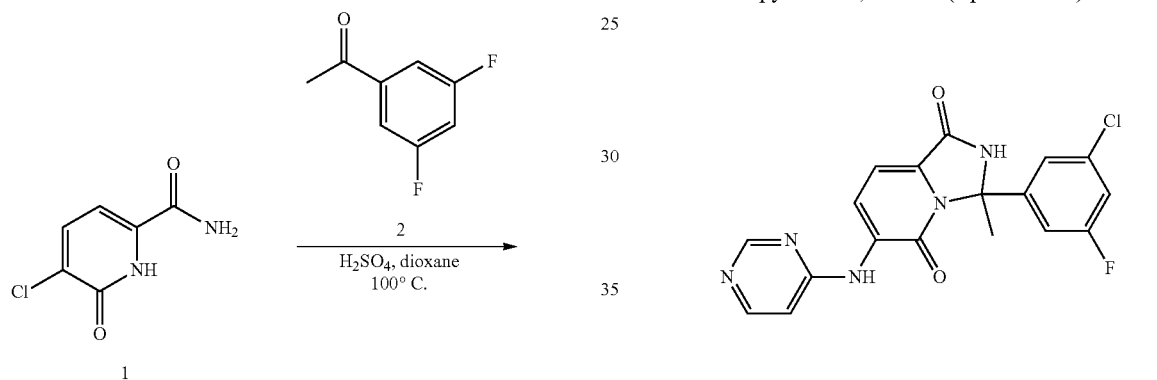

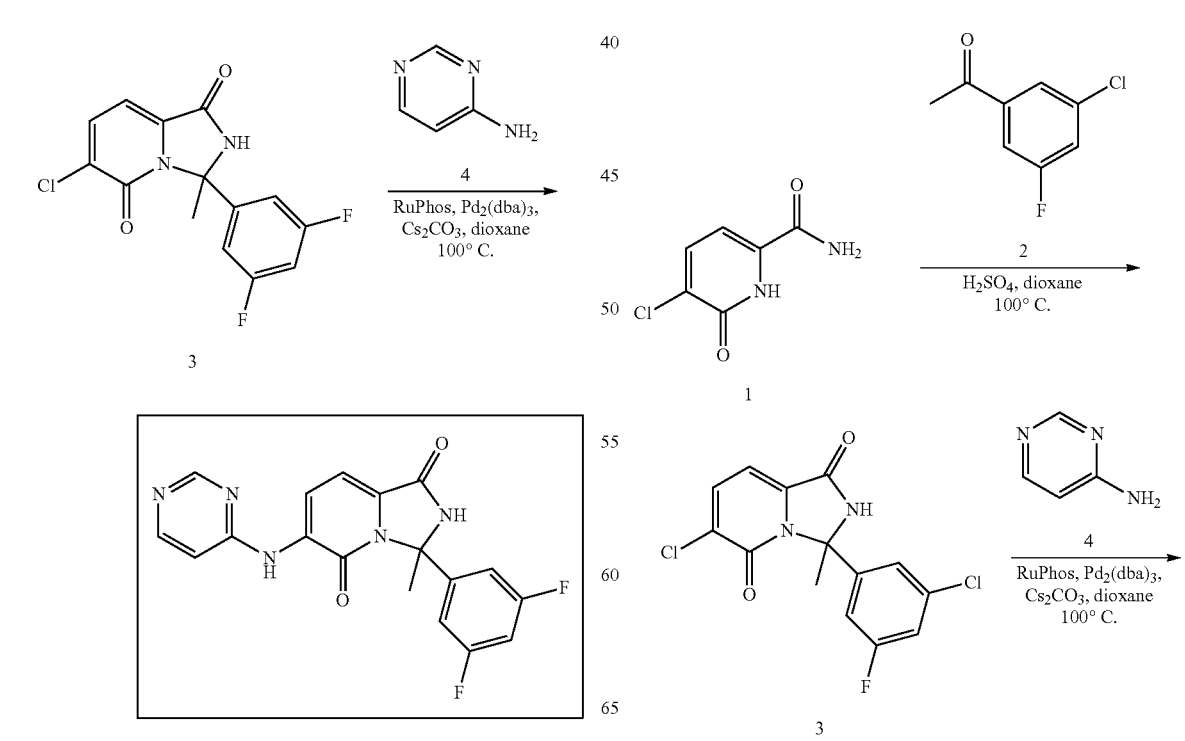

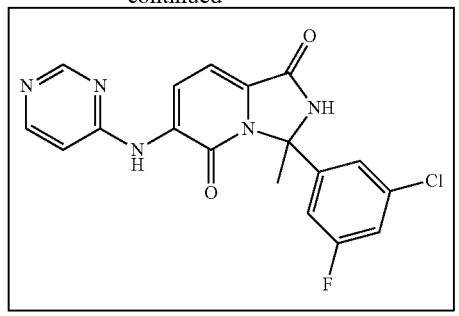

Synthesis of 6-chloro-3-(3-chloro-5-fluorophenyl)-3-methyl-2,3-dihydroimidazo[1,5-a]pyridine-1,5-dione (3)

The synthesis of intermediate 3 was carried out as described above using the general protocol of Procedure A. Yield: 0.2 g, 21%; MS (ESI) m/z 326[M+1]+.

Synthesis of 3-(3-chloro-5-fluorophenyl)-3-methyl-6-(pyrimidin-4-ylamino)-2,3-dihydroimidazo[1,5-a]pyridine-1,5-dione (Cpd. No. 28)

The synthesis of compound 28 was carried out as described above using the general protocol of Procedure B. Yellow solid; Yield: 0.065 g, 27%; MS (ESI) m/z 286.25 [M+1]+; 1H NMR (400 MHz, DMSO-d6) δ 10.10 (s, 1H), 9.39 (s, 1H), 8.86-8.74 (m, 2H), 8.36 (d, J=5.8 Hz, 1H), 7.53-7.45 (m, 1H), 7.33-7.24 (m, 3H), 7.22 (s, 1H), 2.23 (s, 3H).

Example 29

Synthesis of N-[6-[(3-isopropyl-3-methyl-1,5-dioxo-2H-imidazo[1,5-a]pyridin-6-yl)amino]pyrimidin-4-yl]cyclopropanecarboxamide (Cpd. No. 29)

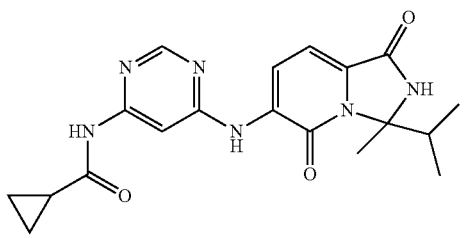 [SMILES: CC(C)C1(C)NC(=O)c2ccc(Nc3cc(NC(=O)C4CC4)ncn3)c(=O)n21]

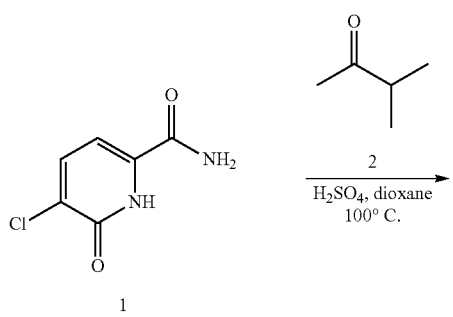

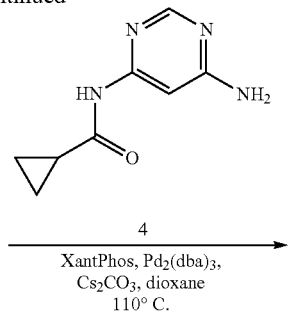

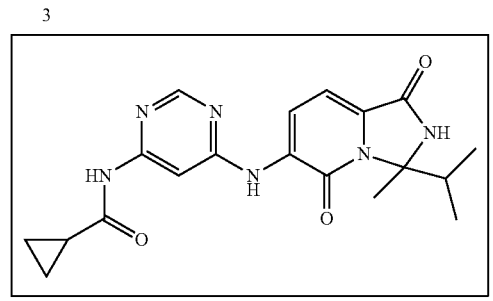

Synthesis of 6-chloro-3-isopropyl-3-methyl-2H-imidazo[1,5-a]pyridine-1,5-dione (3)

The synthesis of intermediate 3 was carried out as described above using the general protocol of Procedure A. Off-white solid. Yield: 0.80 g, 82%; MS (ESI) m/z 241.08 [M+1]+; 1H NMR (400 MHz, DMSO-d6): δ 9.94 (s, 1H), 7.95 (d, J=8.0 Hz, 1H), 6.71 (m, 1H), 3.01 (m, 1H), 1.79 (s, 3H), 1.03 (d, J=6.8 Hz, 3H), 0.42 (d, J=6.4 Hz, 3H).

Synthesis of N-[6-[(3-isopropyl-3-methyl-1,5-dioxo-2H-imidazo[1,5-a]pyridin-6-yl)-amino]pyrimidin-4-yl]cyclopropanecarboxamide (Cpd. No. 29)

The synthesis of compound 29 was carried out as described above using the general protocol of Procedure B. Off-white solid; Yield: 0.060 g, 13%; MS (ESI) m/z 383.30 [M+1]+; 1H NMR (400 MHz, DMSO-d6) δ 10.88 (s, 1H), 9.65 (s, 1H), 9.20 (s, 1H), 8.66 (d, J=7.6 Hz, 1H), 8.51 (s, 1H), 7.87 (s, 1H), 6.84 (d, J=7.6 Hz, 1H), 3.08 (m, 1H), 2.02 (m, 1H), 1.82 (s, 3H), 1.04 (d, J=6.8 Hz, 3H), 0.83 (d, J=6.0 Hz, 4H), 0.46 (d, J=6.4 Hz, 3H).

Example 30

Synthesis of N-[6-[[3-(3-fluorophenyl)-3-methyl-1,5-dioxo-2H-imidazo[1,5-a]pyridin-6-yl]amino]pyrimidin-4-yl]cyclopropanecarboxamide (Cpd. No. 30)

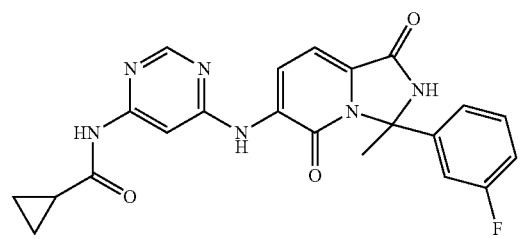 [SMILES: CC1(c2cccc(F)c2)NC(=O)c2ccc(Nc3cc(NC(=O)C4CC4)ncn3)c(=O)n21]

Example 31

Synthesis of 6-[[6-[(E)-2-cyclopropylvinyl]pyrimidin-4-yl]amino]-3-methyl-3-(trifluoromethyl)-2H-imidazo[1,5-a]pyridine-1,5-dione (Cpd. No. 31)

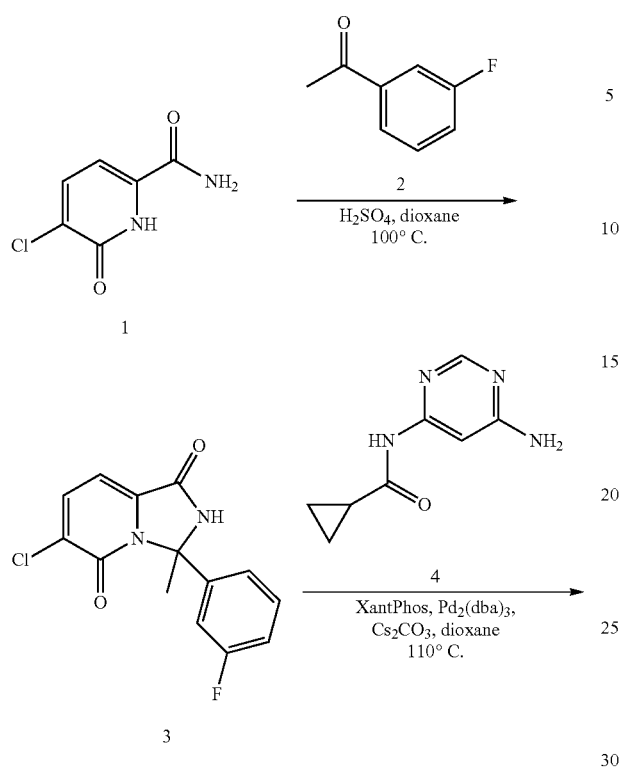

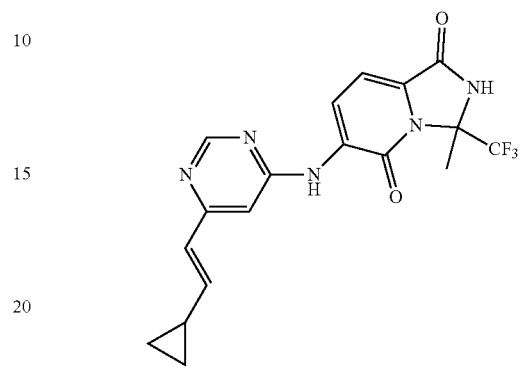

Synthesis of 6-chloro-3-methyl-3-(trifluoromethyl)-2H-imidazo[1,5-a]pyridine-1,5-dione (3)

The synthesis of intermediate 3 was carried out as described above using the general protocol of Procedure A. White solid; Yield: 300 mg, 59%; MS (ESI) m/z 293.13 [M+1]+.

Synthesis of N-[6-[[3-(3-fluorophenyl)-3-methyl-,5-dioxo-2H-imidazo[1,5-a]pyridin-6-yl]amino]pyrimidin-4-yl]cyclopropanecarboxamide (Cpd. No. 30)

The synthesis of compound 30 was carried out as described above using the general protocol of Procedure B. White solid; Yield: 100 mg, 22%; MS (ESI) m/z 435.28 [M+1]+; 1H NMR (400 MHz, DMSO-d6) δ 10.86 (s, 1H), 10.03 (s, 1H), 9.17 (s, 1H), 8.69 (d, J=7.6 Hz, 1H), 8.50 (s, 1H), 7.81 (s, 1H), 7.43 (m, 1H), 7.23 (m, 2H), 7.14 (m, 1H), 6.85 (d, J=7.6 Hz, 1H), 2.24 (s, 3H), 2.01 (m, 1H), 0.82 (d, J=6.0 Hz, 4H).

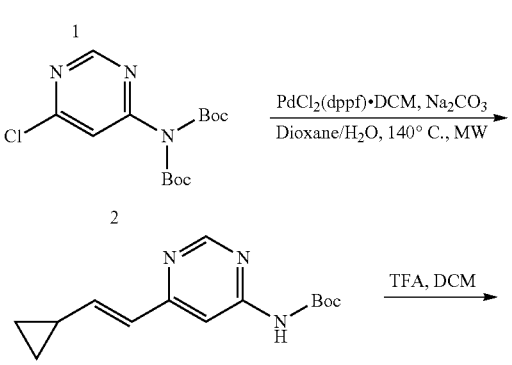

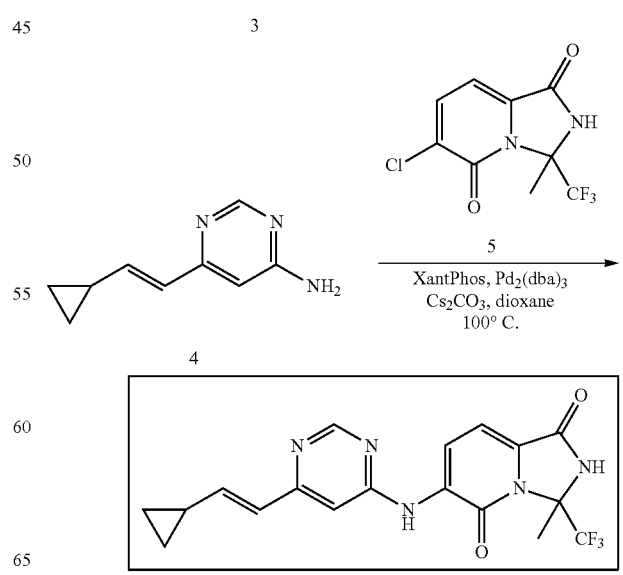

Synthesis of tert-butyl N-[6-[(E)-2-cyclopropylvinyl]pyrimidin-4-yl]carbamate (3)

A mixture of [(E)-2-cyclopropylvinyl]boronic acid (1, 1.0 g, 8.93 mmol), tert-butyl N-tert-butoxycarbonyl-N-(6-chloropyrimidin-4-yl)carbamate (2, 3.24 g, 9.83 mmol), sodium carbonate (2.84 g, 26.8 mmol), 1,4-dioxane (10 mL) and water (3 mL) in a microwave vial was degassed with argon for 10 minutes. To this mixture 1,1-bis(diphenylphosphino)ferrocene-palladium(II)dichloride dichloromethane complex (0.73 g, 0.89 mmol) was added and purged with argon for 5 minutes. After sealing, the vial was irradiated in a microwave reactor at 130° C. for 45 minutes. The reaction mixture was diluted with water (20 mL) and extracted with ethyl acetate (3×30 mL). The organics were washed with water (2×10 mL) and saturated brine solution (1×10 mL). The organics were then separated, dried with sodium sulfate, and filtered before concentration to dryness. The crude residue was purified by column chromatography (silica, ethyl acetate/hexanes=25%) to obtain tert-butyl N-[6-[(E)-2-cyclopropylvinyl]pyrimidin-4-yl]carbamate (3) as a light brown solid. Yield: 370 mg, 16%; MS (ESI) m/z 262.22 [M+1-Boc]$^+$; $^1$H NMR (400 MHz, DMSO-d$_6$) δ 10.23 (s, 1H), 8.60 (s, 1H), 7.63 (s, 1H), 6.50 (m, 2H), 1.48 (s, 9H), 0.91 (m, 2H), 0.64 (m, 2H)

Synthesis of 6-[(E)-2-cyclopropylvinyl]pyrimidin-4-amine (4)

A solution of tert-butyl N-[6-[(E)-2-cyclopropylvinyl]pyrimidin-4-yl]carbamate (3, 350 mg, 1.34 mmol) in dichloromethane (10 mL) at 0° C., trifluoroacetic acid (1.5 mL, 1.34 mmol) was added and stirred at 25° C. for 16 h. The solvent was removed under reduced pressure and the mixture made basic with the residue with aqueous ammonia. Filtration and washing with diethyl ether provided (6-[(E)-2-cyclopropylvinyl]pyrimidin-4-amine (4) as a brown solid. Yield: 170 mg, 79%; MS (ESI) m/z 162.10 [M+1]$^+$; $^1$H NMR (400 MHz, DMSO-d$_6$) δ 8.19 (s, 1H), 6.70 (brs, 2H), 6.32-6.27 (m, 2H), 6.17 (s, 1H), 1.60 (m, 1H), 0.84 (m, 2H), 0.55 (m, 2H).

Synthesis of 6-[[6-[(E)-2-cyclopropylvinyl]pyrimidin-4-yl]amino]-3-methyl-3-(trifluoromethyl)-2H-imidazo[1,5-a]pyridine-1,5-dione (Cpd. No. 31)

The synthesis of compound 31 was carried out as described above using the general protocol of Procedure B. Light brown solid; Yield: 70 mg, 19%; MS (ESI) m/z 392.26 [M+1]$^+$; $^1$H NMR (400 MHz, DMSO-d$_6$) δ 10.50 (brs, 1H), 9.42 (s, 1H), 8.78 (d, J=7.6 Hz, 1H), 8.63 (s, 1H), 7.19 (s, 1H), 7.00 (d, J=8.0 Hz, 1H), 6.46 (m, 2H), 2.13 (s, 3H), 1.69 (m, 1H), 0.90 (m, 2H), 0.62 (m, 2H).

Example 32

Synthesis of 3,3-dimethyl-6-(7H-pyrrolo[2,3-d]pyrimidin-7-yl)-2,3-dihydroimidazo[1,5-a]pyridine-1,5-dione (Cpd. No. 32)

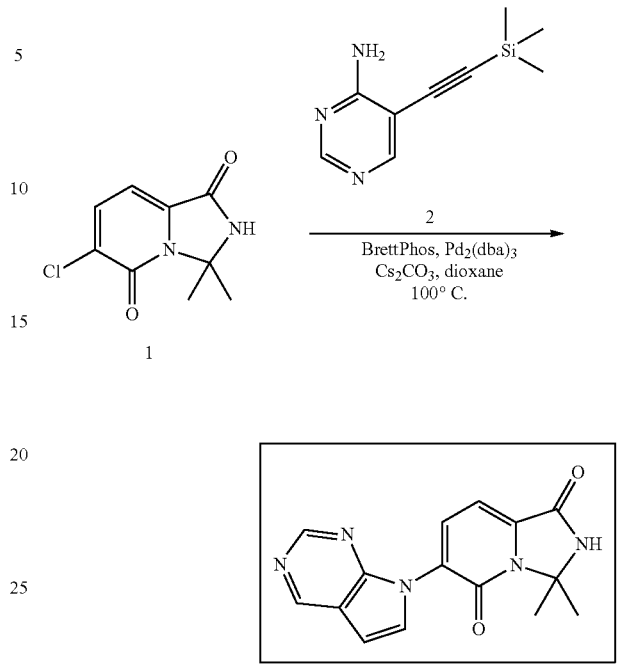

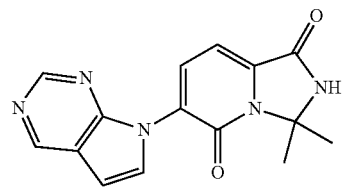 [SMILES: CC1(C)NC(=O)c2ccc(-n3ccc4cncnc43)c(=O)n21]

Synthesis of 3,3-dimethyl-6-(7H-pyrrolo[2,3-d]pyrimidin-7-yl)-2,3-dihydroimidazo[1,5-a]pyridine-1,5-dione (Cpd. No. 32)

The synthesis of compound 32 was carried out as described above using the general protocol of Procedure B. Yellow solid; Yield: 0.13 g, 42%; MS (ESI) m/z 296[M+1]$^+$; $^1$H NMR (400 MHz, DMSO-d$_6$) δ 10.1 (s, 1H), 9.15 (s, 1H), 8.83 (s, 1H), 8.18-8.27 (m, 1H), 7.98-7.87 (m, 1H), 6.99 (d, J=5.9 Hz, 1H), 6.87 (d, J=7.7 Hz, 1H), 1.88 (s, 6H).

Example 33

Synthesis of 3-(3,5-dichlorophenyl)-3-methyl-6-(pyrimidin-4-ylamino)-2,3-dihydroimidazo[1,5-a]pyridine-1,5-dione (Cpd. No. 33)

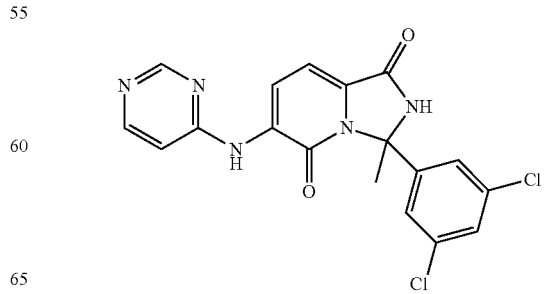

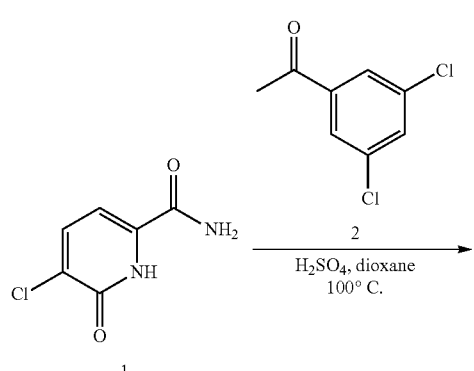

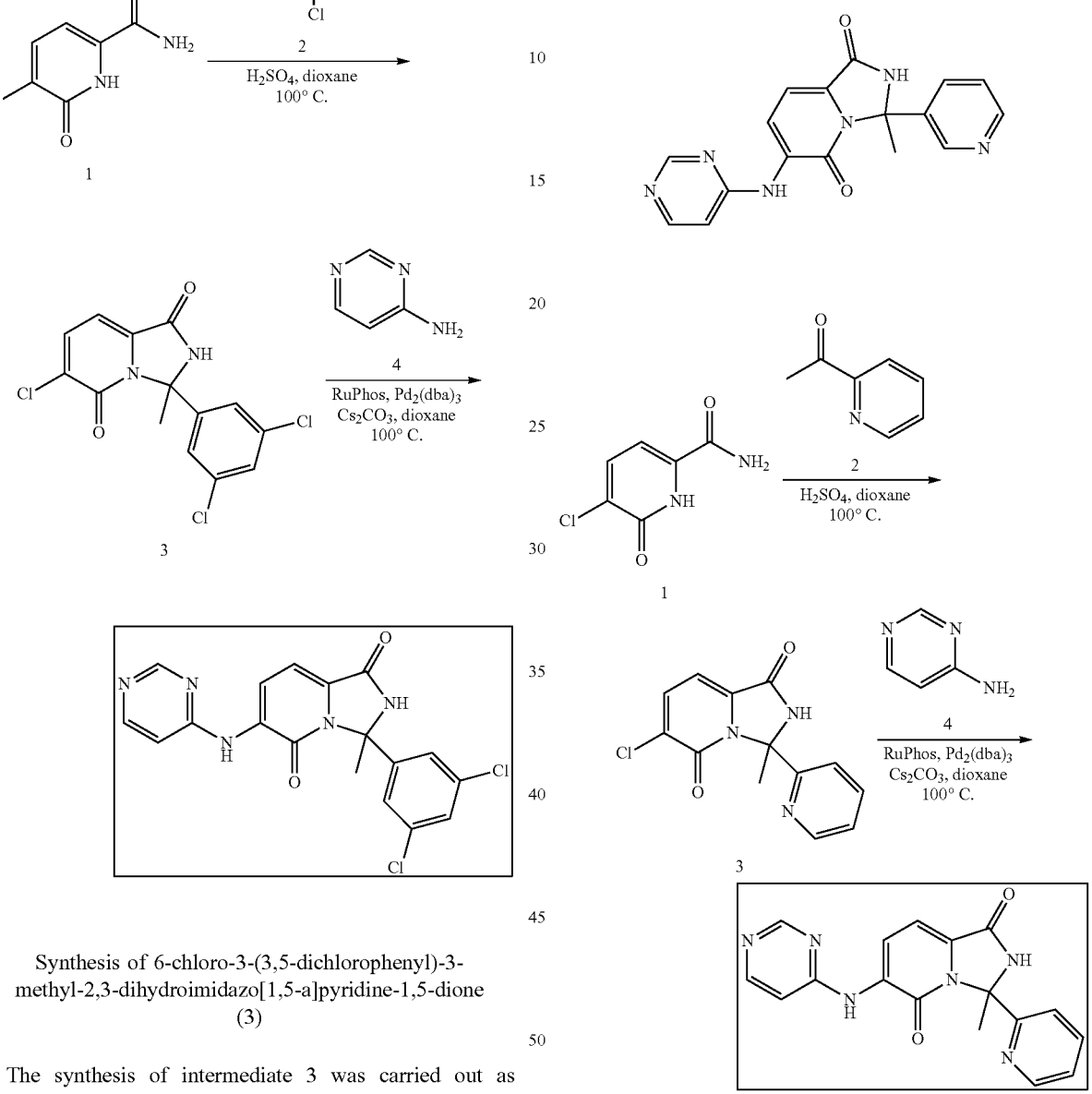

Synthesis of 6-chloro-3-(3,5-dichlorophenyl)-3-methyl-2,3-dihydroimidazo[1,5-a]pyridine-1,5-dione (3)

The synthesis of intermediate 3 was carried out as described above using the general protocol of Procedure A. Yield: 0.21 g, 21%.

Synthesis of 3-(3,5-dichlorophenyl)-3-methyl-6-(pyrimidin-4-ylamino)-2,3-dihydroimidazo[1,5-a]pyridine-1,5-dione (Cpd. No. 33)

The synthesis of compound 33 was carried out as described above using the general protocol of Procedure B. Yellow solid; Yield: 0.042 g, 17%; MS (ESI) m/z 402[M+1]$^+$; $^1$H NMR (400 MHz, DMSO-d$_6$) δ 10.09 (s, 1H), 9.38 (s, 1H), 8.85-8.74 (m, 2H), 8.36 (d, J=5.9 Hz, 1H), 7.66 (t, J=1.9 Hz, 1H), 7.44 (d, J=1.9 Hz, 2H), 7.29 (d, J=6.0 Hz, 1H), 7.02 (d, J=7.7 Hz, 1H), 2.23 (s, 3H).

Example 34

Synthesis of 3-methyl-3-(pyridin-2-yl)-6-(pyrimidin-4-ylamino)-2,3-dihydroimidazo[1,5-a]pyridine-1,5-dione (Cpd. No. 34)

Synthesis of 6-chloro-3-methyl-3-(pyridin-2-yl)-2,3-dihydroimidazo[1,5-a]pyridine-1,5-dione (3)

The synthesis of intermediate 3 was carried out as described above using the general protocol of Procedure A. Yield: 0.26 g, 33%; MS (ESI) m/z 276[M+1]$^+$.

Synthesis of 3-methyl-3-(pyridin-2-yl)-6-(pyrimidin-4-ylamino)-2,3-dihydroimidazo[1,5-a]pyridine-1,5-dione (Cpd. No. 34)

The synthesis of compound 34 was carried out as described above using the general protocol of Procedure B.

Off-white solid; Yield: 0.012 g, 5%; MS (ESI) m/z 335.10 [M+1]⁺; ¹H NMR (400 MHz, DMSO-$d_6$) δ 9.96 (s, 1H), 9.28 (s, 1H), 8.83-8.73 (m, 2H), 8.55-8.48 (m, 1H), 8.34 (d, J=5.9 Hz, 1H), 7.88-7.84 (m, 1H), 7.57 (d, J=8.0 Hz, 1H), 7.37 (dd, J=7.6, 4.7 Hz, 1H), 7.25 (d, J=5.9 Hz, 1H), 6.97 (d, J=7.6 Hz, 1H), 2.29 (s, 3H).

Example 35

Synthesis of 8-chloro-3-methyl-6-(pyrimidin-4-ylamino)-3-(trifluoromethyl)-2H-imidazo[1,5-a]pyridine-1,5-dione (Cpd. No. 35)

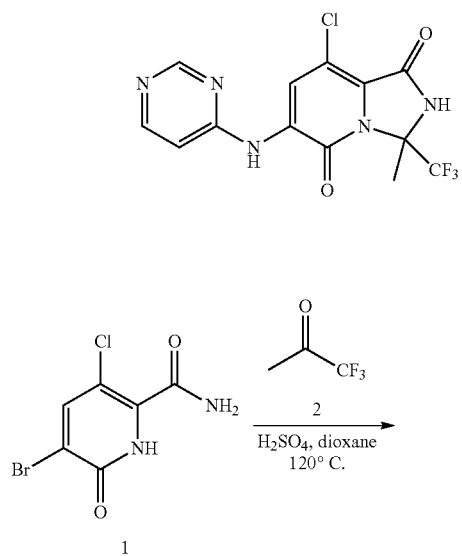

Synthesis of 6-bromo-8-chloro-3-methyl-3-(trifluoromethyl)-2H-imidazo[1,5-a]pyridine-1,5-dione (3)

The synthesis of intermediate 3 was carried out as described above using the general protocol of Procedure A. Off white solid; Yield: 1.8 g, 66%; MS (ESI) m/z 346.6 [M+1]⁺; ¹H NMR (400 MHz, DMSO-$d_6$) δ 10.90 (s, 1H), 8.36 (s, 1H), 2.06 (s, 3H).

Synthesis of 8-chloro-3-methyl-6-(pyrimidin-4-ylamino)-3-(trifluoromethyl)-2H-imidazo-[1,5-a]pyridine-1,5-dione (Cpd. No. 35)

The synthesis of compound 35 was carried out as described above using the general protocol of Procedure B. Off-white solid; Yield: 0.52 g, 35%; MS (ESI) m/z 360.22 [M+1]⁺; ¹H NMR (400 MHz, DMSO-$d_6$) δ 10.60 (s, 1H), 9.82 (s, 1H), 8.87 (s, 1H), 8.81 (m, 1H), 8.47 (d, J=6.0 Hz, 1H), 7.46 (d, J=6.0 Hz, 1H), 2.12 (s, 3H).

Example 36

Synthesis of 2',2'-dimethyl-6-(pyrimidin-4-ylamino)spiro[2H-imidazo[1,5-a]pyridine-3,1'-cyclopentane]-1,5-dione (Cpd. No. 36)

Synthesis of 6-chloro-2',2'-dimethyl-spiro[2H-imidazo[1,5-a]pyridine-3, 1'-cyclopentane]-1,5-dione (3)

The synthesis of intermediate 3 was carried out as described above using the general protocol of Procedure A. Cream colored solid; Yield: 0.12 g, 16%; MS (ESI) m/z 267.15 [M+1]+.

Synthesis of 2',2'-dimethyl-6-(pyrimidin-4-ylamino)spiro[2H-imidazo[1,5-a]pyridine-3,1'-cyclopentane]-1,5-dione (Cpd. No. 36)

The synthesis of compound 36 was carried out as described above using the general protocol of Procedure B. Off-white solid; Yield: 17 mg, 9%; MS (ESI) m/z 326.30 [M+1]+; $^1$H NMR (400 MHz, DMSO-$d_6$) δ 9.66 (s, 1H), 9.48 (s, 1H), 8.78 (d, J=7.6 Hz, 1H), 8.76 (s, 1H), 8.37 (d, J=6.0 Hz, 1H), 7.40 (d, J=6.06 Hz, 1H), 6.87 (d, J=7.6 Hz, 1H), 2.94 (m, 1H), 2.50-1.66 (m, 6H), 1.03 (s, 3H), 0.72 (s, 3H).

Example 37

Synthesis of 6-[(8-cyclopropyl-9H-purin-6-yl)amino]-3-methyl-3-(trifluoromethyl)-2H-imidazo[1,5-a]pyridine-1,5-dione (Cpd. No. 37)

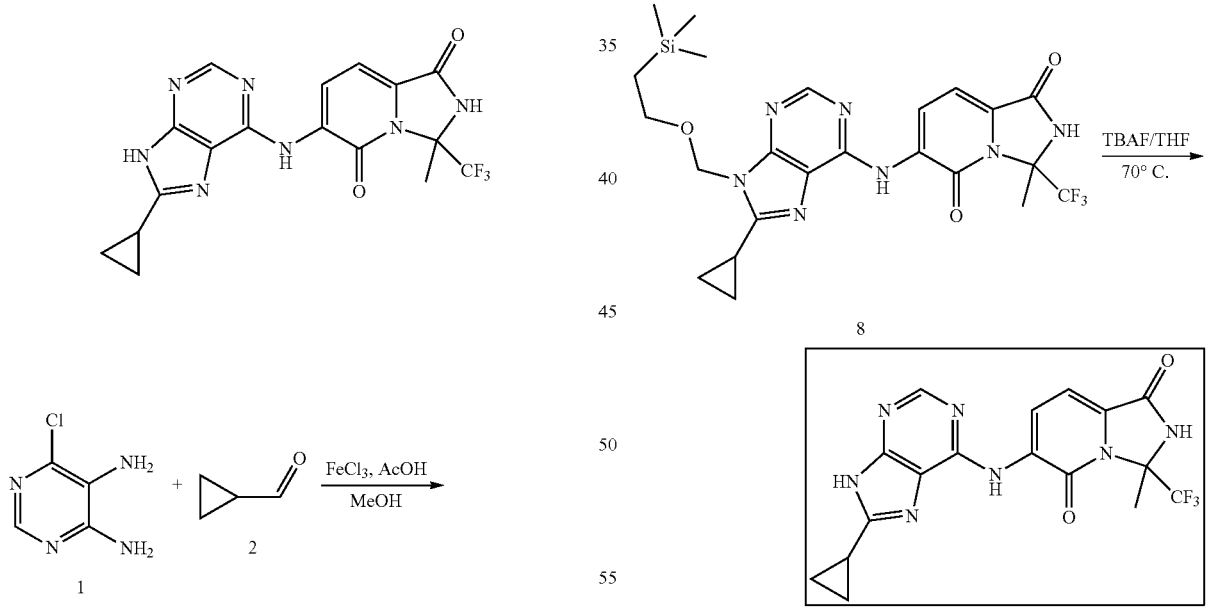

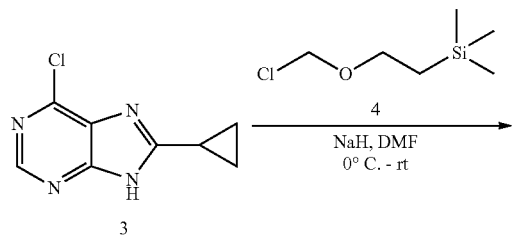

Synthesis of 6-chloro-8-cyclopropyl-9H-purine (3)

To a solution of 6-chloropyrimidine-4,5-diamine (1, 2.0 g, 13.84 mmol) and cyclopropanecarbaldehyde (2, 1.16 g, 16.6 mmol) in methanol (100 mL), acetic acid (1.0 mL) was added and stirred at room temperature for 2 h. To this mixture was added iron(III) chloride (11.22 g, 69.18 mmol) and stirring was continued for 24 h. The solvents were removed under reduced pressure and the crude residue was purified via column chromatography (silica, ethyl acetate/hexanes=70%) to afford 6-chloro-8-cyclopropyl-9H-purine (3) as a white solid. Yield: 1.2 g, 45%; MS (ESI) m/z 195.14 [M+1]$^+$; $^1$H NMR (400 MHz, DMSO-d$_6$) δ 13.65 (s, 1H), 8.60 (s, 1H), 2.19 (m, 1H), 1.18 (m, 4H).

Synthesis of 2-[(6-chloro-8-cyclopropyl-purin-9-yl)methoxy]ethyl-trimethyl-silane (5)

To a stirred suspension of sodium hydride (0.18 g, 7.71 mmol) in dimethylformamide (10 mL) at 0° C., 6-chloro-8-cyclopropyl-9H-purine (3, 1.0 g, 5.14 mmol) was added and stirred for 30 m. To this mixture, 2-(chloromethoxy)ethyl-trimethyl-silane (4, 2.0 mL, 6.17 mmol) was added dropwise and allowed to stir at room temperature for 16 h. The reaction mixture was quenched with ice cold water (20 mL) and extracted with ethyl acetate (3×50 mL). The combined organic layers were separated and dried with magnesium sulfate before concentration to dryness. The crude residue was purified via column chromatography ethyl acetate/hexanes=70%) to afford 2-[(6-chloro-8-cyclopropyl-purin-9-yl)methoxy]ethyl-trimethyl-silane (5) as an off-white solid. Yield: 0.84 g, 50%; MS (ESI) m/z 325.30 [M+1]$^+$; $^1$H NMR (400 MHz, CDCl$_3$) δ 8.65 (s, 1H), 5.73 (s, 2H), 3.61 (m, 2H), 2.44 (m, 1H), 1.43 (m, 2H), 1.26 (m, 2H), 0.88 (m, 2H), 0.05 (s, 9H).

Synthesis of 8-cyclopropyl-9-(2-trimethylsilylethoxymethyl)purin-6-amine (6)

In a sealed tube a stirred suspension of 2-[(6-chloro-8-cyclopropyl-purin-9-yl)methoxy]ethyl-trimethyl-silane (5, 0.8 g, 2.46 mmol) and 30% aqueous ammonia (10 mL) in ethanol (10 mL) was heated at 120° C. for 14 h. After TLC showed consumption of 5, ethanol was removed under reduced pressure and the residue was washed with water (10 mL) and diethyl ether (10 mL) to obtain 8-cyclopropyl-9-(2-trimethylsilylethoxymethyl)purin-6-amine (6) as a white solid. Yield: 703 mg, 93%; MS (ESI) m/z 306.30 [M+1]$^+$; $^1$H NMR (400 MHz, CDCl$_3$) δ 8.00 (s, 1H), 7.10 (s, 2H), 5.64 (s, 2H), 3.57 (m, 2H), 2.24 (m, 1H), 1.08 (m, 4H), 0.83 (m, 2H), 0.09 (s, 9H).

Synthesis of 6-[[8-cyclopropyl-9-(2-trimethylsilylethoxymethyl)purin-6-yl]amino]-3-methyl-3-(trifluoromethyl)-2H-imidazo[1,5-a]pyridine-1,5-dione (8)

The synthesis of intermediate 8 was carried out as described above using the general protocol of Procedure B. Yellow solid; Yield: 300 mg, 50%; MS (ESI) m/z 536.26 [M+1]$^+$.

Synthesis of 6-[(8-cyclopropyl-9H-purin-6-yl)amino]-3-methyl-3-(trifluoromethyl)-2H-imidazo[1,5-a]pyridine-1,5-dione (Cpd. No. 37)

To a solution of 6-[[8-cyclopropyl-9-(2-trimethylsilylethoxymethyl)purin-6-yl]amino]-3-methyl-3-(trifluoromethyl)-2H-imidazo[1,5-a]pyridine-1,5-dione (8, 0.25 g, 0.47 mmol) in tetrahydrofuran (50 mL) was added tetrabutylammonium fluoride hydrate (0.61 g, 2.33 mmol). The mixture was heated at 70° C. for 4 h. After TLC showed consumption of 8, the reaction mixture was diluted with water (50 mL) and extracted with ethyl acetate (2×50 mL). The combined organic layers were dried over sodium sulfate and concentrated under reduced pressure. The crude mixture was purified via column chromatography (silica, methanol/dichloromethane=2%) to afford 6-[(8-cyclopropyl-9H-purin-6-yl)amino]-3-methyl-3-(trifluoromethyl)-2H-imidazo[1,5-a]pyridine-1,5-dione (Cpd. No. 37) as yellow solid. Yield: 135 mg, 71%; MS (ESI) m/z 406.29 [M+1]$^+$; $^1$H NMR (400 MHz, DMSO-d$_6$) δ 13.24 (s, 1H), 10.55 (s, 1H), 8.80 (d, J=7.6 Hz, 1H), 8.64 (s, 1H), 8.49 (s, 1H), 7.10 (d, J=7.6 Hz, 1H), 2.16 (m, 1H), 2.15 (s, 3H), 1.12 (m, 4H).

Example 38

Synthesis of N-[6-[(8-chloro-1,5-dioxo-spiro[2H-imidazo[1,5-a]pyridine-3,1'-cyclopentane]-6-yl)amino]pyrimidin-4-yl]cyclopropanecarboxamide (Cpd. No. 38)

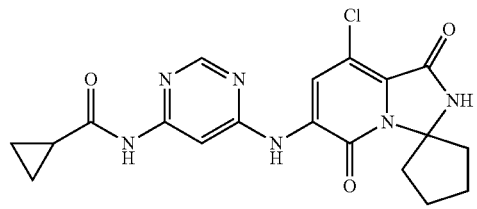 [SMILES: O=C1NC2(CCCC2)n2c1c(Cl)cc(Nc1cc(NC(=O)C3CC3)ncn1)c2=O]

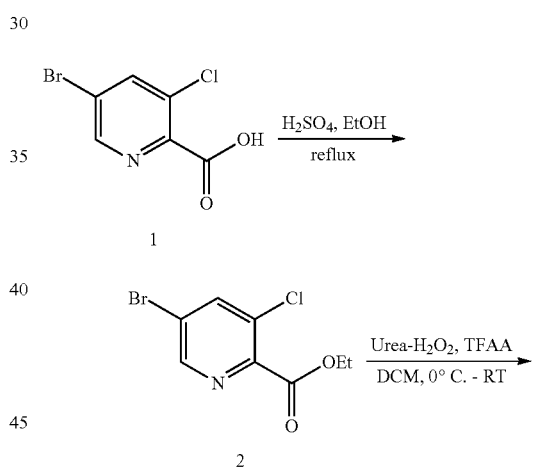

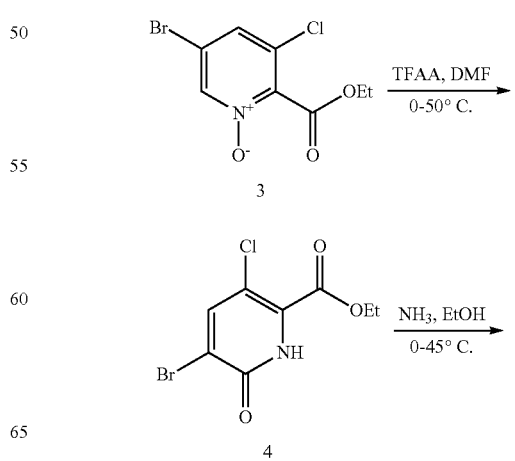

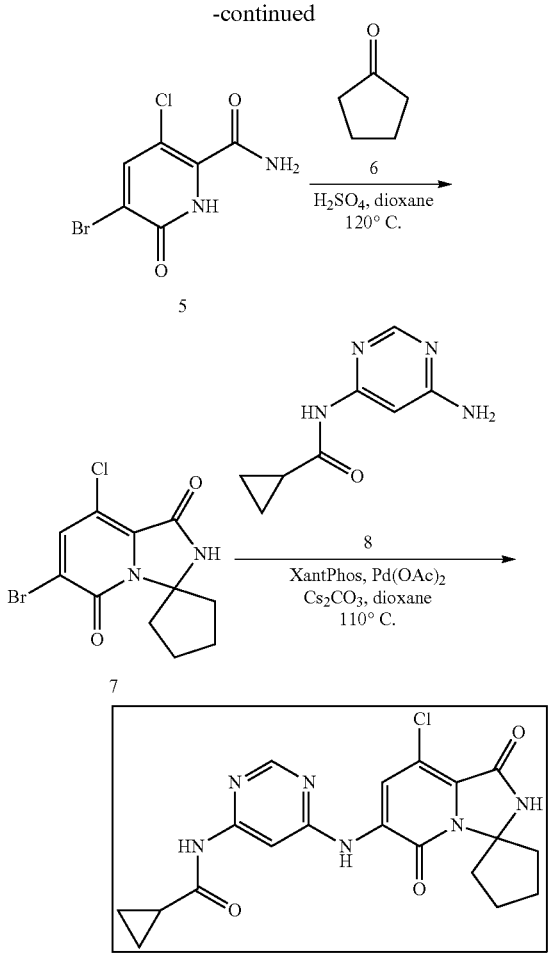

Synthesis of ethyl 5-bromo-3-chloro-pyridine-2-carboxylate (2)

To a stirred solution of 5-bromo-3-chloro-pyridine-2-carboxylic acid (1, 150.0 g, 634.38 mmol) in ethanol (1.5 L) was added sulfuric acid (93.26 g, 951.58 mmol) at room temperature. The reaction mass was stirred at 80° C. overnight. After consumption of starting material as indicated by TLC, the reaction mixture was cooled to room temperature and solvent was removed under reduced pressure. The resulting residue was neutralized with saturated aqueous sodium bicarbonate solution and extracted with ethyl acetate (2×1 L). The organic layers were then separated, combined, dried with magnesium sulfate and concentrated to dryness in vacuum to afford ethyl 5-bromo-3-chloro-pyridine-2-carboxylate (2) as an off white solid. Yield: 163 g, 97%; $^1$H NMR (400 MHz, DMSO-$d_6$) δ 8.69 (m, 1H), 8.08 (m, 1H), 7.81 (m, 1H), 4.47 (m, 2H), 1.43 (t, J=7.2 Hz, 3H).

Synthesis of ethyl 5-bromo-3-chloro-1-oxido-pyridin-1-ium-2-carboxylate (3)

To a stirred solution of ethyl 5-bromo-3-chloro-pyridine-2-carboxylate (2, 151.0 g, 570.89 mmol) in dichloromethane (1.73 L) was added trifluoroacetic anhydride (30.0 mL, 1.14 mol) and urea hydrogen peroxide (112.69 g, 1.20 mol) at 0° C. The reaction was stirred overnight at room temperature. After completion of the reaction, the reaction mixture was neutralized with a potassium phosphate dibasic solution. A sodium bisulfite solution was added followed by extraction with dichloromethane (2×100 mL). The organic layers were separated, combined, dried with magnesium sulfate, filtered and concentrated to dryness under vacuum to afford ethyl 5-bromo-3-chloro-1-oxido-pyridin-1-ium-2-carboxylate 3 as an off white solid. Yield: 150.5 g, 94%; MS (ESI) m/z 281.8 [M+1]$^+$; $^1$H NMR (400 MHz, DMSO-$d_6$) δ 8.26 (d, J=1.2 Hz, 1H), 7.48 (d, J=1.2 Hz, 1H), 4.50 (q, J=7.12 Hz, 2H), 1.42 (t, J=12.12 Hz, 3H).

Synthesis of ethyl 5-bromo-3-chloro-6-oxo-1H-pyridine-2-carboxylate (4)

To a stirred solution of ethyl 5-bromo-3-chloro-1-oxido-pyridin-1-ium-2-carboxylate (3, 150 g, 534.8 mmol) in dimethylformamide (900 mL) at 0° C. was added trifluoroacetic anhydride (224.63 g, 1.07 mmol). The temperature of the reaction mixture was raised to 50° C. and stirring was continued for 1 h. After the oxidation was complete, the reaction mass was quenched with a saturated aqueous sodium bicarbonate solution and product was extracted with dichloromethane (2×100 mL). The organic layers were separated, combined, dried with magnesium sulfate and concentrated to dryness under vacuum to afford ethyl 5-bromo-3-chloro-6-oxo-1H-pyridine-2-carboxylate (4) as a yellow solid. Yield: 75 g, 50%; MS (ESI) m/z 281.8 [M+1]$^+$; $^1$H NMR (400 MHz, DMSO-$d_6$) δ 10.44-10.02 (m, 1H), 7.86 (s, 1H), 4.47 (q, J=7.2 Hz, 2H), 1.43 (t, J=5.6 Hz, 3H).

Synthesis of 5-bromo-3-chloro-6-oxo-1H-pyridine-2-carboxamide (5)

In a round bottom flask containing ethyl 5-bromo-3-chloro-6-oxo-1H-pyridine-2-carboxylate (4, 75.0 g, 267.38 mmol) was added liquid ammonia (150.0 mL, 267.38 mmol) in ethanol (100 mL) at 0° C. The reaction mixture was stirred at 45° C. for 2 h. At this time the mixture was concentrated to remove the ethanolic ammonia. The crude solids were washed with diethyl ether (500 mL) and dissolved in refluxing methanol (1 L) and filtered hot. The filtrate was concentrated under reduced pressure until ⅓ of solvent volume remained. Diethyl ether was added until all solids precipitated. The solid was filtered and dried under vacuum to afford 5-bromo-3-chloro-6-oxo-1H-pyridine-2-carboxamide (5) as a light brown solid. Yield: 45 g, 69%; MS (ESI) m/z 248.9 [M−1]$^−$; $^1$H NMR (400 MHz, DMSO-$d_6$) δ 7.92-7.82 (m, 1H), 7.61-7.59 (m, 1H), 7.36 (s, 1H).

Synthesis 6-bromo-8-chloro-spiro[2H-imidazo[1,5-a]pyridine-3,1'-cyclopentane]-1,5-dione (7)

The synthesis of intermediate 7 was carried out as described above using the general protocol of Procedure A. Off-white solid; Yield: 450 mg, 87%; MS (ESI) m/z 317.03 [M+1]$^+$; $^1$H NMR (400 MHz, DMSO-$d_6$) δ 10.39 (s, 1H), 8.25 (s, 1H), 2.73 (m, 4H), 2.21 (m, 2H), 1.93 (m, 2H).

Synthesis of N-[6-[(8-chloro-1,5-dioxo-spiro[2H-imidazo[1,5-a]pyridine-3,1'-cyclopentane]-6-yl)amino]pyrimidin-4-yl]cyclopropanecarboxamide (Cpd. No. 38)

The synthesis of compound 38 was carried out as described above using the general protocol of Procedure B. White solid; Yield: 50 mg, 17%; MS (ESI) m/z 415.32 [M+1]$^+$; $^1$H NMR (400 MHz, DMSO-$d_6$) δ 10.92 (s, 1H), 10.08 (s, 1H), 9.52 (s, 1H), 8.72 (s, 1H), 8.59 (s, 1H), 7.98 (s, 1H), 2.78 (m, 2H), 2.02 (m, 3H), 1.83 (m, 2H), 1.72 (m, 2H), 0.84 (d, J=6.0 Hz, 4H).

Example 39

Synthesis of 8'-chloro-6'-(pyrimidin-4-ylamino)-2'H-spiro[cyclopentane-1,3'-imidazo[1,5-a]pyridine]-1',5'-dione (Cpd. No. 39)

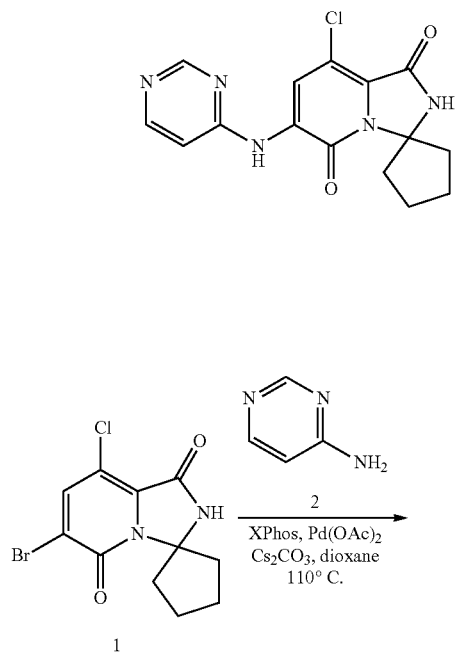

Synthesis of 8'-chloro-6'-(pyrimidin-4-ylamino)-2'H-spiro[cyclopentane-1,3'-imidazo[1,5-a]pyridine]-1',5'-dione (Cpd. No. 39)

The synthesis of compound 39 was carried out as described above using the general protocol of Procedure B. Off white solid; Yield: 0.07 g, 30%; MS (ESI) m/z 332.28 [M+1]; $^1$H NMR (400 MHz, DMSO-d$_6$) δ 10.11 (s, 1H), 9.67 (s, 1H), 8.84 (s, 1H), 8.79 (s, 1H), 8.43 (d, J=5.6 Hz, 1H), 7.43 (d, J=5.6, 1H), 2.77 (m, 2H), 1.98 (m, 2H), 1.82 (m, 2H), 1.74 (m, 2H).

Example 40

Synthesis of 3,3-dimethyl-6-(5H-pyrrolo[2,3-d]pyrimidin-7(6H)-yl)-2,3-dihydroimidazo[1,5-a]pyridine-1,5-dione (Cpd. No. 40)

Synthesis of 3,3-dimethyl-6-(5H-pyrrolo[2,3-d]pyrimidin-7(6H)-yl)-2,3-dihydroimidazo-[1,5-a]pyridine-1,5-dione (Cpd. No. 40)

To a stirred solution of 3,3-dimethyl-6-(7H-pyrrolo [2,3-d] pyrimidin-7-yl)-2, 3-dihydroimidazo [1,5-a] pyridine-1,5-dione (1, 0.095 g, 0.32 mmol) in methanol (25 ml), 10% palladium on carbon (25 mg) was added. The reaction mixture was hydrogenated under balloon pressure hydrogen gas for 24 h. The progress of the reaction was monitored by TLC. After complete consumption of starting material, reaction mixture was filtered through a pad of celite and the filtrate was concentrated under reduced pressure to obtain a crude residue. The residue was purified by prep HPLC to afford the product as a light yellow solid. Yield: 8.0 mg, 8%; MS (ESI) m/z 298.20 [M+1]$^+$; $^1$H NMR (400 MHz, DMSO-d$_6$) δ 8.35 (s, 1H), 8.15 (s, 1H), 7.96 (d, J=7.4 Hz, 1H), 6.81 (d, J=7.5 Hz, 1H), 4.17 (t, J=8.6 Hz, 2H), 3.13 (t, J=8.6 Hz, 2H), 2.59 (s, 2H), 1.79 (s, 6H).

Example 41

Synthesis of 3-(2-aminoethyl)-3-methyl-6-(pyrimidin-4-ylamino)-2H-imidazo[1,5-a]pyridine-1,5-dione (Cpd. No. 41)

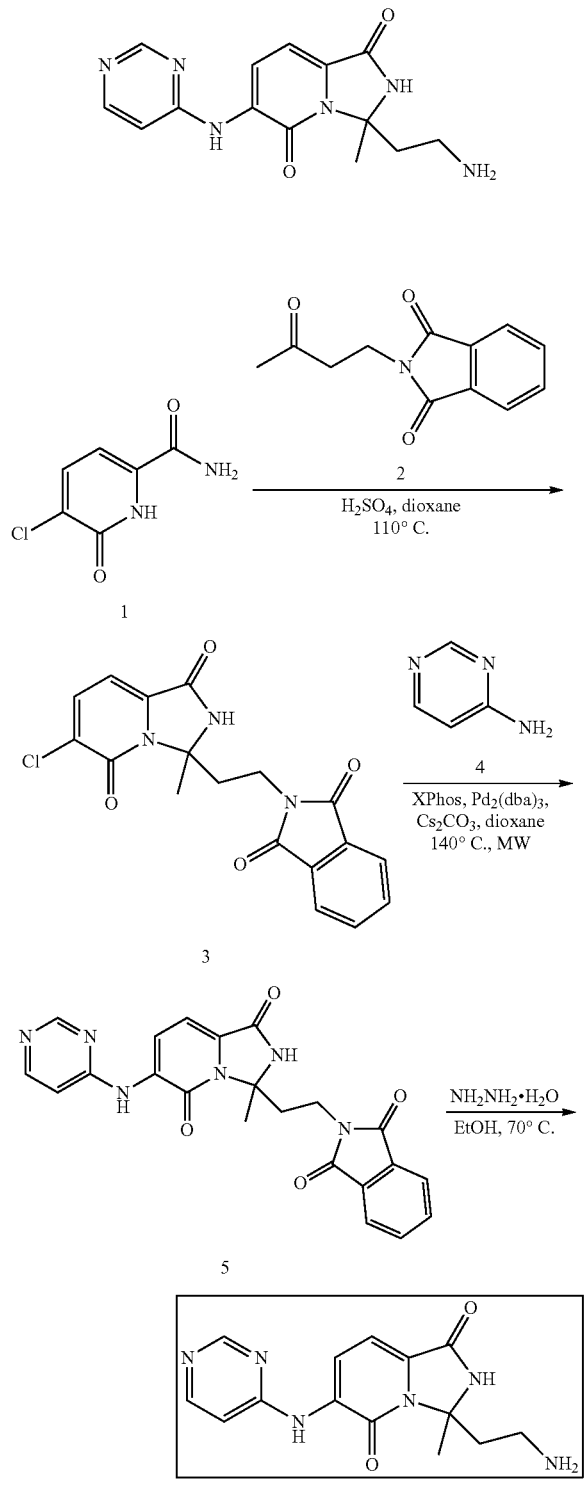

Synthesis of 6-chloro-3-[2-(1,3-dioxoisoindolin-2-yl)ethyl]-3-methyl-2H-imidazo[1,5-a]pyridine-1,5-dione (3)

The synthesis of intermediate 3 was carried out as described above using the general protocol of Procedure A. Brown solid; Yield: 3.01 g, 59%; MS (ESI) m/z 372.0 [M+1]$^+$.

Synthesis of 3-[2-(1,3-dioxoisoindolin-2-yl)ethyl]-3-methyl-6-(pyrimidin-4-ylamino)-2H-imidazo[1,5-a]pyridine-1,5-dione (5)

The synthesis of intermediate 5 was carried out as described above using the genera protocol of Procedure B. Yellow solid; Yield: 1.03 g, 36%; MS (ESI) m/z 431.31 [M+1]$^+$.

Synthesis of 3-(2-aminoethyl)-3-methyl-6-(pyrimidin-4-ylamino)-2H-imidazo[1,5-a]pyridine-1,5-dione (Cpd. No. 41)

The synthesis of compound 41 was carried out as described above using the general protocol of Procedure C. Cream-colored solid; Yield: 300 mg, 54%; MS (ESI) m/z 301.32 [M+1]$^+$; $^1$H NMR (400 MHz, DMSO-d$_6$) δ 9.41 (brs, 1H), 8.77 (d, J=7.6 Hz, 1H), 8.76 (s, 1H), 8.37 (d, J=6.0 Hz, 1H), 7.37 (d, J=5.6 Hz, 1H), 6.86 (d, J=7.6 Hz, 1H), 4.39 (brs, 2H), 2.59 (m, 1H), 2.41 (m, 1H), 2.22 (m, 1H), 2.15 (m, 1H), 1.80 (s, 3H).

Example 42

Synthesis of N-[6-[(8-chloro-3-cyclopentyl-3-methyl-1,5-dioxo-2H-imidazo[1,5-a]pyridin-6-yl)amino]pyrimidin-4-yl]cyclopropanecarboxamide (Cpd. No. 42)

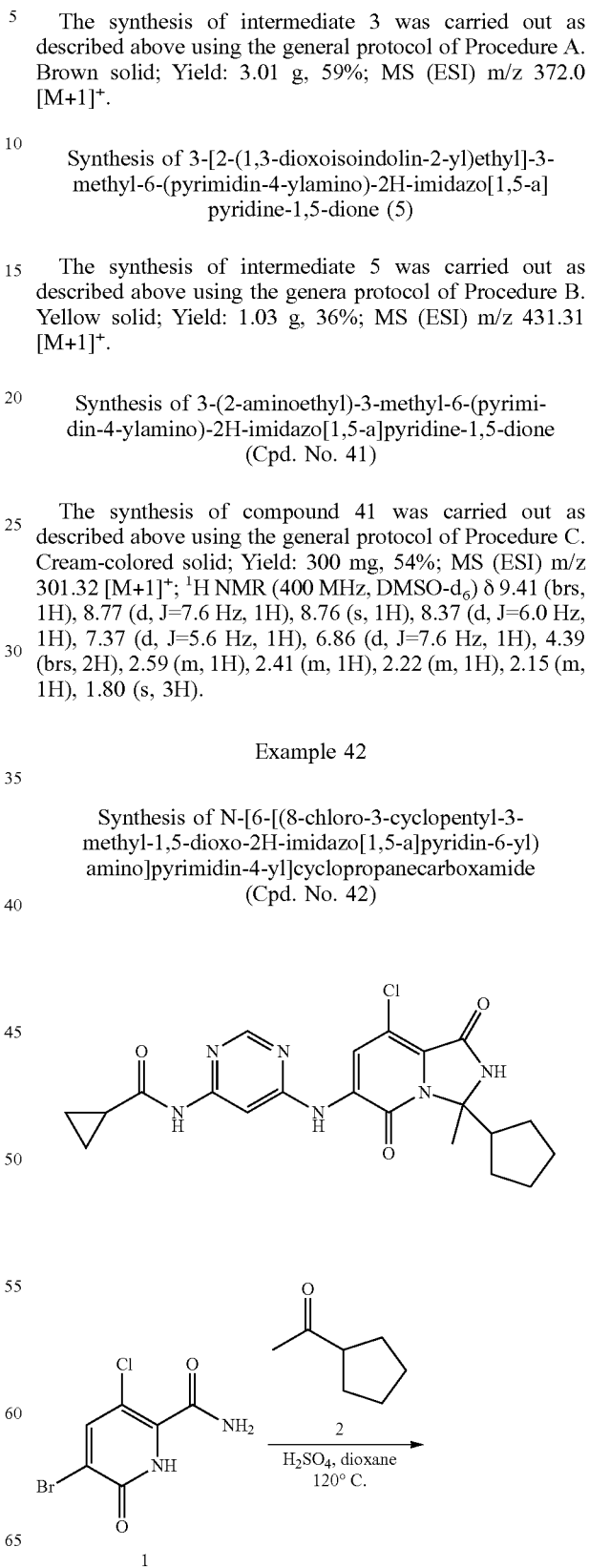

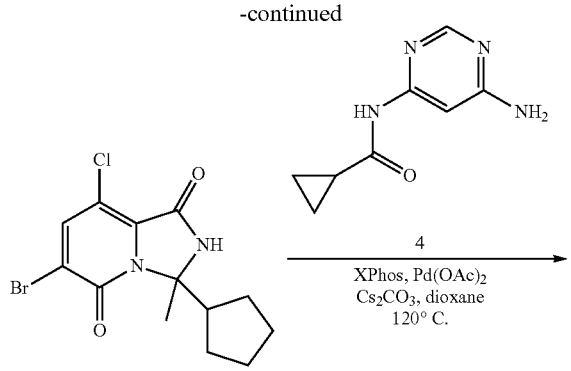

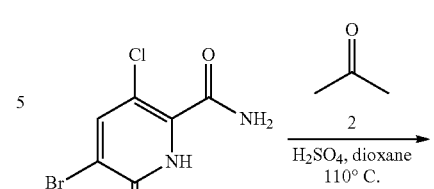

Synthesis of 6-bromo-8-chloro-3-cyclopentyl-3-methyl-2H-imidazo[1,5-a]pyridine-1,5-dione (3)

The synthesis of intermediate 3 was carried out as described above using the general protocol of Procedure A. Light brown solid; Yield: 605 mg, 54%; MS (ESI) m/z 346.98 [M+1]$^+$.

Synthesis of N-[6-[(8-chloro-3-cyclopentyl-3-methyl-1,5-dioxo-2H-imidazo[1,5-a]pyridin-6-yl)amino]pyrimidin-4-yl]cyclopropanecarboxamide (Cpd. No. 42)

The synthesis of compound 42 was carried out as described above using the general protocol of Procedure B. Off-white solid; Yield: 16 mg, 5%; MS (ESI) m/z 443.35 [M+1]$^+$; $^1$H NMR (400 MHz, DMSO-d$_6$) δ 10.93 (s, 1H), 9.78 (s, 1H), 9.46 (s, 1H), 8.70 (s, 1H), 8.59 (s, 1H), 7.97 (s, 1H), 3.39 (m, 1H), 2.01 (m, 1H), 1.82 (s, 3H), 1.77 (m, 1H), 1.57-1.37 (m, 5H), 1.14 (m, 1H), 0.83 (m, 5H).

Example 43

Synthesis of N-[6-[(8-chloro-3,3-dimethyl-1,5-dioxo-2H-imidazo[1,5-a]pyridin-6-yl)amino]pyrimidin-4-yl]cyclopropanecarboxamide (Cpd. No. 43)

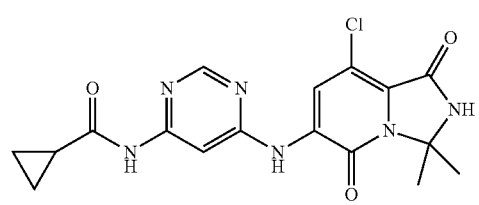 [SMILES: CC1(C)NC(=O)c2c(Cl)cc(Nc3cc(NC(=O)C4CC4)ncn3)c(=O)n21]

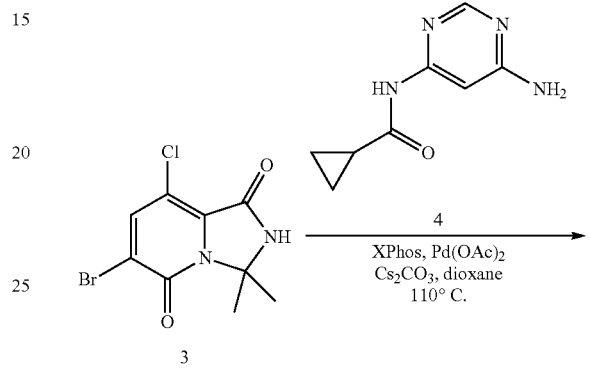

Synthesis of 6-bromo-8-chloro-3,3-dimethyl-2H-imidazo[1,5-a]pyridine-1,5-dione (3)

The synthesis of intermediate 3 was carried out as described above using the general protocol of Procedure A. White solid; Yield: 390 mg, 48%; MS (ESI) m/z 288.93 [M−1]$^-$; $^1$H NMR (400 MHz, DMSO-d$_6$) δ 10.03 (s, 1H), 8.24 (s, 1H), 1.75 (s, 6H).

Synthesis of N-[6-[(8-chloro-3,3-dimethyl-1,5-dioxo-2H-imidazo[1,5-a]pyridin-6-yl)-amino]pyrimidin-4-yl]cyclopropanecarboxamide (Cpd. No. 43)

The synthesis of compound 43 was carried out as described above using the general protocol of Procedure B. Light yellow solid; Yield: 42 mg, 17%; MS (ESI) m/z 389.28 [M+1]$^+$; $^1$H NMR (400 MHz, DMSO-d$_6$) δ 10.92 (s, 1H), 9.74 (s, 1H), 9.49 (s, 1H), 8.70 (s, 1H), 8.59 (s, 1H), 7.98 (s, 1H), 2.02 (m, 1H), 1.79 (s, 6H), 0.84 (d, J=6.0 Hz, 4H).

Example 44

Synthesis of N-(6-((8'-chloro-1',5'-dioxo-1',5'-dihydro-2'H-spiro[cyclobutane-1,3'-imidazo[1,5-a]pyridin]-6'-yl)amino)pyrimidin-4-yl)cyclopropanecarboxamide (Cpd. No. 44)

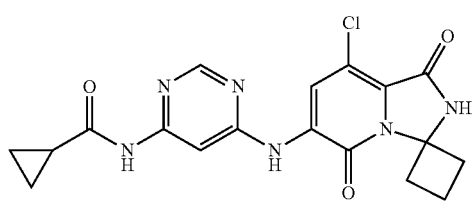 [SMILES: O=C1NC2(CCC2)n2c1c(Cl)cc(Nc1cc(NC(=O)C3CC3)ncn1)c2=O]

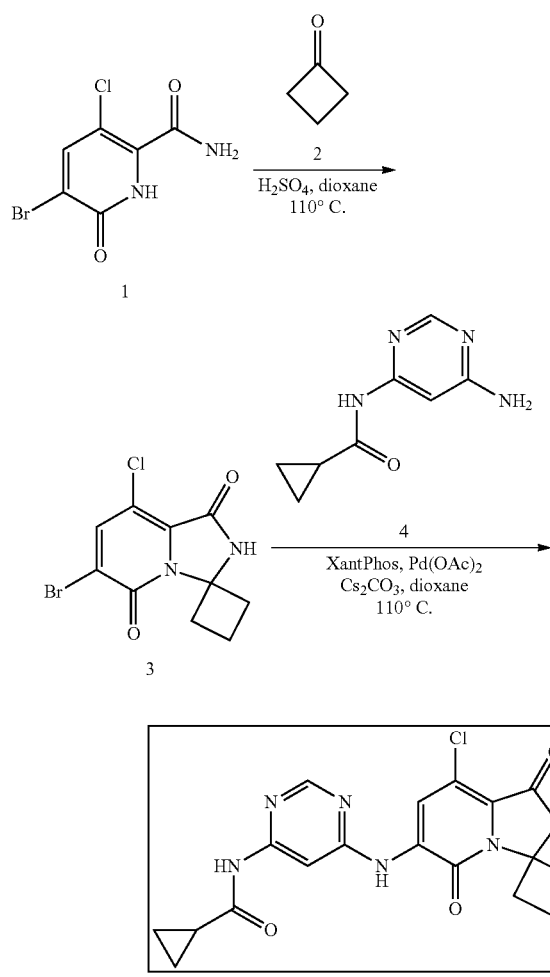

Synthesis of 6'-bromo-8'-chloro-2'H-spiro[cyclobutane-1,3'-imidazo[1,5-a]pyridine]-1',5'-dione (3)

The synthesis of intermediate 3 was carried out as described above using the general protocol of Procedure A. Brown solid; Yield: 0.260 g, 72%; MS (ESI) m/z 300.94 [M−1]⁻; 1H NMR (400 MHz, DMSO-d₆) δ 10.5 (s, 1H), 8.24 (s, 1H), 3.45 (m, 2H), 2.28 (m, 2H), 2.10 (m, 1H), 1.89 (m, 1H).

Synthesis of N-(6-((8'-chloro-1',5'-dioxo-1',5'-dihydro-2'H-spiro[cyclobutane-1, 3'-imidazo-[1,5-a]pyridin]-6'-yl)amino)pyrimidin-4-yl)cyclopropanecarboxamide (Cpd. No. 44)

The synthesis of compound 44 was carried out as described above using the general protocol of Procedure B. Light yellow solid; Yield: 0.110 g, 33%; MS (ESI) m/z 401.27 [M+1]⁺; ¹H NMR (400 MHz, DMSO-d₆) δ 10.94 (s, 1H), 10.24 (s, 1H), 9.59 (s, 1H), 8.71 (s, 1H), 8.59 (s, 1H), 8.00 (s, 1H), 3.26 (m, 2H), 2.34 (m, 2H), 2.15 (m, 1H), 2.04 (m, 1H), 1.89 (m, 1H), 0.82 (m, 4H).

Example 45

Synthesis of N-(6-((8'-chloro-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (Cpd. No. 45)

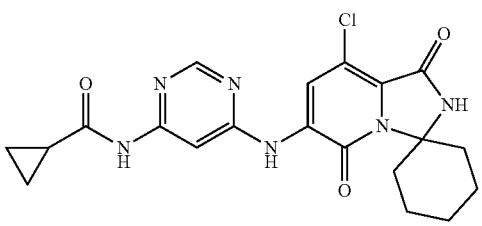 [SMILES: O=C1NC2(CCCCC2)n2c1c(Cl)cc(Nc1cc(NC(=O)C3CC3)ncn1)c2=O]

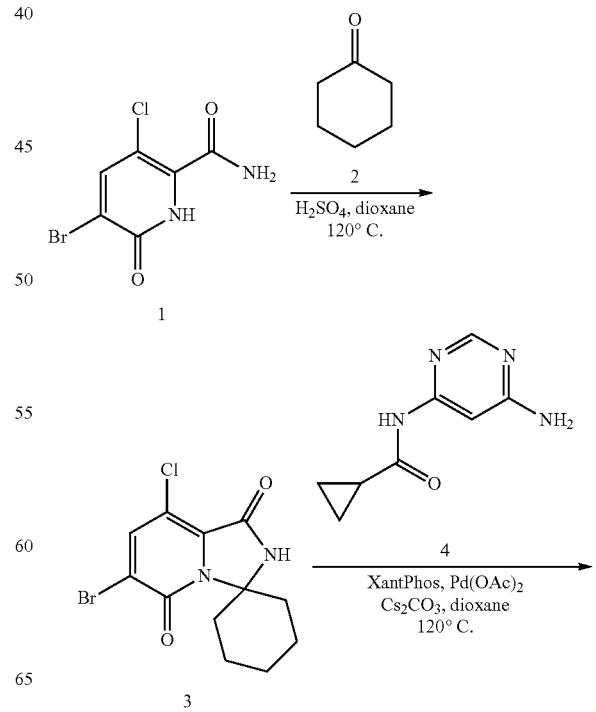

-continued

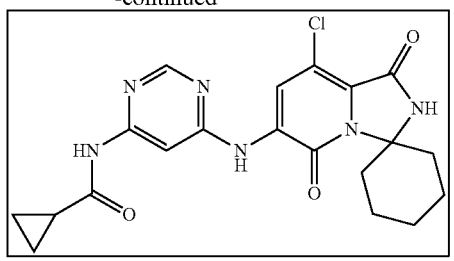

Synthesis of 6'-bromo-8'-chloro-2'H-spiro[cyclohexane-1,3'-imidazo[1,5-a]pyridine]-1',5'-dione (3)

The synthesis of intermediate 3 was carried out as described above using the general protocol of Procedure A. Off white solid; Yield: 1.93 g, 64%; MS (ESI) m/z 330.99 [M+1]; $^1$H NMR (400 MHz, DMSO-d$_6$) δ 10.59 (s, 1H), 8.24 (s, 1H), 2.84 (t, J=10.74, 2H), 1.74 (m, 2H), 1.63 (m, 3H), 1.53 (m, 2H), 1.20 (m, 1H).

Synthesis of N-(6-((8'-chloro-1',5'-dioxo-1',5'-dihydro-2'H-spiro[cyclohexane-1, 3'-imidazo[1,5-a]pyridin]-6'-yl)amino)pyrimidin-4-yl)cyclopropanecarboxamide (Cpd. No. 45)

The synthesis of compound 45 was carried out as described above using the general protocol of Procedure B. Yellow solid; Yield: 0.051 g, 2.07%; MS (ESI) m/z 429.34 [M+1]$^+$; $^1$H NMR (400 MHz, DMSO-d6) δ 10.93 (s, 1H), 10.29 (s, 1H), 9.43 (s, 1H), 8.70 (s, 1H), 8.58 (s, 1H), 7.97 (s, 1H), 2.93 (t, J=11.16 Hz, 2H), 2.02 (m, 1H), 1.75 (m, 2H), 1.64 (m, 3H), 1.54 (m, 2H), 1.21 (m, 1H), 0.84 (m, 4H).

Example 46

Synthesis of N-[6-[[8-chloro-3-methyl-1,5-dioxo-3-(2,2,2-trifluoroethyl)-2H-imidazo[1,5-a]pyridin-6-yl]amino]pyrimidin-4-yl]cyclopropanecarboxamide (Cpd. No. 46)

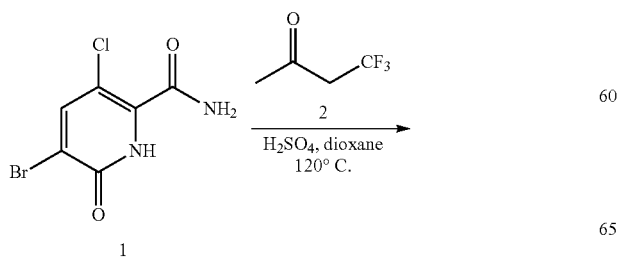

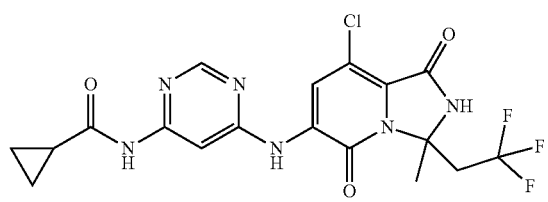 [SMILES: CC1(CC(F)(F)F)NC(=O)c2c(Cl)cc(Nc3cc(NC(=O)C4CC4)ncn3)c(=O)n21]

-continued

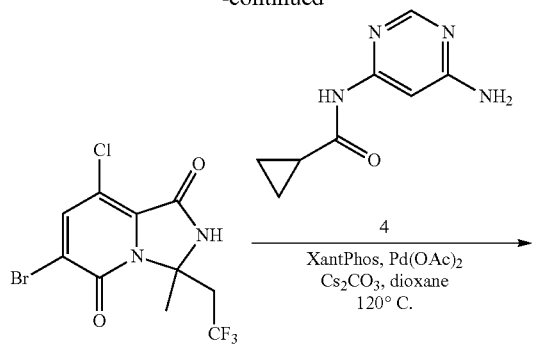

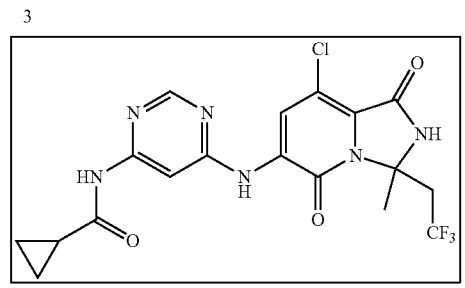

Synthesis of 6-bromo-8-chloro-3-methyl-3-(2,2,2-trifluoroethyl)-2H-imidazo[1,5-a]-pyridine-1,5-dione (3)

The synthesis of intermediate 3 was carried out as described above using the general protocol of Procedure A. Brown solid; Yield: 325 mg, 57%; MS (ESI) m/z 358.95 [M+1]$^+$.

Synthesis of N-[6-[[8-chloro-3-methyl-1,5-dioxo-3-(2,2,2-trifluoroethyl)-2H-imidazo[1,5-a]pyridin-6-yl]amino]pyrimidin-4-yl]cyclopropanecarboxamide (Cpd. No. 46)

The synthesis of compound 46 was carried out as described above using the general protocol of Procedure B. Light brown solid; Yield: 120 mg, 32%; MS (ESI) m/z 457.31 [M+1]$^+$; $^1$H NMR (400 MHz, DMSO-d$_6$) δ 10.95 (s, 1H), 9.92 (s, 1H), 9.59 (s, 1H), 8.75 (s, 1H), 8.60 (s, 1H), 8.01 (s, 1H), 3.69 (m, 1H), 3.12 (m, 1H), 2.02 (m, 1H), 1.87 (s, 3H), 0.84 (d, J=6.0 Hz, 4H).

Example 47

Synthesis of 8-chloro-3,3-dimethyl-6-(pyrimidin-4-ylamino)-2,3-dihydroimidazo[1,5-a]pyridine-1,5-dione (Cpd. No. 47)

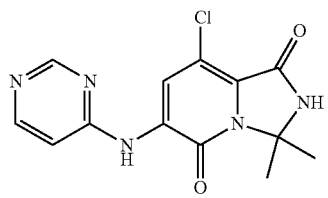 [SMILES: CC1(C)NC(=O)c2c(Cl)cc(Nc3ccncn3)c(=O)n21]

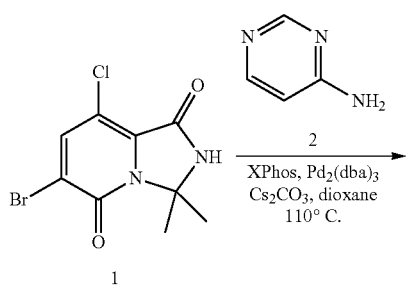

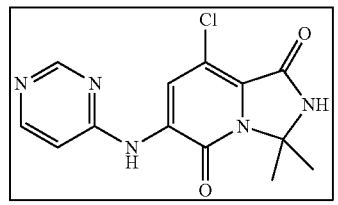

Synthesis of 8-chloro-3,3-dimethyl-6-(pyrimidin-4-ylamino)-2,3-dihydroimidazo[1,5-a]pyridine-1,5-dione (Cpd. No. 47)

The synthesis of compound 47 was carried out as described above using the general protocol of Procedure B. Off white solid; Yield: 0.020 g, 10%; MS (ESI) m/z 306.25 [M+1]$^+$; $^1$H NMR (400 MHz, DMSO-d$_6$) δ 9.78 (s, 1H), 9.64 (s, 1H), 8.84 (s, 1H), 8.79 (s, 1H), 8.43 (d, J=5.6 Hz, 1H), 7.44 (d, J=5.2 Hz, 1H), 1.81 (s, 6H).

Example 48

Synthesis of 8-chloro-3-cyclopentyl-3-methyl-6-(pyrimidin-4-ylamino)-2H-imidazo[1,5-a]pyridine-1,5-dione (Cpd. No. 48)

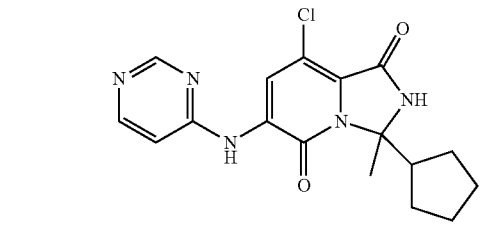 [SMILES: CC1(C2CCCC2)NC(=O)c2c(Cl)cc(Nc3ccncn3)c(=O)n21]

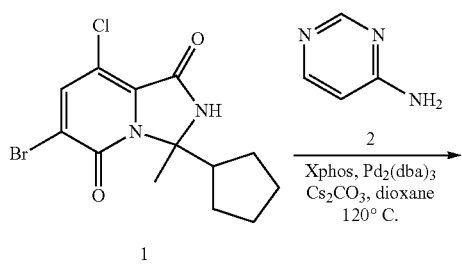

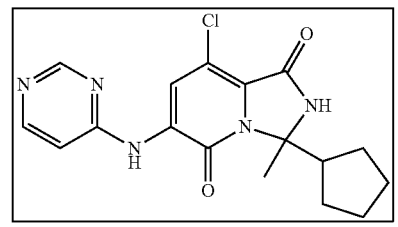

Synthesis of 8-chloro-3-cyclopentyl-3-methyl-6-(pyrimidin-4-ylamino)-2H-imidazo[1,5-a]pyridine-1,5-dione (Cpd. No. 48)

The synthesis of compound 48 was carried out as described above using the general protocol of Procedure B. Light yellow solid; Yield: 0.019 g, 6%; MS (ESI) m/z 360.23 [M+1]$^+$; $^1$H NMR (400 MHz, DMSO-d$_6$) δ 9.83 (s, 1H), 9.63 (s, 1H), 8.84 (s, 1H), 8.79 (s, 1H), 8.44 (d, J=5.7 Hz, 1H), 7.43 (d, J=5.6 Hz, 1H), 3.38 (m, 1H), 1.84 (s, 3H), 1.79 (m, 1H), 1.51 (m, 5H), 1.13 (m, 1H), 0.83 (m, 1H).

Example 49

Synthesis of N-(6-((8-chloro-3-methyl-1,5-dioxo-3-(trifluoromethyl)-1,2,3,5-tetrahydroimidazo[1,5-a]pyridin-6-yl)amino)pyrimidin-4-yl)cyclopropanecarboxamide (Cpd. No. 49)

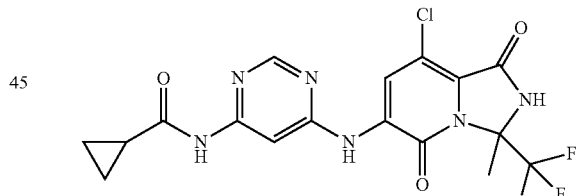

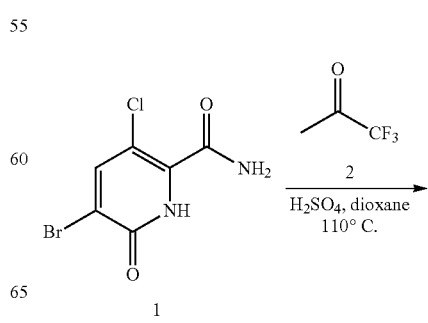

-continued

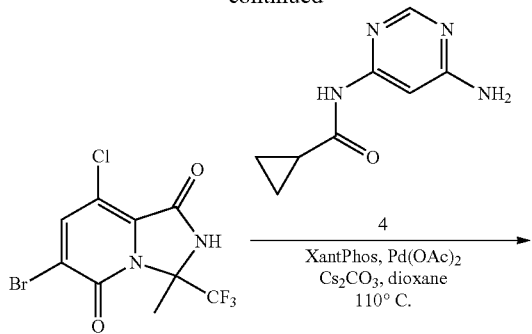

Synthesis of 6-bromo-8-chloro-3-methyl-3-(trifluoromethyl)-2,3-dihydroimidazo[1,5-a]pyridine-1,5-dione (3)

The synthesis of intermediate 3 was carried out as described above using the general protocol of Procedure A. Light brown solid; Yield: 0.7 g, crude; MS (ESI) m/z 342.97 [M−1]⁻

Synthesis of N-(6-((8-chloro-3-methyl-1,5-dioxo-3-(trifluoromethyl)-1,2,3,5-tetrahydroimidazo[1,5-a]pyridin-6-yl)amino-4-yl)cyclopropanecarboxamide (Cpd. No. 49)

The synthesis of compound 49 was carried out as described above using the general protocol of Procedure B. Light yellow solid. Yield: 0.16 g, 42%; MS (ESI) m/z 443.27 [M+1]⁺; $^1$H NMR (400 MHz, DMSO-d$_6$) δ 10.95 (s, 1H), 10.55 (bs, 1H), 9.72 (s, 1H), 8.74 (s, 1H), 8.61 (s, 1H), 8.04 (s, 1H), 2.11 (s, 3H), 2.03 (m, 1H), 0.84 (d, J=6.0 Hz, 4H).

Example 50

Synthesis of N-[6-[(8-chloro-4',4'-difluoro-1,5-dioxo-spiro[2H-imidazo[1,5-a]pyridine-3,1'-cyclohexane]-6-yl)amino]pyrimidin-4-yl]cyclopropanecarboxamide (Cpd. No. 50)

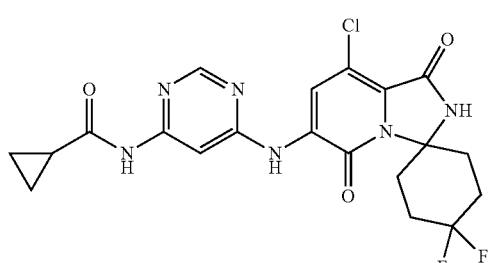

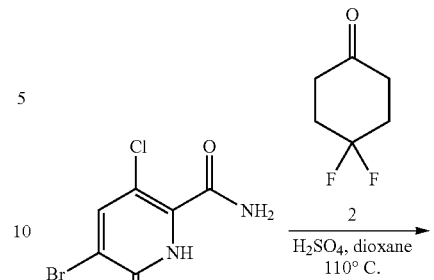

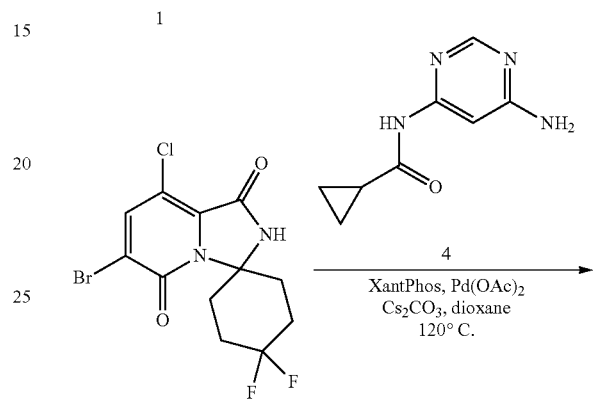

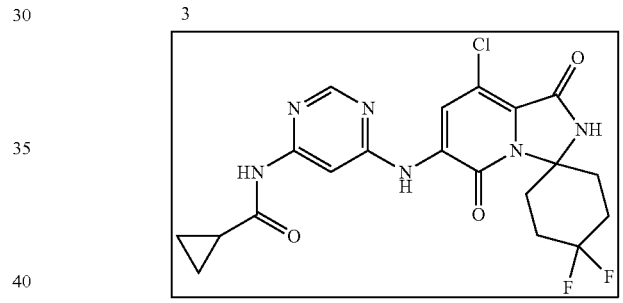

Synthesis of 6-bromo-8-chloro-4',4'-difluoro-spiro[2H-imidazo[1,5-a]pyridine-3,1'-cyclohexane]-1,5-dione (3)

The synthesis of intermediate 3 was carried out as described above using the general protocol of Procedure A. Off-white solid; Yield: 0.41 g, 93%; MS (ESI) m/z 366.94 [M+1]⁺; $^1$H NMR (400 MHz, DMSO-d$_6$) δ 9.79 (s, 1H), 7.89 (s, 1H), 2.12 (m, 6H), 1.66 (m, 2H).

Synthesis of N-[6-[(8-chloro-4',4'-difluoro-1,5-dioxo-spiro[2H-imidazo[1,5-a]pyridine-3,1'-cyclohexane]-6-yl)amino]pyrimidin-4-yl]cyclopropanecarboxamide (Cpd. No. 50)

The synthesis of compound 50 was carried out as described above using the general protocol of Procedure B. Light yellow solid; Yield: 0.098 g, 39%; MS (ESI) m/z 465.16 [M+1]⁺; $^1$H NMR (400 MHz, DMSO-d$_6$) δ 10.92 (s, 1H), 10.47 (s, 1H), 9.52 (s, 1H), 8.72 (s, 1H), 8.59 (s, 1H), 7.98 (s, 1H), 3.30-3.20 (m, 2H), 2.35-2.15 (m, 4H), 2.05-1.98 (m, 1H), 1.75-1.67 (m, 2H), 0.97-0.80 (m, 4H).

Example 51

Synthesis of N-[6-[[8-chloro-3-(3-chlorophenyl)-3-methyl-1,5-dioxo-2H-imidazo[1,5-a]pyridin-6-yl]amino]pyrimidin-4-yl]cyclopropanecarboxamide (Cpd. No. 51)

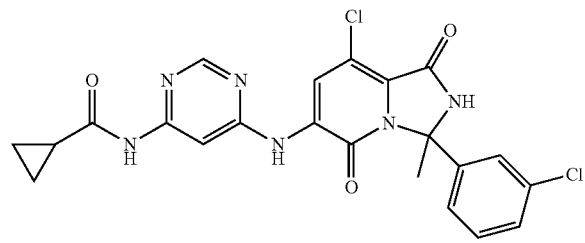 [SMILES: CC1(c2cccc(Cl)c2)NC(=O)c2c(Cl)cc(Nc3cc(NC(=O)C4CC4)ncn3)c(=O)n21]

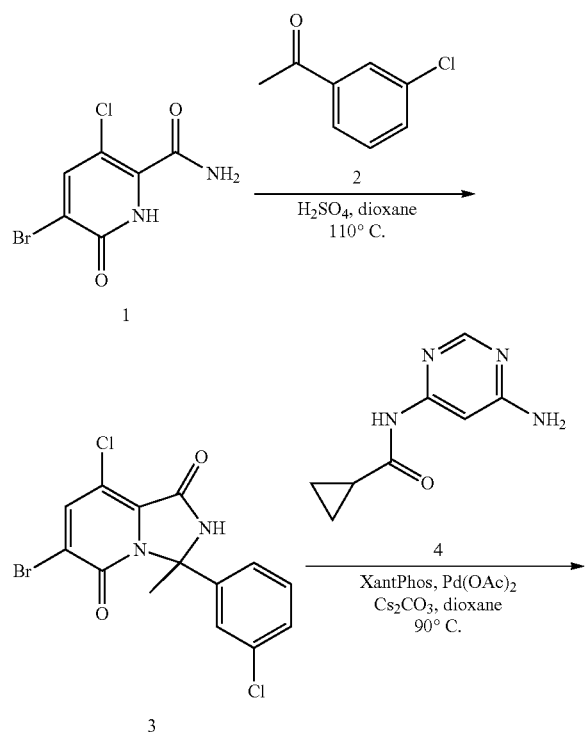

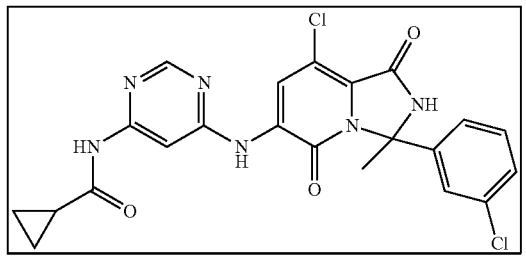

Synthesis of 6-bromo-8-chloro-3-(3-chlorophenyl)-3-methyl-2H-imidazo[1,5-a]pyridine-1,5-dione (3)

The synthesis of intermediate 3 was carried out as described above using the general protocol of Procedure A. White solid; Yield: 0.13 g, 17%; MS (ESI) m/z 386.83 [M+1]$^+$; 1H NMR (400 MHz, DMSO-d$_6$) δ 10.38 (s, 1H), 8.32 (s, 1H), 7.52 (s, 1H), 7.43 (m, 2H), 7.34 (d, J=7.6 Hz, 1H), 2.18 (s, 3H).

Synthesis of N-[6-[[8-chloro-3-(3-chlorophenyl)-3-methyl-1,5-dioxo-2H-imidazo[1,5-a]pyridin-6-yl]amino]pyrimidin-4-yl]cyclopropanecarboxamide (Cpd. No. 51)

The synthesis of compound 51 was carried out as described above using the general protocol of Procedure B. Light yellow solid; Yield: 0.04 g, 25%; MS (ESI) m/z 485.30 [M+1]$^+$; $^1$H NMR (400 MHz, DMSO-d$_6$) δ 10.90 (s, 1H), 10.09 (s, 1H), 9.44 (s, 1H), 8.75 (s, 1H), 8.59 (s, 1H), 7.90 (s, 1H), 7.52 (s, 1H), 7.43 (m, 2H), 7.34 (d, J=7.2 Hz, 1H), 2.23 (s, 3H), 2.00 (m, 1H), 0.82 (m, 4H).

Example 52

Synthesis of N-[6-[[8-chloro-3-(3-fluorophenyl)-3-methyl-1,5-dioxo-2H-imidazo[1,5-a]pyridin-6-yl]amino]pyrimidin-4-yl]cyclopropanecarboxamide (Cpd. No. 52)

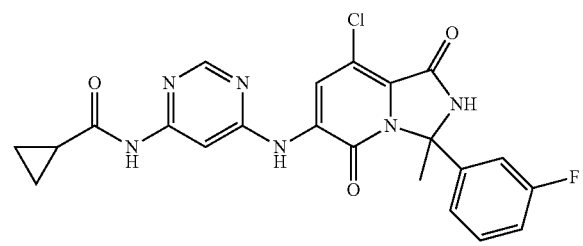 [SMILES: CC1(c2cccc(F)c2)NC(=O)c2c(Cl)cc(Nc3cc(NC(=O)C4CC4)ncn3)c(=O)n21]

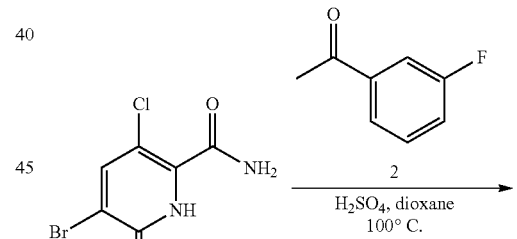

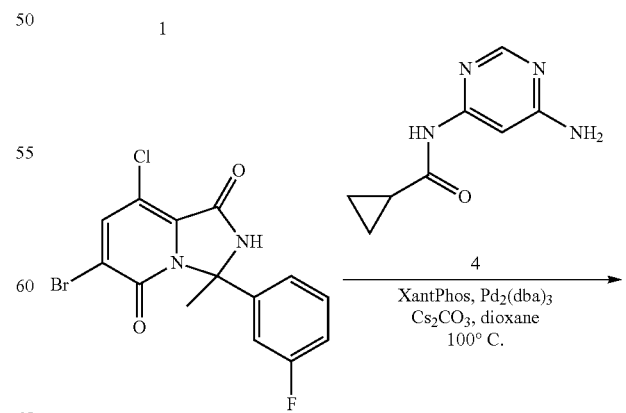

-continued

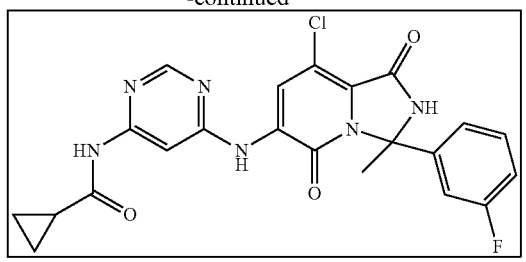

Synthesis of 6-bromo-8-chloro-3-(3-fluorophenyl)-3-methyl-2H-imidazo[1,5-a]pyridine-1,5-dione (3)

The synthesis of intermediate 3 was carried out as described above using the general protocol of Procedure A. White solid; Yield: 0.18 g, 20%; MS (ESI) m/z 373.01 [M+1]+; $^1$H NMR (400 MHz, DMSO-$d_6$) δ 10.38 (s, 1H), 8.31 (s, 1H), 7.43 (m, 1H), 7.31 (d, J=10.3 Hz, 1H), 7.22 (m, 2H), 2.19 (s, 3H).

Synthesis of N-[6-[[8-chloro-3-(3-fluorophenyl)-3-methyl-1,5-dioxo-2H-imidazo[1,5-a]pyridin-6-yl]amino]pyrimidin-4-yl]cyclopropanecarboxamide (Cpd. No. 52)

The synthesis of compound 52 was carried out as described above using the general protocol of Procedure B. White solid; Yield: 0.035 g, 15%; MS (ESI) m/z 469.34 [M+1]+; $^1$H NMR (400 MHz, DMSO-$d_6$) δ 10.91 (s, 1H), 10.10 (s, 1H), 9.44 (s, 1H), 8.75 (s, 1H), 8.59 (s, 1H), 7.90 (s, 1H), 7.42 (m, 1H), 7.32 (m, 1H), 7.23 (m, 2H), 2.23 (s, 3H), 2.00 (m, 1H), 0.823 (m, 4H).

Example 53

Synthesis of (3'S)-3'-amino-6-(pyrimidin-4-ylamino)spiro[2H-imidazo[1,5-a]pyridine-3,1'-cyclohexane]-1,5-dione (Cpd. No. 53)

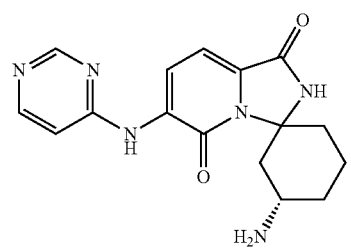 [SMILES: N[C@H]1CCCC2(C1)NC(=O)c1ccc(Nc3ccncn3)c(=O)n12]

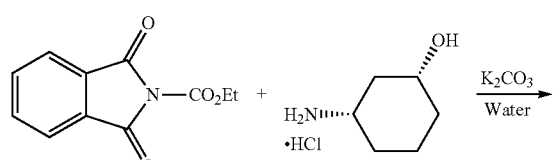

-continued

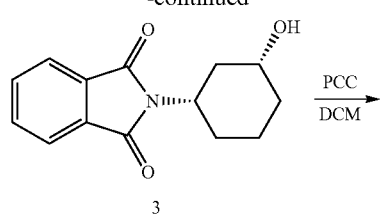

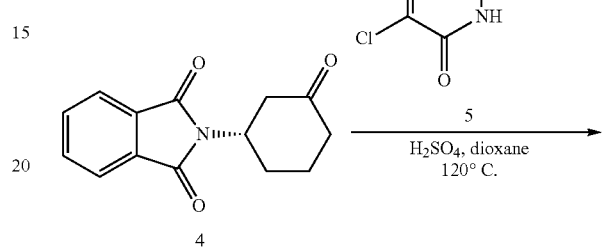

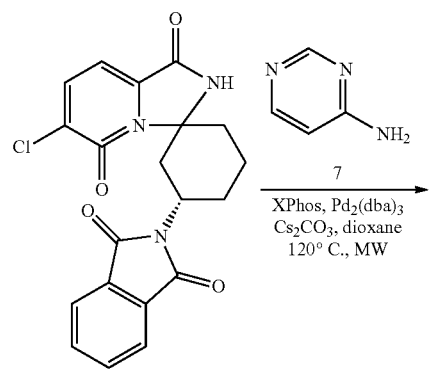

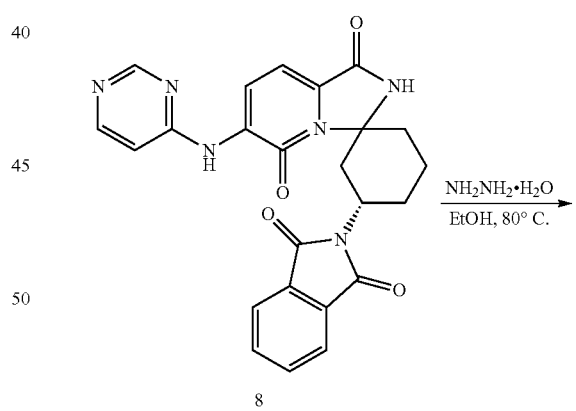

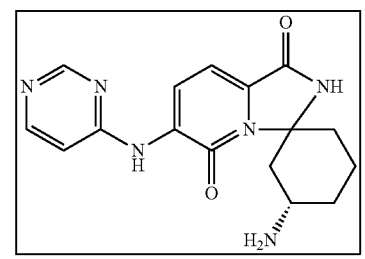

Synthesis of 2-[(1S,3R)-3-hydroxycyclohexyl]isoindoline-1,3-dione (3)

To a solution of (1R, 3S)-3-aminocyclohexanol hydrochloride (2, 1.0 g, 6.57 mmol) in water (50 mL) at 0° C., ethyl 1,3-dioxoisoindoline-2-carboxylate (1, 1.6 g, 7.3 mmol) was added. The mixture was allowed to stir at 25° C. for 3 hours while monitoring by TLC. After completion, the suspension was filtered and the residue was washed with water (50 mL) and dried to obtain 2-[(3R)-3-hydroxycyclohexyl]isoindoline-1,3-dione (3) as a white solid. Yield: 1.45 g, 81%; $^1$H NMR (400 MHz, DMSO-$d_6$) δ 7.83 (m, 4H), 4.77 (m, 1H), 3.99 (m, 1H), 2.04-1.29 (m, 9H).

Synthesis of (S)-2-(3-oxocyclohexyl)isoindoline-1,3-dione (4)

To a stirred solution of 2-[(3R)-3-hydroxycyclohexyl]isoindoline-1,3-dione (3, 1.4 g, 5.71 mmol) in dichloromethane (50 mL) at 0° C., was added pyridinium chlorochromate (3.69 g, 17.12 mmol). The mixture was allowed to stir at 25° C. for 5 hours while monitoring by TLC. The reaction mixture was made basic (pH 8) with saturated aqueous sodium bicarbonate solution and extracted with dichloromethane (2×150 mL). The combined organic layers were dried over sodium sulfate and concentrated under reduced pressure to obtain 2-(3-oxocyclohexyl)isoindoline-1,3-dione (4) as a brown solid. Yield: 1.31 g, 94%; MS (ESI) m/z 244.15 [M+1]$^+$.

Synthesis of (3'S)-6-chloro-3'-(1,3-dioxoisoindolin-2-yl)spiro[2H-imidazo[1,5-a]pyridine-3,1'-cyclohexane]-1,5-dione (6)

The synthesis of intermediate 6 was carried out as described above using the general protocol of Procedure A. Cream colored solid; Yield: 1.51 g, 71%; MS (ESI) m/z 398.19 [M+1]$^+$.

Synthesis of (3'S)-3'-(1,3-dioxoisoindolin-2-yl)-6-(pyrimidin-4-ylamino)spiro[2H-imidazo[1,5-a]pyridine-3,1'-cyclohexane]-1,5-dione (8)

The synthesis of intermediate 8 was carried out as described above using the general protocol of Procedure B. Yellow solid; Yield: 104 mg, 45%; MS (ESI) m/z 457.0 [M+1]$^+$; $^1$H NMR (400 MHz, DMSO-$d_6$) δ 10.54 (s, 1H), 9.47 (s, 1H), 8.76 (s, 2H), 8.37 (s, 1H), 7.84 (m, 4H), 7.38 (s, 1H), 6.91 (m, 1H), 4.60 (m, 1H), 3.96 (m, 1H), 3.32 (m, 1H), 3.06 (m, 1H), 2.32 (m, 1H), 1.99-1.56 (m, 5H).

Synthesis of (3'S)-3'-amino-6-(pyrimidin-4-ylamino)spiro[2H-imidazo[1,5-a]pyridine-3,1'-cyclohexane]-1,5-dione (Cpd. No. 53)

The synthesis of compound 53 was carried out as described above using the general protocol of Procedure C. Pale greenish solid; Yield: 60.0 mg, 21%; MS (ESI) m/z 327.35 [M+1]$^+$; $^1$H NMR (400 MHz, DMSO-$d_6$): δ 9.37 (s, 1H), 8.78 (d, J=7.6 Hz, 1H), 8.76 (s, 1H), 8.37 (d, J=6.0 Hz, 1H), 7.37 (d, J=5.6 Hz, 1H), 6.89 (d, J=7.6 Hz, 1H), 2.89 (m, 2H), 2.72 (m, 1H), 1.82 (m, 2H), 1.65 (m, 2H), 1.46 (m, 1H), 1.05 (m, 1H).

Example 54

Synthesis of 8-chloro-6-(pyrimidin-4-ylamino)spiro[2H-imidazo[1,5-a]pyridine-3,3'-piperidine]-1,5-dione hydrochloride (Cpd. No. 54)

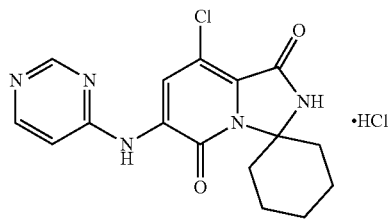 [SMILES: O=C1NC2(CCCCC2)n2c1c(Cl)cc(Nc1ccncn1)c2=O ; Cl]

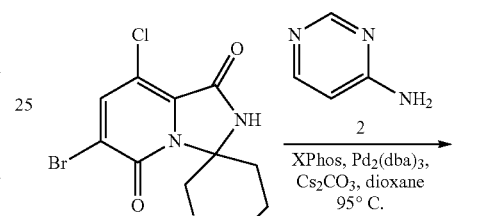

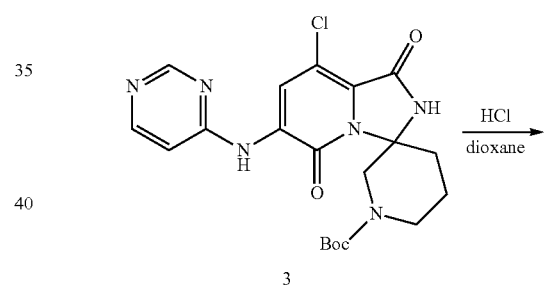

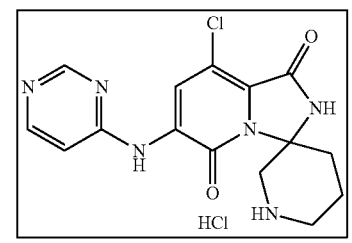

Synthesis of tert-butyl 8-chloro-1,5-dioxo-6-(pyrimidin-4-ylamino)spiro[2H-imidazo[1,5-a]pyridine-3,3'-piperidine]-1'-carboxylate (3)

The synthesis of intermediate 3 was carried out as described above using the general protocol of Procedure B. Light yellow solid; Yield: 0.08 g, 50%; MS (ESI) m/z 447.17 [M+1]$^+$; $^1$H NMR (400 MHz, DMSO-$d_6$) δ 10.51 (s, 1H), 9.63 (s, 1H), 8.85 (s, 1H), 8.79 (s, 1H), 8.44 (d, J=5.8 Hz, 1H), 7.45 (d, J=5.6 Hz, 1H), 4.14 (m, 2H), 3.89 (m, 1H), 3.05 (m, 1H), 2.90 (m, 1H), 1.93 (m, 3H), 1.41 (s, 9H).

115

Synthesis of 8-chloro-6-(pyrimidin-4-ylamino)spiro[2H-imidazo[1,5-a]pyridine-3,3'-piperidine]-1,5-dione hydrochloride (Cpd. No. 54)

The synthesis of compound 54 was carried out as described above using the general protocol of Procedure D. Light brown solid; Yield: 0.024 g, 35%; MS (ESI) m/z 347.31 [M+1]$^+$; $^1$H NMR (400 MHz, DMSO-d$_6$) δ 10.23 (s, 1H), 9.99 (s, 1H), 9.72 (bs, 1H), 9.48 (bs, 1H), 8.99 (bs, 1H), 8.78 (s, 1H), 8.53 (bs, 1H), 7.54 (bs, 1H), 4.15 (m, 1H), 3.52 (m, 1H), 3.38 (m, 1H), 3.03 (m, 1H), 2.92 (m, 1H), 2.17 (m, 1H), 2.04 (m, 1H), 1.84 (m, 1H).

Example 55

Synthesis of 8-chloro-3-methyl-6-(pyrimidin-4-ylamino)-3-(2,2,2-trifluoroethyl)-2H-imidazo[1,5-a]pyridine-1,5-dione (Cpd. No. 55)

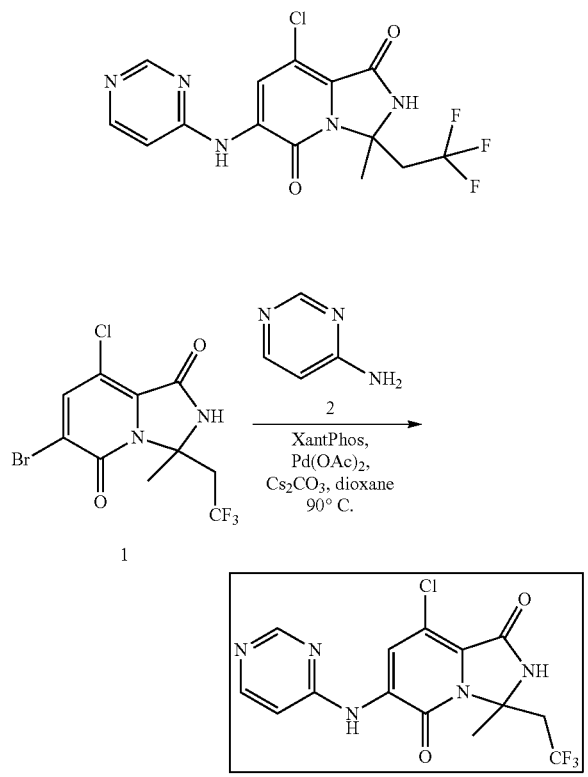

Synthesis of 8-chloro-3-methyl-6-(pyrimidin-4-ylamino)-3-(2, 2, 2-trifluoroethyl)-2H-imidazo[1,5-a]pyridine-1,5-dione (Cpd. No. 55)

The synthesis of compound 55 was carried out as described above using the general protocol of Procedure B. Light yellow solid; Yield: 0.1 g, 30%; MS (ESI) m/z 374.25 [M+1]$^+$; $^1$H NMR (400 MHz, DMSO-d$_6$) δ 9.95 (s, 1H), 9.70 (s, 1H), 8.86 (s, 1H), 8.83 (s, 1H), 8.45 (d, J=5.6 Hz, 1H), 7.45 (d, J=5.6 Hz, 1H), 3.73 (m, 1H), 3.14 (m, 1H), 1.89 (s, 3H).

116

Example 56

Synthesis of N-(6-((8-chloro-1,5-dioxo-1,5-dihydro-2H-spiro[imidazo[1,5-a]pyridine-3,4'-piperidin]-6-yl)amino)pyrimidin-4-yl)cyclopropanecarboxamide hydrochloride (Cpd. No. 56)

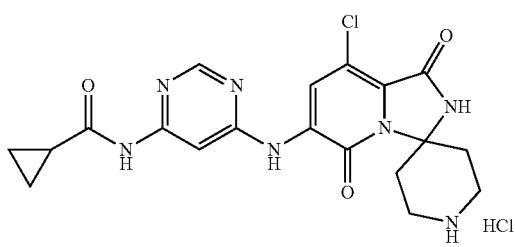 [SMILES: O=C1NC2(CCNCC2)n2c1c(Cl)cc(Nc1cc(NC(=O)C3CC3)ncn1)c2=O ; Cl]

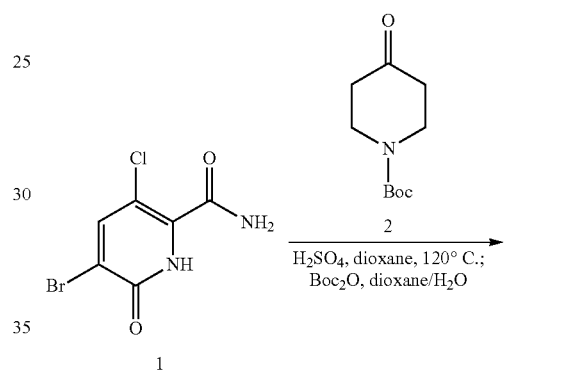

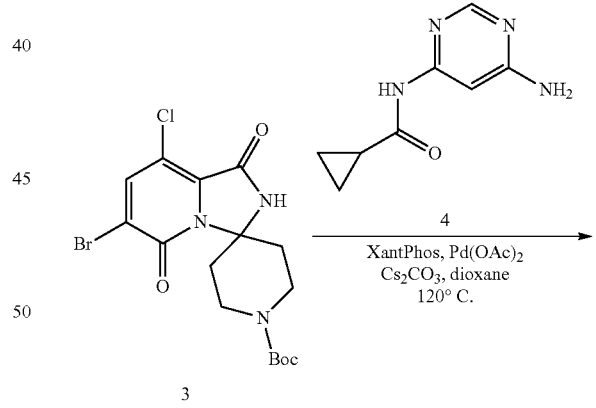

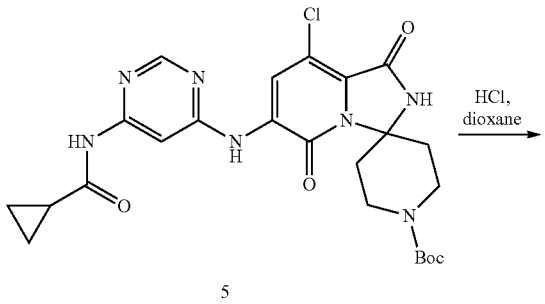

-continued

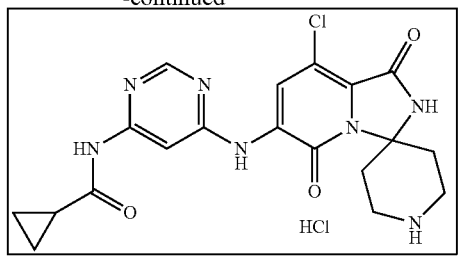

Synthesis of tert-butyl 6-bromo-8-chloro-1,5-dioxo-1,5-dihydro-2H-spiro[imidazo[1,5-a]pyridine-3,4'-piperidine]-1'-carboxylate (3)

Procedure E: To a stirred solution of 5-bromo-3-chloro-6-oxo-1H-pyridine-2-carboxamide (1, 0.4 g, 1.59 mmol) in 1,4-dioxane (12 mL) was added tert-butyl 4-oxopiperidine-1-carboxylate (2, 1.58 g, 7.95 mmol) in a vial at room temperature. Concentrated sulfuric acid (0.16 g, 1.59 mmol) was then added dropwise. The vial was sealed and heated to 120° C. for 3 h. The reaction mixture was quenched with water (20 mL) and extracted with ethyl acetate (2×15 mL). The organic layers were separated and the aqueous layer was diluted with 1,4-dioxane (30 mL), water (25 mL) and treated with di-tert-butyl dicarbonate (0.44 g, 2.03 mmol) dropwise at 0° C. The reaction mixture was stirred at room temperature overnight. After consumption of starting material the reaction was extracted with 10% methanol in dichloromethane (2×25 mL). The organic layers were dried with magnesium sulfate, filtered and concentrated to dryness. The crude residue was then purified by flash column chromatography using neutral alumina eluting with 2% methanol in dichloromethane. The desired fractions were concentrated to dryness in vacuo to afford tert-butyl 6-bromo-8-chloro-1,5-dioxo-1,5-dihydro-2H-spiro [imidazo[1,5-a]pyridine-3,4'-piperidine]-1'-carboxylate (3) as a yellow solid. Yield: 0.26 g, 44%; MS (ESI) m/z 430.11 [M−1]−; 1H NMR (400 MHz, DMSO-d6) δ 10.77 (s, 1H), 8.27 (m, 1H), 4.04 (s, 2H), 2.92 (m, 4H), 1.57 (m, 2H), 1.42 (s, 9H).

Synthesis of tert-butyl 8-chloro-6-((6-(cyclopropanecarboxamido)pyrimidin-4-yl)amino)-1,5-dioxo-1,5-dihydro-2H-spiro[imidazo[1,5-a]pyridine-3,4'-piperidine]-1'-carboxylate (5)

The synthesis of intermediate 5 was carried out as described above using the general protocol of Procedure B. Yellow solid; Yield: 0.14 g, 44%; MS (ESI) m/z 530.36 [M+1]+; 1H NMR (400 MHz, DMSO-d6) δ 10.93 (s, 1H), 10.49 (s, 1H), 9.51 (s, 1H), 8.72 (s, 1H), 8.59 (s, 1H), 8.00 (s, 1H), 4.05 (m, 2H), 3.20 (m, 1H), 3.09 (m, 3H), 2.02 (m, 1H), 1.58 (m, 2H), 1.43 (s, 9H), 0.84 (m, 4H).

Synthesis of N-(6-((8-chloro-1,5-dioxo-1,5-dihydro-2H-spiro[imidazo[1,5-a]pyridine-3,4'-piperidin]-6-yl)amino)pyrimidin-4-yl)cyclopropanecarboxamide hydrochloride (Cpd. No. 56)

The synthesis of compound 56 was carried out as described above using the general protocol of Procedure D.

Yellow solid; Yield: 0.10 g, 87%; MS (ESI) m/z 430.38 [M+1]+; 1H NMR (400 MHz, DMSO-d6) δ 10.98 (s, 1H), 10.54 (s, 1H), 9.43 (s, 1H), 9.33 (d, J=9.6 Hz, 1H), 8.77 (d, J=11.6 Hz, 1H), 8.73 (s, 1H), 8.60 (s, 1H), 8.00 (s, 1H), 3.48 (s, 2H), 3.32 (m, 2H), 3.18 (m, 2H), 2.02 (m, 1H), 1.86 (d, J=12.4 Hz, 2H), 0.84 (m, 4H).

Example 57

Synthesis of 8-chloro-3-(3-fluorophenyl)-3-methyl-6-(pyrimidin-4-ylamino)-2H-imidazo[1,5-a]pyridine-1,5-dione (Cpd. No. 57)

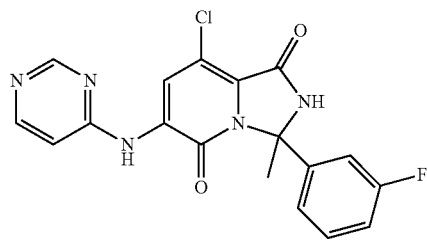 [SMILES: CC1(c2cccc(F)c2)NC(=O)c2c(Cl)cc(Nc3ccncn3)c(=O)n21]

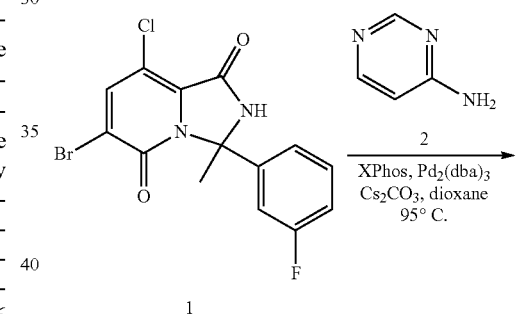

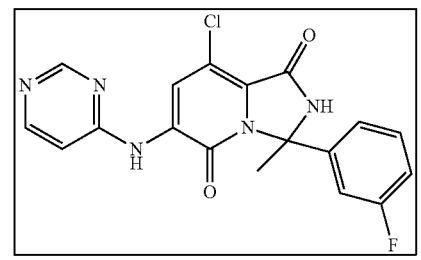

Synthesis of 8-chloro-3-(3-fluorophenyl)-3-methyl-6-(pyrimidin-4-ylamino)-2H-imidazo[1,5-a]pyridine-1,5-dione (Cpd. No. 57)

The synthesis of compound 57 was carried out as described above using the general protocol of Procedure B. White solid; Yield: 0.025 g, 10%; MS (ESI) m/z 386.31 [M+1]+; 1H NMR (400 MHz, DMSO-d6) δ 10.14 (s, 1H), 9.56 (s, 1H), 8.84 (s, 1H), 8.82 (s, 1H), 8.41 (d, J=5.9 Hz, 1H), 7.42 (m, 1H), 7.33 (m, 2H), 7.22 (m, 2H), 2.24 (s, 3H).

Example 58

Synthesis of 8-chloro-3-(3-chlorophenyl)-3-methyl-6-(pyrimidin-4-ylamino)-2H-imidazo[1,5-a]pyridine-1,5-dione (Cpd. No. 58)

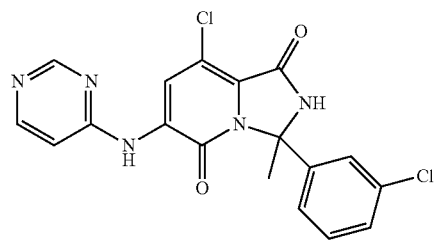 [SMILES: CC1(c2cccc(Cl)c2)NC(=O)c2c(Cl)cc(Nc3ccncn3)c(=O)n21]

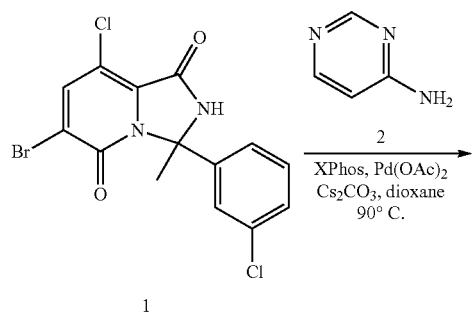

Synthesis of 8-chloro-3-(3-chlorophenyl)-3-methyl-6-(pyrimidin-4-ylamino)-2H-imidazo[1,5-a]pyridine-1,5-dione (Cpd. No. 58)

The synthesis of compound 58 was carried out as described above using the general protocol of Procedure B. Light yellow solid; Yield: 0.07 g, 32%; MS (ESI) m/z 402.25 [M+1]$^+$; $^1$H NMR (400 MHz, DMSO-d$_6$) δ 10.14 (s, 1H), 9.57 (s, 1H), 8.84 (s, 1H), 8.82 (s, 1H), 8.41 (d, J=5.9 Hz, 1H), 7.54 (s, 1H), 7.43 (m, 2H), 7.35 (m, 2H), 2.24 (s, 3H).

Example 59

Synthesis of 6-((6-((1-cyclopropyl-2,2,2-trifluoroethyl)amino)pyrimidin-4-yl)amino)-3-methyl-3-(trifluoromethyl)-2,3-dihydroimidazo[1,5-a]pyridine-1,5-dione (Cpd. No. 59)

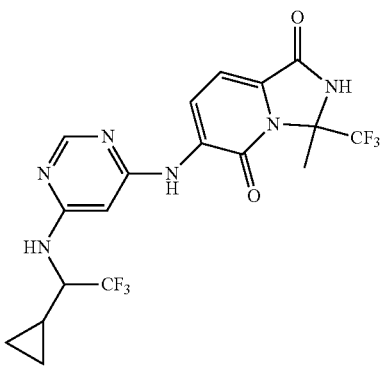 [SMILES: CC1(C(F)(F)F)NC(=O)c2ccc(Nc3cc(NC(C4CC4)C(F)(F)F)ncn3)c(=O)n21]

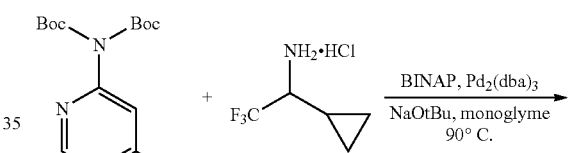

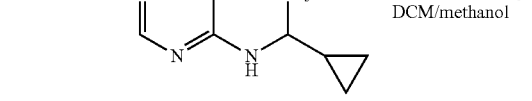

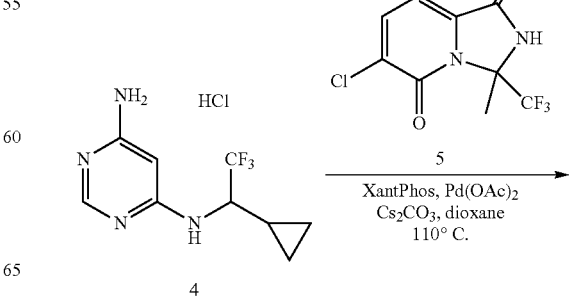

-continued

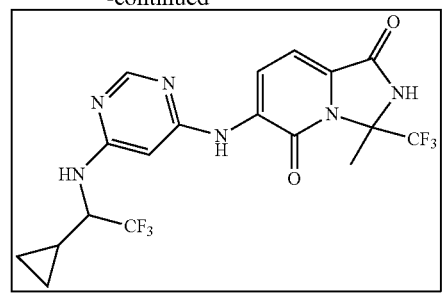

Synthesis of tert-butyl N-tert-butoxycarbonyl-N-[6-[(1-cyclopropyl-2,2,2-trifluoro-ethyl)amino]pyrimidin-4-yl]carbamate (3)

To a solution of tert-butyl N-tert-butoxycarbonyl-N-(6-chloropyrimidin-4-yl)carbamate (1, 0.50 g, 1.52 mmol) and 1-cyclopropyl-2,2,2-trifluoro-ethanamine hydrochloride (2, 0.40 g, 2.27 mmol) in monoglyme (15 mL) in a vial, sodium tert-butoxide (0.729 g, 7.58 mmol) was added. After purging with argon gas for 30 minutes, BINAP (0.14 g, 0.23 mmol) and tris(dibenzylideneacetone)dipalladium(0) (69 mg, 0.080 mmol) were added. The vial was sealed and the contents heated at 90° C. for 24 h. Solvent was removed and the crude mixture was by flash chromatography eluting with a 10-12% gradient of Ethyl acetate in hexane. The desired fractions were concentrated under pressure to obtain tert-butyl N-tert-butoxycarbonyl-N-[6-[(1-cyclopropyl-2,2,2-trifluoro-ethyl)amino]pyrimidin-4-yl]-carbamate (3) as an off-white solid. Yield: 110 mg, 17%; $^1$H NMR (400 MHz, DMSO-$d_6$) δ 9.78 (s, 1H), 8.15 (s, 1H), 7.79 (d, J=9.2 Hz, 1H), 7.10 (s, 1H), 4.47 (m, 1H), 1.46 (s, 1H), 0.61 (m, 1H), 0.49 (m, 2H), 0.39 (m, 1H).

Synthesis of N$^4$-(1-cyclopropyl-2, 2,2-trifluoro-ethyl)pyrimidine-4, 6-diamine hydrochloride (4)

Procedure F: To a solution of tert-butyl N-tert-butoxycarbonyl-N-[6-[(1-cyclopropyl-2,2,2-trifluoro-ethyl)amino]pyrimidin-4-yl]-carbamate (3, 250 mg, 0.58 mmol) in dichloromethane (2 mL) and methanol (2 mL) was added 4 M hydrogenchloride in 1,4-dioxane (5 mL). The reaction was stirred at room temperature overnight. The solvents were evaporated under reduced pressure, the resultant residue was triturated with dichloromethane. The solids were placed in a round bottom flask and aqueous ammonia was added adjusting the pH to 8-9. The solvent content was reduced added and water was added. The solids were filtered and dried to afford N$^4$-(1-cyclopropyl-2,2,2-trifluoro-ethyl)pyrimidine-4,6-diamine hydrochloride (4) as a light brown solid. Yield: 130 mg, crude; MS (ESI) m/z 233 [M+1-HCl]$^+$.

Synthesis of 6-[[6-[(1-cyclopropyl-2, 2,2-trifluoro-ethyl)amino]pyrimidin-4-yl]amino]-3-methyl-3-(trifluoromethyl)-2H-imidazo[1,5-a]pyridine-1,5-dione (Cpd. No. 59)

The synthesis of compound 59 was carried out as described above using the general protocol of Procedure B. Off-white solid; Yield: 33 mg, 19%; MS (ESI) m/z 463.36 [M+1]$^+$; $^1$H NMR (400 MHz, DMSO-$d_6$) δ 10.44 (brs, 1H), 9.05 (s, 1H), 8.62 (d, J=7.6 Hz, 1H), 8.26 (s, 1H), 7.80 (d, J=8.8 Hz, 1H), 6.96 (d, J=8.0 Hz, 1H), 6.43 (s, 1H), 4.36 (brs, 1H), 2.12 (s, 3H), 1.12 (m, 1H), 0.67 (m, 1H), 0.51 (m, 2H), 0.35 (m, 1H).

Example 60

Synthesis of N-(6-((8-chloro-1,5-dioxo-1,5-dihydro-2H-spiro[imidazo[1,5-a]pyridine-3,3'-piperidin]-6-yl)amino)pyrimidin-4-yl)cyclopropanecarboxamide hydrochloride (Cpd. No. 60)

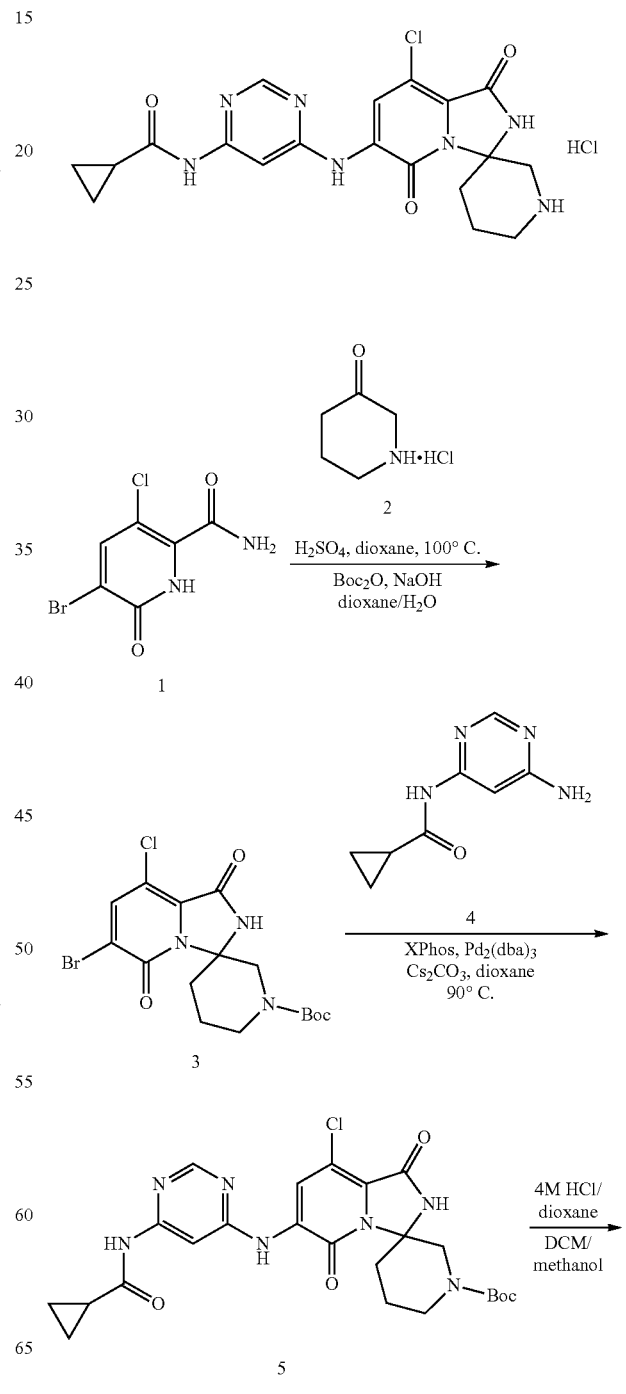

-continued

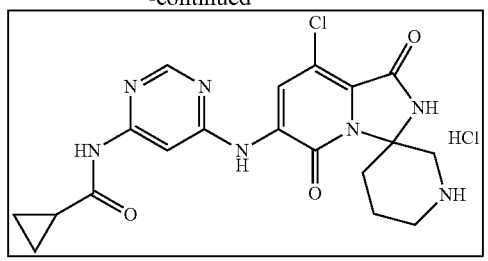

Synthesis of tert-butyl 6-bromo-8-chloro-1,5-dioxo-spiro[2H-imidazo[1,5-a]pyridine-3,3'-piperidine]-1'-carboxylate (3)

To a stirred solution of 5-bromo-3-chloro-6-oxo-1H-pyridine-2-carboxamide (1, 0.7 g, 2.78 mmol) in 1,4-dioxane (10 mL) in a vial, piperidin-3-one hydrochloride (2, 1.13 g, 8.35 mmol) was added at room temperature. To this solution concentrated sulfuric acid (0.27 g, 2.78 mmol) was added dropwise. The reaction vial was sealed and heated to 100° C. for 48 h. After completion the solvent was removed under reduced pressure and the resultant reaction mass was diluted with water (20 mL) and the aqueous layer was washed with ethyl acetate (3×20 mL). The aqueous solution (20.0 mL) of 6-bromo-8-chloro-spiro[2H-imidazo[1,5-a]pyridine-3,3'-piperidine]-1,5-dione (~0.5 g) was treated with sodium hydroxide (90 mg, 2.26 mmol). di-tert-butyl dicarbonate (0.39 g, 1.80 mmol) in 1,4-dioxane (20 mL) was added and the reaction mixture was stirred at 25° C. for 6 h. Once completed the solvent was removed under reduced pressure. The aqueous layer was extracted with ethyl acetate (2×25 mL) and the organic layers were washed with water (2×10 mL). The organic layers were separated and dried with sodium sulfate, filtered and concentrated to dryness. The crude residue was purified by flash column chromatography eluting with 2% methanol in dichloromethane. The desired fractions were concentrated to dryness to afford tert-butyl 6-bromo-8-chloro-1,5-dioxo-spiro [2H-imidazo [1,5-a]pyridine-3,3'-piperidine]-1'-carboxylate (3) as white solid. Yield: 0.4 g; MS (ESI) m/z 432 [M+1]$^+$.

Synthesis of tert-butyl 8-chloro-6-(((6-(cyclopropanecarboxamido)pyrimidin-4-yl)amino)-1,5-dioxo-1,5-dihydro-2H-spiro[imidazo[1,5-a]pyridine-3,3'-piperidine]-1'-carboxylate (5)

The synthesis of intermediate 5 was carried out as described above using the general protocol of Procedure B. Light yellow solid; Yield: 0.07 g, 19%; MS (ESI) m/z 530.0 [M+1]$^+$; $^1$H NMR (400 MHz, DMSO-d$_6$) δ 10.94 (s, 1H), 9.48 (s, 1H), 8.72 (s, 1H), 8.60 (s, 1H), 7.99 (s, 1H), 4.05 (m, 2H), 3.9 (m, 1H), 3.32 (m, 2H), 2.95 (m, 1H), 2.01 (m, 3H), 1.35 (s, 9H), 0.84 (m, 4H).

Synthesis of N-(6-((8-chloro-1,5-dioxo-1,5-dihydro-2H-spiro[imidazo[1,5-a]pyridine-3,3'-piperidin]-6-yl)amino)pyrimidin-4-yl)cyclopropanecarboxamide hydrochloride (Cpd. No. 60)

The synthesis of compound 60 was carried out as described above using the general protocol of Procedure F. Light brown solid; Yield: 22 mg, 35%; MS (ESI) m/z 430.39 [M+1]$^+$; $^1$H NMR (400 MHz, DMSO-d$_6$): δ 10.98 (s, 1H), 10.04 (s, 1H), 9.55 (s, 1H), 9.19 (bs, 1H), 8.75 (s, 1H), 8.61 (s, 1H), 8.02 (s, 1H), 4.17 (m, 1H), 3.35 (m, 2H), 3.02 (m, 2H), 2.08 (m, 3H), 1.81 (m, 1H), 0.84 (s, 4H).

Example 61

Synthesis of N-(6-((8-chloro-1,5-dioxo-1,2',3',5,5',6'-hexahydro-2H-spiro[imidazo[1,5-a]pyridine-3,4'-pyran]-6-yl)amino)pyrimidin-4-yl)cyclopropanecarboxamide (Cpd. No. 61)

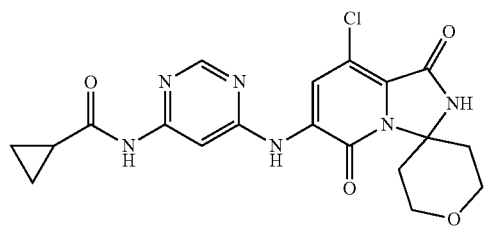 [SMILES: O=C1NC2(CCOCC2)n2c1c(Cl)cc(Nc1cc(NC(=O)C3CC3)ncn1)c2=O]

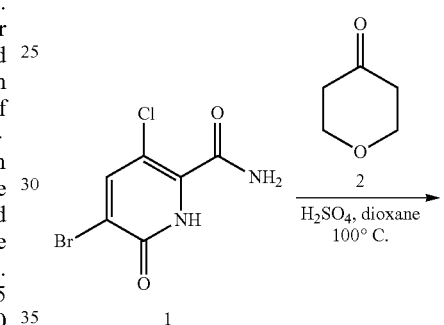

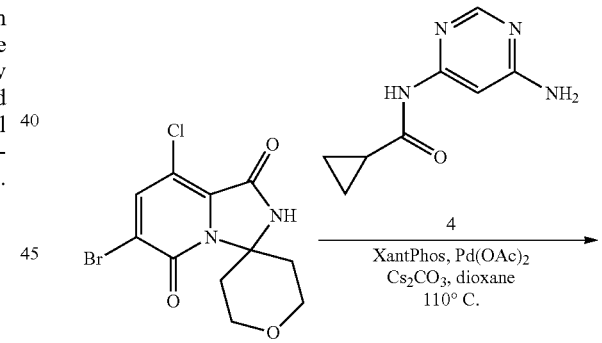

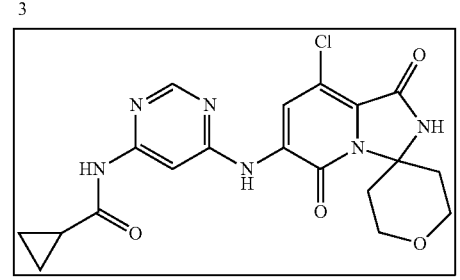

Synthesis of 6-bromo-8-chloro-2',3',5',6'-tetrahydro-2H-spiro[imidazo[1,5-a]pyridine-3,4'-pyran]-1,5-dione (3)

The synthesis of intermediate 3 was carried out as described above using the general protocol of Procedure A.

Light brown solid; Yield: 1.0 g, crude; MS (ESI) m/z 330.8 [M−1]⁻; 1H NMR (400 MHz, DMSO-$d_6$) δ 10.84 (s, 1H), 8.28 (s, 1H), 3.92 (m, 2H), 3.64 (m, 2H), 3.09 (m, 2H), 1.52 (m, 2H).

Synthesis of N-(6-((8-chloro-1,5-dioxo-1,2',3',5,5',6'-hexahydro-2H-spiro[imidazo[1,5-a]pyridine-3,4'-pyran]-6-yl)amino)pyrimidin-4-yl)cyclopropanecarboxamide (Cpd. No. 61)

The synthesis of compound 61 was carried out as described above using the general protocol of Procedure B. Light yellow solid; Yield: 0.11 g, 21%; MS (ESI) m/z 431.36 [M+1]⁺; ¹H NMR (400 MHz, DMSO-$d_6$) δ 10.94 (s, 1H), 10.54 (s, 1H), 9.51 (s, 1H), 8.72 (s, 1H), 8.59 (s, 1H), 8.0 (s, 1H), 3.94 (m, 2H), 3.68 (t, J=12.4 Hz, 2H), 3.19 (m, 2H), 2.05 (m, 1H), 1.52 (d, J=12.4 Hz, 2H), 0.81 (d, J=6.0 Hz, 4H).

Example 62

Synthesis of N-[6-[(8-chloro-1',1'-difluoro-1,5-dioxo-spiro[2H-imidazo[1,5-a]pyridine-3,3'-cyclobutane]-6-yl)amino]pyrimidin-4-yl]cyclopropanecarboxamide (Cpd. No. 62)

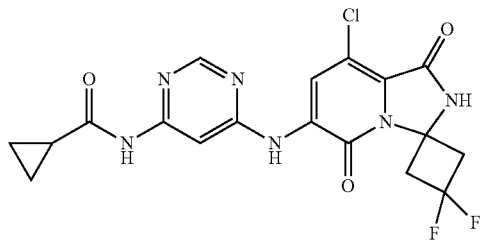 [SMILES: O=C1NC2(CC(F)(F)C2)n2c1c(Cl)cc(Nc1cc(NC(=O)C3CC3)ncn1)c2=O]

Synthesis of 6-bromo-8-chloro-1',1'-difluoro-spiro[2H-imidazo[1,5-a]pyridine-3,3'-cyclobutane]-1,5-dione (3)

The synthesis of intermediate 3 was carried out as described above using the general protocol of Procedure A. Brown solid; Yield: 0.4 g, 59%; MS (ESI) m/z 337 [M+1]⁺.

Synthesis of N-[6-[(8-chloro-1',1'-difluoro-1,5-dioxo-spiro[2H-imidazo[1,5-a]pyridine-3,3'-cyclobutane]-6-yl)amino]pyrimidin-4-yl]cyclopropanecarboxamide (Cpd. No. 62)

The synthesis of compound 62 was carried out as described above using the general protocol of Procedure B. White solid; Yield: 0.025 g, 11%; MS (ESI) m/z 437.4 [M+1]⁺; ¹H NMR (400 MHz, DMSO-$d_6$) δ 10.92 (s, 1H), 10.39 (s, 1H), 9.74 (s, 1H), 8.74 (s, 1H), 8.59 (s, 1H), 8.03 (s, 1H), 4.22-4.15 (m, 1H), 3.13-2.90 (m, 1H), 2.07-1.96 (m, 1H), 0.85-0.77 (s, 4H).

Example 63

Synthesis of 8-chloro-2',2'-dimethyl-6-(pyrimidin-4-ylamino) spiro [2H-imidazo[1,5-a] pyridine-3,1'-cyclopentane]-1,5-dione (Cpd. No. 63)

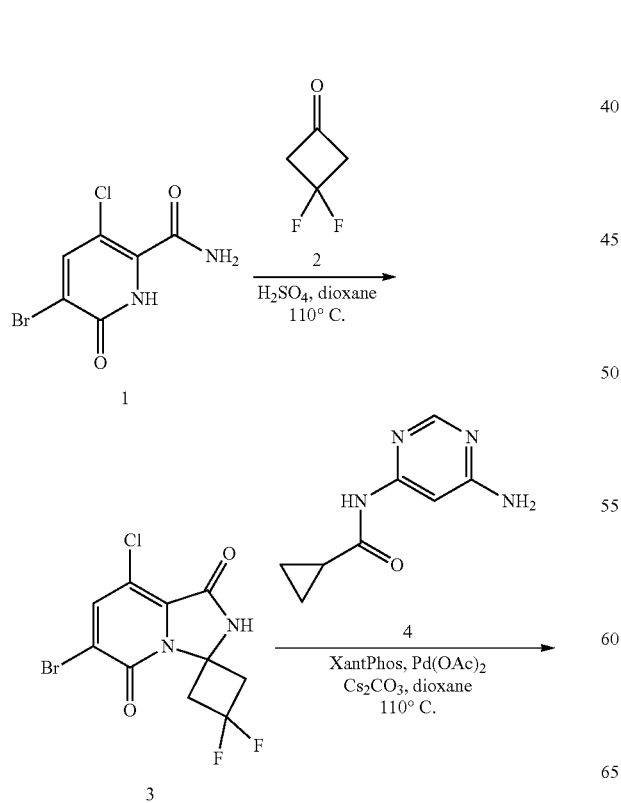

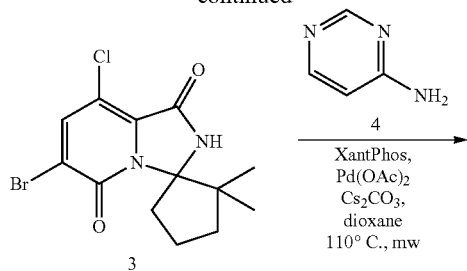

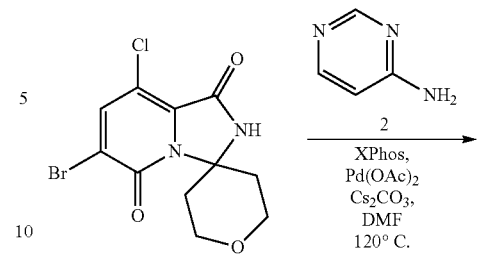

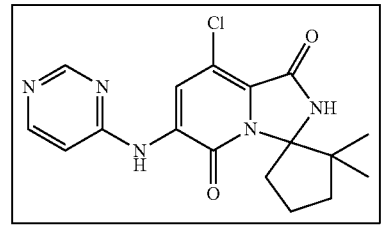

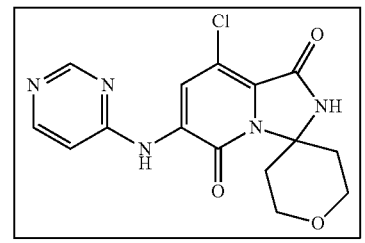

Synthesis of 6-bromo-8-chloro-2',2'-dimethyl-spiro[2H-imidazo[1,5-a]pyridine-3,1'-cyclopentane]-1,5-dione (3)

The synthesis of intermediate 3 was carried out as described above using the general protocol of Procedure A. Cream-colored solid; Yield: 0.2 g, 14%; 1H NMR (400 MHz, DMSO-d$_6$) δ 10.03 (s, 1H), 8.29 (s, 1H), 2.96-2.91 (m, 1H), 2.67 (m, 1H), 2.05-1.92 (m, 4H), 1.63-1.58 (m, 1H), 0.99 (s, 3H), 0.65 (s, 3H).

Synthesis of 8-chloro-2',2'-dimethyl-6-(pyrimidin-4-ylamino)spiro[2H-imidazo[1,5-a]pyridine-3,1'-cyclopentane]-1,5-dione (Cpd. No. 63)

The synthesis of compound 63 was carried out as described above using the general protocol of Procedure B. Microwave reactor was used for heating in place of the conventional oil bath heating. Off white solid; Yield: 0.03 g, 29%; MS (ESI) m/z 360.29 [M+1]$^+$; $^1$H NMR (400 MHz, DMSO-d$_6$) δ 9.76 (s, 1H), 9.66 (s, 1H), 8.84 (s, 1H), 8.81 (s, 1H), 8.44 (d, 1H), 7.47 (d, 1H), 3.00-2.92 (m, 1H), 2.44-2.42 (m, 1H), 2.14-2.10 (m, 1H), 1.99-1.90 (m, 1H), 1.65-1.62 (m, 1H), 1.02 (s, 3H), 0.67, (s, 3H).

Example 64

Synthesis of 8-chloro-6-(pyrimidin-4-ylamino)-2',3',56'-tetrahydro-2H-spiro[imidazo[1,5-a]pyridine-3,4'-pyran]-1,5-dione (Cpd. No. 64)

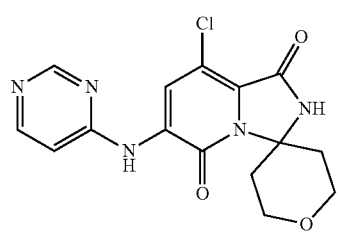 [SMILES: O=C1NC2(CCOCC2)n2c1c(Cl)cc(Nc1ccncn1)c2=O]

Synthesis of 8-chloro-6-(pyrimidin-4-ylamino)-2',3',5',6'-tetrahydro-2H-spiro[imidazo[1,5-a]pyridine-3,4'-pyran]-1,5-dione (Cpd. No. 64)

The synthesis of compound 64 was carried out as described above using the general protocol of Procedure B. Light yellow solid; Yield: 0.10 g, 32%; MS (ESI) m/z 348.27 [M+1]$^+$; $^1$H NMR (400 MHz, DMSO-d$_6$) δ 10.56 (s, 1H), 9.65 (s, 1H), 8.84 (d, J=12.0 Hz, 2H), 8.44 (s, 1H), 7.47 (s, 1H), 3.94 (m, 2H), 3.70 (m, 2H), 3.19 (m, 2H), 1.54 (d, J=11.4 Hz, 2H).

Example 65

Synthesis of N-(6-((8-chloro-1,5-dioxo-1,5-dihydro-2H-spiro[imidazo[1,5-a]pyridine-3,3'-thietan]-6-yl)amino)pyrimidin-4-yl)cyclopropanecarboxamide (Cpd. No. 65)

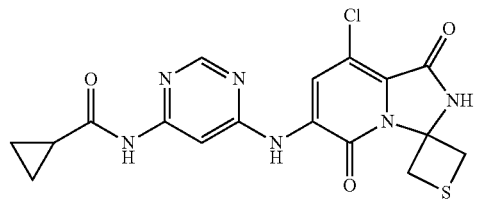 [SMILES: O=C1NC2(CSC2)n2c1c(Cl)cc(Nc1cc(NC(=O)C3CC3)ncn1)c2=O]

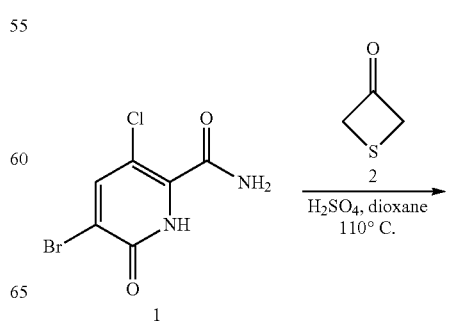

-continued

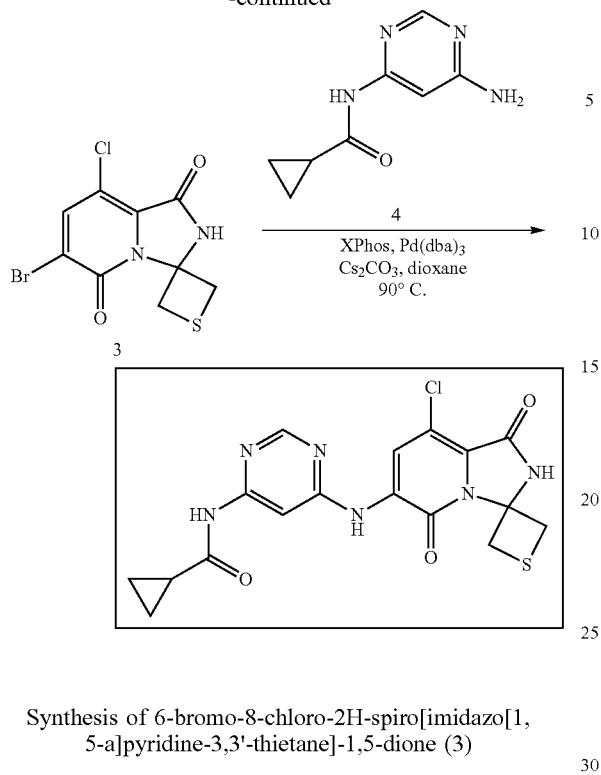

Synthesis of 6-bromo-8-chloro-2H-spiro[imidazo[1,5-a]pyridine-3,3'-thietane]-1,5-dione (3)

The synthesis of intermediate 3 was carried out as described above using the general protocol of Procedure A. Dark brown solid; Yield: 0.25 g, 20%; MS (ESI) m/z 318.96 [M−1]⁻; 1H NMR (400 MHz, DMSO-d$_6$) δ 11.10 (bs, 1H), 8.27 (s, 1H), 4.65 (s, 2H), 3.32 (s, 2H).

Synthesis of N-(6-((8-chloro-1,5-dioxo-1,5-dihydro-2H-spiro[imidazo[1,5-a]pyridine-3,3'-thietan]-6-yl)amino)pyrimidin-4-yl)cyclopropanecarboxamide (Cpd. No. 65)

The synthesis of compound 65 was carried out as described above using the general protocol of Procedure B. Off white solid; Yield: 0.05 g, 30%; MS (ESI) m/z 419.26 [M+1]⁺; $^1$H NMR (400 MHz, DMSO-d$_6$) δ 10.95 (s, 1H), 10.80 (s, 1H), 9.65 (s, 1H), 8.69 (s, 1H), 8.59 (s, 1H), 8.02 (s, 1H), 4.66 (s, 2H), 3.32 (s, 2H), 2.03 (m, 1H), 0.85 (s, 4H).

Example 66

Synthesis of 8-chloro-2'-fluoro-6-(pyrimidin-4-ylamino)spiro[2H-imidazo[1,5-a]pyridine-3,1'-cyclohexane]-1,5-dione (Cpd. No. 66)

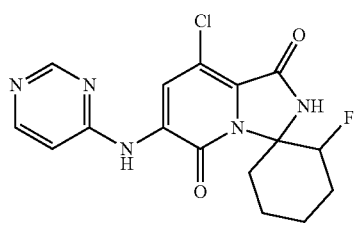 [SMILES: O=C1NC2(CCCCC2F)n2c1c(Cl)cc(Nc1ccncn1)c2=O]

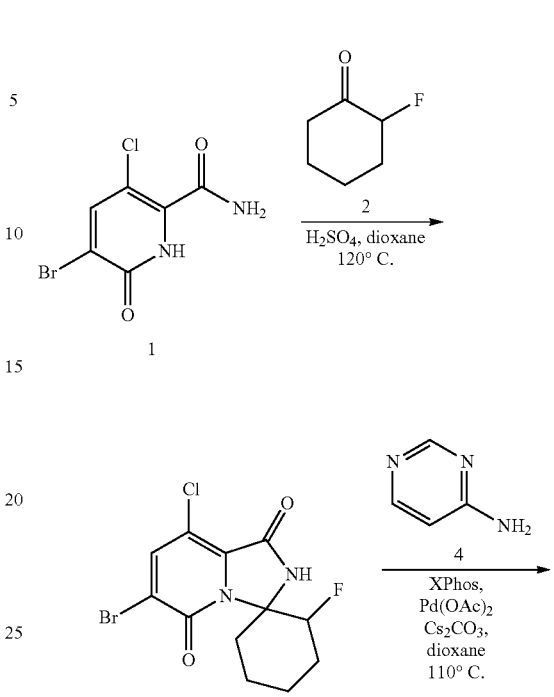

Synthesis of 6-bromo-8-chloro-2'-fluoro-spiro[2H-imidazo[1,5-a]pyridine-3,1'-cyclohexane]-1,5-dione (3)

The synthesis of intermediate 3 was carried out as described above using the general protocol of Procedure A. Light brown solid; Yield: 0.40 g, 57%; MS (ESI) m/z 349 [M−1]⁻.

Synthesis of 8-chloro-2'-fluoro-6-(pyrimidin-4-ylamino)spiro[2H-imidazo[1,5-a]pyridine-3,1'-cyclohexane]-1,5-dione (Cpd. No. 66)

The synthesis of compound 66 was carried out as described above using the general protocol of Procedure B. Off white solid; Yield: 0.1 g, 38%; MS (ESI) m/z 364.29 [M+1]⁺; $^1$H NMR (400 MHz, DMSO-d$_6$) δ 10.31 (s, 1H), 9.65 (s, 1H), 8.85 (d, J=12 Hz, 1H) 8.45 (d, J=4 Hz, 1H) 7.46 (d, J=8 Hz, 1H), 5.74-5.58 (m, 1H), 2.98-2.92 (m, 1H), 2.14-2.12 (m, 1H), 1.80-1.23 (m, 1H).

Example 67

Synthesis of 3,3,8-trimethyl-6-(pyrimidin-4-ylamino)-2H-imidazo[1,5-a]pyridine-1,5-dione (Cpd. No. 67)

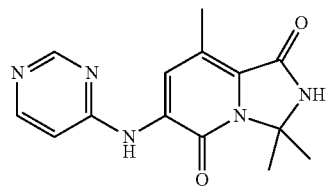 [SMILES: Cc1cc(Nc2ccncn2)c(=O)n2c1C(=O)NC2(C)C]

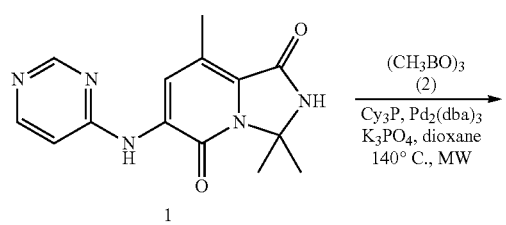

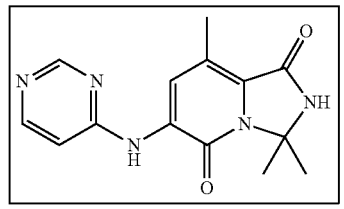

Synthesis of 3,3, 8-trimethyl-6-(pyrimidin-4-ylamino)-2H-imidazo[1,5-a]pyridine-1,5-dione (Cpd. No. 67)

Procedure G: A vial was charged with 8-chloro-3,3-dimethyl-6-(pyrimidin-4-ylamino)-2H-imidazo[1,5-a]pyridine-1,5-dione (1, 0.20 g, 0.65 mmol), trimethylboroxine (2, 0.16 g, 1.31 mmol) and potassium phosphate (0.28 g, 1.31 mmol) in 1,4-dioxane (10 mL) at room temperature under argon. Then reaction mixture was purged with argon for 10 min. followed by addition of tris(dibenzylideneacetone)dipalladium(0) (60 mg, 0.07 mmol) and tricyclohexylphosphine (18 mg, 0.07 mmol). The vial was sealed and heated at 140° C. in a microwave reactor for 1 h. The reaction mixture was concentrated to dryness and the crude residue was subjected to flash column chromatography using silica gel 100-200 mesh with a solvent gradient of 0.2-0.5% methanol in dichloromethane. The desired fractions were collected and concentrated to dryness under vacuum. The solid obtained was stirred in n-pentane and filtered. The resulting product 3,3,8-trimethyl-6-(pyrimidin-4-ylamino)-2H-imidazo[1,5-a]pyridine-1,5-dione (Cpd. No. 67) was obtained as an off-white solid. Yield: 0.035 g, 18%; MS (ESI) m/z 286.3 [M+1]$^+$; $^1$H NMR (400 MHz, DMSO-d$_6$) δ 9.57 (s, 1H), 9.39 (s, 1H), 8.77 (s, 1H), 8.60 (s, 1H), 8.37 (d, J=5.76 Hz, 1H), 7.77 (d, J=5.64 Hz, 1H), 2.44 (s, 3H), 1.79 (s, 6H).

Example 68

Synthesis 8-cyclopropyl-3,3-dimethyl-6-(pyrimidin-4-ylamino)-2H-imidazo[1,5-a]pyridine-1,5-dione (Cpd. No. 68)

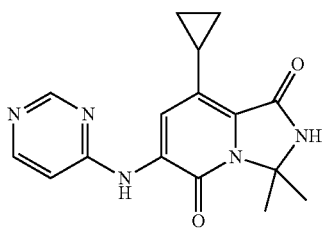 [SMILES: CC1(C)NC(=O)c2c(C3CC3)cc(Nc3ccncn3)c(=O)n21]

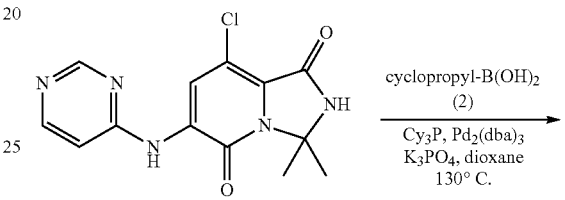

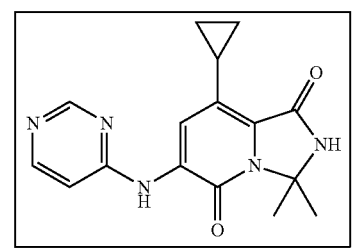

Synthesis 8-cyclopropyl-3,3-dimethyl-6-(pyrimidin-4-ylamino)-2H-imidazo[1,5-a]pyridine-1,5-dione (Cpd. No. 68)

The synthesis of compound 68 was carried out as described above using the general protocol of Procedure G. Off white solid; Yield: 0.032 g, 16%; MS (ESI) m/z 312.3 [M+1]$^+$; $^1$H NMR (400 MHz, DMSO-d$_6$) δ 9.57 (s, 1H), 9.40 (s, 1H), 8.75 (s, 1H), 8.37 (d, J=5.6 Hz, 1H), 8.26 (s, 1H), 7.35 (d, J=5.8 Hz, 1H), 3.17-3.15 (m, 1H), 1.80 (s, 6H), 1.10-0.98 (m, 2H), 0.69-0.68 (m, 2H).

Example 69

Synthesis of 8-fluoro-3,3-dimethyl-6-(pyrimidin-4-ylamino)-2H-imidazo[1,5-a]pyridine-1,5-dione (Cpd. No. 69)

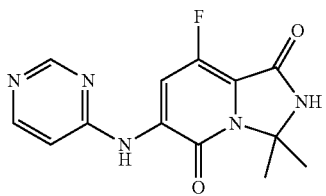 [SMILES: CC1(C)NC(=O)c2c(F)cc(Nc3ccncn3)c(=O)n21]

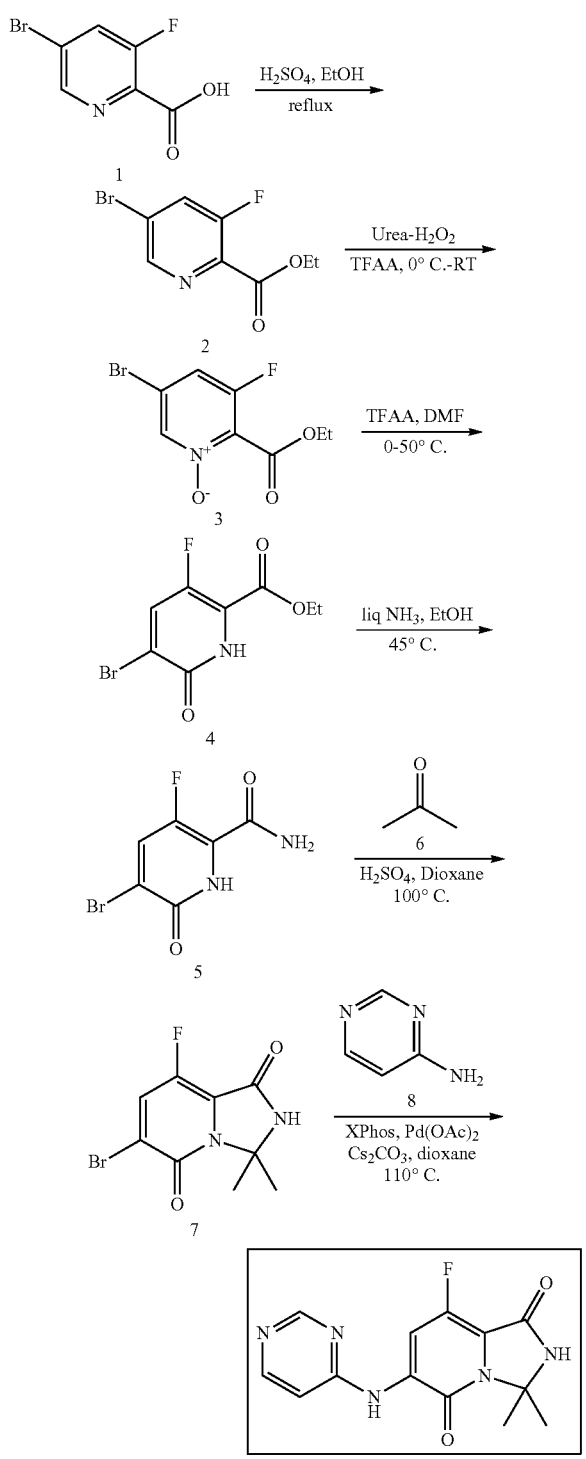

Synthesis of ethyl 5-bromo-3-fluoro-pyridine-2-carboxylate (2)

To a stirred solution of 5-bromo-3-fluoro-pyridine-2-carboxylic acid (1, 1.0 g, 4.55 mmol) in ethanol (20 mL) was added sulfuric acid (0.67 g, 6.82 mmol) at room temperature. The reaction mixture was stirred at reflux overnight. After consumption of starting materials as indicated by TLC, the reaction mixture was cooled to room temperature, and the solvent was removed under vacuum. The residue was neutralized with a saturated aqueous sodium bicarbonate solution and extracted with ethyl acetate (2×100 mL). The organic layers were separated and dried with magnesium sulfate, filtered and concentrated to dryness under vacuum to afford ethyl 5-bromo-3-fluoro-pyridine-2-carboxylate (2) as an off-white solid. Yield: 1.0 g, 89%; MS (ESI) m/z 249.9 [M+1]$^+$; $^1$H NMR (400 MHz, DMSO-d$_6$) δ 8.61 (m, 1H), 7.77-7.75 (m, 1H), 4.51 (q, J=7.16 Hz, 2H), 1.43 (t, J=7.12 Hz, 3H).

Synthesis of ethyl 5-bromo-3-fluoro-1-oxido-pyridin-1-ium-2-carboxylate (3)

To a stirred solution of ethyl 5-bromo-3-fluoro-pyridine-2-carboxylate (2, 0.9 g, 3.63 mmol) in dichloromethane (50 mL) at 0° C. was added trifluoroacetic anhydride (1.52 g, 7.26 mmol), urea hydrogen peroxide (0.72 g, 7.62 mmol). The reaction mixture was stirred at room temperature overnight. After the oxidation was complete the reaction mixture was neutralized with a dipotassium hydrogenphosphate solution and quenched with a sodium bisulfite solution. The product was extracted with dichloromethane (2×100 mL). The organic layers were separated, dried with magnesium sulfate, filtered and concentrated to dryness under vacuum to afford ethyl 5-bromo-3-fluoro-1-oxido-pyridin-1-ium-2-carboxylate (3) as an off-white solid. Yield: 0.9 g, 89%; MS (ESI) m/z 265.95 [M+1]$^+$; $^1$H NMR (400 MHz, DMSO-d$_6$) δ: 8.22 (s, 1H), 7.30-7.26 (m, 1H), 4.50 (q, J=7.2 Hz, 2H), 1.42 (t, J=7.2 Hz, 3H).

Synthesis of ethyl 5-bromo-3-fluoro-6-oxo-1H-pyridine-2-carboxylate (4)

To a stirred solution of ethyl 5-bromo-3-fluoro-1-oxido-pyridin-1-ium-2-carboxylate (3, 0.85 g, 3.21 mmol) in dimethylformamide (15 mL) was added trifluoroacetic anhydride (1.35 g, 6.42 mmol) at 0° C. The reaction mixture was warmed to 50° C. and stirred for 1 h, quenched with saturated aqueous sodium bicarbonate solution and extracted with dichloromethane (2×100 mL). The organic layers were separated, dried with magnesium sulfate, filtered and concentrated to dryness under vacuum to afford ethyl 5-bromo-3-fluoro-6-oxo-1H-pyridine-2-carboxylate (4) as a yellow solid. Yield: 0.8 g, 94%; MS (ESI) m/z 264 [M+1]$^+$; $^1$H NMR (400 MHz, DMSO-d$_6$) δ 7.86 (m, 1H), 4.47 (q, J=7.2 Hz, 2H), 1.43 (t, J=7.2 Hz, 3H).

Synthesis of 5-bromo-3-fluoro-6-oxo-1H-pyridine-2-carboxamide (5)

In a round bottom flask charged with ethyl 5-bromo-3-fluoro-6-oxo-1H-pyridine-2-carboxylate (4, 0.8 g, 3.03 mmol) at 0° C. was added liquid ammonia (15 mL, 3.03 mmol) in ethanol (5 mL). The stirred reaction mixture was warmed to 45° C. for 2 h. After the ester was completely consumed liquid ammonia and ethanol was evaporated under reduced pressure. Methanol was added and the mixture was refluxed for 2 h and filtered while hot. The volume of the filtrate was reduced by ⅔ and to the remaining methanol was added diethyl ether until solid precipitated. The solid was filtered and dried under vacuum to afford 5-bromo-3-fluoro-6-oxo-1H-pyridine-2-carboxamide (5) as a light brown solid. Yield: 0.6 g, 85%; 1H NMR (400 MHz, DMSO-d$_6$) δ 7.88-7.86 (m, 1H), 7.67 (s, 1H), 7.50 (s, 1H).

Synthesis of 6-bromo-8-fluoro-3,3-dimethyl-2H-imidazo[1,5-a]pyridine-1,5-dione (7)

The synthesis of intermediate 7 was carried out as described above using the general protocol of Procedure A. Off-white solid; Yield: 0.24 g, 34%; MS (ESI) m/z 275.07 [M+1]$^+$; $^1$H NMR (400 MHz, DMSO-d$_6$) δ 7.87 (d, J=7.44 Hz, 1H), 7.06 (s, 1H), 1.96 (s, 6H).

Synthesis of 8-fluoro-3,3-dimethyl-6-(pyrimidin-4-ylamino)-2H-imidazo[1,5-a]pyridine-1,5-dione (Cpd. No. 69)

The synthesis of compound 69 was carried out as described above using the general protocol of Procedure B. Off-white solid; Yield: 0.032 g, 13%; MS (ESI) m/z 290.32 [M+1]$^+$; $^1$H NMR (400 MHz, DMSO-d$_6$) δ 9.72 (s, 1H), 9.61 (s, 1H), 8.83 (d, J=5.1 Hz, 1H), 8.79 (s, 1H), 8.45 (d, J=5.7 Hz, 1H), 7.46 (d, J=5.6 Hz, 1H), 1.82 (s, 6H).

Example 70

Synthesis of 6'-((6-aminopyrimidin-4-yl)amino)-8'-chloro-2'H-spiro[cyclohexane-1,3'-imidazo[1,5-a]pyridine]-1',5'-dione (Cpd. No. 70)

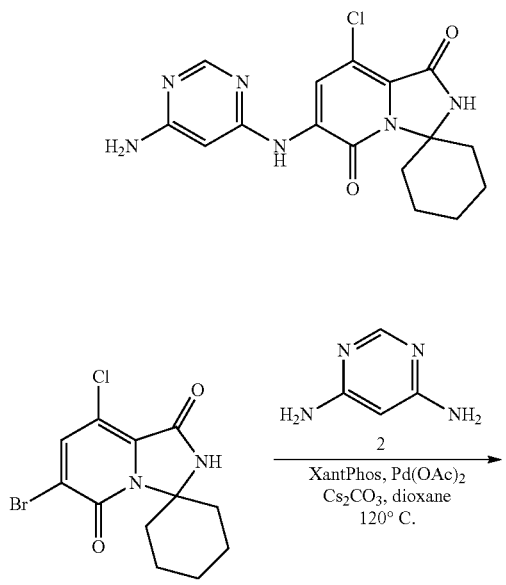

Synthesis of 6'-((6-aminopyrimidin-4-yl)amino)-8'-chloro-2'H-spiro[cyclohexane-1,3'-imidazo[1,5-a]pyridine]-1',5'-dione (Cpd. No. 70)

The synthesis of compound 70 was carried out as described above using the general protocol of Procedure B. Yield: 22 mg; MS (ESI) m/z 361.33 [M+1]$^+$; $^1$H NMR (400 MHz, DMSO-d$_6$) δ 10.22 (s, 1H), 8.90 (s, 1H), 8.63 (s, 1H), 8.20 (s, 1H), 6.61 (s, 2H), 6.24 (s, 1H), 2.94 (t, J=11.36 Hz, 2H), 1.65 (m, 5H), 1.51 (d, J=12.1 Hz, 2H), 1.21 (m, 1H).

Example 71

Synthesis of 8-ethyl-3,3-dimethyl-6-(pyrimidin-4-ylamino)-2H-imidazo[1,5-a]pyridine-1,5-dione (Cpd. No. 71)

Synthesis of 8-ethyl-3,3-dimethyl-6-(pyrimidin-4-ylamino)-2H-imidazo[1,5-a]pyridine-1,5-dione (Cpd. No. 71)

The synthesis of compound 71 was carried out as described above using the general protocol of Procedure G. Off white solid; Yield: 0.04 g, 12%; MS (ESI) m/z 300.3 [M+1]$^+$; $^1$H NMR (400 MHz, DMSO-d$_6$) δ 9.58 (s, 1H), 9.40 (s, 1H), 8.78 (s, 1H), 8.67 (s, 1H), 8.38 (d, J=5.84 Hz, 1H), 7.38 (d, J=5.36 Hz, 1H), 2.89 (q, J=7.76 Hz, 2H), 1.79 (s, 6H), 1.11 (t, J=7.36 Hz, 3H).

Example 72

Synthesis of 8-chloro-3-methyl-3-(3-pyridyl)-6-(pyrimidin-4-ylamino)-2H-imidazo[1,5-a]pyridine-1,5-dione (Cpd. No. 72)

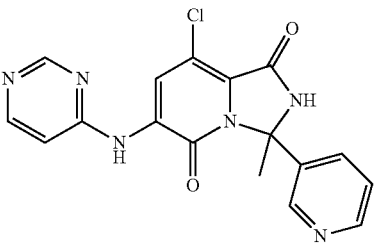 [SMILES: CC1(c2cccnc2)NC(=O)c2c(Cl)cc(Nc3ccncn3)c(=O)n21]

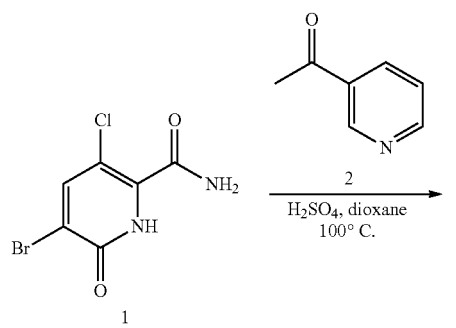

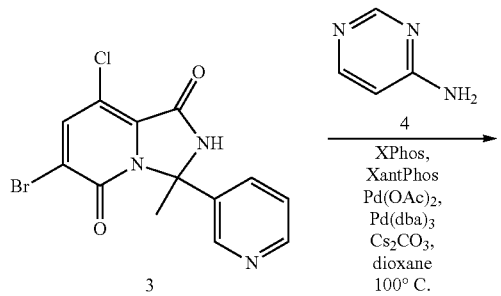

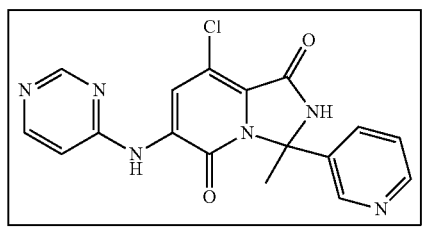

Synthesis of 6-bromo-8-chloro-3-methyl-3-(3-pyridyl)-2H-imidazo[1,5-a]pyridine-1,5-dione (3)

The synthesis of intermediate 3 was carried out as described above using the general protocol of Procedure A. Yellow solid; Yield: 0.4 g, 57%; MS (ESI) m/z 354.02 [M+1]$^+$; $^1$H NMR (400 MHz, DMSO-d$_6$) δ 10.4 (bs, 1H), 8.70 (s, 1H), 8.57 (d, J=4 Hz, 1H), 8.31 (s, 1H), 7.82 (d, J=8.0 Hz, 1H), 7.42-7.39 (m, 1H), 2.22 (s, 3H).

Synthesis of 8-chloro-3-methyl-3-(3-pyridyl)-6-(pyrimidin-4-ylamino)-2H-imidazo[1,5-a]pyridine-1,5-dione (Cpd. No. 72)

Procedure H: To a solution of 6-bromo-8-chloro-3-methyl-3-(3-pyridyl)-2H-imidazo[1,5-a]pyridine-1,5-dione (100 mg, 0.28 mmol) and pyrimidin-4-amine (30 mg, 0.31 mmol) in 1,4-dioxane (12 mL) was added cesium carbonate (276 mg, 0.85 mmol). The reaction was purged with argon for 15 min. XPhos (13 mg, 0.03 mmol), XantPhos (16 mg, 0.030 mmol), palladium acetate (6 mg, 0.030 mmol) and tris(dibenzylideneacetone)dipalladium(0) (26 mg, 0.030 mmol) were added and purging was continued for another 10 min. The reaction was stirred at 100° C. for 16 h. After completion the reaction mass was diluted with 10% methanol in dichloromethane and passed through celite pad. The crude filtrate was then purified by flash column chromatography using 10% methanol in dichloromethane. The desired fractions were concentrated to dryness under vacuum to obtain 8-chloro-3-methyl-3-(3-pyridyl)-6-(pyrimidin-4-ylamino)-2H-imidazo[1,5-a]pyridine-1,5-dione as pale yellow solid. Yield: 0.059 g, 57%; MS (ESI) m/z 369.29 [M+1]$^+$; $^1$H NMR (400 MHz, DMSO-d$_6$) δ 10.16 (s, 1H), 9.57 (s, 1H), 8.84 (d, J=6.2 Hz, 1H), 8.75 (d, J=2.24 Hz, 1H), 8.56-8.55 (m, 1H), 7.82 (d, J=8.2 Hz, 1H), 7.42-7.38 (m, 1H), 2.27 (s, 3H).

Example 73

Synthesis of N-(6-((8-chloro-3-methyl-1,5-dioxo-3-(pyridin-4-yl)-1,2,3,5-tetrahydroimidazo[1,5-a]pyridin-6-yl)amino)pyrimidin-4-yl)cyclopropanecarboxamide (Cpd. No. 73)

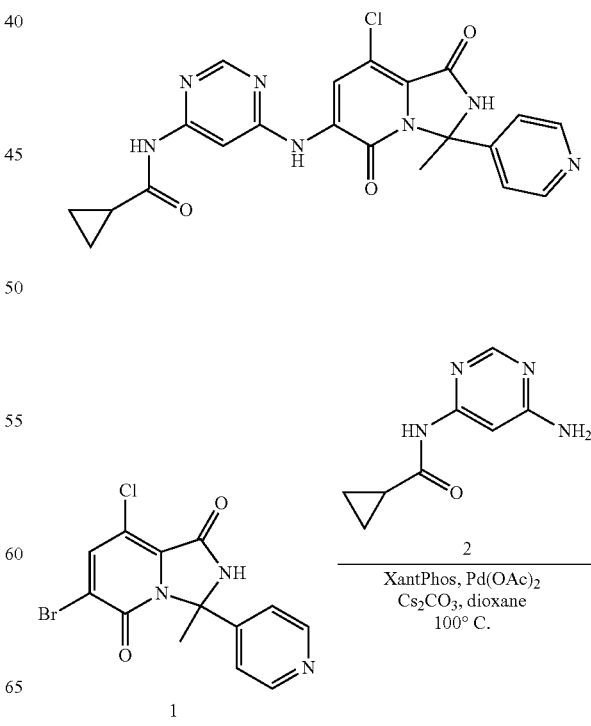

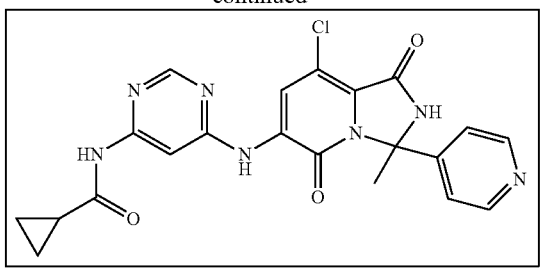

Synthesis of N-(6-((8-chloro-3-methyl-1,5-dioxo-3-(pyridin-4-yl)-1,2,3,5-tetrahydroimidazo[1,5-a]pyridin-6-yl)amino)pyrimidin-4-yl)cyclopropanecarboxamide (Cpd. No. 73)

The synthesis of compound 73 was carried out as described above using the general protocol of Procedure B. Off-white solid; Yield: 0.030 g, 16%; MS (ESI) m/z 352.34 [M+1]⁺; ¹H NMR (400 MHz, DMSO-d₆) δ 10.91 (brs, 1H), 10.15 (s, 1H), 9.45 (brs, 1H), 8.76 (s, 1H), 8.58 (m, 3H), 7.90 (s, 1H), 7.40 (brs, 2H), 2.21 (s, 3H), 2.05-1.95 (m, 1H), 0.90-0.75 (m, 4H).

Example 74

Synthesis of 8-chloro-3-methyl-3-(2-pyridyl)-6-(pyrimidin-4-ylamino)-2H-imidazo[1,5-a]pyridine-1,5-dione (Cpd. No. 74)

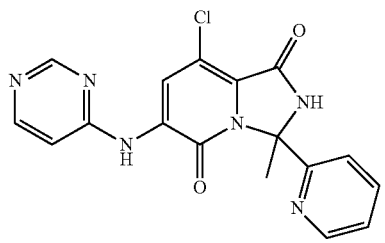 [SMILES: CC1(c2ccccn2)NC(=O)c2c(Cl)cc(Nc3ccncn3)c(=O)n21]

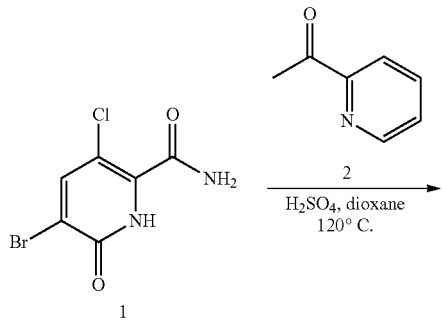

Synthesis of 6-bromo-8-chloro-3-methyl-3-(pyridin-2-yl)-2,3-dihydroimidazo[1,5-a]pyridine-1,5-dione (3)

The synthesis of intermediate 3 was carried out as described above using the general protocol of Procedure A. White solid; Yield: 0.30 g, 42%; MS (ESI) m/z 354 [M+1]⁺.

Synthesis of 8-chloro-3-methyl-3-(2-pyridyl)-6-(pyrimidin-4-ylamino)-2H-imidazo[1,5-a]pyridine-1,5-dione (Cpd. No. 74)

The synthesis of compound 74 was carried out as described above using the general protocol of Procedure H. Off-white solid; Yield: 55 mg, 35%; 1H NMR (400 MHz, DMSO-d₆) δ 10.05 (bs, 1H), 9.51 (bs, 1H), 8.84 (d, J=11.1 Hz, 2H), 8.52 (d, J=3.28 Hz, 1H), 8.40 (d, J=5.72 Hz, 1H), 7.88-7.84 (m, 1H), 7.66 (d, J=8.12 Hz, 1H), 7.38-7.35 (m, 1H), 7.24 (d, J=5.84 Hz, 1H), 2.26 (s, 3H).

Example 75

Synthesis of 8-chloro-3-methyl-3-(4-pyridyl)-6-(pyrimidin-4-ylamino)-2H-imidazo[1,5-a]pyridine-1,5-dione (Cpd. No. 75)

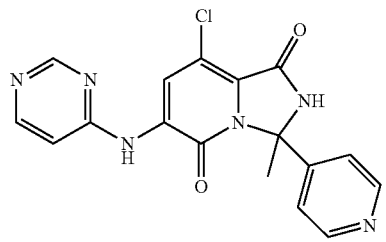 [SMILES: CC1(c2ccncc2)NC(=O)c2c(Cl)cc(Nc3ccncn3)c(=O)n21]

141

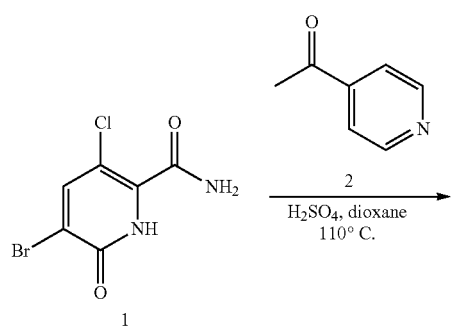

142

Example 76

Synthesis of N-(6-((8-chloro-3-methyl-1,5-dioxo-3-(pyridin-2-yl)-1,2,3,5-tetrahydroimidazo[1,5-a]pyridin-6-yl)amino)pyrimidin-4-yl)cyclopropanecarboxamide (Cpd. No. 76)

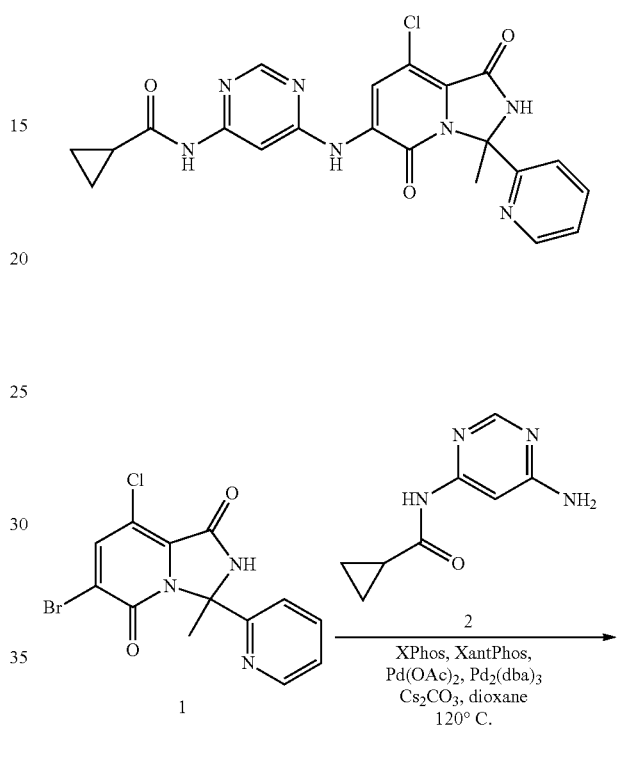

Synthesis of 6-bromo-8-chloro-3-methyl-3-(pyridin-4-yl)-2, 3-dihydroimidazo[1,5-a]pyridine-1,5-dione (3)

The synthesis of intermediate 3 was carried out as described above using the general protocol of Procedure A. Off-white solid; Yield: 0.36 g, 51%; MS (ESI) m/z 354.02 [M+1]$^+$; $^1$H NMR (400 MHz, DMSO-d$_6$) δ 10.4 (bs, 1H), 8.57 (d, J=5.2 Hz, 2H), 8.33 (s, 1H), 7.40 (d, J=4.5 Hz, 2H), 2.17 (s, 3H).

Synthesis of 8-chloro-3-methyl-3-(4-pyridyl)-6-(pyrimidin-4-ylamino)-2H-imidazo[1,5-a]pyridine-1, 5-dione (Cpd. No. 75)

The synthesis of compound 75 was carried out as described above using the general protocol of Procedure B. Off-white solid; Yield: 59 mg, 57%; MS (ESI) m/z 369.29 [M+1]$^+$; $^1$H NMR (400 MHz, DMSO-d$_6$) δ 10.18 (bs, 1H), 9.58 (s, 1H), 8.84 (d, J=2.88 Hz, 2H), 8.59 (d, J=5.64 Hz, 2H), 8.41 (d, J=5.88 Hz, 1H), 7.43 (d, J=5.76 Hz, 2H), 7.34 (d, J=5.76 Hz, 1H), 2.23 (s, 3H).

Synthesis of N-(6-((8-chloro-3-methyl-1,5-dioxo-3-(pyridin-2-yl)-1,2,3,5-tetrahydroimidazo[1,5-a]pyridin-6-yl)amino)pyrimidin-4-yl)cyclopropanecarboxamide (Cpd. No. 76)

The synthesis of compound 76 was carried out as described above using the general protocol of Procedure H. Off-white solid; Yield: 15 mg, 8%; MS (ESI) m/z 452.35 [M+1]$^+$; $^1$H NMR (400 MHz, DMSO-d$_6$) δ 10.90 (s, 1H), 10.01 (s, 1H), 9.36 (s, 1H), 8.73 (s, 1H), 8.58 (s, 1H), 8.51 (d, J=4.32 Hz, 1H), 7.85 (m, 2H), 7.63 (d, J=7.96 Hz, 1H), 7.37 (m, 1H), 2.27 (s, 3H), 1.99 (m, 1H), 0.81 (m, 4H).

Example 77

Synthesis of N-[6-[[8-chloro-3-methyl-1,5-dioxo-3-(3-pyridyl)-2H-imidazo[1,5-a]pyridin-6-yl]amino]pyrimidin-4-yl]cyclopropanecarboxamide (Cpd. No. 77)

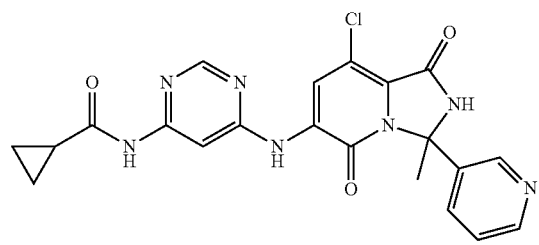 [SMILES: CC1(c2cccnc2)NC(=O)c2c(Cl)cc(Nc3cc(NC(=O)C4CC4)ncn3)c(=O)n21]

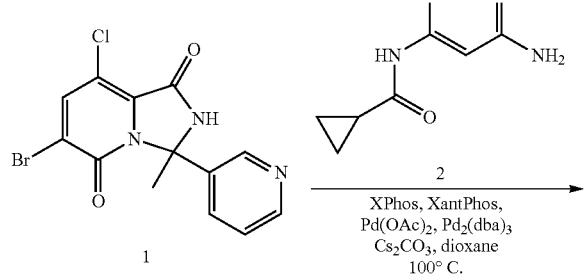

Synthesis of N-[6-[[8-chloro-3-methyl-1,5-dioxo-3-(3-pyridyl)-2H-imidazo[1,5-a]pyridin-6-yl]amino]pyrimidin-4-yl]cyclopropanecarboxamide (Cpd. No. 77)

The synthesis of compound 77 was carried out as described above using the general protocol of Procedure H. Pale yellow solid; Yield: 58 mg, 15%; MS (ESI) m/z 452.36 [M+1]$^+$; $^1$H NMR (400 MHz, DMSO-d$_6$) δ 10.99 (bs, 1H), 10.12 (bs, 1H), 9.44 (s, 1H), 8.75 (s, 1H), 8.73 (d, J=2.0 Hz, 1H), 8.58 (s, 1H), 8.56 (d, J=3.7 Hz, 1H), 7.90 (s, 1H), 7.42-7.38 (m, 1H), 2.26 (s, 3H), 2.02-1.96 (m, 1H), 0.82-0.81 (m, 4H).

Example 78

Synthesis of N-(6-((8'-chloro-2-fluoro-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (Cpd. No. 78)

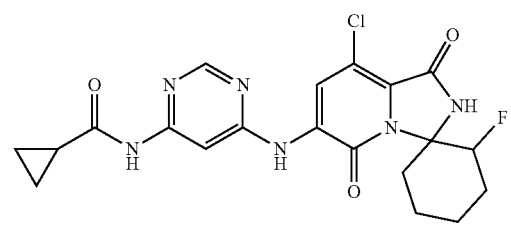 [SMILES: O=C1NC2(CCCCC2F)n2c1c(Cl)cc(Nc1cc(NC(=O)C3CC3)ncn1)c2=O]

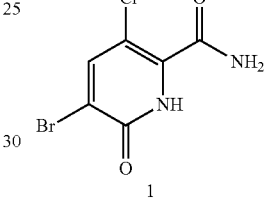

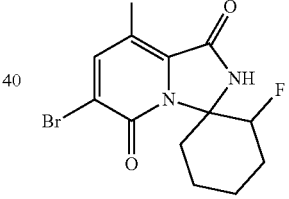

Synthesis of 6'-bromo-8'-chloro-2-fluoro-2'H-spiro[cyclohexane-1,3'-imidazo[1,5-a]pyridine]-1',5'-dione (3)

The synthesis of intermediate 3 was carried out as described above using the general protocol of Procedure A. Off-white solid; Yield: 0.31 g; MS (ESI) m/z 348.8 [M+1]$^+$.

Synthesis of N-(6-((8'-chloro-2-fluoro-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (Cpd. No. 78)

The synthesis of compound 78 was carried out as described above using the general protocol of Procedure B. Light yellow solid; Yield: 50 mg, 16%; MS (ESI) m/z 447.34 [M+1]$^+$; $^1$H NMR (400 MHz, DMSO-d$_6$) δ 10.95 (s, 1H), 10.27 (s, 1H), 9.51 (s, 1H), 8.74 (s, 1H), 8.60 (s, 1H), 7.99 (s, 1H), 5.64 (m, 1H), 2.95 (m, 1H), 2.1 (m, 1H), 2.02 (m, 1H), 1.72 (m, 4H), 1.57 (m, 1H), 1.39 (m, 1H), 0.84 (d, J=5.12 Hz, 4H).

Example 79

Synthesis of 3,3-dimethyl-6-(pyrimidin-4-ylamino)-8-vinyl-2H-imidazo[1,5-a]pyridine-1,5-dione (Cpd. No. 79)

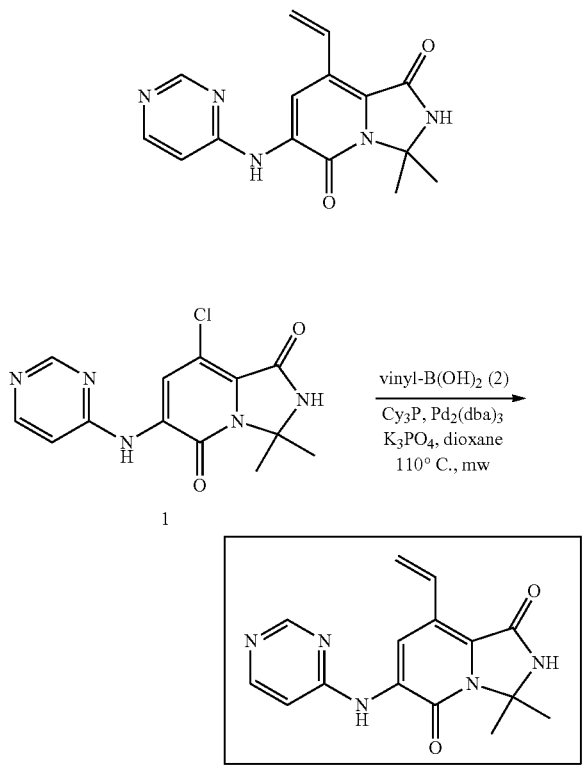

Synthesis of 3,3-dimethyl-6-(pyrimidin-4-ylamino)-8-vinyl-2H-imidazo[1,5-a]pyridine-1,5-dione (Cpd. No. 79)

The synthesis of compound 79 was carried out as described above using the general protocol of Procedure G. Pale yellow solid; Yield: 50 mg, 17%; MS (ESI) m/z 298.3 [M+1]$^+$; $^1$H NMR (400 MHz, DMSO-d$_6$) δ 9.74 (s, 1H), 9.47 (s, 1H), 9.14 (s, 1H), 8.81 (s, 1H), 8.40 (d, J=5.88 Hz, 1H), 7.85 (dd, J=11.04 Hz, 1H), 7.40 (d, J=5.88 Hz, 1H), 5.75 (d, J=6.12 Hz, 1H), 5.37 (d, J=11.24 Hz, 1H), 1.81 (s, 6H).

Example 80

Synthesis of N-(6-((8-chloro-3-methyl-1,5-dioxo-3-(3-(trifluoromethyl)phenyl)-1,2,3,5-tetrahydroimidazo[1,5-a]pyridin-6-yl)amino)pyrimidin-4-yl)cyclopropanecarboxamide (Cpd. No. 80)

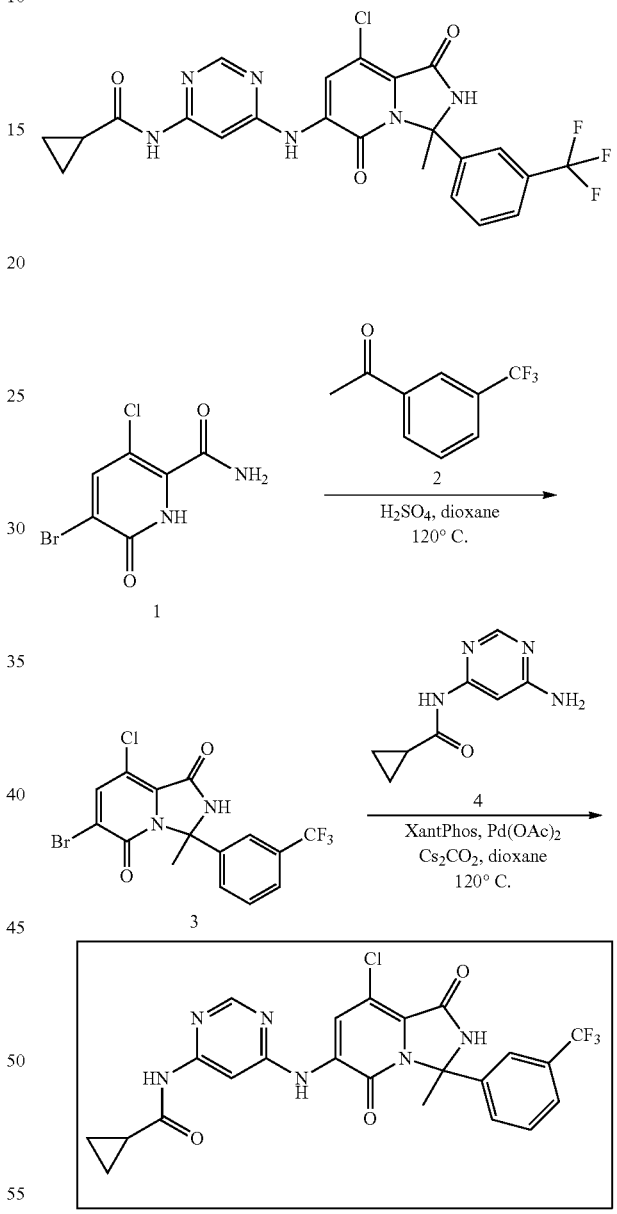

Synthesis of 6-bromo-8-chloro-3-methyl-3-(3-(trifluoromethyl)phenyl)-2,3-dihydroimidazo[1,5-a]pyridine-1,5-dione (3)

The synthesis of intermediate 3 was carried out as described above using the general protocol of Procedure A. Off-white solid; Yield: 0.12 g, 14%; MS (ESI) m/z 419 [M−1]$^-$.

Synthesis of N-(6-((8-chloro-3-methyl-1,5-dioxo-3-(3-(trifluoromethyl)phenyl)-1,2,3,5-tetrahydroimidazo[1,5-a]pyridin-6-yl)amino)pyrimidin-4-yl)cyclopropanecarboxamide (Cpd. No. 80)

The synthesis of compound 80 was carried out as described above using the general protocol of Procedure B. Off-white solid; Yield: 16 mg, 11%; MS (ESI) m/z 519 [M+1]$^+$; $^1$H NMR (400 MHz, DMSO-d$_6$) δ 8.75 (s, 1H), 8.58 (s, 1H), 7.90 (s, 1H), 7.82 (s, 1H), 7.75 (d, J=7.4 Hz, 1H), 7.68 (d, J=7.92 Hz, 1H), 7.62 (d, J=7.7 Hz, 1H), 2.27 (s, 3H), 1.98 (m, 1H), 0.81 (m, 4H).

Example 81

Synthesis of 8-methoxy-3,3-dimethyl-6-(pyrimidin-4-ylamino)-2H-imidazo[1,5-a]pyridine-1,5-dione (Cpd. No. 81)

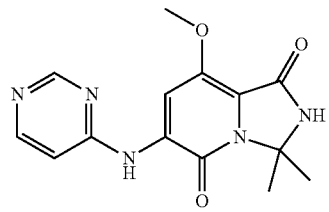 [SMILES: COc1cc(Nc2ccncn2)c(=O)n2c1C(=O)NC2(C)C]

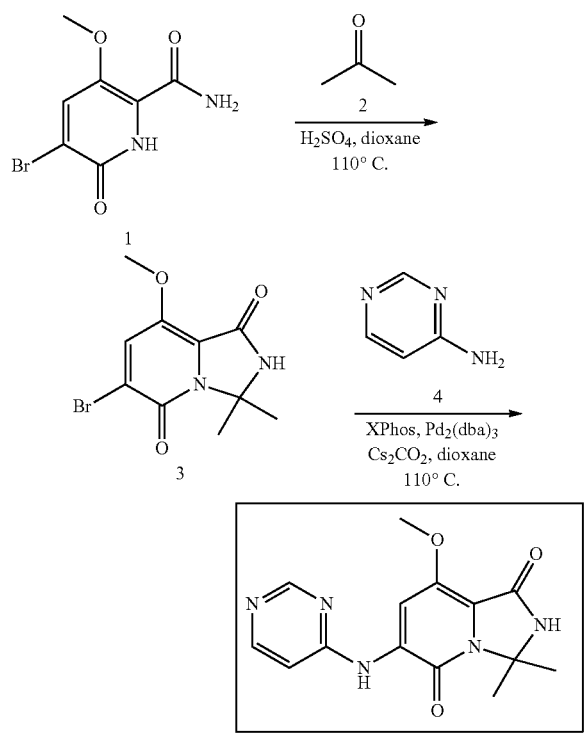

Synthesis of 6-bromo-8-methoxy-3,3-dimethyl-2H-imidazo[1,5-a]pyridine-1,5-dione (3)

The synthesis of intermediate 3 was carried out as described above using the general protocol of Procedure A. Light brown solid; Yield: 0.5 g, 41%; $^1$H NMR (400 MHz, DMSO-d$_6$) δ 7.87 (s, 1H), 6.75 (bs, 1H), 3.94 (s, 3H), 1.93 (s, 6H).

Synthesis of 8-methoxy-3,3-dimethyl-6-(pyrimidin-4-ylamino)-2H-imidazo[1,5-a]pyridine-1,5-dione (Cpd. No. 81)

The synthesis of compound 81 was carried out as described above using the general protocol of Procedure B. Yellow solid; Yield: 0.060 g, 15%; $^1$H NMR (400 MHz, DMSO-d$_6$) δ 9.50-9.41 (bs, 1H), 8.79 (s, 1H), 8.39 (d, J=4.0 Hz, 1H), 7.40 (d, J=8.0 Hz, 1H), 7.13 (bs, 1H), 3.85 (s, 3H), 1.76 (s, 6H).

Example 82

Synthesis of 3,3-dimethyl-8-methylsulfanyl-6-(pyrimidin-4-ylamino)-2H-imidazo[1,5-a]pyridine-1,5-dione (Cpd. No. 82)

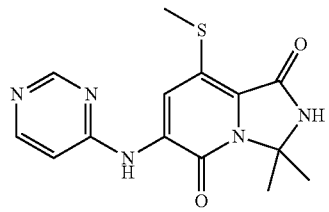

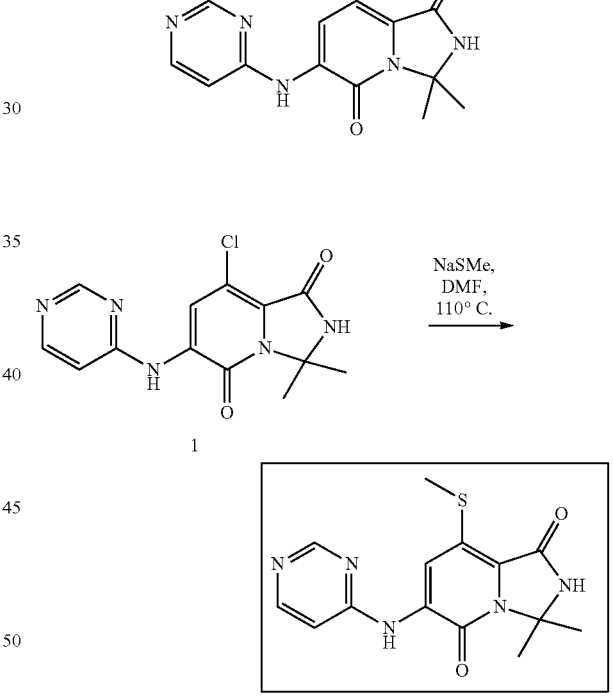

Synthesis of 3,3-dimethyl-8-methylsulfanyl-6-(pyrimidin-4-ylamino)-2H-imidazo[1,5-a]pyridine-1,5-dione (Cpd. No. 82)

To a vial was added 8-chloro-3,3-dimethyl-6-(pyrimidin-4-ylamino)-2H-imidazo[1,5-a]pyridine-1,5-dione (1, 0.30 g, 0.98 mmol) in dimethylformamide (5 mL). Sodium thiomethoxide (0.14 g, 1.96 mmol) was added at room temperature, the vial was sealed and heated at 110° C. for 36 h. The reaction mixture was quenched with an aqueous ammonium chloride solution and extracted with 10% methanol in dichloromethane. The organic layers were separated, combined, dried over sodium sulfate, filtered and concentrated it to dryness. Solids were precipitated by the addition of ice, filtered and dried. The solid material was subjected to preparative HPLC to afford 3,3-dimethyl-8-methylsulfanyl-6-(pyrimidin-4-ylamino)-2H-imidazo[1,5-a]pyridine-1,5-dione (Cpd. No. 82) as a yellow solid. Yield: 0.060 g, 19%; MS (ESI) m/z 318.42 [M+1]+; 1H NMR (400 MHz, DMSO-$d_6$) δ 10.02 (s, 1H), 9.66 (s, 1H), 8.92 (s, 1H), 8.84 (s, 1H), 8.45 (d, J=6.0 Hz, 1H), 7.47 (d, J=6.4 Hz, 1H), 2.47 (s, 3H), 1.80 (s, 6H).

Example 83

Synthesis of N-(6-((8-chloro-3-methyl-1,5-dioxo-3-(m-tolyl)-1,2,3,5-tetrahydroimidazo[1,5-a]pyridin-6-yl)amino)pyrimidin-4-yl)cyclopropanecarboxamide (Cpd. No. 83)

Synthesis of 6-bromo-8-chloro-3-methyl-3-(m-tolyl)-2,3-dihydroimidazo[1,5-a]pyridine-1,5-dione (3)

The synthesis of intermediate 3 was carried out as described above using the general protocol of Procedure A. Off-white solid; Yield: 0.30 g, 41%; MS (ESI) m/z 367 [M+1]+; 1H NMR (400 MHz, DMSO-$d_6$) δ 10.32 (s, 1H), 8.29 (s, 1H), 7.26 (m, 1H), 7.16 (m, 3H), 2.30 (s, 3H), 2.18 (s, 3H).

Synthesis of N-(6-((8-chloro-3-methyl-1,5-dioxo-3-(m-tolyl)-1,2,3,5-tetrahydroimidazo-[1,5-a]pyridin-6-yl)amino)pyrimidin-4-yl)cyclopropanecarboxamide (Cpd. No. 83)

The synthesis of compound 83 was carried out as described above using the general protocol of Procedure H. Pale yellow solid; Yield: 60 mg, 16%; MS (ESI) m/z 465.49 [M+1]+; 1H NMR (400 MHz, DMSO-$d_6$) δ 10.90 (s, 1H), 10.04 (s, 1H), 9.40 (s, 1H), 8.73 (s, 1H), 8.58 (s, 1H), 7.88 (s, 1H), 7.26 (m, 1H), 7.21 (m, 1H), 7.12 (m, 2H), 2.29 (s, 3H), 2.28 (s, 3H) 1.99 (m, 1H), 0.82 (m, 4H).

Example 84

Synthesis of N-[6-[(3-tert-butyl-8-chloro-3-methyl-1,5-dioxo-2H-imidazo[1,5-a]pyridin-6-yl)amino]pyrimidin-4-yl]cyclopropanecarboxamide (Cpd. No. 84)

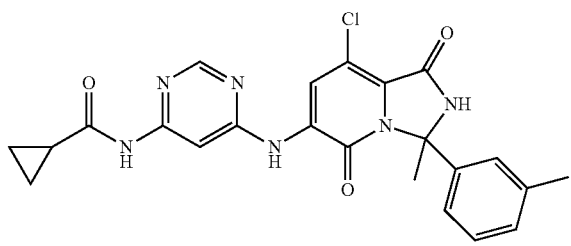 [SMILES: Cc1cccc(C2(C)NC(=O)c3c(Cl)cc(Nc4cc(NC(=O)C5CC5)ncn4)c(=O)n32)c1]

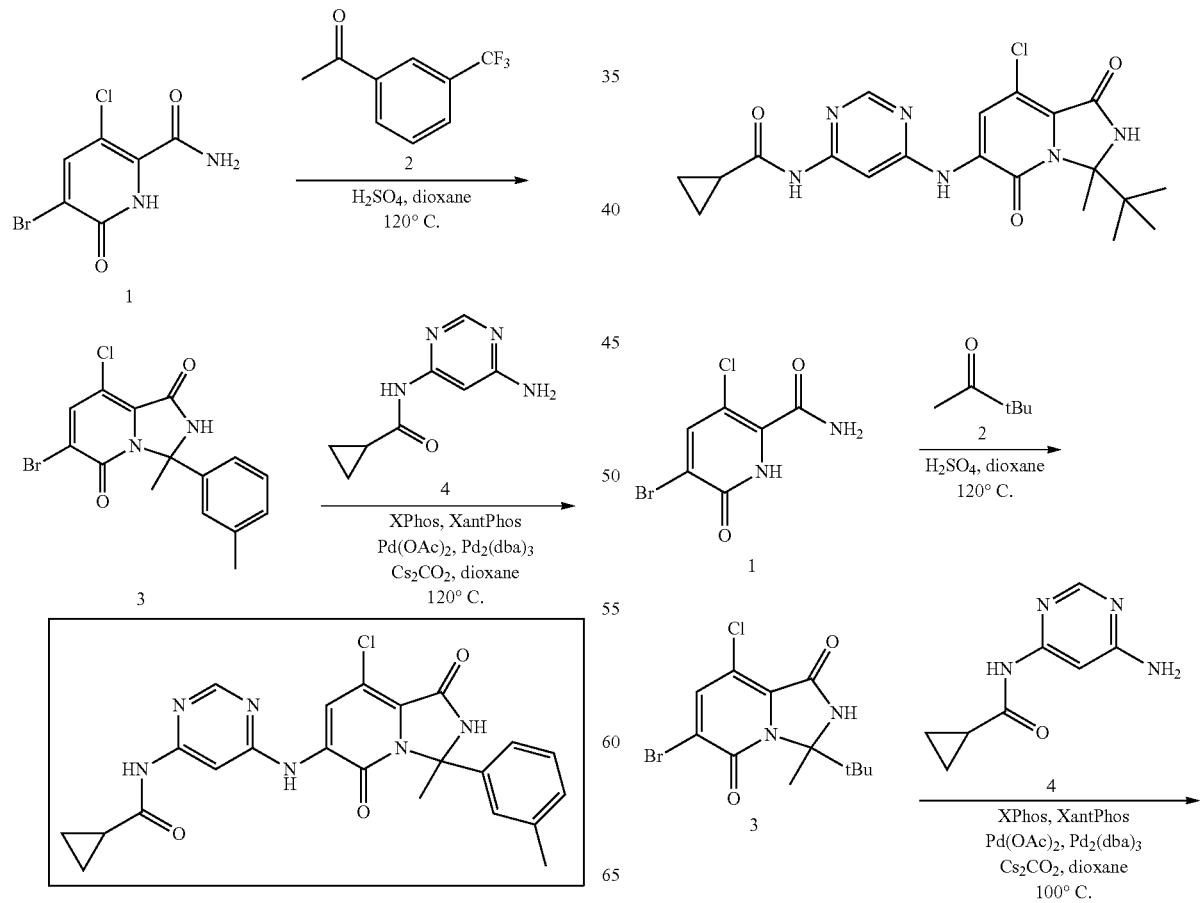

-continued

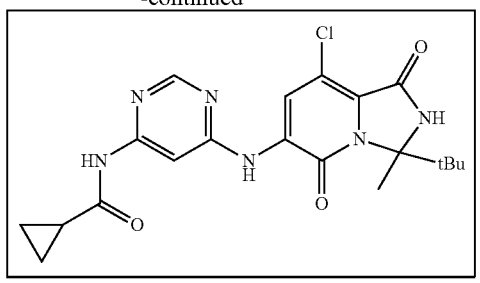

Synthesis of 6-bromo-3-tert-butyl-8-chloro-3-methyl-2H-imidazo[1,5-a]pyridine-1,5-dione (3)

The synthesis of intermediate 3 was carried out as described above using the general protocol of Procedure A. Yellow solid; Yield: 150 mg, 28%; MS (ESI) m/z 332.8 [M+1]+.

Synthesis of N-[6-[(3-tert-butyl-8-chloro-3-methyl-1,5-dioxo-2H-imidazo[1,5-a]pyridin-6-yl)amino]pyrimidin-4-yl]cyclopropanecarboxamide (Cpd. No. 84)

The synthesis of compound 84 was carried out as described above using the general protocol of Procedure H. Brown solid; Yield: 0.060 g, 31%; MS (ESI) m/z 431.42 [M+1]+; $^1$H NMR (400 MHz, DMSO-d$_6$) δ 10.91 (s, 1H), 9.73 (s, 1H), 9.49 (s, 1H), 8.67 (s, 1H), 8.58 (s, 1H), 7.98 (s, 1H), 2.02 (m, 1H), 1.92 (s, 1H), 0.98 (s, 9H), 0.83 (m, 4H).

Example 85

Synthesis of N-[6-[[8-chloro-1,5-dioxo-3-(trifluoromethyl)-2,3-dihydroimidazo[1,5-a]pyridin-6-yl]amino]pyrimidin-4-yl]cyclopropanecarboxamide (Cpd. No. 85)

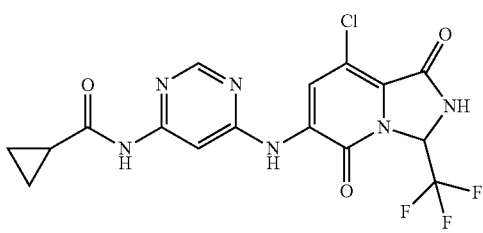 [SMILES: O=C1NC(C(F)(F)F)n2c1c(Cl)cc(Nc1cc(NC(=O)C3CC3)ncn1)c2=O]

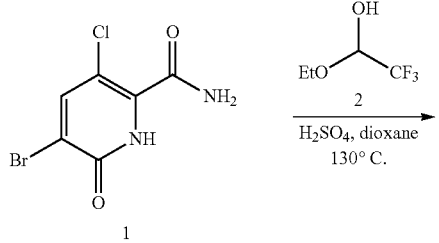

-continued

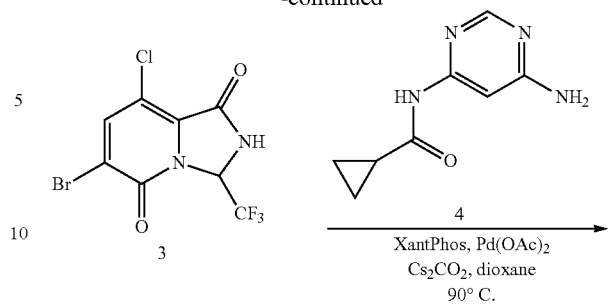

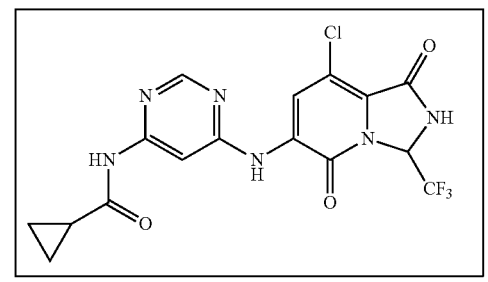

Synthesis of 6-bromo-8-chloro-3-(trifluoromethyl)-2,3-dihydroimidazo[1,5-a]pyridine-1,5-dione (3)

The synthesis of intermediate 3 was carried out as described above using the general protocol of Procedure A. Brown solid; Yield: 200 mg, 61%; 1H NMR (400 MHz, DMSO-d$_6$) δ 10.93 (s, 1H), 8.34 (m, 1H), 6.57 (m, 1H).

Synthesis of N-[6-[[8-chloro-1,5-dioxo-3-(trifluoromethyl)-2,3-dihydroimidazo[1,5-a]pyridin-6-yl]amino]pyrimidin-4-yl]cyclopropanecarboxamide (Cpd. No. 85)

The synthesis of compound 85 was carried out as described above using the general protocol of Procedure B. Pale yellow solid; Yield: 0.035 g, 14%; MS (ESI) m/z 429.33 [M+1]+; $^1$H NMR (400 MHz, DMSO-d$_6$) δ 10.95 (s, 1H), 10.58 (s, 1H), 9.80 (s, 1H), 8.76 (s, 1H), 8.61 (s, 1H), 8.06 (s, 1H), 6.61 (d, J=3.0 Hz, 1H), 2.02 (m, 1H), 0.84 (m, 4H).

Example 86

Synthesis of N-[6-[(8-chloro-1,5-dioxo-spiro [2H-imidazo[1,5-a]pyridine-3,3'-azetidine]-6-yl) amino]pyrimidin-4-yl] cyclopropanecarboxamide hydrochloride (Cpd. No. 86)

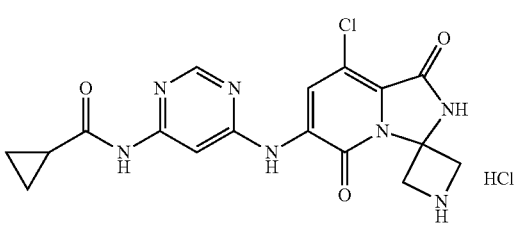 [SMILES: O=C1NC2(CNC2)n2c1c(Cl)cc(Nc1cc(NC(=O)C3CC3)ncn1)c2=O ; Cl]

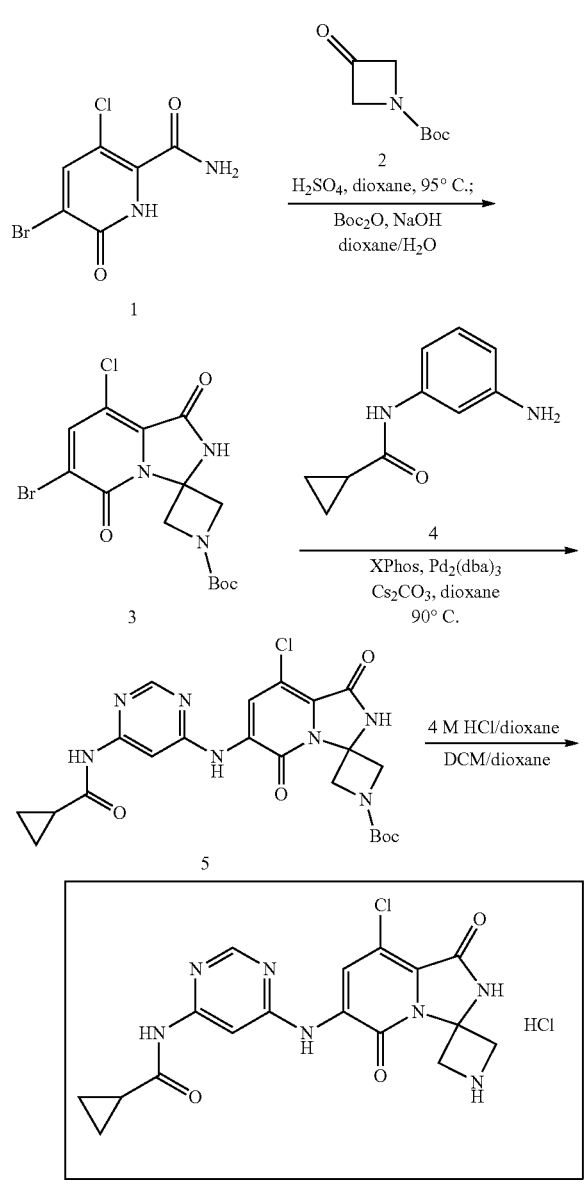

Synthesis of tert-butyl 6-bromo-8-chloro-1,5-dioxo-spiro[2H-imidazo[1,5-a]pyridine-3,3'-azetidine]-1'-carboxylate (3)

To a stirred solution of 5-bromo-3-chloro-6-oxo-1H-pyridine-2-carboxamide (1, 1.0 g, 3.98 mmol) in 1,4-dioxane (12 mL) in a vial was added tert-butyl 3-oxoazetidine-1-carboxylate (2, 2.72 g, 15.91 mmol) at room temperature. Concentrated sulfuric acid (0.39 g, 3.98 mmol) was then added dropwise. The vial was sealed and heated to 95° C. for 16 h. The reaction mixture was concentrated, water (30 mL) was added and extracted with ethyl acetate (2×30 mL). The organic layers were separated and discarded.

To a stirred solution of 6-bromo-8-chloro-spiro[2H-imidazo[1,5-a]pyridine-3,3'-azetidine]-1,5-dione (0.41 g, 1.35 mmol) in 1,4-dioxane (30 mL) and water (25 mL, 1.35 mmol) was added di-tert-butyl dicarbonate (0.59 g, 2.71 mmol). The solution was cooled to 0° C. and 2 M aqueous sodium hydroxide solution was added dropwise with stirring. The reaction mixture was stirred at room temperature overnight. After consumption of starting material as indicated by TLC, the mixture was extracted with 10% methanol in dichloromethane (2×25 mL). The organic layers were separated and dried over magnesium sulfate, filtered and concentrated to dryness. The crude residue was then purified by flash column chromatography using neutral alumina with 2% methanol in dichloromethane. The desired fractions were concentrated to dryness under vacuum to afford tert-butyl 6-bromo-8-chloro-1,5-dioxo-spiro[2H-imidazo[1,5-a]pyridine-3,3'-azetidine]-1'-carboxylate (3) as a yellow solid. Yield: 180 mg, 33%; MS (ESI) m/z 404.03 [M+1]$^+$; $^1$H NMR (400 MHz, DMSO-d$_6$) δ 10.53 (s, 1H), 8.28 (s, 1H), 4.88-4.68 (m, 2H), 3.97-3.89 (m, 2H), 1.42 (s, 9H).

Synthesis of tert-butyl 8-chloro-6-[[6-(cyclopropanecarbonylamino)pyrimidin-4-yl]amino]-1,5-dioxo-spiro[2H-imidazo[1,5-a]pyridine-3,3'-azetidine]-1'-carboxylate (5)

The synthesis of intermediate 5 was carried out as described above using the general protocol of Procedure B. Yellow solid; Yield: 0.065 g; 29%; 1H NMR (400 MHz, DMSO-d$_6$) δ 10.93 (s, 1H), 10.46 (s, 1H), 9.63 (s, 1H), 8.71 (s, 1H), 8.59 (s, 1H), 8.10 (s, 1H), 4.89-4.84 (m, 2H), 3.97-3.95 (m, 2H), 2.02-2.0 (m, 1H), 1.42 (s, 9H), 0.79-0.75 (m, 4H).

Synthesis of N-[6-[(8-chloro-1,5-dioxo-spiro[2H-imidazo[1,5-a]pyridine-3,3'-azetidine]-6-yl)amino]pyrimidin-4-yl]cyclopropanecarboxamide hydrochloride (Cpd. No. 86)

The synthesis of compound 86 was carried out as described above using the general protocol of Procedure F. Light yellow solid; Yield: 0.03 g; 61%; MS (ESI) m/z 402.34 [M+1]$^+$; $^1$H NMR (400 MHz, DMSO-d$_6$) δ 11.04 (s, 1H), 10.41 (s, 1H), 9.67 (s, 1H) 9.5 (bs, 1H), 8.79 (s, 1H), 8.74 (s, 1H), 8.06 (s, 1H).

Example 87

Synthesis of 6-[(6-aminopyrimidin-4-yl) amino]-8-chloro-3-(3-fluorophenyl)-3-methyl-2H-imidazo[1,5-a]pyridine-1,5-dione (Cpd. No. 87)

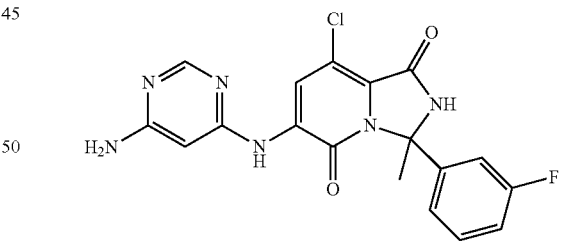

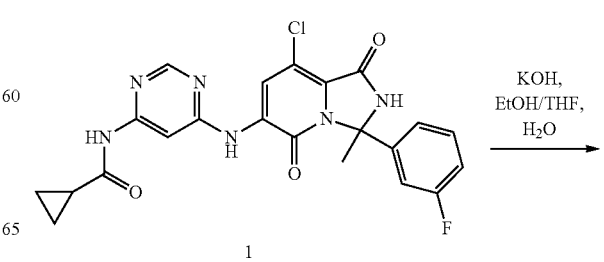

-continued

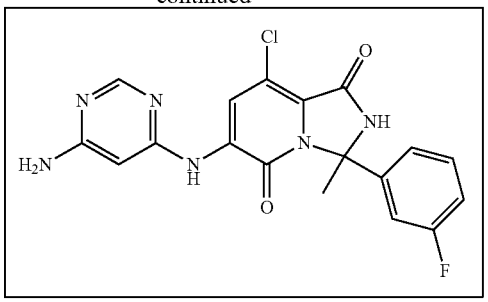

Synthesis of 6-[(6-aminopyrimidin-4-yl) amino]-8-chloro-3-(3-fluorophenyl)-3-methyl-2H-imidazo[1,5-a]pyridine-1,5-dione (Cpd. No. 87)

Procedure I: In a vial containing N-[6-[[8-chloro-3-(3-fluorophenyl)-3-methyl-1,5-dioxo-2H-imidazo[1,5-a]pyridin-6-yl]amino]pyrimidin-4-yl]cyclopropanecarboxamide (1, 0.23 g, 0.49 mmol) in tetrahydrofuran (5 mL), water (5 mL) and ethanol (10 mL) at room temperature was added a concentrated aqueous solution of potassium hydroxide (0.14 g, 2.45 mmol). Then reaction mixture was stirred for 16 h and was extracted with ethyl acetate (3×50 mL). The organic layers were then separated and dried over sodium sulfate, filtered and concentrated to dryness. The crude residue was subjected to flash column chromatography with 2% methanol in dichloromethane. The desired fractions were concentrated to dryness. The resulting solid was washed with pentane and diethyl ether to afford the product as a yellow solid. Yield: 0.095 g, 48%; MS (ESI) m/z 401.40 [M+1]$^+$; $^1$H NMR (400 MHz, DMSO-d$_6$) δ 10.02 (brs, 1H), 8.86 (s, 1H), 8.68 (s, 1H), 8.19 (s, 1H), 7.45-7.38 (m, 1H), 7.30 (d, J=8.8 Hz, 1H), 7.23-7.15 (m, 2H), 6.58 (brs, 2H), 6.17 (s, 1H), 2.21 (s, 1H).

Example 88

Synthesis of 6-[(6-aminopyrimidin-4-yl)amino]-8-chloro-3,3-dimethyl-2H-imidazo[1,5-a]pyridine-1,5-dione (Cpd. No. 88)

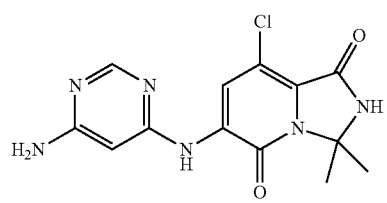 [SMILES: CC1(C)NC(=O)c2c(Cl)cc(Nc3cc(N)ncn3)c(=O)n21]

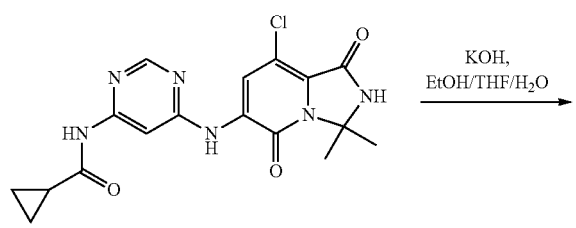

-continued

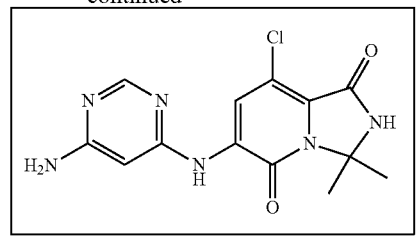

Synthesis of 6-[(6-aminopyrimidin-4-yl)amino]-8-chloro-3,3-dimethyl-2H-imidazo[1,5-a]pyridine-1,5-dione (Cpd. No. 88)

The synthesis of compound 88 was carried out as described above using the general protocol of Procedure I. Light yellow solid; Yield: 0.14 g, 68%; MS (ESI) m/z 321.34 [M+1]$^+$; $^1$H NMR (400 MHz, DMSO-d$_6$) δ 9.64 (s, 1H), 8.92 (s, 1H), 8.64 (s, 1H), 8.20 (s, 1H), 6.60 (s, 2H), 6.25 (s, 1H), 1.79 (s, 6H).

Synthesis of 6-[(6-aminopyrimidin-4-yl) amino]-8-chloro-3,3-dimethyl-2H-imidazo[1,5-a]pyridine-1,5-dione hydrogenchloride (hydrogenchloride salt of Cpd. No. 88)

To 6-[(6-aminopyrimidin-4-yl)amino]-8-chloro-3,3-dimethyl-2H-imidazo[1,5-a]pyridine-1,5-dione (Cpd. No. 88, 0.55 g, 1.71 mmol), in dichloromethane (10 mL), methanol (10 mL) a vial was added 4 M hydrogenchloride in 1,4-dioxane (10 mL). After stirring overnight at room temperature the reaction mixture was concentrated under vacuum, filtered, washed with methanol then diethyl ether and dried under vacuum to afford the product as a light yellow solid. Yield: 0.61 g, 100%; MS (ESI) m/z 319.43 [M+1]$^+$; $^1$H NMR (400 MHz, DMSO-d$_6$) δ 9.83 (s, 1H), 9.77 (s, 1H), 8.48 (s, 1H), 8.42 (s, 1H), 7.75 (s, 2H), 6.49 (s, 1H), 1.79 (s, 6H).

Example 89

Synthesis of 8-chloro-3-(3-chlorophenyl)-3-methyl-6-[[6-(methylamino)pyrimidin-4-yl]amino]-2H-imidazo[1,5-a]pyridine-1,5-dione (Cpd. No. 89)

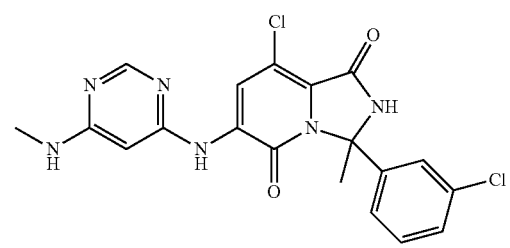 [SMILES: CNc1cc(Nc2cc(Cl)c3n(c2=O)C(C)(c2cccc(Cl)c2)NC3=O)ncn1]

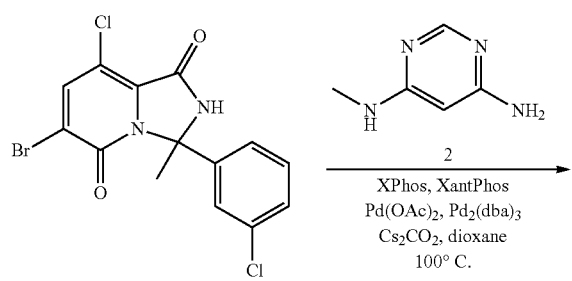

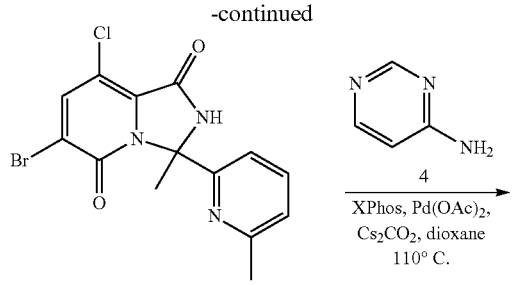

Synthesis of 8-chloro-3-(3-chlorophenyl)-3-methyl-6-[[6-(methylamino)pyrimidin-4-yl]amino]-2H-imidazo[1,5-a]pyridine-1,5-dione (Cpd. No. 89)

The synthesis of compound 89 was carried out as described above using the general protocol of Procedure H. Yellow solid; Yield: 50 mg, 16%; MS (ESI) m/z 431.32 [M+1]$^+$; $^1$H NMR (400 MHz, DMSO-d$_6$) δ 10.03 (s, 1H), 8.89 (s, 1H), 8.70 (s, 1H), 8.25 (s, 1H), 7.51 (s, 1H), 7.41 (m, 2H), 7.37 (m, 1H), 7.05 (s, 1H), 6.24 (s, 1H), 2.68 (s, 3H), 2.19 (s, 3H).

Example 90

Synthesis of 8-chloro-3-methyl-3-(6-methyl-2-pyridyl)-6-(pyrimidin-4-ylamino)-2H-imidazo[1,5-a]pyridine-1,5-dione (Cpd. No. 90)

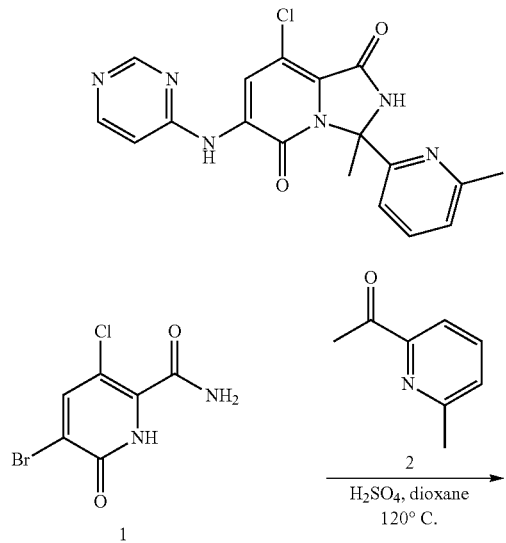

Synthesis of 6-bromo-8-chloro-3-methyl-3-(6-methyl-2-pyridyl)-2H-imidazo[1,5-a]pyridine-1,5-dione (3)

The synthesis of intermediate 3 was carried out as described above using the general protocol of Procedure A. Brown solid; Yield: 0.41 g, 56%; MS (ESI) m/z 370 [M+1]$^+$; $^1$H NMR (400 MHz, DMSO-d$_6$) δ 10.28 (m, 1H), 8.30 (s, 1H), 7.73 (m, 1H), 7.39 (m, 1H), 7.24 (m, 1H), 2.29 (s, 3H), 2.20 (s, 3H).

Synthesis of 8-chloro-3-methyl-3-(6-methyl-2-pyridyl)-6-(pyrimidin-4-ylamino)-2H-imidazo[1,5-a]pyridine-1,5-dione (Cpd. No. 90)

The synthesis of compound 90 was carried out as described above using the general protocol of Procedure B. Light yellow solid; Yield: 0.15 g, 48%; MS (ESI) m/z 383.37 [M+1]$^+$; $^1$H NMR (400 MHz, DMSO-d$_6$) δ 10.00 (s, 1H), 9.48 (s, 1H), 8.83 (s, 1H), 8.81 (s, 1H), 8.39 (d, J=11.92 Hz, 1H), 7.72 (t, J=7.78 Hz, 1H), 7.37 (m, 1H), 7.31 (m, 1H), 7.22 (m, 1H), 2.38 (s, 3H), 2.25 (s, 3H).

Example 91

Synthesis of N-[6-[[8-chloro-3-(3-fluorophenyl)-1,5-dioxo-2,3-dihydroimidazo[1,5-a]pyridin-6-yl]amino]pyrimidin-4-yl]cyclopropanecarboxamide (Cpd. No. 91)

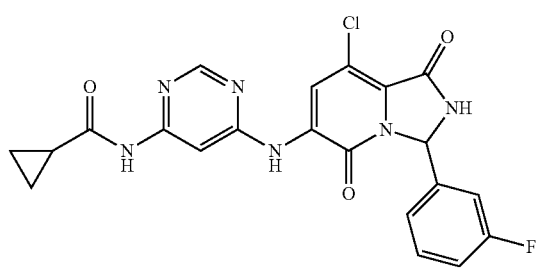 [SMILES: O=C1NC(c2cccc(F)c2)n2c1c(Cl)cc(Nc1cc(NC(=O)C3CC3)ncn1)c2=O]

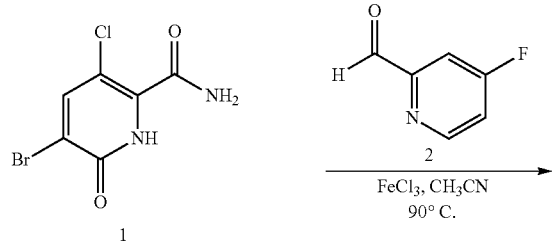

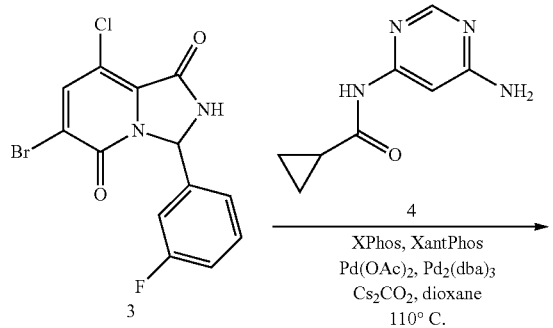

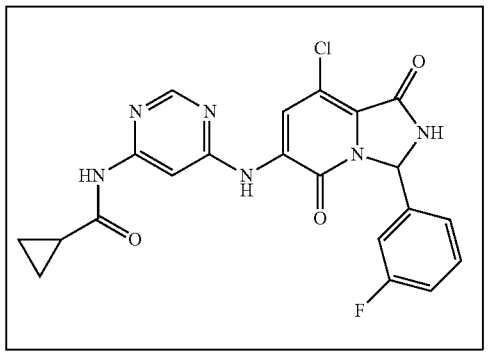

Synthesis of 6-bromo-8-chloro-3-(3-fluorophenyl)-
2,3-dihydroimidazo[1,5-a]pyridine-1,5-dione (3)

A mixture of 5-bromo-3-chloro-6-oxo-1H-pyridine-2-carboxamide (1, 0.4 g, 1.59 mmol), 3-fluorobenzaldehyde (2, 0.69 g, 5.57 mmol), acetonitrile (15 mL) and iron(III) chloride (1.81 g, 11.13 mmol) in a sealed tube was heated at 90° C. for 16 h. Once TLC showed consumption of the starting material, the mixture was cooled and filtered through a celite bed. The celite was washed with acetonitrile and the filtrate was concentrated under vacuum. The crude residue was subjected to flash column chromatography eluting with 35% ethyl acetate in hexane. The desired fractions were collected, concentrated and dried under high vacuum to afford 6-bromo-8-chloro-3-(3-fluorophenyl)-2,3-dihydroimidazo[1,5-a]pyridine-1,5-dione (3) as a yellow solid. Yield: 0.35 g, 61%; MS (ESI) m/z 357.20 [M+1]$^+$.

Synthesis of N-[6-[[8-chloro-3-(3-fluorophenyl)-1,
5-dioxo-2,3-dihydroimidazo[1,5-a]-pyridin-6-yl]
amino]pyrimidin-4-yl]cyclopropanecarboxamide
(Cpd. No. 91)

The synthesis of compound 91 was carried out as described above using the general protocol of Procedure H. Yellow solid; Yield: 46 mg, 18%. MS (ESI) m/z 455.33 [M+1]$^+$; $^1$H NMR (400 MHz, DMSO-d$_6$) δ 10.89 (s, 1H), 10.06 (s, 1H), 9.47 (s, 1H), 8.76 (s, 1H), 8.58 (s, 1H), 7.90 (s, 1H), 7.44 (m, 1H), 7.41 (m, 1H), 7.24 (m, 2H), 6.62 (s, 1H), 2.00 (t, J=5.68 Hz, 1H), 0.81 (m, 4H).

Example 92

Synthesis of 6-[(6-aminopyrimidin-4-yl)amino]-3-
(3-chlorophenyl)-3,8-dimethyl-2H-imidazo[1,5-a]
pyridine-1,5-dione (Cpd. No. 92)

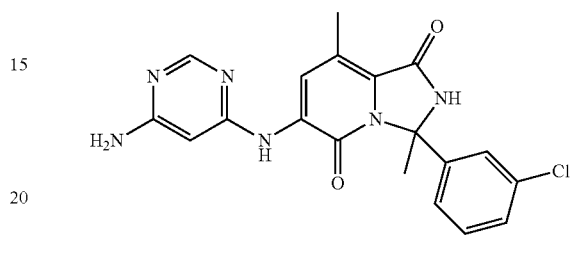

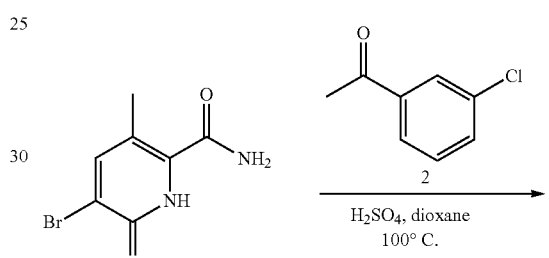

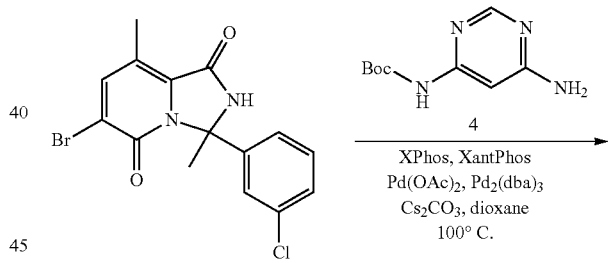

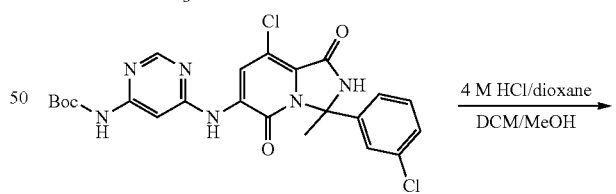

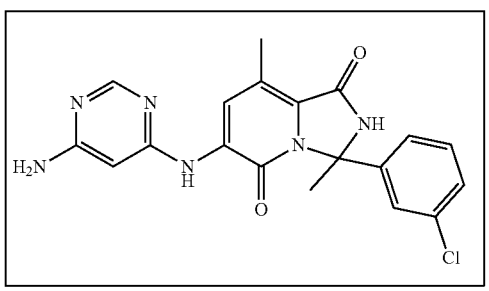

Synthesis of 6-bromo-3-(3-chlorophenyl)-3,8-dimethyl-2H-imidazo[1,5-a]pyridine-1,5-dione (3)

The synthesis of intermediate 3 was carried out as described above using the general protocol of Procedure A. Cream colored solid; Yield: 0.25 g, 39%; MS (ESI) m/z 397.23 [M+1]+.

Synthesis of tert-butyl N-[6-[[3-(3-chlorophenyl)-3,8-dimethyl-1,5-dioxo-2H-imidazo[1,5-a]pyridin-6-yl]amino]pyrimidin-4-yl]carbamate (5)

The synthesis of intermediate 5 was carried out as described above using the general protocol of Procedure H. Off-white semi-solid; Yield: 0.26 g, 31%; MS (ESI) m/z 497.06[M+1]+.

Synthesis of 6-[(6-aminopyrimidin-4-yl)amino]-3-(3-chlorophenyl)-3, 8-dimethyl-2H-imidazo[1,5-a]pyridine-1,5-dione (Cpd. No. 92)

The synthesis of compound 92 was carried out as described above using the general protocol of Procedure F. Yellow solid; Yield: 0.077 g, 37%; MS (ESI) m/z 397.13 [M+1]+; 1H NMR (400 MHz, DMSO-d6) δ 9.80 (s, 1H), 8.57 (s, 1H), 8.46 (s, 1H), 8.15 (s, 1H), 7.41 (m, 3H), 7.27 (d, J=6.3 Hz, 1H), 6.50 (s, 2H), 6.10 (s, 1H), 2.47 (s, 3H), 2.20 (s, 3H).

Example 93

Synthesis of 6-[(6-aminopyrimidin-4-yl)amino]-8-chloro-3-(3-chlorophenyl)-3-methyl-2H-imidazo[1,5-a]pyridine-1,5-dione (Cpd. No. 93)

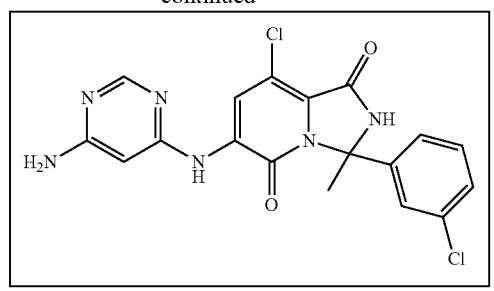

Synthesis of 6-[(6-aminopyrimidin-4-yl)amino]-8-chloro-3-(3-chlorophenyl)-3-methyl-2H-imidazo[1,5-a]pyridine-1,5-dione (Cpd. No. 93)

The synthesis of compound 93 was carried out as described above using the general protocol of Procedure I. Yellow solid; Yield: 0.17 g, 57%; MS (ESI) m/z 417.08 [M+1]+; 1H NMR (400 MHz, DMSO-d6) δ 8.55 (s, 1H), 8.15 (s, 1H), 7.39-7.35 (m, 3H), 6.08 (s, 1H), 2.17 (s, 3H).

Example 94

Synthesis of 6-[(6-aminopyrimidin-4-yl)amino]-8-chloro-spiro[2H-imidazo[1,5-a]pyridine-3,1'-cyclopentane]-1,5-dione (Cpd. No. 94)

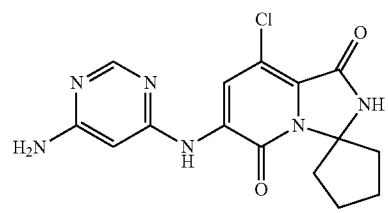 [SMILES: Nc1cc(Nc2cc(Cl)c3n(c2=O)C2(CCCC2)NC3=O)ncn1]

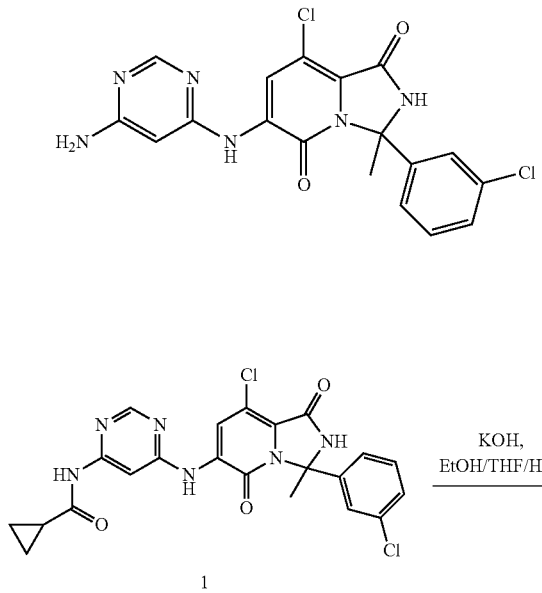

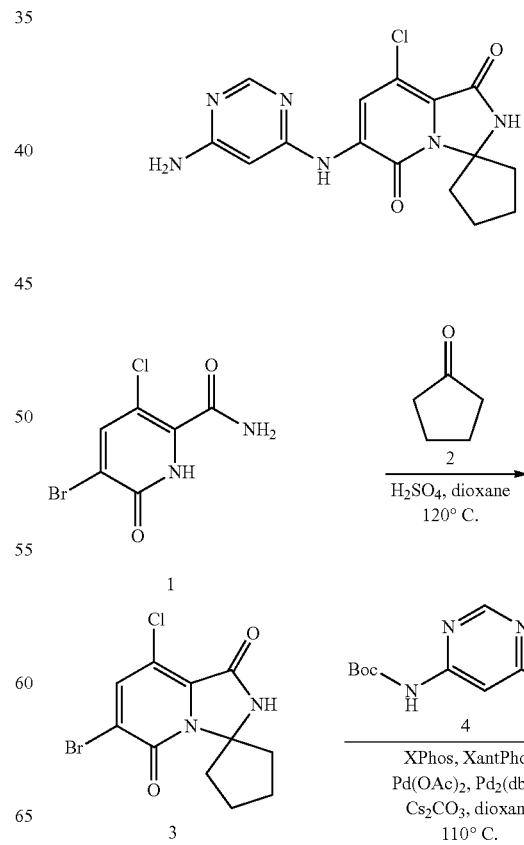

-continued

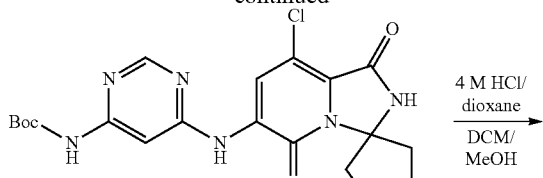

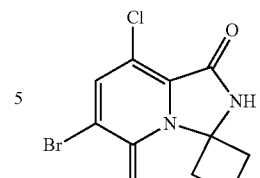

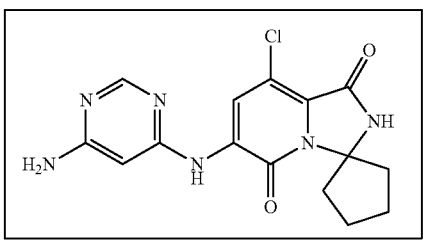

Synthesis of 6-bromo-8-chloro-spiro[2H-imidazo[1,5-a]pyridine-3,1'-cyclopentane]-1,5-dione (3)

The synthesis of intermediate 3 was carried out as described above using the general protocol of Procedure A. Off-white solid; Yield: 380 mg; 60%; MS (ESI) m/z 315.06 [M−1]⁻.

Synthesis of tert-butyl N-[6-[(8-chloro-1,5-dioxo-spiro[2H-imidazo[1,5-a]pyridine-3,1'-cyclopentane]-6-yl)amino]pyrimidin-4-yl]carbamate (5)

The synthesis of intermediate 5 was carried out as described above using the general protocol of Procedure H. Light yellow solid; Yield: 0.30 g, 71%. MS (ESI) m/z 447.03 [M+1]⁺.

Synthesis of 6-[(6-aminopyrimidin-4-yl)amino]-8-chloro-spiro[2H-imidazo[1,5-a]pyridine-3,1'-cyclopentane]-1,5-dione (Cpd. No. 94)

The synthesis of compound 94 was carried out as described above using the general protocol of Procedure F. Light yellow solid; Yield: 0.07 g, 45%. MS (ESI) m/z 347.14 [M+1]⁺; ¹H NMR (400 MHz, DMSO-d₆) δ 10.04 (s, 1H), 9.15 (s, 1H), 8.60 (s, 1H), 8.26 (s, 1H), 6.85 (s, 2H), 6.30 (s, 1H), 2.77 (s, 2H), 1.97 (s, 2H), 1.77 (m, 4H).

Example 95

Synthesis of N-[6-[(8-chloro-1,1',5-trioxo-spiro[2H-imidazo[1,5-a]pyridine-3,3'-thietane]-6-yl)amino]pyrimidin-4-yl]cyclopropanecarboxamide (Cpd. No. 95)

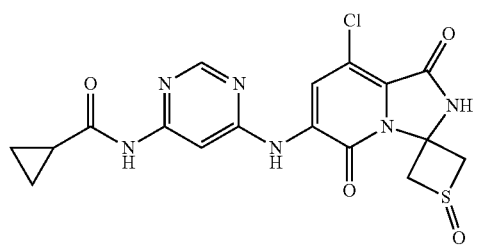 [SMILES: O=C1NC2(CS(=O)C2)n2c1c(Cl)cc(Nc1cc(NC(=O)C3CC3)ncn1)c2=O]

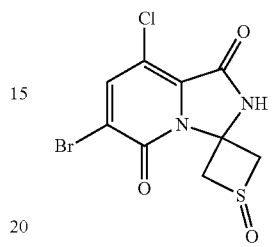

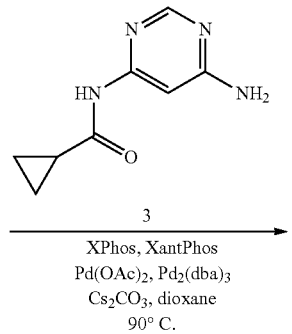

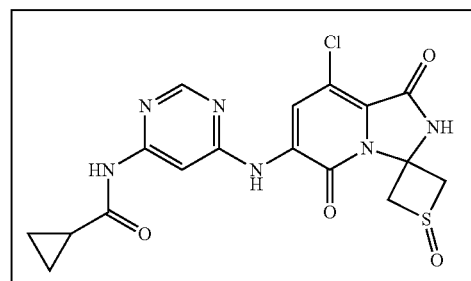

Synthesis of 6-bromo-8-chloro-1'-oxo-spiro[2H-imidazo[1,5-a]pyridine-3,3'-thietane]-1,5-dione (2)

A 30% solution of hydrogen peroxide (0.53 g, 15.55 mmol) was added dropwise to 6-bromo-8-chloro-spiro[2H-imidazo[1,5-a]pyridine-3,3'-thietane]-1,5-dione (1, 1.0 g, 3.11 mmol) dissolved in acetone (15 mL). Acetic acid (18.66 mg, 0.31 mmol) was added and the mixture was stirred at room temperature for 16 h. After TLC showed consumption of starting materials, the reaction mixture was concentrated under reduced pressure. The solids were washed with diethyl ether and dichloromethane. The solid was filtered and dried under vacuum to afford 6-bromo-8-chloro-1'-oxo-spiro [2H-imidazo [1,5-a]pyridine-3,3'-thietane]-1,5-dione (2) as an off-white solid. Yield: 0.4 g, 38%; MS (ESI) m/z 335 [M+1]⁺; ¹H NMR (400 MHz, DMSO-d₆) δ 8.32 (s, 1H), 4.62 (d, J=12 Hz, 2H), 3.54 (d, J=16 Hz, 2H).

Synthesis of N-[6-[(8-chloro-1,1',5-trioxo-spiro[2H-imidazo[1,5-a]pyridine-3,3'-thietane]-6-yl)amino]pyrimidin-4-yl]cyclopropanecarboxamide (Cpd. No. 95)

The synthesis of compound 95 was carried out as described above using the general protocol of Procedure H. Light yellow solid; Yield: 0.08 g, 24%; MS (ESI) m/z 435.4 [M+1]⁺; ¹H NMR (400 MHz, DMSO-d₆) δ 10.91 (bs, 1H), 10.45-10.32 (m, 1H), 8.76 (bs, 1H), 8.59 (bs, 1H), 8.04 (bs, 1H), 4.66-4.63 (m, 2H), 3.59-3.56 (m, 2H), 2.01 (bs, 1H), 0.84 (s, 4H).

Example 96

Synthesis of 8-chloro-1',1'-dimethyl-6-(pyrimidin-4-ylamino)spiro[2H-imidazo[1,5-a]pyridine-3,2'-cyclohexane]-1,5-dione (Cpd. No. 96)

Off white solids; Yield: 25 mg, 10%; MS (ESI) m/z 374.19 [M+1]$^+$; $^1$H NMR (400 MHz, DMSO-d$_6$) δ 9.98 (bs, 1H), 9.60 (s, 1H), 8.84 (s, 1H) 8.76 (s, 1H) 8.43 (d, J=4 Hz, 1H), 7.47 (d, J=4 Hz, 1H), 3.61-3.50 (m, 1H), 1.75-1.36 (m, 7H), 1.25 (s, 3H), 0.64 (s, 3H).

Example 97

Synthesis of N-(6-((8-chloro-3-methyl-1,5-dioxo-3-phenyl-1,2,3,5-tetrahydroimidazo[1,5-a]pyridin-6-yl)amino)pyrimidin-4-yl)cyclopropanecarboxamide (Cpd. No. 97)

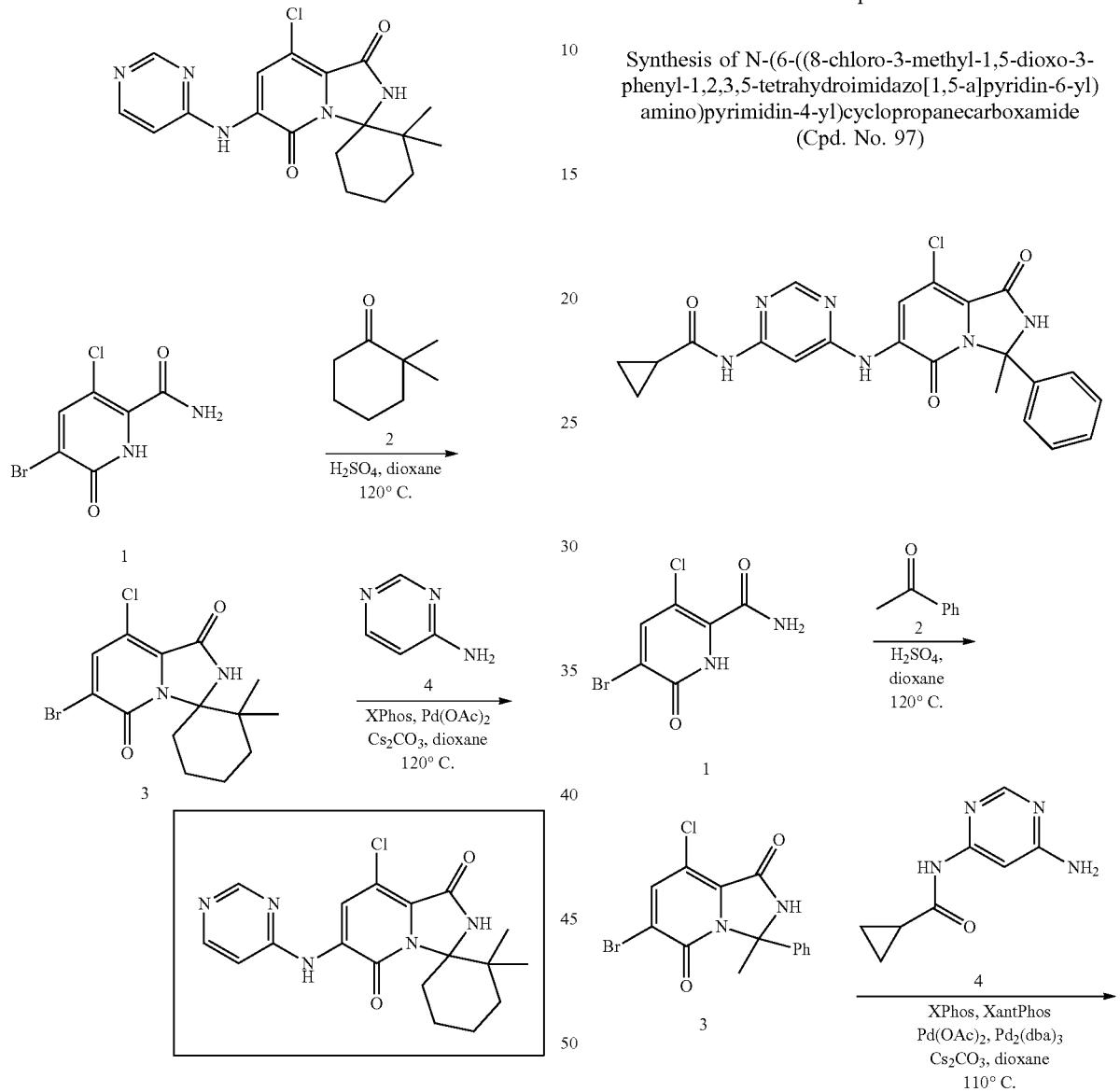

Synthesis of 6-bromo-8-chloro-1',1'-dimethyl-spiro[2H-imidazo[1,5-a]pyridine-3,2'-cyclohexane]-1,5-dione (3)

The synthesis of intermediate 3 was carried out as described above using the general protocol of Procedure A. Light brown solid; Yield: 0.41 g, 57%; MS (ESI) m/z 360.8 [M+1]$^+$.

Synthesis of 8-chloro-1',1'-dimethyl-6-(pyrimidin-4-ylamino)spiro[2H-imidazo[1,5-a]pyridine-3,2'-cyclohexane]-1,5-dione (Cpd. No. 96)

The synthesis of compound 96 was carried out as described above using the general protocol of Procedure B.

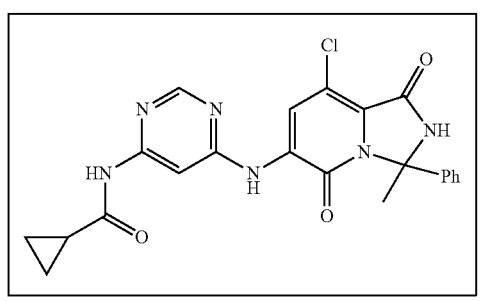

Synthesis of 6-bromo-8-chloro-3-methyl-3-phenyl-2H-imidazo[1,5-a]pyridine-1,5-dione (3)

The synthesis of intermediate 3 was carried out as described above using the general protocol of Procedure A. Green solid; Yield: 525 mg, 75%; MS (ESI) m/z 353.21 [M+1]+.

Synthesis of N-[6-[(8-chloro-3-methyl-1,5-dioxo-3-phenyl-2H-imidazo[1,5-a]pyridin-6-yl)amino]pyrimidin-4-yl]cyclopropanecarboxamide (Cpd. No. 97)

The synthesis of compound 97 was carried out as described above using the general protocol of Procedure H. Light yellow solid; Yield: 97 mg, 15%. MS (ESI) m/z 451.13 [M+1]+; $^1$H NMR (400 MHz, DMSO-$d_6$) δ 10.89 (s, 1H), 10.06 (s, 1H), 9.39 (s, 1H), 8.73 (s, 1H), 8.58 (s, 1H), 7.88 (s, 1H), 7.39 (s, 5H), 2.24 (s, 3H), 1.99 (s, 1H), 0.81 (s, 4H).

Example 98

Synthesis of of 6-[(6-aminopyrimidin-4-yl)amino]-8-methyl-spiro[2H-imidazo[1,5-a]pyridine-3,1'-cyclopentane]-1,5-dione hydrochloride (Cpd. No. 98)

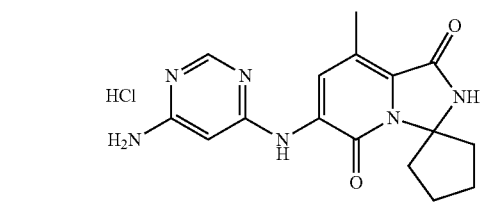 [SMILES: Cl ; Cc1cc(Nc2cc(N)ncn2)c(=O)n2c1C(=O)NC21CCCC1]

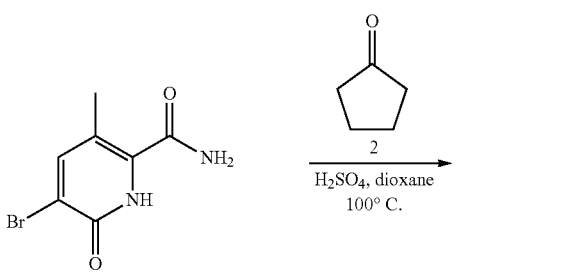

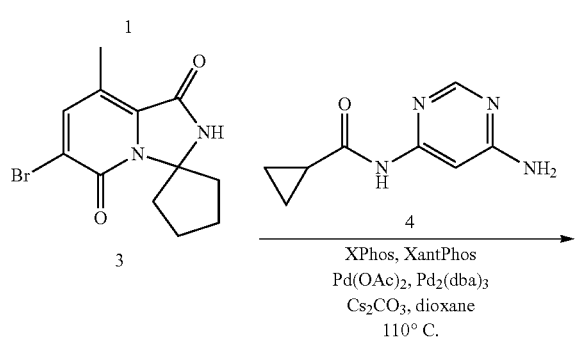

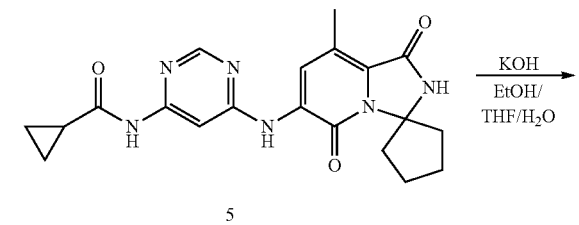

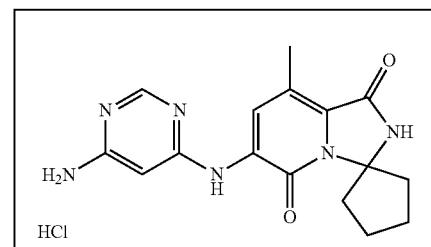

Synthesis of 6-bromo-8-methyl-spiro[2H-imidazo[1,5-a]pyridine-3,1'-cyclopentane]-1,5-dione (3)

The synthesis of intermediate 3 was carried out as described above using the general protocol of Procedure A. Off-white solid; Yield: 1.8 g, 70%; MS (ESI) m/z 297.15 [M+1]+.

Synthesis of N-[6-[(8-methyl-1,5-dioxo-spiro[2H-imidazo[1,5-a]pyridine-3,1'-cyclopentane]-6-yl)amino]pyrimidin-4-yl]cyclopropanecarboxamide (5)

The synthesis of intermediate 5 was carried out as described above using the general protocol of Procedure H. White solid; Yield: 1.30 g, 58%; MS (ESI) m/z 395.37 [M+1]+; $^1$H NMR (400 MHz, DMSO-$d_6$) δ 10.86 (s, 1H), 9.88 (s, 1H), 9.20 (s, 1H), 8.51 (d, J=15.96 Hz, 2H), 7.86 (s, 1H), 2.81 (m, 2H), 2.45 (m, 3H), 2.09 (m, 3H), 1.82 (m, 2H), 1.67 (m, 2H), 0.72 (m, 4H).

Synthesis of 6-[(6-aminopyrimidin-4-yl)amino]-8-methyl-spiro[2H-imidazo[1,5-a]-pyridine-3,1'-cyclopentane]-1,5-dione hydrochloride (Cpd. No. 98)

The synthesis of compound 98 was carried out as described above using the general protocol of Procedure I. White solid; Yield: 0.76 g, 87%; MS (ESI) m/z 327.49 [M+1]+; $^1$H NMR (400 MHz, DMSO-$d_6$) δ 10.02 (s, 1H), 9.75 (s, 1H), 8.46 (s, 1H), 8.12 (s, 1H), 7.88 (s, 2H), 6.39 (s, 1H), 2.77 (m, 2H), 2.41 (s, 3H), 1.96 (m, 2H), 1.83 (m, 2H), 1.70 (m, 2H).

Example 99

Synthesis of 6-[(6-aminopyrimidin-4-yl)amino]-8-chloro-4',4'-difluoro-spiro[2H-imidazo[1,5-a]pyridine-3,1'-cyclohexane]-1,5-dione hydrochloride (Cpd. No. 99)

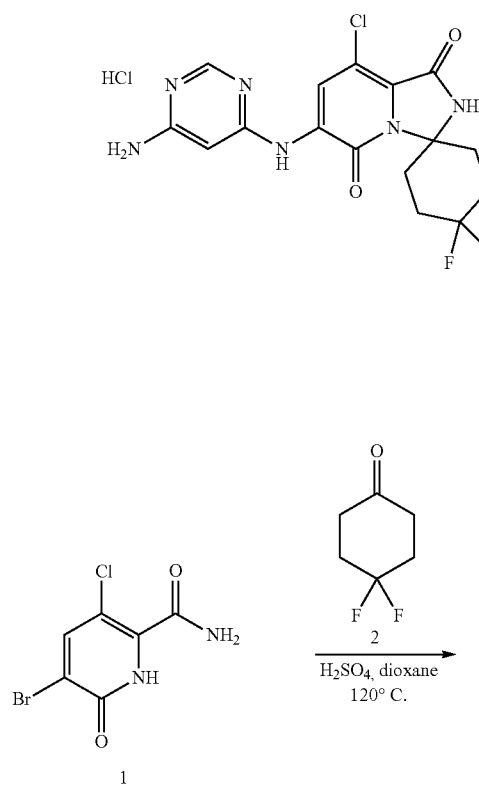

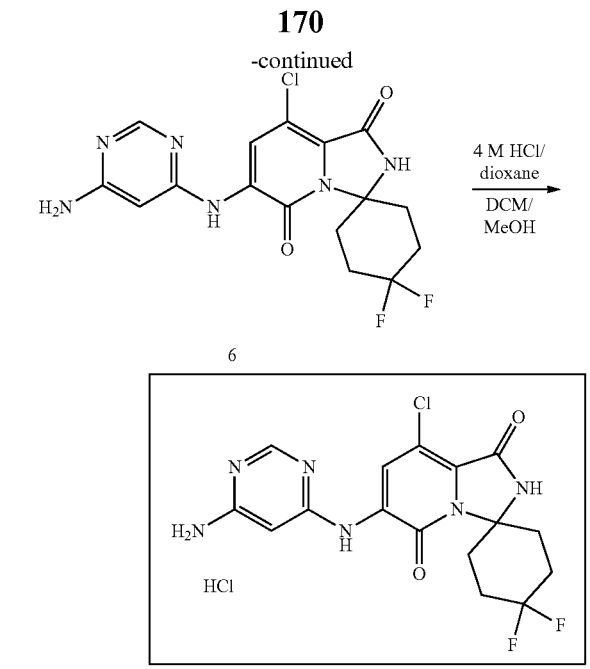

Synthesis of 6-bromo-8-chloro-4',4'-difluoro-spiro[2H-imidazo[1,5-a]pyridine-3,1' cyclohexane]-1,5-dione (3)

The synthesis of intermediate 3 was carried out as described above using the general protocol of Procedure A. Off-white solid; Yield: 5.9 g. 80%; MS (ESI) m/z 364.92 [M−1]⁻.

Synthesis of N-[6-[(8-chloro-4',4'-difluoro-1,5-dioxo-spiro[2H-imidazo[1,5-a]pyridine-3,1'-cyclohexane]-6-yl)amino]pyrimidin-4-yl]cyclopropanecarboxamide (5)

The synthesis of intermediate 5 was carried out as described above using the general protocol of Procedure B. Off-white solid; Yield: 4.71 g, 63%; MS (ESI) m/z 465.38 [M+1]⁺; $^1$H NMR (400 MHz, DMSO-$d_6$) δ 10.92 (s, 1H), 10.47 (s, 1H), 9.51 (s, 1H), 8.71 (s, 1H), 8.59 (s, 1H), 7.98 (s, 1H), 3.32 (m, 2H), 2.24 (m, 4H), 2.02 (m, 1H), 1.71 (m, 2H), 0.64 (m, 4H).

Synthesis of 6-[(6-aminopyrimidin-4-yl)amino]-8-chloro-4',4'-difluoro-spiro[2H-imidazo[1,5-a]pyridine-3,1'-cyclohexane]-1,5-dione (6)

The synthesis of intermediate 6 was carried out as described above using the general protocol of Procedure I. Light yellow solid; Yield: 0.35 g, 41%; MS (ESI) m/z 397.33 [M+1]⁺.

Synthesis of 6-[(6-aminopyrimidin-4-yl)amino]-8-chloro-4',4'-difluoro-spiro[2H-imidazo-[1,5-a]pyridine-3,1'-cyclohexane]-1,5-dione hydrochloride (Cpd. No. 99)

The synthesis of compound 99 was carried out as described above using the general protocol of Procedure F. Yellow solid; Yield: 0.66 g, 92%; MS (ESI) m/z 397.17 [M+1]⁺; $^1$H NMR (400 MHz, DMSO-$d_6$) δ 10.56 (s, 1H), 9.87 (s, 1H), 8.51 (s, 1H), 8.43 (s, 1H), 7.89 (s, 2H), 6.52 (s, 1H), 3.22 (m, 2H), 2.21 (m, 4H), 1.74 (d, J=12.12 Hz, 2H).

Example 100

Synthesis of 8-chloro-6-((7-cyclopropylpyrido[4,3-d]pyrimidin-4-yl)amino)-3,3-dimethyl-2,3-dihydroimidazo[1,5-a]pyridine-1,5-dione (Cpd. No. 100)

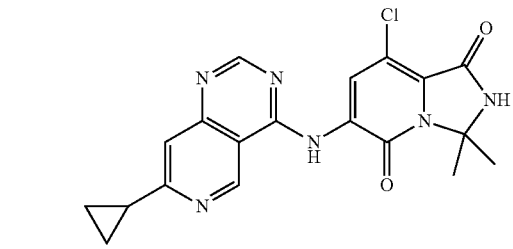 [SMILES: CC1(C)NC(=O)c2c(Cl)cc(Nc3ncnc4cc(C5CC5)ncc34)c(=O)n21]

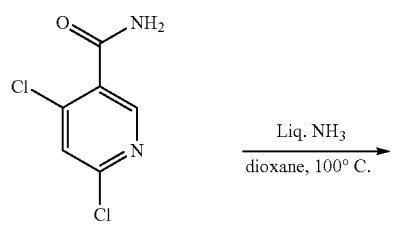

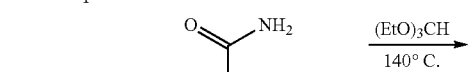

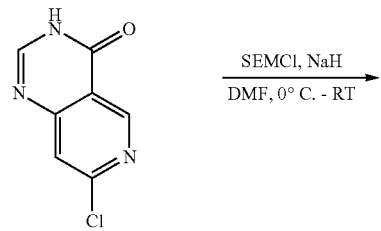

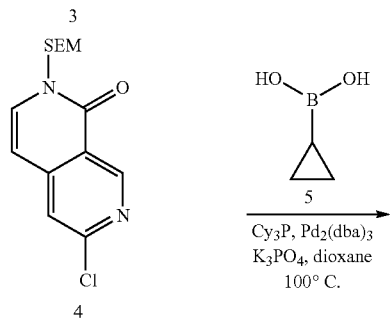

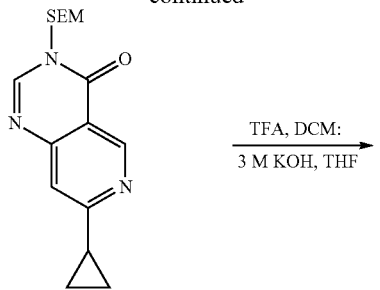

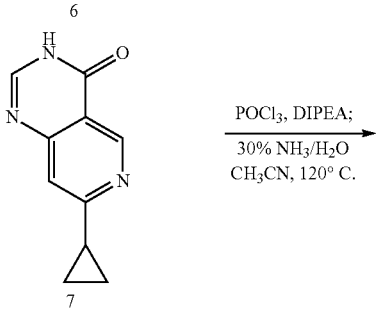

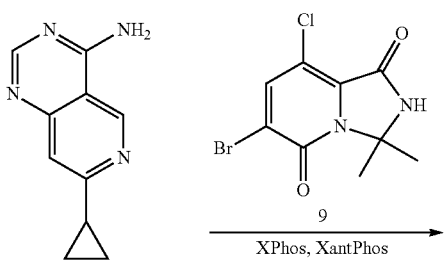

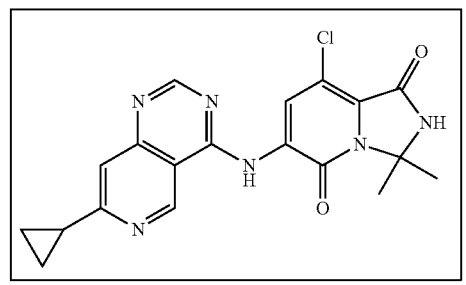

Synthesis of 4-amino-6-chloro-pyridine-3-carboxamide (2)

To a well stirred solution of 4,6-dichloropyridine-3-carboxamide (11.0 g, 57.59 mmol) in 1,4-dioxane (20 mL) in steel bomb was added the liquid ammonia (50 mL, 57.59 mmol). The steel bomb was closed and heated the reaction to 100° C. for 9 h. The progress of the displacement reaction was monitored by TLC and LCMS. After completion the solid formed was filtered. The filtrate was also concentrated as it also contains 50% product. The combined solids were dried under vacuum to afford 4-amino-6-chloro-pyridine-3-carboxamide (2) as a light brown solid. Yield: 10.6 g, crude, 47%; 1H NMR (400 MHz, DMSO-$d_6$) δ 8.36 (s, 1H), 7.97 (s, 1H), 7.50 (s, 1H), 7.37 (s, 1H), 6.65 (s, 1H).

Synthesis of 7-chloro-3H-pyrido[4,3-d]pyrimidin-4-one (3)

4-Amino-6-chloro-pyridine-3-carboxamide (2, 4.5 g, 26.23 mmol) was added to a pressure tube and triethylorthoformate (30 mL) was added. The reaction vessel was sealed and heated to 140° C. for 11 h. After the cyclization was complete, the reaction mixture was concentrated under reduced pressure, and to the solid obtained was added diethyl ether. The solid was filtered, washed with diethyl ether and dried in vacuum to afford 7-chloro-3H-pyrido[4,3-d]pyrimidin-4-one (3) as brown solid. MS (ESI) m/z 181.90 [M+1]$^+$.

Synthesis of 7-chloro-3-(2-trimethylsilylethoxymethyl)pyrido[4,3-d]pyrimidin-4-one (4)

In a dried round bottom flask under $N_2$ atmosphere was added 7-chloro-3H-pyrido[4,3-d]pyrimidin-4-one (3, 9.0 g, 49.56 mmol) to dimethylformamide (50 mL). The solution was stirred at 0° C. and sodium hydride (1.78 g, 74.35 mmol) was added portion-wise over 10 min. The anionic suspension was stirred for 1 h at 0° C. followed by the addition of 2-(trimethylsilyl)ethoxymethyl chloride (12.4 g, 74.35 mmol) at 0° C. The reaction mixture was stirred at room temperature for 5 h. After consumption of starting materials as indicated by TLC, the reaction mixture was quenched with ice. A solid precipitates. It was filtered and washed with excess n-pentane. The solid was dried under vacuum to afford 7-chloro-3-(2-trimethylsilylethoxymethyl)pyrido[4,3-d]pyrimidin-4-one (4) as a brown solid. Yield: 9.1 g, 59%; 1H NMR (400 MHz, DMSO-$d_6$) δ 9.17 (s, 1H), 8.72 (s, 1H), 7.79 (s, 1H), 5.49 (s, 2H), 3.65 (t, J=16 Hz, 2H), 0.90 (t, J=16 Hz, 2H), −0.03 (s, 9H).

Synthesis of 7-cyclopropyl-3-(2-trimethylsilylethoxymethyl)pyrido[4,3-d]pyrimidin-4-one (6)

The synthesis of intermediate 6 was carried out as described above using the general protocol of Procedure G. Yellow liquid; Yield: 2.1 g, 52%; MS (ESI) m/z 319 [M+1]$^+$; $^1$H NMR (400 MHz, DMSO-$d_6$) δ 9.16 (s, 1H), 8.57 (s, 1H), 7.52 (s, 1H), 7.27 (s, 1H), 5.33 (s, 2H), 3.63-3.59 (m, 2H), 2.32-2.26 (m, 1H) 1.07-1.05 (m, 4H), 0.89 (t, J=8.0 Hz, 1H), 0.04 (s, 9H).

Synthesis of 7-cyclopropyl-3H-pyrido[4,3-d]pyrimidin-4-one (7)

To 7-cyclopropyl-3-(2-trimethylsilylethoxymethyl)pyrido[4,3-d]pyrimidin-4-one (6, 2.0 g, 6.3 mmol) in dichloromethane (10 mL) at 0° C. was added a 20% trifluoroacetic acid solution in dichloromethane (10 mL, 6.3 mmol). The reaction mixture was warmed to room temperature and stirred for 3 h. After complete deprotection as indicated by TLC the reaction mixture was concentrated, taken up in dichloromethane and concentrated. This process was repeated 2-3 times. Tetrahydrofuran (20 mL) was added to the crude residue and cooled to 0° C. 3 M potassium hydroxide solution (10 mL, 6.3 mmol) was added to the solution bringing the pH to 9-10. The suspension was stirred for 6-7 h. The reaction was concentrated, the residue was diluted with 10% methanol in dichloromethane and the organic layers were washed with 10 mL water and 10 mL of a saturated brine solution. The organic layers were separated, dried over magnesium sulfate, filtered and concentration to dryness to afford 7-cyclopropyl-3H-pyrido [4,3-d]pyrimidin-4-one (7) as a brown solid. Yield: 1.00 g, 85%; MS (ESI) m/z 188.18 [M+1]$^+$; $^1$H NMR (400 MHz, DMSO-$d_6$) δ 12.57 (bs, 1H), 9.15 (s, 1H), 8.32 (s, 1H), 7.38 (s, 1H), 2.27 (bs, 1H), 1.03 (bs, 4H).

Synthesis of 7-cyclopropylpyrido[4,3-d]pyrimidin-4-amine (8)

To 7-cyclopropyl-3H-pyrido[4,3-d]pyrimidin-4-one (7, 1.0 g, 5.34 mmol) in a round bottom flask under a nitrogen atmosphere was added N,N-diisopropylethylamine (9.45 mL, 53.42 mmol) at 0° C. To this stirred mixture was slowly added phosphorus(V) oxychloride (7.48 mL, 80.13 mmol). The reaction mixture was stirred at room temperature for 2-3 h until a clear solution was obtained. The solution was concentrated under reduced pressure under inert conditions, taken up in excess toluene and reconcentrated. This process was repeated sev N,N-diisopropylethylamine eral times. The residue was dissolved in acetonitrile to it was added 30% aqueous ammonia (30 mL). The mixture was heated to 120° C. for 16 h in sealed tube. The reaction mixture was diluted with 10% methanol in dichloromethane and extracted from the aqueous ammonia. The organic layers were separated, dried over Sodium sulfate, filtered and concentrated to dryness. The crude residue was given Methanol washing. The solid obtained was dried to afford 7-cyclopropylpyrido[4,3-d]pyrimidin-4-amine (8) as a brown solid. Yield: 0.60 g, 60%; MS (ESI) m/z 375.8 [M+1]$^+$; $^1$H NMR (400 MHz, DMSO-$d_6$) δ 9.34 (s, 1H), 8.43 (s, 1H), 8.26-7.99 (m, 2H), 7.39 (s, 1H), 1.75 (s, 1H), 1.01-0.84 (s, 4H).

Synthesis of 8-chloro-6-[(7-cyclopropylpyrido[4,3-d]pyrimidin-4-yl)amino]-3,3-dimethyl-2H-imidazo[1,5-a]pyridine-1,5-dione (Cpd. No. 100)

The synthesis of compound 100 was carried out as described above using the general protocol of Procedure H. Pale yellow solid; Yield: 0.37 g, 58%; MS (ESI) m/z 397.48 [M+1]$^+$; $^1$H NMR (400 MHz, DMSO-$d_6$) δ 9.46 (s, 1H), 8.85 (s, 1H), 8.75 (s, 1H), 7.58 (s, 1H), 2.32-2.29 (m, 1H), 1.82 (s, 6H), 1.08-1.02 (m, 4H).

Example 101

Synthesis of 6-((6-aminopyrimidin-4-yl)amino)-3-(3-fluorophenyl)-3,8-dimethyl-2,3-dihydroimidazo[1,5-a]pyridine-1,5-dione (Cpd. No. 101)

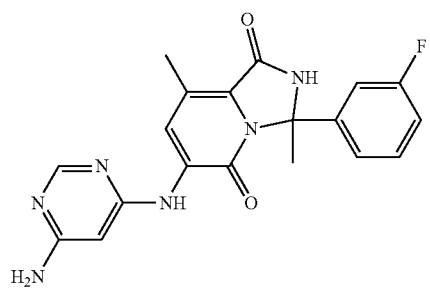 [SMILES: Cc1cc(Nc2cc(N)ncn2)c(=O)n2c1C(=O)NC2(C)c1cccc(F)c1]

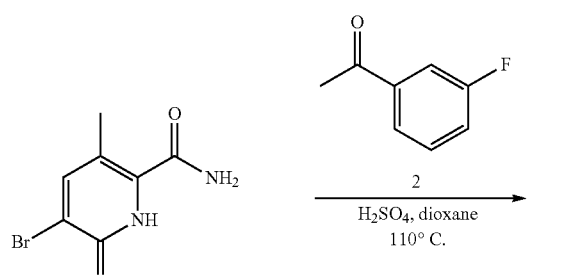

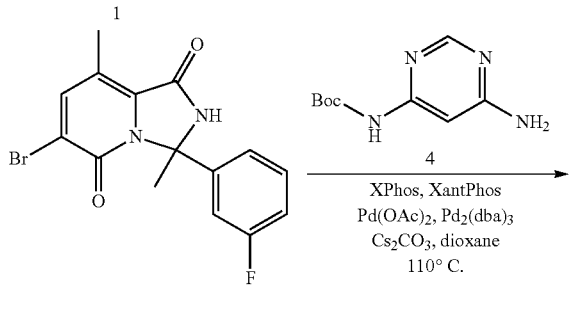

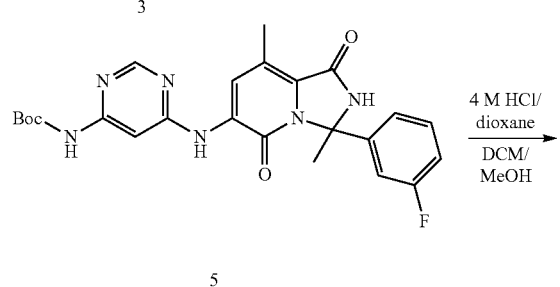

Synthesis of 6-bromo-3-(3-fluorophenyl)-3, 8-dimethyl-2,3-dihydroimidazo[1,5-a]pyridine-1,5-dione (3)

The synthesis of intermediate 3 was carried out as described above using the general protocol of Procedure A. Yellow solid; Yield: 0.35 g, 46%; MS (ESI) m/z: 351.17 [M+1]$^+$; $^1$H NMR (400 MHz, DMSO-d$_6$) δ 10.17 (s, 1H), 8.08 (s, 1H), 7.42 (m, 1H), 7.21 (m, 2H), 7.13 (d, J=8.0 Hz, 1H), 2.43 (s, 3H), 2.1 (s, 3H).

Synthesis of tert-butyl (6-((3-(3-fluorophenyl)-3, 8-dimethyl-1,5-dioxo-1,2,3,5-tetrahydroimidazo[1,5-a]pyridin-6-yl)amino)pyrimidin-4-yl)carbamate (5)

The synthesis of intermediate 5 was carried out as described above using the general protocol of Procedure H. Yellow solid; Yield: 0.15 g, 34%; MS (ESI) m/z 481.47 [M+1]$^+$; $^1$H NMR (400 MHz, DMSO-d$_6$) δ 10.0-9.80 (brs, 2H), 9.01 (brs, 1H), 8.47 (s, 1H), 8.43 (s, 1H), 7.52 (s, 1H), 7.38 (m, 1H), 7.10-7.22 (m, 3H), 2.43 (s, 3H), 2.16 (s, 3H), 1.46 (s, 9H).

Synthesis of 6-((6-aminopyrimidin-4-yl)amino)-3-(3-fluorophenyl)-3, 8-dimethyl-2,3-dihydroimidazo [1,5-a]pyridine-1,5-dione (Cpd. No. 101)

The synthesis of compound 101 was carried out as described above using the general protocol of Procedure F. Off-white solid; Yield: 0.09 g, 76%; MS (ESI) m/z 381.50 [M+1]$^+$; $^1$H NMR (400 MHz, DMSO-d$_6$) δ 9.82 (s, 1H), 8.60 (s, 1H), 8.45 (s, 1H), 8.17 (s, 1H), 7.42 (m, 1H), 7.25-7.10 (m, 3H), 6.54 (brs, 2H), 6.10 (s, 1H), 2.47 (s, 3H), 2.20 (s, 3H).

Example 102

Synthesis of 6-((6-aminopyrimidin-4-yl)amino)-3,3, 8-trimethyl-2,3-dihydroimidazo[1,5-a]pyridine-1,5-dione hydrochloride (Cpd. No. 102)

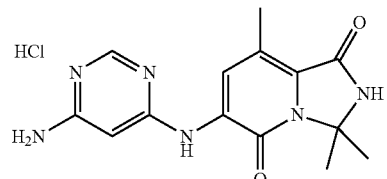

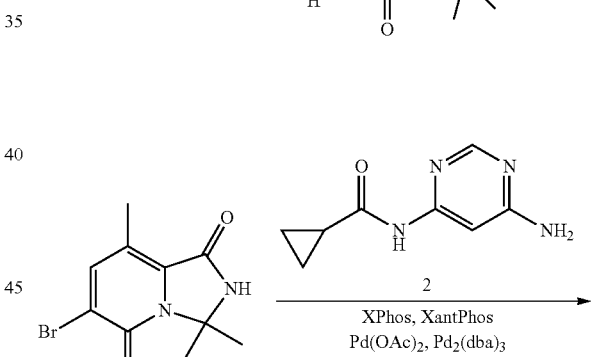

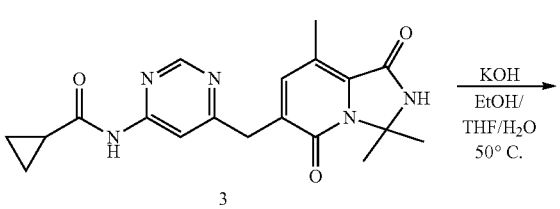

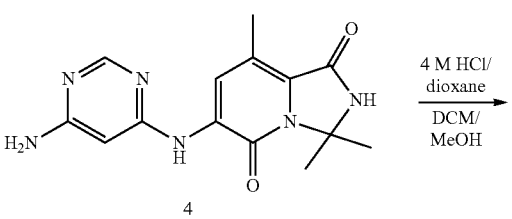

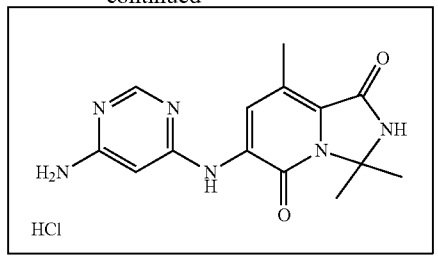

Synthesis of N-(6-((3,3,8-trimethyl-1,5-dioxo-1,2,3,5-tetrahydroimidazo[1,5-a]pyridin-6-yl)amino)pyrimidin-4-yl)cyclopropanecarboxamide (3)

The synthesis of intermediate 3 was carried out as described above using the general protocol of Procedure H. Yellow solid; Yield: 0.85 g, 50%; MS (ESI) m/z 369.0 [M+1]$^+$; $^1$H NMR (400 MHz, DMSO-d$_6$) δ 10.86 (s, 1H), 9.52 (s, 1H), 9.16 (s, 1H), 8.53 (s, 1H), 8.47 (s, 1H), 7.86 (s, 1H), 5.75 (s, 1H), 2.42 (s, 3H), 2.02 (m, 1H), 1.77 (s, 6H), 0.88-0.80 (m, 4H).

Synthesis of 6-((6-aminopyrimidin-4-yl)amino)-3,3,8-trimethyl-2,3-dihydroimidazo[1,5-a]pyridine-1,5-dione (4)

The synthesis of intermediate 4 was carried out as described above using the general protocol of Procedure I. Yellow solid; Yield: 0.55 g, 80%; MS (ESI) m/z 301.29 [M+1]$^+$; $^1$H NMR (400 MHz, DMSO-d$_6$) δ 9.46 (s, 1H), 8.61 (s, 1H), 8.38 (s, 1H), 8.16 (s, 1H), 6.53 (brs, 2H), 6.16 (s, 1H), 2.40 (s, 3H), 1.77 (s, 6H).

Synthesis of 6-((6-aminopyrimidin-4-yl)amino)-3,3,8-trimethyl-2,3-dihydroimidazo[1,5-a]pyridine-1,5-dione hydrochloride (Cpd. No. 102)

The synthesis of compound 102 was carried out as described above using the general protocol of Procedure F. Yellow solid; Yield: 0.60 g, 97%; MS (ESI) m/z 301.25 [M+1]$^+$; $^1$H NMR (400 MHz, DMSO-d$_6$) δ 9.71 (s, 1H), 9.67 (s, 1H), 8.45 (s, 1H), 8.12 (s, 1H), 7.95-7.70 (brs, 2H), 6.39 (s, 1H), 2.41 (s, 3H), 1.77 (s, 6H).

Example 103

Synthesis of 6-[(6-aminopyrimidin-4-yl)amino]-4',4'-difluoro-8-methyl-spiro[2H-imidazo[1,5-a]pyridine-3,1'-cyclohexane]-1,5-dione hydrochloride (Cpd. No. 103)

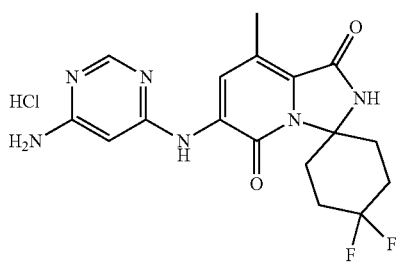 [SMILES: Cl ; Cc1cc(Nc2cc(N)ncn2)c(=O)n2c1C(=O)NC21CCC(F)(F)CC1]

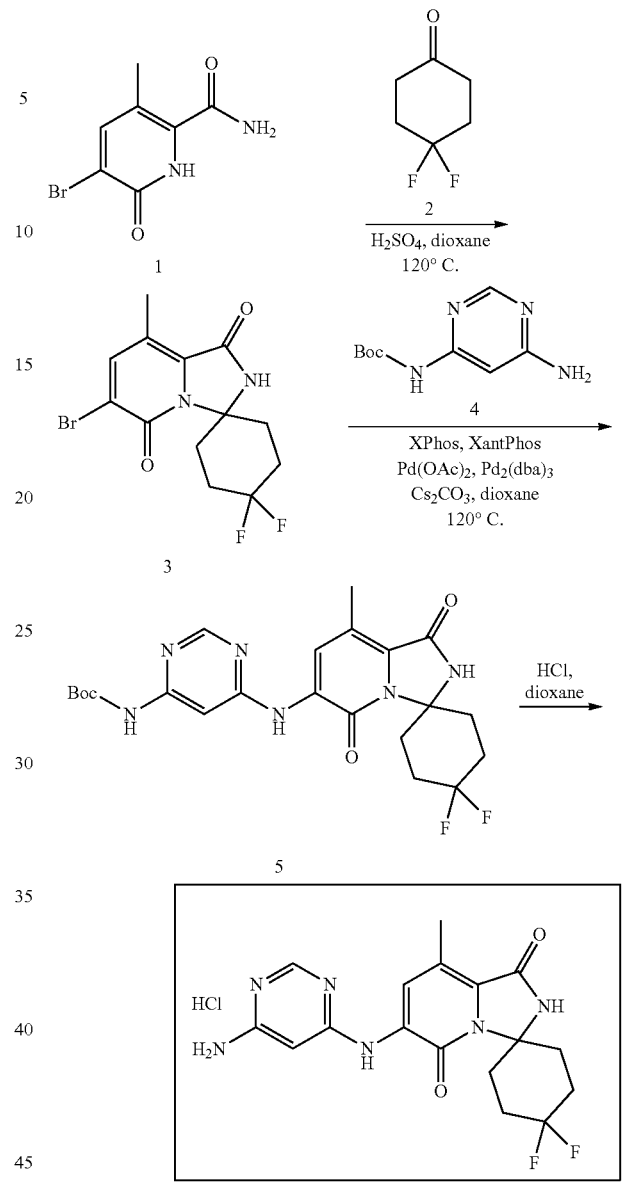

Synthesis of 6-bromo-4',4'-difluoro-8-methyl-spiro[2H-imidazo[1,5-a]pyridine-3,1'-cyclohexane]-1,5-dione (3)

The synthesis of intermediate 3 was carried out as described above using the general protocol of Procedure A. Off-white solid; Yield: 1.2 g, 53%; MS (ESI) m/z 346.99 [M+1]$^+$.

Synthesis of tert-butyl N-[6-[(4',4'-difluoro-8-methyl-1,5-dioxo-spiro[2H-imidazo[1,5-a]pyridine-3,1'-cyclohexane]-6-yl)amino]pyrimidin-4-yl]carbamate (5)

The synthesis of intermediate 5 was carried out as described above using the general protocol of Procedure H. Yellow solid; Yield: 0.8 g, 58%; MS (ESI) m/z 477.48 [M+1]$^+$.

Synthesis of 6-[(6-aminopyrimidin-4-yl)amino]-4',4'-difluoro-8-methyl-spiro[2H-imidazo[1,5-a]pyridine-3,1'-cyclohexane]-1,5-dione hydrochloride (Cpd. No. 103)

The synthesis of compound 103 was carried out as described above using the general protocol of Procedure D. Yellow solid; Yield: 0.75 g, 97%; MS (ESI) m/z 377.40 [M+1]$^+$; $^1$H NMR (400 MHz, DMSO-d$_6$) δ 10.40 (s, 1H), 9.73 (s, 1H), 8.46 (s, 1H), 8.15 (s, 1H), 7.87 (brs, 2H), 6.40 (s, 1H), 3.30 (m, 2H), 2.43 (s, 3H), 2.32-2.29 (m, 1H), 2.20-2.10 (m, 3H), 1.65 (m, 2H).

Example 104

Synthesis of 8-chloro-6-(pyrimidin-4-ylamino)spiro[2H-imidazo[1,5-a]pyridine-3,4'-piperidine]-1,5-dione hydrochloride (Cpd. No. 104)

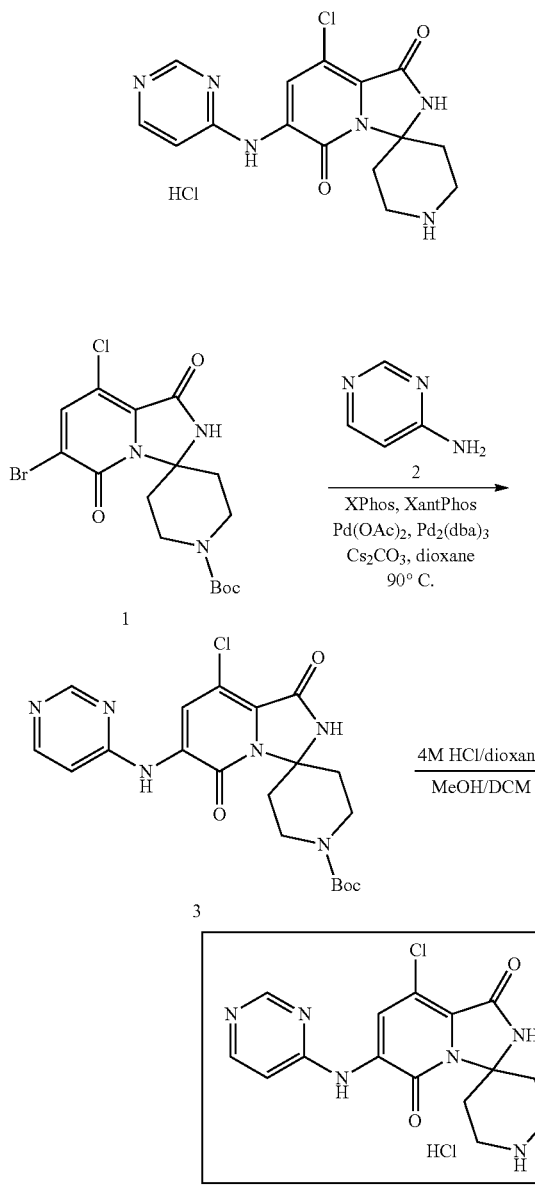

Synthesis of tert-butyl 8-chloro-1,5-dioxo-6-(pyrimidin-4-ylamino)spiro[2H-imidazo[1,5-a]pyridine-3,4'-piperidine]-1'-carboxylate (3)

The synthesis of intermediate 3 was carried out as described above using the general protocol of Procedure H. Yellow solid; Yield: 0.8 g, 52%; MS (ESI) m/z 447 [M+1]$^+$.

Synthesis of 8-chloro-6-(pyrimidin-4-ylamino)spiro[2H-imidazo[1,5-a]pyridine-3,4'-piperidine]-1,5-dione hydrochloride (Cpd. No. 104)

The synthesis of compound 104 was carried out as described above using the general protocol of Procedure F. Pale yellow solid; Yield: 0.6 g, 93%; MS (ESI) m/z 347.37 [M+1]$^+$; $^1$H NMR (400 MHz, DMSO-d$_6$) δ 10.69 (s, 1H), 10.52 (brs, 1H), 9.46 (m, 1H), 8.72 (s, 1H), 8.52 (d, J=6.0 Hz, 1H), 7.57 (d, J=5.6 Hz, 1H), 3.50-3.45 (m, 2H), 3.36-3.12 (m, 4H), 1.91-1.86 (m, 2H).

Example 105

Synthesis of 6-[(6-aminopyrimidin-4-yl)amino]-3-tert-butyl-8-chloro-3-methyl-2H-imidazo[1,5-a]pyridine-1,5-dione hydrochloride (Cpd. No. 105)

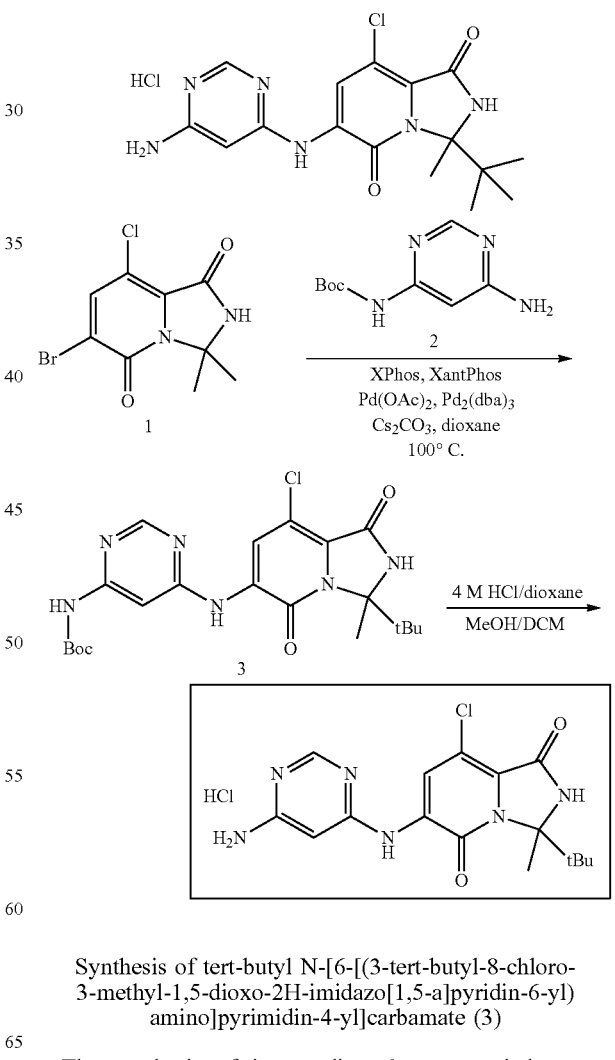

Synthesis of tert-butyl N-[6-[(3-tert-butyl-8-chloro-3-methyl-1,5-dioxo-2H-imidazo[1,5-a]pyridin-6-yl)amino]pyrimidin-4-yl]carbamate (3)

The synthesis of intermediate 3 was carried out as described above using the general protocol of Procedure H.

Yellow solid; Yield: 0.21 g, 50%; MS (ESI) m/z 431.39 [M+1]+; 1H NMR (400 MHz, DMSO-d6) δ 10.04 (s, 1H), 9.73 (s, 1H), 9.50 (s, 1H), 8.57 (s, 1H), 8.51 (s, 1H), 7.77 (s, 1H), 1.92 (s, 3H), 1.48 (s, 9H), 0.99 (s, 9H).

Synthesis of 6-[(6-aminopyrimidin-4-yl)amino]-3-tert-butyl-8-chloro-3-methyl-2H-imidazo[1,5-a]pyridine-1,5-dione hydrochloride (Cpd. No. 105)

The synthesis of compound 105 was carried out as described above using the general protocol of Procedure F. Yellow solid; Yield: 0.08 g, 54%; MS (ESI) m/z 363.46 [M+1]+; 1H NMR (400 MHz, DMSO-d6) δ 9.82 (s, 2H), 8.51 (s, 1H), 8.40 (s, 1H), 7.89 (brs, 2H), 6.54 (s, 1H), 1.92 (s, 3H), 0.99 (s, 9H).

Example 106

Synthesis of 6-((6-aminopyrimidin-4-yl)amino)-8-methyl-2H-spiro[imidazo[1,5-a]pyridine-3,4'-piperidine]-1,5-dione dihydrochloride (Cpd. No. 106)

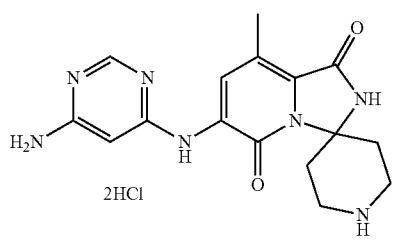 [SMILES: Cc1cc(Nc2cc(N)ncn2)c(=O)n2c1C(=O)NC21CCNCC1]

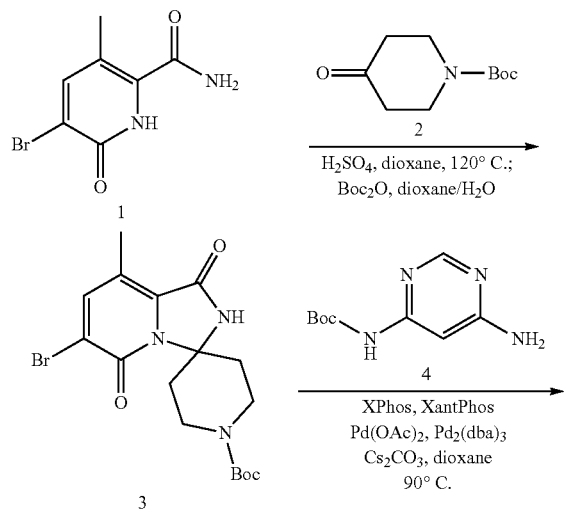

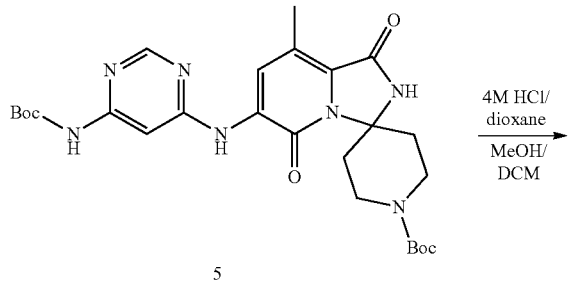

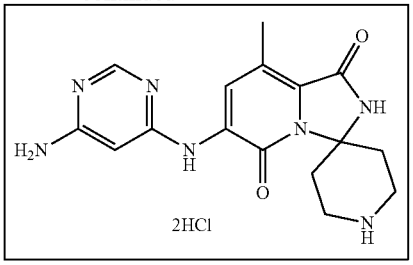

Synthesis of tert-butyl 6-bromo-8-methyl-1,5-dioxo-1,5-dihydro-2H-spiro[imidazo[1,5-a]pyridine-3,4'-piperidine]-1'-carboxylate (3)

The synthesis of intermediate 3 was carried out as described above using the general protocol of Procedure E. Off-white solid; Yield: 1.7 g, 43%; MS (ESI) m/z 409.9 [M−1]−; 1H NMR (400 MHz, DMSO-d6) δ 10.57 (s, 1H), 8.04 (s, 1H), 4.03 (brs, 2H), 3.56 (brs, 1H), 3.11 (brs, 4H), 2.23 (s, 3H), 1.42 (s, 9H).

Synthesis of tert-butyl 6-(((6-((tert-butoxycarbonyl)amino)pyrimidin-4-yl)amino)-8-methyl-1,5-dioxo-1,5-dihydro-2H-spiro[imidazo[1,5-a]pyridine-3,4'-piperidine]-1'-carboxylate (5)

The synthesis of intermediate 5 was carried out as described above using the general protocol of Procedure H. Yellow solid; Yield: 1.6 g, 60%; MS (ESI) m/z 542.2 [M+1]+; 1H NMR (400 MHz, DMSO-d6) δ 10.27 (brs, 1H), 9.98 (s, 1H), 9.19 (s, 1H), 8.50-8.45 (m, 2H), 7.66 (s, 1H), 4.05 (brs, 1H), 3.32 (m, 2H), 2.24 (s, 3H), 1.48 (s, 9H), 1.43 (s, 9H).

Synthesis of 6-((6-aminopyrimidin-4-yl)amino)-8-methyl-2H-spiro[imidazo[1,5-a]-pyridine-3,4'-piperidine]-1,5-dione dihydrochloride (Cpd. No. 106)

The synthesis of compound 106 was carried out as described above using the general protocol of Procedure F. Pale yellow solid; Yield: 1.02 g, 83%; MS (ESI) m/z 342.2 [M+1]+; 1H NMR (400 MHz, DMSO-d6) δ 10.42 (brs, 1H), 9.55 (brs, 1H), 9.24 (brs, 1H), 8.78 (brs, 1H), 8.41 (s, 1H), 8.16 (s, 1H), 7.58 (brs, 2H), 6.37 (s, 1H), 3.48-3.40 (m, 2H), 3.40-3.28 (m, 2H), 3.20-3.10 (m, 1H), 2.38 (s, 3H), 1.73 (m, 2H).

Example 107

Synthesis of 6'-((6-aminopyrimidin-4-yl)amino)-8'-methyl-2'H-spiro[cyclohexane-1,3'-imidazo[1,5-a]pyridine]-1',5'-dione hydrochloride (Cpd. No. 107)

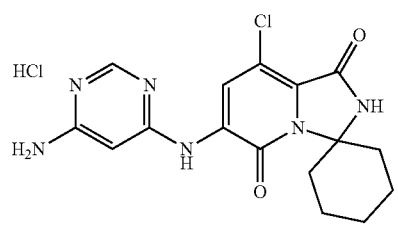 [SMILES: Cl ; Nc1cc(Nc2cc(Cl)c3n(c2=O)C2(CCCCC2)NC3=O)ncn1]

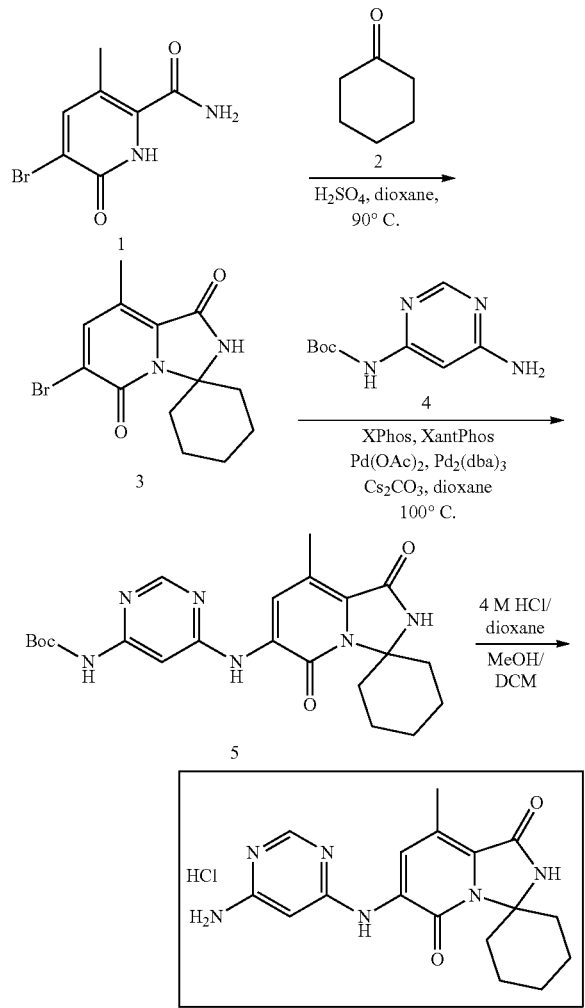

(s, 1H), 3.00-2.90 (m, 2H), 2.42 (s, 3H), 1.80-1.60 (m, 5H), 1.42 (d, J=12 Hz, 2H), 1.25-1.12 (m, 1H).

Example 108

Synthesis of 6-((6-aminopyrimidin-4-yl)amino)-8-chloro-2H-spiro[imidazo[1,5-a]pyridine-3,4'-piperidine]-1,5-dione dihydrochloride (Cpd. No. 108)

Synthesis of 6'-bromo-8'-methyl-2'H-spiro[cyclo-hexane-1,3'-imidazo[1,5-a]pyridine]-1',5'-dione (3)

The synthesis of intermediate 3 was carried out as described above using the general protocol of Procedure A. Off-white solid; Yield: 2.4 g, 71%; MS (ESI) m/z 311.18 [M+1]⁺.

Synthesis of tert-butyl (6-((8'-methyl-1',5'-dioxo-1', 5'-dihydro-2'H-spiro[cyclohexane-1,3'-imidazo[1,5-a]pyridin]-6'-yl)amino)pyrimidin-4-yl)carbamate (5)

The synthesis of intermediate 5 was carried out as described above using the general protocol of Procedure H. Off-white solid; Yield: 2.10 g, 30%.

Synthesis of 6'-((6-aminopyrimidin-4-yl)amino)-8'-methyl-2'H-spiro[cyclohexane-1,3'-imidazo[1,5-a]pyridine]-1',5'-dione hydrochloride (Cpd. No. 107)

The synthesis of compound 107 was carried out as described above using the general protocol of Procedure F. Off-white solid; Yield: 0.55 g, 64%; MS (ESI) m/z 341.50; [M+1]⁺; ¹H NMR (400 MHz, DMSO-d₆) δ 10.20 (s, 1H), 9.68 (s, 1H), 8.45 (s, 1H), 8.10 (s, 1H), 7.88 (brs, 2H), 6.39

Synthesis of tert-butyl 6-[[6-(tert-butoxycarbonylamino)pyrimidin-4-yl]amino]-8-chloro-1,5-dioxo-spiro[2H-imidazo[1,5-a]pyridine-3,4'-piperidine]-1'-carboxylate (3)

The synthesis of intermediate 3 was carried out as described above using the general protocol of Procedure H. Off-white solid; Yield: 1.6 g, 54%; MS (ESI) m/z 562.2 [M+1]⁺; ¹H NMR (400 MHz, DMSO-d₆) δ 10.47 (s, 1H), 10.05 (s, 1H), 9.49 (s, 1H), 8.72 (s, 1H), 8.51 (s, 1H), 7.78 (s, 1H), 4.09 (brs, 1H), 3.33 (m, 4H), 1.74 (brs, 1H), 1.48 (s, 9H), 1.43 (s, 9H).

Synthesis of 6-((6-aminopyrimidin-4-yl)amino)-8-chloro-2H-spiro[imidazo[1,5-a]pyridine-3,4'-piperidine]-1,5-dione dihydrochloride (Cpd. No. 108)

The synthesis of compound 108 was carried out as described above using the general protocol of Procedure F. Pale yellow solid; Yield: 0.8 g, 96%; MS (ESI) m/z 362.16 [M+1]$^+$; $^1$H NMR (400 MHz, DMSO-d$_6$) δ 10.64 (s, 1H), 9.82 (s, 1H), 9.49-9.46 (m, 1H), 9.01-8.98 (m, 1H), 8.51 (s, 1H), 8.40 (s, 1H), 7.91 (brs, 2H), 6.54 (s, 1H), 3.54-3.47 (m, 2H), 3.38-3.18 (m, 4H), 1.88-1.85 (m, 2H).

Example 109

Synthesis of 8-chloro-6-(pyrimidin-4-ylamino)spiro [2H-imidazo[1,5-a]pyridine-3,1'-cyclohexane]-1,5-dione hydrochloride (Cpd. No. 109)

Synthesis of 8-chloro-6-(pyrimidin-4-ylamino)spiro [2H-imidazo[1,5-a]pyridine-3,1'-cyclohexane]-1,5-dione (3)

The synthesis of intermediate 3 was carried out as described above using the general protocol of Procedure H. Off-white solid; Yield: 0.8 g, 64%; MS (ESI) m/z 346.04 [M+1]$^+$; $^1$H NMR (400 MHz, DMSO-d$_6$) δ 10.32 (s, 1H), 9.61 (s, 1H), 8.84 (s, 1H), 8.43 (d, J=6.4 Hz, 1H), 7.45 (d, J=6.4 Hz, 1H), 2.9 (t, J=9.2 Hz, 2H), 1.65-1.54 (m, 6H), 1.25-1.23 (m, 2H).

Synthesis of 8-chloro-6-(pyrimidin-4-ylamino)spiro [2H-imidazo[1,5-a]pyridine-3,1'-cyclohexane]-1,5-dione hydrochloride (Cpd. No. 109)

The synthesis of compound 109 was carried out as described above using the general protocol of Procedure F. Light yellow solid; Yield: 0.6 g, 77%; MS (ESI) m/z 346.04 [M+1]$^+$; $^1$H NMR (400 MHz, DMSO-d$_6$) δ 10.41 (s, 1H), 10.23 (s, 1H), 9.0 (s, 1H), 8.71 (s, 1H), 8.48 (d, J=6.4 Hz, 1H), 7.52 (d, J=6.4 Hz, 1H), 2.9 (t, J=9.2 Hz, 2H), 1.78-1.54 (m, 6H), 1.23-1.27 (m, 2H).

Example 110

Synthesis of 8-chloro-4',4'-difluoro-6-(pyrimidin-4-ylamino)spiro[2H-imidazo[1,5-a]pyridine-3,1'-cyclohexane]-1,5-dione hydrochloride (Cpd. No. 110)

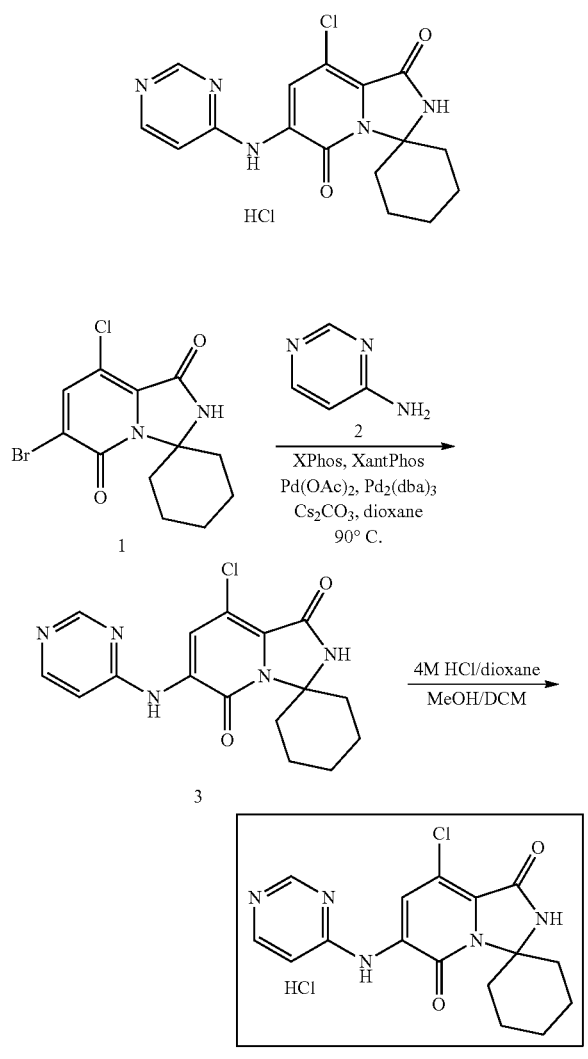

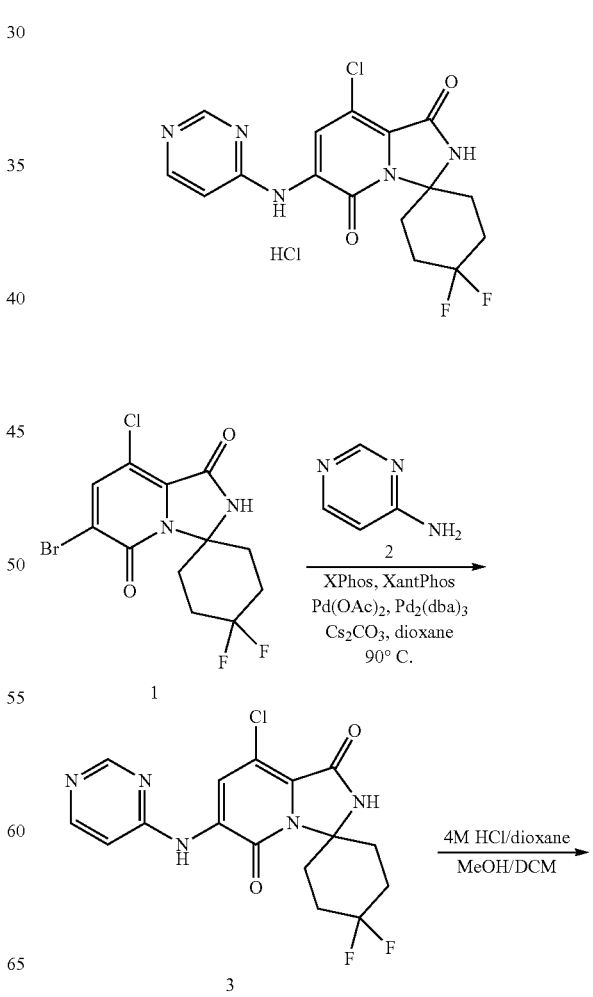

-continued

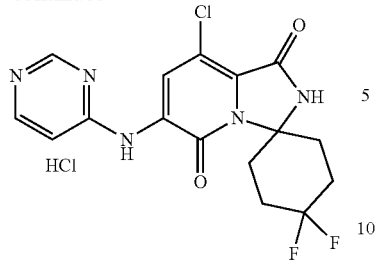

HCl

Synthesis of 8-chloro-4',4'-difluoro-6-(pyrimidin-4-ylamino)spiro[2H-imidazo[1,5-a]pyridine-3,1'-cyclohexane]-1,5-dione (3)

The synthesis of intermediate 3 was carried out as described above using the general protocol of Procedure H. Yellow solid; Yield: 0.85 g, 35%; MS (ESI) m/z 382.36 [M+1]$^+$; $^1$H NMR (400 MHz, DMSO-d$_6$) δ 10.51 (s, 1H), 9.68 (s, 1H), 8.80-8.84 (m, 2H), 8.44 (d, J=6.8 Hz, 1H), 7.44 (d, J=6.4.0 Hz, 1H), 3.34-3.17 (m, 2H), 2.32-2.17 (m, 4H), 1.76-1.72 (m, 2H).

Synthesis of 8-chloro-4',4'-difluoro-6-(pyrimidin-4-ylamino)spiro[2H-imidazo[1,5-a]pyridine-3,1'-cyclohexane]-1,5-dione hydrochloride (Cpd. No. 110)

The synthesis of compound 110 was carried out as described above using the general protocol of Procedure F. Yellow solid; Yield: 0.81 g, 87%; MS (ESI) m/z 382.4 [M+1]$^+$; $^1$H NMR (400 MHz, DMSO-d$_6$) δ 10.64 (s, 1H), 10.45 (s, 1H), 9.05 (s, 1H), 8.71 (s, 1H), 8.52 (d, J=6.8 Hz, 1H), 7.56 (d, J=6.4 Hz, 1H), 3.30-3.20 (m, 2H), 2.35-2.15 (m, 4H), 1.80-1.72 (m, 2H).

Example 111

Synthesis of 6-[(6-aminopyrimidin-4-yl)amino]-6',8-dichloro-spiro[2H-imidazo[1,5-a]pyridine-3,1'-indane]-1,5-dione hydrochloride (Cpd. No. 111)

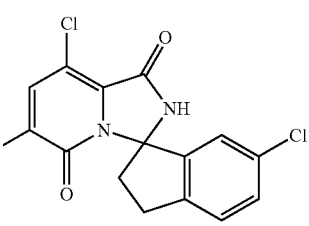

HCl

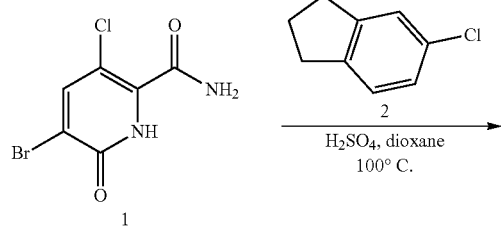

-continued

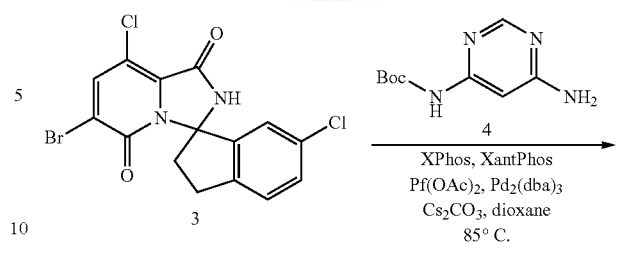

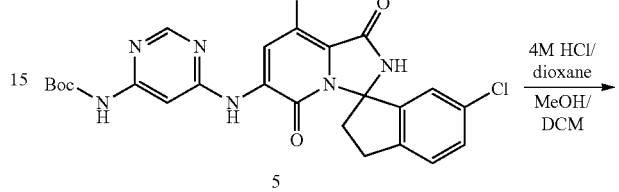

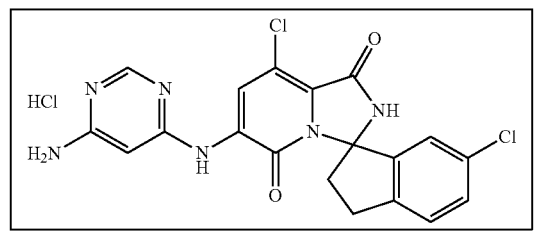

Synthesis of 6-bromo-6',8-dichloro-spiro[2H-imidazo[1,5-a]pyridine-3,1'-indane]-1,5-dione (3)

The synthesis of intermediate 3 was carried out as described above using the general protocol of Procedure A. Off-white solid; Yield: 0.52 g, 35%; MS (ESI) m/z: 399.23 [M+1]$^+$; $^1$H NMR (400 MHz, DMSO-d$_6$) δ 10.35 (s, 1H), 8.28 (s, 1H), 7.39 (m, 3H), 3.23 (m, 1H), 3.08 (m, 2H), 2.43 (m, 1H).

Synthesis of tert-butyl N-[6-[(6',8-dichloro-1,5-dioxo-spiro[2H-imidazo[1,5-a]pyridine-3,1'-indane]-6-yl)amino]pyrimidin-4-yl]carbamate (5)

The synthesis of intermediate 5 was carried out as described above using the general protocol of Procedure H. Off-white solid; Yield: 0.38 g, 56%; MS (ESI) m/z 529.2 [M+1]$^+$; $^1$H NMR (400 MHz, DMSO-d$_6$) δ 10.07 (s, 1H), 9.99 (s, 1H), 9.42 (s, 1H), 8.72 (s, 1H), 8.50 (s, 1H), 7.65 (s, 1H), 7.37 (m, 3H), 3.10 (m, 2H), 3.01 (m, 2H), 1.45 (s, 9H).

Synthesis of 6-[(6-aminopyrimidin-4-yl)amino]-6',8-dichloro-spiro[2H-imidazo[1,5-a]pyridine-3,1'-indane]-1,5-dione hydrochloride (Cpd. No. 111)

The synthesis of compound 111 was carried out as described above using the general protocol of Procedure F. Pale yellow solid; Yield: 0.17 g, 55%; MS (ESI) m/z 429.3 [M+1]$^+$; $^1$H NMR (400 MHz, DMSO-d$_6$) δ 10.18 (s, 1H), 9.78 (s, 1H), 8.52 (s, 1H), 8.44 (s, 1H), 7.91 (brs, 2H), 7.38 (m, 3H), 6.42 (s, 1H), 3.30 (m, 1H), 3.21 (m, 1H), 2.96 (m, 1H), 2.47 (m, 1H).

Example 112

Synthesis of 8-chloro-6-[(5-fluoropyrimidin-4-yl)amino]spiro[2H-imidazo[1,5-a]pyridine-3,1'-cyclohexane]-1,5-dione (Cpd. No. 112)

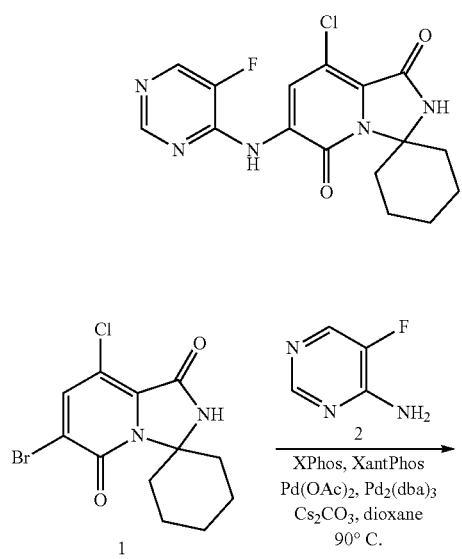

Synthesis of 8-chloro-6-[(5-fluoropyrimidin-4-yl)amino]spiro[2H-imidazo[1,5-a]pyridine-3,1'-cyclohexane]-1,5-dione (Cpd. No. 112)

The synthesis of compound 112 was carried out as described above using the general protocol of Procedure H. Yellow solid; Yield: 0.14 g, 43%; MS (ESI) m/z 364.3 [M+1]$^+$; $^1$H NMR (400 MHz, DMSO-d$_6$) δ 10.41 (s, 1H), 8.73 (s, 1H), 8.62 (s, 2H), 8.54 (s, 1H), 2.95-2.87 (m, 2H), 1.80-1.54 (m, 7H), 1.30-1.18 (m, 1H).

Example 113

Synthesis of 8-chloro-6-(pyrimidin-4-ylamino)spiro[2H-imidazo[1,5-a]pyridine-3,2'-indane]-1,1',5-trione (Cpd. No. 113)

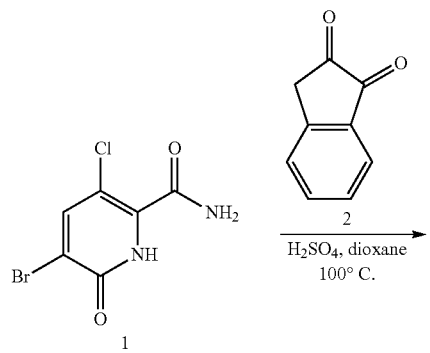

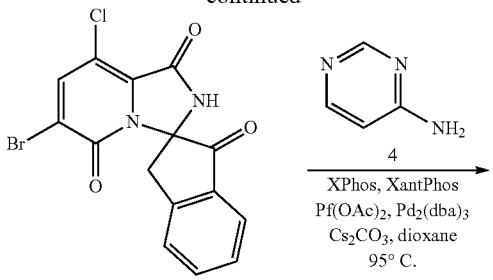

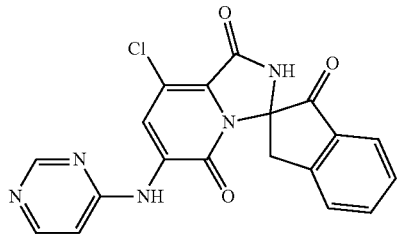 [SMILES: O=C1NC2(Cc3ccccc3C2=O)n2c1c(Cl)cc(Nc1ccncn1)c2=O]

Synthesis of 6-bromo-8-chloro-spiro[2H-imidazo[1,5-a]pyridine-3, 2'-indane]-1,1',5-trione (3)

The synthesis of intermediate 3 was carried out as described above using the general protocol of Procedure A. Brown solid; Yield: 0.12 g, 28%; MS (ESI) m/z 378.94 [M+1]$^+$; $^1$H NMR (400 MHz, DMSO-d$_6$) δ 10.40 (s, 1H), 8.40 (s, 1H), 7.88-7.81 (m, 2H), 7.70 (d, J=7.32, 1H), 7.57 (t, J=7.36, 1H), 4.12 (d, J=18.32, 1H), 3.43 (d, J=18.08, 1H).

Synthesis of 8-chloro-6-(pyrimidin-4-ylamino)spiro[2H-imidazo[1,5-a]pyridine-3, 2'-indane]-1,1',5-trione (Cpd. No. 113)

The synthesis of compound 113 was carried out as described above using the general protocol of Procedure H. Yellow solid; Yield: 0.065 g, 26%; MS (ESI) m/z 394.06 [M+1]$^+$; $^1$H NMR (400 MHz, DMSO-d$_6$) δ 10.05 (brs, 1H), 9.64 (s, 1H), 8.85 (s, 2H), 8.41 (d, J=5.68 Hz, 1H), 7.86-7.80 (m, 2H), 7.69 (d, J=7.44 Hz, 1H), 7.55 (t, J=7.44, 1H), 7.30 (d, J=5.92 Hz, 1H), 4.15 (d, J=18.2 Hz, 1H), 3.50 (d, J=18.44 Hz, 1H).

Example 114

Synthesis of 6-((6-aminopyrimidin-4-yl)amino)-8-chloro-6'-fluoro-2',3'-dihydro-2H-spiro[imidazo[1,5-a]pyridine-3,1'-indene]-1,5-dione hydrochloride (Cpd. No. 114)

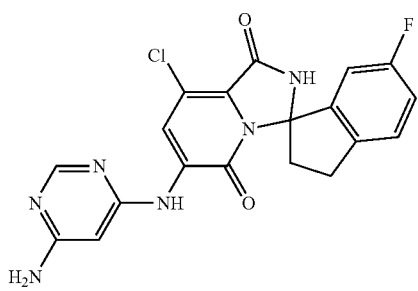 [SMILES: Nc1cc(Nc2cc(Cl)c3n(c2=O)C2(CCc4ccc(F)cc42)NC3=O)ncn1]

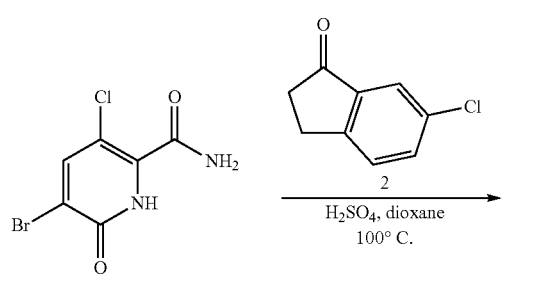

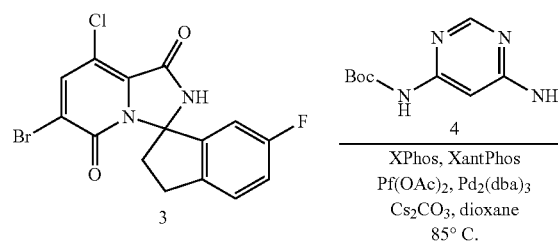

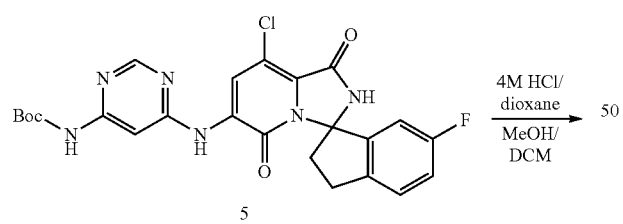

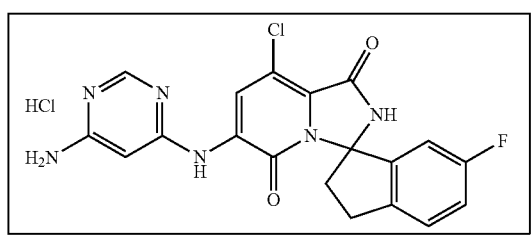

Synthesis of 6-bromo-8-chloro-6'-fluoro-2',3'-dihydro-2H-spiro[imidazo[1,5-a]pyridine-3,1'-indene]-1,5-dione (3)

The synthesis of intermediate 3 was carried out as described above using the general protocol of Procedure A. White solid; Yield: 0.46 g, 32%; MS (ESI) m/z 381.19 [M+1]$^+$; $^1$H NMR (400 MHz, DMSO-d$_6$) δ 10.37 (s, 1H), 8.31-8.28 (s, 1H), 7.37-7.34 (m, 1H), 7.20-7.16 (m, 2H), 3.22 (m, 1H), 3.06-2.97 (m, 2H), 2.42-2.35 (m, 1H).

Synthesis of tert-butyl (6-((8-chloro-6'-fluoro-1,5-dioxo-1,2',3',5-tetrahydro-2H-spiro[imidazo[1,5-a]pyridine-3,1'-inden]-6-yl)amino)pyrimidin-4-yl)carbamate (5)

The synthesis of intermediate 5 was carried out as described above using the general protocol of Procedure H. Off white solid; Yield: 320 mg, 53%; MS (ESI) m/z 513.35 [M+1]$^+$.

Synthesis of 6-((6-aminopyrimidin-4-yl)amino)-8-chloro-6'-fluoro-2',3'-dihydro-2H-spiro[imidazo[1,5-a]pyridine-3,1'-indene]-1,5-dione hydrochloride (Cpd. No. 114)

The synthesis of compound 114 was carried out as described above using the general protocol of Procedure F. Yellow solid; Yield: 0.089 g, 37%; MS (ESI) m/z 413.32 [M+1]$^+$; $^1$H NMR (400 MHz, DMSO-d$_6$) δ 10.16 (s, 1H), 9.72 (s, 1H), 8.49-8.46 (d, 2H), 7.86-7.69 (bs, 2H), 7.36 (m, 1H), 7.19 (m, 1H), 7.11 (m, 1H), 6.41 (s, 1H), 3.31-3.35 (m, 2H), 3.17-2.96 (m, 2H).

Example 115

Synthesis of 8-chloro-6-[(5-chloropyrimidin-4-yl)amino]spiro[2H-imidazo[1,5-a]pyridine-3,1'-cyclohexane]-1,5-dione (Cpd. No. 115)

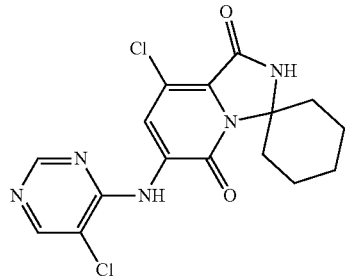 [SMILES: O=C1NC2(CCCCC2)n2c1c(Cl)cc(Nc1ncncc1Cl)c2=O]

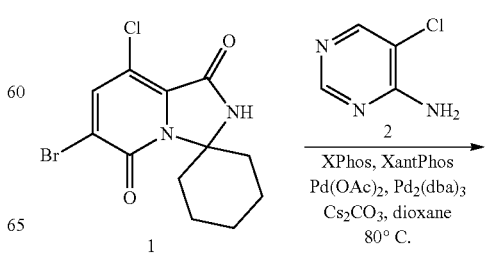

-continued

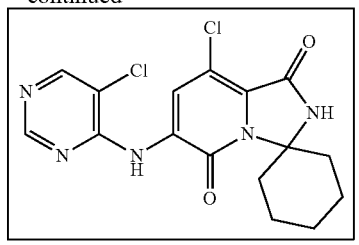

Synthesis of 8-chloro-6-[(5-chloropyrimidin-4-yl)amino]spiro[2H-imidazo[1,5-a]pyridine-3,1'-cyclohexane]-1,5-dione (Cpd. No. 115)

The synthesis of compound 115 was carried out as described above using the general protocol of Procedure H. Yellow solid; Yield: 75 mg, 13%; MS (ESI) m/z 380.23 [M+1]$^+$; $^1$H NMR (400 MHz, DMSO-d$_6$) δ 10.44 (s, 1H), 8.85 (s, 1H), 8.80 (s, 1H), 8.72 (s, 1H), 8.66 (s, 1H), 2.93-2.88 (m, 2H), 1.77-1.74 (m, 2H), 1.65-1.61 (m, 3H), 1.57-1.57 (m, 2H), 1.04-1.02 (m, 1H).

Example 116

Synthesis of 8-chloro-6-[(6-methylpyrimidin-4-yl)amino]spiro[2H-imidazo[1,5-a]pyridine-3,1'-cyclohexane]-1,5-dione (Cpd. No. 116)

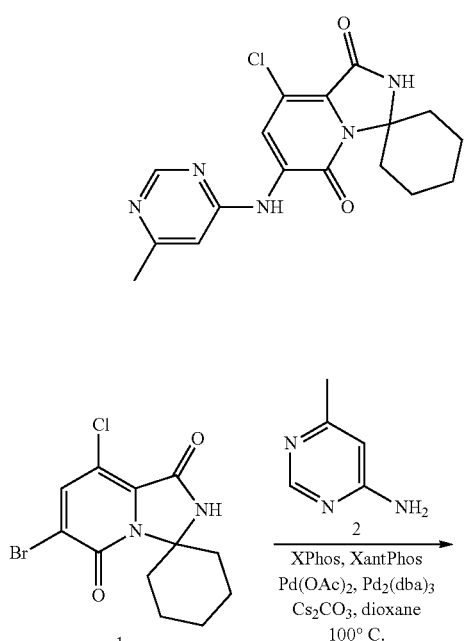

Synthesis of 8-chloro-6-[(6-methylpyrimidin-4-yl)amino]spiro[2H-imidazo[1,5-a]pyridine-3,1'-cyclohexane]-1,5-dione (Cpd. No. 116)

The synthesis of compound 116 was carried out as described above using the general protocol of Procedure H. Yellow solid; Yield: 190 mg, 58%; MS (ESI) m/z 359.81 [M+1]$^+$; $^1$H NMR (400 MHz, DMSO-d$_6$) δ 10.29 (s, 1H), 10.08 (s, 1H), 9.41 (s, 1H), 8.76 (s, 1H), 8.71 (s, 1H), 7.27 (s, 1H), 2.98-2.91 (m, 2H), 2.33 (s, 3H), 1.77-1.74 (m, 2H), 1.67-1.58 (m, 3H), 1.55-1.52 (m, 2H) 1.26-1.19 (m, 1H).

Example 117

Synthesis of 6'-((7H-purin-6-yl)amino)-8'-chloro-2'H-spiro[cyclohexane-1,3'-imidazo[1,5-a]pyridine]-1',5'-dione (Cpd. No. 117)

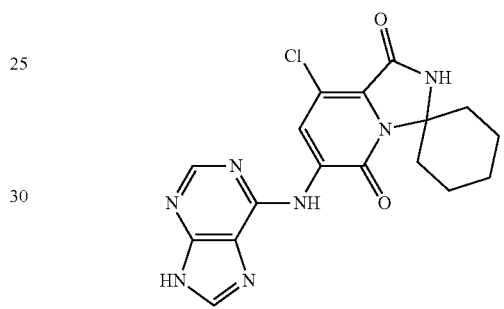

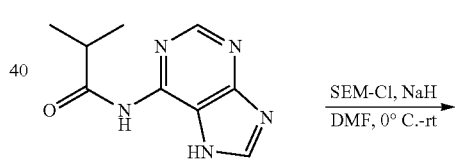

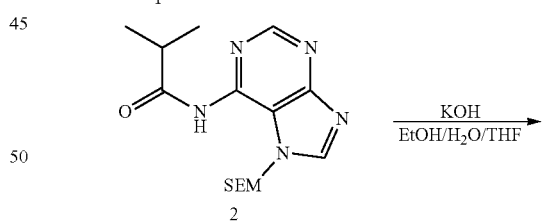

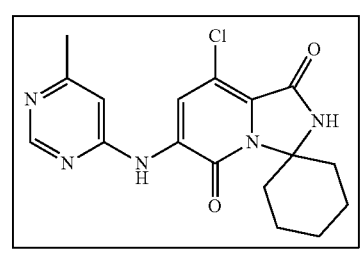

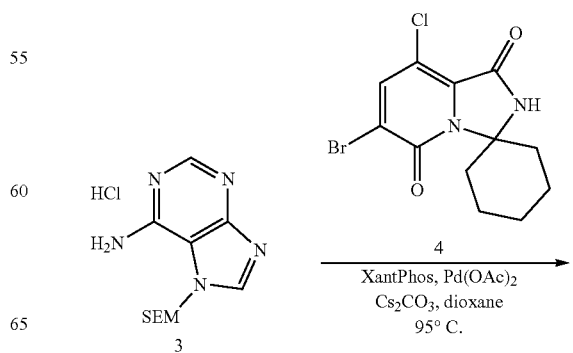

195

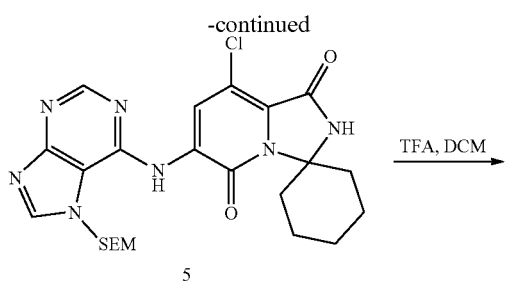

5

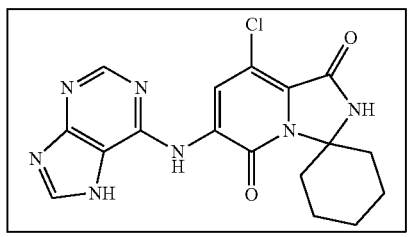

Synthesis of N-(7-((2-(trimethylsilyl)ethoxy)methyl)-7H-purin-6-yl)isobutyramide (2)

To a stirred solution of 2-methyl-N-(7H-purin-6-yl)propanamide (1, 5 g, 24.36 mmol) in dimethylformamide (20 mL), sodium hydride (0.88 g, 36.55 mmol) was added portion wise in 10 minutes at 0° C. The above suspension was stirred for 10 minutes at 0° C. followed by addition of 2-(trimethylsilyl)ethoxymethyl chloride (4.87 g, 29.24 mmol) slowly at 0° C. under nitrogen atmosphere. The reaction was stirred at room temperature for 16 h. After completion of the reaction, the mixture was quenched with saturated aqueous solution of ammonium chloride and product was extracted with dichloromethane (2×50 mL). The organics were then separated, dried (magnesium sulfate) and concentrated to dryness under vacuum and the crude was purified by flash chromatography eluting with 2% methanol in dichloromethane. Concentration of the desired fractions afford 2-methyl-N-[7-(2-trimethylsilylethoxymethyl)purin-6-yl]propanamide (2) as white solid. Yield: 2 g, 24%.

Synthesis of 7-((2-(trimethylsilyl)ethoxy)methyl)-7H-purin-6-amine hydrochloride (3)

The synthesis of intermediate 3 was carried out as described above using the general protocol of Procedure I. White solid; Yield: 3.0 g, 73%; MS (ESI) m/z 266.31[M+1]$^+$; $^1$H NMR (400 MHz, DMSO-d$_6$) δ 8.26 (s, 1H), 8.16 (s, 1H), 7.26 (brs, 2H), 5.50 (s, 2H), 3.52 (t, J=1.56 Hz, 2H), 0.835 (t, J=1.56 Hz, 2H), 0.088 (s, 9H).

Synthesis of 8'-chloro-6'-((7-((2-(trimethylsilyl)ethoxy)methyl)-7H-purin-6-yl)amino)-2'H-spiro[cyclohexane-1,3'-imidazo[1,5-a]pyridine]-1',5'-dione (5)

The synthesis of intermediate 5 was carried out as described above using the general protocol of Procedure B. Yellow solid; Yield: 0.10 g, 26%; MS (ESI) m/z 516.44 [M+1]$^+$; $^1$H NMR (400 MHz, DMSO-d$_6$) δ 10.42 (s, 1H), 9.07 (s, 1H), 9.03 (s, 1H), 8.71 (s, 1H), 8.58 (s, 1H), 5.74 (s, 2H), 3.61 (t, J=1.6 Hz, 2H), 0.852 (t, J=1.64 Hz, 2H), 0.081 (s, 9H).

196

Synthesis of 6'-((7H-purin-6-yl)amino)-8'-chloro-2'H-spiro[cyclohexane-1,3'-imidazo[1,5-a]pyridine]-1',5'-dione (Cpd. No. 117)

8-Chloro-6-[[7-(2-trimethylsilylethoxy)purin-6-yl]amino]spiro[2H-imidazo[1,5-a]pyridine-3,1'-cyclohexane]-1,5-dione (5, 0.6 g, 1.2 mmol) was dissolved in dichloromethane (10 mL) in a flask and trifluoroacetic acid (1.36 g, 11.95 mmol) was added dropwise and stirred the mixture at room temperature overnight. After completion, evaporated the solvent under reduced pressure and the crude was basified by saturated aqeous solution of sodium bicarbonate to pH 8 and extracted with dichloromethane (2×50 mL). The organic layer was dried over anhy. Sodium sulfate and concentrated to afford crude. The crude was purified by flash column chromatography eluting with 2.5% methanol in dichloromethane. The desired fractions were concentrated to dryness under vacuum to afford 8-chloro-6-(7H-purin-6-ylamino)spiro[2H-imidazo[1,5-a]pyridine-3, 1'-cyclohexane]-1,5-dione (Cpd. No. 117) as a yellow solid. Yield: 0.06 g, 13%; MS (ESI) m/z 386.39 [M+1]$^+$; $^1$H NMR: (400 MHz, DMSO-d$_6$) δ 10.43 (m, 1H), 10.37 (s, 1H), 8.88 (s, 1H), 8.64 (s, 1H), 8.43 (s, 1H), 2.94 (t, J=2.32 Hz, 2H), 1.77 (m, 2H), 1.63 (m, 3H), 1.57 (d, J=12.8 Hz, 2H), 1.23 (m, 1H).

Example 118

Synthesis of 6-[(6-aminopyrimidin-4-yl)amino]-3-cyclopentyl-3-methyl-1,5-dioxo-imidazo[1,5-a]pyridine-2-carbonitrile (Cpd. No. 118)

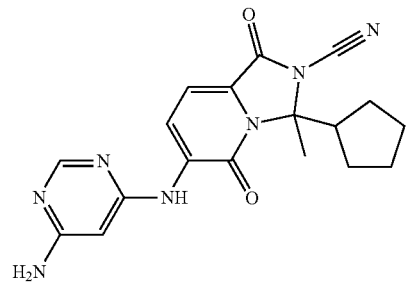 [SMILES: CC1(C2CCCC2)N(C#N)C(=O)c2ccc(Nc3cc(N)ncn3)c(=O)n21]

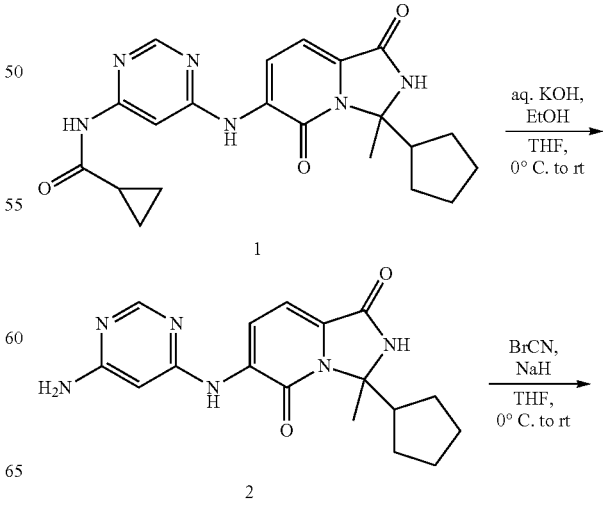

-continued

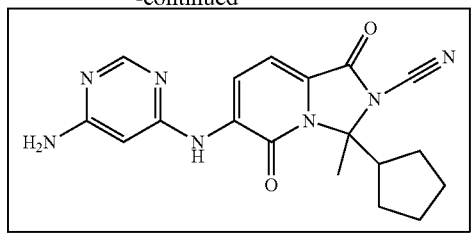

Synthesis of 6-[(6-aminopyrimidin-4-yl)amino]-3-cyclopentyl-3-methyl-2H-imidazo[1,5-a]pyridine-1,5-dione (2)

The synthesis of intermediate 2 was carried out as described above using the general protocol of Procedure I. Yellow solid; Yield: 0.36 g, 71%; MS (ESI) m/z 341.16 [M+1]$^+$; 1H NMR (400 MHz, DMSO-d$_6$) δ 9.61 (s, 1H), 8.62 (s, 1H), 8.57 (d, J=7.64, 1H), 8.15 (s, 1H), 6.80 (d, J=7.68, 1H), 6.51 (s, 2H), 6.16 (s, 1H), 3.4 (m, 1H), 1.82 (s, 3H), 1.63-1.41 (m, 5H), 1.1 (m, 1H), 0.87-0.75 (m, 2H).

Synthesis of 6-[(6-aminopyrimidin-4-yl)amino]-3-cyclopentyl-3-methyl-1,5-dioxo-imidazo[1,5-a]pyridine-2-carbonitrile (Cpd. No. 118)

In a 2-neck round bottom flask 6-[(6-aminopyrimidin-4-yl)amino]-3-cyclopentyl-3-methyl-2H-imidazo[1,5-a]pyridine-1,5-dione (2, 0.28 g, 0.82 mmol) was taken in dry tetrahydrofuran (15 mL). The reaction mixture was cooled to 0° C. and sodium hydride (164 mg, 4.11 mmol) was added in portions. After stirring for 10 min at room temperature, cyanogen bromide (436 mg, 4.11 mmol) was added and the resulting reaction mixture was stirred at room temperature for 20 h. The reaction mixture was quenched with aqeous ammonium chloride solution and then concentrated to get the crude mass. This crude was purified by flash chromatography eluting with 2% methanol in dichloromethane. The compound was washed with pentane and dried under vacuum to afford 6-[(6-aminopyrimidin-4-yl)amino]-3-cyclopentyl-3-methyl-1,5-dioxo-imidazo[1,5-a]pyridine-2-carbonitrile (Cpd. No. 118) as yellow solid. Yield: 0.018 g, 6%; MS (ESI) m/z 366.16 [M+1]$^+$; $^1$H NMR (400 MHz, DMSO-d$_6$) δ 9.08 (s, 1H), 8.71 (d, J=7.84, 1H), 8.19 (s, 1H), 7.28 (d, J=7.96, 1H), 6.65 (s, 2H), 6.29 (s, 1H), 3.49-3.43 (m, 1H), 2.21 (s, 3H), 1.94 (m, 1H), 1.7-1.58 (m, 4H), 1.48 (m, 1H), 1.23 (m, 1H), 1.06-1.02 (m, 1H).

Example 119

Synthesis of 6-[(6-aminopyrimidin-4-yl) amino]-8-chloro-3-(3-fluorophenyl)-2,3-dihydroimidazo [1,5-a] pyridine-1,5-dione (Cpd. No. 119)

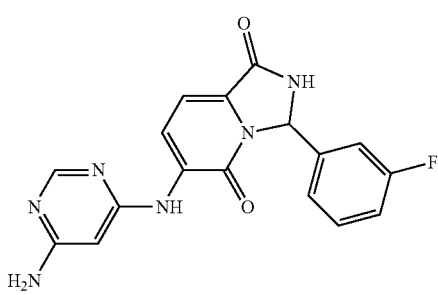 [SMILES: Nc1cc(Nc2ccc3n(c2=O)C(c2cccc(F)c2)NC3=O)ncn1]

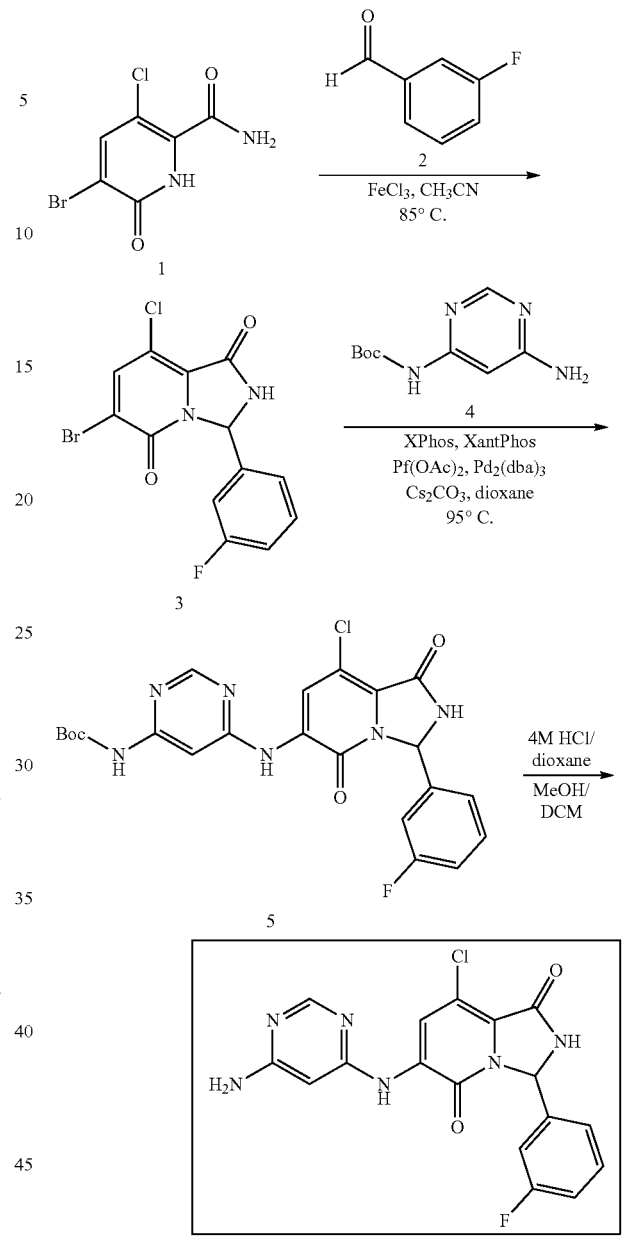

Synthesis of 6-bromo-8-chloro-3-(3-fluorophenyl)-2,3-dihydroimidazo[1,5-a]pyridine-1,5-dione (3)

To a suspension of 5-bromo-3-chloro-6-oxo-1H-pyridine-2-carboxamide (1, 0.5 g, 1.99 mmol) in acetonitrile (15 mL), 3-fluorobenzaldehyde (0.86 g, 6.96 mmol) and ferric chloride (2.25 g, 13.92 mmol) were added in a vial. The vial was sealed and heated the reaction mass to 85° C. for 16 h. After completion, the reaction mass was cooled to room temperature, filtered through celite bed, washed with 5% methanol in dichloromethane followed by concentration to get crude. The crude was then purified by column chromatography eluting with 5% methanol in dichloromethane to afford 8-chloro-3-(3-fluorophenyl)-2, 3-dihydroimidazo[1,5-a] pyridine-1,5-dione as white solid. Yield: 0.45 g, 63%; MS (ESI) m/z 256.17 [M+1]$^+$.

Synthesis of tert-butyl (6-((8-chloro-3-(3-fluorophenyl)-1,5-dioxo-1,2,3,5-tetrahydroimidazo[1,5-a]pyridin-6-yl)amino)pyrimidin-4-yl)carbamate (5)

The synthesis of intermediate 5 was carried out as described above using the general protocol of Procedure H. Yellow solid; Yield: 0.15 g, 33%; MS (ESI) m/z 487.43 [M+1]⁺.

Synthesis of 6-[(6-aminopyrimidin-4-yl) amino]-8-chloro-3-(3-fluorophenyl)-2, 3-dihydroimidazo[1,5-a]pyridine-1,5-dione (Cpd. No. 119)

The synthesis of compound 119 was carried out as described above using the general protocol of Procedure F. Off white solid; Yield: 0.012 g, 10%; MS (ESI) m/z 387.29 [M+]⁺; ¹H NMR (400 MHz, DMSO-d₆) δ 9.98 (s, 1H), 8.90 (s, 1H), 8.70 (s, 1H), 8.20 (s, 1H), 7.43 (m, 1H), 7.33 (m, 1H), 7.19 (s, 2H), 6.61 (s, 1H), 6.58 (s, 2H), 6.17 (s, 1H).

Example 120

Synthesis of 8'-chloro-2,2-dimethyl-6'-(pyrimidin-4-ylamino)-2'H-spiro[cyclobutane-1,3'-imidazo[1,5-a]pyridine]-1',5'-dione (Cpd. No. 120)

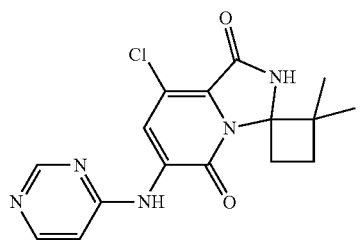 [SMILES: CC1(C)CCC12NC(=O)c1c(Cl)cc(Nc3ccncn3)c(=O)n12]

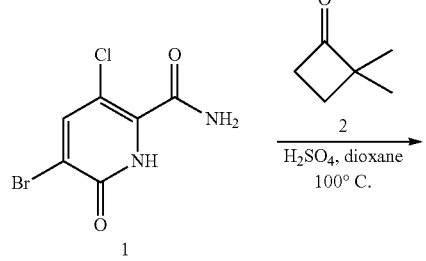

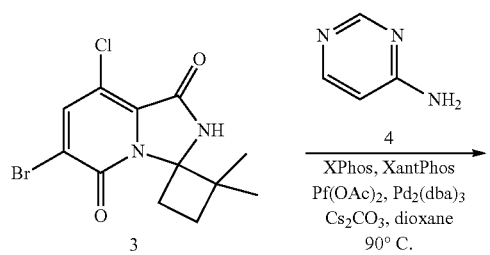

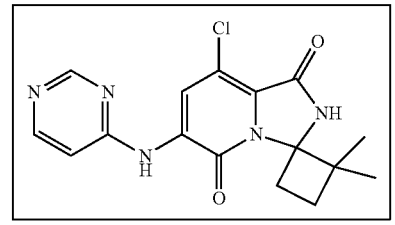

Synthesis 6'-bromo-8'-chloro-2,2-dimethyl-2'H-spiro[cyclobutane-1,3'-imidazo[1,5-a]pyridine]-1',5'-dione (3)

The synthesis of intermediate 3 was carried out as described above using the general protocol of Procedure A. Off white solid; Yield: 0.51 g; 64%; MS (ESI) m/z 331.59 [M+1]⁺.

Synthesis 8'-chloro-2,2-dimethyl-6'-(pyrimidin-4-ylamino)-2'H-spiro[cyclobutane-1,3'-imidazo[1,5-a]pyridine]-1',5'-dione (Cpd. No. 120)

The synthesis of compound 120 was carried out as described above using the general protocol of Procedure H. Light yellow solid; Yield: 0.12 g, 39%; MS (ESI) m/z 346.80 [M+1]+; ¹H NMR (400 MHz, DMSO-d₆) δ 10.03 (s, 1H), 9.75 (s, 1H), 8.85 (s, 1H), 8.80 (s, 1H), 8.84 (d, J=16.88 Hz, 1H), 7.48 (d, J=5.72 Hz, 2H), 3.13-3.08 (m, J=9.44 Hz, 1H), 2.66-2.59 (m, J=9.64 Hz, 1H), 1.20 (s, 3H), 0.98 (s, 3H).

Example 121

Synthesis of 6'-((6-Aminopyrimidin-4-yl) amino)-8'-chloro-2,2-dimethyl-2'H-spiro[cyclobutane-1,3'-imidazo[1,5-a]pyridine]-1',5'-dione (Cpd. No. 121)

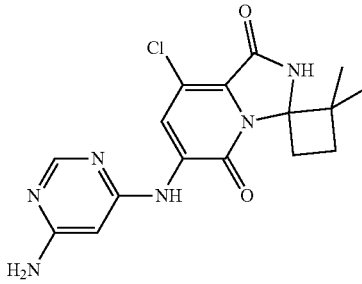

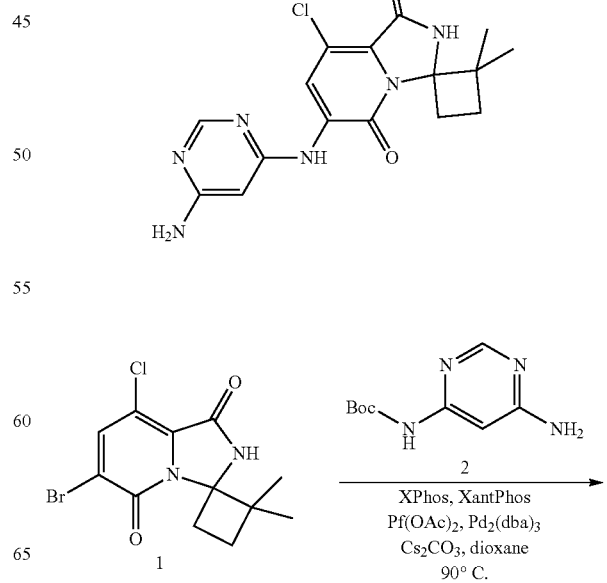

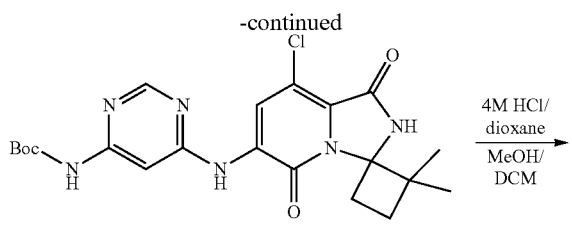

Synthesis of tert-butyl (6-((8'-chloro-2, 2-dimethyl-1',5'-dioxo-1',5'-dihydro-2'H-spiro[cyclobutane-1,3'-imidazo[1,5-a]pyridin]-6'-yl)amino)pyrimidin-4-yl)carbamate (3)

The synthesis of intermediate 3 was carried out as described above using the general protocol of Procedure H. Off white solid; Yield: 0.31 g, crude; MS (ESI) m/z 461.90 [M+1]⁺.

Synthesis of 6'-((6-aminopyrimidin-4-yl) amino)-8'-chloro-2,2-dimethyl-2'H-spiro[cyclobutane-1,3'-imidazo[1,5-a]pyridine]-1',5'-dione (Cpd. No. 121)

The synthesis of compound 121 was carried out as described above using the general protocol of Procedure F. Yellow solid; Yield: 0.070 g, 30%; MS (ESI) m/z 361.92 [M+1]⁺; ¹H NMR: (400 MHz, DMSO-d₆) δ 9.94 (s, 1H), 9.07 (s, 1H), 8.67 (s, 1H), 8.21 (s, 1H), 6.61 (s, 2H), 3.12-3.05 (m, J=2.48 Hz, 1H), 2.66-2.58 (m, J=5.4 Hz, 1H), 1.55-1.50 (m, J=3.0 Hz, 1H), 1.19 (s, 3H), 0.96 (s, 3H).

Example 122

Synthesis of 6-[(6-amino-5-chloro-pyrimidin-4-yl)amino]-8-chloro-spiro[2H-imidazo[1,5-a]pyridine-3,1'-cyclohexane]-1,5-dione hydrochloride (Cpd. No. 122)

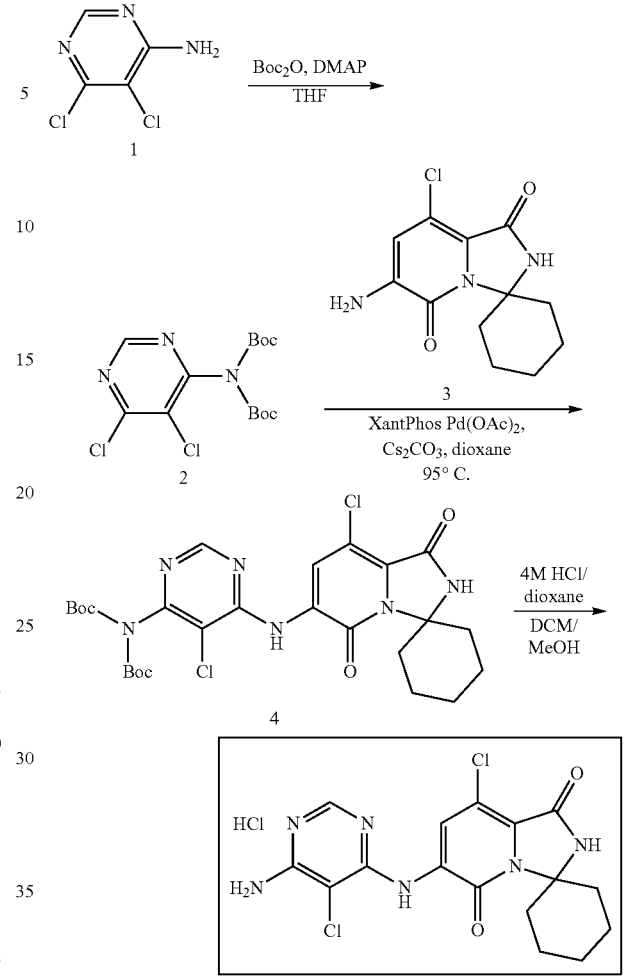

Synthesis tert-butyl N-tert-butoxycarbonyl-N-(5,6-dichloropyrimidin-4-yl)carbamate (2)

Procedure J: To a stirred solution of 5, 6-dichloropyrimidin-4-amine (1, 3.0 g, 18.29 mmol) in tetrahydrofuran (30 mL), 4-dimethylaminopyridine (0.16 g, 1.31 mmol) and di-tert-butyl dicarbonate (8.77 g, 40.2 mmol) were added at room temperature. The reaction mass was stirred at room temperature for overnight. After completion, distilled out the solvent. The above residue was diluted with water and extracted with ethyl acetate (2×50 mL). The organics were then separated and dried (magnesium sulfate) and concentrated to dryness under vacuum to afford ethyl tert-butyl N-tert-butoxycarbonyl-N-(5,6-dichloropyrimidin-4-yl)carbamate (2) as white solid. Yield: 3.1 g, 47%; MS (ESI) m/z 364.3 [M+1]⁺; ¹H NMR (400 MHz, DMSO-d₆) δ 9.04 (s, 1H), 1.40 (s, 18H).

Synthesis of tert-butyl N-tert-butoxycarbonyl-N-[5-chloro-6-[(8-chloro-1,5-dioxo-spiro[2H-imidazo[1,5-a]pyridine-3,1'-cyclohexane]-6-yl)amino]pyrimidin-4-yl]carbamate (4)

The synthesis of intermediate 4 was carried out as described above using the general protocol of Procedure B. Yellow solid; Yield: 0.10 g, 26%; MS (ESI) m/z 595.45

[M+1]+; 1H NMR (400 MHz, DMSO-d6) δ 10.46 (s, 1H), 8.99 (s, 1H), 8.95 (s, 1H), 8.66 (s, 1H), 2.90 (m, 2H), 1.65 (m, 7H), 1.46 (s, 18H), 1.20 (m, 1H).

Synthesis of 6-[(6-amino-5-chloro-pyrimidin-4-yl) amino]-8-chloro-spiro[2H-imidazo[1,5-a]pyridine-3,1'-cyclohexane]-1,5-dione hydrochloride (Cpd. No. 122)

The synthesis of compound 122 was carried out as described above using the general protocol of Procedure F. Yellow solid; Yield: 0.059 g, 81%; MS (ESI) m/z 395.35 [M+1]+; 1H NMR: (400 MHz, DMSO-d6) δ 10.35 (s, 1H), 8.62 (s, 1H), 8.55 (s, 1H), 8.23 (s, 2H), 7.27 (s, 1H), 2.91 (t, J=2.28, 2H), 1.75 (m, 2H), 1.63 (m, 3H), 1.53 (d, J=12.8 Hz, 2H), 1.23 (m, 1H).

Example 123

Synthesis of 6'-((7H-pyrrolo[2,3-d]pyrimidin-4-yl) amino)-8'-chloro-2'H-spiro[cyclohexane-1,3'-imidazo[1,5-a]pyridine]-1',5'-dione hydrochloride (Cpd. No. 123)

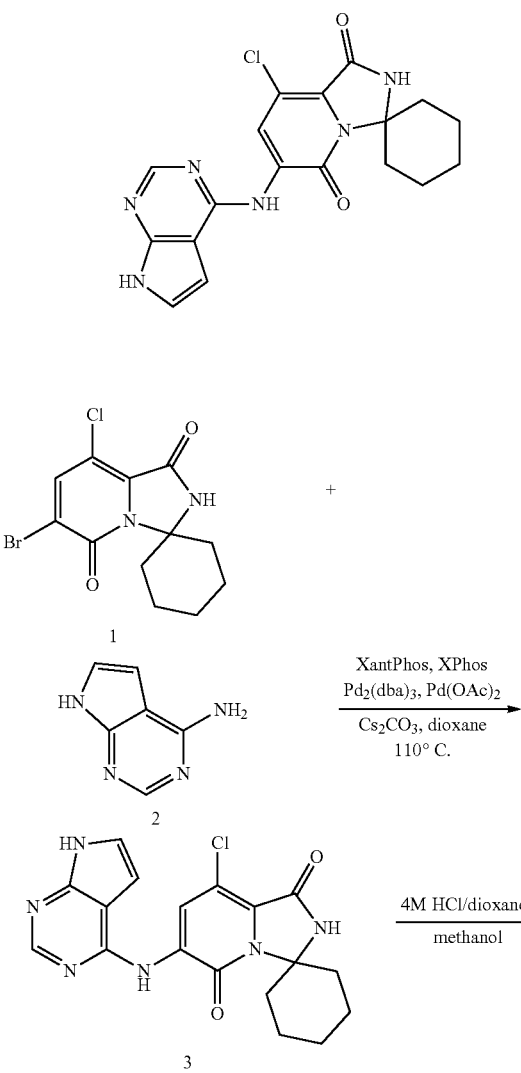

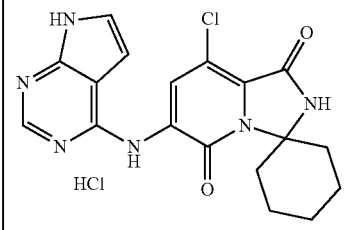

Synthesis of 6'-((7H-pyrrolo[2,3-d]pyrimidin-4-yl) amino)-8'-chloro-2'H-spiro[cyclohexane-1,3'-imidazo[1,5-a]pyridine]-1',5'-dione (3)

The synthesis of intermediate 3 was carried out as described above using the general protocol of Procedure H. Yellow solid; Yield: 0.60 g, crude; MS (ESI) m/z 385.19 [M+1]+

Synthesis of 6'-((7H-pyrrolo[2,3-d]pyrimidin-4-yl) amino)-8'-chloro-2'H-spiro[cyclohexane-1,3'-imidazo[1,5-a]pyridine]-1',5'-dione hydrochloride (Cpd. No. 123)

To a stirred solution of 8-chloro-6-(7H-pyrrolo[2,3-d]pyrimidin-4-ylamino)spiro[2H-imidazo[1,5-a]pyridine-3,1'-cyclohexane]-1,5-dione (3, 0.6 g, 1.56 mmol) in methanol (6 mL) 4 M hydrogenchloride in dioxane (4 mL) was added under cooling and stirred the reaction mixture at room temperature for overnight. After completion filtered the reaction mass using sintered funnel and washed with ethanol (10 mL). The solid obtained was dried under high vacuum to afford 8-chloro-6-(7H-pyrrolo[2,3-d]pyrimidin-4-ylamino)spiro[2H-imidazo[1,5-a]pyridine-3, 1'-cyclohexane]-1,5-dione hydrochloride (Cpd. No. 123) as light yellow solid; Yield: 0.21 g, 32%; MS (ESI) m/z 385.31 [M+1]+; 1H NMR (400 MHz, DMSO-d6) δ 12.24 (s, 1H), 10.39 (s, 1H), 9.12 (s, 1H), 8.75 (s, 1H), 8.50 (s, 1H), 7.43 (s, 1H), 6.88 (s, 1H), 2.95 (t, J=11.14 Hz, 2H), 1.76 (m, 2H), 1.62 (m, 5H), 1.22 (m, 1H).

Example 124

Synthesis of 8-chloro-3,3-dimethyl-6-(pyrido[4,3-d]pyrimidin-4-ylamino)-2,3-dihydroimidazo[1,5-a]pyridine-1,5-dione (Cpd. No. 124)

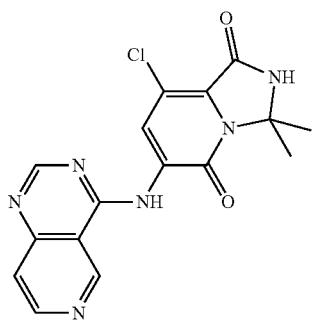 [SMILES: CC1(C)NC(=O)c2c(Cl)cc(Nc3ncnc4ccncc34)c(=O)n21]

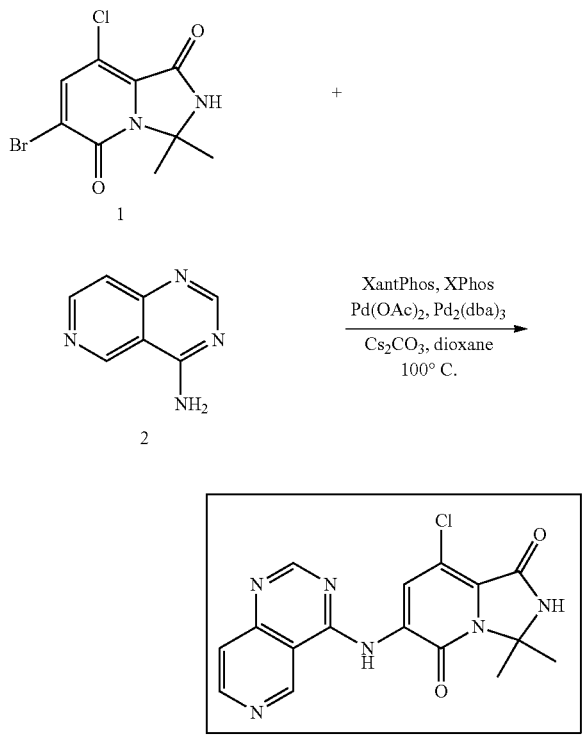

Synthesis of 8-chloro-3,3-dimethyl-6-(pyrido[4,3-d]pyrimidin-4-ylamino)-2,3-dihydroimidazo[1,5-a]pyridine-1,5-dione (Cpd. No. 124)

The synthesis of compound 124 was carried out as described above using the general protocol of Procedure H. Yellow solid; Yield: 0.060 g, 16%; MS (ESI) m/z 357.77 [M+1]$^+$; $^1$H NMR (400 MHz, DMSO-d$_6$) δ 9.91 (s, 2H), 9.69 (s, 1H), 8.96 (s, 1H), 8.90-8.86 (d, 1H), 8.87 (s, 1H), 7.73 (d, 1H), 1.84 (s, 6H).

Example 125

Synthesis of 8'-chloro-6'-((2-methylpyrimidin-4-yl)amino)-2'H-spiro[cyclohexane-1,3'-imidazo[1,5-a]pyridine]-1',5'-dione hydrochloride (Cpd. No. 125)

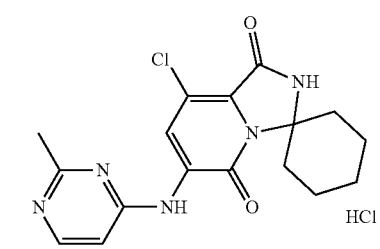 [SMILES: Cc1nccc(Nc2cc(Cl)c3n(c2=O)C2(CCCCC2)NC3=O)n1 ; Cl]

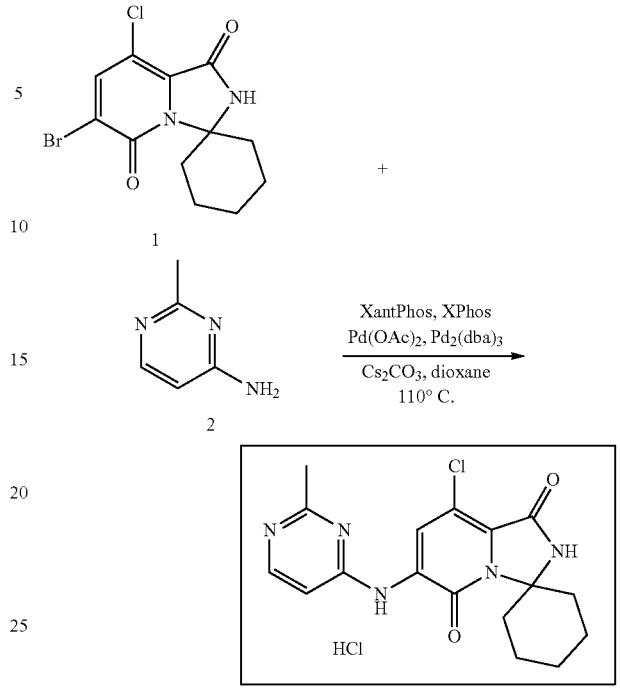

Synthesis of 8'-chloro-6'-((2-methylpyrimidin-4-yl)amino)-2'H-spiro[cyclohexane-1,3'-imidazo[1,5-a]pyridine]-1',5'-dione hydrochloride (Cpd. No. 125)

The synthesis of compound 125 was carried out as described above using the general protocol of Procedure H. Off white solid; Yield: 0.16 g, 45%; MS (ESI) m/z 360.38 [M+1]$^+$; $^1$H NMR (400 MHz, DMSO-d$_6$) δ 10.55 (s, 1H), 10.47 (s, 1H), 8.67 (s, 1H), 8.45 (m, 1H), 7.44 (d, J=4.8 Hz, 1H), 2.91 (t, J=11.74 Hz, 2H), 2.65 (s, 3H), 1.76 (m, 2H), 1.65 (m, 3H), 1.56 (m, 2H), 1.19 (m, 1H).

Example 126

Synthesis of 6-((6-aminopyrimidin-4-yl)amino)-8-chloro-2H-spiro[imidazo[1,5-a]pyridine-3,6'-[1,4]diazepane]-1,5-dione (Cpd. No. 126)

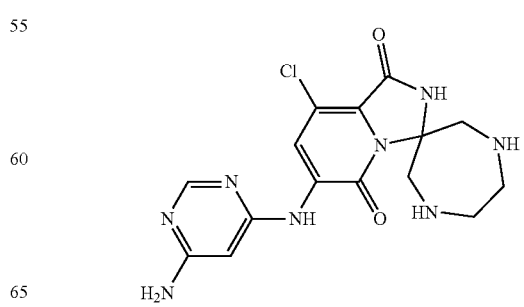

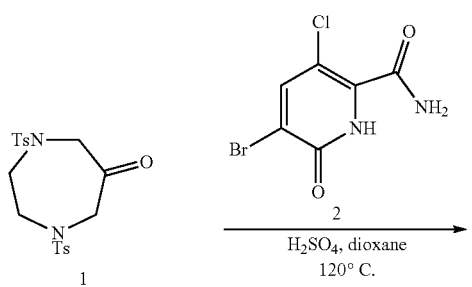
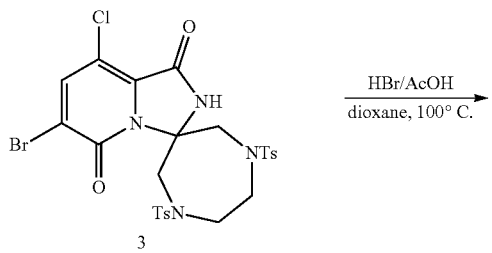
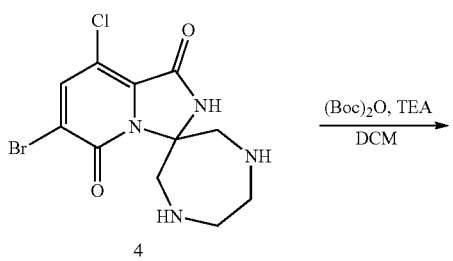
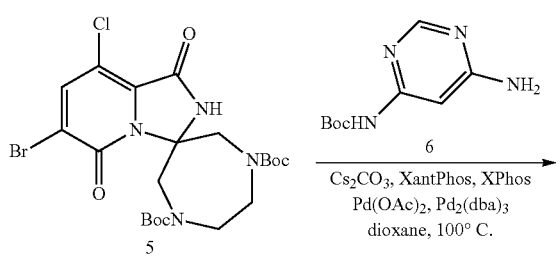
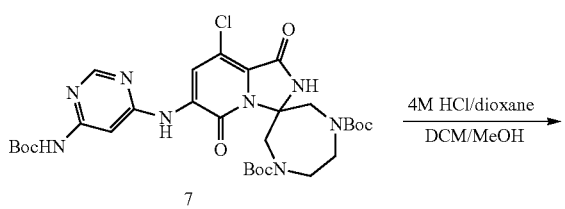
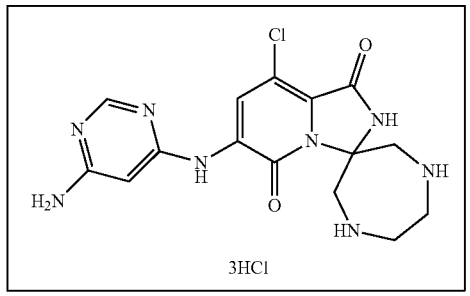

Synthesis of 6-bromo-8-chloro-1',4'-ditosyl-2H-spiro[imidazo[1,5-a]pyridine-3, 6'-[1,4]diazepane]-1,5-dione (3)

The synthesis of intermediate 3 was carried out as described above using the general protocol of Procedure A. White solid; Yield: 1.7 g, 43%; MS (ESI) m/z 442.31 [M+1]$^+$.

Synthesis of 6-bromo-8-chloro-2H-spiro[imidazo[1,5-a]pyridine-3, 6'-[1,4]diazepane]-1,5-dione (4)

To a stirred solution of hydrogenbromide (1.43 g, 15.24 mmol) in acetic acid in 1,4-dioxane (30 mL), 6-bromo-8-chloro-1',4'-ditosyl-2H-spiro[imidazo[1,5-a]pyridine-3,6'-[1,4]diazepane]-1,5-dione (1 g, 1.52 mmol) was added at room temperature. The vial was sealed and heated the reaction mass to 100° C. for 16 h. After completion, solvent was removed under reduced pressure and crude was triturated with dichloromethane to afford 6-bromo-8-chloro-2H-spiro[imidazo[1,5-a]pyridine-3,6'-[1,4]diazepane]-1,5-dione (4) as brown solid. Yield: 0.5 g, 94%; MS (ESI) m/z 362.28 [M+1]$^+$.

Synthesis of di-tert-butyl 6-bromo-8-chloro-1,5-dioxo-1,5-dihydro-2H-spiro[imidazo[1,5-a]pyridine-3,6'-[1,4]diazepane]-1',4'-dicarboxylate (5)

To a stirred solution of di-tert-butyl dicarbonate (0.94 g, 4.32 mmol) in dichloromethane (30 mL) in a vial at room temperature, 6-bromo-8-chloro-2H-spiro[imidazo[1,5-a]pyridine-3,6'-[1,4]diazepane]-1,5-dione (4, 0.5 g, 1.44 mmol) and triethylamine (0.73 g, 7.19 mmol) were added. The vial was sealed and stirred the reaction mass at room temperature for 16 h. After completion, the solvent was removed and the crude was triturated with hexane to afford di-tert-butyl 6-bromo-8-chloro-1,5-dioxo-1,5-dihydro-2H-spiro[imidazo[1,5-a]pyridine-3,6'-[1,4]diazepane]-1',4'-dicarboxylate (5) as yellow solid. Yield: 0.45 g, 57%; MS (ESI) m/z 547.13 [M+1]$^+$.

Synthesis of di-tert-butyl 6-((6-(((tert-butoxycarbonyl)amino)pyrimidin-4-yl)amino)-8-chloro-1,5-dioxo-1,5-dihydro-2H-spiro[imidazo[1,5-a]pyridine-3, 6'-[1,4]diazepane]-1',4'-dicarboxylate (7)

The synthesis of intermediate 7 was carried out as described above using the general protocol of Procedure H. Yellow solid; Yield: 0.41 g, 74%; MS (ESI) m/z 677.32 [M+1]$^+$.

Synthesis of 6-((6-aminopyrimidin-4-yl)amino)-8-chloro-2H-spiro[imidazo[1,5-a]pyridine-3,6'-[1,4]diazepane]-1,5-dione (Cpd. No. 126)

The synthesis of compound 126 was carried out as described above using the general protocol of Procedure F. Off white solid; Yield: 0.04 g, 18%; MS (ESI) m/z 377.32 [M+1]$^+$; $^1$H NMR (400 MHz, DMSO-d$_6$) δ 9.87 (s, 1H), 8.98 (s, 1H), 8.66 (s, 1H), 8.20 (s, 1H), 6.61 (s 2H), 6.25 (s, 1H), 3.61-3.58 (m, 2H), 2.95-2.91 (m, 2H), 2.82 (s, 4H), 2.66-2.61 (m, 2H).

Example 127

Synthesis of 6'-((1H-pyrazolo[3,4-d]pyrimidin-4-yl)amino)-8'-chloro-2'H-spiro [cyclohexane-1,3'-imidazo[1,5-a]pyridine]-1',5'-dione (Cpd. No. 127)

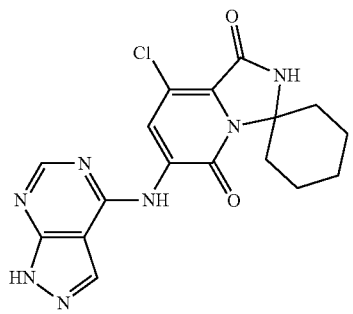 [SMILES: O=C1NC2(CCCCC2)n2c1c(Cl)cc(Nc1ncnc3[nH]ncc13)c2=O]

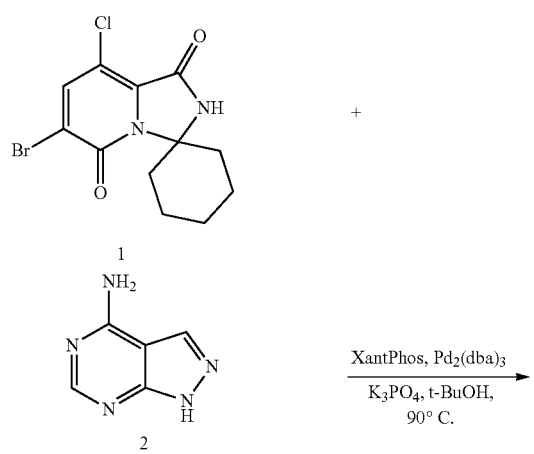

Synthesis of 6'-((1H-pyrazolo[3,4-d]pyrimidin-4-yl)amino)-8'-chloro-2'H-spiro [cyclohexane-1,3'-imidazo[1,5-a]pyridine]-1',5'-dione (Cpd. No. 127)

The synthesis of compound 127 was carried out as described above using the general protocol of Procedure B. Yield: 0.037 g, 6%; MS (ESI) m/z 386.36 [M+1]$^+$; $^1$H NMR (400 MHz, DMSO-d$_6$) δ 10.39 (s, 1H), 9.55 (s, 1H), 8.91 (s, 1H), 8.61 (s, 2H), 2.97 (m, 2H), 1.76-1.56 (m, 7H), 1.23 (m, 1H).

Example 128

Synthesis of 6-[(6-aminopyrimidin-4-yl)amino]-8-chloro-1'-methyl-spiro[2H-imidazo[1,5-a]pyridine-3,4'-piperidine]-1,5-dione hydrochloride (Cpd. No. 128)

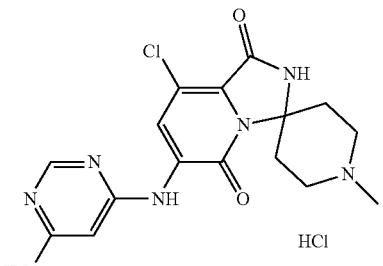

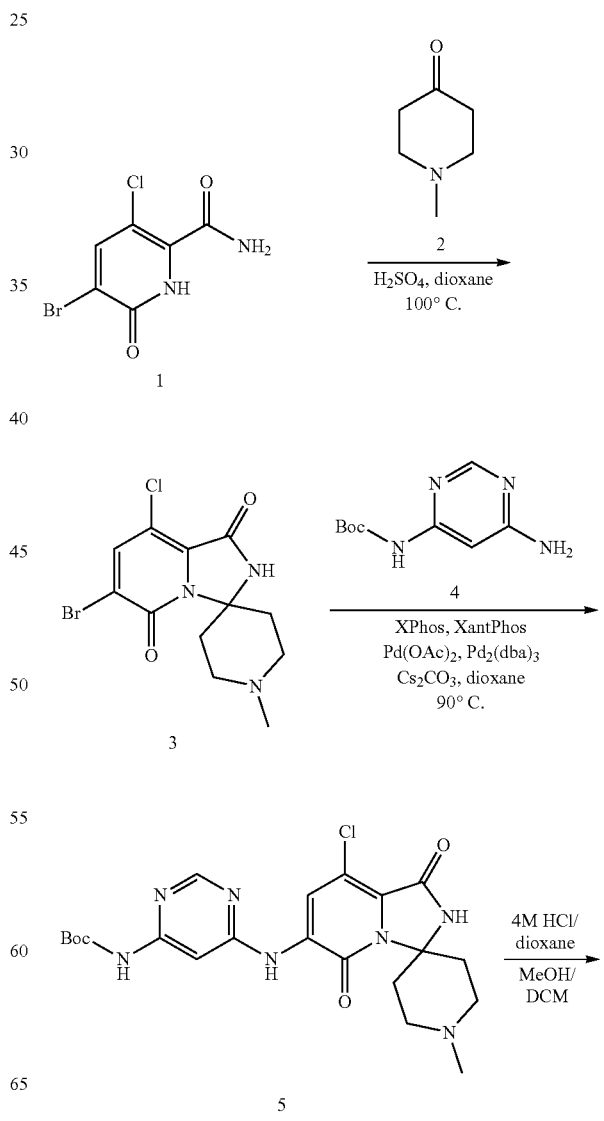

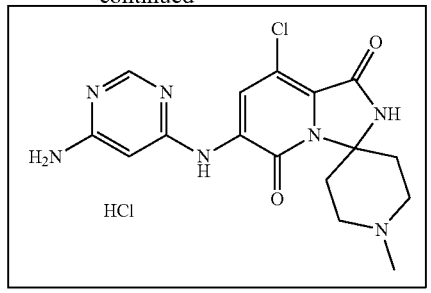

Synthesis of 6-bromo-8-chloro-1'-methyl-spiro[2H-imidazo[1,5-a]pyridine-3,4'-piperidine]-1,5-dione (3)

The synthesis of intermediate 3 was carried out as described above using the general protocol of Procedure A. Light brown solid; Yield: 1.0 g, 36%; MS (ESI) m/z 346.13 [M+1]+.

Synthesis of tert-butyl N-[6-[(8-chloro-1'-methyl-1,5-dioxo-spiro[2H-imidazo[1,5-a]pyridine-3,4'-piperidine]-6-yl)amino]pyrimidin-4-yl]carbamate (5)

The synthesis of intermediate 5 was carried out as described above using the general protocol of Procedure H. Off white solid; Yield: 60 mg, 14%; 1H NMR (400 MHz, DMSO-d6) δ 10.33 (s, 1H), 9.63 (s, 1H), 8.84 (s, 1H), 8.80 (s, 1H), 8.44-8.42 (d, J=8.0 Hz, 1H), 7.47-7.45 (d, J=8.0 Hz, 1H), 7.39-7.38 (m, 1H), 5.75 (s, 2H), 3.24-3.17 (m, 2H), 2.80-2.66 (m, 2H), 2.39-2.35 (m, 2H), 2.32 (s, 3H), 1.50-1.47 (m, 2H), 1.23 (s, 9H).

Synthesis of 6-[(6-aminopyrimidin-4-yl)amino]-8-chloro-1'-methyl-spiro[2H-imidazo[1,5-a]pyridine-3,4'-piperidine]-1,5-dione hydrochloride (Cpd. No. 128)

The synthesis of compound 128 was carried out as described above using the general protocol of Procedure F. Off white solid; Yield: 0.032 g, 62%; MS (ESI) m/z 375.82 [M+1]+; 1H NMR (400 MHz, DMSO-d6) δ 10.72 (brs, 1H), 10.60 (s, 1H), 9.80 (s, 1H), 8.49 (s, 1H), 8.44 (s, 1H), 7.81 (brs, 2H), 6.53 (s, 1H), 3.66-3.33 (m, 6H), 2.78 (s, 3H), 1.91-1.88 (m, 2H).

Example 129

Synthesis of 8-chloro-1'-methyl-6-(pyrimidin-4-ylamino)spiro[2H-imidazo[1,5-a]pyridine-3,4'-piperidine]-1,5-dione (Cpd. No. 129)

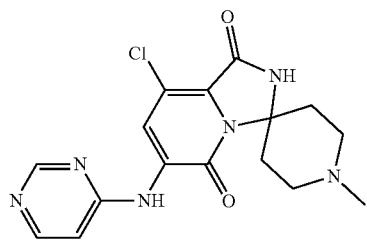 [SMILES: CN1CCC2(CC1)NC(=O)c1c(Cl)cc(Nc3ccncn3)c(=O)n12]

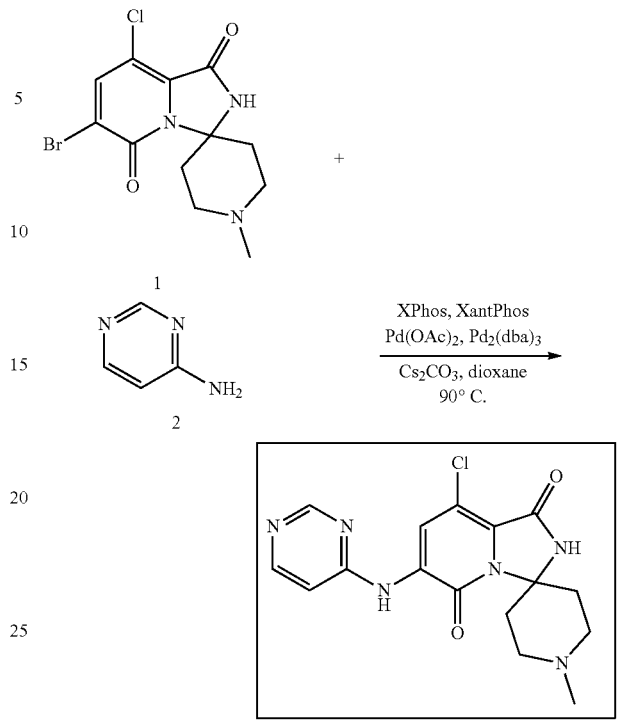

Synthesis of 8-chloro-1'-methyl-6-(pyrimidin-4-ylamino)spiro[2H-imidazo[1,5-a]pyridine-3,4'-piperidine]-1,5-dione (Cpd. No. 129)

The synthesis of compound 129 was carried out as described above using the general protocol of Procedure H. Off white solid; Yield: 65 mg, 31%; MS (ESI) m/z 360.80 [M+1]+; 1H NMR (400 MHz, DMSO-d6) δ 10.32 (s, 1H), 9.62 (s, 1H), 8.43-8.42 (d, J=5.6 Hz, 1H), 7.47-7.45 (d, J=4.8 Hz, 1H), 3.25-3.17 (m, 2H), 2.80-2.78 (m, 2H), 2.39-2.33 (m, 2H), 2.24 (s, 3H), 1.50-1.47 (m, 2H).

Example 130

Synthesis of 1',8-dimethyl-6-(pyrimidin-4-ylamino)-2H-spiro[imidazo[1,5-a]pyridine-3,3'-piperidine]-1,5-dione (Cpd. No. 130)

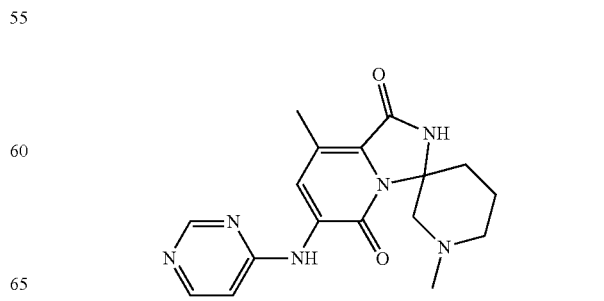

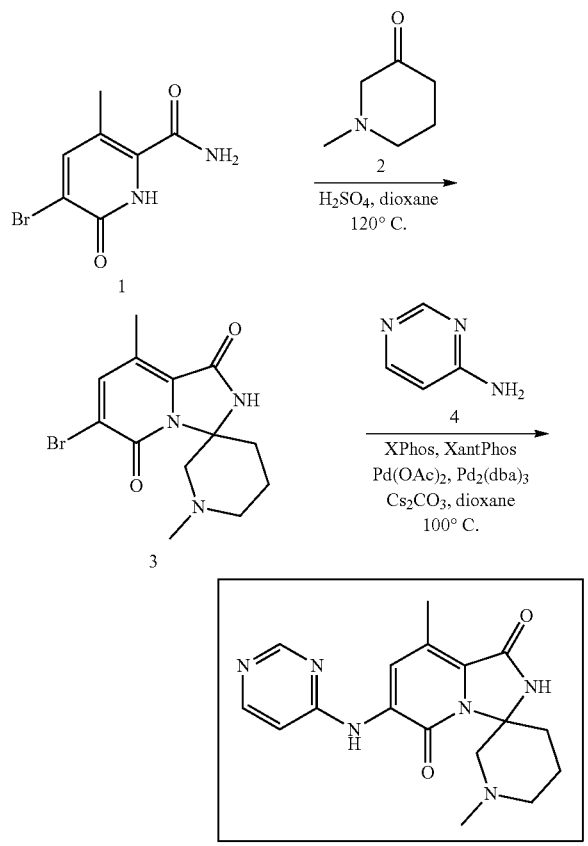

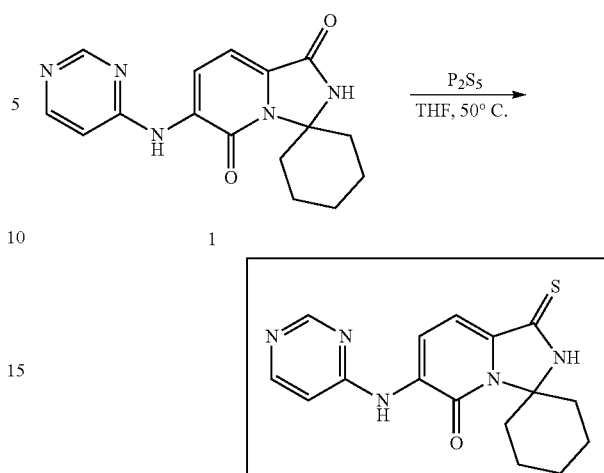

Synthesis of 6-bromo-1',8-dimethyl-spiro[2H-imidazo[1,5-a]pyridine-3,3'-piperidine]-1,5-dione (3)

The synthesis of intermediate 3 was carried out as described above using the general protocol of Procedure A. White solid; Yield: 0.7 g, 25%; MS (ESI) m/z 326.19 [M+1]$^+$.

Synthesis of 1',8-dimethyl-6-(pyrimidin-4-ylamino)-2H-spiro[imidazo[1,5-a]pyridine-3,3'-piperidine]-1,5-dione (Cpd. No. 130)

The synthesis of compound 130 was carried out as described above using the general protocol of Procedure H. Yellow solid; Yield: 190 mg, 58%; MS (ESI) m/z 359.81 [M+1]$^+$; $^1$H NMR (400 MHz, DMSO-d$_6$) δ 9.93 (s, 1H), 9.35 (s, 1H), 8.77 (s, 1H), 8.59 (s, 1H), 8.37-8.38 (d, J=5.88 Hz, 1H), 7.35-7.36 (d, J=5.88 Hz, 1H), 3.01 (m, 2H), 2.95 (m, 1H), 2.50 (s, 2H), 2.45 (s, 3H), 2.25 (s, 3H), 1.91-1.97 (m, 2H), 1.71-1.73 (m, 1H), 1.48-1.51 (m, 1H).

Example 131

Synthesis of 6'-(pyrimidin-4-ylamino)-1'-thioxo-1',2'-dihydro-5'H-spiro[cyclohexane-1,3'-imidazo[1,5-a]pyridin]-5'-one (Cpd. No. 131)

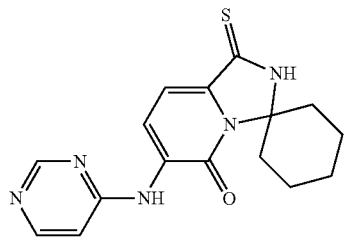 [SMILES: O=c1c(Nc2ccncn2)ccc2n1C1(CCCCC1)NC2=S]

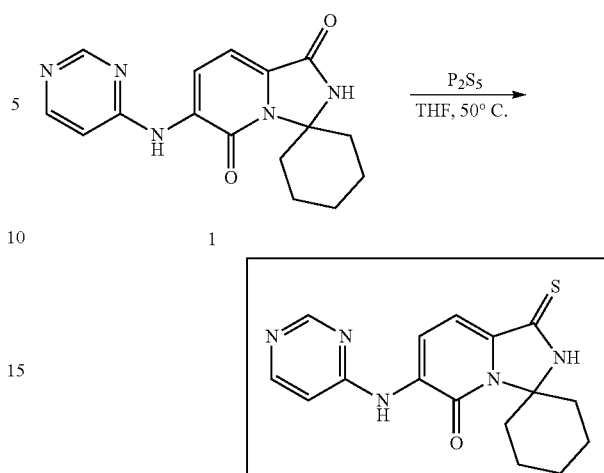

Synthesis of 6'-(pyrimidin-4-ylamino)-1'-thioxo-1',2'-dihydro-5'H-spiro[cyclohexane-1, 3'-imidazo[1,5-a]pyridin]-5'-one (Cpd. No. 131)

A vial containing tetrahydrofuran (10 mL) was charged with 6-(pyrimidin-4-ylamino)spiro[2H-imidazo[1,5-a]pyridine-3, 1'-cyclohexane]-1,5-dione (1, 0.6 g, 1.93 mmol) and phosphorus pentasulfide (857 mg, 3.85 mmol). Seal the vial and heat the reaction mixture at 50° C. for 16 h. After completion, the reaction mass was diluted with 5% methanol in dichloromethane (100 mL), washed with water (2×100 mL) and brine solution (100 mL), dried over anhydrous sodium sulfate, concentrated under vacuum. Crude material was purified by flash chromatography in silica gel in 3-4% methanol in dichloromethane, fraction were combined concentrated under reduced pressure. The product was triturated with methanol, filtered washed with methanol (3 mL), ether (5 mL), dried under high vacuum to obtain the desired product 6'-(pyrimidin-4-ylamino)-1'-thioxo-1',2'-dihydro-5'H-spiro[cyclohexane-1,3'-imidazo[1,5-a]pyridin]-5'-one (Cpd. No. 131) as light yellow solid. Yield: 0.050 g, 8%; MS (ESI) m/z 328.41 [M+1]$^+$; $^1$HNMR (400 MHz, DMSO-d$_6$) δ 12.26 (s, 1H), 9.46 (s, 1H), 8.80-8.77 (d, 2H), 8.39-8.38 (d, 1H), 7.39-7.38 (d, 1H), 7.07-7.06 (d, 1H), 2.97 (t, 2H), 1.78-1.72 (m, 5H), 1.59-1.56 (d, 1H), 1.26 (m, 1H).

Example 132

Synthesis of 8'-chloro-1'-(methoxyimino)-6'-(pyrimidin-4-ylamino)-1',2'-dihydro-5'H-spiro[cyclohexane-1,3'-imidazo[1,5-a]pyridin]-5'-one (Cpd. No. 132)

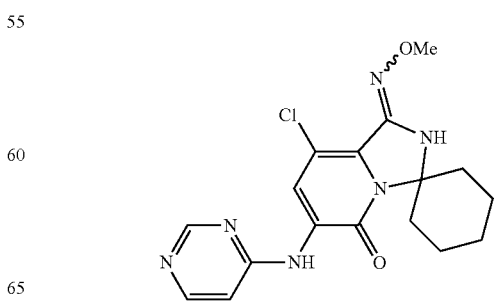

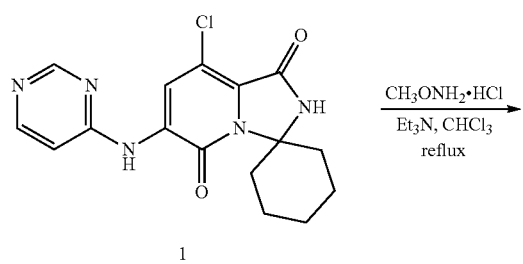

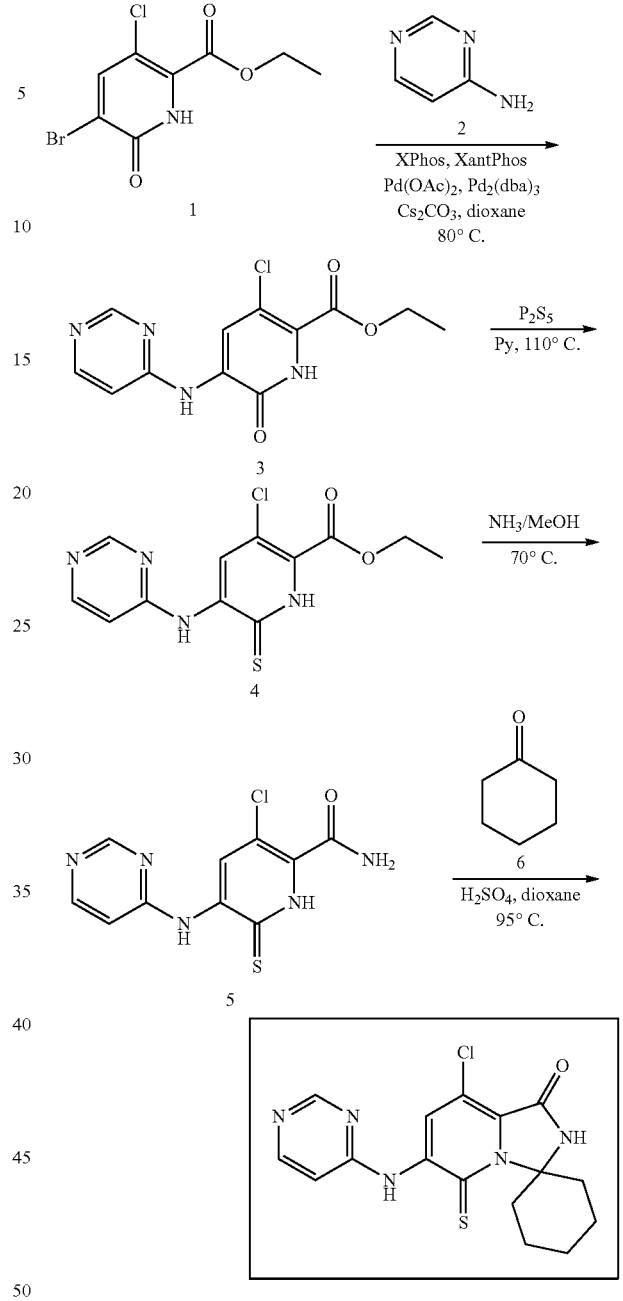

Synthesis of 8'-chloro-1'-(methoxyimino)-6'-(pyrimidin-4-ylamino)-1',2'-dihydro-5'H-spiro[cyclohexane-1, 3'-imidazo[1,5-a]pyridin]-5'-one (Cpd. No. 132)

To a solution of 8'-chloro-6'-(pyrimidin-4-ylamino)-2'H-spiro[cyclohexane-1,3'-imidazo[1,5-a]pyridine]-1',5'-dione (1, 1 g, 2.89 mmol) in chloroform (30 mL) was added triethylamine (1.21 mL, 8.67 mmol) and O-methylhydroxylamine hydrochloride (241 mg, 2.89 mmol). The reaction was stirred at reflux overnight. The resulting mixture was cooled to room temperature and washed with water. The organic layer was dried over magnesium sulfate, filtered and concentrated. The crude was purified via flash column chromatography to afford 8'-chloro-1'-(methoxyimino)-6'-(pyrimidin-4-ylamino)-1',2'-dihydro-5'H-spiro[cyclohexane-1,3'-imidazo[1,5-a]pyridin]-5'-one (Cpd. No. 132).

Example 133

Synthesis of 8'-chloro-6'-(pyrimidin-4-ylamino)-5'-thioxo-2'H-spiro[cyclohexane-1,3'-imidazo[1,5-a]pyridin]-1'(5'H)-one (Cpd. No. 133)

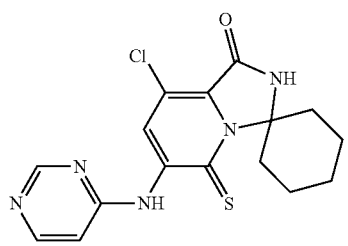 [SMILES: O=C1NC2(CCCCC2)n2c1c(Cl)cc(Nc1ccncn1)c2=S]

Synthesis of ethyl 3-chloro-6-oxo-5-(pyrimidin-4-ylamino)-1, 6-dihydropyridine-2-carboxylate (3)

The synthesis of intermediate 3 was carried out as described above using the general protocol of Procedure H. Yellow solid; Yield: 0.42 g, 20%; MS (ESI) m/z 295 [M+1]$^+$

Synthesis of ethyl 3-chloro-5-(pyrimidin-4-ylamino)-6-thioxo-1,6-dihydropyridine-2-carboxylate (4)

A vial was charged with 3-chloro-6-oxo-5-(pyrimidin-4-ylamino)-1,6-dihydropyridine-2-carboxylate (3, 0.35, 1.2 mmol) and pyridine (10 mL) was added. To the above mixture phosphorus pentasulfide (0.53 g, 2.4 mmol) was added and reaction was heated at 110° C. for 16 h. TLC showed presence of starting material and phosphorus pentasulfide (0.265 g, 1.2 mmol) was added again and heated the reaction to 115° C. for 24 h. The pyridine was removed under reduced pressure and water (20 mL) was added and extracted with 5% methanol in dichloromethane (100 mL). The organic layer was washed with sodium bicarbonate and brine and layer was concentrated to dryness to afford ethyl 3-chloro-5-(pyrimidin-4-ylamino)-6-thioxo-1,6-dihydropyridine-2-carboxylate (4) as brownish yellow solid and used directly without further purification. Yield: 350 mg, crude; MS (ESI) m/z 310.94 [M+1]$^+$.

Synthesis of 3-chloro-5-(pyrimidin-4-ylamino)-6-thioxo-1,6-dihydropyridine-2-carboxamide (5)

Procedure K: A vial was charged with 3-chloro-5-(pyrimidin-4-ylamino)-6-thioxo-1,6-dihydropyridine-2-carboxylate (4, 0.35 g, 1.2 mmol) and methanolic ammonia (12 mL) was added. The mixture was slowly heated at 60-65° C. for 40 h when TLC showed complete conversion of starting material. The mixture was cooled and concentrated under reduced pressure and triturated with diethyl ether (10 mL) to afford 3-chloro-5-(pyrimidin-4-ylamino)-6-thioxo-1,6-dihydropyridine-2-carboxamide (5) as reddish brown solid. Yield: 350 mg, crude; MS (ESI) m/z 282.04 [M+1]$^+$.

Synthesis of 8'-chloro-6'-(pyrimidin-4-ylamino)-5'-thioxo-2'H-spiro[cyclohexane-1,3'-imidazo[1,5-a]pyridin]-1'(5'H)-one (Cpd. No. 133)

The synthesis of compound 133 was carried out as described above using the general protocol of Procedure A. Yellow solid; Yield: 17 mg, 4%; MS (ESI) m/z 362.06 [M+1]$^+$. 1H NMR (400 MHz, DMSO-d$_6$) δ 10.64 (brs, 1H), 9.93 (s, 1H), 9.00 (s, 1H), 8.90 (s, 1H), 8.51 (d, J=5.6 Hz, 1H), 7.43 (d, J=6.0 Hz, 1H), 4.22-3.12 (m, 2H), 1.84-1.78 (m, 2H), 1.75-1.60 (m, 3H), 1.54-1.47 (m, 2H), 1.30-1.22 (m, 1H).

Example 134

Synthesis of 8'-chloro-5'-(methoxyimino)-6'-(pyrimidin-4-ylamino)-2'H-spiro[cyclohexane-1,3'-imidazo[1,5-a]pyridin]-1'(5'H)-one (Cpd. No. 134)

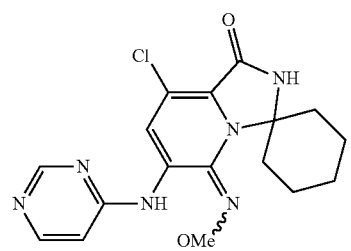 [SMILES: CON=c1c(Nc2ccncn2)cc(Cl)c2n1C1(CCCCC1)NC2=O]

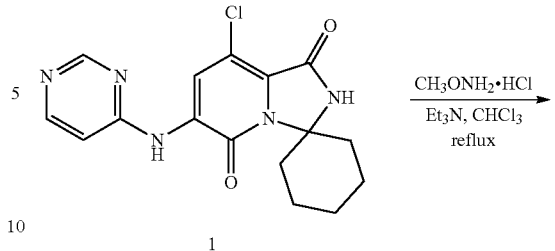

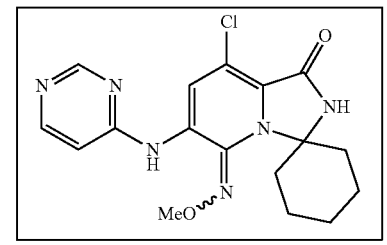

Synthesis of 8'-chloro-5'-(methoxyimino)-6'-(pyrimidin-4-ylamino)-2'H-spiro[cyclohexane-1,3'-imidazo[1,5-a]pyridin]-1'(5'H)-one (Cpd. No. 134)

To a solution of 8'-chloro-6'-(pyrimidin-4-ylamino)-2'H-spiro[cyclohexane-1,3'-imidazo[1,5-a]pyridine]-1',5'-dione (1, 1 g, 2.89 mmol) in chloroform (30 mL) is added triethylamine (1.21 mL, 8.67 mmol) and O-methylhydroxylamine hydrochloride (241 mg, 2.89 mmol). The reaction is stirred at reflux overnight. The resulting mixture is cooled to room temperature and washed with water. The organic layer is dried over magnesium sulfate, filtered and concentrated. The crude is purified via flash column chromatography to afford 8'-chloro-5'-(methoxyimino)-6'-(pyrimidin-4-ylamino)-2'H-spiro[cyclohexane-1,3'-imidazo[1,5-a]pyridin]-1'(5'H)-one (Cpd. No. 134).

Example 135

Synthesis of 8'-chloro-2'-cyclopropyl-6'-(pyrimidin-4-ylamino)-2'H-spiro[cyclohexane-1,3'-imidazo[1,5-a]pyridine]-1',5'-dione (Cpd. No. 135)

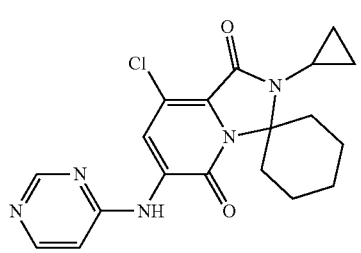 [SMILES: O=C1c2c(Cl)cc(Nc3ccncn3)c(=O)n2C2(CCCCC2)N1C1CC1]

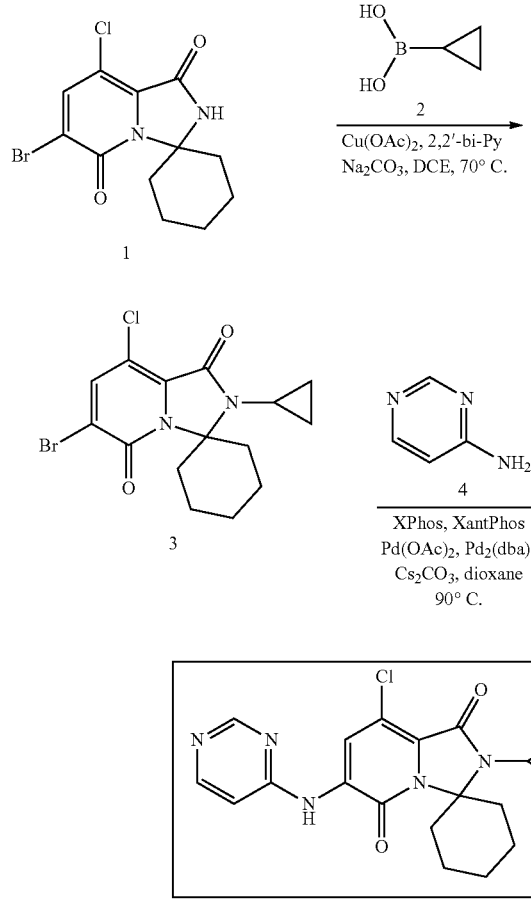

Synthesis of 6'-bromo-8'-chloro-2'-cyclopropyl-2'H-spiro[cyclohexane-1,3'-imidazo[1,5-a]pyridine]-1',5'-dione (3)

To a solution of 6'-bromo-8'-chloro-2'H-spiro[cyclohexane-1,3'-imidazo[1,5-a]pyridine]-1',5'-dione (1, 1 g, 3.02 mmol) in 1,2-dichloroethane (15 mL) is added cyclopropylboronic acid (2, 0.58 g, 6.80 mmol), copper(II) acetate (0.59 g, 3.23 mmol), 2,2'-bi-pyridyl (0.50 g, 3.23 mmol) and sodium carbonate (0.73 g, 6.86 mmol). The reaction is stirred at 70° C. overnight. The reaction is cooled to room temperature. The resulting mixture is quenched with saturated aqueous ammonium chloride solution and extracted with dichloromethane. The organic is dried over magnesium sulfate, filtered and concentrated. The crude is purified via column chromatography to afford 6'-bromo-8'-chloro-2'-cyclopropyl-2'H-spiro[cyclohexane-1,3'-imidazo[1,5-a]pyridine]-1',5'-dione (3).

Synthesis of 8'-chloro-2'-cyclopropyl-6'-(pyrimidin-4-ylamino)-2'H-spiro[cyclohexane-1,3'-imidazo[1,5-a]pyridine]-1',5'-dione (Cpd. No. 135)

The synthesis of compound 135 is carried out as described above using the general protocol of Procedure H.

Example 136

Synthesis of 8'-chloro-2'-(pyridin-3-yl)-6'-(pyrimidin-4-ylamino)-2'H-spiro[cyclohexane-1,3'-imidazo[1,5-a]pyridine]-1',5'-dione (Cpd. No. 136)

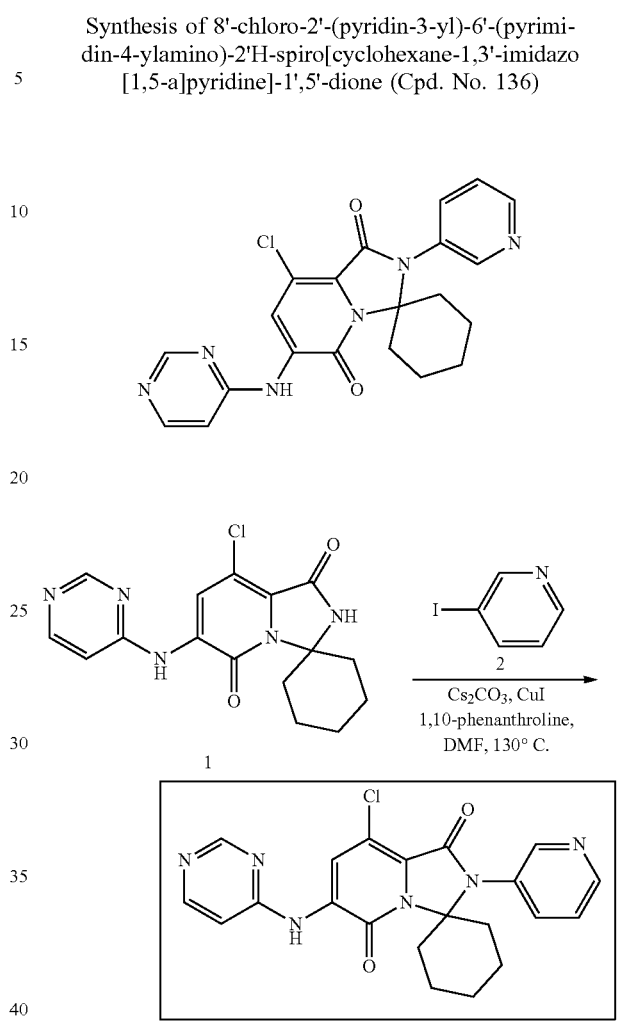

Synthesis of 8'-chloro-2'-(pyridin-3-yl)-6'-(pyrimidin-4-ylamino)-2'H-spiro[cyclohexane-1,3'-imidazo[1,5-a]pyridine]-1',5'-dione (Cpd. No. 136)

To a solution of 8'-chloro-6'-(pyrimidin-4-ylamino)-2'H-spiro[cyclohexane-1,3'-imidazo[1,5-a]pyridine]-1',5'-dione (1, 450 mg, 1.3 mmol) and 3-iodopyridine (800 mg, 3.9 mmol) in dimethylformamide (10 mL) in a vial, cesium carbonate (550 mg, 1.6 mmol) was added and the mixture was degassed with argon for 15 min. To this mixture 1,10,-phenanthroline (37 mg, 0.2 mmol), copper(I) iodide (12 mg, 0.05 mmol), XantPhos (26 mg, 0.065 mmol) were added and the reaction was heated the mixture at 130° C. for 26 h. TLC showed consumption of starting material, the reaction mixture was filtered over celite bed and washed with 5% methanol in dichloromethane followed by concentration of the filtrate. Obtained solid was purified by Combi-Flash chromatography on neutral alumina using 3% methanol/dichloromethane as a eluent, appropriate fractions were concentrated under reduced pressure to afford 8'-chloro-2'-(pyridin-3-yl)-6'-(pyrimidin-4-ylamino)-2'H-spiro[cyclohexane-1,3'-imidazo[1,5-a]pyridine]-1',5'-dione (Cpd. No. 136) as yellow solid. Yield: 0.025 g, 4.6%; MS (ESI) m/z 423.12 [M+1]$^+$; $^1$H NMR (400 MHz, DMSO-d$_6$) δ 10.59 (s, 1H), 8.61 (d, J=2.0 Hz, 1H), 8.58 (s, 1H), 8.49 (d, J=4.8 Hz, 1H), 8.33 (d, J=6.0 Hz, 1H), 8.03 (s, 1H), 7.82 (d, J=8.8 Hz, 1H), 7.47 (dd, J=4.4, 8.8 Hz, 1H), 6.65 (d, J=6.0 Hz, 1H), 2.85-2.79 (m, 2H), 1.74-1.53 (m, 6H), 1.17-1.14 (m, 1H).

Example 137

Synthesis of 7'-fluoro-6'-(pyrimidin-4-ylamino)-2'H-spiro[cyclohexane-1,3'-imidazo[1,5-a]pyridine]-1',5'-dione (Cpd. No. 137)

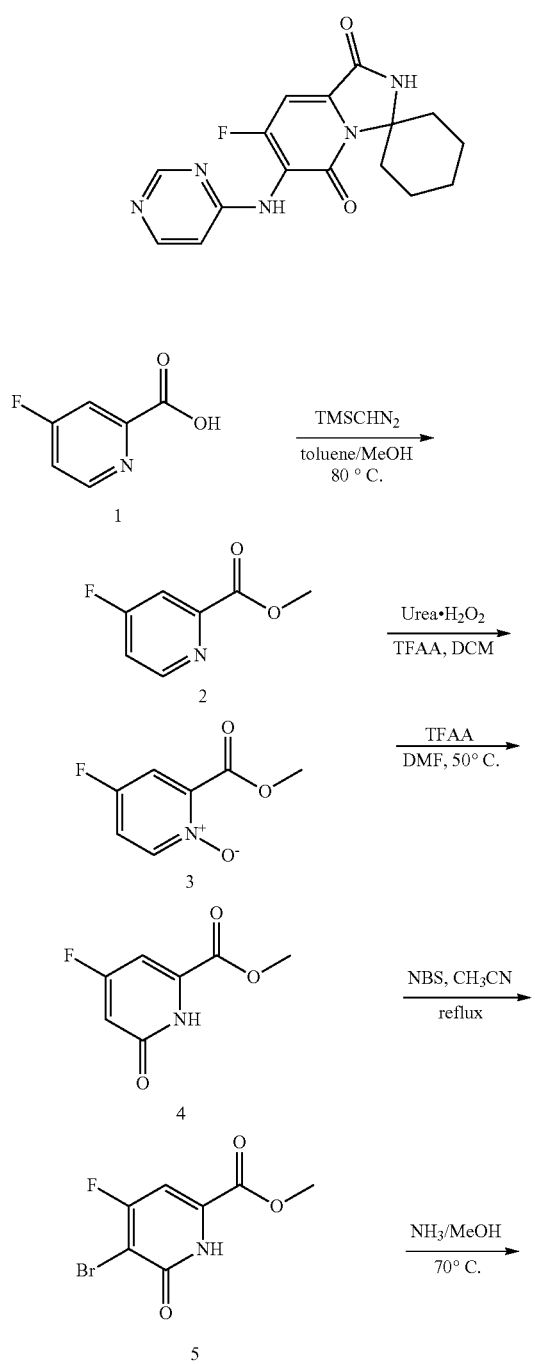

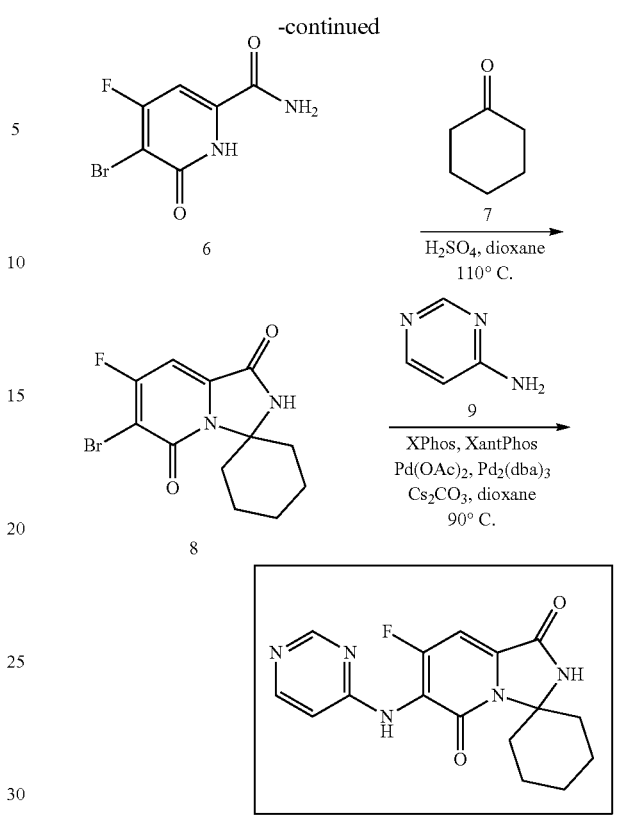

Synthesis of methyl 4-fluoropicolinate (2)

To a solution of 4-fluoropicolinic acid (1, 1 g, 7.09 mmol) in toluene (20 mL) and methanol (5 mL) at room temperature is added (trimethylsilyl)diazomethane (2 M in hexanes, 5.32 mL, 10.64 mmol) dropwise. The reaction is stirred at 80° C. for 2 h. The resulting mixture is concentrated and purified via flash chromatography to afford methyl 4-fluoropicolinate (2).

Synthesis of 4-fluoro-2-(methoxycarbonyl)pyridine 1-oxide (3)

To a solution of methyl 4-fluoropicolinate (2, 1 g, 6.45 mmol) in dichloromethane (30 mL) is added urea hydrogen peroxide (1.27 g, 13.54 mmol) and trifluoroacetic anhydride (1.79 mL, 12.9 mmol). The reaction is stirred at room temperature for 2 h. The resulting mixture is pour into 0.5 M hydrochloric acid and extracted with dichloromethane. The organic layer is washed with saturated aqueous sodium bicarbonate solution, dried over magnesium sulfate, filtered and concentrated. The crude is purified via flash chromatography to afford methyl 4-fluoro-2-(methoxycarbonyl)pyridine 1-oxide (3).

Synthesis of methyl 4-fluoro-6-oxo-1,6-dihydropyridine-2-carboxylate (4)

To a solution of methyl 4-fluoro-2-(methoxycarbonyl) pyridine 1-oxide (3, 1 g, 5.84 mmol) in dimethylformamide (25 mL) is added trifluoroacetic anhydride (1.62 mL, 11.68 mmol). The reaction is stirred at 50° C. for 3 h. The resulting mixture is concentrated and purified via flash chromatography to afford methyl 4-fluoro-6-oxo-1,6-dihydropyridine-2-carboxylate (4).

Synthesis of methyl 5-bromo-4-fluoro-6-oxo-1,6-dihydropyridine-2-carboxylate (5)

To a solution of methyl 4-fluoro-6-oxo-1,6-dihydropyridine-2-carboxylate (4, 1 g, 5.84 mmol) in acetonitrile (25 mL) is added N-bromosuccinimide (1.56 g, 8.76 mmol). The reaction is stirred at reflux for 2 h. The resulting mixture is pour into half saturated aqueous sodium bisulfite and extracted with ethyl acetate. The organic layers are combined, dried over magnesium sulfate, filtered and concentrated. The crude is purified via flash chromatography to afford methyl 5-bromo-4-fluoro-6-oxo-1,6-dihydropyridine-2-carboxylate (5).

Synthesis of 5-bromo-4-fluoro-6-oxo-1,6-dihydropyridine-2-carboxamide (6)

The synthesis of intermediate 6 is carried out as described above using the general protocol of Procedure K.

Synthesis of 6'-bromo-7'-fluoro-2'H-spiro[cyclohexane-1,3'-imidazo[1,5-a]pyridine]-1',5'-dione (8)

The synthesis of intermediate 8 is carried out as described above using the general protocol of Procedure A.

Synthesis of 7'-fluoro-6'-(pyrimidin-4-ylamino)-2'H-spiro[cyclohexane-1,3'-imidazo[1,5-a]pyridine]-1',5'-dione (Cpd. No. 137)

The synthesis of compound 137 is carried out as described above using the general protocol of Procedure H.

Example 138

Synthesis of 8-phenyl-6-(pyrimidin-4-ylamino)spiro[2H-imidazo[1,5-a]pyridine-3,1'-cyclohexane]-1,5-dione (Cpd. No. 138)

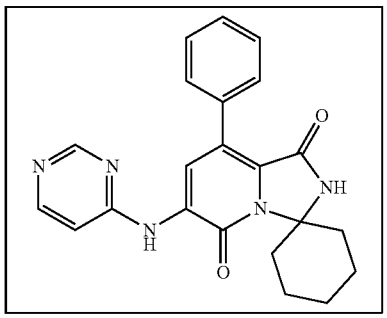

Synthesis of 8-phenyl-6-(pyrimidin-4-ylamino)spiro[2H-imidazo[1,5-a]pyridine-3,1'-cyclohexane]-1,5-dione (Cpd. No. 138)

The synthesis of compound 138 was carried out as described above using the general protocol of Procedure G. Off white solid; Yield: 0.15 g, 67%; MS (ESI) m/z 388.48 [M+1]$^+$; $^1$H NMR (400 MHz, DMSO-$d_6$) δ 10.16 (s, 1H), 9.49 (s, 1H), 8.74 (s, 1H), 8.71 (s, 1H), 8.38 (d, J=5.84 Hz, 1H), 7.47-7.35 (m, 6H), 3.10-3.04 (m, 2H), 1.76-1.49 (m, 7H), 1.04-1.02 (m, 1H).

Example 139

Synthesis of 8'-(oxetan-2-yl)-6'-(pyrimidin-4-ylamino)-2'H-spiro[cyclohexane-1,3'-imidazo[1,5-a]pyridine]-1',5'-dione (Cpd. No. 139)

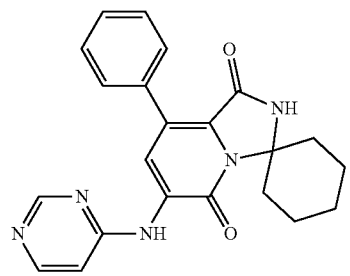 [SMILES: O=C1NC2(CCCCC2)n2c1c(-c1ccccc1)cc(Nc1ccncn1)c2=O]

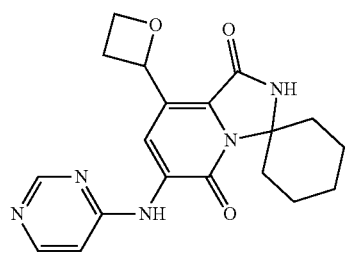 [SMILES: O=C1NC2(CCCCC2)n2c1c(C1CCO1)cc(Nc1ccncn1)c2=O]

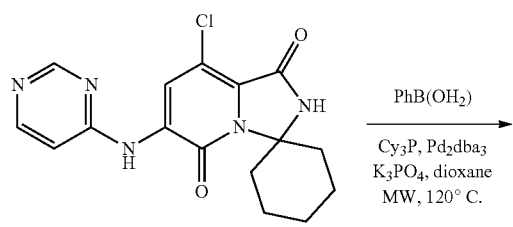

PhB(OH$_2$)

Cy$_3$P, Pd$_2$dba$_3$
K$_3$PO$_4$, dioxane
MW, 120° C.

PMBCl, NaH

DMF

225
-continued

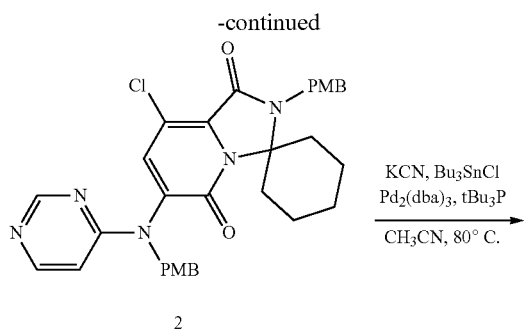
2

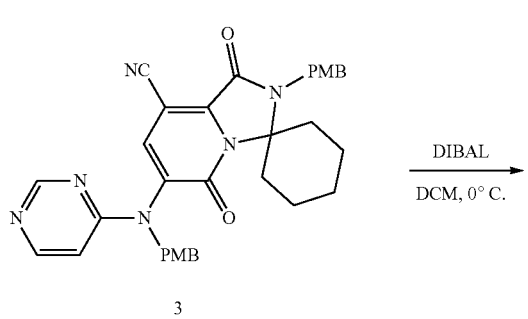
3

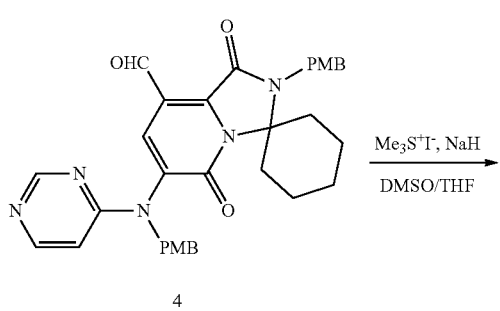
4

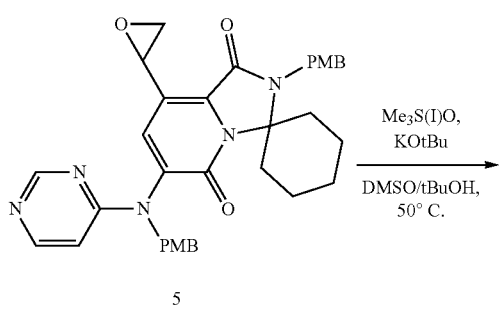
5

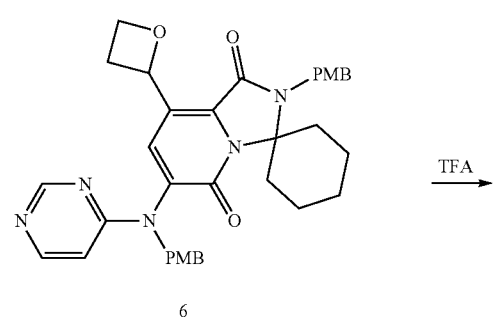
6

226
-continued

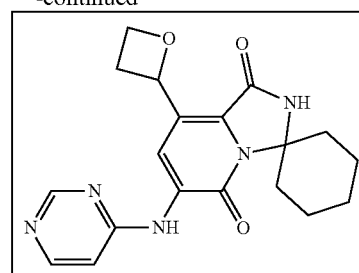

Synthesis of 8'-chloro-2'-(4-methoxybenzyl)-6'-((4-methoxybenzyl)(pyrimidin-4-yl)amino)-2'H-spiro[cyclohexane-1,3'-imidazo[1,5-a]pyridine]-1',5'-dione (2)

To a solution of 8'-chloro-6'-(pyrimidin-4-ylamino)-2'H-spiro[cyclohexane-1,3'-imidazo[1,5-a]pyridine]-1',5'-dione (1, 1 g, 2.89 mmol) in dimethylformamide (15 mL) is added sodium hydride (0.21 g, 8.67 mmol) and 4-methoxybenzyl chloride (1.57 mL, 11.56 mmol). The reaction is stirred at room temperature overnight. The resulting mixture is poured into iced water and extracted with dichloromethane. The organic layer is dried over magnesium sulfate, filtered and concentrated. The crude is purified via column chromatography to afford 8'-chloro-2'-(4-methoxybenzyl)-6'-((4-methoxybenzyl)(pyrimidin-4-yl)amino)-2' H-spiro[cyclohexane-1,3'-imidazo[1,5-a]pyridine]-1',5'-dione (2).

Synthesis of 2'-(4-methoxybenzyl)-6'-((4-methoxybenzyl)(pyrimidin-4-yl)amino)-1',5'-dioxo-1',5'-dihydro-2'H-spiro[cyclohexane-1,3'-imidazo[1,5-a]pyridine]-8'-carbonitrile (3)

To a solution of 8'-chloro-2'-(4-methoxybenzyl)-6'-((4-methoxybenzyl)(pyrimidin-4-yl)amino)-2'H-spiro[cyclohexane-1,3'-imidazo[1,5-a]pyridine]-1',5'-dione (2, 1 g, 1.71 mmol)) in acetonitrile (20 mL) is added potassium cyanide (0.17 g, 2.56 mmol), tributyltin chloride (0.038 mL, 0.14 mmol). The mixture is degassed and followed by the addition of tris(dibenzylideneacetone)dipalladium(0) (64 mg, 0.07 mmol) and tri-tert-butylphosphine (63 mg, 0.31 mmol). The mixture is degassed two more times. The reaction is stirred at 80° C. overnight. The resulting mixture is cooled to room temperature and filtered through a pad of celite. The filtrate is concentrated and purified via column chromatography to afford 2'-(4-methoxybenzyl)-6'-((4-methoxybenzyl)(pyrimidin-4-yl) amino)-1',5'-dioxo-1',5'-dihydro-2'H-spiro[cyclohexane-1,3'-imidazo[1,5-a]pyridine]-8'-carbonitrile (3).

Synthesis of 2'-(4-methoxybenzyl)-6'-((4-methoxybenzyl)(pyrimidin-4-yl)amino)-1',5'-dioxo-1',5'-dihydro-2'H-spiro[cyclohexane-1,3'-imidazo[1,5-a]pyridine]-8'-carbaldehyde (4)

To a solution of 2'-(4-methoxybenzyl)-6'-((4-methoxybenzyl)(pyrimidin-4-yl)amino)-1',5'-dioxo-1',5'-dihydro-2'H-spiro[cyclohexane-1,3'-imidazo[1,5-a]pyridine]-8'-carbonitrile (3, 1 g, 1.73 mmol) in dichloromethane (20 mL) at 0° C. is added diisobutylaluminum hydride (1 M in dichloromethane, 3.46 mL, 3.46 mmol) dropwise. The reacton is stirred at 0° C. for 2 h. The resulting mixture is poured into saturated aqueous Rochelle's salt solution. The biphasic mixture is stirred overnight and filtered. The filtrate is extracted with dichloromethane. The organic is dried over magnesium sulfate, filtered and concentrated. The crude is purified via column chromatography to afford 2'-(4-methoxybenzyl)-6'-((4-methoxybenzyl)(pyrimidin-4-yl)amino)-1',5'-dioxo-1',5'-dihydro-2'H-spiro[cyclohexane-1,3'-imidazo[1,5-a]pyridine]-8'-carbaldehyde (4).

Synthesis of 2'-(4-methoxybenzyl)-6'-((4-methoxybenzyl)(pyrimidin-4-yl)amino)-8'-(oxiran-2-yl)-2'H-spiro[cyclohexane-1,3'-imidazo[1,5-a]pyridine]-1',5'-dione (5)

A suspension of sodium hydride (50% dispersion washed free of mineral oil, 90 mg, 1.87 mmol) in dimethylsulfoxide (2 mL) is heated to 65° C. under argon for 1 h. The oil bath is removed and to the clear solution is added tetrahydrofuran (2 mL). The solution is cooled to −15° C. and treated with a solution of trimethylsulfonium iodide (0.35 g, 1.72 mmol) in dimethylsulfoxide (2 mL). After 3 min a solution of 2'-(4-methoxybenzyl)-6'-((4-methoxybenzyl)(pyrimidin-4-yl)amino)-1',5'-dioxo-1',5'-dihydro-2'H-spiro[cyclohexane-1,3'-imidazo[1,5-a]pyridine]-8'-carbaldehyde (4, 1 g, 1.72 mmol) in 3 ml. of tetrahydrofuran is added. The reaction is stirred overnight. The resulting mixture is poured into water and extracted with ethyl acetate. The extracts are washed with water, dried and evaporated to afford 2'-(4-methoxybenzyl)-6'-((4-methoxybenzyl)(pyrimidin-4-yl)amino)-8'-(oxiran-2-yl)-2'H-spiro[cyclohexane-1,3'-imidazo[1,5-a]pyridine]-1',5'-dione (5).

Synthesis of 2'-(4-methoxybenzyl)-6'-((4-methoxybenzyl)(pyrimidin-4-yl)amino)-8'-(oxetan-2-yl)-2'H-spiro[cyclohexane-1,3'-imidazo[1,5-a]pyridine]-1',5'-dione (6)

Potassium tert-butoxide (0.23 g, 2.02 mmol) is added to a solution of trimethylsulfoxonium iodide (0.44 g, 2.02 mmol) in tert-butanol (10 mL) at room temperature. After 15 min, a solution of 2'-(4-methoxybenzyl)-6'-((4-methoxybenzyl)(pyrimidin-4-yl)amino)-8'-(oxiran-2-yl)-2'H-spiro[cyclohexane-1,3'-imidazo[1,5-a]pyridine]-1',5'-dione (5, 1 g, 1.68 mmol) in dimethylsulfoxide (5 mL) is added dropwise. The reaction is stirred at 50° C. overnight. The resulting mixture is quenched with brine and extracted with ethyl acetate. The combined extracts are dried over magnesium sulfate. After filtration and concentration, the residue is purified by flash column to afford 2'-(4-methoxybenzyl)-6'-((4-methoxybenzyl)(pyrimidin-4-yl)amino)-8'-(oxetan-2-yl)-2'H-spiro[cyclohexane-1,3'-imidazo[1,5-a]pyridine]-1',5'-dione (6).

Synthesis of 8'-(oxetan-2-yl)-6'-(pyrimidin-4-ylamino)-2'H-spiro[cyclohexane-1,3'-imidazo[1,5-a]pyridine]-1',5'-dione (Cpd. No. 139)

2'-(4-Methoxybenzyl)-6'-((4-methoxybenzyl)(pyrimidin-4-yl)amino)-8'-(oxetan-2-yl)-2'H-spiro[cyclohexane-1,3'-imidazo[1,5-a]pyridine]-1',5'-dione (6, 100 mg, 0.16 mmol) is dissolved in trifluoroacetic acid (5 mL). The reaction is stirred at room temperature overnight. The resulting mixture is concentrated and purified via column chromatography to afford 8'-(oxetan-2-yl)-6'-(pyrimidin-4-ylamino)-2'H-spiro[cyclohexane-1,3'-imidazo[1,5-a]pyridine]-1',5'-dione (Cpd. No. 139).

Example 140

Synthesis of 8-chloro-3-methyl-6-(pyrimidin-4-ylamino)-3-vinyl-2,3-dihydroimidazo[1,5-a]pyridine-1,5-dione (Cpd. No. 140)

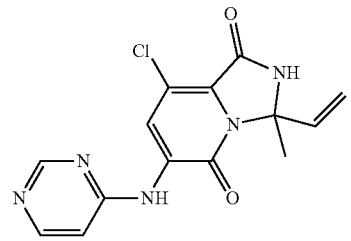 [SMILES: C=CC1(C)NC(=O)c2c(Cl)cc(Nc3ccncn3)c(=O)n21]

Synthesis of 6-bromo-8-chloro-3-methyl-3-vinyl-2,3-dihydroimidazo[1,5-a]pyridine-1,5-dione (3)

The synthesis of intermediate 3 is carried out as described above using the general protocol of Procedure A.

Synthesis of 8-chloro-3-methyl-6-(pyrimidin-4-ylamino)-3-vinyl-2,3-dihydroimidazo[1,5-a]pyridine-1,5-dione (Cpd. No. 140)

The synthesis of compound 140 is carried out as described above using the general protocol of Procedure H.

Example 141

Synthesis of 8-chloro-3-methyl-3-(prop-1-yn-1-yl)-6-(pyrimidin-4-ylamino)-2,3-dihydroimidazo[1,5-a]pyridine-1,5-dione (Cpd. No. 141)

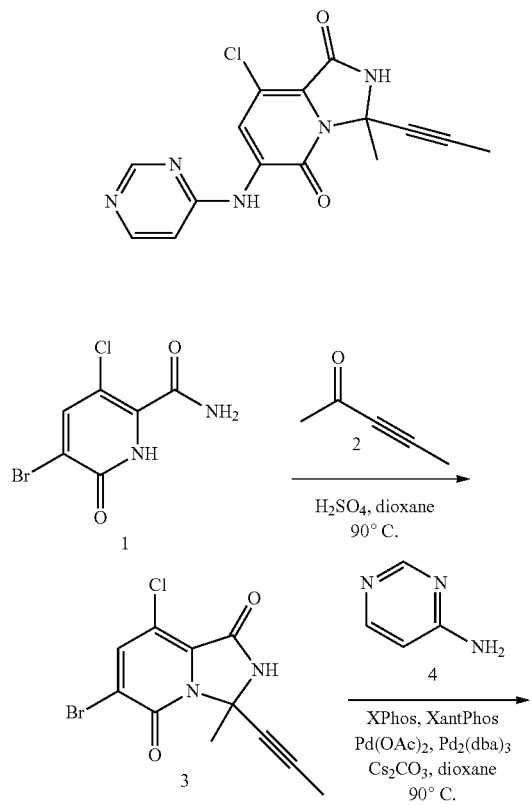

Synthesis of 6-bromo-8-chloro-3-methyl-3-(prop-1-yn-1-yl)-2,3-dihydroimidazo[1,5-a]pyridine-1,5-dione (3)

The synthesis of intermediate 3 is carried out as described above using the general protocol of Procedure A.

Synthesis of 8-chloro-3-methyl-3-(prop-1-yn-1-yl)-6-(pyrimidin-4-ylamino)-2,3-dihydroimidazo[1,5-a]pyridine-1,5-dione (Cpd. No. 141)

The synthesis of compound 141 is carried out as described above using the general protocol of Procedure H.

Example 142

Synthesis of 4-((8'-chloro-1',5'-dioxo-1',5'-dihydro-2'H-spiro[cyclohexane-1,3'-imidazo[1,5-a]pyridin]-6'-yl)amino)pyrimidine-5-carbonitrile (Cpd. No. 142)

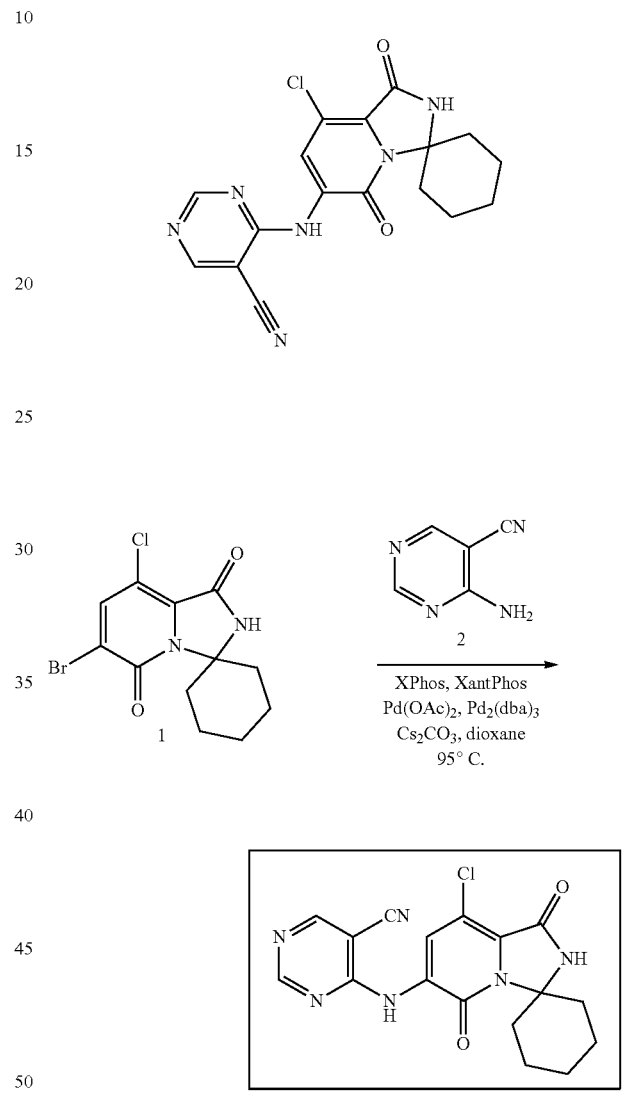

Synthesis of 4-((8'-chloro-1',5'-dioxo-1',5'-dihydro-2'H-spiro[cyclohexane-1,3'-imidazo[1,5-a]pyridin]-6'-yl)amino)pyrimidine-5-carbonitrile (Cpd. No. 142)

The synthesis of compound 142 was carried out as described above using the general protocol of Procedure H. Yellow solid; Yield: 0.25 g, 76%; MS (ESI) m/z 371.38 [M+1]$^+$; $^1$H NMR (400 MHz, DMSO-d$_6$) δ 10.48 (s, 1H), 9.06 (s, 1H), 9.03 (s, 1H), 8.98 (s, 1H), 8.59 (s, 1H), 2.93-2.87 (m, 2H), 1.93-1.88 (m, 2H), 1.75-1.54 (m, 5H), 1.27-1.23 (m, 1H).

Example 143

Synthesis of 8'-chloro-6'-((5-(1-methyl-1H-pyrazol-4-yl)pyrimidin-4-yl)amino)-2'H-spiro[cyclohexane-1,3'-imidazo[1,5-a]pyridine]-1',5'-dione (Cpd. No. 143)

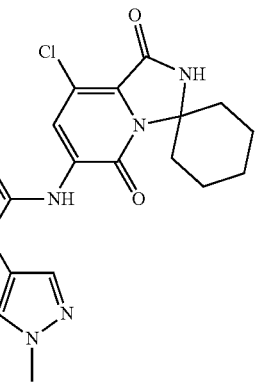

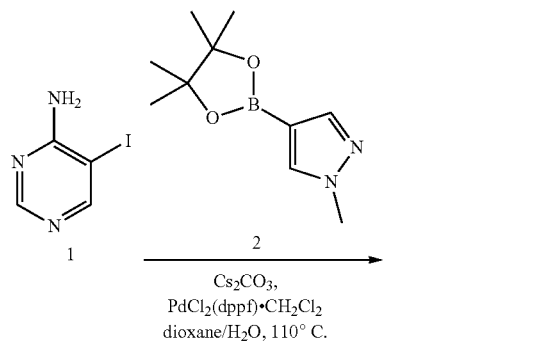

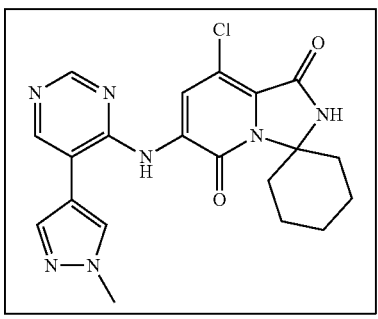

Synthesis of 5-(1-methyl-1H-pyrazol-4-yl)pyrimidin-4-amine (3)

To a solution of 5-iodopyrimidin-4-amine (1, 0.5 g, 2.26 mmol) and 1-methyl-4-(4,4,5,5-tetramethyl-1,3,2-dioxaborolan-2-yl)pyrazole (2, 0.56 g, 2.71 mmol) in dioxane/water (15 mL, 9:1.5) in a vial, was added cesium carbonate (1.84 g, 5.66 mmol) and the mixture was degassed with argon for 15 min. To this mixture was added [1,1'-bis(diphenylphosphino)ferrocene]dichloropalladium(II), complex with dichloromethane (0.09 g, 0.11 mmol) and then heated to 110° C. for 16 h. TLC showed consumption of starting material, cooled the reaction mixture to ambient temperature, filtered the mass over celite bed, washed with dichloromethane (30 mL) followed by concentration of filtrate. The crude compound was purified by flash column chromatography eluting with 3% methanol in dichloromethane. The desired fractions were concentrated to dryness to afforded as 5-(1-methylpyrazol-4-yl)pyrimidin-4-amine (3) as off white solid; Yield: 0.2 g, 50%; MS (ESI) m/z 176.08 [M+1]$^+$; $^1$H NMR (400 MHz, DMSO-$d_6$) δ 8.28 (s, 1H), 8.13 (s, 1H), 8.01 (s, 1H), 7.70 (s, 1H), 6.61 (s, 2H), 3.87 (s, 3H).

Synthesis of 8'-chloro-6'-((5-(1-methyl-1H-pyrazol-4-yl)pyrimidin-4-yl)amino)-2'H-spiro[cyclohexane-1,3'-imidazo[1,5-a]pyridine]-1',5'-dione (Cpd. No. 143)

The synthesis of compound 143 was carried out as described above using the general protocol of Procedure H. Pale yellow solid; Yield: 0.14 g, 36%; MS (ESI) m/z 426.44 [M+1]$^+$; $^1$H NMR (400 MHz, DMSO-$d_6$) δ 10.35 (s, 1H), 8.83 (s, 1H), 8.76-8.73 (s, 2H), 8.46 (s, 1H), 8.17 (s, 1H), 7.85 (s, 1H), 3.96 (s, 3H), 2.86 (m, 2H), 1.74-1.49 (m, 7H), 1.25 (m, 1H).

Example 144

Synthesis of 8'-chloro-6'-((5-ethynylpyrimidin-4-yl)amino)-2'H-spiro[cyclohexane-1,3'-imidazo[1,5-a]pyridine]-1',5'-dione (Cpd. No. 144)

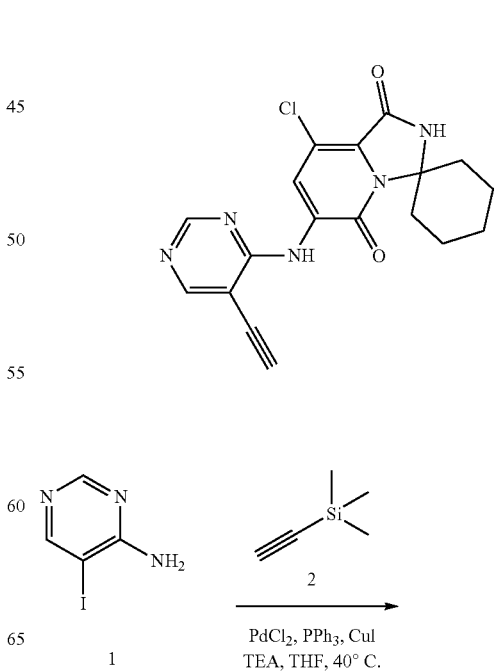

233

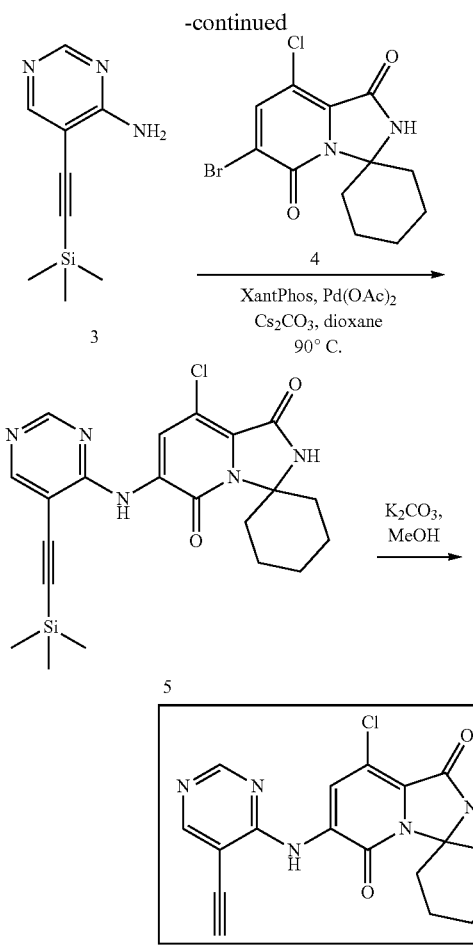

Synthesis of 5-((trimethylsilyl)ethynyl)pyrimidin-4-amine (3)

5-Iodopyrimidin-4-amine (1, 1 g, 4.52 mmol), copper(I) iodide (172 mg, 0.90 mmol), ethynyl(trimethyl) silane (2, 0.67 g, 6.79 mmol), triphenylphosphine (119 mg, 0.45 mmol), triethylamine (0.914 mg, 9.04 mmol) and palladium (II) chloride (80 mg, 0.45 mmol) were taken in a flask and tetrahydrofuran was added followed by degassing with argon for 5 minutes. The reaction mixture was stirred at 40° C. for 16 h. After completion, reaction mixture was filtered over celite bed and resulting filtrate was concentrated to afford 5-(2-trimethylsilylethynyl)pyrimidin-4-amine (3) as a brown solid. Yield: 0.76 g, 88%; MS (ESI) m/z 192.1 [M+1]+.

Synthesis of 8'-chloro-6'-((5-((trimethylsilyl)ethynyl)pyrimidin-4-yl)amino)-2'H-spiro[cyclohexane-1,3'-imidazo[1,5-a]pyridine]-1',5'-dione (5)

The synthesis of intermediate 5 was carried out as described above using the general protocol of Procedure B. Yellow solid. Yield: 0.30 g, 45%; MS (ESI) m/z 441.99 [M+1]+; $^1$H NMR (400 MHz, DMSO-$d_6$) δ 10.40 (s, 1H), 9.06 (s, 1H), 8.88 (s, 1H), 8.67 (m, 2H), 5.80 (m, 1H), 2.94-2.89 (m, 2H), 1.74-1.57 (m, 7H), 1.23 (m, 1H), 0.34 (s, 9H).

234

Synthesis of 8'-chloro-6'-((5-ethynylpyrimidin-4-yl)amino)-2'H-spiro[cyclohexane-1,3'-imidazo[1,5-a]pyridine]-1',5'-dione (Cpd. No. 144)

A flask was charged with 8'-chloro-6'-((5-((trimethylsilyl)ethynyl)pyrimidin-4-yl)amino)-2'H-spiro[cyclohexane-1,3'-imidazo[1,5-a]pyridine]-1',5'-dione (5, 300 mg, 0.67 mmol) and methanol (20 mL) followed by addition of potassium carbonate (469 mg, 3.39 mmol) at room temperature and reaction mixture was stirred for 16 h. After completion, solvent was concentrated under reduced pressure and the resulting residue was further washed with water followed by diethyl ether and pentane to afford 8'-chloro-6'-((5-ethynylpyrimidin-4-yl)amino)-2'H-spiro[cyclohexane-1,3'-imidazo[1,5-a]pyridine]-1',5'-dione (Cpd. No. 144) as yellow solid. Yield: 100 mg, 40%; MS (ESI) m/z 370.09 [M+1]+; $^1$H NMR (400 MHz, DMSO-$d_6$) δ 10.42 (s, 1H), 8.99 (s, 1H), 8.90 (s, 1H), 8.70 (s, 2H), 5.22 (s, 1H), 2.90 (brs, 2H), 1.73-1.64 (m, 2H), 1.61-1.56 (m, 3H), 1.56-1.53 (m, 2H), 1.27 (m, 1H).

Example 145

Synthesis of 6'-((1H-pyrazolo[3,4-d]pyrimidin-4-yl)amino)-8'-chloro-2'H-spiro [cyclohexane-1,3'-imidazo[1,5-a]pyridine]-1',5'-dione (Cpd. No. 145)

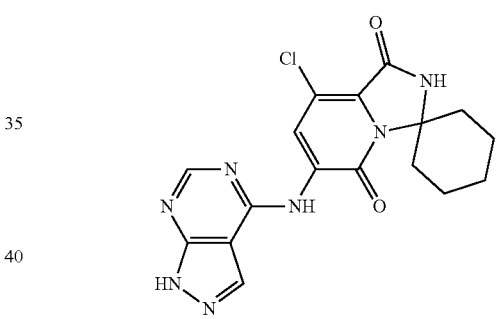

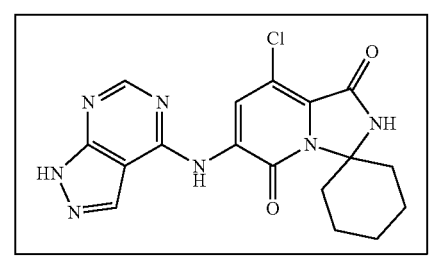

Synthesis of 6'-((1H-pyrazolo[3,4-d]pyrimidin-4-yl)amino)-8'-chloro-2'H-spiro [cyclohexane-1,3'-imidazo[1,5-a]pyridine]-1',5'-dione (Cpd. No. 145)

To a suspension of 6-bromo-8-chloro-spiro[2H-imidazo[1,5-a]pyridine-3,1'-cyclohexane]-1,5-dione (1, 0.5 g, 1.51 mmol), 1H-pyrazolo[3,4-d]pyrimidin-4-amine (2, 0.2 g, 1.51 mmol) in tert-butanol (20 mL) in a vial, potassium phosphate (0.96 g, 4.54 mmol) was added and the reaction mixture was degassed with argon for 15 min. To this mixture XantPhos (4 mg, 0.08 mmol) and Pd$_2$(dba)$_3$ (7 mg, 0.08 mmol) was added and the reaction mixture was further degassed with argon for 5 min. The reaction mixture was heated at 90° C. for 18 h. TLC showed consumption of starting material, the reaction mixture was filtered over celite bed and washed with dichloromethane followed by concentration of the filtrate. The crude was stirred with methanol (10 mL) and filtered. The resulting solid was further washed with diethyl ether (20 mL) and dried under vacuum to afford 8-chloro-6-(1H-pyrazolo[3,4-d]pyrimidin-4-ylamino)spiro[2H-imidazo[1,5-a]pyridine-3,1'-cyclohexane]-1,5-dione (Cpd. No. 145). Yield: 0.037 g, 6%; MS (ESI) m/z 386.36 [M+1]$^+$; $^1$H NMR (400 MHz, DMSO-d$_6$) δ 10.39 (s, 1H), 9.55 (s, 1H), 8.91 (s, 1H), 8.61 (s, 2H), 2.97 (m, 2H), 1.76-1.56 (m, 7H), 1.23 (m, 1H).

Example 146

Synthesis of 8-chloro-6-(3H-triazolo[4,5-d]pyrimidin-7-ylamino)spiro[2H-imidazo[1,5-a]pyridine-3,1'-cyclohexane]-1,5-dione (Cpd. No. 146)

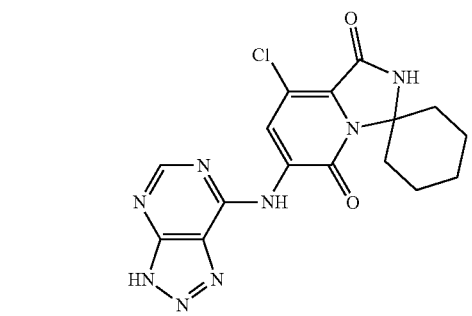 [SMILES: O=C1NC2(CCCCC2)n2c1c(Cl)cc(Nc1ncnc3[nH]nnc13)c2=O]

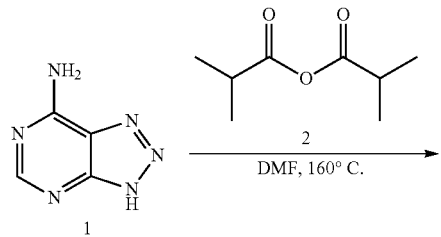

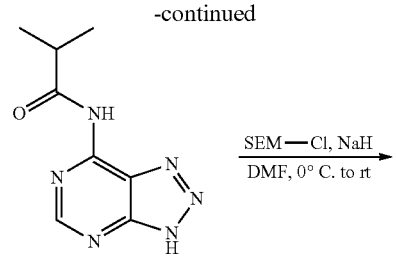

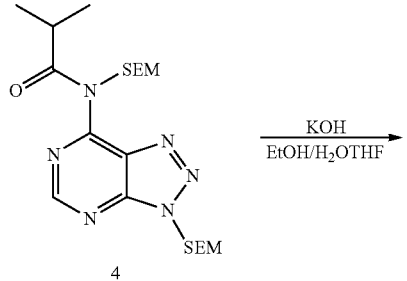

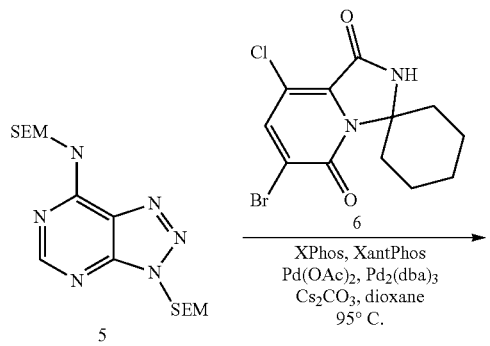

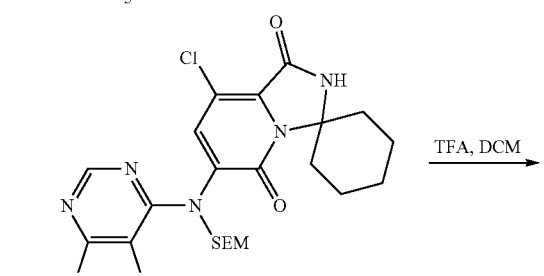

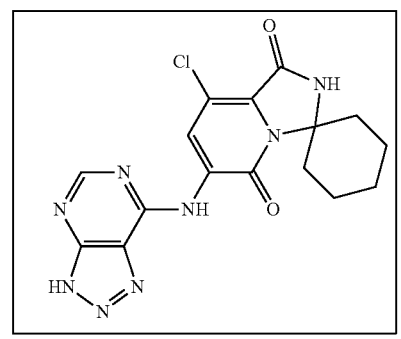

Synthesis of 2-methyl-N-(3H-triazolo[4,5-d]pyrimidin-7-yl)propanamide (3)

To a vial 3H-triazolo[4,5-d]pyrimidin-7-amine (1, 2.0 g, 14.69 mmol) was added in dimethylformamide (20 mL)

followed by addition of 2-methylpropanoyl 2-methylpropanoate (2, 6.97 g, 44.08 mmol). The reaction mixture was stirred at 160° C. for 1 h. After completion, the reaction was cooled to room temperature and diluted with water (100 mL). The precipitated white solid was filtered and dried under vacuum to offer 2-methyl-N-(3H-triazolo[4,5-d]pyrimidin-7-yl)propanamide (3) as white solid. Yield: 2.5 g, 82%; MS (ESI) m/z 205.2 [M+1]+; $^{1}$H NMR (400 MHz, DMSO-$d_6$) δ 15.75 (m, 2H), 11.57 (s, 1H), 8.80 (s, 1H), 2.94-2.97 (m, 1H), 1.20 (d, J=6.8 Hz, 6H).

Synthesis of N-((2-(trimethylsilyl)ethoxy)methyl)-N-(3-((2-(trimethylsilyl)ethoxy)methyl)-3H-[1,2,3]triazolo[4,5-d]pyrimidin-7-yl)isobutyramide (4)

To a stirred solution of 2-methyl-N-(3H-triazolo[4,5-d]pyrimidin-7-yl)propanamide (3, 1.5 g, 7.27 mmol) in dimethylformamide (20 mL), sodium hydride (0.26 g, 10.91 mmol) was added portion wise in 10 min at 0° C. The above suspension was stirred for 10 min at 0° C. and 2-(trimethylsilyl)ethoxymethyl chloride (1.82 g, 10.91 mmol) was added at the same temperature under nitrogen. The reaction was stirred at room temperature for 6 h. After completion, the reaction mass was quenched with saturated aqueous solution of ammonium chloride and crude was extracted with dichloromethane (2×50 mL). The organics were then separated, dried (magnesium sulfate) and concentrated to dryness under vacuum and the crude was purified by flash chromatography eluting with 5% ethyl acetate in hexane. Concentration of the desired fractions provides 2-methyl-N-(2-trimethylsilylethoxy)-N-[3-(2-trimethylsilylethoxy)triazolo[4,5-d]pyrimidin-7-yl]propanamide (4) as transparent viscous oil. Yield: 1.1 g, 44%; MS (ESI) m/z 467.42 [M+1]+.

Synthesis of N,3-bis((2-(trimethylsilyl)ethoxy)methyl)-3H-[1,2,3]triazolo[4,5-d]pyrimidin-7-amine (5)

The synthesis of intermediate 5 was carried out as described above using the general protocol of Procedure I. Yellow solid; Yield: 0.8 g, 94%; MS (ESI) m/z 397 [M+1]+.

Synthesis of 8'-chloro-6'-(((2-(trimethylsilyl)ethoxy)methyl)(3-((2-(trimethylsilyl)ethoxy)methyl)-3H-[1,2,3]triazolo[4, 5-d]pyrimidin-7-yl)amino)-2'H-spiro[cyclohexane-1,3'-imidazo[1,5-a]pyridine]-1',5'-dione (7)

The synthesis of intermediate 7 was carried out as described above using the general protocol of Procedure H. Brown solid; Yield: 0.3 g, crude.

Synthesis of 8-chloro-6-(3H-triazolo[4,5-d]pyrimidin-7-ylamino)spiro[2H-imidazo[1,5-a]pyridine-3,1'-cyclohexane]-1,5-dione (Cpd. No. 146)

To a stirred solution of 8-chloro-6-[2-trimethylsilylethoxymethyl-[3-(2-trimethylsilylethoxymethyl)triazolo[4,5-d]pyrimidin-7-yl]amino]spiro[2H-imidazo[1,5-a]pyridine-3,1'-cyclohexane]-1,5-dione (7, 0.3 g, 0.46 mmol) in dichloromethane (15 mL), trifluoroacetic acid (5 mL, 4.63 mmol) was added drop wise at 0° C. The reaction mass was stirred for overnight at room temperature. After completion, reaction mass was concentrated and co-evaporated with diethyl ether. The crude was then dissolved in tetrahydrofuran/ethanol solution and potassium hydroxide (5 mL, 0.46 mmol) solution (3 M in water) was added and stirred the mixture for 16 h. After completion of the reaction the aqueous layer was separated and organic layer was dried over sodium sulfate, filtered and concentrated to get crude. The crude was washed with methanol and n-pentane and dried to afford 8-chloro-6-(3H-triazolo[4,5-d]pyrimidin-7-ylamino)spiro[2H-imidazo[1,5-a]pyridine-3,1'-cyclohexane]-1,5-dione (Cpd. No. 146) as brown solid. Yield: 70 mg, 39%; MS (ESI) m/z 387.39 [M+1]+; $^{1}$H NMR: (400 MHz, DMSO-$d_6$) δ 10.45 (brs, 1H), 9.29 (s, 1H), 8.88 (s, 1H), 7.77 (s, 1H), 2.94 (t, J=2.32, 2H), 1.79-1.76 (m, 2H), 1.67-1.51 (m, 5H), 1.27-1.23 (m, 1H).

Example 147

Synthesis of 8-((6-aminopyrimidin-4-yl)amino)-10-methyl-2,3,4,5-tetrahydropyrido[1,2-a][1,4]diazepine-1,7-dione (Cpd. No. 147)

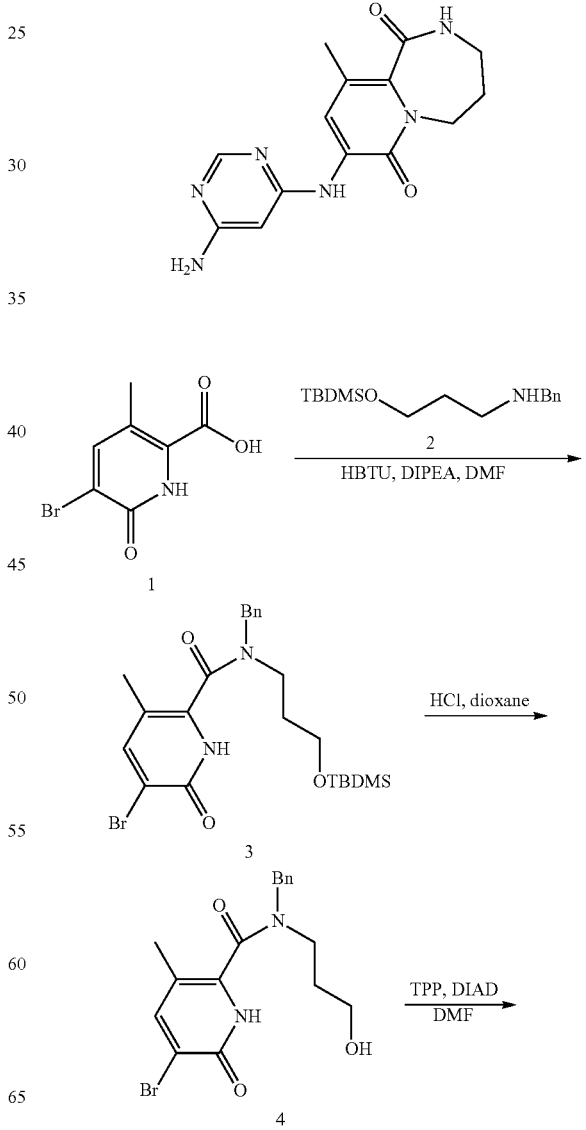

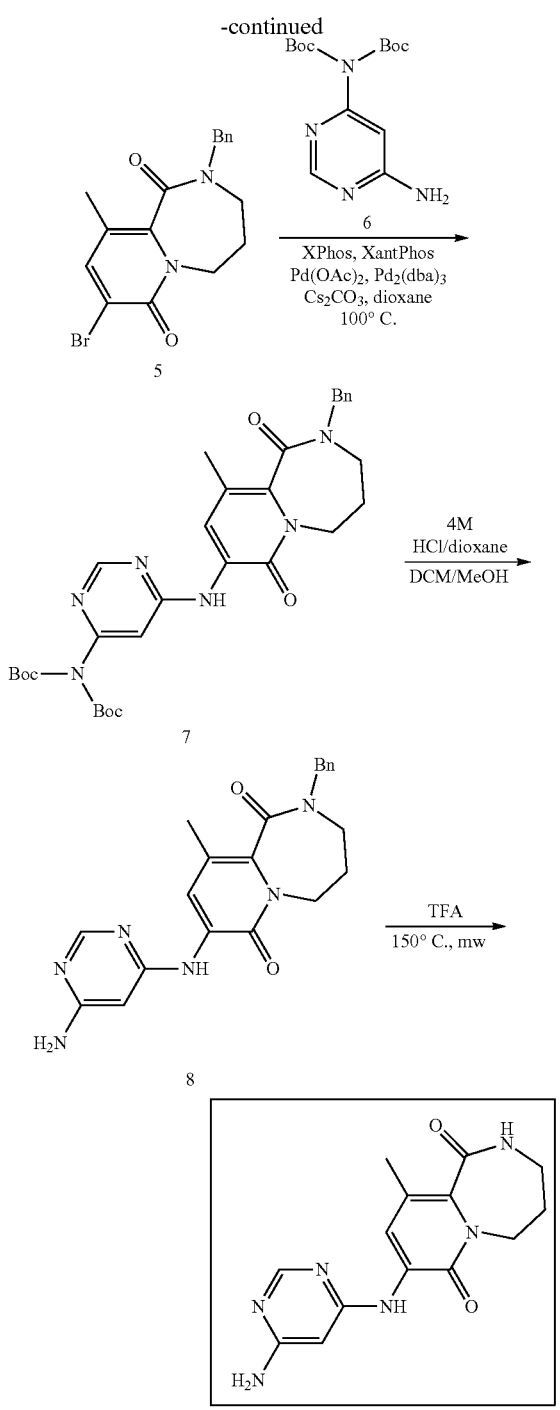

Synthesis of N-benzyl-5-bromo-N-(3-((tert-butyldimethylsilyl)oxy)propyl)-3-methyl-6-oxo-1,6-dihydropyridine-2-carboxamide (3)

To a stirred solution of N-benzyl-3-((tert-butyldimethylsilyl)oxy)propan-1-amine (2, 3.0 g, 12.9 mmol) in dimethylformamide (50 mL), 5-bromo-3-methyl-6-oxo-1,6-dihydropyridine-2-carboxylic acid (1, 3.6 g, 12.9 mmol), HBTU (6.4 g, 16.9 mmol) and N,N-diisopropylethylamine (2.2 g, 16.9 mmol) were added in a vial at room temperature and stirred the mixture for 16 h. TLC showed completion of reaction, the reaction mixture was quenched with aqueous sodium bicarbonate solution and extracted with ethyl acetate (250 mL). The organic layer was dried over sodium sulfate and solvent was removed under reduced pressure to afford N-benzyl-5-bromo-N-(3-((tert-butyldimethylsilyl)oxy)propyl)-3-methyl-6-oxo-1, 6-dihydropyridine-2-carboxamide (3) as yellow liquid. Yield: 3.0 g, 47%; MS (ESI) m/z 495.24 [M−1]⁻.

Synthesis of N-benzyl-5-bromo-N-(3-hydroxypropyl)-3-methyl-6-oxo-1, 6-dihydropyridine-2-carboxamide (4)

To a stirred solution of N-benzyl-5-bromo-N-(3-((tert-butyldimethylsilyl)oxy) propyl)-3-methyl-6-oxo-1,6-dihydropyridine-2-carboxamide (3, 3.0 g, 6.0 mmol) in dioxane (20 mL), hydrogenchloride in dioxane (20 mL) was added at room temperature and the mixture was stirred for 16 h. After completion, the solvent was removed and the reaction was basified with aqueous sodium bicarbonate solution and extracted with 5% methanol/dichloromethane (3×200 mL). The organic layer was dried over sodium sulfate and solvent was removed under reduced pressure to get N-benzyl-5-bromo-N-(3-hydroxypropyl)-3-methyl-6-oxo-1, 6-dihydropyridine-2-carboxamide (4) as brown liquid. Yield: 2.2 g, 95%; MS (ESI) m/z 381.22 [M−1]⁻.

Synthesis of 2-benzyl-8-bromo-10-methyl-2, 3, 4, 5-tetrahydropyrido [1, 2-a][1,4]diazepine-1, 7-dione (5)

To a stirred solution of N-benzyl-5-bromo-N-(3-hydroxypropyl)-3-methyl-6-oxo-1,6-dihydropyridine-2-carboxamide (4, 1.5 g, 3.9 mmol) in tetrahydrofuran (30 mL), triphenylphosphine (1.5 g, 5.9 mmol) and diisopropyl azodicarboxylate (1.2 g, 5.9 mmol) were added at 0° C. The reaction was stirred at room temperature for 16 h. After completion, solvent was removed under reduced pressure and crude was purified by flash chromatography eluting with 40% ethyl acetate in hexane. Appropriate fractions were concentrated under reduced pressure to afford 2-benzyl-8-bromo-10-methyl-2,3,4,5-tetrahydropyrido[1,2-a][1,4]diazepine-1,7-dione (5) as yellow solid. Yield: 0.9 g, 64%; MS (ESI) m/z 361.18 [M+1]⁺.

Synthesis of 8-((6-(di-(tert-butoxycarbonyl)-amino) pyrimidin-4-yl)amino)-2-benzyl-10-methyl-2,3,4,5-tetrahydropyrido[1,2-a][1,4]diazepine-1, 7-dione (7)

The synthesis of intermediate 7 was carried out as described above using the general protocol of Procedure H. Yellow solid; Yield: 0.9 g, 69%; MS (ESI) m/z 591.66 [M+1]⁺.

Synthesis of 8-((6-aminopyrimidin-4-yl)amino)-2-benzyl-10-methyl-2, 3,4,5-tetrahydropyrido[1,2-a][1,4]diazepine-1, 7-dione (8)

The synthesis of intermediate 8 was carried out as described above using the general protocol of Procedure F. Yellow solid; Yield: 0.59 g, 99%; MS (ESI) m/z 391.32 [M+1]⁺.

Synthesis of 8-((6-aminopyrimidin-4-yl)amino)-10-methyl-2,3,4,5-tetrahydropyrido[1,2-a][1,4]diazepine-1,7-dione (Cpd. No. 147)

A vial was charged with 8-((6-aminopyrimidin-4-yl)amino)-2-benzyl-10-methyl-2,3,4,5-tetrahydropyrido[1,2-a]

[1,4]diazepine-1,7-dione (8, 0.3 g, 76.9 mmol) and trifluoroacetic acid (7.0 mL) was added and the reaction mixture was heated under microwave at 150° C. for 20 min. TLC showed completion of the reaction and the mixture was cooled to ambient temperature and this was then basified with aqueous sodium bicarbonate solution and extracted with 5% methanol/dichloromethane (3×200 mL). The organic layer was dried over sodium sulfate and solvent was removed under reduced pressure to afford 8-((6-aminopyrimidin-4-yl)amino)-10-methyl-2,3,4,5-tetrahydropyrido[1,2-a][1,4]diazepine-1,7-dione (Cpd. No. 147) as a brown solid. Yield: 0.06 g, 26%; MS (ESI) m/z 301.15 [M+1]$^+$; $^1$H NMR (400 MHz, DMSO-d$_6$) δ 8.51 (s, 1H), 8.44 (m, 2H), 8.15 (s, 1H), 6.52 (m, 2H), 6.13 (s 1H), 5.05 (m, 1H), 3.17 (m, 2H), 2.95 (m, 1H), 2.13 (s, 3H), 1.87 (m, 2H).

Example 148

Synthesis of 3,3-di-tert-butyl-8-chloro-6-(pyrimidin-4-ylamino)-2,3-dihydroimidazo[1,5-a]pyridine-1,5-dione (Cpd. No. 148)

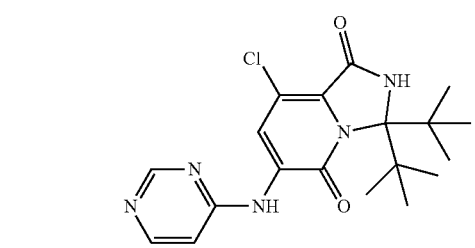 [SMILES: CC(C)(C)C1(C(C)(C)C)NC(=O)c2c(Cl)cc(Nc3ccncn3)c(=O)n21]

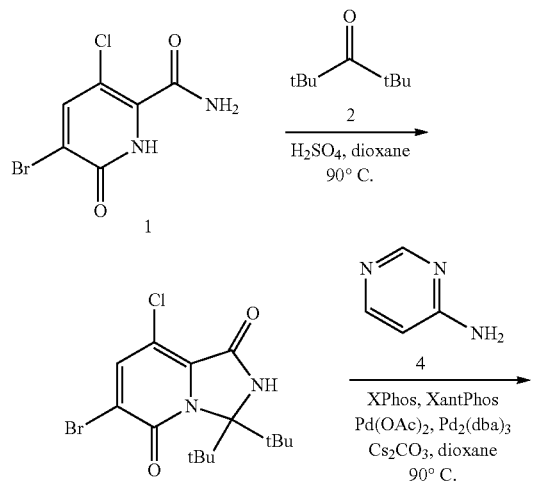

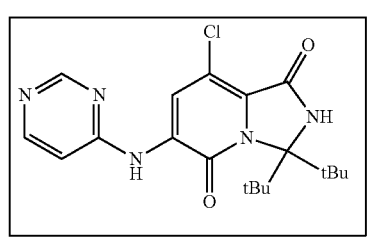

Synthesis of 6-bromo-3,3-di-tert-butyl-8-chloro-2,3-dihydroimidazo[1,5-a]pyridine-1,5-dione (3)

The synthesis of intermediate 3 is carried out as described above using the general protocol of Procedure A.

Synthesis of 3,3-di-tert-butyl-8-chloro-6-(pyrimidin-4-ylamino)-2,3-dihydroimidazo[1,5-a]pyridine-1,5-dione (Cpd. No. 148)

The synthesis of compound 148 is carried out as described above using the general protocol of Procedure H.

Example 149

Synthesis of 8-chloro-6-(pyrimidin-4-ylamino)-3,3-di(thiophen-2-yl)-2,3-dihydroimidazo[1,5-a]pyridine-1,5-dione (Cpd. No. 149)

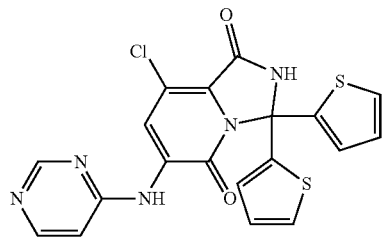 [SMILES: O=C1NC(c2cccs2)(c2cccs2)n2c1c(Cl)cc(Nc1ccncn1)c2=O]

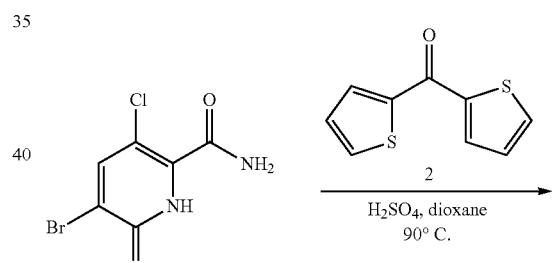

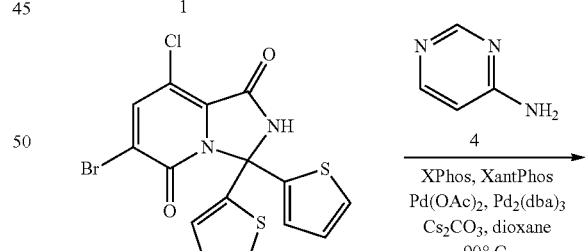

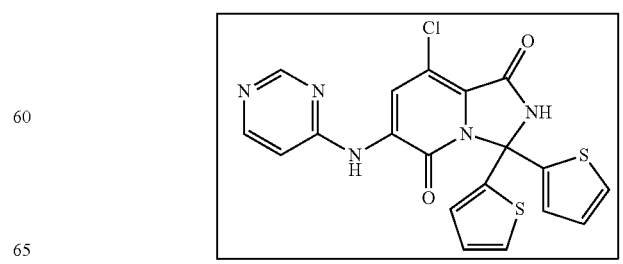

243

Synthesis of 6-bromo-8-chloro-3,3-di(thiophen-2-yl)-2,3-dihydroimidazo[1,5-a]pyridine-1,5-dione (3)

The synthesis of intermediate 3 is carried out as described above using the general protocol of Procedure A.

Synthesis of 8-chloro-6-(pyrimidin-4-ylamino)-3,3-di(thiophen-2-yl)-2,3-dihydroimidazo[1,5-a]pyridine-1,5-dione (Cpd. No. 149)

The synthesis of compound 149 is carried out as described above using the general protocol of Procedure H.

Example 150

Synthesis of 8-chloro-6-(pyrimidin-4-ylamino)-3,3-di(thiophen-3-yl)-2,3-dihydroimidazo[1,5-a]pyridine-1,5-dione (Cpd. No. 150)

244

Synthesis of 6-bromo-8-chloro-3,3-di(thiophen-3-yl)-2,3-dihydroimidazo[1,5-a]pyridine 1,5-dione (3)

The synthesis of intermediate 3 is carried out as described above using the general protocol of Procedure A.

Synthesis of 8-chloro-6-(pyrimidin-4-ylamino)-3,3-di(thiophen-3-yl)-2, 3-dihydroimidazo[1,5-a]pyridine-1,5-dione (Cpd. No. 150)

The synthesis of compound 150 is carried out as described above using the general protocol of Procedure H.

Example 151

Synthesis of 8-chloro-3,3-dipropyl-6-(pyrimidin-4-ylamino)-2H-imidazo[1,5-a]pyridine-1,5-dione (Cpd. No. 151)

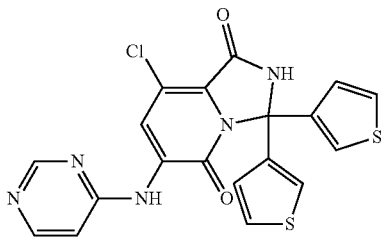 [SMILES: O=C1NC(c2ccsc2)(c2ccsc2)n2c1c(Cl)cc(Nc1ccncn1)c2=O]

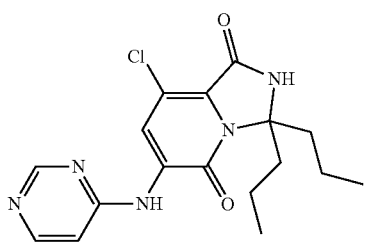 [SMILES: CCCC1(CCC)NC(=O)c2c(Cl)cc(Nc3ccncn3)c(=O)n21]

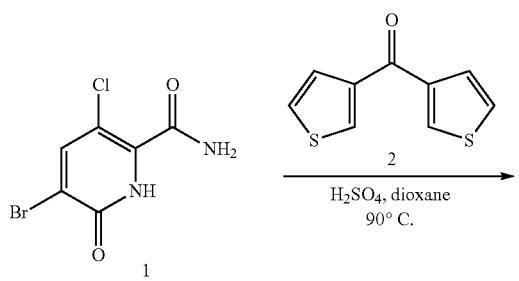

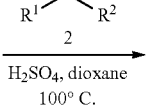

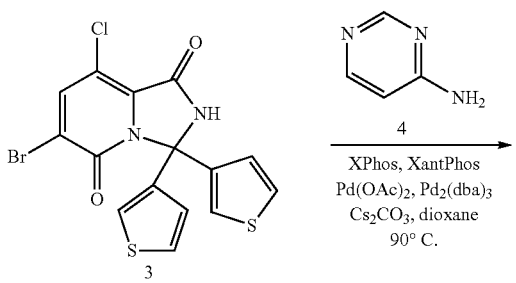

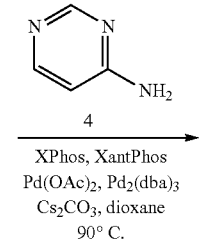

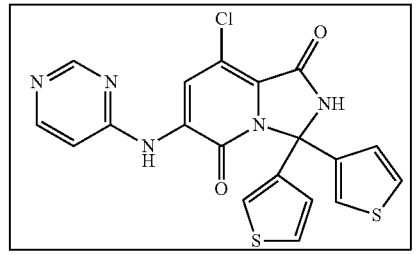

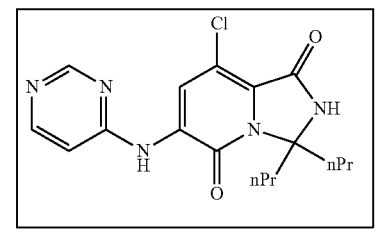

Synthesis of 6-bromo-8-chloro-3,3-dipropyl-2,3-dihydroimidazo[1,5-a]pyridine-1,5-dione (3)

The synthesis of intermediate 3 was carried out as described above using the general protocol of Procedure A. Off white solid; Yield: 0.23 g, 66%; MS (ESI) m/z 347.01 [M+1]$^+$.

Synthesis of 8-chloro-3,3-dipropyl-6-(pyrimidin-4-ylamino)-2H-imidazo[1,5-a]pyridine-1,5-dione (Cpd. No. 151)

The synthesis of compound 151 was carried out as described above using the general protocol of Procedure H. Off white solid; Yield: 0.14 g, 57%; MS (ESI) m/z 362.13 [M+1]$^+$; $^1$H-NMR (400 MHz, DMSO-d$_6$) δ 9.64 (s, 1H), 9.59 (s, 1H), 8.85 (s, 1H), 8.81 (s, 1H), 8.44 (d, J=5.88 Hz, 1H), 7.42 (d, J=5.88, 1H), 2.54 (m, 2H), 1.86 (t, J=10.9 Hz, 2H), 1.15 (m, 2H), 0.82 (m, 8H).

Example 152

Synthesis of 3,3-bis(2-aminoethyl)-8-chloro-6-(pyrimidin-4-ylamino)-2,3-dihydroimidazo[1,5-a]pyridine-1,5-dione (Cpd. No. 152)

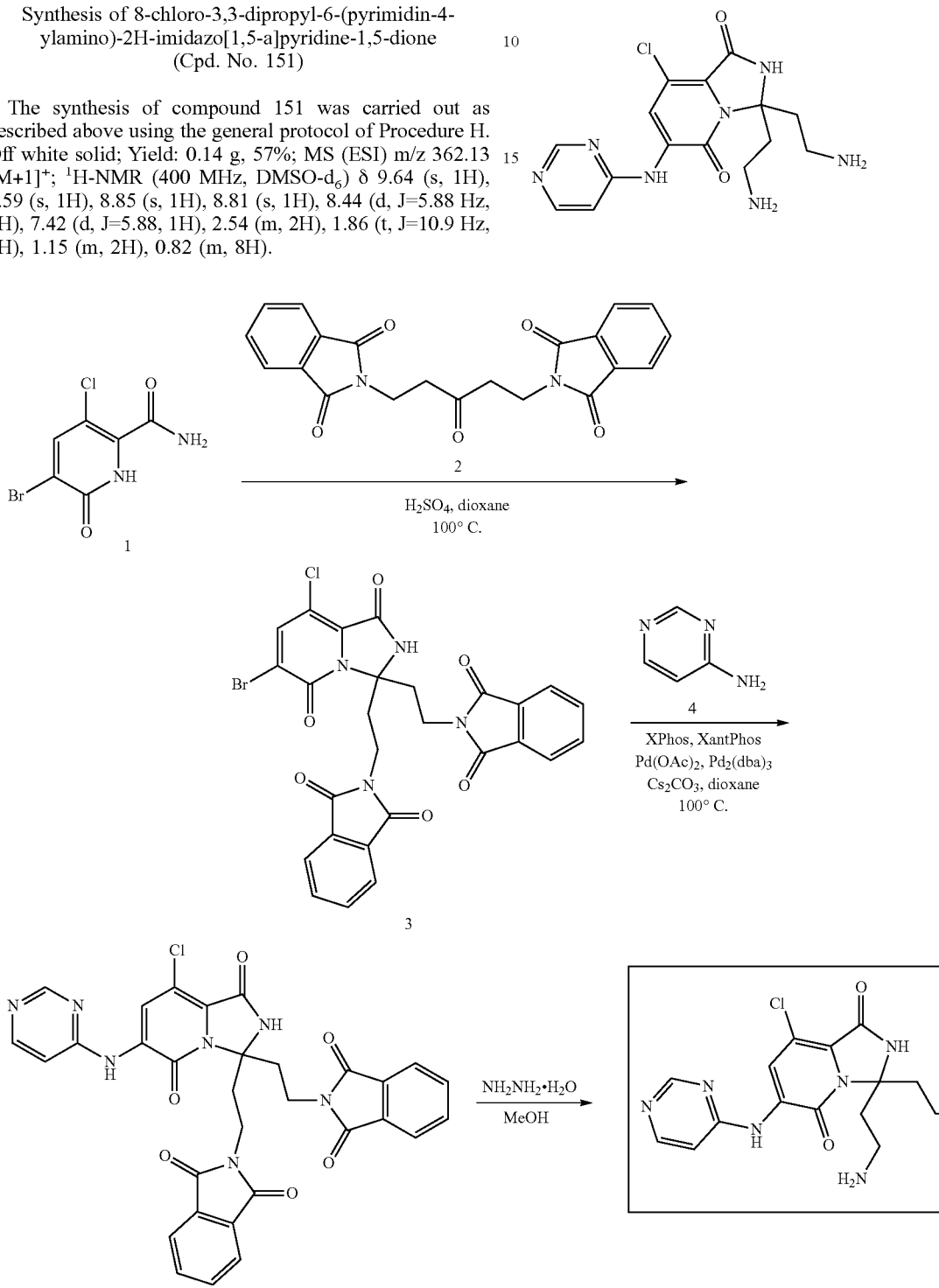

247

Synthesis of 2,2'-((6-bromo-8-chloro-1,5-dioxo-1,2,3,5-tetrahydroimidazo[1,5-a]pyridine-3,3-diyl)bis(ethane-2,1-diyl))bis(isoindoline-1,3-dione) (3)

The synthesis of intermediate 3 is carried out as described above using the general protocol of Procedure A.

Synthesis of 2,2'-((8-chloro-1,5-dioxo-6-(pyrimidin-4-ylamino)-1,2,3,5-tetrahydroimidazo[1,5-a]pyridine-3,3-diyl)bis(ethane-2,1-diyl))bis(isoindoline-1,3-dione) (5)

The synthesis of intermediate 5 is carried out as described above using the general protocol of Procedure H.

Synthesis of 3,3-bis(2-aminoethyl)-8-chloro-6-(pyrimidin-4-ylamino)-2,3-dihydroimidazo[1,5-a]pyridine-1,5-dione (Cpd. No. 152)

The synthesis of compound 152 is carried out as described above using the general protocol of Procedure C.

Example 153

Synthesis of 8-chloro-3,3-bis(2-hydroxyethyl)-6-(pyrimidin-4-ylamino)-2,3-dihydroimidazo[1,5-a]pyridine-1,5-dione (Cpd. No. 153)

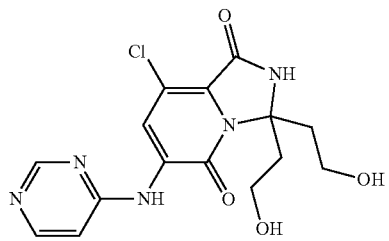 [SMILES: O=C1NC(CCO)(CCO)n2c1c(Cl)cc(Nc1ccncn1)c2=O]

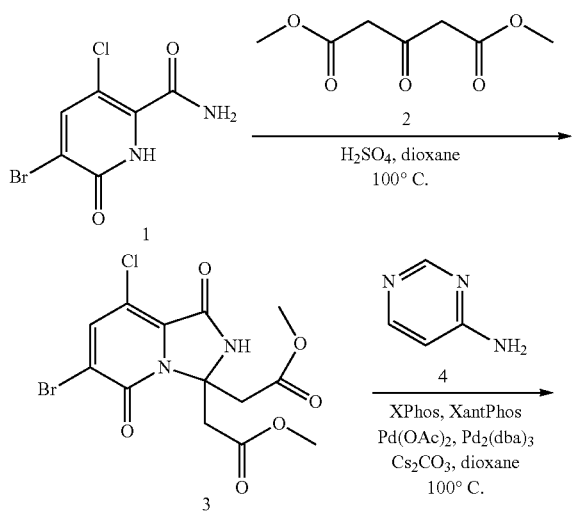

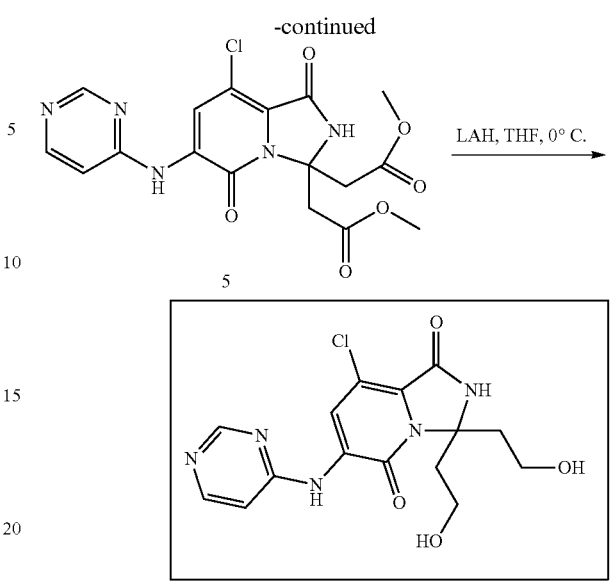

Synthesis of dimethyl 2,2'-(6-bromo-8-chloro-1,5-dioxo-1,2,3,5-tetrahydroimidazo[1,5-a]pyridine-3,3-diyl)diacetate (3)

The synthesis of intermediate 3 was carried out as described above using the general protocol of Procedure A. Off white solid; Yield: 0.65 g, 27%; MS (ESI) m/z 407.18 [M−1]⁻.

Synthesis of dimethyl 2,2'-(8-chloro-1,5-dioxo-6-(pyrimidin-4-ylamino)-1,2,3,5-tetrahydroimidazo[1,5-a]pyridine-3,3-diyl)diacetate (5)

The synthesis of intermediate 5 was carried out as described above using the general protocol of Procedure H. Off white solid; Yield: 0.34 g, 51%; MS (ESI) m/z 422.49 [M+1]⁺.

Synthesis of of 8-chloro-3,3-bis(2-hydroxyethyl)-6-(pyrimidin-4-ylamino)-2,3-dihydroimidazo[1,5-a]pyridine-1,5-dione (Cpd. No. 153)

To a slurry of lithium aluminum hydride (71 mg, 1.9 mmol) in tetrahydrofuran (3 mL) at 0° C. a solution of dimethyl 2,2'-(8-chloro-1,5-dioxo-6-(pyrimidin-4-ylamino)-1,2,3,5-tetrahydroimidazo[1,5-a]pyridine-3,3-diyl)diacetate (5, 280 mg, 0.66 mmol) in tetrahydrofuran (2 mL) was added slowly. After consumption of starting material the reaction mixture was quenched with 10% sodium hydroxide solution (1 mL), diluted with 10 ml of ethyl acetate. The organic layer was separated and dried over anhydrous sodium sulfate and concentrated under reduce pressure to afford the residue. The residue was purified prep HPLC to afford 8-chloro-3,3-bis(2-hydroxyethyl)-6-(pyrimidin-4-ylamino)-2,3-dihydroimidazo[1,5-a]pyridine-1,5-dione (Cpd. No. 153) as yellow solid. Yield: 0.047 g, 19%; MS (ESI) m/z 366.09 [M+1]⁺; ¹H NMR (400 MHz, DMSO-d₆) δ 9.58-9.57 (brs, 1H), 8.83 (s, 1H), 8.75 (s, 1H), 8.42 (d, J=5.6 Hz, 1H), 7.44-7.42 (d, J=5.6 Hz, 1H), 4.44 (brs, 2H), 3.34-3.26 (m, 4H), 2.79-3.73 (m, 2H), 2.11-2.08 (m, 2H).

Example 154

Synthesis of 3,3-bis(aminomethyl)-8-chloro-6-(pyrimidin-4-ylamino)-2,3-dihydroimidazo[1,5-a]pyridine-1,5-dione (Cpd. No. 154)

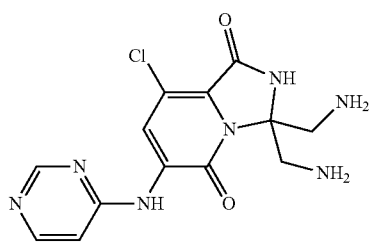 [SMILES: NCC1(CN)NC(=O)c2c(Cl)cc(Nc3ccncn3)c(=O)n21]

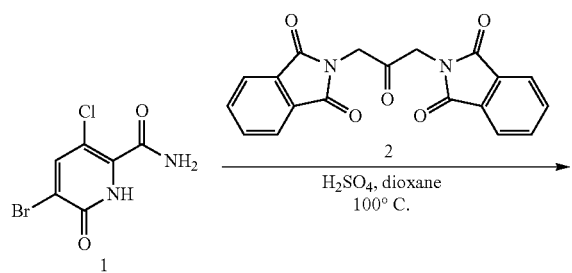

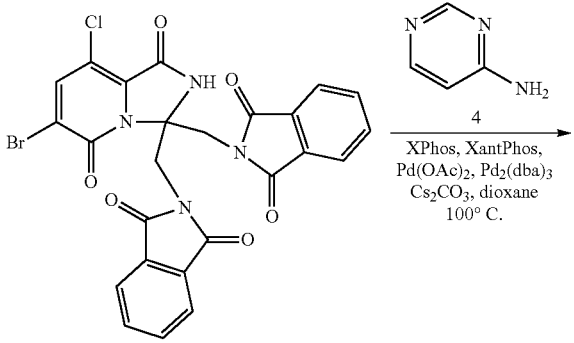

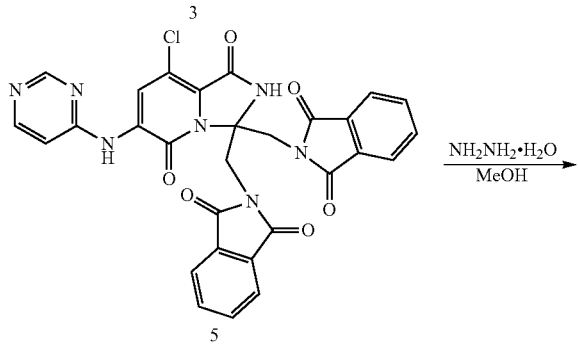

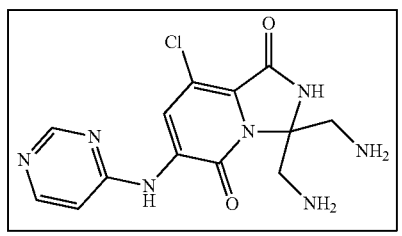

Synthesis of 2,2'-((6-bromo-8-chloro-1,5-dioxo-1,2,3,5-tetrahydroimidazo[1,5-a]pyridine-3,3-diyl)bis(methylene))bis(isoindoline-1,3-dione) (3)

The synthesis of intermediate 3 is carried out as described above using the general protocol of Procedure A.

Synthesis of 2,2'-((8-chloro-1,5-dioxo-6-(pyrimidin-4-ylamino)-1,2,3,5-tetrahydroimidazo[1,5-a]pyridine-3,3-diyl)bis(methylene))bis(isoindoline-1,3-dione) (5)

The synthesis of intermediate 5 is carried out as described above using the general protocol of Procedure H.

Synthesis of 3,3-bis(aminomethyl)-8-chloro-6-(pyrimidin-4-ylamino)-2,3-dihydroimidazo[1,5-a]pyridine-1,5-dione (Cpd. No. 154)

The synthesis of compound 154 is carried out as described above using the general protocol of Procedure C.

Example 155

Synthesis of 8-chloro-1'-(2-hydroxyethyl)-6-(pyrimidin-4-ylamino)-2H-spiro[imidazo[1,5-a]pyridine-3,4'-piperidine]-1,5-dione (Cpd. No. 155)

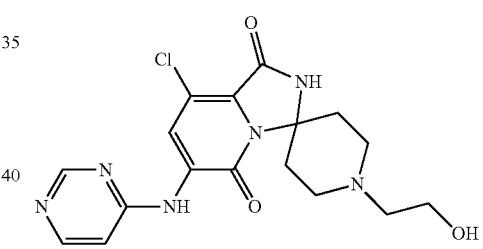

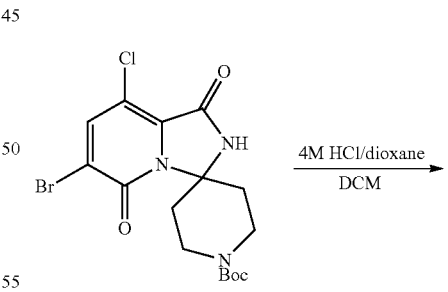

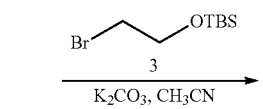

251

-continued

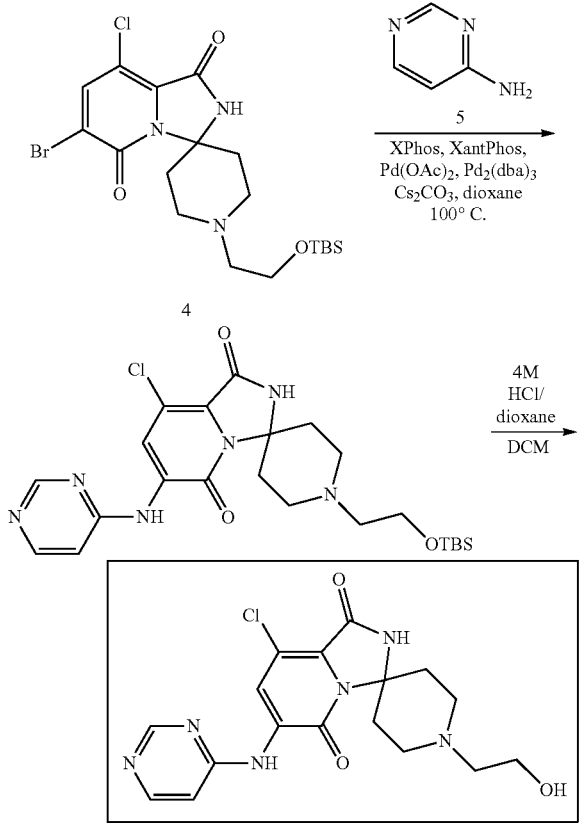

Synthesis of 6-bromo-8-chloro-spiro[2H-imidazo[1,5-a]pyridine-3,4'-piperidine]-1,5-dione hydrochloride (2)

The synthesis of intermediate 2 was carried out as described above using the general protocol of Procedure F. Off white solid; Yield: 3.5 g, 95%; MS (ESI) m/z 332.1 [M+1]$^+$; $^1$H NMR (400 MHz, DMSO-d$_6$) δ 10.89 (s, 1H), 9.45 (brs, 1H), 8.67 (brs, 1H), 8.30 (s, 1H), 3.70-3.36 (m, 4H), 2.59-2.57 (m, 2H), 1.89-1.85 (m, 2H).

Synthesis of 6-bromo-1'-[2-[tert-butyl(dimethyl)silyl]oxyethyl]-8-chloro-spiro[2H-imidazo[1,5-a]pyridine-3,4'-piperidine]-1,5-dione (4)

A flask was charged with 6-bromo-8-chloro-spiro[2H-imidazo[1,5-a]pyridine-3,4'-piperidine]-1,5-dione hydrochloride (2, 0.5 g, 1.35 mmol) and acetonitrile (15 mL) was added. The reaction mass was cooled to 0° C. and potassium carbonate (281 mg, 2.03 mmol) and (2-bromoethoxy)(tert-butyl)dimethylsilane (3, 388 mg, 1.62 mmol) were added and reaction mass was heated at 80° C. for 2 days. After completion, the solvent was removed to get the crude compound. The crude compound was purified by flash column with 0.2% methanol in dichloromethane. The desired fractions were concentrated to give 6-bromo-1'-[2-[tert-butyl(dimethyl)silyl]oxyethyl]-8-chloro-spiro[2H-imidazo[1,5-a]pyridine-3,4'-piperidine]-1,5-dione (4) as a brown solid. Yield: 0.3 g, 45%; MS (ESI) m/z 373.01 [M+1]$^+$; $^1$H NMR (400 MHz, DMSO-d$_6$) δ 10.62 (s, 1H),

252

8.25 (s, 1H), 3.69-3.63 (m, 4H), 3.10-2.83 (m, 4H), 1.52 (m, 2H), 1.04 (s, 9H), 0.058 (s, 6H).

Synthesis of 1'-[2-[tert-butyl(dimethyl)silyl]oxyethyl]-8-chloro-6-(pyrimidin-4-ylamino)spiro[2H-imidazo[1,5-a]pyridine-3,4'-piperidine]-1,5-dione (6)

The synthesis of intermediate 6 was carried out as described above using the general protocol of Procedure H. Yellow solid; Yield: 0.15 g, 49%; MS (ESI) m/z 505 [M+1]$^+$; $^1$H NMR (400 MHz, DMSO-d$_6$) δ 10.37 (s, 1H), 9.63-9.60 (m, 1H), 8.84-8.75 (m, 2H), 8.43-8.36 (d, J=5.8 Hz, 1H), 7.47 (d, J=5.8 Hz, 1H), 3.72-3.70 (m, 2H), 3.26-3.22 (m, 4H), 2.98-2.90 (m, 4H), 1.53-1.46 (m, 2H), 1.33-1.29 (m, 2H), 0.95 (s, 9H), 0.058 (s, 6H).

Synthesis of 8-chloro-1'-(2-hydroxyethyl)-6-(pyrimidin-4-ylamino)spiro[2H-imidazo[1,5-a]pyridine-3,4'-piperidine]-1,5-dione (Cpd. No. 155)

The synthesis of compound 155 was carried out as described above using the general protocol of Procedure F. Yellow solid; Yield: 0.035 g, 49%; MS (ESI) m/z 391.34 [M+1]$^+$; $^1$H NMR (400 MHz, DMSO-d$_6$) δ 10.50 (s, 1H), 9.59 (m, 1H), 8.84 (d, J=16.48 Hz, 2H), 8.43-8.36 (d, J=5.8 Hz, 1H), 7.47 (d, J=5.8 Hz, 1H), 4.43 (brs, 2H), 3.53 (brs, 2H), 3.21-3.16 (m, 2H), 2.98-2.90 (m, 2H), 2.46-2.41 (m, 2H), 1.48-1.46 (m, 2H).

Example 156

Synthesis of 8-chloro-1'-(2,2-difluoroethyl)-6-(pyrimidin-4-ylamino)spiro[2H-imidazo[1,5-a]pyridine-3,4'-piperidine]-1,5-dione (Cpd. No. 156)

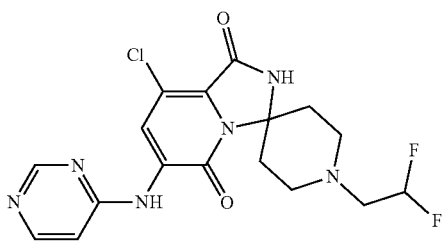 [SMILES: O=C1NC2(CCN(CC(F)F)CC2)n2c1c(Cl)cc(Nc1ccncn1)c2=O]

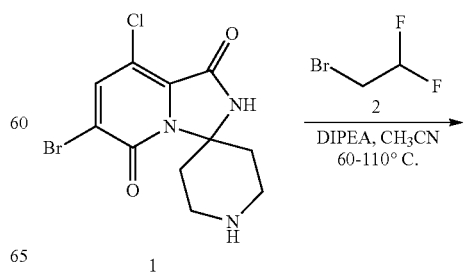

-continued

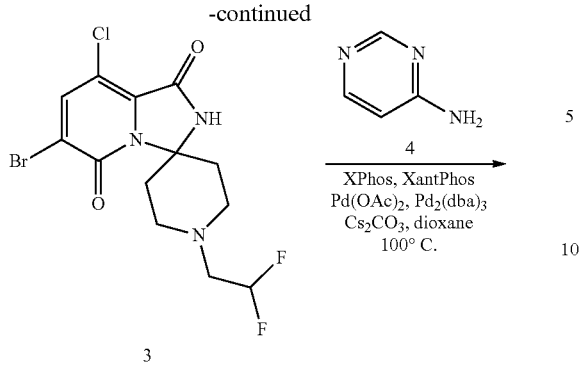

Synthesis of 6-bromo-8-chloro-1'-(2,2-difluoroethyl) spiro[2H-imidazo[1,5-a]pyridine-3,4'-piperidine]-1,5-dione (3)

A flask was charged with 6-bromo-8-chloro-spiro[2H-imidazo[1,5-a]pyridine-3,4'-piperidine]-1,5-dione hydrochloride (1, 0.5 g, 1.35 mmol) and acetonitrile (15 mL) was added. The reaction was cooled to 0° C. and N,N-diisopropylethylamine (1.17 mL, 6.77 mmol) was added drop wise followed by addition of 2-bromo-1,1-difluoro-ethane (2, 589 mg, 4.06 mmol). The reaction was stirred at 60-110° C. for 48 h. After completion, the solvent was removed under reduced pressure to get the crude. The crude was purified by flash column using 1-3% methanol in dichloromethane. The desired fractions were concentrated to get 6-bromo-8-chloro-1'-(2,2-difluoroethyl)spiro[2H-imidazo[1,5-a]pyridine-3,4'-piperidine]-1,5-dione (3) as brown solid. Yield: 0.27 g, 50%; MS (ESI) m/z 396.11 [M+1]$^+$; $^1$H NMR (400 MHz, DMSO-d$_6$) δ 10.66 (s, 1H), 8.25 (s, 1H), 6.29 (t, J=55.68 Hz, 1H), 3.12-3.06 (m, 2H), 2.84-2.79 (m, 2H), 2.66-2.60 (m, 2H) 1.49-1.46 (m, 2H).

Synthesis of 8-chloro-1'-(2,2-difluoroethyl)-6-(pyrimidin-4-ylamino)spiro[2H-imidazo[1,5-a]pyridine-3,4'-piperidine]-1,5-dione (Cpd. No. 156)

The synthesis of compound 156 was carried out as described above using the general protocol of Procedure H. Yellow solid; Yield: 0.13 g, 50%; MS (ESI) m/z 411.38 [M+1]$^+$; $^1$H NMR (400 MHz, DMSO-d$_6$) δ 10.39 (s, 1H), 9.60 (s, 1H), 8.84 (s, 1H), 8.80 (s, 1H), 8.43-8.36 (d, J=6.28 Hz, 1H), 7.47 (d, J=5.8 Hz, 1H), 6.32 (t, J=56.0 Hz, 1H), 3.26-3.22 (m, 2H), 2.98-2.90 (m, 2H), 2.88-2.79 (m, 2H), 2.70-2.64 (m, 2H), 1.51-1.48 (m, 2H).

Example 157

Synthesis of 8-chloro-6-(pyrimidin-4-ylamino)-1'-(2,2,2-trifluoroethyl)-2H-spiro[imidazo[1,5-a]pyridine-3,4'-piperidine]-1,5-dione (Cpd. No. 157)

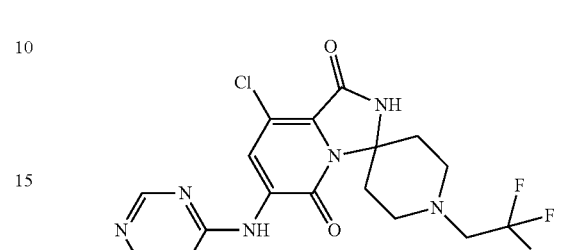

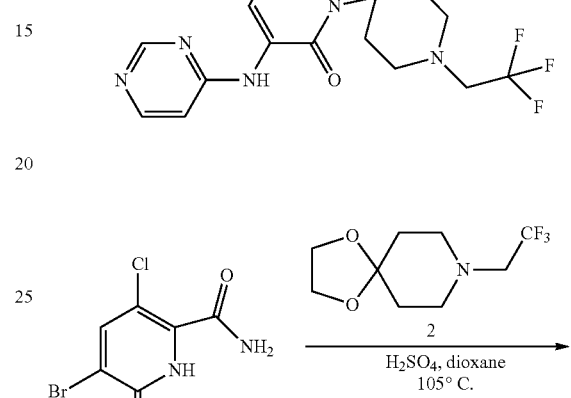

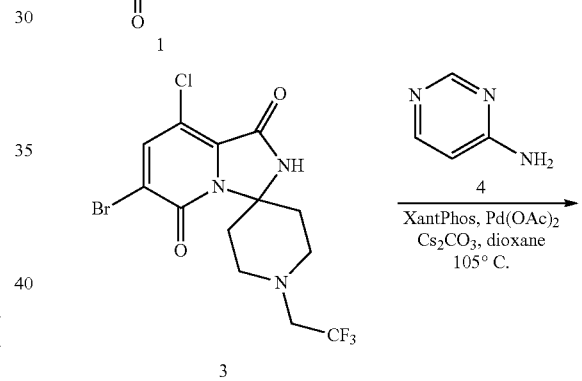

Synthesis of 6-bromo-8-chloro-1'-(2,2,2-trifluoroethyl)-2H-spiro[imidazo[1,5-a]pyridine-3,4'-piperidine]-1,5-dione (3)

The synthesis of intermediate 3 was carried out as described above using the general protocol of Procedure A. Off White solid; Yield: 1.1 g, 50%; MS (ESI) m/z 414.28 [M−1]$^-$.

Synthesis of 8-chloro-6-(pyrimidin-4-ylamino)-1'-(2,2,2-trifluoroethyl)-2H-spiro[imidazo[1,5-a]pyridine-3,4'-piperidine]-1,5-dione (Cpd. No. 157)

The synthesis of compound 157 was carried out as described above using the general protocol of Procedure B. Yellow solid; Yield: 0.21 g, 41%; MS (ESI) m/z 429.24 [M+1]$^+$; $^1$H NMR (400 MHz, DMSO-d$_6$) δ 10.44 (s, 1H), 9.61 (s, 1H), 8.84-8.80 (m, 2H), 8.44-8.43 (m, 1H), 7.46-7.44 (m, 1H), 3.28-3.17 (m, 4H), 2.97-2.95 (m, 2H), 2.86-2.79 (m, 2H), 1.51-1.48 (d, 2H).

Example 158

Synthesis of 8'-chloro-8-methyl-6'-(pyrimidin-4-ylamino)-2'H-8-azaspiro[bicyclo[3.2.1]octane-3,3'-imidazo[1,5-a]pyridine]-1',5'-dione (Cpd. No. 158)

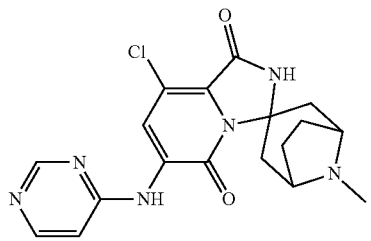 [SMILES: CN1C2CCC1CC1(C2)NC(=O)c2c(Cl)cc(Nc3ccncn3)c(=O)n21]

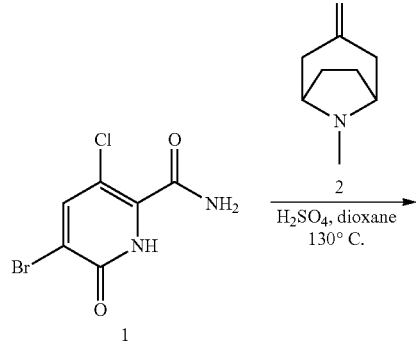

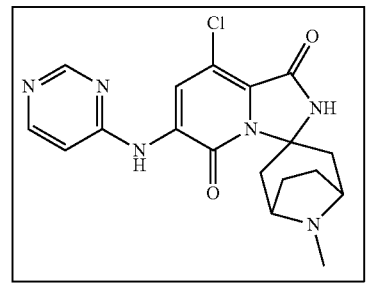

Synthesis of 6'-bromo-8'-chloro-8-methyl-2'H-8-azaspiro[bicyclo[3.2.1]octane-3,3'-imidazo[1,5-a]pyridine]-1',5'-dione (3)

The synthesis of intermediate 3 was carried out as described above using the general protocol of Procedure A. Brown solid; Yield: 0.15 g, 10%; MS (ESI) m/z 372.21 [M+1]$^+$.

Synthesis of 8'-chloro-8-methyl-6'-(pyrimidin-4-ylamino)-2'H-8-azaspiro[bicyclo[3.2.1]octane-3,3'-imidazo[1,5-a]pyridine]-1',5'-dione (Cpd. No. 158)

The synthesis of compound 158 was carried out as described above using the general protocol of Procedure B. Yellow solid; Yield: 0.029 g, 20%; MS (ESI) m/z 387.35 [M+1]$^+$; $^1$H NMR (400 MHz, DMSO-d$_6$) δ 9.64 (s, 1H), 9.53 (s, 1H), 8.84 (s, 1H), 8.80 (s, 1H), 8.43 (d, J=5.88 Hz, 1H), 7.46 (d, J=5.84 Hz, 1H), 3.23 (m, 4H), 2.59 (s, 3H), 1.94 (s, 4H). 1.40 (d, J=12.8 Hz, 2H).

Example 159

Synthesis of 8'-chloro-6'-(pyrimidin-4-ylamino)-2'H-8-azaspiro[bicyclo[3.2.1]octane-3,3'-imidazo[1,5-a]pyridine]-1',5'-dione (Cpd. No. 159)

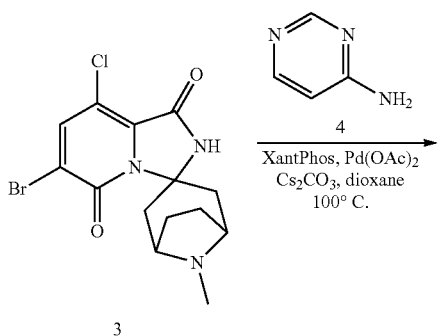

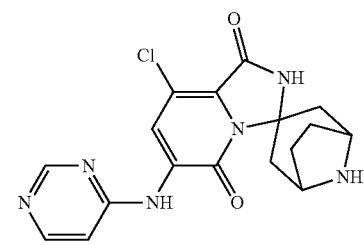 [SMILES: O=C1NC2(CC3CCC(C2)N3)n2c1c(Cl)cc(Nc1ccncn1)c2=O]

257

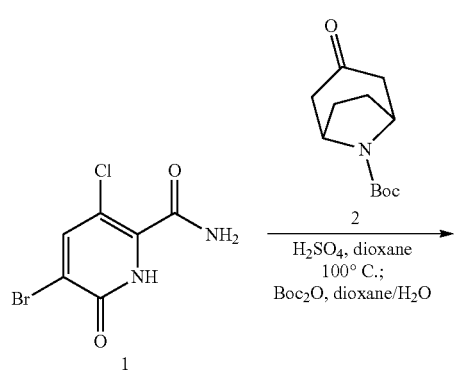

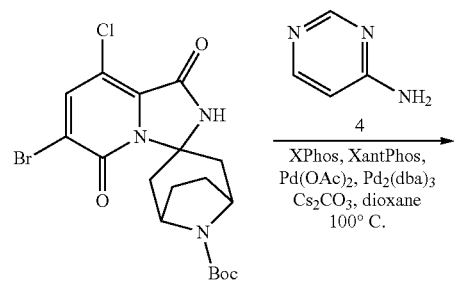

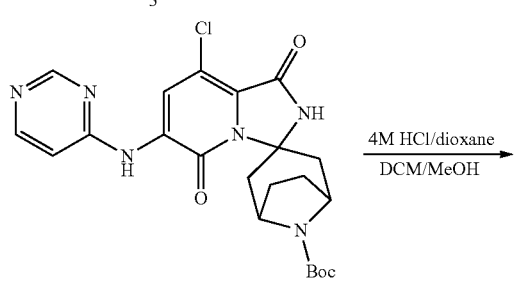

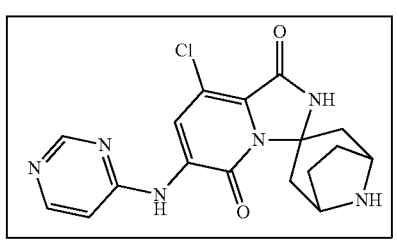

Synthesis of tert-butyl 6'-bromo-8'-chloro-1',5'-dioxo-1',5'-dihydro-2'H-8-azaspiro[bicyclo[3.2.1]octane-3,3'-imidazo[1,5-a]pyridine]-8-carboxylate (3)

The synthesis of intermediate 3 is carried out as described above using the general protocol of Procedure E.

Synthesis of tert-butyl 8'-chloro-1',5'-dioxo-6'-(pyrimidin-4-ylamino)-1',5'-dihydro-2'H-8-azaspiro[bicyclo[3.2.1]octane-3,3'-imidazo[1,5-a]pyridine]-8-carboxylate (5)

The synthesis of intermediate 5 is carried out as described above using the general protocol of Procedure H.

258

Synthesis of 8'-chloro-6'-(pyrimidin-4-ylamino)-2'H-8-azaspiro[bicyclo[3.2.1]octane-3,3'-imidazo[1,5-a]pyridine]-1',5'-dione (Cpd. No. 159)

The synthesis of compound 159 is carried out as described above using the general protocol of Procedure F.

Example 160

Synthesis of 2-(8-chloro-1,5-dioxo-6-(pyrimidin-4-ylamino)-1,5-dihydro-2H-spiro[imidazo[1,5-a]pyridine-3,4'-piperidin]-1'-yl)acetonitrile (Cpd. No. 160)

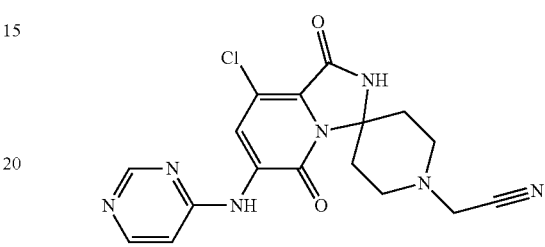

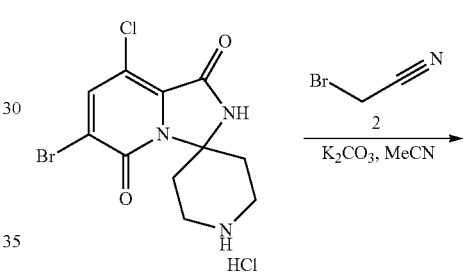

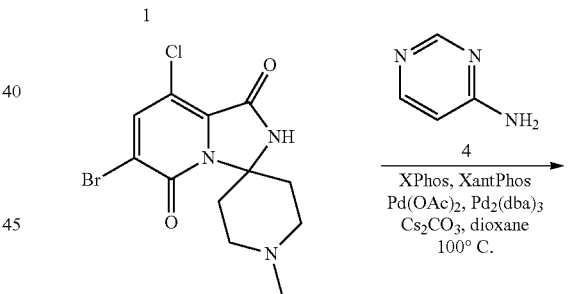

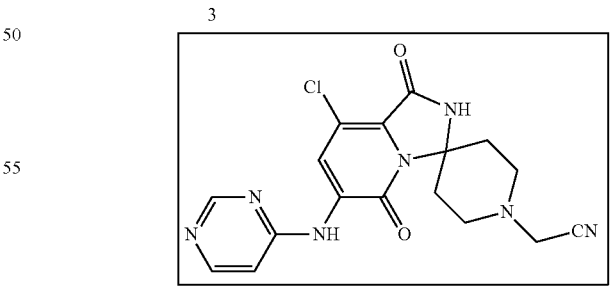

Synthesis of 2-(6-bromo-8-chloro-1,5-dioxo-1,5-dihydro-2H-spiro[imidazo[1,5-a]pyridine-3,4'-piperidin]-1'-yl)acetonitrile (3)

A flask was charges with 6-bromo-8-chloro-spiro[2H-imidazo[1,5-a]pyridine-3,4'-piperidine]-1,5-dione hydrochloride (1, 0.5 g, 1.35 mmol) and acetonitrile (15 mL) was added. The reaction mass was cooled to 0° C. and potassium carbonate (281 mg, 2.03 mmol) was added followed by addition of 2-bromoacetonitrile (2, 218 mg, 1.63 mmol). The reaction mass was stirred at room temperature for 10 h. After completion, the solvent was removed under reduced pressure to get the crude. The crude was purified by Biotage snap using 1-3% methanol in dichloromethane. The desired fractions were concentrated to get 3-(6-bromo-8-chloro-1,5-dioxo-spiro[2H-imidazo[1,5-a]pyridine-3,4'-piperidine]-1'-yl)propanenitrile (3) as brown solid. Yield: 0.42 g, 83%; MS (ESI) m/z 373.18 [M+1]$^+$; $^1$H NMR (400 MHz, DMSO-d$_6$) δ 10.83 (s, 1H), 8.25 (s, 1H), 3.75 (s, 2H), 3.15-3.10 (m, 2H), 2.87-2.72 (m, 2H), 2.66-2.60 (m, 2H) 1.57-1.54 (m, 2H).

Synthesis of 2-[8-chloro-1,5-dioxo-6-(pyrimidin-4-ylamino)spiro[2H-imidazo[1,5-a]pyridine-3,4'-piperidine]-1'-yl]acetonitrile (Cpd. No. 160)

The synthesis of compound 160 was carried out as described above using the general protocol of Procedure H. Yellow solid; Yield: 0.2 g, 49%; MS (ESI) m/z 385.97 [M+1]$^+$; $^1$H NMR (400 MHz, DMSO-d$_6$) δ 10.50 (s, 1H), 9.62 (s, 1H), 8.84 (s, 1H), 8.80 (s, 1H), 8.43-8.36 (d, J=6.28 Hz, 1H), 7.47 (d, J=5.8 Hz, 1H), 3.75 (s, 2H), 3.26-3.22 (m, 2H), 2.98-2.90 (m, 2H), 2.67-2.61 (m, 2H), 1.60-1.57 (m, 2H).

Example 161

Synthesis of 8-chloro-1'-(pyrimidin-4-yl)-6-(pyrimidin-4-ylamino)-2H-spiro[imidazo[1,5-a]pyridine-3,4'-piperidine]-1,5-dione (Cpd. No. 161)

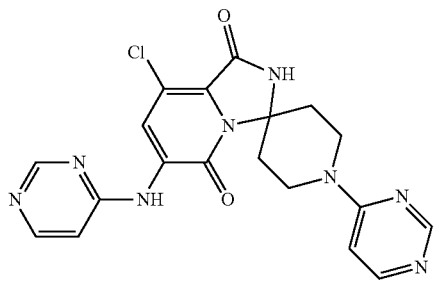 [SMILES: O=C1NC2(CCN(c3ccncn3)CC2)n2c1c(Cl)cc(Nc1ccncn1)c2=O]

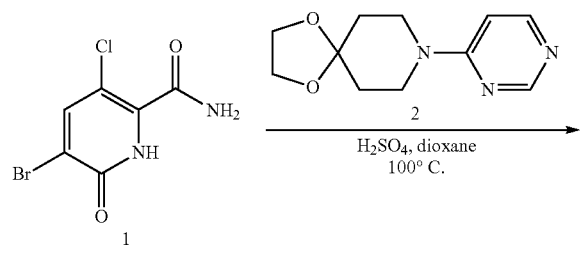

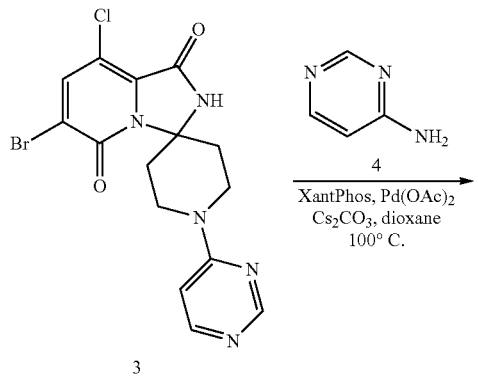

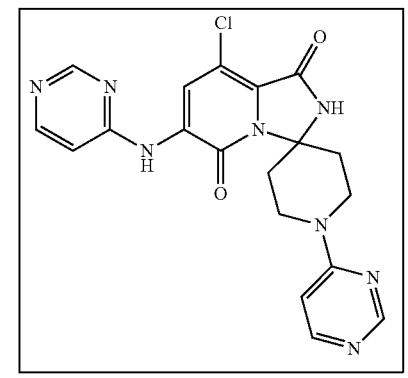

Synthesis of 6-bromo-8-chloro-1'-(pyrimidin-4-yl)-2H-spiro[imidazo[1,5-a]pyridine-3, 4'-piperidine]-1, 5-dione (3)

The synthesis of intermediate 3 was carried out as described above using the general protocol of Procedure A. Yellow solid. Yield: 0.1 g, 61%; MS (ESI) m/z 410.02 [M+1]$^+$.

Synthesis of 8-chloro-1'-(pyrimidin-4-yl)-6-(pyrimidin-4-ylamino)-2H-spiro[imidazo[1,5-a]pyridine-3, 4'-piperidine]-1,5-dione (Cpd. No. 161)

The synthesis of compound 161 was carried out as described above using the general protocol of Procedure B. Yellow solid. Yield: 0.06 g, 23%; MS (ESI) m/z 425.34 [M+1]$^+$; $^1$H NMR (400 MHz, DMSO-d$_6$) δ 10.65 (s, 1H), 9.59 (s, 1H), 8.83 (s, 1H), 8.79 (s, 1H), 8.56 (s, 1H), 8.41 (d, J=5.84 Hz, 1H), 8.25 (d, J=6.08 Hz, 1H), 7.39 (d, J=5.72 Hz, 1H), 7.00 (d, J=6.01 Hz, 1H), 4.53 (brs, 2H), 3.28 (m, 2H), 3.05 (m, 2H), 1.68 (d, J=12.6 Hz, 1H).

Example 162

Synthesis of 8-chloro-4'-(methylamino)-6-(pyrimidin-4-ylamino)spiro[2H-imidazo[1,5-a]pyridine-3,1'-cyclohexane]-1,5-dione hydrochloride (Cpd. No. 162)

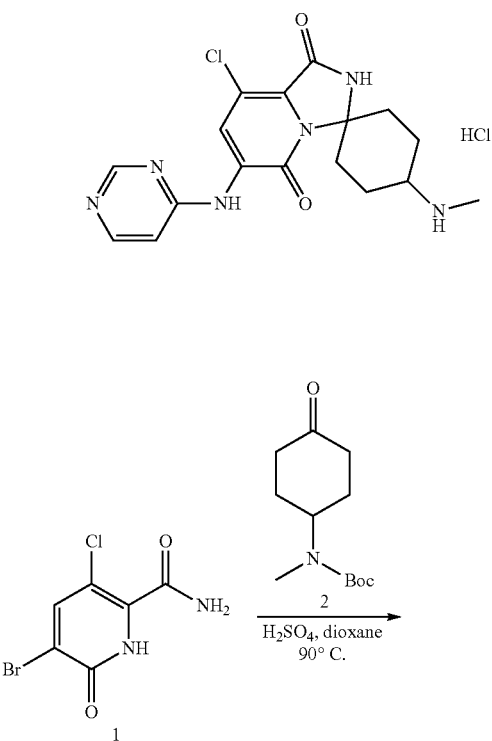

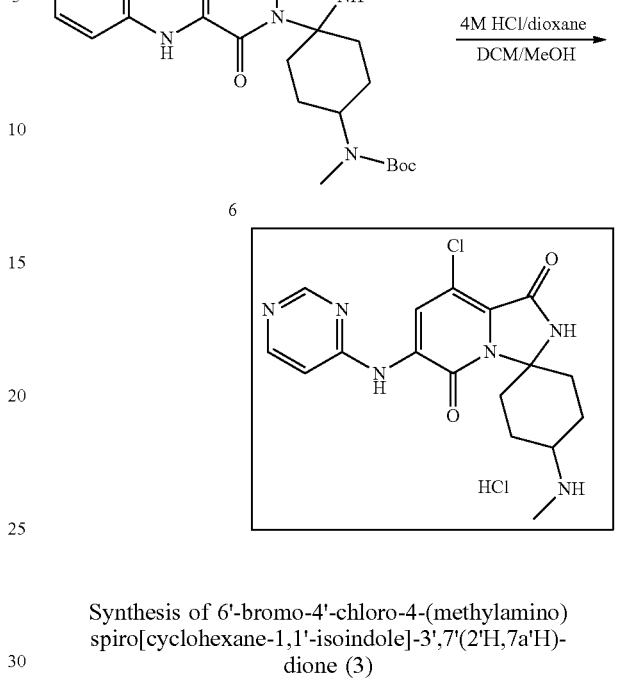

Synthesis of 6'-bromo-4'-chloro-4-(methylamino)spiro[cyclohexane-1,1'-isoindole]-3',7'(2'H,7a'H)-dione (3)

The synthesis of intermediate 3 was carried out as described above using the general protocol of Procedure A. Yield: 0.72 g, crude; MS (ESI) m/z 359.65 [M−1]⁻.

Synthesis of tert-butyl N-(6-bromo-8-chloro-1,5-dioxo-spiro[2H-imidazo[1,5-a]pyridine-3,4'-cyclohexane]-1'-yl)-N-methyl-carbamate (4)

To a mixture of 6-bromo-8-chloro-4'-(methylamino)spiro[2H-imidazo[1,5-a]pyridine-3,1'-cyclohexane]-1,5-dione (3, 0.72 g, 1.99 mmol) in 1,4-dioxane (10 mL) and water (10 mL), potassium hydroxide (0.56 g, 9.94 mmol) was added followed by addition of tert-butoxycarbonyl tert-butyl carbonate (651 mg, 2.98 mmol) and stirred the mixture at room temperature for 24 h. On completion of reaction, the resulting mixture was filtered. The precipitate was dissolved it in 10% methanol in dichloromethane. Organic layer was washed with water and brine, dried over anhydrous sodium sulfate, filtered and concentrated under reduced pressure to get tert-butyl N-(6-bromo-8-chloro-1,5-dioxo-spiro[2H-imidazo[1,5-a]pyridine-3,4'-cyclohexane]-1'-yl)-N-methyl-carbamate (4) as white solid. Yield: 0.9 g, 98%; $^1$H-NMR (400 MHz, DMSO-$d_6$) δ 10.76 (s, 1H), 8.26 (s, 1H), 4.00-3.97 (m, 1H), 2.98 (brs, 2H), 2.73 (s, 3H), 1.98-1.81 (m, 2H), 1.73-1.60 (m, 4H), 1.41 (s, 9H).

Synthesis of tert-butyl N-[8-chloro-1,5-dioxo-6-(pyrimidin-4-ylamino)spiro[2H-imidazo[1,5-a]pyridine-3, 4'-cyclohexane]-1'-yl]-N-methyl-carbamate (6)

The synthesis of intermediate 6 was carried out as described above using the general protocol of Procedure H. Off white solid; Yield: 0.11 g, 21%; MS (ESI) m/z 475.31 [M+1]⁺; $^1$H NMR (400 MHz, DMSO-$d_6$) δ 10.51 (s, 1H), 9.67 (s, 1H), 8.84 (s, 1H), 8.80 (s, 1H), 8.44 (d, J=5.6, 1H),

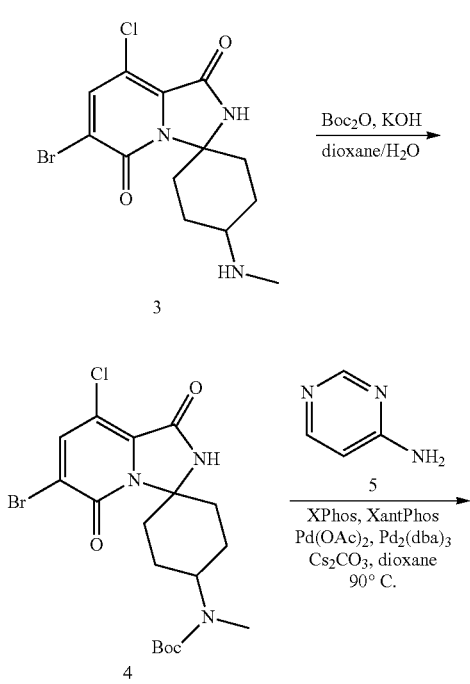

7.46 (s, 1H), 3.94-3.87 (m, 1H), 3.12-3.06 (m, 2H) 2.75 (s, 3H), 1.89-1.85 (m, 3H), 1.66-1.64 (m, 4H), 1.41 (s, 3H).

Synthesis of 8-chloro-4'-(methylamino)-6-(pyrimidin-4-ylamino)spiro[2H-imidazo[1,5-a]pyridine-3,1'-cyclohexane]-1,5-dione hydrochloride (Cpd. No. 162)

The synthesis of compound 162 was carried out as described above using the general protocol of Procedure F. Yellow solid; Yield: 0.060 g, 69%; MS (ESI) m/z 375.26 [M+1]$^+$; $^1$H NMR (400 MHz, DMSO-d$_6$) δ 9.07 (s, 1H), 8.60 (s, 1H), 8.46 (d, J=6.8 Hz, 1H), 7.58 (d, J=6.0 Hz, 1H), 3.16-3.13 (m, 1H), 3.04-2.98 (m, 2H), 2.57 (s, 3H), 2.13-2.10 (m, 2H), 1.72-1.66 (m, 4H).

Example 163

Synthesis of 1'-acetyl-8-chloro-6-(pyrimidin-4-ylamino)-2H-spiro [imidazo [1,5-a]pyridine-3,4'-piperidine]-1,5-dione (Cpd. No. 163)

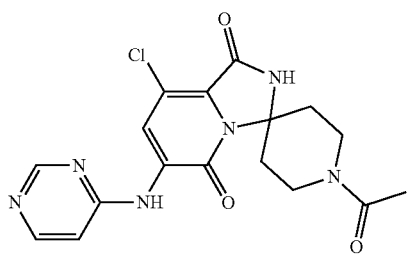 [SMILES: CC(=O)N1CCC2(CC1)NC(=O)c1c(Cl)cc(Nc3ccncn3)c(=O)n12]

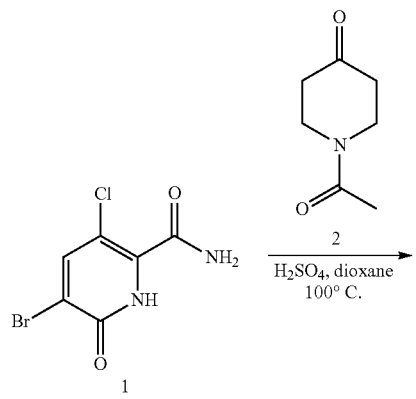

Synthesis of 1'-acetyl-6-bromo-8-chloro-2H-spiro[imidazo[1,5-a]pyridine-3,4'-piperidine]-1,5-dione (3)

The synthesis of intermediate 3 was carried out as described above using the general protocol of Procedure A. Off white solid; Yield: 0.60 g, 81%; MS (ESI) m/z 375.41 [M+1]$^+$.

Synthesis 1'-acetyl-8-chloro-6-(pyrimidin-4-ylamino)-2H-spiro[imidazo[1,5-a]pyridine-3,4'-piperidine]-1,5-dione (Cpd. No. 163)

The synthesis of compound 163 was carried out as described above using the general protocol of Procedure H. Yellow solid; Yield: 0.35 g, 43%; MS (ESI) m/z 389 [M+1]$^+$; $^1$H NMR (400 MHz, DMSO-d$_6$) δ 10.55 (s, 1H), 9.66 (s, 1H), 8.84 (s, 1H), 8.79 (s, 1H), 8.43 (d, J=5.84 Hz, 1H), 7.43 (d, J=5.92 Hz, 1H), 4.50 (d, J=12.64 Hz, 1H), 3.96 (d, J=2.95 Hz, 1H), 3.10-3.07 (m, 1H), 3.06-3.03 (m, 1H), 2.06 (s, 3H), 1.68-1.59 (m, 2H).

Example 164

Synthesis of 8'-chloro-1',5'-dioxo-6'-(pyrimidin-4-ylamino)-1',5'-dihydro-2'H-spiro[cyclohexane-1,3'-imidazo[1,5-a]pyridine]-4-carbonitrile (Cpd. No. 164)

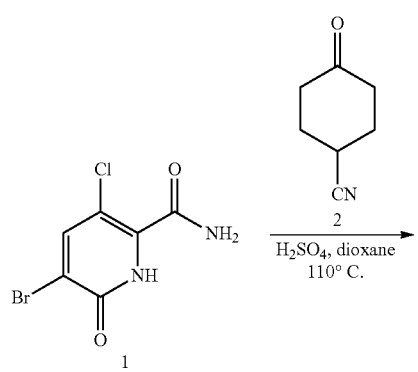

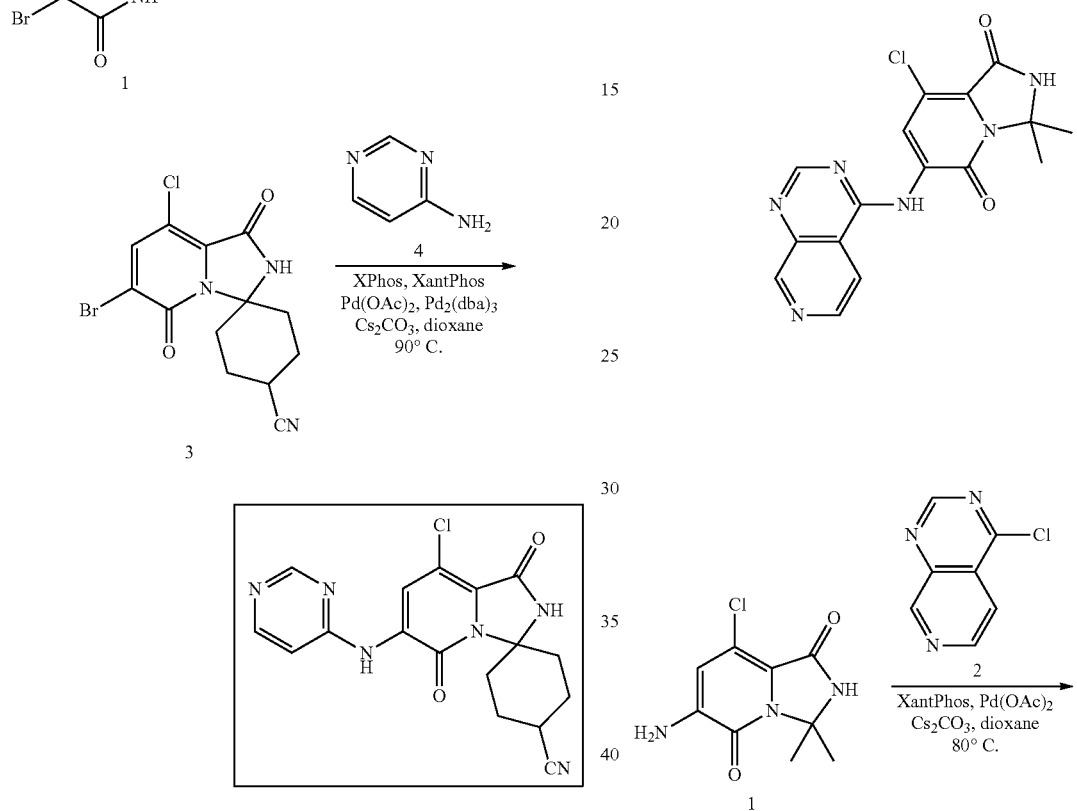

Example 165

Synthesis of 8-chloro-3,3-dimethyl-6-(pyrido[3,4-d]pyrimidin-4-ylamino)-2,3-dihydroimidazo[1,5-a]pyridine-1,5-dione (Cpd. No. 165)

Synthesis of 6'-bromo-8'-chloro-1',5'-dioxo-1',5'-dihydro-2'H-spiro[cyclohexane-1,3'-imidazo[1,5-a]pyridine]-4-carbonitrile (3)

The synthesis of intermediate 3 was carried out as described above using the general protocol of Procedure A. Off white solid; Yield: 0.75 g, 53%; MS (ESI) m/z 354.08 [M−1]⁻.

Synthesis of 8'-chloro-1',5'-dioxo-6'-(pyrimidin-4-ylamino)-1',5'-dihydro-2'H-spiro[cyclohexane-1,3'-imidazo[1,5-a]pyridine]-4-carbonitrile (Cpd. No. 164)

The synthesis of compound 164 was carried out as described above using the general protocol of Procedure H. Yellow solid; Yield: 0.21 g, 29%; MS (ESI) m/z 371.18 [M+1]⁺; $^1$H NMR (400 MHz, DMSO-$d_6$) δ 10.36 (s, 1H), 9.58 (s, 1H), 8.84-8.78 (m, 2H), 8.44-8.39 (m, 1H), 7.44-7.43 (m, 1H), 3.00-2.94 (m, 2H), 2.82-2.76 (m, 1H), 2.15-2.12 (m, 2H), 1.99-1.90 (m, 3H), 1.67-1.64 (m, 2H).

Synthesis of 8-chloro-3,3-dimethyl-6-(pyrido[3,4-d]pyrimidin-4-ylamino)-2,3-dihydroimidazo[1,5-a]pyridine-1,5-dione (Cpd. No. 165)

The synthesis of compound 165 was carried out as described above using the general protocol of Procedure B. Yellow solid; Yield: 25 mg, 8%; MS (ESI) m/z 357.34 [M+1]⁺; $^1$H NMR (400 MHz, DMSO-$d_6$) δ 10.05 (brs, 1H), 10.37 (s, 1H), 9.17 (s, 1H), 8.61 (m, 2H), 8.18 (d, J=5.24 Hz, 1H), 1.82 (s, 6H).

Example 166

Synthesis of 8-chloro-3,3-dimethyl-6-(pyrimido[5,4-c]pyridazin-8-ylamino)-2,3-dihydroimidazo[1,5-a]pyridine-1,5-dione (Cpd. No. 166)

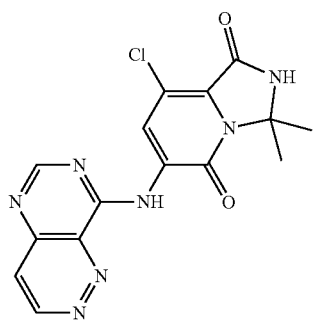 [SMILES: CC1(C)NC(=O)c2c(Cl)cc(Nc3ncnc4ccnnc34)c(=O)n21]

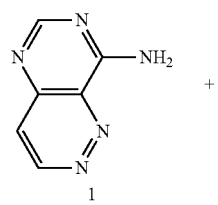

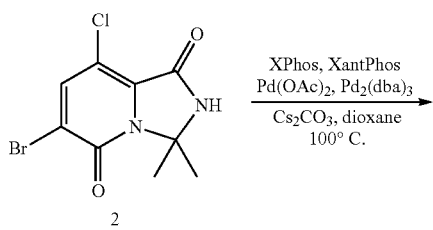

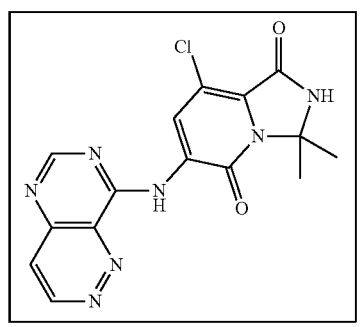

Synthesis of 8-chloro-3,3-dimethyl-6-(pyrimido[5,4-c]pyridazin-8-ylamino)-2,3-dihydroimidazo[1,5-a]pyridine-1,5-dione (Cpd. No. 166)

The synthesis of compound 166 is carried out as described above using the general protocol of Procedure H.

Example 167

Synthesis of 8-chloro-3,3-dimethyl-6-(pyrimido[5,4-d]pyrimidin-4-ylamino)-2,3-dihydroimidazo[1,5-a]pyridine-1,5-dione (Cpd. No. 167)

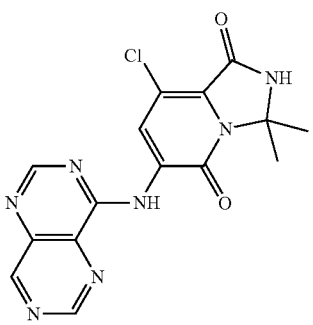 [SMILES: CC1(C)NC(=O)c2c(Cl)cc(Nc3ncnc4cncnc34)c(=O)n21]

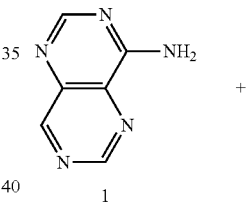

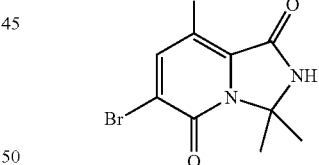

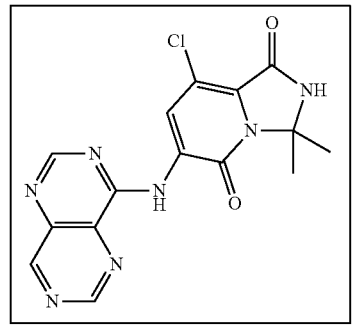

Synthesis of 8-chloro-3,3-dimethyl-6-(pyrimido[5,4-d]pyrimidin-4-ylamino)-2,3-dihydroimidazo[1,5-a]pyridine-1,5-dione (Cpd. No. 167)

The synthesis of compound 167 is carried out as described above using the general protocol of Procedure H.

Example 168

Synthesis of (Z)-8-chloro-6-((6-(2-cyclopropyl-3,3,3-trifluoroprop-1-en-1-yl)pyrimidin-4-yl)amino)-3-(3-fluorophenyl)-3-methyl-2,3-dihydroimidazo[1,5-a]pyridine-1,5-dione (Cpd. No. 168)

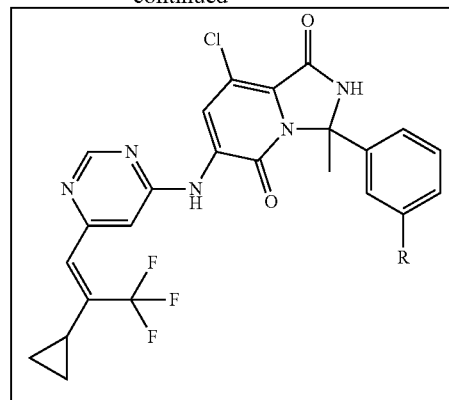

Synthesis of (Z)-8-chloro-6-((6-(2-cyclopropyl-3,3,3-trifluoroprop-1-en-1-yl)pyrimidin-4-yl)amino)-3-(3-fluorophenyl)-3-methyl-2, 3-dihydroimidazo[1,5-a]pyridine-1,5-dione (Cpd. No. 168)

The synthesis of compound 168 is carried out as described above using the general protocol of Procedure H.

Example 169

Synthesis of 6'-((6-amino-5-fluoropyrimidin-4-yl)amino)-8'-chloro-2'H-spiro[cyclohexane-1,3'-imidazo[1,5-a]pyridine]-1',5'-dione hydrochloride (Cpd. No. 169)

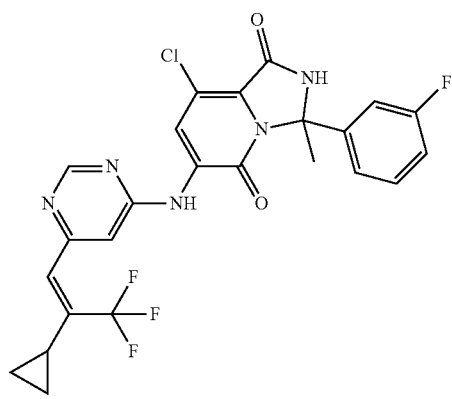 [SMILES: CC1(c2cccc(F)c2)NC(=O)c2c(Cl)cc(Nc3cc(/C=C(/C4CC4)C(F)(F)F)ncn3)c(=O)n21]

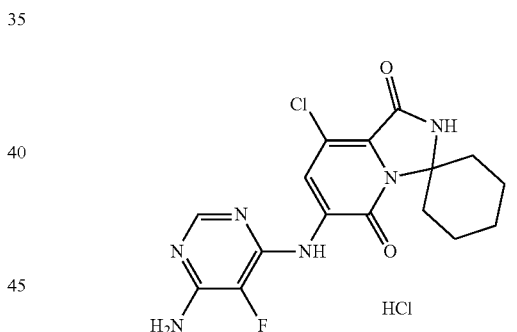

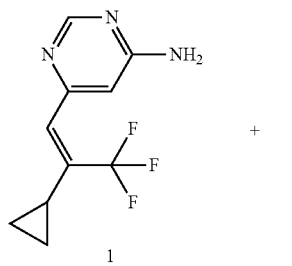

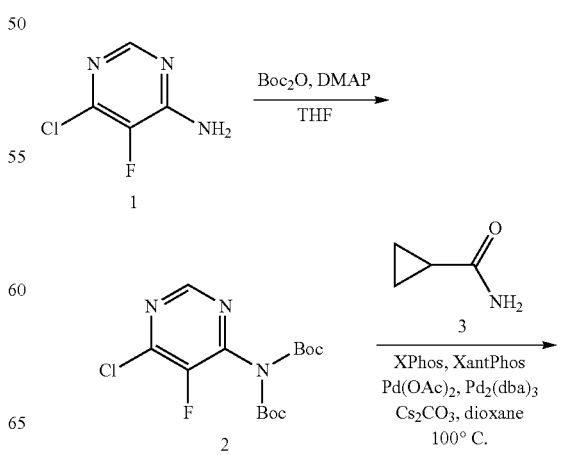

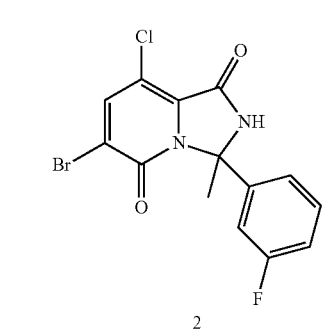

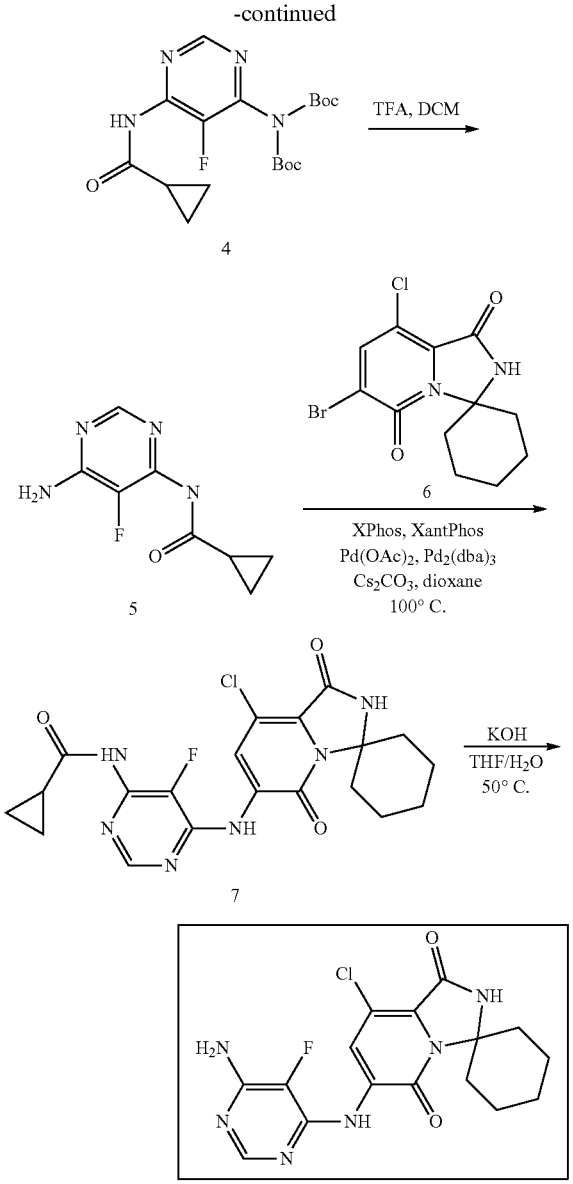

Synthesis of tert-butyl N-tert-butoxycarbonyl-N-(6-chloro-5-fluoropyrimidin-4-yl)carbamate (2)

The synthesis of intermediate 2 was carried out as described above using the general protocol of Procedure J. Off white solid; Yield: 2.3 g, 97%; MS (ESI) m/z 348 [M+1]$^+$.

Synthesis of tert-butyl N-tert-butoxycarbonyl-N-[6-(cyclopropanecarbonylamino)-5-fluoro-pyrimidin-4-yl]carbamate (4)

The synthesis of intermediate 4 was carried out as described above using the general protocol of Procedure H. Off white solid; Yield: 0.9 g, 38%; MS (ESI) m/z 397.29 [M+1]$^+$; $^1$H NMR (400 MHz, DMSO-d$_6$) δ 8.6 (s, 1H), 7.83 (s, 1H), 2.41 (brs, 1H), 1.46 (s, 18H), 1.30 (m, 4H).

Synthesis of N-(6-amino-5-fluoro-pyrimidin-4-yl)cyclopropanecarboxamide (5)

To a stirred solution of tert-butyl N-tert-butoxycarbonyl-N-[6-(cyclopropanecarbonylamino)-5-fluoro-pyrimidin-4-yl]carbamate (4, 0.89 g, 2.25 mmol) in dichloromethane (20 mL), trifluoroacetic acid (20 mL, 2.25 mmol) was added at 0° C. and stirred the reaction mass at room temperature for 16 h. After completion the reaction, trifluoroacetic acid was distilled and the crude compound was basified with liquid ammonia. The solid precipitated out was filtered and dried to afford N-(6-amino-5-fluoro-pyrimidin-4-yl)cyclopropanecarboxamide (5) as off white solid. Yield: 0.4 g, 90%; MS (ESI) m/z 197.06 [M+1]$^+$; $^1$H NMR (400 MHz, DMSO-d$_6$) δ 10.37 (s, 1H), 7.99 (s, 1H), 7.16 (s, 2H), 7.04 (s, 1H), 2.06 (m, 1H), 0.82-0.78 (m, 4H).

Synthesis of N-[6-[(8-chloro-1,5-dioxo-spiro[2H-imidazo[1,5-a]pyridine-3,1'-cyclohexane]-6-yl)amino]-5-fluoro-pyrimidin-4-yl]cyclopropanecarboxamide (7)

The synthesis of intermediate 7 was carried out as described above using the general protocol of Procedure H. Yellow solid; Yield: 0.22 g, 40%; MS (ESI) m/z 447 [M+1]$^+$; $^1$H NMR (400 MHz, DMSO-d$_6$) δ 10.87 (s, 1H), 10.45 (s, 1H), 8.59-8.53 (m, 1H), 8.50-8.42 (m, 2H), 2.90 (m, 2H), 1.98-1.98 (m, 1H), 1.77-1.53 (m, 8H), 0.82-0.84 (m, 4H).

Synthesis of 6'-((6-amino-5-fluoropyrimidin-4-yl)amino)-8'-chloro-2'H-spiro[cyclohexane-1,3'-imidazo[1,5-a]pyridine]-1',5'-dione hydrochloride (Cpd. No. 169)

The synthesis of compound 169 was carried out as described above using the general protocol of Procedure I. Off white solid; Yield: 110 mg, 65%; MS (ESI) m/z 378.9 [M+1]$^+$; $^1$H NMR: (400 MHz, DMSO-d$_6$) δ 10.34 (brs, 1H), 8.51 (s, 1H), 8.16 (s, 1H), 8.08 (s, 1H), 7.10 (s, 1H), 2.94 (t, J=2.32, 2H), 1.79-1.76 (m, 2H), 1.67-1.51 (m, 5H), 1.27-1.23 (m, 1H).

Example 170

Synthesis of 6-[(6-aminopyrimidin-4-yl)amino]-1',8-dimethyl-spiro[2H-imidazo[1,5-a]pyridine-3,3'-piperidine]-1,5-dione (Cpd. No. 170)

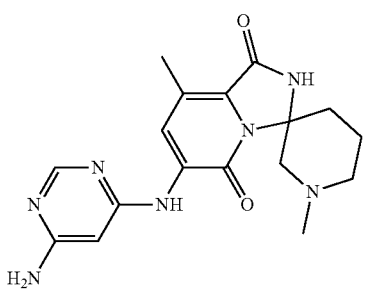 [SMILES: Cc1cc(Nc2cc(N)ncn2)c(=O)n2c1C(=O)NC21CCCN(C)C1]

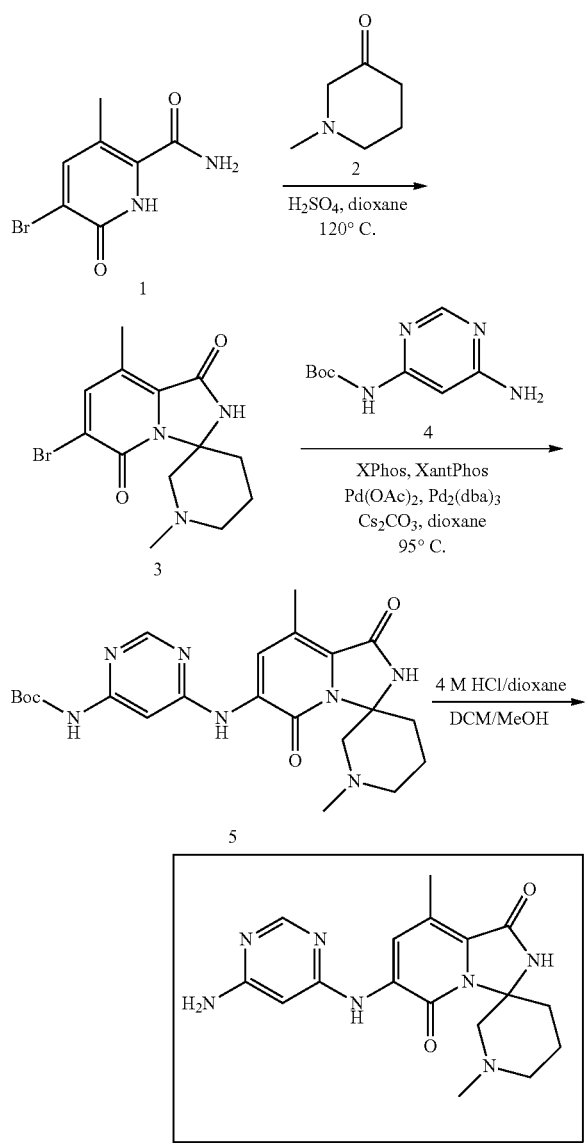

Synthesis of 6-bromo-1',8-dimethyl-2H-spiro[imidazo[1,5-a]pyridine-3,3'-piperidine]-1,5-dione (3)

The synthesis of intermediate 3 was carried out as described above using the general protocol of Procedure A. White solid; Yield: 0.7 g, 25%; MS (ESI) m/z 326.19 [M+1]$^+$.

Synthesis of tert-butyl (6-((1',8-dimethyl-1,5-dioxo-1,5-dihydro-2H-spiro[imidazo[1,5-a]pyridine-3,3'-piperidin]-6-yl)amino)pyrimidin-4-yl)carbamate (5)

The synthesis of intermediate 5 was carried out as described above using the general protocol of Procedure H. Yellow solid; Yield: 0.25 g, 64%; 1H NMR (400 MHz, DMSO-d$_6$) δ 10.92 (s, 1H), 9.80 (s, 1H), 9.10 (s, 1H), 8.52-8.46 (m, 2H), 7.84 (m, 1H), 3.00-2.98 (m, 2H), 2.81-2.79 (m, 1H), 2.43 (s, 3H), 2.21 (s, 3H), 2.03-1.90 (m, 3H), 1.70 (m, 1H), 1.48-1.4 (s, 9H).

Synthesis of 6-[(6-aminopyrimidin-4-yl)amino]-1',8-dimethyl-spiro[2H-imidazo[1,5-a]pyridine-3,3'-piperidine]-1,5-dione (Cpd. No. 170)

The synthesis of compound 170 was carried out as described above using the general protocol of Procedure F. Yellow solid; Yield: 0.1 g, 34%; MS (ESI) m/z 356.47 [M+1]$^+$; $^1$H NMR (400 MHz, DMSO-d$_6$) δ 9.82 (s, 1H), 8.59 (s, 1H), 8.38 (s, 1H), 8.16 (s, 1H), 6.52 (s, 2H), 6.14 (s, 1H), 3.32-3.30 (m, 1H), 2.98 (s, 1H), 2.80 (s, 1H), 2.50 (s, 1H), 2.41 (s, 3H), 2.20 (s, 3H), 1.91 (s, 2H), 1.76-1.69 (m, 1H), 1.48-1.45 (m, 1H).

Example 171

Synthesis of 8-chloro-6-(pyrimidin-4-ylamino)-2',3'-dihydro-1'H,2H-spiro[imidazo[1,5-a]pyridine-3,4'-isoquinoline]-1,5-dione (Cpd. No. 171)

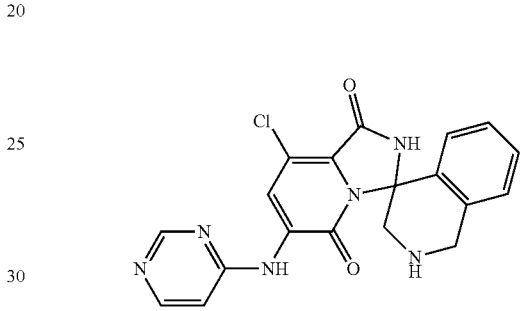

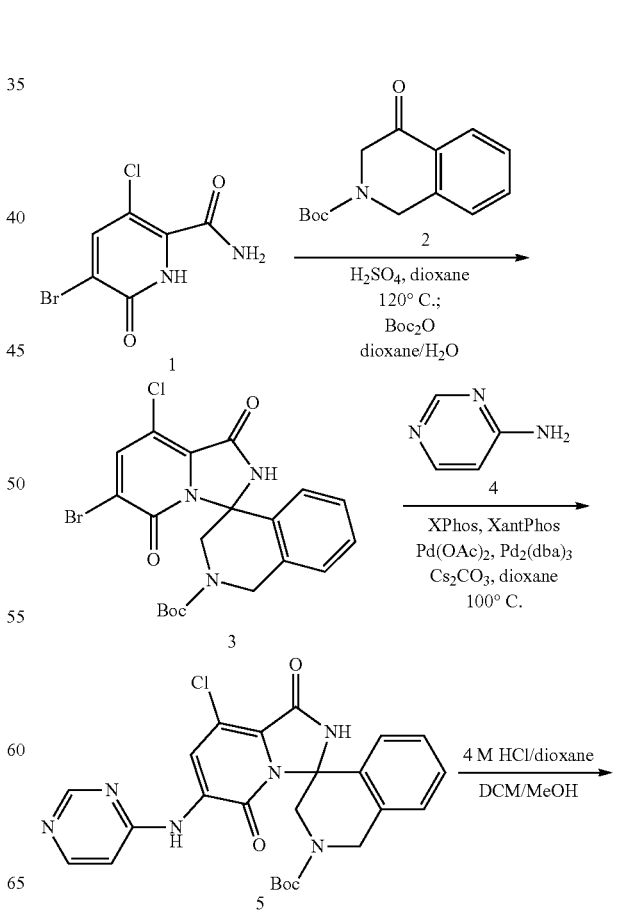

275
-continued

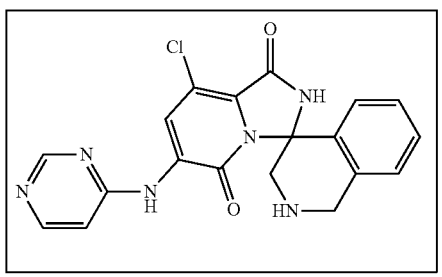

Synthesis of tert-butyl 6-bromo-8-chloro-1,5-dioxo-1,5-dihydro-1'H,2H-spiro[imidazo[1,5-a]pyridine-3,4'-isoquinoline]-2'(3'H)-carboxylate (3)

The synthesis of intermediate 3 is carried out as described above using the general protocol of Procedure E.

Synthesis of tert-butyl 8-chloro-1,5-dioxo-6-(pyrimidin-4-ylamino)-1,5-dihydro-1'H,2H-spiro[imidazo[1,5-a]pyridine-3,4'-isoquinoline]-2'(3'H)-carboxylate (5)

The synthesis of intermediate 5 is carried out as described above using the general protocol of Procedure H.

Synthesis of 8-chloro-6-(pyrimidin-4-ylamino)-2',3'-dihydro-1'H,2H-spiro[imidazo[1,5-a]pyridine-3,4'-isoquinoline]-1,5-dione (Cpd. No. 171)

The synthesis of compound 171 is carried out as described above using the general protocol of Procedure F.

Example 172

Synthesis of 6-((6-aminopyrimidin-4-yl)amino)-8-chloro-2',3'-dihydro-1'H,2H-spiro[imidazo[1,5-a]pyridine-3,4'-isoquinoline]-1,5-dione (Cpd. No. 172)

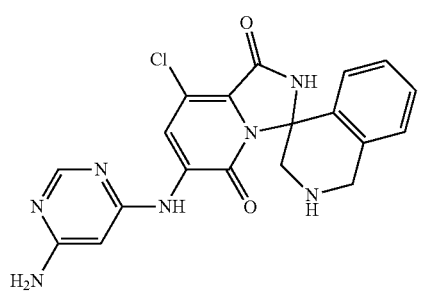 [SMILES: Nc1cc(Nc2cc(Cl)c3n(c2=O)C2(CNCc4ccccc42)NC3=O)ncn1]

276

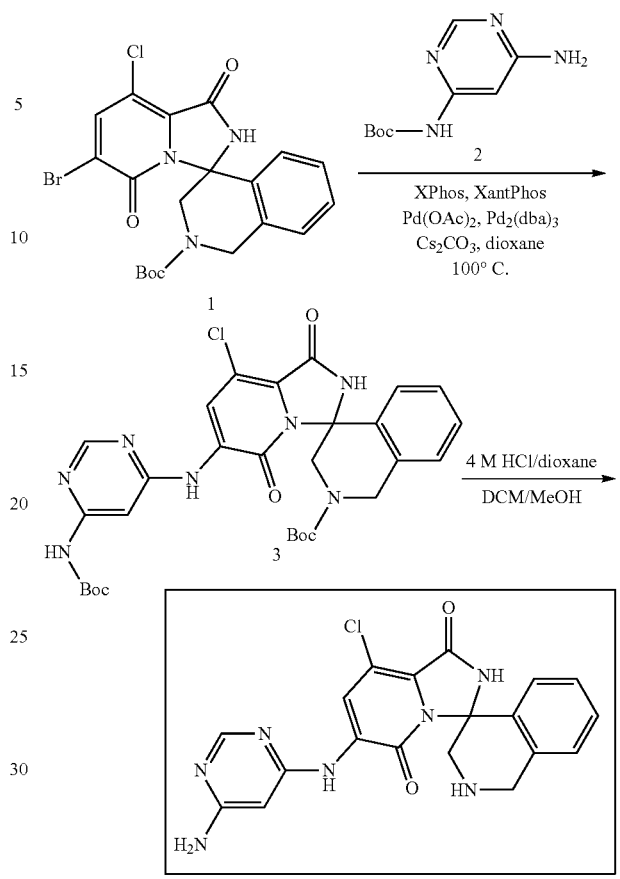

Synthesis of tert-butyl 6-((6-((tert-butoxycarbonyl)amino)pyrimidin-4-yl)amino)-8-chloro-1,5-dioxo-1,5-dihydro-1'H,2H-spiro[imidazo[1,5-a]pyridine-3,4'-isoquinoline]-2'(3'H)-carboxylate (3)

The synthesis of intermediate 3 is carried out as described above using the general protocol of Procedure H.

Synthesis of 6-((6-aminopyrimidin-4-yl)amino)-8-chloro-2',3'-dihydro-1'H,2H-spiro[imidazo[1,5-a]pyridine-3,4'-isoquinoline]-1,5-dione (Cpd. No. 172)

The synthesis of compound 172 is carried out as described above using the general protocol of Procedure F.

Example 173

Synthesis of 8-chloro-6'-fluoro-6-(pyrimidin-4-ylamino)-2',3'-dihydro-1'H,2H-spiro[imidazo[1,5-a]pyridine-3,4'-isoquinoline]-1,5-dione (Cpd. No. 173)

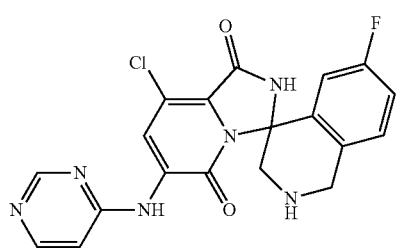 [SMILES: O=C1NC2(CNCc3ccc(F)cc32)n2c1c(Cl)cc(Nc1ccncn1)c2=O]

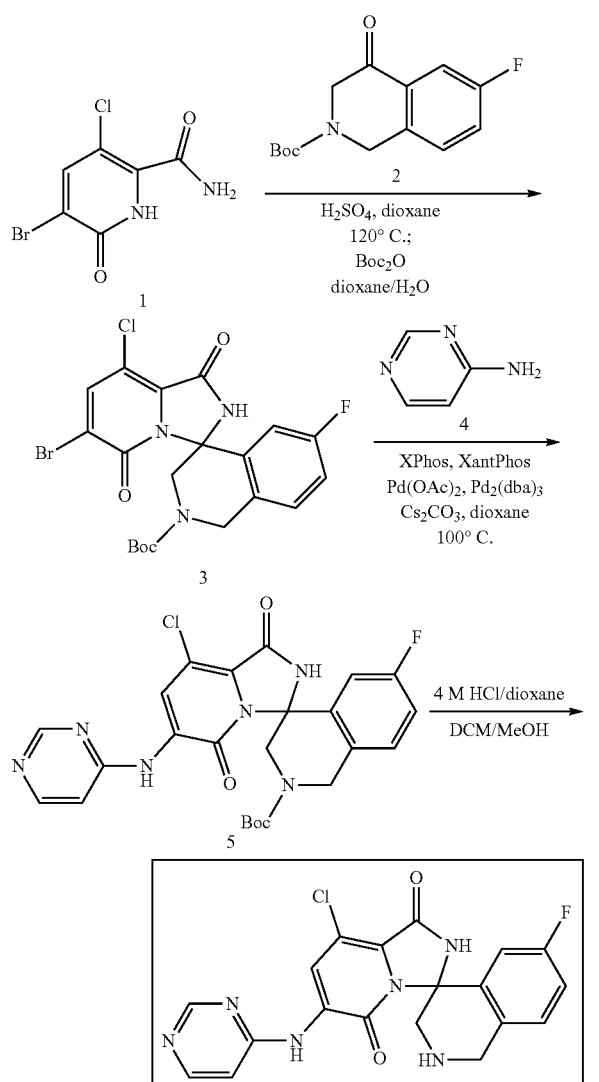

Synthesis of tert-butyl 6-bromo-8-chloro-6'-fluoro-1,5-dioxo-1,5-dihydro-1'H,2H-spiro[imidazo[1,5-a]pyridine-3,4'-isoquinoline]-2'(3'H)-carboxylate (3)

The synthesis of intermediate 3 is carried out as described above using the general protocol of Procedure E.

Synthesis of tert-butyl 8-chloro-6'-fluoro-1,5-dioxo-6-(pyrimidin-4-ylamino)-1,5-dihydro-1'H,2H-spiro[imidazo[1,5-a]pyridine-3,4'-isoquinoline]-2'(3'H)-carboxylate (5)

The synthesis of intermediate 5 is carried out as described above using the general protocol of Procedure H.

Synthesis of 8-chloro-6'-fluoro-6-(pyrimidin-4-ylamino)-2',3'-dihydro-1'H,2H-spiro[imidazo[1,5-a]pyridine-3,4'-isoquinoline]-1,5-dione (Cpd. No. 173)

The synthesis of compound 173 is carried out as described above using the general protocol of Procedure F.

Example 174

Synthesis of 6-((6-aminopyrimidin-4-yl)amino)-8-chloro-6'-fluoro-2',3'-dihydro-1'H,2H-spiro[imidazo[1,5-a]pyridine-3,4'-isoquinoline]-1,5-dione (Cpd. No. 174)

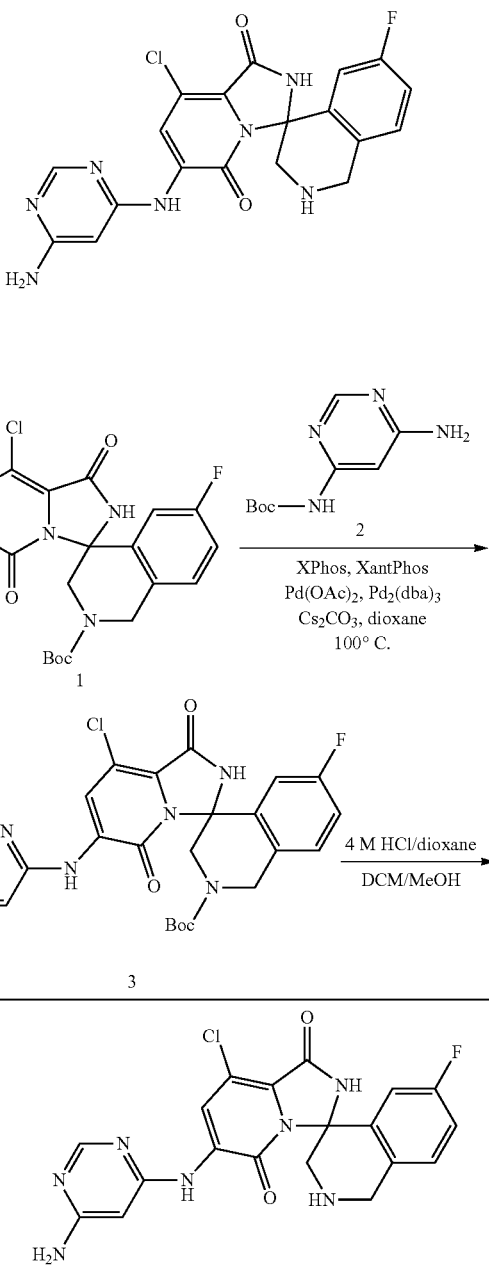

Synthesis of tert-butyl 6-((6-((tert-butoxycarbonyl)amino)pyrimidin-4-yl)amino)-8-chloro-6'-fluoro-1,5-dioxo-1,5-dihydro-1'H,2H-spiro[imidazo[1,5-a]pyridine-3,4'-isoquinoline]-2'(3'H)-carboxylate (3)

The synthesis of intermediate 3 is carried out as described above using the general protocol of Procedure H.

Synthesis of 6-((6-aminopyrimidin-4-yl)amino)-8-chloro-6'-fluoro-2',3'-dihydro-1'H,2H-spiro[imidazo[1,5-a]pyridine-3,4'-isoquinoline]-1,5-dione (Cpd. No. 174)

The synthesis of compound 174 is carried out as described above using the general protocol of Procedure F.

Example 175

Synthesis of 8-chloro-6-(pyrimidin-4-ylamino)-2H-spiro[imidazo[1,5-a]pyridine-3,3'-indoline]-1,5-dione (Cpd. No. 175)

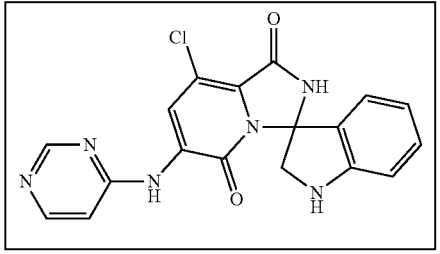

Synthesis of tert-butyl 6-bromo-8-chloro-1,5-dioxo-1,5-dihydro-2H-spiro[imidazo[1,5-a]pyridine-3,3'-indoline]-1'-carboxylate (3)

The synthesis of intermediate 3 is carried out as described above using the general protocol of Procedure E.

Synthesis of tert-butyl 8-chloro-1,5-dioxo-6-(pyrimidin-4-ylamino)-1,5-dihydro-2H-spiro[imidazo[1,5-a]pyridine-3,3'-indoline]-1'-carboxylate (5)

The synthesis of intermediate 5 is carried out as described above using the general protocol of Procedure H.

Synthesis of 8-chloro-6-(pyrimidin-4-ylamino)-2H-spiro[imidazo[1,5-a]pyridine-3,3'-indoline]-1,5-dione (Cpd. No. 175)

The synthesis of compound 175 is carried out as described above using the general protocol of Procedure F.

Example 176

Synthesis of 8-chloro-5'-fluoro-6-(pyrimidin-4-ylamino)-2H-spiro[imidazo[1,5-a]pyridine-3,3'-indoline]-1,5-dione (Cpd. No. 176)

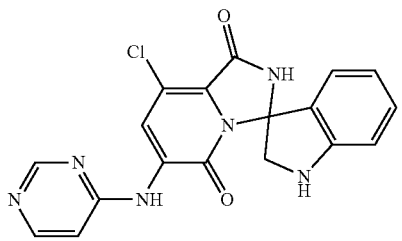 [SMILES: O=C1NC2(CNc3ccccc32)n2c1c(Cl)cc(Nc1ccncn1)c2=O]

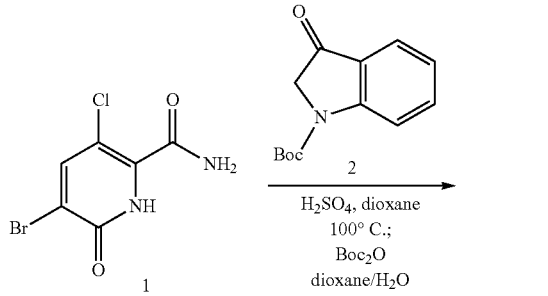

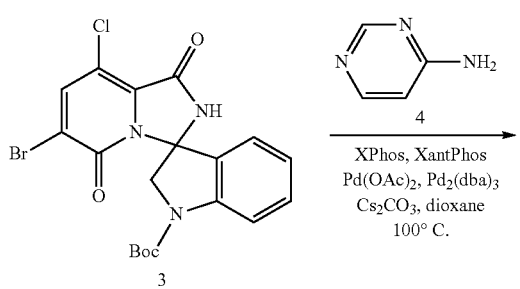

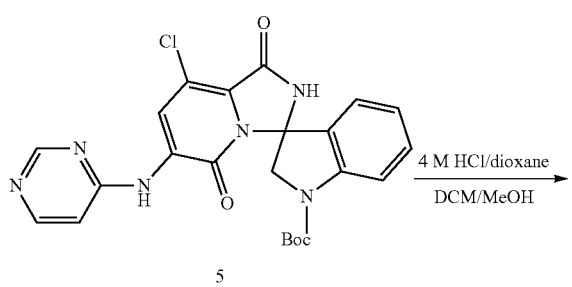

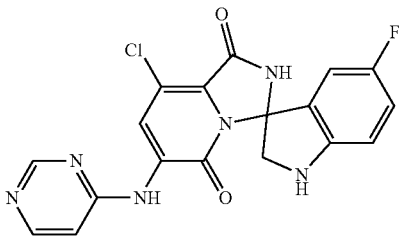 [SMILES: O=C1NC2(CNc3ccc(F)cc32)n2c1c(Cl)cc(Nc1ccncn1)c2=O]

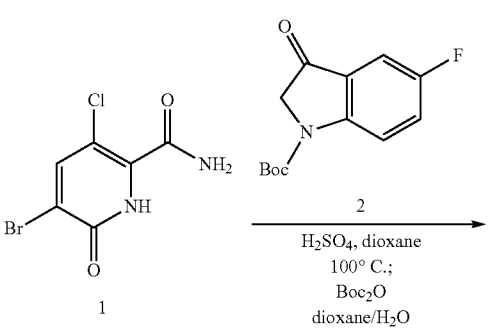

281
-continued

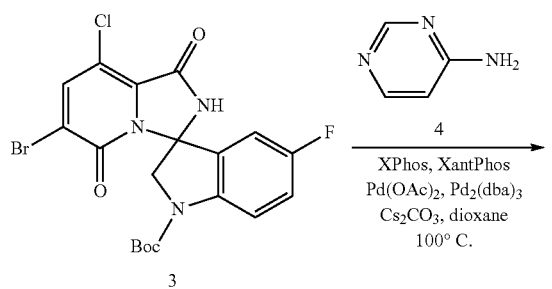

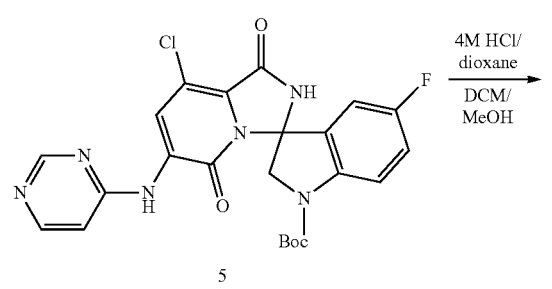

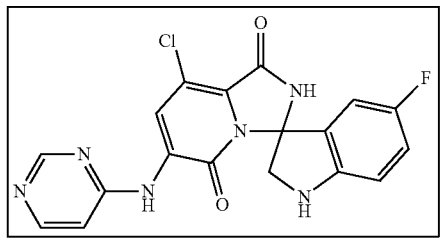

Synthesis of tert-butyl 6-bromo-8-chloro-5'-fluoro-1,5-dioxo-1,5-dihydro-2H-spiro[imidazo[1,5-a]pyridine-3,3'-indoline]-1'-carboxylate (3)

The synthesis of intermediate 3 is carried out as described above using the general protocol of Procedure E.

Synthesis of tert-butyl 8-chloro-5'-fluoro-1,5-dioxo-6-(pyrimidin-4-ylamino)-1,5-dihydro-2H-spiro[imidazo[1,5-a]pyridine-3,3'-indoline]-1'-carboxylate (5)

The synthesis of intermediate 5 is carried out as described above using the general protocol of Procedure H.

Synthesis of 8-chloro-5'-fluoro-6-(pyrimidin-4-ylamino)-2H-spiro[imidazo[1,5-a]pyridine-3,3'-indoline]-1,5-dione (Cpd. No. 176)

The synthesis of compound 176 is carried out as described above using the general protocol of Procedure F.

282

Example 177

Synthesis of 8-chloro-4',4'-difluoro-6-(pyrimidin-4-ylamino)-2H-spiro[imidazo[1,5-a]pyridine-3,3'-piperidine]-1,5-dione (Cpd. No. 177)

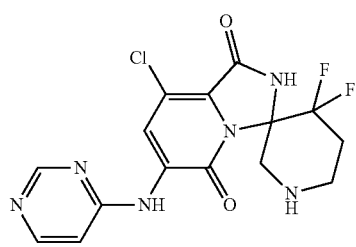 [SMILES: O=C1NC2(CNCCC2(F)F)n2c1c(Cl)cc(Nc1ccncn1)c2=O]

Synthesis of tert-butyl 6-bromo-8-chloro-4',4'-difluoro-1,5-dioxo-1,5-dihydro-2H-spiro[imidazo[1,5-a]pyridine-3,3'-piperidine]-1'-carboxylate (3)

The synthesis of intermediate 3 is carried out as described above using the general protocol of Procedure E.

Synthesis of tert-butyl 8-chloro-4',4'-difluoro-1,5-dioxo-6-(pyrimidin-4-ylamino)-1,5-dihydro-2H-spiro[imidazo[1,5-a]pyridine-3,3'-piperidine]-1'-carboxylate (5)

The synthesis of intermediate 5 is carried out as described above using the general protocol of Procedure H.

Synthesis of 8-chloro-4',4'-difluoro-6-(pyrimidin-ylamino)-2H-spiro[imidazo[1,5-a]pyridine-3,3'-piperidine]-1,5-dione (Cpd. No. 177)

The synthesis of compound 177 is carried out as described above using the general protocol of Procedure F.

Example 178

Synthesis of 6-((6-aminopyrimidin-4-yl)amino)-8-chloro-4',4'-difluoro-2H-spiro[imidazo[1,5-a]pyridine-3,3'-piperidine]-1,5-dione (Cpd. No. 178)

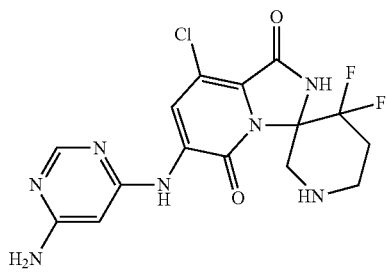 [SMILES: Nc1cc(Nc2cc(Cl)c3n(c2=O)C2(CNCCC2(F)F)NC3=O)ncn1]

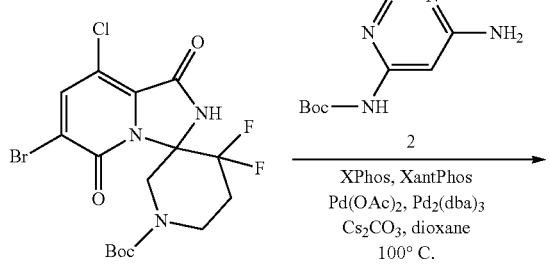

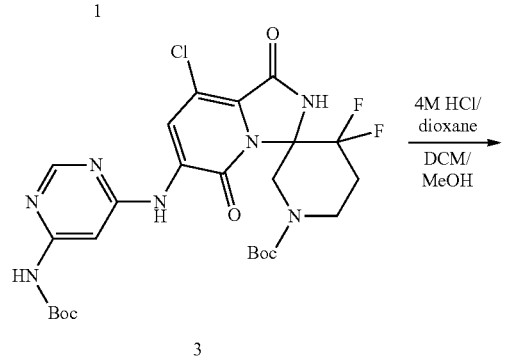

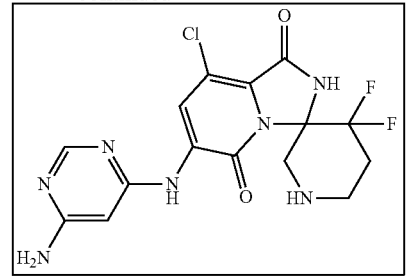

Synthesis of tert-butyl 6-((6-((tert-butoxycarbonyl)amino)pyrimidin-4-yl)amino)-8-chloro-4',4'-difluoro-1,5-dioxo-1,5-dihydro-2H-spiro[imidazo[1,5-a]pyridine-3,3'-piperidine]-1'-carboxylate (3)

The synthesis of intermediate 3 is carried out as described above using the general protocol of Procedure H.

Synthesis of 6-((6-aminopyrimidin-4-yl)amino)-8-chloro-4,4'-difluoro-2H-spiro[imidazo[1,5-a]pyridine-3,3'-piperidine]-1,5-dione (Cpd. No. 178)

The synthesis of compound 178 is carried out as described above using the general protocol of Procedure F.

Example 179

Synthesis of 8'-chloro-2,2-dimethyl-6'-(pyrimidin-4-ylamino)-4,5-dihydro-2H,2'H-spiro[furan-3,3'-imidazo[1,5-a]pyridine]-1',5'-dione (Cpd. No. 179)

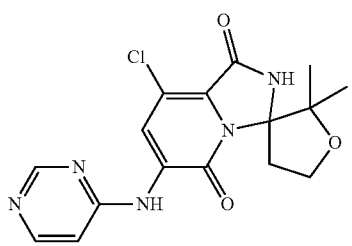 [SMILES: CC1(C)OCCC12NC(=O)c1c(Cl)cc(Nc3ccncn3)c(=O)n12]

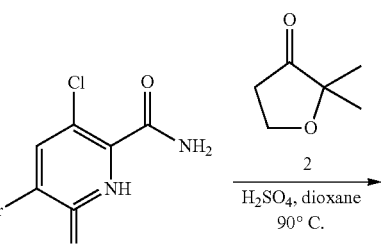

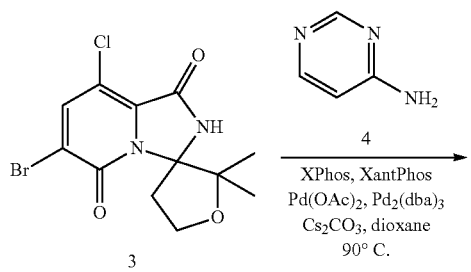

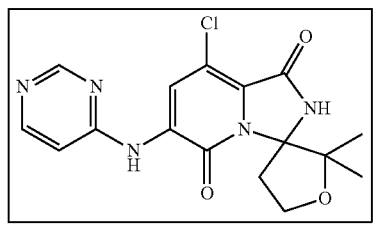

Synthesis of 6'-bromo-8'-chloro-2, 2-dimethyl-4, 5-dihydro-2H, 2'H-spiro[furan-3,3'-imidazo[1,5-a]pyridine]-1',5'-dione (3)

The synthesis of intermediate 3 is carried out as described above using the general protocol of Procedure A.

Synthesis of 8'-chloro-2,2-dimethyl-6'-(pyrimidin-4-ylamino)-4,5-dihydro-2H,2'H-spiro[furan-3,3'-imidazo[1,5-a]pyridine]-1',5'-dione (Cpd. No. 179)

The synthesis of compound 179 is carried out as described above using the general protocol of Procedure H.

Example 180

Synthesis of 6'-((6-aminopyrimidin-4-yl)amino)-8'-chloro-2,2-dimethyl-4,5-dihydro-2H,2'H-spiro[furan-3,3'-imidazo[1,5-a]pyridine]-1',5'-dione (Cpd. No. 180)

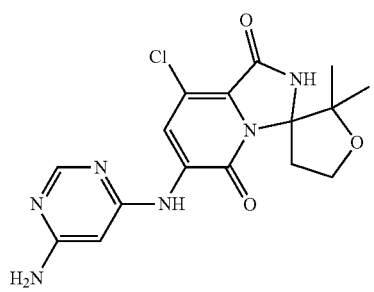 [SMILES: CC1(C)OCCC12NC(=O)c1c(Cl)cc(Nc3cc(N)ncn3)c(=O)n12]

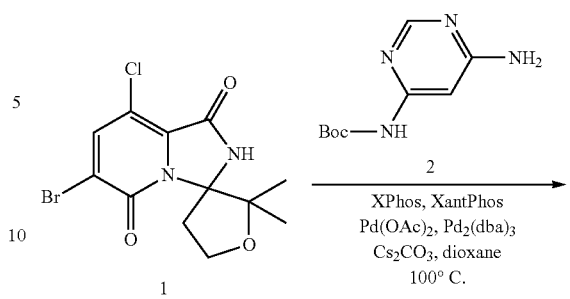

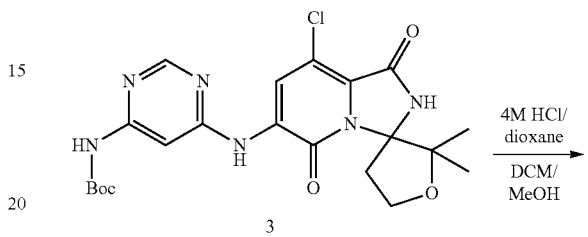

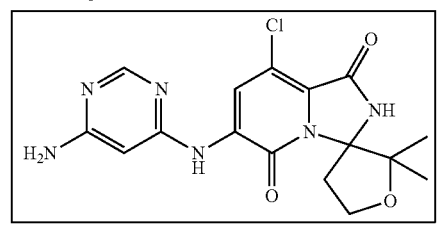

Synthesis of tert-butyl (6-((8'-chloro-2,2-dimethyl-1',5'-dioxo-1',4,5,5'-tetrahydro-2H,2'H-spiro[furan-3,3'-imidazo[1,5-a]pyridin-6'-yl)amino)pyrimidin-4-yl)carbamate (3)

The synthesis of intermediate 3 is carried out as described above using the general protocol of Procedure H.

Synthesis of 6'-((6-aminopyrimidin-4-yl)amino)-8'-chloro-2,2-dimethyl-4,5-dihydro-2H,2'H-spiro[furan-3,3'-imidazo[1,5-a]pyridine]-1',5'-dione (Cpd. No. 180)

The synthesis of compound 180 is carried out as described above using the general protocol of Procedure F.

Example 181

Synthesis of 3,3-dimethyl-1,5-dioxo-6-(pyrimidin-4-ylamino)-2H-imidazo[1,5-a]pyridine-8-carbonitrile (Cpd. No. 181)

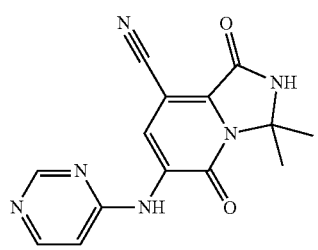 [SMILES: CC1(C)NC(=O)c2c(C#N)cc(Nc3ccncn3)c(=O)n21]

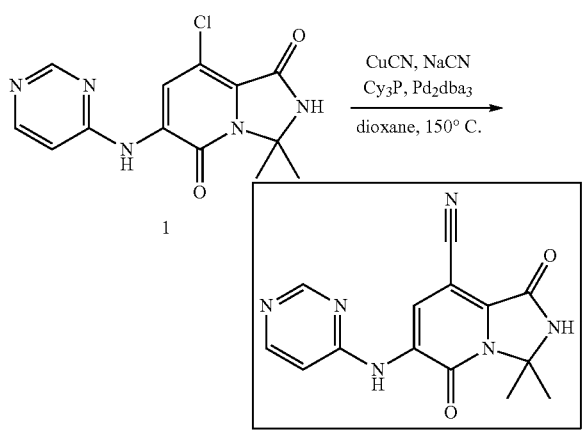

Synthesis of 3,3-dimethyl-1,5-dioxo-6-(pyrimidin-4-ylamino)-2H-imidazo[1,5-a]pyridine-8-carbonitrile (Cpd. No. 181)

To a vial was added 8-chloro-3,3-dimethyl-6-(pyrimidin-4-ylamino)-2H-imidazo[1,5-a]pyridine-1,5-dione (1, 1000 mg, 3.27 mmol), copper(I) cyanide (293 mg, 3.27 mmol) and sodium cyanide (160 mg, 3.27 mmol) in 1,4-dioxane (10 mL) at room temperature under argon. The reaction was purged with argon for 5-10 min, followed by addition of tricyclohexylphosphine (92 mg, 0.33 mmol) and tris(dibenzylideneacetone)dipalladium(0) (299 mg, 0.33 mmol) under argon. The vial was then sealed and heated at 150° C. for 48 h. After completion the reaction was quenched with sat solution of potassium permanganate and extracted the crude compound with 10% methanol in dichloromethane. The organic layer was concentrated to dryness and crude was purified by flash column chromatography (silica gel 100-200 mesh) using 2% methanol in dichloromethane. The desired fractions were concentrated to dryness under vacuum to obtain 3,3-dimethyl-1,5-dioxo-6-(pyrimidin-4-ylamino)-2H-imidazo[1,5-a]pyridine-8-carbonitrile (Cpd. No. 181) as off white solid. Yield: 0.2 g, 20%; MS (ESI) m/z 297.36 [M+1]$^+$; $^1$H NMR (400 MHz, DMSO-$d_6$) δ 10.20 (s, 1H), 9.69 (s, 1H), 8.90 (s, 1H), 8.85 (s, 1H), 8.44 (d, J=5.84 Hz, 1H), 7.44 (d, J=5.36 Hz, 1H), 1.82 (s, 6H).

Example 182

Synthesis of 6'-((2-aminopyridin-4-yl)amino)-8'-methyl-2'H-spiro[cyclohexane-1,3'-imidazo[1,5-a]pyrazine]-1',5'-dione (Cpd. No. 182)

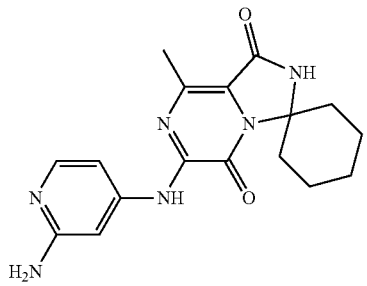 [SMILES: Cc1nc(Nc2ccnc(N)c2)c(=O)n2c1C(=O)NC21CCCCC1]

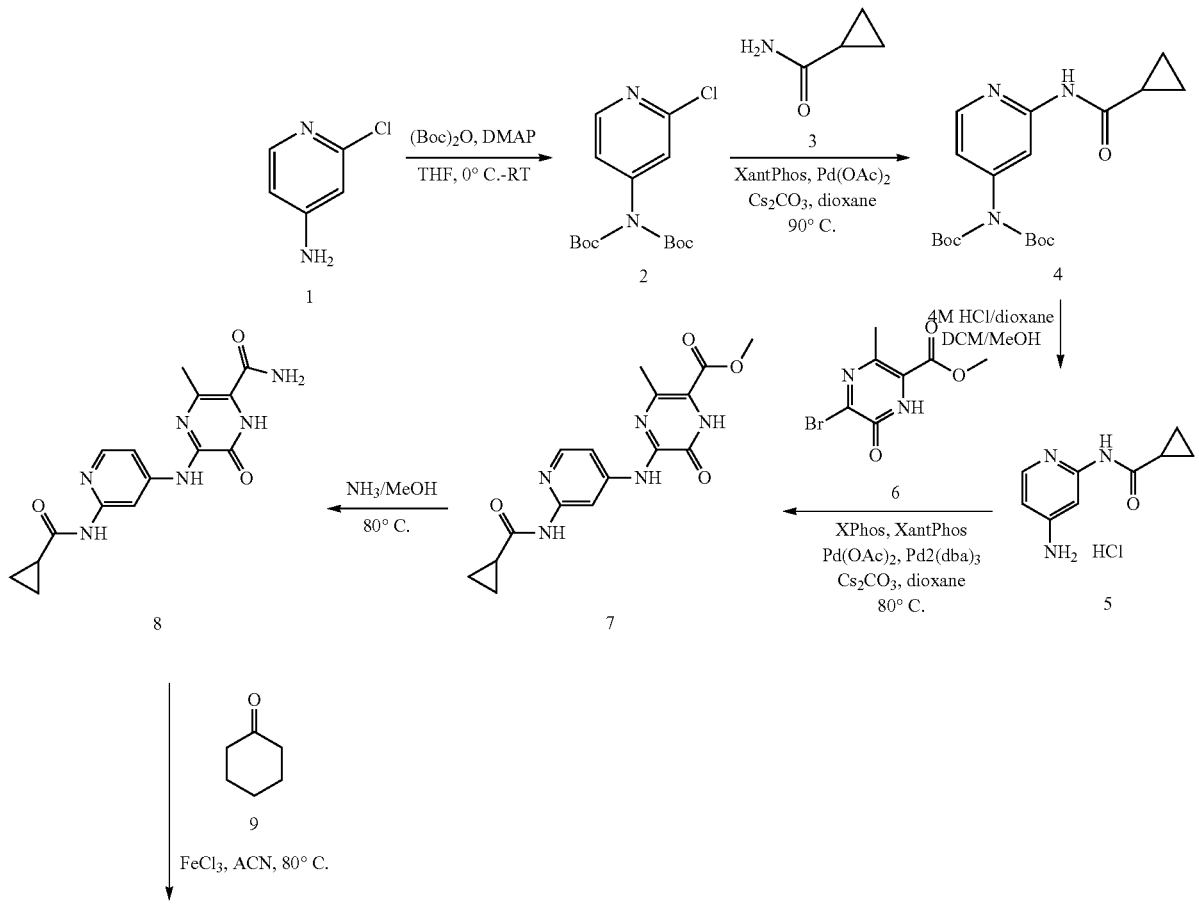

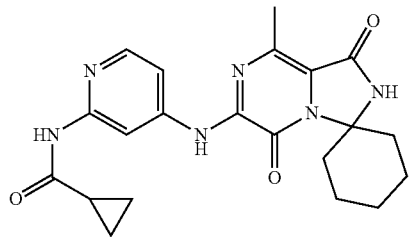 → 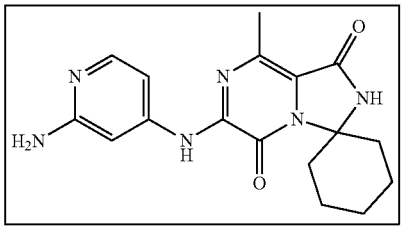

10

Synthesis of N,N-ditertbutoxycarbonyl-2-chloropyridin-4-amine (2)

The synthesis of intermediate 2 was carried out as described above using the general protocol of Procedure J. Light brown solid; Yield: 5.3 g, 70%; MS (ESI) m/z 329.21 [M+1]$^+$.

Synthesis of N, N-di-tertbutoxycarbonyl(2-(cyclopropanecarboxamido))pyridin-4-amine (4)

The synthesis of intermediate 4 was carried out as described above using the general protocol of Procedure B. Light brown solid; Yield: 2.5 g, 51%; MS (ESI) r/z 378.61 [M+1]$^+$.

Synthesis of N-(4-aminopyridin-2-yl)cyclopropanecarboxamide hydrochloride (5)

The synthesis of intermediate 5 was carried out as described above using the general protocol of Procedure F. Off white solid; Yield: 1.6 g, crude; MS (ESI) r/z 178.45 [M+1]$^+$.

Synthesis of methyl 5-((2-(cyclopropanecarboxamido)pyridin-4-yl)amino)-3-methyl-6-oxo-1,6-dihydropyrazine-2-carboxylate (7)

The synthesis of intermediate 7 was carried out as described above using the general protocol of Procedure H. Yellow solid; Yield: 1.5 g, 48%; MS (ESI) r/z 344.05 [M+1]$^+$.

Synthesis of 5-((2-(cyclopropanecarboxamido)pyridin-4-yl)amino)-3-methyl-6-oxo-1,6-dihydropyrazine-2-carboxamide (8)

The synthesis of intermediate 8 was carried out as described above using the general protocol of Procedure K. Yield: 600 mg, crude; MS (ESI) m/z 329.06 [M+1]$^+$.

Synthesis of N-(4-(((8'-methyl-1',5'-dioxo-1',5'-dihydro-2'H-spiro[cyclohexane-1, 3'-imidazo[1,5-a]pyrazin]-6'-yl)amino-2-yl)cyclopropanecarboxamide (10)

5-((2-(cyclopropanecarboxamido)pyridin-4-yl)amino)-3-methyl-6-oxo-1,6-dihydropyrazine-2-carboxamide (8, 600 mg, 1.83 mmol) and cyclohexanone (538 mg, 5.48 mmol) were charged in acetonitrile in a 20 mL microwave vial. Iron(III) chloride (889 mg, 1.83 mmol) was added and heated the reaction mixture at 80° C. for 16 h. On completion of the reaction, solvent was removed under vacuum and purified the compound by silica gel (200-400 mesh) column chromatography eluting with 5% methanol in dichloromethane. Appropriate column fractions were concentrated under reduced pressure to afford N-(4-(((8'-methyl-1',5'-dioxo-1',5'-dihydro-2'H-spiro[cyclohexane-1,3'-imidazo[1,5-a]pyrazin]-6'-yl)amino)pyridin-2-yl)cyclopropanecarboxamide (10, 100 mg, crude) as light brown crude solid which was directly forwarded to next step. MS (ESI) r/z 409.43 [M+1]$^+$.

Synthesis of 6'-((2-aminopyridin-4-yl)amino)-8'-methyl-2'H-spiro[cyclohexane-1,3'-imidazo[1,5-a]pyrazine]-1',5'-dione (Cpd. No. 182)

The synthesis of compound 182 was carried out as described above using the general protocol of Procedure I. Off white solid; Yield: 2 mg; MS (ESI) m/z 341.21[M+1]$^+$; $^1$H NMR (400 MHz, DMSO-d$_6$) δ 12.59 (s, 1H), 10.36 (s, 1H), 10.18, (s, 1H), 8.09 (s, 1H), 7.79 (s, 1H), 7.77 (s, 2H), 7.27 (s, 1H), 2.82-2.76 (m, 2H), 2.50 (s, 3H), 1.77-1.74 (m, 2H), 1.70-1.60 (m, 3H), 1.55-1.52 (m, 2H), 1.23-1.19 (m, 1H).

Example 183

Synthesis of 3'-amino-6-((6-aminopyrimidin-4-yl)amino)-8-chloro-6'-fluoro-2',3'-dihydro-2H-spiro[imidazo[1,5-a]pyridine-3,1'-indene]-1,5-dione (Cpd. No. 183)

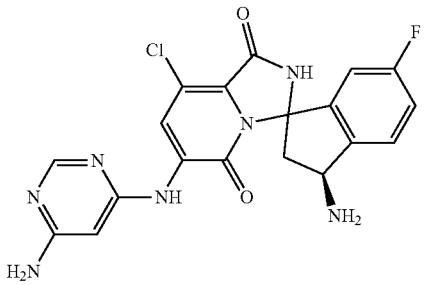 [SMILES: Nc1cc(Nc2cc(Cl)c3n(c2=O)C2(C[C@H](N)c4ccc(F)cc42)NC3=O)ncn1]

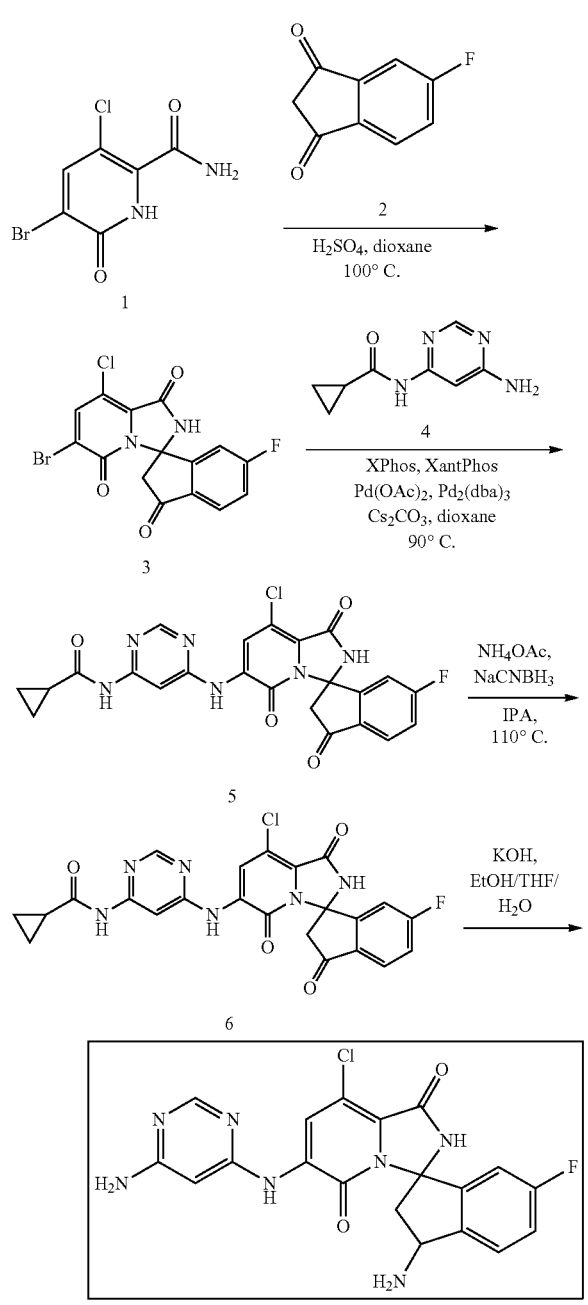

Synthesis of 6-bromo-8-chloro-6'-fluoro-2H-spiro[imidazo[1,5-a]pyridine-3, 1'-indene]-1,3',5(2'H)-trione (3)

The synthesis of intermediate 3 is carried out as described above using the general protocol of Procedure A.

Synthesis of N-(6-((8-chloro-6'-fluoro-1,3',5-trioxo-1,2',3',5-tetrahydro-2H-spiro[imidazo[1,5-a]pyridine-3,1'-inden]-6-yl)amino)pyrimidin-4-yl) cyclopropanecarboxamide (5)

The synthesis of intermediate 5 is carried out as described above using the general protocol of Procedure H.

Synthesis of N-(6-((3'-amino-8-chloro-6'-fluoro-1,5-dioxo-1,2',3',5-tetrahydro-2H-spiro[imidazo[1,5-a]pyridine-3,1'-inden]-6-yl)amino)pyrimidin-4-yl)cyclopropanecarboxamide (6)

To a solution of N-(6-((3'-amino-8-chloro-6'-fluoro-1,5-dioxo-1,2',3',5-tetrahydro-2H-spiro[imidazo[1,5-a]pyridine-3,1'-inden]-6-yl)amino)pyrimidin-4-yl)cyclopropanecarboxamide (6, 1 g, 2.02 mmol) in 2-propanol (20 mL) was added ammonium acetate (0.47 g, 6.06 mmol) and sodium cyanoborohydride (1.02 g, 16.16 mmol). The reaction was stirred at 110° C. overnight. The resulting mixture was cooled to room temperature and poured into saturated aqueous sodium bicarbonate solution. The mixture was extracted with dichloromethane. The organic layer was dried over magnesium sulfate, filtered and concentrated. The crude was purified via column chromatography to afford N-(6-((3'-amino-8-chloro-6'-fluoro-1,5-dioxo-1,2',3',5-tetrahydro-2H-spiro[imidazo[1,5-a]pyridine-3, 1'-inden]-6-yl)amino)pyrimidin-4-yl)cyclopropanecarboxamide (6).

Synthesis of 3'-amino-6-((6-aminopyrimidin-4-yl)amino)-8-chloro-6'-fluoro-2',3'-dihydro-2H-spiro[imidazo[1,5-a]pyridine-3,1'-indene]-1,5-dione (Cpd. No. 183)

The synthesis of compound 183 is carried out as described above using the general protocol of Procedure I.

Example 184

Synthesis of N-(6-((8-chloro-3-(3-chlorophenyl)-3-methyl-1,5-dioxo-1,2,3,5-tetrahydroimidazo[1,5-a]pyridin-6-yl)amino)pyrimidin-4-yl)cyanamide (Cpd. No. 184)

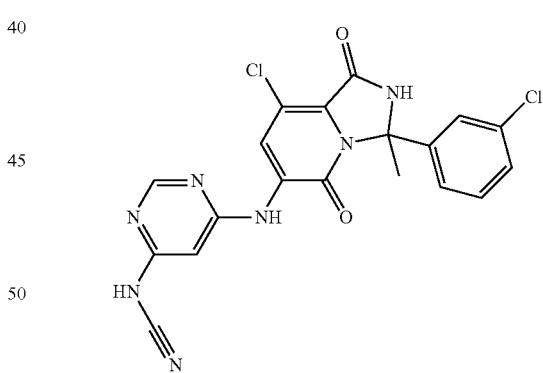

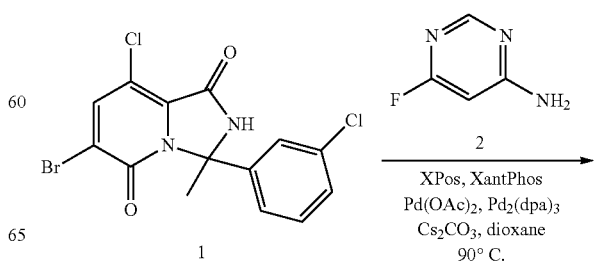

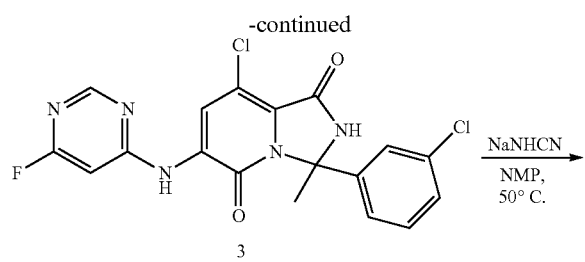

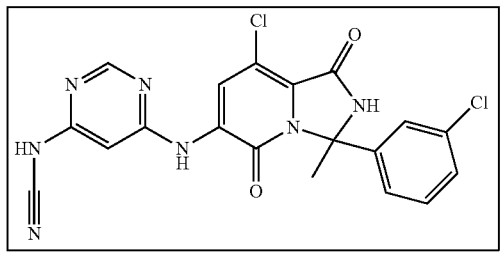

Synthesis of 8-chloro-3-(3-chlorophenyl)-6-((6-fluoropyrimidin-4-yl)amino)-3-methyl-2, 3-dihydroimidazo[1,5-a]pyridine-1,5-dione (3)

The synthesis of intermediate 3 is carried out as described above using the general protocol of Procedure H.

Synthesis of N-(6-((8-chloro-3-(3-chlorophenyl)-3-methyl-1,5-dioxo-1,2,3,5-tetrahydroimidazo[1,5-a]pyridin-6-yl)amino)pyrimidin-4-yl)cyanamide (Cpd. No. 184)

To a solution of 8-chloro-3-(3-chlorophenyl)-6-((6-fluoropyrimidin-4-yl)amino)-3-methyl-2,3-dihydroimidazo[1,5-a]pyridine-1,5-dione (3, 100 mg, 0.24 mmol) in N-methyl-2-pyrrolidinone (4 mL) was added sodium hydrogencyanamide (46 mg, 0.72 mmol). The reaction was stirred at 50° C. for 2 h. The resulting mixture was cooled to room temperature, poured into water and acidified to pH=5.5 with concentrated hydrochloric acid. The mixture was filtered. The solid crude was purified via HPLC to afford N-(6-((8-chloro-3-(3-chlorophenyl)-3-methyl-1,5-dioxo-1,2,3,5-tetrahydroimidazo[1,5-a]pyridin-6-yl)amino)pyrimidin-4-yl)cyanamide (Cpd. No. 184).

Example 185

Synthesis of 8'-chloro-6'-(pyrimidin-4-ylamino)-2'H-spiro[bicyclo[2.2.1]heptane-7,3'-imidazo[1,5-a]pyridine]-1',5'-dione (Cpd. No. 185)

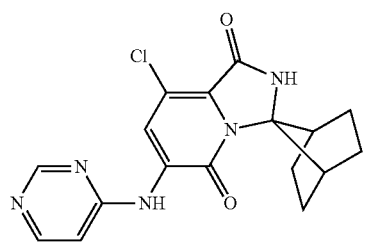 [SMILES: O=C1NC2(C3CCC2CC3)n2c1c(Cl)cc(Nc1ccncn1)c2=O]

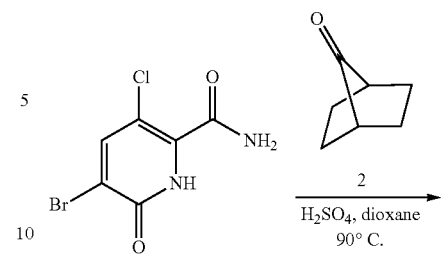

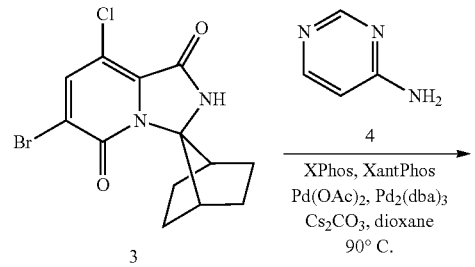

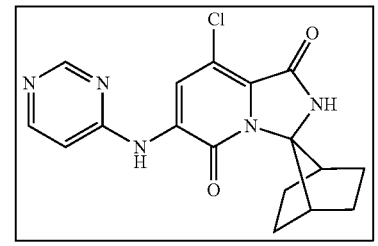

Synthesis of 6'-bromo-8'-chloro-2'H-spiro[bicyclo[2.2.1]heptane-7,3'-imidazo[1,5-a]pyridine]-1',5'-dione (3)

The synthesis of intermediate 3 is carried out as described above using the general protocol of Procedure A.

Synthesis of 8'-chloro-6'-(pyrimidin-4-ylamino)-2'H-spiro[bicyclo[2.2.1]heptane-7,3'-imidazo[1,5-a]pyridine]-1',5'-dione (Cpd. No. 185)

The synthesis of compound 185 is carried out as described above using the general protocol of Procedure H.

Example 186

Synthesis of 6'-((6-aminopyrimidin-4-yl)amino)-8'-chloro-2'H-spiro[bicyclo[2.2.1]heptane-7,3'-imidazo[1,5-a]pyridine]-1',5'-dione (Cpd. No. 186)

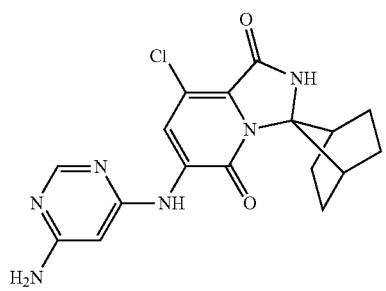 [SMILES: Nc1cc(Nc2cc(Cl)c3n(c2=O)C2(NC3=O)C3CCC2CC3)ncn1]

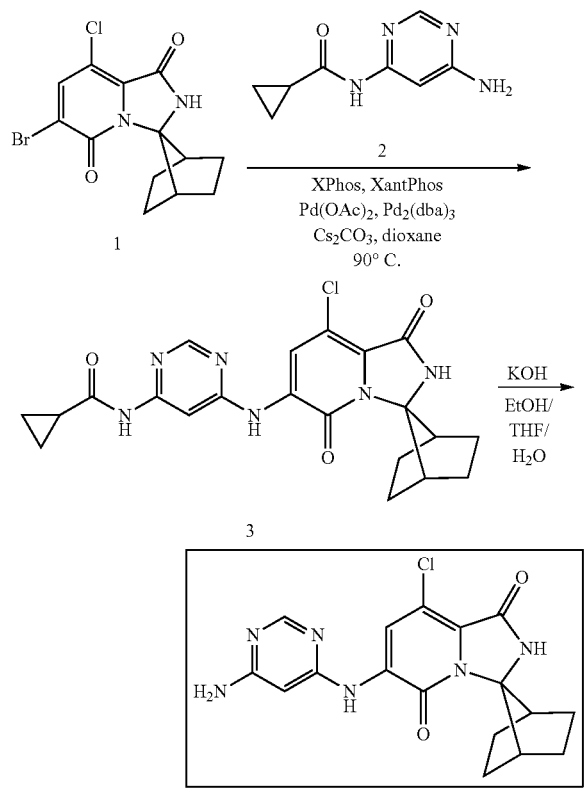

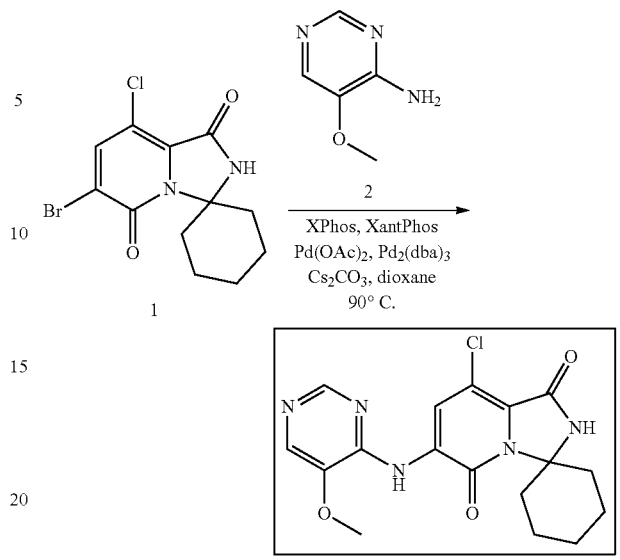

Synthesis of N-(6-((8'-chloro-1',5'-dioxo-1',5'-di-hydro-2'H-spiro[bicyclo[2.2.1]heptane-7,3'-imidazo[1,5-a]pyridin]-6'-yl)amino)pyrimidin-4-yl)cyclopropanecarboxamide (3)

The synthesis of intermediate 3 is carried out as described above using the general protocol of Procedure H.

Synthesis of 6'-((6-aminopyrimidin-4-yl)amino)-8'-chloro-2'H-spiro[bicyclo[2.2.1]heptane-7,3'-imidazo[1,5-a]pyridine]-1',5'-dione (Cpd. No. 186)

The synthesis of compound 186 is carried out as described above using the general protocol of Procedure I.

Example 187

Synthesis of 8-chloro-6-[(5-methoxypyrimidin-4-yl)amino]spiro[2H-imidazo[1,5-a]pyridine-3,1'-cyclohexane]-1,5-dione (Cpd. No. 187)

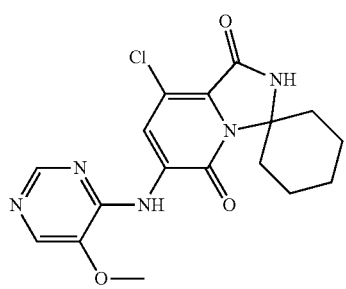 [SMILES: COc1cncnc1Nc1cc(Cl)c2n(c1=O)C1(CCCCC1)NC2=O]

Synthesis of 8-chloro-6-[(5-methoxypyrimidin-4-yl)amino]spiro[2H-imidazo[1,5-a]pyridine-3,1'-cyclohexane]-1,5-dione (Cpd. No. 187)

The synthesis of compound 187 was carried out as described above using the general protocol of Procedure H. Grey solid; Yield: 0.052 g, 17%; MS (ESI) m/z 376.31 [M+1]$^+$; $^1$H NMR (400 MHz, DMSO-d$_6$) δ 10.36 (s, 1H), 8.69 (s, 1H), 8.64 (s, 1H), 8.53 (s, 1H), 8.29 (s, 1H), 4.01 (s, 3H), 3.46-3.40 (m, 1H), 2.93-2.87 (m, 2H) 1.77-1.74 (m, 2H), 1.64-1.61 (m, 3H), 1.55-1.52 (m, 2H), 1.23 (m, 1H).

Example 188

Synthesis of 6'-((6-amino-5-ethylpyrimidin-4-yl)amino)-8'-chloro-2'H-spiro[cyclohexane-1,3'-imidazo[1,5-a]pyridine]-1',5'-dione hydrochloride (Cpd. No. 188)

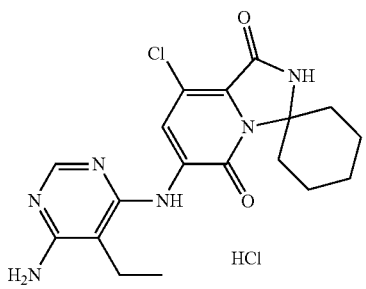 [SMILES: CCc1c(N)ncnc1Nc1cc(Cl)c2n(c1=O)C1(CCCCC1)NC2=O ; Cl]

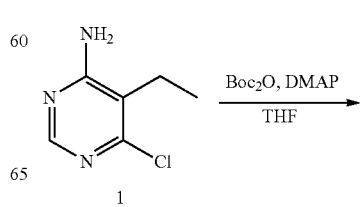

-continued

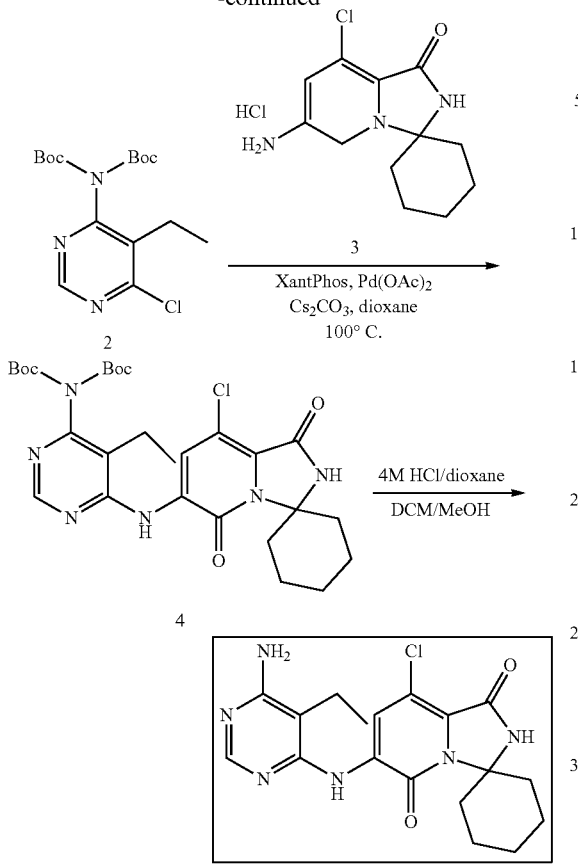

Synthesis tert-butyl N-tert-butoxycarbonyl-N-(6-chloro-5-ethyl-pyrimidin-4-yl)carbamate (2)

The synthesis of intermediate 2 was carried out as described above using the general protocol of Procedure J. Light brown solid. Yield: 3.5 g, 96%; MS (ESI) m/z 358.5 [M+1]$^+$; $^1$H NMR (400 MHz, DMSO-d$_6$) δ 8.71 (s, 1H), 2.70 (m, 3H), 1.4 (m, 18H), 1.20 (m, 3H).

Synthesis of tert-butyl N-tert-butoxycarbonyl-N-[6-[(8-chloro-1,5-dioxo-spiro[2H-imidazo[1,5-a]pyridine-3,1'-cyclohexane]-6-yl)amino]-5-ethyl-pyrimidin-4-yl]carbamate (4)

The synthesis of intermediate 4 was carried out as described above using the general protocol of Procedure B. Yellow solid. Yield: 0.48 g, 42%; MS (ESI) m/z 589.45 [M+1]$^+$; $^1$H NMR (400 MHz, DMSO-d$_6$) δ 10.40 (s, 1H), 8.75 (s, 1H), 8.71 (s, 1H), 8.54 (s, 1H), 2.94 (m, 2H), 2.59 (m, 2H), 1.74 (m, 2H), 1.65 (m, 2H), 1.57 (m, 2H), 1.14 (m, 18H), 1.25 (m, 1H), 1.22 (m, 4H).

Synthesis of 6'-((6-amino-5-ethylpyrimidin-4-yl)amino)-8'-chloro-2'H-spiro[cyclohexane-1,3'-imidazo[1,5-a]pyridine]-1',5'-dione hydrochloride (Cpd. No. 188)

The synthesis of compound 188 was carried out as described above using the general protocol of Procedure F. Yellow solid. Yield: 0.32 g, 94%; MS (ESI) m/z 389.06 [M+1]$^+$; $^1$H NMR (400 MHz, DMSO-d$_6$) δ 10.49 (s, 1H), 8.59 (s, 1H), 8.44-8.33 (m, 2H), 7.74 (brs, 2H), 2.93-2.90 (m, 2H), 2.66 (m, 2H), 1.77-1.74 (m, 3H), 1.55-1.52 (m, 2H), 1.25-1.22 (m, 1H), 1.10 (t, J=14.8 Hz, 3H).

Example 189

Synthesis of 6'-((6-amino-5-isopropylpyrimidin-4-yl)amino)-8'-chloro-2'H-spiro[cyclohexane-1,3'-imidazo[1,5-a]pyridine]-1',5'-dione (Cpd. No. 189)

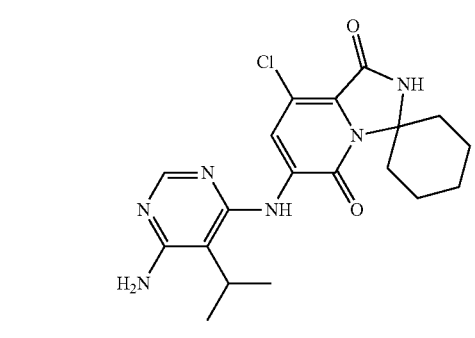 [SMILES: CC(C)c1c(N)ncnc1Nc1cc(Cl)c2n(c1=O)C1(CCCCC1)NC2=O]

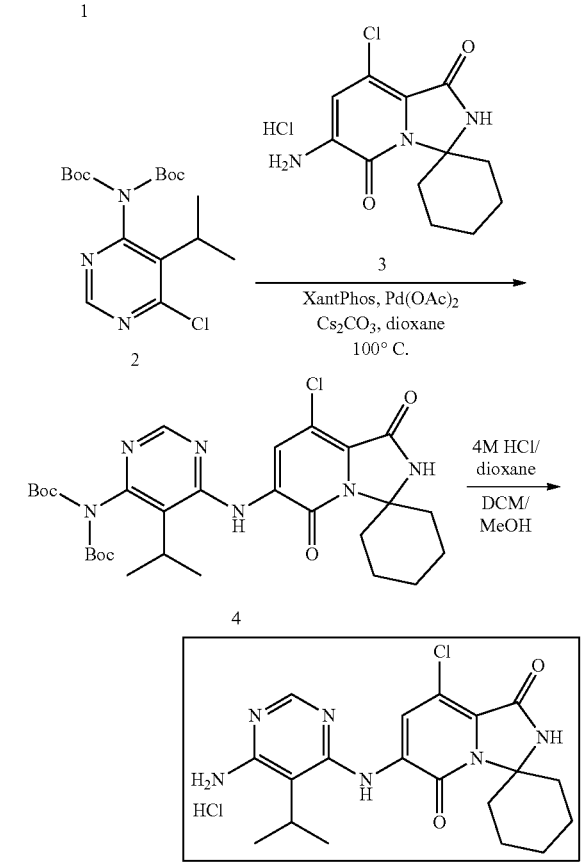

Synthesis of tert-butyl N-tert-butoxycarbonyl-N-(6-chloro-5-isopropyl-pyrimidin-4-yl)carbamate (2)

The synthesis of intermediate 2 was carried out as described above using the general protocol of Procedure J. White solid; Yield: 4.5 g, 90%; MS (ESI) m/z 372.3 [M+1]⁺; ¹H NMR (400 MHz, DMSO-d₆) δ 8.92 (s, 1H), 3.32-3.20 (m, 1H), 1.52-1.20 (m, 24H).

Synthesis of tert-butyl N-tert-butoxycarbonyl-N-[6-[(8-chloro-1,5-dioxo-spiro[2H-imidazo[1,5-a]pyridine-3,1'-cyclohexane]-6-yl)amino]-5-isopropyl-pyrimidin-4-yl]carbamate (4)

The synthesis of intermediate 4 was carried out as described above using the general protocol of Procedure B. Yellow solid; Yield: 0.41 g, 30%; MS (ESI) m/z 603.55 [M+1]⁺; ¹H NMR (400 MHz, DMSO-d₆) δ 10.40 (s, 1H), 8.75-8.72 (m, 2H), 8.67 (s, 1H), 3.32-3.19 (m, 1H), 2.94 (m, 2H), 1.74 (m, 2H), 1.65 (m, 3H), 1.57 (m, 2H), 1.14 (m, 24H), 1.20-1.00 (m, 1H).

Synthesis of 6'-((6-amino-5-isopropylpyrimidin-4-yl)amino)-8'-chloro-2'H-spiro[cyclohexane-1,3'-imidazo[1,5-a]pyridine]-1',5'-dione hydrochloride (Cpd. No. 189)

The synthesis of compound 189 was carried out as described above using the general protocol of Procedure F. Yellow solid; Yield: 0.30 g, 93%; MS (ESI) m/z 403.17 [M+1]⁺; ¹H NMR (400 MHz, DMSO-d₆) δ 10.38 (s, 1H), 9.51 (s, 1H), 8.45 (s, 2H), 7.69-7.68 (brs, 2H), 3.59-3.56 (m, 2H), 2.93-2.87 (m, 2H), 1.77-1.74 (m, 2H), 1.68-1.65 (m, 3H), 1.56 (m, 2H), 1.36 (m, 6H), 1.26 (m, 1H).

Example 190

Synthesis of 8'-chloro-6'-(7H-pyrrolo[2,3-d]pyrimidin-7-yl)-2'H-spiro[cyclohexane-1,3'-imidazo[1,5-a]pyridine]-1',5'-dione (Cpd. No. 190)

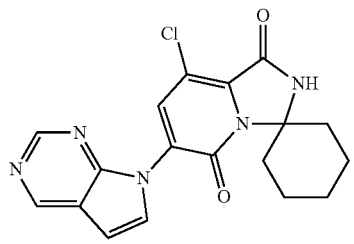 [SMILES: O=C1NC2(CCCCC2)n2c1c(Cl)cc(-n1ccc3cncnc31)c2=O]

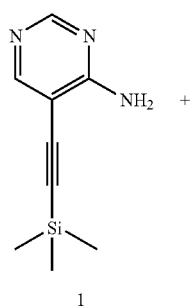

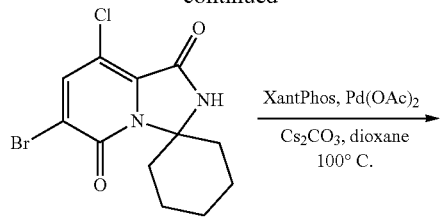

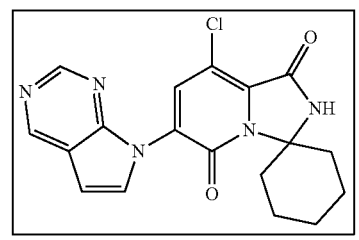

Synthesis of 8'-chloro-6'-(7H-pyrrolo[2,3-d]pyrimidin-7-yl)-2'H-spiro[cyclohexane-1,3'-imidazo[1,5-a]pyridine]-1',5'-dione (Cpd. No. 190)

The synthesis of compound 190 was carried out as described above using the general protocol of Procedure B. Yellow solid. Yield: 0.070 g, 7%; MS (ESI) m/z 370.09 [M+1]⁺; ¹H NMR (400 MHz, DMSO-d₆) δ 10.66 (s, 1H), 9.11 (s, 1H), 8.87 (s, 1H), 8.26 (s, 1H), 7.93 (d, J=3.56 Hz, 2H), 6.82 (d, J=3.56 Hz, 2H), 2.94-2.89 (m, 2H), 1.74-1.57 (m, 7H), 1.23 (m, 1H).

Example 191

Synthesis of 8'-chloro-6'-(pyrimidin-4-ylamino)-2-(trifluoromethyl)-2'H-spiro[cyclohexane-1,3'-imidazo[1,5-a]pyridine]-1',5'-dione (Cpd. No. 191)

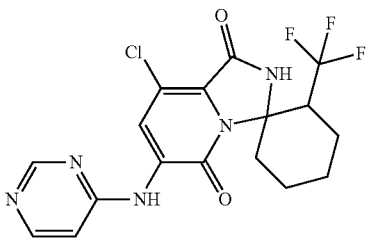 [SMILES: O=C1NC2(CCCCC2C(F)(F)F)n2c1c(Cl)cc(Nc1ccncn1)c2=O]

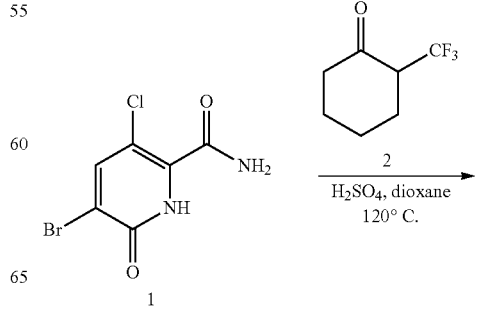

-continued

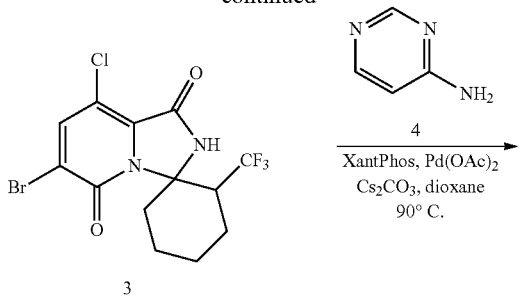

3

Synthesis of 6'-bromo-8'-chloro-2-(trifluoromethyl)-2'H-spiro[cyclohexane-1,3'-imidazo[1,5-a]pyridine]-1',5'-dione (3)

The synthesis of intermediate 3 was carried out as described above using the general protocol of Procedure A. Off white solid; Yield: 0.40 g, 43%; MS (ESI) m/z 400.59 [M+1]+.

Synthesis of 8'-chloro-6'-(pyrimidin-4-ylamino)-2-(trifluoromethyl)-2'H-spiro[cyclohexane-1,3'-imidazo[1,5-a]pyridine]-1',5'-dione (Cpd. No. 191)

The synthesis of compound 191 was carried out as described above using the general protocol of Procedure B. White solid; Yield: 0.030 g, 8%; MS (ESI) m/z 346.80 [M+1]+; $^1$H NMR (400 MHz, DMSO-$d_6$) δ 10.53 (s, 1H), 9.66 (s, 1H), 8.84 (d, J=9.6 Hz, 2H), 8.45 (d, J=5.92 Hz, 1H), 7.44 (d, J=4.8 Hz, 1H), 4.03 (m, 1H), 2.88 (m, 1H), 2.04 (m, 1H), 1.80 (m, 3H), 1.67 (m, 1H), 1.41 (s, 1H).

Example 192

Synthesis of 8-chloro-3-methyl-3-(2-methylprop-1-enyl)-6-(pyrimidin-4-ylamino)-2H-imidazo[1,5-a]pyridine-1,5-dione (Cpd. No. 192)

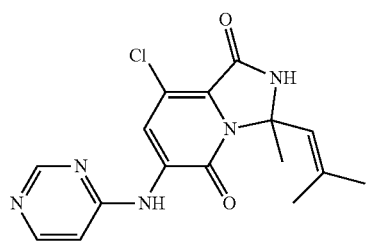 [SMILES: CC(C)=CC1(C)NC(=O)c2c(Cl)cc(Nc3ccncn3)c(=O)n21]

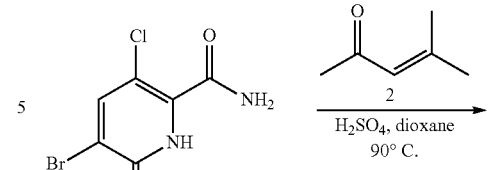

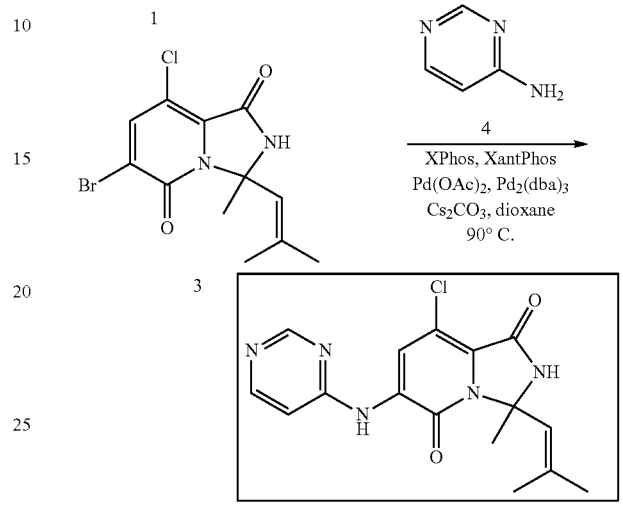

Synthesis of 6-bromo-8-chloro-3-methyl-3-(2-methylprop-1-enyl)-2H-imidazo[1,5-a]pyridine-1,5-dione (3)

The synthesis of intermediate 3 was carried out as described above using the general protocol of Procedure A. Light brown thick liquid. Yield: 1.5 g, 28%; MS (ESI) m/z 329 [M−1]−.

Synthesis of 8-chloro-3-methyl-3-(2-methylprop-1-enyl)-6-(pyrimidin-4-ylamino)-2H-imidazo[1,5-a]pyridine-1,5-dione (Cpd. No. 192)

The synthesis of compound 192 was carried out as described above using the general protocol of Procedure H. White solid; Yield: 65 mg, 31%; MS (ESI) m/z 360.80 [M+1]+; $^1$H NMR (400 MHz, DMSO-$d_6$) δ 10.32 (s, 1H), 9.62 (s, 1H), 8.43 (d, J=5.6 Hz, 1H), 7.47 (d, J=4.8 Hz, 1H), 3.25-3.17 (m, 2H), 280-2.78 (m, 2H), 2.39-2.33 (m, 2H), 2.24 (s, 3H), 1.50-1.47 (m, 2H).

Example 193

Synthesis of 6'-((6-amino-5-methylpyrimidin-4-yl)amino)-8'-chloro-2'H-spiro[cyclohexane-1,3'-imidazo[1,5-a]pyridine]-1',5'-dione hydrochloride (Cpd. No. 193)

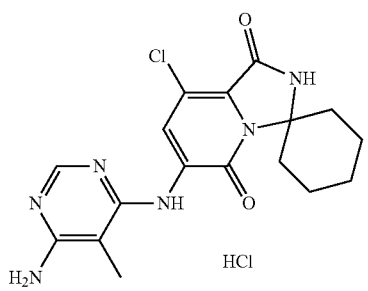 [SMILES: Cc1c(N)ncnc1Nc1cc(Cl)c2n(c1=O)C1(CCCCC1)NC2=O ; Cl]

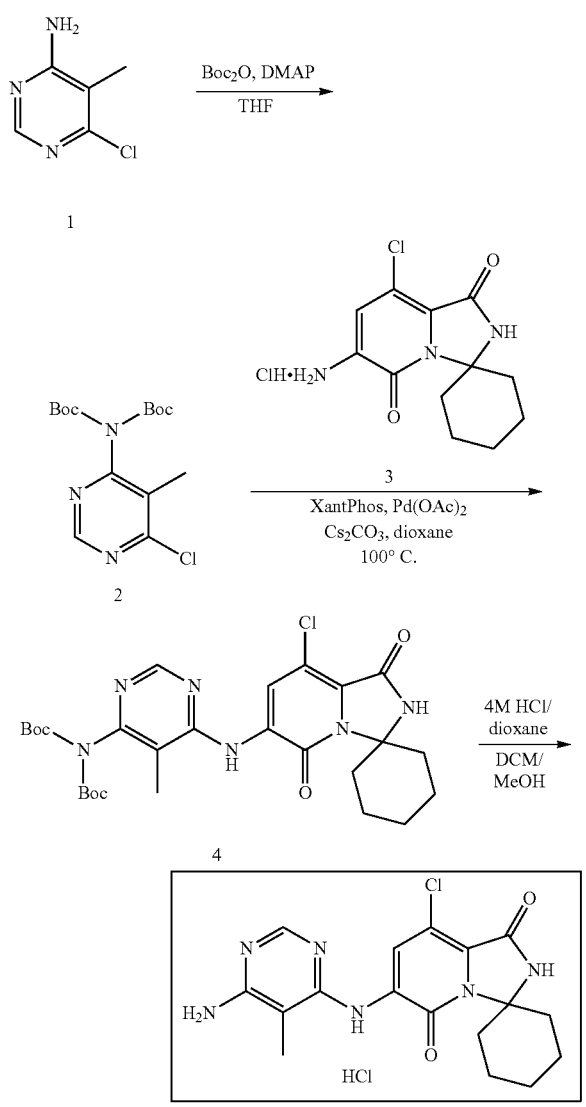

Synthesis of tert-butyl N-tert-butoxycarbonyl-N-(6-chloro-5-methyl-pyrimidin-4-yl)carbamate (2)

The synthesis of intermediate 2 was carried out as described above using the general protocol of Procedure J. White solid; Yield: 1.1 g, 94%; MS (ESI) m/z 344.27 [M+1]$^+$; $^1$H NMR (400 MHz, DMSO-d$_6$) δ 8.90 (s, 1H), 2.22 (s, 1H), 1.38 (s, 18H).

Synthesis of tert-butyl N-tert-butoxycarbonyl-N-[6-[(8-chloro-1,5-dioxo-spiro[2H-imidazo[1,5-a]pyridine-3,1'-cyclohexan e]-6-yl)amino]-5-methyl-pyrimidin-4-yl]carbamate (4)

The synthesis of intermediate 4 was carried out as described above using the general protocol of Procedure B. Yellow solid; Yield: 0.20 g, 35%; MS (ESI) m/z 575.32 [M+1]$^+$; $^1$H NMR (400 MHz, DMSO-d$_6$) δ 10.41 (s, 1H), 8.73 (s, 2H), 8.46 (s, 1H), 2.14 (s, 3H), 1.77-1.66 (m, 7H), 1.46 (m, 18H), 1.20 (m, 1H).

Synthesis of 6'-((6-amino-5-methylpyrimidin-4-yl)amino)-8'-chloro-2'H-spiro[cyclohexane-1,3'-imidazo[1,5-a]pyridine]-1',5'-dione hydrochloride (Cpd. No. 193)

The synthesis of compound 193 was carried out as described above using the general protocol of Procedure F. Yellow solid; Yield: 0.11 g, 80%; MS (ESI) m/z 375.26 [M+1]$^+$; $^1$H NMR (400 MHz, DMSO-d$_6$) δ 10.41 (s, 1H), 8.47 (s, 2H), 8.40 (s, 1H), 7.79 (brs, 2H), 2.93-2.87 (m, 1H), 2.07 (s, 1H), 1.77-1.74 (m, 2H), 1.65-1.56 (m, 3H), 1.56-1.53 (m, 2H), 1.09 (m, 1H).

Example 194

Synthesis of 8'-chloro-6'-((5-ethylpyrimidin-4-yl)amino)-2'H-spiro[cyclohexane-1,3'-imidazo[1,5-a]pyridine]-1',5'-dione (Cpd. No. 194)

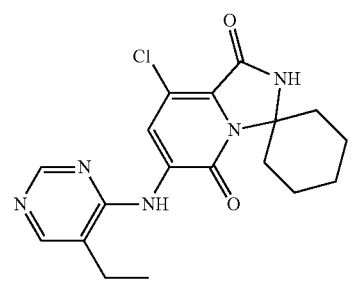 [SMILES: CCc1cncnc1Nc1cc(Cl)c2n(c1=O)C1(CCCCC1)NC2=O]

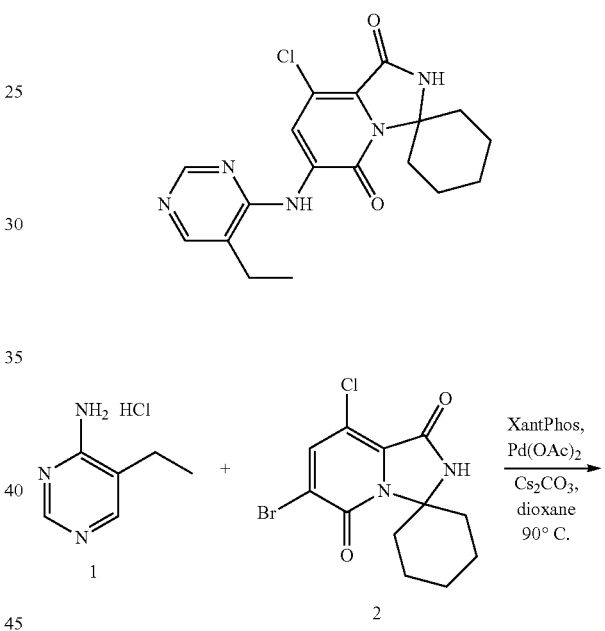

Synthesis of 8'-chloro-6'-((5-ethylpyrimidin-4-yl)amino)-2'H-spiro[cyclohexane-1,3'-imidazo[1,5-a]pyridine]-1',5'-dione (Cpd. No. 194)

The synthesis of compound 194 was carried out as described above using the general protocol of Procedure B. Yellow solid; Yield: 0.026 g, 22%; MS (ESI) m/z 374.21 [M+1]$^+$; $^1$H NMR (400 MHz, DMSO-d$_6$) δ 10.37 (s, 1H), 8.78 (s, 1H), 8.72 (s, 1H), 8.39 (s, 1H), 8.34 (s, 1H), 2.95-2.89 (m, 2H), 2.70-2.64 (m, 2H), 1.77-1.74 (m, 2H), 1.69-1.65 (m, 3H), 1.57-1.54 (m, 2H), 1.26 (m, 4H).

Example 195

Synthesis of 6'-((6-amino-5-methoxypyrimidin-4-yl)amino)-8'-chloro-2'H-spiro[cyclohexane-1,3'-imidazo[1,5-a]pyridine]-1',5'-dione hydrochloride (Cpd. No. 195)

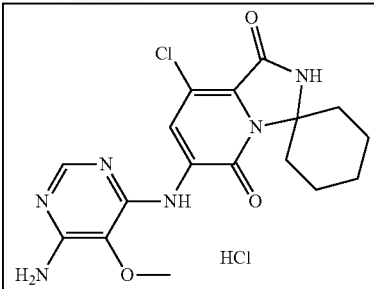

Synthesis of tert-butyl N-tert-butoxycarbonyl-N-(6-chloro-5-methoxy-pyrimidin-4-yl)carbamate (2)

The synthesis of intermediate 2 was carried out as described above using the general protocol of Procedure J. Off white solid; Yield: 092 g, 59%; MS (ESI) m/z 360.12 [M+1]$^+$; $^1$H NMR (400 MHz; DMSO-d$_6$) δ 1.44 (s, 18H), 3.92 (s, 3H), 8.64 (s, 1H).

Synthesis of tert-butyl N-tert-butoxycarbonyl-N-[6-[(8-chloro-1,5-dioxo-spiro[2H-imidazo[1,5-a]pyridine-3,1'-cyclohexane]-6-yl)amino]-5-methoxy-pyrimidin-4-yl]carbamate (4)

The synthesis of intermediate 4 was carried out as described above using the general protocol of Procedure B. Yellow solid; Yield: 0.14 g; 23%; MS (ESI) m/z 591.23 [M+1]$^+$; $^1$H NMR (400 MHz, DMSO-d$_6$) δ 10.40 (s, 1H), 8.78 (s, 1H), 8.67 (s, 1H), 8.6 (s, 1H), 3.87 (s, 3H), 2.92 (m, 2H), 1.81-1.54 (m, 7H), 1.40 (s, 18H), 1.23 (m, 1H)

Synthesis of 6'-((6-amino-5-methoxypyrimidin-4-yl)amino)-8'-chloro-2'H-spiro[cyclohexane-1,3'-imidazo[1,5-a]pyridine]-1',5'-dione hydrochloride (Cpd. No. 195)

The synthesis of compound 195 was carried out as described above using the general protocol of Procedure F. Off white solid; Yield: 0.075 g, 80%; MS (ESI) m/z 391.12 [M+1]$^+$; $^1$H NMR (400 MHz, DMSO-d$_6$) δ 10.35 (s, 1H), 8.53 (s, 1H), 8.48 (s, 1H), 8.19 (s, 1H), 7.33 (brs, 2H), 3.74 (s, 3H), 2.91 (m, 2H), 1.76-1.52 (m, 7H), 1.26 (m, 1H).

Example 196

Synthesis of 8'-chloro-6'-((5-ethoxypyrimidin-4-yl)amino)-2'H-spiro[cyclohexane-1,3'-imidazo[1,5-a]pyridine]-1',5'-dione (Cpd. No. 196)

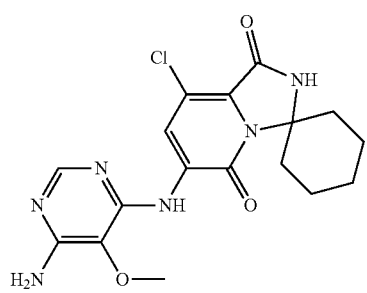 [SMILES: COc1c(N)ncnc1Nc1cc(Cl)c2n(c1=O)C1(CCCCC1)NC2=O]

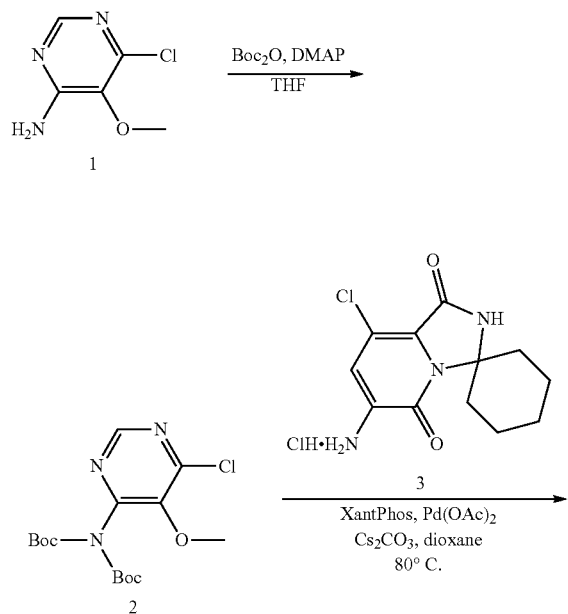

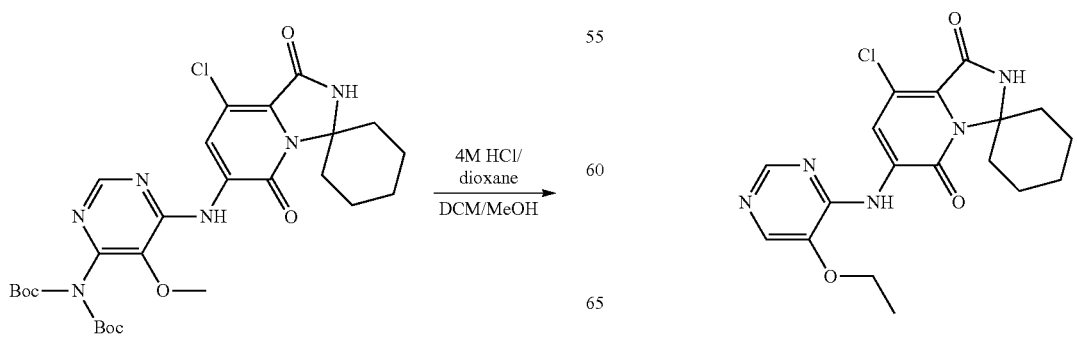

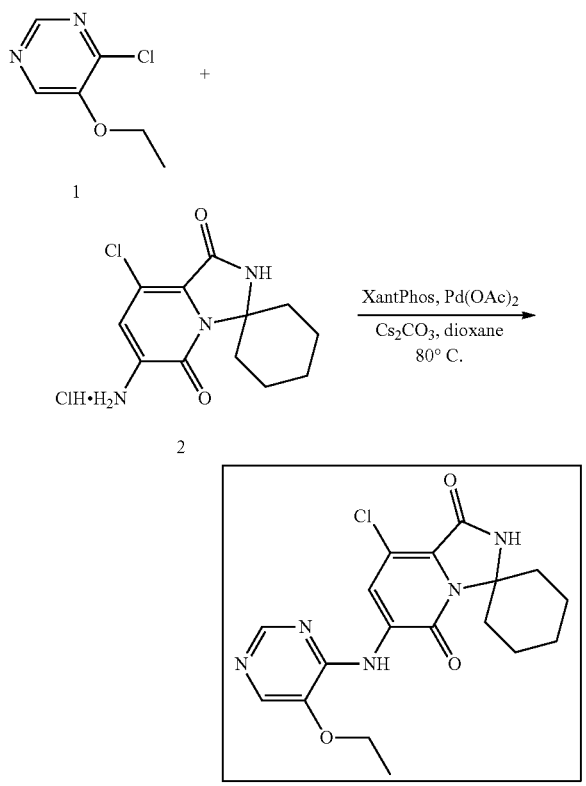

Synthesis of 8'-chloro-6'-((5-ethoxypyrimidin-4-yl)amino)-2'H-spiro[cyclohexane-1,3'-imidazo[1,5-a]pyridine]-1',5'-dione (Cpd. No. 196)

The synthesis of compound 196 was carried out as described above using the general protocol of Procedure B. Yellow solid; Yield: 0.055 g, 20%; MS (ESI) m/z 390.13 [M+1]$^+$; $^1$H NMR (400 MHz, DMSO-d$_6$) δ 10.42 (s, 1H), 8.82 (s, 1H), 8.75 (s, 1H), 8.62 (s, 1H), 8.33 (s, 1H), 4.30 (q, J=6.96 Hz, 2H), 2.90 (m, 2H), 1.74-1.53 (m, 7H), 1.43 (t, J=6.96 Hz, 3H), 1.25 (m, 1H).

Example 197

Synthesis of 8'-chloro-6'-((5-isopropoxypyrimidin-4-yl)amino)-2'H-spiro[cyclohexane-1,3'-imidazo[1,5-a]pyridine]-1',5'-dione (Cpd. No. 197)

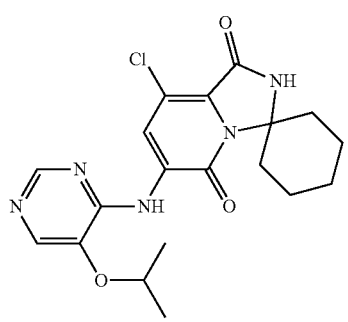 [SMILES: CC(C)Oc1cncnc1Nc1cc(Cl)c2n(c1=O)C1(CCCCC1)NC2=O]

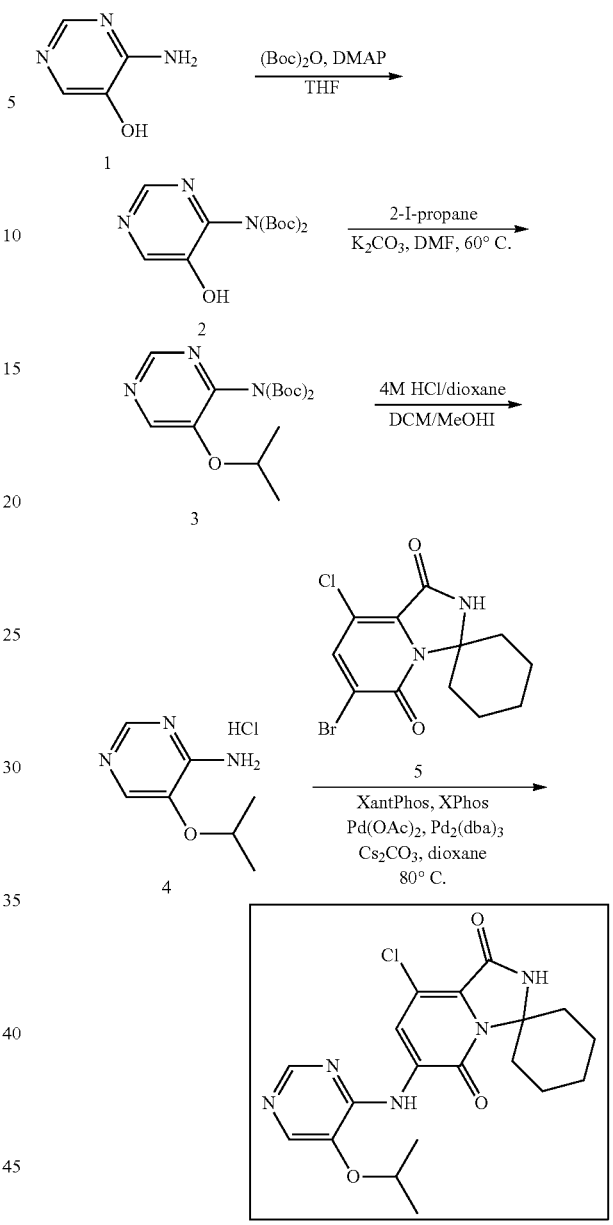

Synthesis of N,N-di-boc-4-aminopyrimidin-5-ol (2)

The synthesis of intermediate 2 was carried out as described above using the general protocol of Procedure J. Brown solid; Yield: 1.2 g, 86%; MS (ESI) m/z 312.15 [M+1]$^+$; $^1$H NMR (400 MHz; CDCl$_3$) δ 8.96 (s, 1H), 8.76 (s, 1H), 1.42 (s, 18H).

Synthesis of N,N-di-boc-5-isopropoxypyrimidin-4-amine (3)

To a solution of N,N-di-boc-4-aminopyrimidin-5-ol (2, 1.0 g, 3.21 mmol) in dimethylformamide (15 mL), potassium carbonate (1.11 g, 8.03 mmol) was added followed by addition of 2-iodo propane (1.64 g, 9.64 mmol). The reaction mixture was stirred at 60° C. for 3 h. The reaction mixture was cooled, diluted with ethyl acetate (50 mL) and washed with cold water (3×20 mL) and brine, dried over sodium sulfate and concentrated under reduced pressure to afford N,N-diboc-5-isopropoxypyrimidin-4-amine (3) as white solid. Yield: 1.1 g, 97%; MS (ESI) m/z 354.20 [M+1]+; ¹H NMR (400 MHz, DMSO-d₆) δ 8.75 (s, 1H), 8.70 (s, 1H), 4.89 (m, 1H), 1.37 (s, 18H), 1.27 (d, J=6.0 Hz, 6H).

Synthesis of 5-isopropoxypyrimidin-4-amine hydrochloride (4)

The synthesis of intermediate 4 was carried out as described above using the general protocol of Procedure F. Off white solid; Yield: 0.55 g, 93%; MS (ESI) m/z 154.09 [M+1]+; ¹H NMR (400 MHz, DMSO-d₆) δ 14.32 (brs, 1H), 9.10-8.60 (m, 2H), 8.48 (s, 1H), 8.31 (brs, 1H), 8.06 (s, 1H), 4.72 (m, 1H), 1.32 (d, J=6.0 Hz, 6H)

Synthesis of 8'-chloro-6'-((5-isopropoxypyrimidin-4-yl)amino)-2'H-spiro[cyclohexane-1,3'-imidazo[1,5-a]pyridine]-1',5'-dione (Cpd. No. 197)

The synthesis of compound 197 was carried out as described above using the general protocol of Procedure H. Yellow solid; Yield: 0.22 g, 61%; MS (ESI) m/z 404.14 [M+1]+; ¹H NMR (400 MHz, DMSO-d₆) δ 10.4 (s, 1H), 8.71 (s, 2H), 8.56 (s, 1H), 8.34 (s, 1H), 4.87 (m, 1H), 2.92 (m, 2H), 1.77-1.53 (m, 7H), 1.37 (d, J=6.0 Hz, 6H), 1.23 (m, 1H).

Example 198

Synthesis of 8'-chloro-2'-cyclopentyl-6'-(pyrimidin-4-ylamino)-2'H-spiro[cyclohexane-1,3'-imidazo[1,5-a]pyridine]-1',5'-dione (Cpd. No. 198)

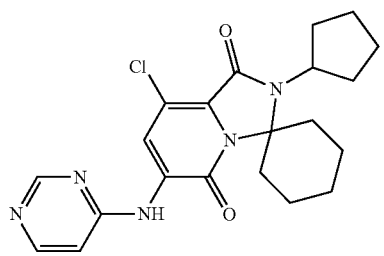 [SMILES: O=C1c2c(Cl)cc(Nc3ccncn3)c(=O)n2C2(CCCCC2)N1C1CCCC1]

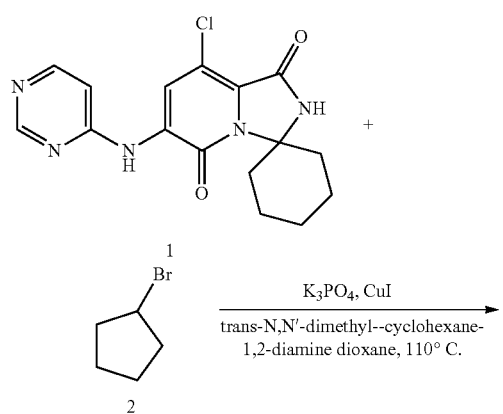

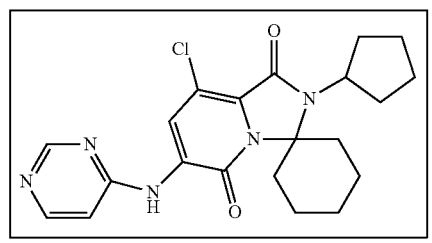

Synthesis of 8'-chloro-2'-cyclopentyl-6'-(pyrimidin-4-ylamino)-2'H-spiro[cyclohexane-1,3'-imidazo[1,5-a]pyridine]-1',5'-dione (Cpd. No. 198)

In a vial 8'-chloro-6'-(pyrimidin-4-ylamino)-2'H-spiro [cyclohexane-1,3'-imidazo[1,5-a]pyridine]-1',5'-dione (0.5 g, 1.44 mmol), bromocyclopentane (0.26 g, 1.73 mmol) and potassium phosphate (0.49 g, 3.62 mmol) were taken in 1,4-dioxane (10 mL). The reaction mixture was purged with argon for 10 min and copper(I) iodide (0.027 g, 0.14 mmol), trans-N,N'-dimethylcyclohexane-1,2-diamine (0.041 g, 0.14 mmol) were added and purging was continued for another 10 min. The reaction was sealed and heated at 110° C. for 24 h. After completion, the reaction was diluted with 5% methanol in dichloromethane (300 mL) and filtered through a celite bed. The filtrate was concentrated. The crude compound was purified by column chromatography using neutral alumina and the compound was eluted with dichloromethane. The solvent was removed under reduced pressure to get solid which was dried under high vacuum to afford 8'-chloro-2'-cyclopentyl-6'-(pyrimidin-4-ylamino)-2'H-spiro[cyclohexane-1,3'-imidazo[1,5-a]pyridine]-1',5'-dione (Cpd. No. 198) as an off white solid. Yield: 0.035 g, 6%; MS (ESI) m/z 414.14 [M+1]+; ¹H NMR (400 MHz, DMSO-d₆) δ 9.50 (s, 1H), 8.81 (s, 1H), 8.77 (s, 1H), 8.40 (d, J=5.84 Hz, 1H), 7.41 (d, J=5.32 Hz, 1H), 5.33 (s, 1H), 2.93 (m, 2H), 1.92 (m, 12H), 1.62 (m, 2H), 1.37 (m, 2H).

Example 199

Synthesis of 6'-((6-aminopyrimidin-4-yl)amino)-8'-methyl-5'-thioxo-2'H-spiro[cyclopentane-1,3'-imidazo[1,5-a]pyridin]-1'(5'H)-one (Cpd. No. 199)

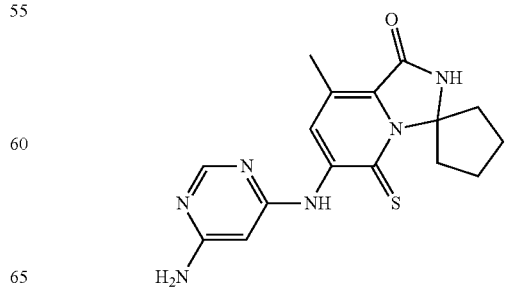

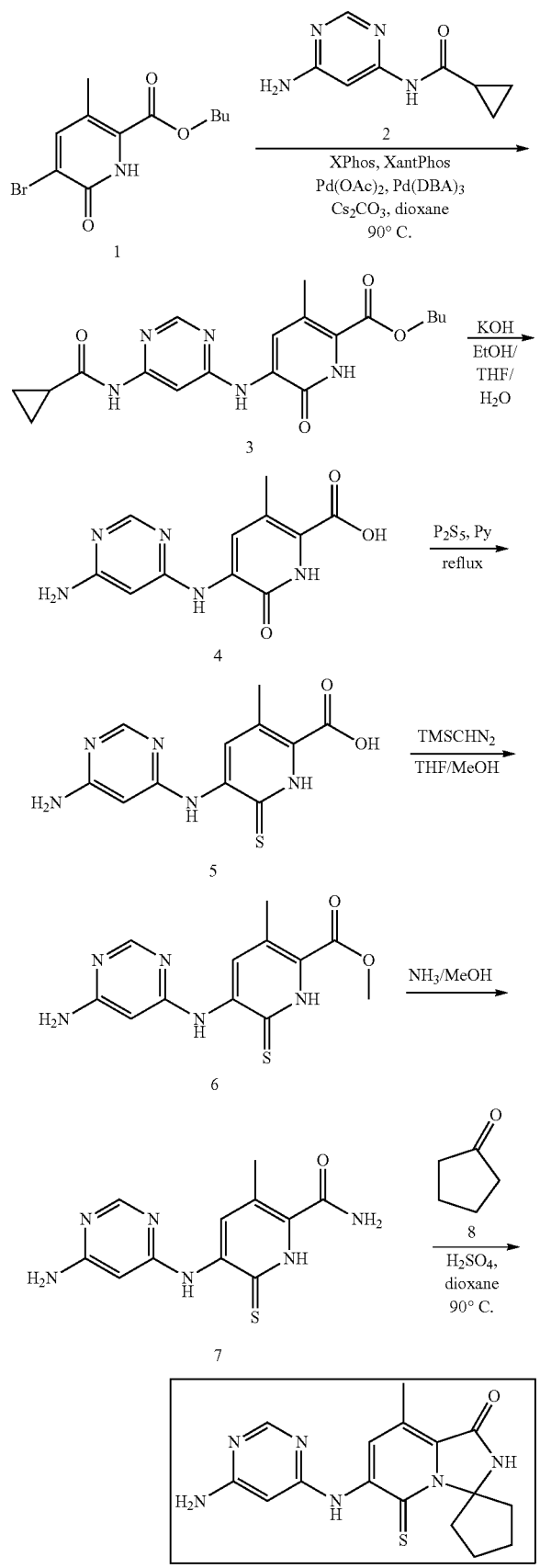

Synthesis of n-butyl 5-((6-(cyclopropanecarbox-amido)pyrimidin-4-yl)amino)-3-methyl-6-oxo-1, 6-dihydropyridine-2-carboxylate (3)

The synthesis of intermediate 3 is carried out as described above using the general protocol of Procedure H.

Synthesis of 5-((6-aminopyrimidin-4-yl)amino)-3-methyl-6-oxo-1, 6-dihydropyridine-2-carboxylic acid (4)

The synthesis of intermediate 3 is carried out as described above using the general protocol of Procedure I.

Synthesis of 5-((6-aminopyrimidin-4-yl)amino)-3-methyl-6-thioxo-1, 6-dihydropyridine-2-carboxylic acid (5)

To a solution of 5-((6-aminopyrimidin-4-yl)amino)-3-methyl-6-oxo-1,6-dihydropyridine-2-carboxylic acid (4, 0.5 g, 1.91 mmol) in pyridine (10 mL) is added phosphorus pentasulfide (1.27 g, 5.73 mmol). The reaction is refluxed overnight. The resulting mixture is cooled to room temperature and concentrated. The crude is purified via column chromatography to afford 5-((6-aminopyrimidin-4-yl)amino)-3-methyl-6-thioxo-1,6-dihydropyridine-2-carboxylic acid (5).

Synthesis of methyl 5-((6-aminopyrimidin-4-yl) amino)-3-methyl-6-thioxo-1, 6-dihydropyridine-2-carboxylate (6)

To a solution of 5-((6-aminopyrimidin-4-yl)amino)-3-methyl-6-thioxo-1,6-dihydropyridine-2-carboxylic acid (5, 0.5 g, 1.72 mmol) in tetrahydrofuran (10 mL) and methanol is added (trimethylsilyl)diazomethane (2 M in hexanes, 1.29 mL, 2.58 mmol). The reaction is stirred at room temperature for 1 h. The resulting mixture is concentrated and purified via column chromatography to afford methyl 5-((6-aminopyrimidin-4-yl)amino)-3-methyl-6-thioxo-1,6-dihydropyridine-2-carboxylate (6).

Synthesis of 5-((6-aminopyrimidin-4-yl)amino)-3-methyl-6-thioxo-1, 6-dihydropyridine-2-carboxamide (7)

The synthesis of intermediate 7 is carried out as described above using the general protocol of Procedure K.

Synthesis of 6'-((6-aminopyrimidin-4-yl)amino)-8'-methyl-5'-thioxo-2'H-spiro[cyclopentane-1,3'-imidazo[1,5-a]pyridin]-1'(5'H)-one (Cpd. No. 199)

The synthesis of compound 199 is carried out as described above using the general protocol of Procedure A.

Example 200

Synthesis of 6'-((6-aminopyrimidin-4-yl)(methyl)amino)-8'-chloro-2'H-spiro[cyclopentane-1,3'-imidazo[1,5-a]pyridine]-1',5'-dione (Cpd. No. 200)

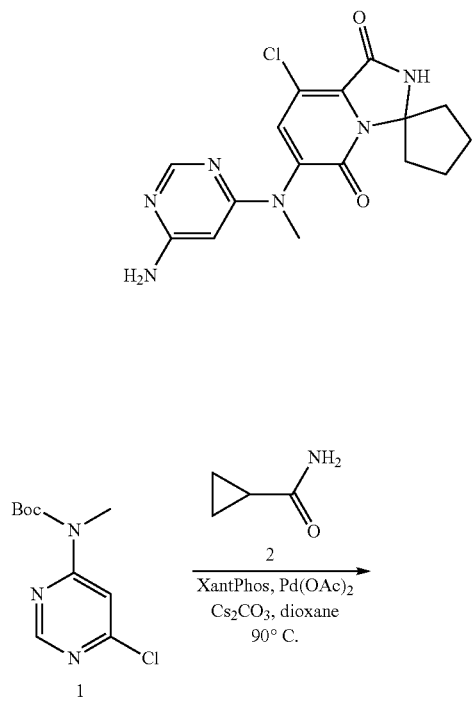

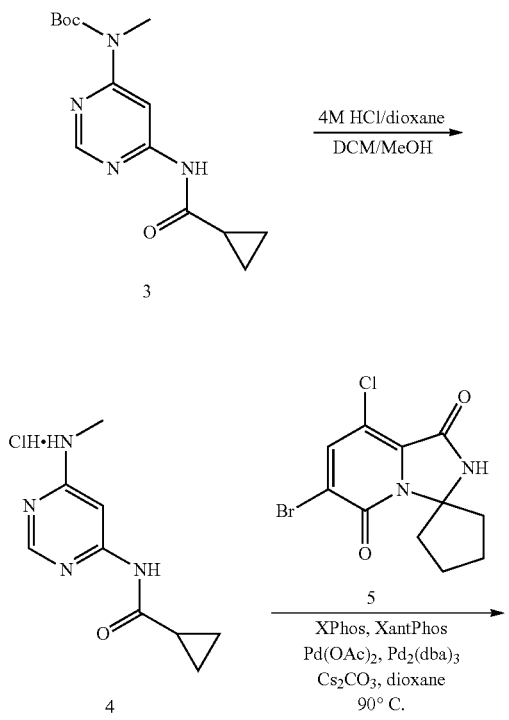

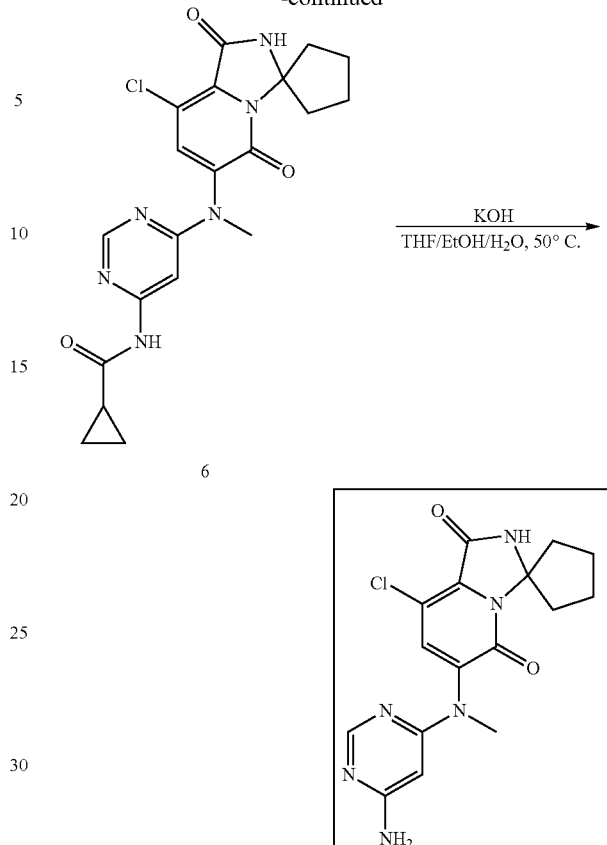

Synthesis of tert-butyl (6-(cyclopropanecarboxamido)pyrimidin-4-yl)(methyl)carbamate (3)

The synthesis of intermediate 3 was carried out as described above using the general protocol of Procedure B. Yellow solid; Yield: 2.5 g, 80%; MS (ESI) m/z 293.51 [M+1]$^+$; $^1$H NMR (400 MHz, DMSO-$d_6$) δ 11.06 (s, 1H), 8.63 (s, 1H), 8.59 (s, 1H), 2.05-1.99 (m, 1H), 1.49 (s, 9H), 0.85-0.83 (m, 4H).

Synthesis of N-(6-(methylamino)pyrimidin-4-yl)cyclopropanecarboxamide hydrochloride (4)

The synthesis of intermediate 4 was carried out as described above using the general protocol of Procedure F. White solid; Yield: 1.4 g, 90%; MS (ESI) m/z 193.30 [M+1]$^+$; $^1$H NMR (400 MHz, DMSO-$d_6$) δ 11.87 (brs, 1H), 9.10 (brs, 1H), 8.45 (s, 1H), 7.05 (brs, 1H), 2.91 (s, 3H), 2.01 (m, 1H), 0.93-0.89 (m, 4H).

Synthesis of N-(6-((8'-chloro-1',5'-dioxo-1',5'-dihydro-2'H-spiro[cyclopentane-1, 3'-imidazo[1,5-a]pyridin]-6'-yl)(methyl)amino)pyrimidin-4-yl)cyclopropanecarboxamide (6)

The synthesis of intermediate 6 was carried out as described above using the general protocol of Procedure H. Yellow solid; Yield: 120 mg, 18%; MS (ESI) m/z 427.01 [M−1]$^−$.

315

Synthesis of 6'-((6-aminopyrimidin-4-yl)(methyl)amino)-8'-chloro-2'H-spiro[cyclopentane-1,3'-imidazo[1,5-a]pyridine]-1',5'-dione (Cpd. No. 200)

The synthesis of compound 200 was carried out as described above using the general protocol of Procedure I. Light brown solid; Yield: 27 mg, 32%; MS (ESI) m/z 361.12 [M+1]$^+$; $^1$H NMR (400 MHz, DMSO-d$_6$) δ 10.46 (s, 1H), 8.29 (s, 1H), 8.04 (s, 1H), 7.59 (brs, 2H), 5.72 (s, 1H), 3.27 (s, 3H), 2.76-2.69 (m, 2H), 1.91-1.84 (m, 2H), 1.82-1.79 (m, 2H), 1.74-1.69 (m, 2H).

Example 201

Synthesis of 6'-(pyrimidin-4-ylamino)-8'-(tetrahydro-2H-pyran-4-yl)-2'H-spiro[cyclohexane-1,3'-imidazo[1,5-a]pyridine]-1',5'-dione (Cpd. No. 201)

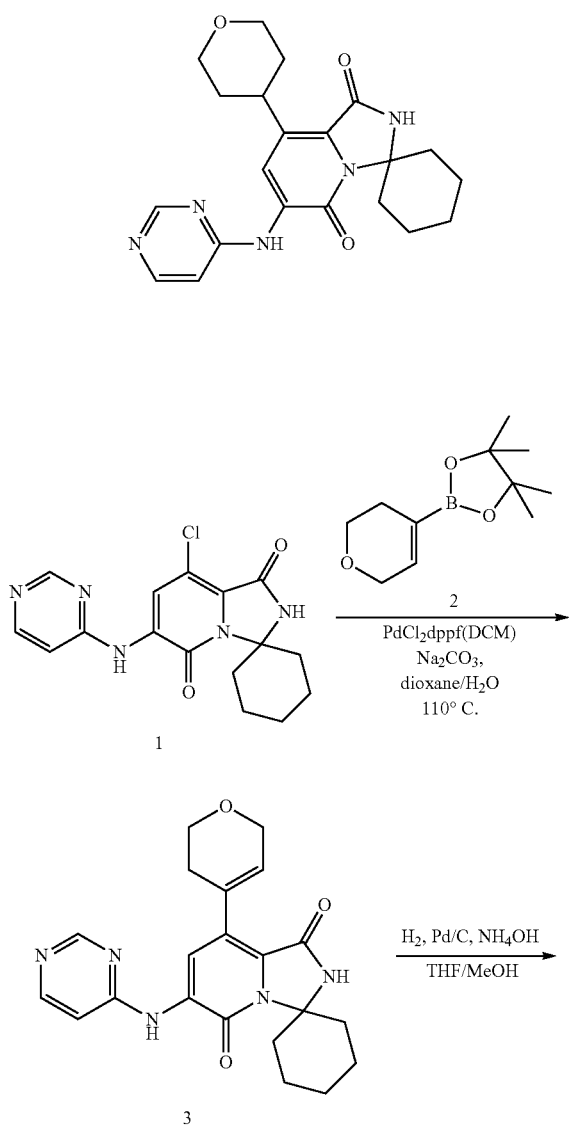

316

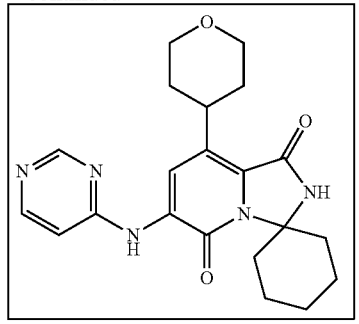

Synthesis of 8'-(3, 6-dihydro-2H-pyran-4-yl)-6'-(pyrimidin-4-ylamino)-2'H-spiro[cyclohexane-1,3'-imidazo[1,5-a]pyridine]-1',5'-dione (3)

A vial was charged with 8'-chloro-6'-(pyrimidin-4-ylamino)-2'H-spiro[cyclohexane-1,3'-imidazo[1,5-a]pyridine]-1',5'-dione (1, 0.50 g, 1.44 mmol) and 2-(3,6-dihydro-2H-pyran-4-yl)-4,4,5,5-tetramethyl-1,3,2-dioxaborolane (2, 0.36 g, 1.73 mmol) in 1,4-dioxane (10 mL). Sodium carbonate (0.46 g, 4.33 mmol) was added followed by water (1.44 mL) and purged the mixture with argon for 10 min. [1,1'-bis(diphenylphosphino)ferrocene]dichloropalladium (II), complex with dichloromethane (0.1 g, 0.144 mmol) was then added and purging was continued for 5 more min. The reaction was sealed and heated at 110° C. for 16 h. After completion of reaction by TLC and LCMS. Water (100 mL) was added and extracted with 10% methanol in dichloromethane (3×150 mL). The organics were washed with brine (1×100 mL). The organics were then separated and dried (sodium sulfate) before concentration to dryness. The crude was then purified by flash column chromatography eluting with 2-3% methanol in dichloromethane. The desired fractions were concentrated to dryness under vacuum to afford 8'-(3,6-dihydro-2H-pyran-4-yl)-6'-(pyrimidin-4-ylamino)-2'H-spiro[cyclohexane-1,3'-imidazo[1,5-a]pyridine]-1',5'-dione (3) as an off white solid. Yield: 0.35 g, 61%; MS (ESI) m/z 394 [M+1]$^+$; $^1$H NMR (400 MHz, DMSO-d$_6$) δ 10.24 (s, 1H), 9.41 (s, 1H), 8.78 (s, 1H), 8.61 (s, 1H), 8.43 (d, J=6.08 Hz, 1H), 7.44 (d, J=5.72 Hz, 1H), 5.75 (s, 1H), 4.18 (s, 2H), 3.79 (s, 2H), 3.05 (m, 2H), 2.45 (m, 2H), 1.84 (m, 6H), 1.56 (s, 2H).

Synthesis of 6'-(pyrimidin-4-ylamino)-8'-(tetrahydro-2H-pyran-4-yl)-2'H-spiro[cyclohexane-1,3'-imidazo[1,5-a]pyridine]-1',5'-dione (Cpd. No. 201)

A double neck round bottom flask was charged with 8'-(3,6-dihydro-2H-pyran-4-yl)-6'-(pyrimidin-4-ylamino)-2'H-spiro[cyclohexane-1,3'-imidazo[1,5-a]pyridine]-1',5'-dione (3, 0.22 g, 0.57 mmol) in methanol (10 mL) and tetrahydrofuran (10 mL). Palladium on carbon (0.10 g) was added followed by ammonium hydroxide (1.0 mL) under nitrogen atmosphere. The reaction was filled with hydrogen and stirred at room temperature for 3 d. After completion of reaction monitored by TLC and LCMS, the reaction mass was diluted with 5% methanol in dichloromethane (100 mL) and passed through celite bed and washed with 10% methanol/dichloromethane (3×50 mL). Solvent was removed under vacuum and crude material was purified by prep HPLC to afford 6'-(pyrimidin-4-ylamino)-8'-(tetrahydro-2H-pyran-4-yl)-2'H-spiro[cyclohexane-1,3'-imidazo[1,5-a]

pyridine]-1',5'-dione (Cpd. No. 201) as a white solid. Yield: 0.11 g, 49%; MS (ESI) m/z 396.4 [M+1]+; 1H NMR (400 MHz, DMSO-d6) δ 10.16 (6, 1H), 9.40 (s, 1H), 8.85 (s, 1H), 8.81 (s, 1H), 8.38 (d, J=5.88 Hz, 1H), 7.37 (d, J=5.88 Hz, 1H), 4.20 (m, 1H), 3.96 (m, 2H), 3.42 (t, J=11.3 Hz, 2H), 3.01 (m, 2H), 1.70 (m, 9H), 1.58 (m, 2H), 1.22 (m, 1H).

Example 202

Synthesis of 6'-((6-amino-5-hydroxypyrimidin-4-yl)amino)-8'-methyl-2'H-spiro[cyclohexane-1,3'-imidazo[1,5-a]pyridine]-1',5'-dione (Cpd. No. 202)

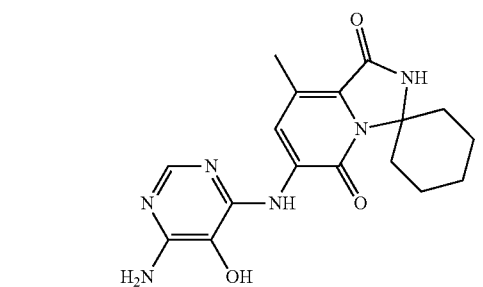 [SMILES: Cc1cc(Nc2ncnc(N)c2O)c(=O)n2c1C(=O)NC21CCCCC1]

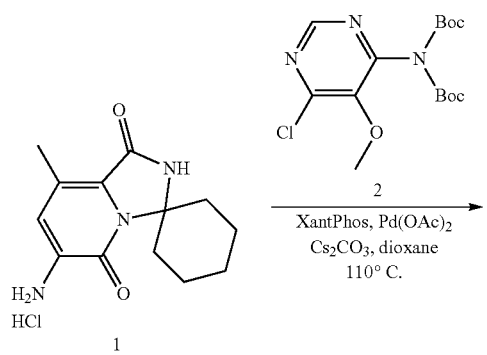

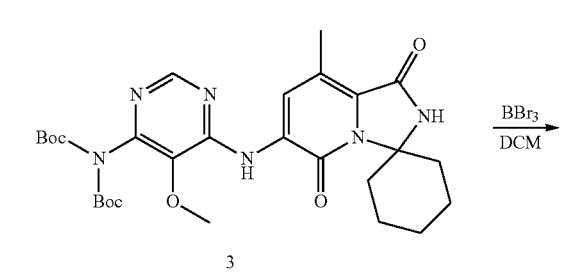

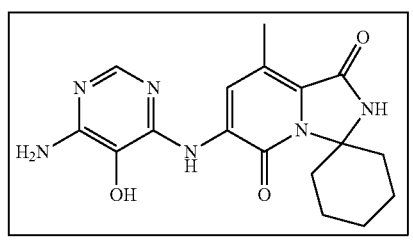

Synthesis of tert-butyl N-tert-butoxycarbonyl-N-(5-methoxy-6-((8'-methyl-1',5'-dioxo-1',5'-dihydro-2'H-spiro[cyclohexane-1,3'-imidazo[1,5-a]pyridin]-6'-yl)amino)pyrimidin-4-yl)carbamate (3)

The synthesis of intermediate 3 was carried out as described above using the general protocol of Procedure B. Yellow solid; Yield: 0.45 g, 64%; MS (ESI) m/z 571.15 [M+1]+.

Synthesis of 6'-((6-amino-5-hydroxypyrimidin-4-yl)amino)-8'-methyl-2'H-spiro[cyclohexane-1,3'-imidazo[1,5-a]pyridine]-1',5'-dione (Cpd. No. 202)

A flask was charged with tert-butyl N-tert-butoxycarbonyl-N-(5-methoxy-6-((8'-methyl-1',5'-dioxo-1',5'-dihydro-2'H-spiro[cyclohexane-1,3'-imidazo[1,5-a]pyridin]-6'-yl)amino)pyrimidin-4-yl)carbamate (3, 0.40 g, 0.70 mmol) and dichloromethane (20 mL) was added and mixture was cooled to −20° C. boron tribromide (0.87 g, 3.50 mmol) was then added to the mixture drop wise. The reaction mass was stirred at room temperature overnight. After completion, water was added to the reaction mixture and quenched with saturated aqueous solution of sodium bicarbonate till pH 8. Yellow solid was precipitated out, filtered and washed with water (20 mL) followed by diethyl ether then finally dried under high vacuum to afford 6'-((6-amino-5-hydroxypyrimidin-4-yl)amino)-8'-methyl-2'H-spiro[cyclohexane-1,3'-imidazo[1,5-a]pyridine]-1',5'-dione (Cpd. No. 202) as yellow solid. Yield: 0.085 g, 34%; MS (ESI) m/z 357.16 [M+1]+; 1H NMR: (400 MHz, DMSO-d6) δ 10.06 (s, 1H), 9.15 (brs, 1H), 8.50 (s, 1H), 8.40 (m, 1H), 8.08 (s, 1H), 6.65 (brs, 2H), 3.00-2.94 (m, 2H), 2.44 (s, 3H), 1.73-1.62 (m, 5H), 1.46-1.43 (m, 2H), 1.24-1.21 (m, 1H).

Example 203

Synthesis of 6'-((6-amino-2-hydroxypyrimidin-4-yl)amino)-8'-methyl-2'H-spiro[cyclohexane-1,3'-imidazo[1,5-a]pyridine]-1',5'-dione (Cpd. No. 203)

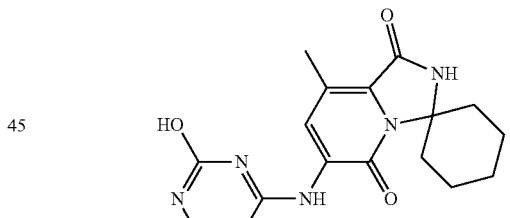

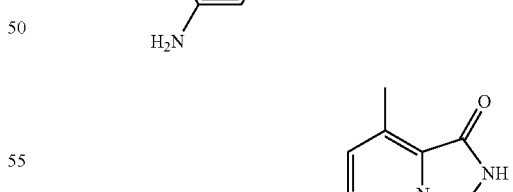

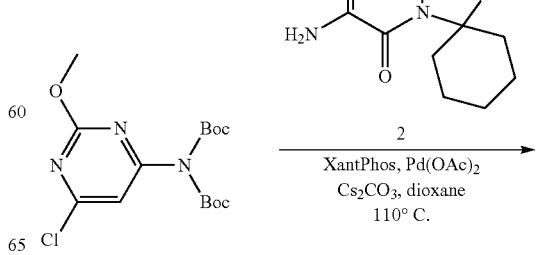

319

-continued

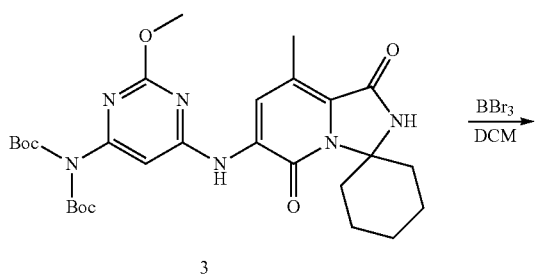

3

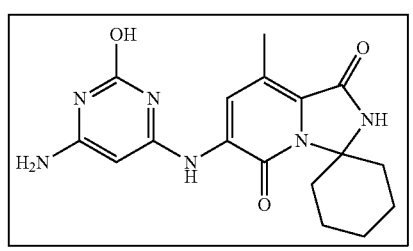

Synthesis of 6'-((6-(di-(tert-butoxycarbonyl)-amino)-2-methoxypyrimidin-4-yl)amino)-8'-methyl-2'H-spiro[cyclohexane-1,3'-imidazo[1,5-a]pyridine]-1',5'-dione (3)

The synthesis of intermediate 3 was carried out as described above using the general protocol of Procedure B. Yellow solid; Yield: 0.77 g, 51%; MS (ESI) m/z 571.21 [M+1]$^+$.

Synthesis of 6'-((6-amino-2-hydroxypyrimidin-4-yl)amino)-8'-methyl-2'H-spiro[cyclohexane-1,3'-imidazo[1,5-a]pyridine]-1',5'-dione (Cpd. No. 203)

To a stirred solution of 6'-((6-(di-(tert-butoxycarbonyl)-amino)-2-methoxypyrimidin-4-yl)amino)-8'-methyl-2'H-spiro[cyclohexane-1,3'-imidazo[1,5-a]pyridine]-1',5'-dione (3, 0.77 g, 1.35 mmol) in dichloromethane (15 mL) at −20° C., boron tribromide (1 mL) was added. The mixture was stirred for another 20 min at the same temperature and then stirred for 48 h at room temperature when TLC showed complete conversion of starting material. The mixture was quenched by addition of methanol (2 mL) and the solvent was removed under reduced pressure to afford the crude. The crude was purified by washing with methanol (5 mL), dichloromethane (5 mL) and pentane (25 mL) to afford 6'-((6-amino-2-hydroxypyrimidin-4-yl)amino)-8'-methyl-2'H-spiro[cyclohexane-1,3'-imidazo[1,5-a]pyridine]-1',5'-dione (Cpd. No. 203) as pale yellow solid. Yield: 0.28 g, 58%; MS (ESI) m/z 357.16 [M+1]$^+$; $^1$H NMR (400 MHz, DMSO-d$_6$) δ 10.03 (brs, 2H), 8.58 (brs, 1H), 8.47 (brs, 1H), 6.46 (brs, 2H), 5.39 (brs, 1H), 3.05-2.92 (m, 2H), 2.40 (s, 3H), 1.80-1.54 (m, 6H), 1.48-1.50 (m, 2H), 1.28-1.16 (m, 1H).

320

Example 204

Synthesis of 6'-((6-aminopyrimidin-4-yl)amino)-2-hydroxy-8'-methyl-2'H-spiro[cyclohexane-1,3'-imidazo[1,5-a]pyridine]-1',5'-dione (Cpd. No. 204)

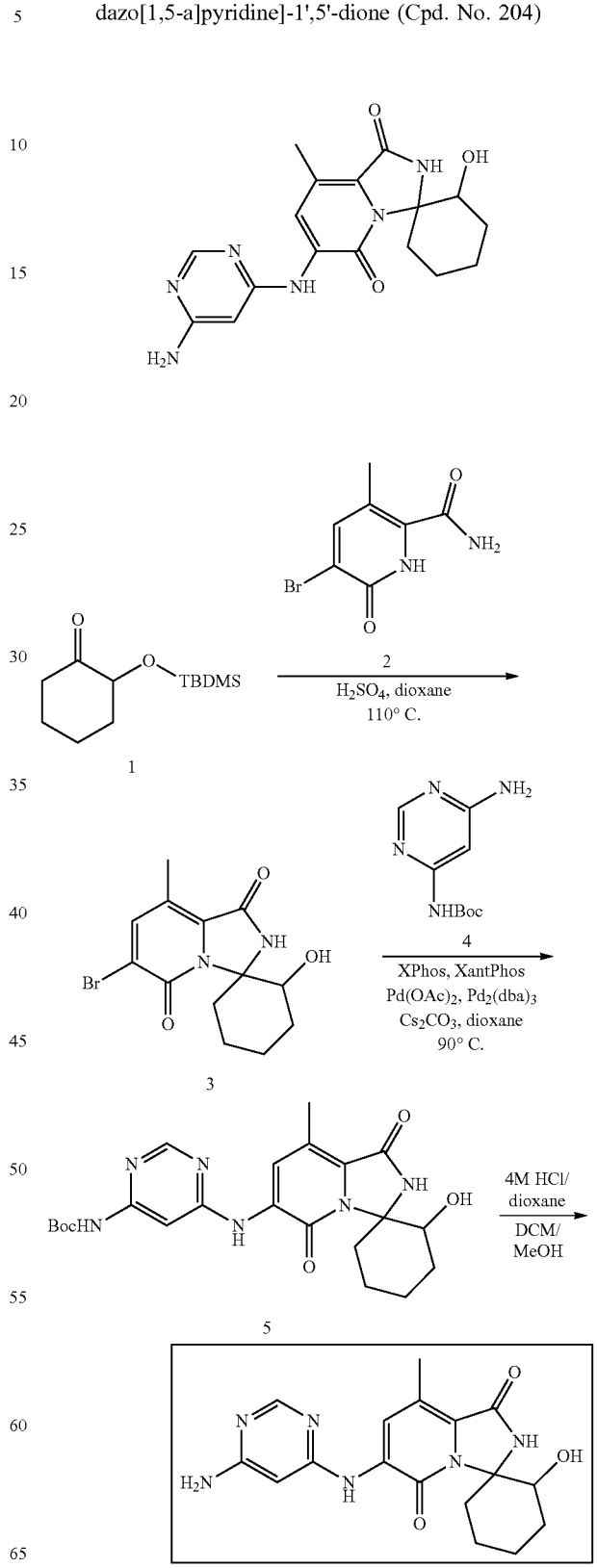

321

Synthesis of 6'-bromo-2-hydroxy-8'-methyl-2'H-spiro[cyclohexane-1,3'-imidazo[1,5-a]pyridine]-1',5'-dione (3)

The synthesis of intermediate 3 was carried out as described above using the general protocol of Procedure A. Pale yellow solid; Yield: 1.3 g, 62%; MS (ESI) m/z 326.97 [M+1]$^+$.

Synthesis of tert-butyl (6-((2-hydroxy-8'-methyl-1', 5'-dioxo-1',5'-dihydro-2'H-spiro[cyclohexane-1,3'-imidazo[1,5-a]pyridin]-6'-yl)amino)pyrimidin-4-yl) carbamate (5)

The synthesis of intermediate 5 was carried out as described above using the general protocol of Procedure H. Pale yellow solid; Yield: 1.1 g, 79%; MS (ESI) m/z 457.34 [M+1]$^+$.

Synthesis of 6'-((6-aminopyrimidin-4-yl)amino)-2-hydroxy-8'-methyl-2'H-spiro[cyclohexane-1,3'-imidazo[1,5-a]pyridine]-1',5'-dione (Cpd. No. 204)

The synthesis of compound 204 was carried out as described above using the general protocol of Procedure F. Yellow solid; Yield: 0.21 g, 25%; MS (ESI) m/z 357.16 [M+1]$^+$; $^1$H NMR (400 MHz, DMSO-d$_6$) δ 9.55 (s, 1H), 8.60 (brs, 1H), 8.30 (s, 1H), 8.19 (brs, 1H), 6.62 (brs, 2H), 6.17 (s, 1H), 5.00-4.95 (m, 1H), 4.70-4.62 (m, 1H), 3.10-3.00 (m, 1H), 1.82-1.48 (m, 6H), 1.38-1.28 (m, 1H).

Example 205

Synthesis of 6'-((6-aminopyrimidin-4-yl)amino)-3-hydroxy-8'-methyl-2'H-spiro[cyclohexane-1,3'-imidazo[1,5-a]pyridine]-1',5'-dione (Cpd. No. 205)

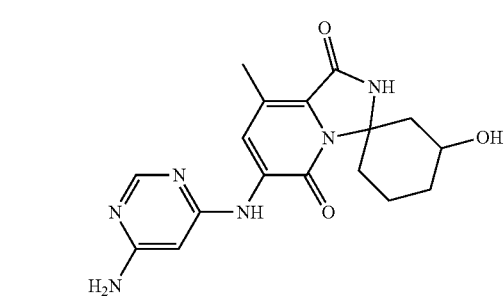 [SMILES: Cc1cc(Nc2cc(N)ncn2)c(=O)n2c1C(=O)NC21CCCC(O)C1]

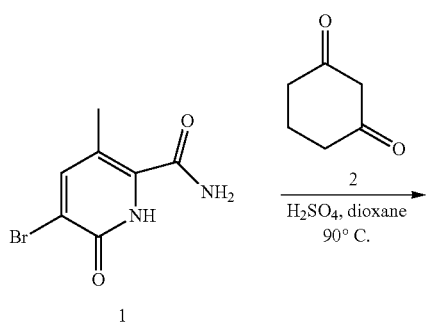

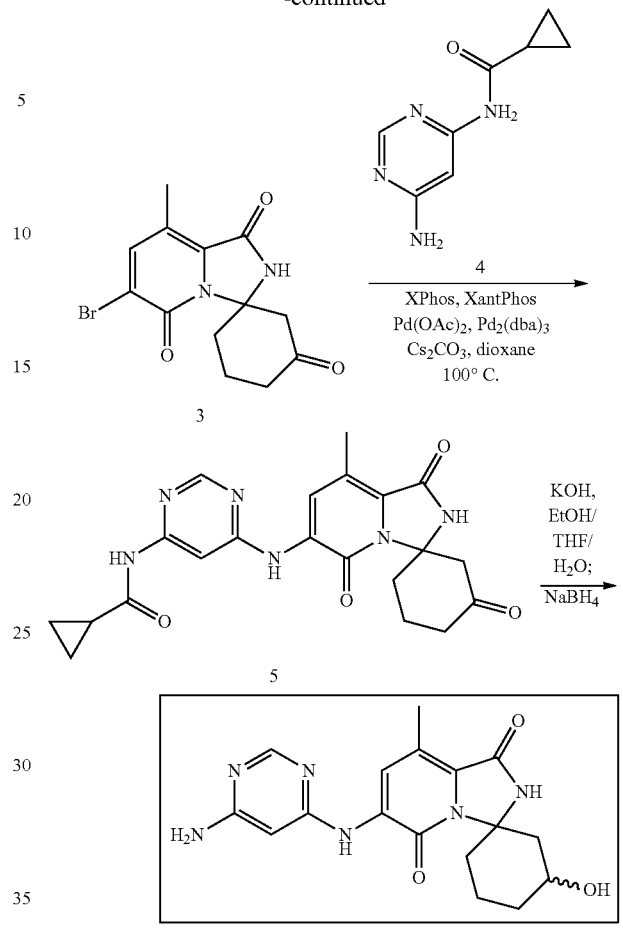

Synthesis of 6'-bromo-8'-methyl-2'H-spiro[cyclohexane-1,3'-imidazo[1,5-a]pyridine]-1',3,5'-trione (3)

The synthesis of intermediate 3 was carried out as described above using the general protocol of Procedure A. Off white solid; Yield: 1.6 g, 22%; MS (ESI) m/z 329.9 [M+1]$^+$.

Synthesis of N-(6-((8'-methyl-1',3,5'-trioxo-1',5'-dihydro-2'H-spiro[cyclohexane-1, 3'-imidazo[1,5-a]pyridin]-6'-yl)amino)pyrimidin-4-yl)cyclopropanecarboxamide (5)

The synthesis of intermediate 5 was carried out as described above using the general protocol of Procedure H. Off white solid; Yield: 0.40 g, 51%; MS (ESI) m/z 457.31 [M+1]$^+$.

Synthesis of 6'-((6-aminopyrimidin-4-yl)amino)-3-hydroxy-8'-methyl-2'H-spiro[cyclohexane-1,3'-imidazo[1,5-a]pyridine]-1',5'-dione (Cpd. No. 205)

A flask containing tetrahydrofuran and ethanol (1:1, 20 mL) was charged with N-(6-((8'-methyl-1',3,5'-trioxo-1',5'-dihydro-2'H-spiro[cyclohexane-1,3'-imidazo[1,5-a]pyridin]-6'-yl)amino)pyrimidin-4-yl)cyclopropanecarboxamide (5, 0.4 g, 0.9 mmol) and 3 M potassium hydroxide solution (8.0 mL) was added to the above reaction. The reaction was stirred at room temperature for 18 h. After complete hydrolysis, sodium borohydride (0.18 g, 0.4 mmol) was added to the above reaction at room temperature. The reaction mass was stirred for 2 h when TLC showed completion of starting material. The solvents were removed under reduced pressure and crude was dissolved in 10% methanol in dichloromethane and neutralized with 10% citric acid. The organic layer was separated and dried over sodium sulfate, filtered and concentrated to obtain solid. The solid was filtered and washed with methanol (5 mL) and pentane (20 mL) and dried under high vacuum to afford 6'-((6-aminopyrimidin-4-yl)amino)-4-hydroxy-8'-methyl-2'H-spiro[cyclohexane-1,3'-imidazo[1,5-a]pyridine]-1',5'-dione (Cpd. No. 205) as yellow solid as a mixture of diastereomers. Yield: 0.045 g, 13%; MS (ESI) m/z 357.19 [M+1]$^+$; $^1$H NMR: (400 MHz, DMSO-d$_6$) δ 9.89 & 8.48 (2 s, 1H each, isomer A & B), 8.59 & 8.57 (2 s, 1H each, isomer A & B), 8.42 (brs, 1H), 8.16 (brs, 1H), 6.52 (brs, 2H), 6.16 (brs, 1H), 5.16 & 4.85 (2 s, 1H each, isomer A & B), 4.22 and 3.73 (2 m, 1H each, isomer A & B), 2.99 & 2.88 (2 m, 2H each, isomer A & B), 2.42 (s, 3H), 1.98-1.11 (m, 6H).

Example 206

Synthesis of 6'-((6-aminopyrimidin-4-yl)amino)-4-hydroxy-8'-methyl-2'H-spiro[cyclohexane-1,3'-imidazo[1,5-a]pyridine]-1',5'-dione hydrochloride (Cpd. No. 206)

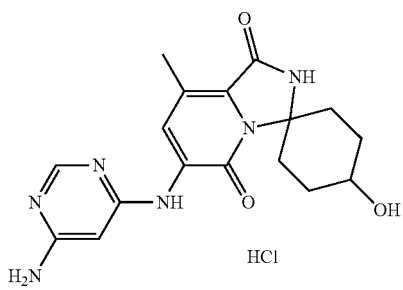 [SMILES: Cc1cc(Nc2cc(N)ncn2)c(=O)n2c1C(=O)NC21CCC(O)CC1 ; Cl]

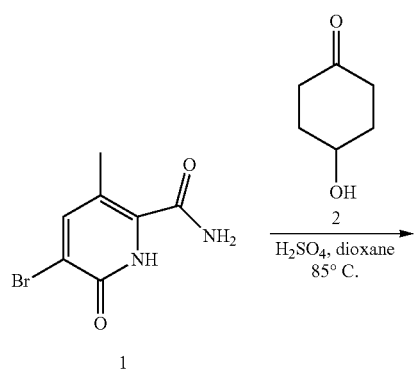

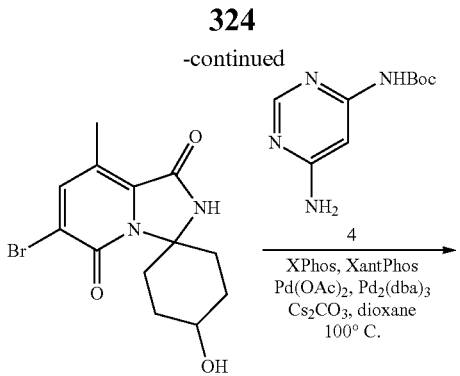

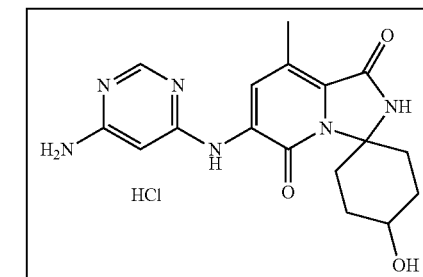

Synthesis of 6'-bromo-4-hydroxy-8'-methyl-2'H-spiro[cyclohexane-1, 3'-imidazo[1,5-a]pyridine]-1', 5'-dione (3)

The synthesis of intermediate 3 was carried out as described above using the general protocol of Procedure A. Off white solid; Yield: 1.0 g, 35%; MS (ESI) m/z 326.91 [M+1]$^+$.

Synthesis of tert-butyl (6-((4-hydroxy-8'-methyl-1', 5'-dioxo-1',5'-dihydro-2'H-spiro[cyclohexane-1,3'-imidazo[1,5-a]pyridin]-6'-yl)amino)pyrimidin-4-yl) carbamate (5)

The synthesis of intermediate 5 was carried out as described above using the general protocol of Procedure H. Off white solid; Yield: 0.45 g, 81%; MS (ESI) m/z 457.31 [M+1]$^+$.

Synthesis of 6'-((6-aminopyrimidin-4-yl)amino)-4-hydroxy-8'-methyl-2'H-spiro[cyclohexane-1,3'-imidazo[1,5-a]pyridine]-1',5'-dione hydrochloride (Cpd. No. 206)

The synthesis of compound 206 was carried out as described above using the general protocol of Procedure F. Yellow solid as a mixture of diastereomers; Yield: 0.049 g, 12%; MS (ESI) m/z 357.09 [M+1]$^+$; $^1$H NMR (400 MHz, DMSO-d$_6$) δ 10.04 & 9.97 (2 s, 1H each, isomer A & B), 8.58 & 8.56 (2 s, 1H each, isomer A & B), 8.38 & 8.35 (2 s, 1H each, isomer A & B), 8.16 (s, 1H), 6.51 (brs, 2H), 6.15 & 6.14 (2 s, 1H each, isomer A & B), 4.78 & 4.46 (2 brs, 1H each, isomer A & B), 3.86 & 3.53 (2 m, 1H each, isomer A & B), 3.41 & 3.09 (2 m, 2H each, isomer A & B), 2.42 (s, 3H), 1.85-1.56 (m, 4H), 143 & 1.17 (2 m, 2H each, isomer A & B).

Example 207

Synthesis of 6'-((6-aminopyrimidin-4-yl)amino)-8'-(hydroxymethyl)-2'H-spiro[cyclohexane-1,3'-imidazo[1,5-a]pyridine]-1',5'-dione (Cpd. No. 207)

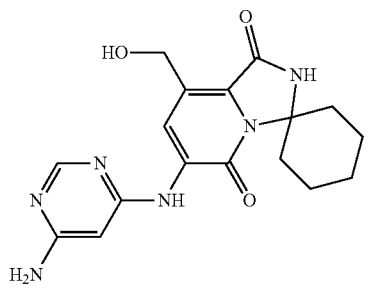 [SMILES: Nc1cc(Nc2cc(CO)c3n(c2=O)C2(CCCCC2)NC3=O)ncn1]

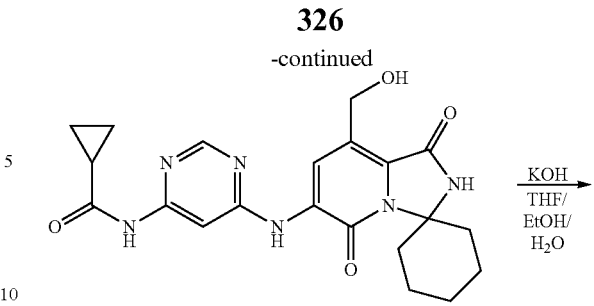

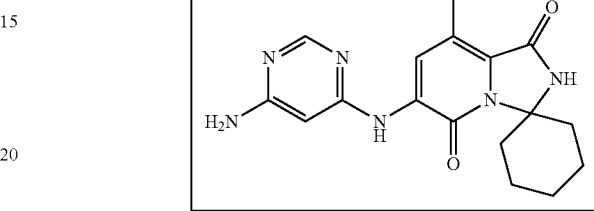

Synthesis of N-(6-((1',5'-dioxo-8'-vinyl-1',5'-dihydro-2'H-spiro[cyclohexane-1, 3'-imidazo[1,5-a]pyridin]-6'-yl)amino)pyrimidin-4-yl)cyclopropanecarboxamide (3)

The synthesis of intermediate 3 was carried out as described above using the general protocol of Procedure G. Brown solid; Yield: 1.5 g, 51%; MS (ESI) m/z 421.22 [M+1]$^+$; $^1$H NMR (400 MHz, DMSO-d$_6$) δ 10.88 (s, 1H), 10.25 (s, 1H), 9.20 (s, 1H), 8.99 (s, 1H), 8.56 (s, 1H), 7.92-7.84 (m, 2H), 5.70 (d, J=17.6 Hz, 1H), 5.34 (d, J=11.6 Hz, 1H), 3.32 (m, 1H), 2.99-2.93 (m, 2H), 2.05-1.98 (m, 2H), 1.72-1.66 (m, 5H), 1.43-1.40 (m, 2H), 1.34-1.16 (m, 1H), 0.85 (m, 4H).

Synthesis of N-(6-((8'-formyl-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (4)

To a stirred solution of N-(6-((1',5'-dioxo-8'-vinyl-1',5'-dihydro-2'H-spiro[cyclohexane-1,3'-imidazo[1,5-a]pyridin]-6'-yl)amino)pyrimidin-4-yl)cyclopropanecarboxamide (3, 2.0 g, 4.75 mmol) and sodium periodate (3.05 g, 14.26 mmol) in dioxane and water (2:1, 30 mL), a solution of osmium tetroxide in butanol (0.60 g, 2.38 mmol) was added drop wise at 0° C. The reaction mass was stirred at room temperature overnight. After TLC showed completion, the solvent was evaporated under reduced pressure and water (100 mL) was added. The mixture was extracted with 10% methanol in dichloromethane (2×50 mL). The organics were then separated and dried (magnesium sulfate) and concentrated to dryness under vacuum to afford N-(6-((8'-formyl-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (4) as brown solid. Yield: 1.2 g, 60%; MS (ESI) m/z 423.26 [M+1]$^+$.

Synthesis of N-(6-((8'-(hydroxymethyl)-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (5)

To a stirred solution of N-(6-((8'-formyl-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (1.2 g, 2.85 mmol) in methanol/tetrahydrofuran (1:2, 30 mL), sodium borohydride was added portion wise at 0° C. The reaction mass was stirred at 0° C. for 2 h. After completion, the reaction mixture was diluted with water (100 mL) and the mixture was extracted with 10% methanol in dichloromethane (2×50 mL). The organics were then separated and dried (magnesium sulfate) and concentrated to dryness under vacuum to afford N-(6-((8'-(hydroxymethyl)-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (5) as brown solid. Yield: 0.7 g, 62%; MS (ESI) m/z 423.43 [M−1]⁻; 1H NMR (400 MHz, DMSO-d$_6$) δ 10.86 (s, 1H), 10.24-10.18 (m, 1H), 8.71-8.62 (m, 1H), 8.56-8.52 (m, 1H), 7.84 (s, 1H), 6.13-5.33 (m, 1H), 4.47-4.33 (m, 3H), 3.16-2.84 (m, 4H), 2.01-1.86 (m, 2H), 1.72-1.66 (m, 5H), 1.43-1.40 (m, 2H), 1.34-1.16 (m, 1H).

Synthesis of 6'-((6-aminopyrimidin-4-yl)amino)-8'-(hydroxymethyl)-2'H-spiro[cyclohexane-1,3'-imidazo[1,5-a]pyridine]-1',5'-dione (Cpd. No. 207)

The synthesis of compound 207 was carried out as described above using the general protocol of Procedure I. Brown solid; Yield: 0.18 g, 29%; MS (ESI) m/z 357.35 [M+1]⁺; $^1$H NMR (400 MHz, DMSO-d$_6$) δ 10.23 (s, 1H), 9.23 (m, 1H), 8.47 (m, 1H), 8.33 (s, 1H), 7.25 (brs, 2H), 6.27 (s, 1H), 5.18 (brs, 1H), 4.81 (s, 2H), 3.01 (m, 2H), 1.73-1.62 (m, 5H), 1.46-1.44 (m, 2H), 1.23 (m, 1H).

Example 208

Synthesis of 6'-((5-cyclopropylpyrimidin-4-yl)amino)-8'-methyl-2'H-spiro[cyclohexane-1,3'-imidazo[1,5-a]pyridine]-1',5'-dione (Cpd. No. 208)

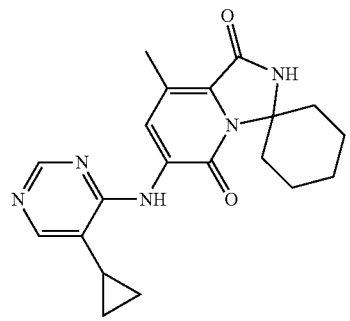 [SMILES: Cc1cc(Nc2ncncc2C2CC2)c(=O)n2c1C(=O)NC21CCCCC1]

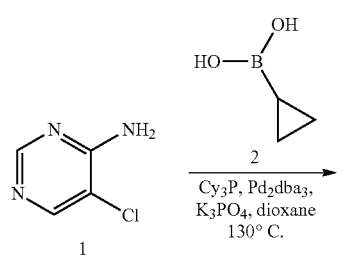

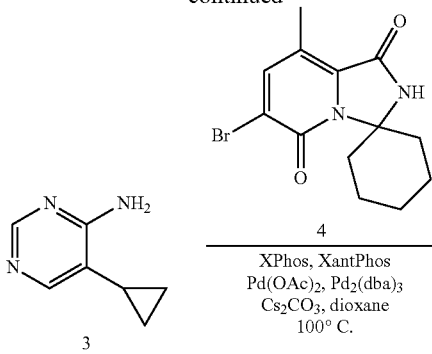

Synthesis of 5-cyclopropylpyrimidin-4-amine (3)

The synthesis of intermediate 3 was carried out as described above using the general protocol of Procedure G. Brown solid; Yield: 0.41 g, 78%; MS (ESI) m/z 136.08 [M+1]⁺; $^1$H NMR (400 MHz, DMSO-d$_6$) δ 8.02 (s, 1H), 7.81 (s, 1H), 6.75 (brs, 2H), 1.57-1.53 (m, 1H), 0.86-0.82 (m, 2H), 0.56-0.53 (m, 2H).

Synthesis of 6'-((5-cyclopropylpyrimidin-4-yl)amino)-8'-methyl-2'H-spiro[cyclohexane-1,3'-imidazo[1,5-a]pyridine]-1',5'-dione (Cpd. No. 208)

The synthesis of compound 208 was carried out as described above using the general protocol of Procedure H. Off white solid; Yield: 0.14 g, 24%; MS (ESI) m/z 366.20 [M+1]⁺; $^1$H NMR (400 MHz, DMSO-d$_6$) δ 10.16 (s, 1H), 8.88 (s, 1H), 8.72 (s, 1H), 8.62 (s, 1H), 8.29 (s, 1H), 3.01-2.96 (m, 2H), 2.5 (s, 3H), 1.84-1.59 (m, 6H), 1.48-1.45 (m, 2H), 1.30-1.27 (m, 1H), 1.05-1.01 (m, 2H), 0.73-0.69 (m, 2H).

Example 209

Synthesis of 8'-methyl-6'-(pyrimidin-4-yloxy)-2'H-spiro[cyclohexane-1,3'-imidazo[1,5-a]pyridine]-1',5'-dione (Cpd. No. 209)

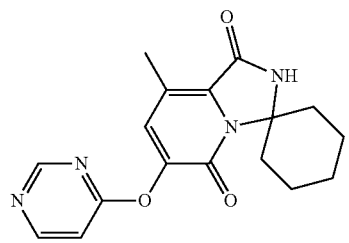 [SMILES: Cc1cc(Oc2ccncn2)c(=O)n2c1C(=O)NC21CCCCC1]

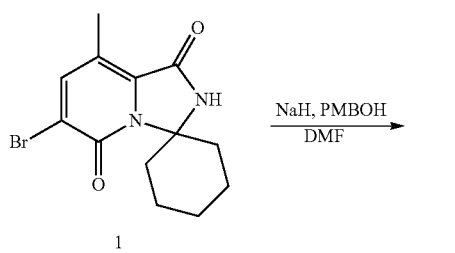

1

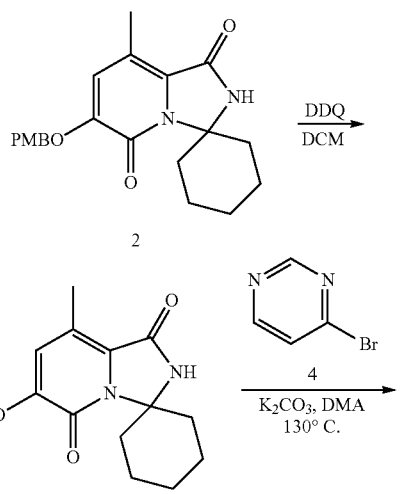

2

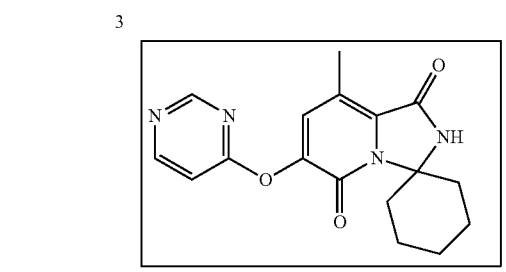

3

Synthesis of 6'-((4-methoxybenzyl)oxy)-8'-methyl-2'H-spiro[cyclohexane-1,3'-imidazo[1,5-a]pyridine]-1',5'-dione (2)

To a solution of 6'-bromo-8'-methyl-2'H-spiro[cyclohexane-1,3'-imidazo[1,5-a]pyridine]-1',5'-dione (2 g, 6.43 mmol) in dimethylformamide (30 mL) is added sodium hydride (0.46 g, 19.29 mmol) and 4-methoxybenzyl alcohol (3.19 mL, 25.72 mmol). The reaction is stirred at room temperature overnight. The resulting mixture is poured into iced water and extracted with dichloromethane. The organic layer is dried over magnesium sulfate, filtered and concentrated. The crude is purified via column chromatography to afford 6'-((4-methoxybenzyl)oxy)-8'-methyl-2'H-spiro[cyclohexane-1,3'-imidazo[1,5-a]pyridine]-1',5'-dione (2).

Synthesis of 6'-hydroxy-8'-methyl-2'H-spiro[cyclohexane-1,3'-imidazo[1,5-a]pyridine]-1',5'-dione (3)

To a solution of 6'-((4-methoxybenzyl)oxy)-8'-methyl-2'H-spiro[cyclohexane-1,3'-imidazo[1,5-a]pyridine]-1',5'-dione (2, 1.5 g, 4.07 mmol) in dichloromethane (20 mL) is added 2,3-dichloro-5,6-dicyano-p-benzoquinone (1.38 g, 6.10 mmol). The reaction is stirred at room temperature for 2 h. The resulting mixture is concentrated and purified via column chromatography to afford 6'-hydroxy-8'-methyl-2'H-spiro[cyclohexane-1,3'-imidazo[1,5-a]pyridine]-1',5'-dione (3).

Synthesis of 8'-methyl-6'-(pyrimidin-4-yloxy)-2'H-spiro[cyclohexane-1,3'-imidazo[1,5-a]pyridine]-1',5'-dione (Cpd. No. 209)

To a solution of 6'-hydroxy-8'-methyl-2'H-spiro[cyclohexane-1,3'-imidazo[1,5-a]pyridine]-1',5'-dione (3, 1 g, 4.03 mmol) in dimethylacetamide (20 mL) is added potassium carbonate (1.67 g, 12.09 mmol) and 4-bromopyrimidine (4, 0.77 g, 4.84 mmol). The reaction is stirred at 130° C. overnight. The resulting mixture is cooled to room temperature, poured into water and extracted with dichloromethane. The organic layer is dried over magnesium sulfate, filtered and concentrated. The crude is purified via column chromatography to afford 8'-methyl-6'-(pyrimidin-4-yloxy)-2'H-spiro[cyclohexane-1,3'-imidazo[1,5-a]pyridine]-1',5'-dione (Cpd. No. 209).

Example 210

Synthesis of 8'-methyl-6'-(pyrimidin-4-ylthio)-2'H-spiro[cyclohexane-1,3'-imidazo[1,5-a]pyridine]-1',5'-dione (Cpd. No. 210)

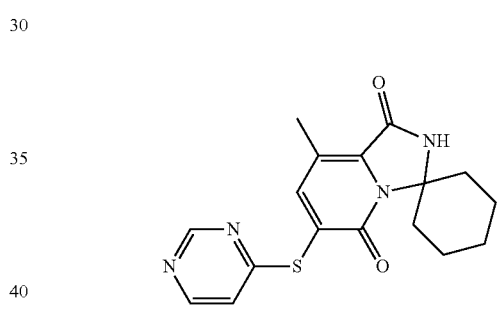

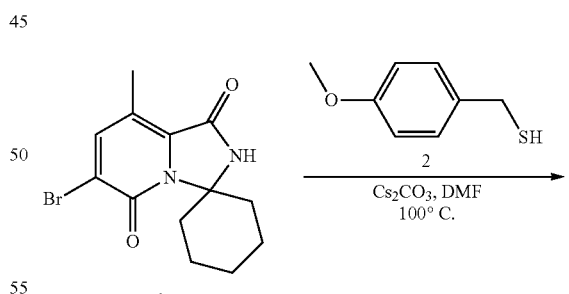

1

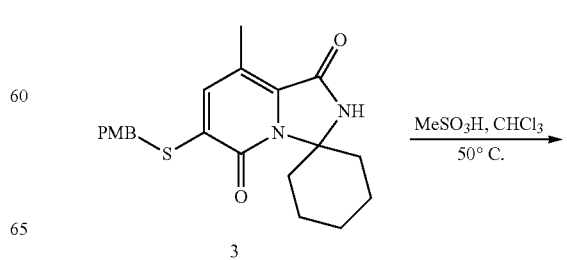

3

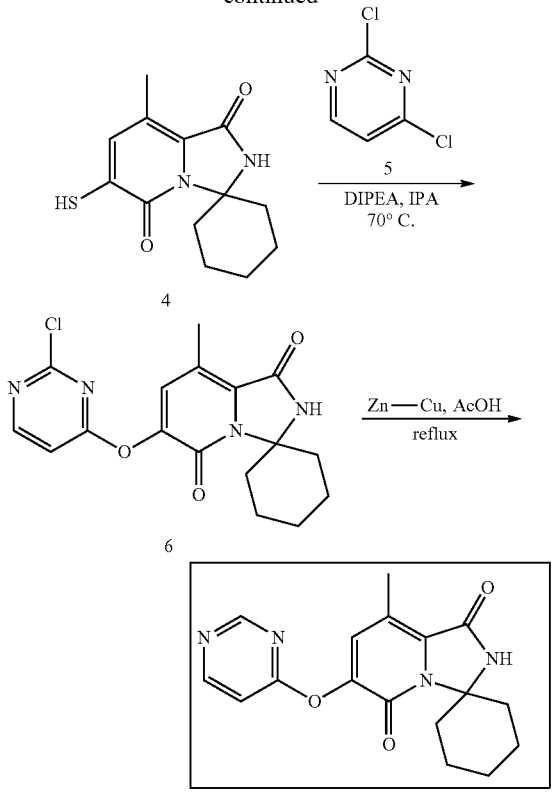

Synthesis of 6'-((4-methoxybenzyl)thio)-8'-methyl-2'H-spiro[cyclohexane-1,3'-imidazo[1,5-a]pyridine]-1',5'-dione (3)

To a solution of 6'-bromo-8'-methyl-2'H-spiro[cyclohexane-1,3'-imidazo[1,5-a]pyridine]-1',5'-dione (1, 2 g, 6.43 mmol) in dimethylformamide (30 mL) is added cesium carbonate (6.28 g, 19.29 mmol) and (4-methoxyphenyl)methanethiol (2, 1.19 g, 7.72 mmol). The reaction is stirred at 100° C. overnight. The resulting mixture is cooled to room temperature, poured into water and extracted with dichloromethane. The organic layer is dried over magnesium sulfate, filtered and concentrated. The crude is purified via column chromatography to afford 6'-((4-methoxybenzyl)thio)-8'-methyl-2'H-spiro[cyclohexane-1,3'-imidazo[1,5-a]pyridine]-1',5'-dione (3).

Synthesis of 6'-mercapto-8'-methyl-2'H-spiro[cyclohexane-1,3'-imidazo[1,5-a]pyridine]-1',5'-dione (4)

To a solution of 6'-((4-methoxybenzyl)thio)-8'-methyl-2'H-spiro[cyclohexane-1,3'-imidazo[1,5-a]pyridine]-1',5'-dione (3, 3.3 g, 8.58 mmol) in chloroform (40 mL) is added methanesulfonic acid (3 mL, 46.23 mmol). The reaction is stirred at 50° C. overnight. The resulting mixture is cooled to room temperature, poured into water and extracted with dichloromethane. The organic layer is dried over magnesium sulfate, filtered and concentrated. The crude is purified via column chromatography to afford 6'-mercapto-8'-methyl-2'H-spiro[cyclohexane-1,3'-imidazo[1,5-a]pyridine]-1',5'-dione (4).

Synthesis of 6'-((2-chloropyrimidin-4-yl)thio)-8'-methyl-2'H-spiro[cyclohexane-1,3'-imidazo[1,5-a]pyridine]-1',5'-dione (6)

To a solution of 6'-mercapto-8'-methyl-2'H-spiro[cyclohexane-1,3'-imidazo[1,5-a]pyridine]-1',5'-dione (4, 0.50 g, 1.89 mmol) in 2-propanol (10 mL) is added N,N-diisopropylethylamine (0.99 mL, 5.67 mmol) and 2,4-dichloropyrimidine (5, 0.34 g, 2.27 mmol). The reaction is stirred at 70° C. overnight. The resulting mixture is cooled to room temperature, poured into water and extracted with dichloromethane. The organic layer is dried over magnesium sulfate, filtered and concentrated. The crude is purified via column chromatography to afford 6'-((2-chloropyrimidin-4-yl)thio)-8'-methyl-2'H-spiro[cyclohexane-1,3'-imidazo[1,5-a]pyridine]-1',5'-dione (6).

Synthesis of 8'-methyl-6'-(pyrimidin-4-ylthio)-2'H-spiro[cyclohexane-1,3'-imidazo[1,5-a]pyridine]-1',5'-dione (Cpd. No. 210)

To a solution of 6'-((2-chloropyrimidin-4-yl)thio)-8'-methyl-2'H-spiro[cyclohexane-1,3'-imidazo[1,5-a]pyridine]-1',5'-dione (6, 0.3 g, 0.80 mmol) in acetic acid (4 mL) is added zinc copper couple (0.5 g). The reaction is stirred at reflux for 4 h. The resulting mixture is cooled to room temperature, filtered and concentrated. The crude is purified via column chromatography to afford 8'-methyl-6'-(pyrimidin-4-ylthio)-2'H-spiro[cyclohexane-1,3'-imidazo[1,5-a]pyridine]-1',5'-dione (Cpd. No. 210).

Example 211

Synthesis of 8'-methyl-6'-(pyrimidine-4-carbonyl)-2'H-spiro[cyclohexane-1,3'-imidazo[1,5-a]pyridine]-1',5'-dione (Cpd. No. 211)

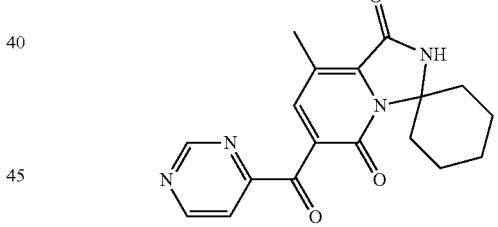

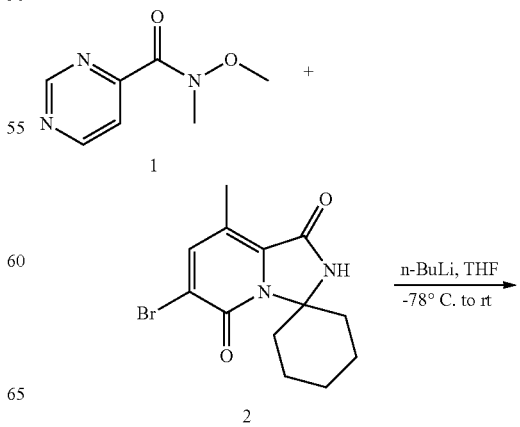

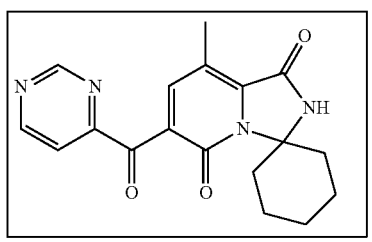

Synthesis of 8'-methyl-6'-(pyrimidine-4-carbonyl)-2'H-spiro[cyclohexane-1,3'-imidazo[1,5-a]pyridine]-1',5'-dione (Cpd. No. 211)

To a solution of 6'-bromo-8'-methyl-2'H-spiro[cyclohexane-1,3'-imidazo[1,5-a]pyridine]-1',5'-dione (2, 0.3 g, 0.96 mmol) in tetrahydrofuran (25 mL), n-butyllithium (0.58 g, 2.89 mmol) was added at −78° C. The reaction mixture was stirred for 30 min. To the mixture N-methoxy-N-methylpyrimidine-4-carboxamide (1, 0.25 g, 1.44 mmol) was added at −78° C. and then the mixture was stirred at room temperature for 16 h. After completion, the reaction was quenched with aqueous solution of ammonium chloride (50 mL) and extracted with dichloromethane (2×50 mL). The organic layer was separated and was hed with brine (25 mL) and the solvent was evaporated under reduced pressure. The crude was purified by silica gel (220-400 mesh) column chromatography using 0.5% methanol in dichloromethane as eluent. The fractions were concentrated to afford 8'-methyl-6'-(pyrimidine-4-carbonyl)-2'H-spiro[cyclohexane-1,3'-imidazo[1,5-a]pyridine]-1',5'-dione as yellow solid. Yield: 0.001 g, 3.0%; MS (ESI) m/z 339.13 [M+1]⁺; $^1$H NMR (400 MHz, DMSO-$d_6$) δ 10.58 (s, 1H), 9.26 (s, 1H), 9.07 (d, J=5.08 Hz, 1H), 9.97 (s, 1H), 7.83 (d, J=5.2 Hz, 1H), 2.85-2.75 (m, 2H), 2.45 (s, 3H), 1.68-162 (m, 2H), 1.60-1.53 (m, 3H), 1.46-1.43 (m, 2H), 1.10-1.09 (m, 1H).

Example 212

Synthesis of 8'-methyl-6'-(pyrimidin-4-ylmethyl)-2'H-spiro[cyclohexane-1,3'-imidazo[1,5-a]pyridine]-1',5'-dione (Cpd. No. 212)

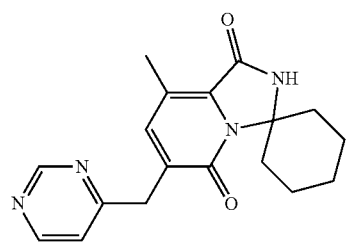 [SMILES: Cc1cc(Cc2ccncn2)c(=O)n2c1C(=O)NC21CCCCC1]

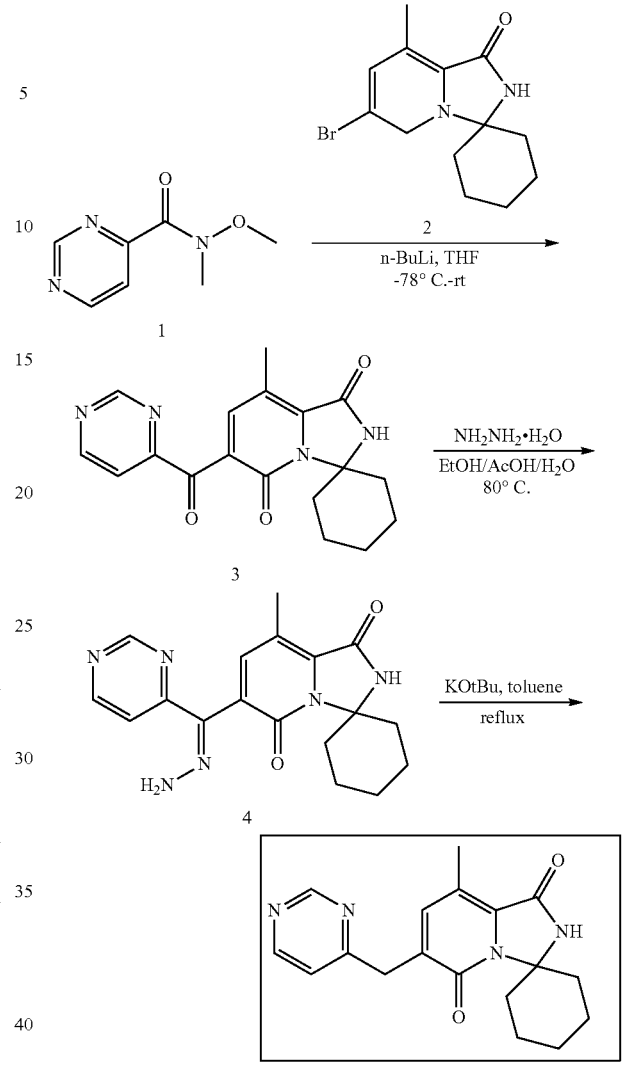

Synthesis of 8'-methyl-6'-(pyrimidine-4-carbonyl)-2'H-spiro[cyclohexane-1,3'-imidazo[1,5-a]pyridine]-1',5'-dione (3)

To a solution of 6'-bromo-8'-methyl-2'H-spiro[cyclohexane-1,3'-imidazo[1,5-a]pyridine]-1',5'-dione (2, 2 g, 6.43 mmol) in tetrahydrofuran (30 mL) at −78° C. is added n-butyllithium (1.6 M in hexanes, 12.06 mL, 19.29 mmol) dropwise, followed by N-methoxy-N-methylpyrimidine-4-carboxamide (1, 1.29 g, 7.72 mmol). The reaction is slowly warmed to room temperature and stirred for 4 h. The reaction is quenched via the slow addition of water. The mixture is warmed to room temperature and extracted with ethyl acetate. The organic layer is dried over magnesium sulfate, filtered and concentrated. The crude is purified via column chromatography to afford 8'-methyl-6'-(pyrimidine-4-carbonyl)-2'H-spiro[cyclohexane-1,3'-imidazo[1,5-a]pyridine]-1',5'-dione (3).

Synthesis of 6'-(hydrazono(pyrimidin-4-yl)methyl)-8'-methyl-2'H-spiro[cyclohexane-1,3'-imidazo[1,5-a]pyridine]-1',5'-dione (4)

To a solution of 8'-methyl-6'-(pyrimidine-4-carbonyl)-2'H-spiro[cyclohexane-1,3'-imidazo[1,5-a]pyridine]-1',5'- dione (3, 0.7 g, 2.07 mmol) in ethanol (4 mL), acetic acid (4 mL) and water (4 mL) is added hydrazine hydrate (0.13 g, 4.14 mmol). The reaction is stirred at 80° C. overnight. The reaction is cooled to room temperature and concentrated. The crude is resuspended in dichloromethane and is washed with saturated aqueous sodium bicarbonate solution. The organic layer is dried over magnesium sulfate, filtered and concentrated. The crude is purified via column chromatography to afford 6'-(hydrazono(pyrimidin-4-yl)methyl)-8'-methyl-2'H-spiro[cyclohexane-1,3'-imidazo[1,5-a]pyridine]-1',5'-dione (4).

Synthesis of 8'-methyl-6'-(pyrimidin-4-ylmethyl)-2'H-spiro[cyclohexane-1,3'-imidazo[1,5-a]pyridine]-1',5'-dione (Cpd. No. 212)

To a solution of 6'-(hydrazono(pyrimidin-4-yl)methyl)-8'-methyl-2'H-spiro[cyclohexane-1,3'-imidazo[1,5-a]pyridine]-1',5'-dione (4, 100 mg, 0.28 mmol) in toluene (4 mL) is added potassium tert-butoxide (94 mg, 0.84 mmol). The reaction is refluxed overnight. The resulting mixture is cooled to room temperature, diluted with dichloromethane and is hed with 1 M ammonium chloride solution. The organic layer is dried over magnesium sulfate, filtered and concentrated. The crude is purified via HPLC to afford 8'-methyl-6'-(pyrimidin-4-ylmethyl)-2'H-spiro[cyclohexane-1,3'-imidazo[1,5-a]pyridine]-1',5'-dione (Cpd. No. 212).

Example 213

Synthesis of 5-((6-aminopyrimidin-4-yl)amino)-3-chloro-1-isobutyl-6-oxo-1,6-dihydropyridine-2-carboxamide (Cpd. No. 213)

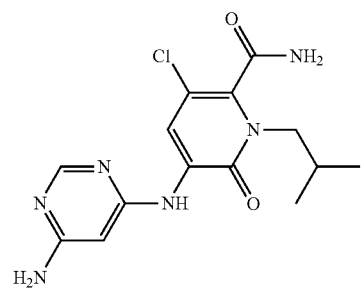 [SMILES: CC(C)Cn1c(C(N)=O)c(Cl)cc(Nc2cc(N)ncn2)c1=O]

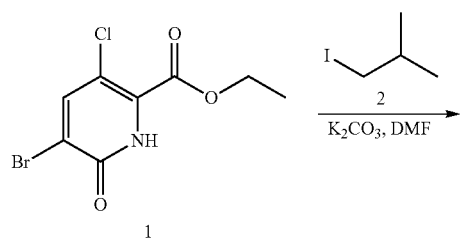

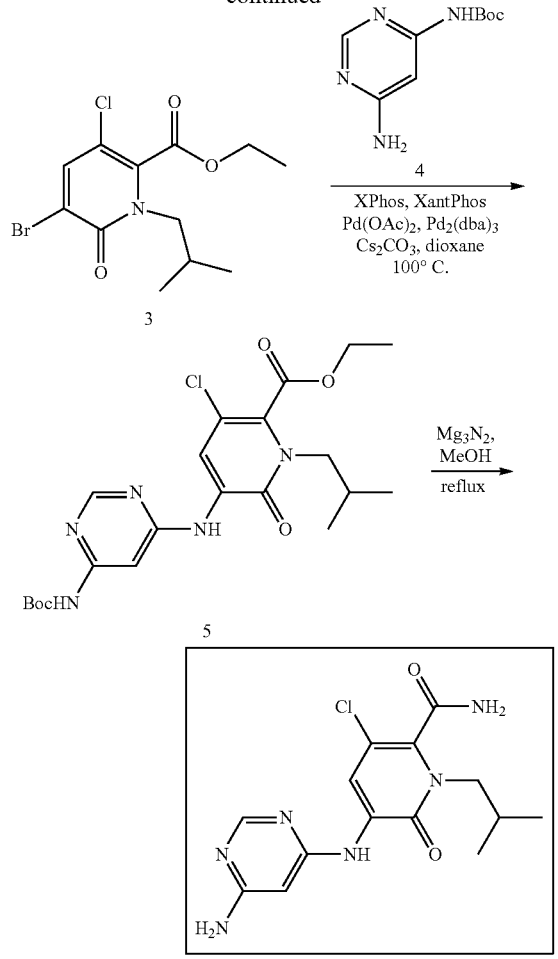

Synthesis of ethyl 5-bromo-3-chloro-1-isobutyl-6-oxo-1,6-dihydropyridine-2-carboxylate (3)

To a solution of ethyl 5-bromo-3-chloro-6-oxo-1,6-dihydropyridine-2-carboxylate (1, 1.0 g, 3.56 mmol) and 1-iodo-2-methylpropane (2, 1.31 g, 7.13 mmol) in dimethylformamide (12 mL) in a vial, potassium carbonate (261 mg, 1.89 mmol) was added and the mixture was stirred at room temperature for 16 h. After completion, the reaction mass was diluted with water (50 mL) and extracted with ethyl acetate (2×50 mL). Combined organic layer was washed with water, brine, dried over anhydrous sodium sulfate and concentrated under vacuum. The crude was purified by silica gel (220-400 mesh) column chromatography using 50% ethyl acetate in hexane as an eluent to afford ethyl 5-bromo-3-chloro-1-isobutyl-6-oxo-1,6-dihydropyridine-2-carboxylate (3) as light yellow solid. Yield: 0.70 g, 58%; MS (ESI) m/z 336.3 [M+1]+.

Synthesis of ethyl 5-((6-((tert-butoxycarbonyl)amino)pyrimidin-4-yl)amino)-3-chloro-1-isobutyl-6-oxo-1,6-dihydropyridine-2-carboxylate (5)

The synthesis of intermediate 5 was carried out as described above using the general protocol of Procedure H. Off white solid; Yield: 0.36 g, 40%; MS (ESI) m/z 466.2 [M+1]+.

Synthesis of 5-((6-aminopyrimidin-4-yl)amino)-3-chloro-1-isobutyl-6-oxo-1,6-dihydropyridine-2-carboxamide (Cpd. No. 213)

To a solution of ethyl 5-(((6-(((tert-butoxycarbonyl)amino)pyrimidin-4-yl)amino)-3-chloro-1-isobutyl-6-oxo-1,6-dihydropyridine-2-carboxylate (5, 300 mg, 0.64 mmol) in methanol (20 mL) was added magnesium nitride (3.25 g, 3.21 mmol) and the reaction was refluxed for 16 h. After completion, solvent was removed under reduced pressure and the resulting residue was stirred in 2N hydrochloric acid for 10 m. The reaction mixture was filtered and the obtained solid was dried under reduced pressure. The crude was purified by prep purification, to afford 5-((6-aminopyrimidin-4-yl)amino)-3-chloro-1-isobutyl-6-oxo-1,6-dihydropyridine-2-carboxamide (Cpd. No. 213) as an off white solid. Yield: 70 mg, 32%; MS (ESI) m/z 336.99 [M+1]$^+$; $^1$H NMR (400 MHz, DMSO-$d_6$) δ 9.46 (s, 1H), 8.33 (s, 1H), 8.27 (s, 1H), 7.87 (s, 1H), 7.59-7.54 (m, 3H), 6.05 (s, 1H), 4.17-4.16 (d, J=6.8 Hz, 2H), 2.08-2.01 (m, 1H), 0.95-0.93 (d, J=6.8 Hz, 6H).

Example 214

Synthesis of 5-((6-aminopyrimidin-4-yl)amino)-3-chloro-6-oxo-1,6-dihydropyridine-2-carboxamide (Cpd. No. 214)

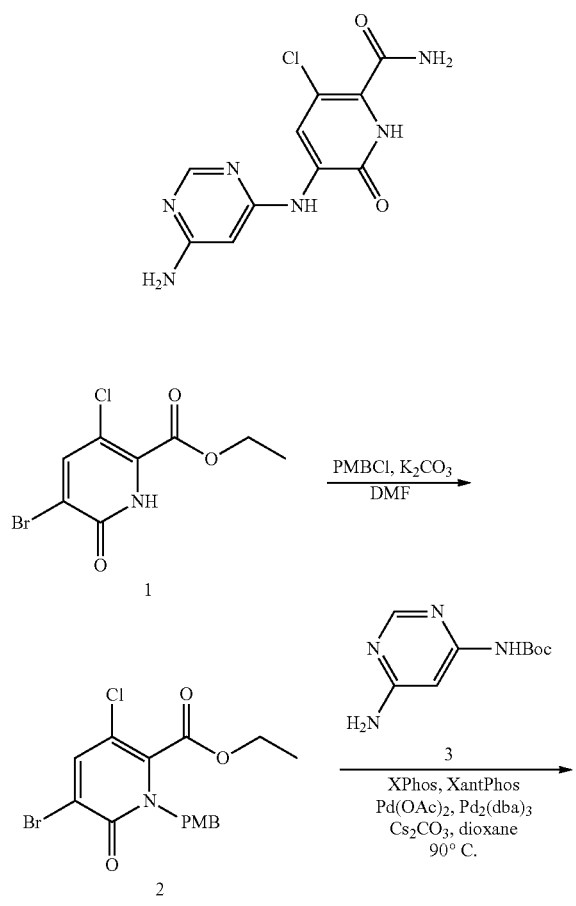

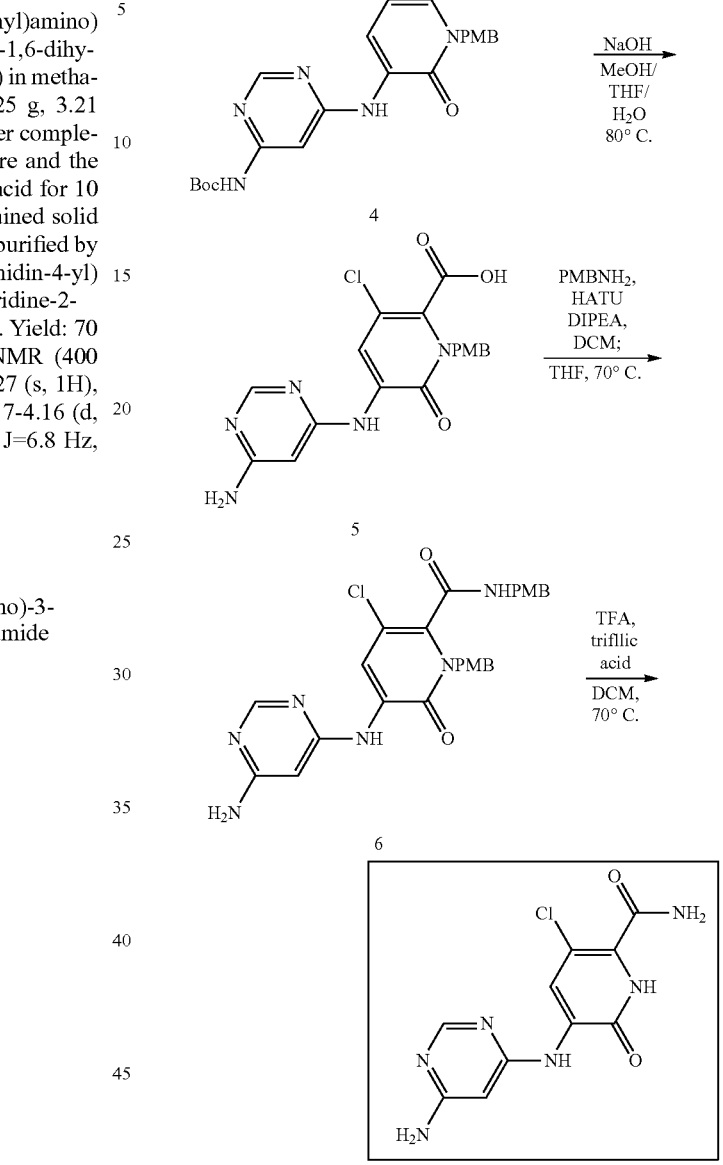

Synthesis of ethyl 5-bromo-3-chloro-1-(4-methoxybenzyl)-6-oxo-1,6-dihydropyridine-2-carboxylate (2)

A solution of ethyl 5-bromo-3-chloro-6-oxo-1,6-dihydropyridine-2-carboxylate (3.0 g, 10.7 mmol), 4-methoxybenzyl chloride (4.19, 26.74 mmol) and potassium carbonate (4.43 g, 32.09 mmol) in dimethylformamide (40 ml) was stirred at room temperature for 16 h. After completion, the reaction mixture was diluted with cold water (20 mL) and extracted with ethyl acetate (3×30 mL). The organic layer was again washed with brine, separated, dried over Sodium sulfate, filtered and concentrated under reduced pressure. The residue was finally purified by flash column chromatography to afford ethyl 5-bromo-3-chloro-1-(4-methoxybenzyl)-6-oxo-1,6-dihydropyridine-2-carboxylate (2) as off white solid. Yield: 1.2 g, 28%; MS (ESI) m/z 399.99 [M+1]⁺; ¹H NMR (400 MHz, DMSO-d₆) δ 8.27 (s, 1H), 7.11 (d, J=8.64 Hz, 2H), 6.89 (d, J=8.6 Hz, 2H), 5.11 (s, 2H), 4.27 (q, J=7.12 Hz, 2H), 3.72 (s, 3H), 1.13 (t, J=7.12 Hz, 3H).

Synthesis of ethyl 5-((6-((tert-butoxycarbonyl)amino)pyrimidin-4-yl)amino)-3-chloro-1-(4-methoxybenzyl)-6-oxo-1,6-dihydropyridine-2-carboxylate (4)

The synthesis of intermediate 4 was carried out as described above using the general protocol of Procedure H. Brown solid; Yield: 0.70 g, 44%; MS (ESI) m/z 530.17 [M+1]⁺; ¹H NMR (400 MHz, DMSO-d₆) δ 10.04 (s, 1H), 9.49 (s, 1H), 8.64 (s, 1H), 8.50 (s, 1H), 7.76 (s, 1H), 7.11 (d, J=8.2 Hz, 2H), 6.89 (d, J=8.44 Hz, 2H), 5.21 (s, 2H), 4.23 (q, J=6.92 Hz, 2H), 3.72 (s, 3H), 1.48 (s, 9H), 1.13 (t, J=7.04 Hz, 3H).

Synthesis of 5-((6-aminopyrimidin-4-yl)amino)-3-chloro-1-(4-methoxybenzyl)-6-oxo-1,6-dihydropyridine-2-carboxylic acid (5)

Sodium hydroxide (0.26 g, 6.6 mmol) was added to a suspension of ethyl 5-((6-((tert-butoxycarbonyl)amino)pyrimidin-4-yl)amino)-3-chloro-1-(4-methoxybenzyl)-6-oxo-1,6-dihydropyridine-2-carboxylate (0.70 g, 1.32 mmol) in methanol/tetrahydrofuran/water (2:1:1, 30 mL). The mixture was stirred at 80° C. for 16 h. After completion, the solvent was evaporated to dryness under reduced pressure. The crude was diluted with 1N hydrochloric acid. The precipitate obtained was collected by filtration, dried, washed with pentane and dried further to afford 5-((6-aminopyrimidin-4-yl)amino)-3-chloro-1-(4-methoxybenzyl)-6-oxo-1,6-dihydropyridine-2-carboxylic acid (5) as brown solid. Yield: 0.45 g, 85%; MS (ESI) m/z 402.09 [M+1]⁺; ¹H NMR (400 MHz, DMSO-d₆) δ 9.62 (s, 1H), 8.43 (s, 1H), 8.33 (s, 1H), 7.67 (brs, 2H), 7.19 (d, J=8.16 Hz, 2H), 6.87 (d, J=8.12 Hz, 2H), 6.39 (s, 1H), 5.18 (s, 2H), 3.71 (s, 3H).

Synthesis of 5-((6-aminopyrimidin-4-yl)amino)-3-chloro-N, 1-bis(4-methoxybenzyl)-6-oxo-1,6-dihydropyridine-2-carboxamide (6)

To a solution of 5-((6-aminopyrimidin-4-yl)amino)-3-chloro-1-(4-methoxybenzyl)-6-oxo-1,6-dihydropyridine-2-carboxylic acid (5, 0.40 g, 0.99 mmol) and 4-methoxybenzylamine (0.16 g, 1.19 mmol) in dimethylformamide (20 mL) was added N,N-diisopropylethylamine (0.39 g, 2.99 mmol) and HATU (0.57 g, 1.99 mmol) at room temperature. The reaction mixture was stirred for 40 h. Progress of the reaction was monitored by LCMS. To the reaction mixture was added tetrahydrofuran (20 mL) and the reaction was refluxed for 7 h. After completion, the reaction was diluted with water (20 mL) and extracted with 10% methanol in dichloromethane (2×30 mL). The combined organic layer was dried over sodium sulfate, filtered and evaporated under reduced pressure to obtain the crude. The crude was purified by flash column chromatography eluting at 1% methanol in dichloromethane. The best fractions were concentrated to afford 5-((6-aminopyrimidin-4-yl)amino)-3-chloro-N, 1-bis(4-methoxybenzyl)-6-oxo-1,6-dihydropyridine-2-carboxamide (6) as yellow solid. Yield: 0.44 g, 84%; MS (ESI) m/z 521.16 [M+1]⁺; ¹H NMR (400 MHz, DMSO-d₆) δ 9.35 (m, 1H), 8.74 (s, 1H), 8.53 (s, 1H), 8.17 (s, 1H), 7.19-7.16 (m, 4H), 6.87-6.80 (m, 4H), 6.53 (s, 2H), 6.17 (s, 1H), 5.07 (s, 2H), 4.34 (s, 2H), 3.73 (s, 6H).

Synthesis of 5-((6-aminopyrimidin-4-yl)amino)-3-chloro-6-oxo-1, 6-dihydropyridine-2-carboxamide (Cpd. No. 214)

To a solution of 5-((6-aminopyrimidin-4-yl)amino)-3-chloro-N, 1-bis(4-methoxybenzyl)-6-oxo-1,6-dihydropyridine-2-carboxamide (6, 0.40 g, 0.77 mmol) in dichloromethane (10 mL) was added trifluoroacetic acid (20 mL) and trifluoromethanesulfonic acid (1 mL) at 0° C. The reaction mixture was stirred at 70° C. for 2 h. After completion, the reaction mixture was concentrated and basified by aq. ammonia at 0° C. The precipitate obtained was collected by filtration, washed with water and dried to obtain the crude. The crude was stirred with methanol, filtered, washed with pentane and dried to afford 5-((6-aminopyrimidin-4-yl)amino)-3-chloro-6-oxo-1,6-dihydropyridine-2-carboxamide (Cpd. No. 214) as yellow solid. Yield: 0.035 g, 16%; MS (ESI) m/z 281.05 [M+1]⁺; ¹H NMR (400 MHz, DMSO-d₆) δ 12.02 (s, 1H), 8.66 (s, 1H), 8.50 (s, 1H), 8.17 (s, 1H), 7.92 (s, 1H), 7.86 (s, 1H), 6.53 (s, 2H), 6.18 (s, 1H).

Example 215

Synthesis of 3'-(pyrimidin-4-ylamino)-4'H-spiro[cyclohexane-1,6'-imidazo[1,5-a]pyrimidine]-4',8'(7'H)-dione (Cpd. No. 215)

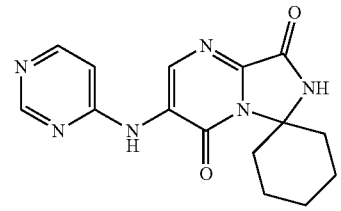 [SMILES: O=C1NC2(CCCCC2)n2c1ncc(Nc1ccncn1)c2=O]

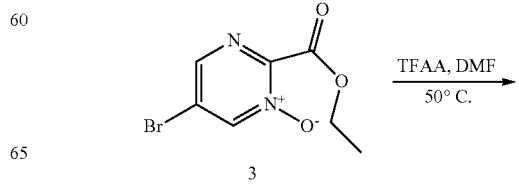

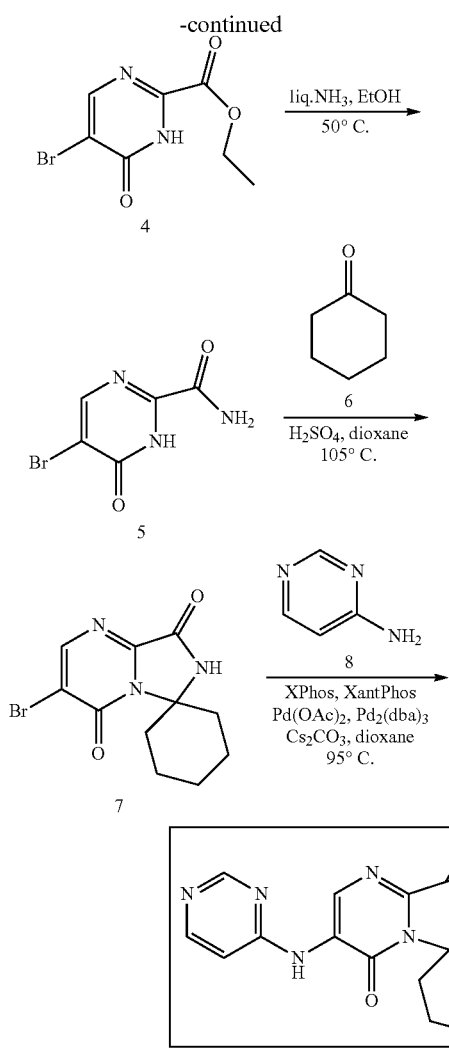

Synthesis of ethyl 5-bromopyrimidine-2-carboxylate (2)

To a solution of 5-bromopyrimidine-2-carboxylic acid (1, 4.0 g, 19.8 mmol) in ethanol (70 mL) at room temperature was added sulfuric acid (0.5 mL). The reaction mixture was heated at 80° C. for 16 h. TLC showed consumption of starting material. Concentrated the reaction mixture under reduce pressure to give residue which was diluted with water (30 mL) and extracted with ethyl acetate (2×100 mL). Combined organic layer was washed with sodium bicarbonate solution (50 mL) and then washed with brine (50 mL), dried over anhydrous sodium sulfate, filtered and concentrate under reduced pressure to afford ethyl 5-bromopyrimidine-2-carboxylate (2) as off white solid. Yield: 3.5 g, 77%; MS (ESI) m/z 230.91 [M+1]$^+$.

Synthesis of 5-bromo-2-(ethoxycarbonyl)pyrimidine 1-oxide (3)

To a 0° C. cooled solution of 1-ethyl 5-bromopyrimidine-2-carboxylate (2, 1.5 g, 6.5 mmol) in dichloromethane (30 mL), trifluoroacetic anhydride (13.69 g, 65 mmol) and Urea hydrogen peroxide (6.1 g, 65 mmol) were added. The reaction mixture was stirred at room temperature for 16 h. TLC showed consumption of starting material, the reaction mixture was diluted with water (10 mL) and neutralized with solid sodium bicarbonate. The solution was extracted with dichloromethane (2×40 mL). The organic layer was dried over anhydrous sodium sulfate, filtered and concentrated under reduced pressure to afford 5-bromo-2-(ethoxycarbonyl) pyrimidine 1-oxide (3) as yellow liquid which was used without further purification. Yield: 0.64 g, crude; MS (ESI) m/z 247.13 [M+1]$^+$.

Synthesis of ethyl 5-bromo-6-oxo-1,6-dihydropyrimidine-2-carboxylate (4)

To a 0° C. cooled solution of 5-bromo-2-(ethoxycarbonyl) pyrimidine 1-oxide (3, 0.62 g, 2.5 mmol) in dimethylformamide (6 mL), trifluoroacetic anhydride (3.1 g, 15 mmol) was added dropwise. The reaction mixture was heated at 50° C. for 18 h. TLC showed consumption of starting material and solvent was removed under reduced pressure. The residue was triturated with methanol (2 mL) and filtered. The solid was washed with diethyl ether and dried under reduced pressure to afford ethyl 5-bromo-6-oxo-1,6-dihydropyrimidine-2-carboxylate (4) as off white solid. Yield: 0.21 g, 34%; MS (ESI) m/z 245.09 [M−1]$^-$.

Synthesis of 5-bromo-6-oxo-1,6-dihydropyrimidine-2-carboxamide (5)

To a solution of ethyl 5-bromo-6-oxo-1,6-dihydropyrimidine-2-carboxylate (4, 0.2 g, 0.81 mmol) in ethanol (4 mL), liquid ammonia (4 mL) was added dropwise at room temperature. The reaction mixture was heated at 50° C. for 16 h. TLC showed consumption of starting material. Solvent was removed under reduced pressure and the residue was treated with methanol (1 mL) and filtered. The solid was washed with diethyl ether and dried under reduced pressure to afford 5-bromo-6-oxo-1,6-dihydropyrimidine-2-carboxamide (5) as off white solid. Yield: 0.14 g, 76%; MS (ESI) m/z 218.87 [M+1]$^+$.

Synthesis of 3'-bromo-4'H-spiro[cyclohexane-1,6'-imidazo[1,5-a]pyrimidine]-4',8'(7'H)-dione (7)

The synthesis of intermediate 7 was carried out as described above using the general protocol of Procedure A. Off white solid; Yield: 0.085 g, 50%; 1H NMR (400 MHz, DMSO-d$_6$) δ 10.96 (s, 1H), 8.55 (s, 1H), 6.94-7.20 (m, 2H), 3.36 (s, 1H), 2.65-2.71 (m, 2H), 1.61-1.73 (m, 2H), 1.19-1.22 (m, 1H).

Synthesis of 3'-(pyrimidin-4-ylamino)-4'H-spiro[cyclohexane-1,6'-imidazo[1,5-a]pyrimidine]-4',8'(7'H)-dione (Cpd. No. 215)

The synthesis of compound 215 was carried out as described above using the general protocol of Procedure H. Yellow solid; Yield: 0.014 g, 17%; MS (ESI) m/z 313.14 [M+1]$^+$; $^1$H NMR (400 MHz, DMSO-d$_6$) δ 10.77 (s, 1H), 9.42 (s, 1H), 9.34 (s, 1H), 8.77 (s, 1H), 8.38 (s, 1H), 7.35 (s, 1H), 2.85-2.72 (m, 2H), 1.85-1.54 (m, 7H), 1.30-1.20 (m, 1H).

Example 216

Synthesis of 8'-methyl-6'-(pyrimidin-4-ylamino)-2'H-spiro[cyclohexane-1,3'-imidazo[1,5-a]pyrazine]-1',5'-dione (Cpd. No. 216)

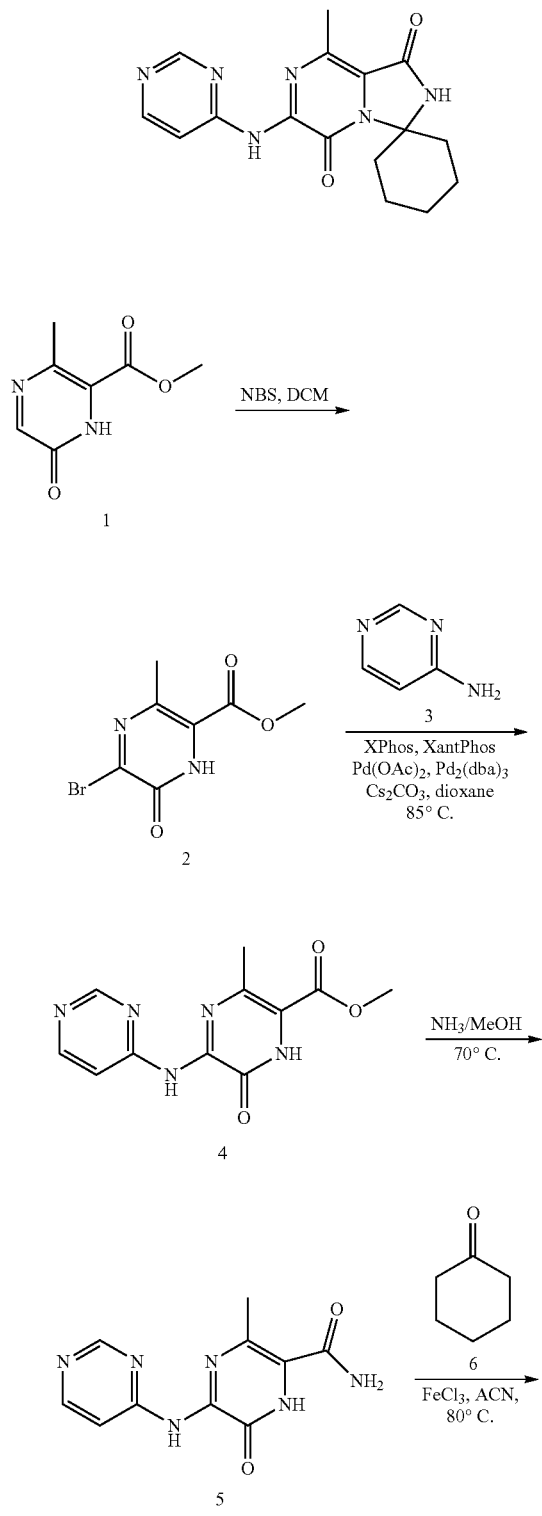

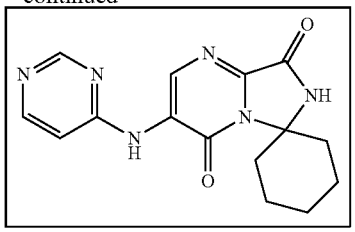

Synthesis of methyl 5-bromo-3-methyl-6-oxo-1,6-dihydropyrazine-2-carboxylate (2)

Methyl 3-methyl-6-oxo-1,6-dihydropyrazine-2-carboxylate (2.0 g, 11.89 mmol) was dissolved in dichloromethane (30 mL) and N-bromosuccinimide (2.12 g, 11.89 mmol) was added. The reaction was allowed to stir at room temperature for 16 h. On completion, the reaction mixture was washed with water and brine, dried over anhydrous sodium sulfate, filtered and concentrated. The solid was washed with ether to afford methyl 5-bromo-3-methyl-6-oxo-1,6-dihydropyrazine-2-carboxylate (2) as light brown solid. Yield: 1.25 g, 42%; MS (ESI) m/z 247.04 [M+1]$^+$; $^1$H NMR (400 MHz, DMSO-d$_6$) δ 12.92 (brs, 1H), 3.87 (s, 4H), 2.50 (s, 3H).

Synthesis of methyl 3-methyl-6-oxo-5-(pyrimidin-4-ylamino)-1,6-dihydropyrazine-2-carboxylate (4)

The synthesis of intermediate 4 was carried out as described above using the general protocol of Procedure H. Yellow solid; Yield: 500 mg, 48%; MS (ESI) m/z 262.22 [M+1]$^+$; $^1$H NMR (400 MHz, DMSO-d$_6$) δ 12.16 (brs, 1H), 9.14 (s, 1H), 8.69-8.68 (d, J=5.6 Hz, 1H), 8.49-8.47 (d, J=5.6 Hz, 1H), 3.80 (s, 3H), 2.50 (s, 3H).

Synthesis of 3-methyl-6-oxo-5-(pyrimidin-4-ylamino)-1,6-dihydropyrazine-2-carboxamide (5)

The synthesis of intermediate 5 was carried out as described above using the general protocol of Procedure K. Brown solid. Yield: 350 mg, 74%; MS (ESI) m/z 247.01 [M+1]$^+$.

Synthesis of 8'-methyl-6'-(pyrimidin-4-ylamino)-2'H-spiro[cyclohexane-1,3'-imidazo[1,5-a]pyrazine]-1',5'-dione (Cpd. No. 216)

To a solution of 3-Methyl-6-oxo-5-(pyrimidin-4-ylamino)-1,6-dihydropyrazine-2-carboxamide (5, 100 mg, 0.41 mmol) and cyclohexanone (199 mg, 2.03 mmol) in acetonitrile in a 20 mL microwave vial was added iron(III) chloride (197 mg, 1.21 mmol). The reaction was heated at 80° C. for 16 h. On completion of the reaction, solvent was removed under vacuum and the crude was purified by silica gel (200-400 mesh) column chromatography eluting with 5% methanol in dichloromethane. Appropriate column fractions were concentrated under reduced pressure to afford 8'-methyl-6'-(pyrimidin-4-ylamino)-2'H-spiro[cyclohexane-1,3'-imidazo[1,5-a]pyrazine]-1',5'-dione (Cpd. No. 216) as off white solid. Yield: 8.5 mg, 6%; MS (ESI) m/z 327.13 [M+1]$^+$; $^1$H NMR (400 MHz, DMSO-d$_6$) δ 10.17 (s, 1H), 9.11 (s, 1H), 8.88 (s, 1H), 8.72 (d, J=4.0 Hz 1H), 8.47 (d, J=4.0 Hz, 1H), 2.85-2.74 (m, 2H), 2.54 (s, 3H), 1.80-1.50 (m, 7H), 1.30-120 (m, 1H).

Example 217

Synthesis of 8-((6-aminopyrimidin-4-yl)amino)-10-methyl-2,3,4,5-tetrahydropyrido[1,2-a][1,4]diazepine-1,7-dione (Cpd. No. 217)

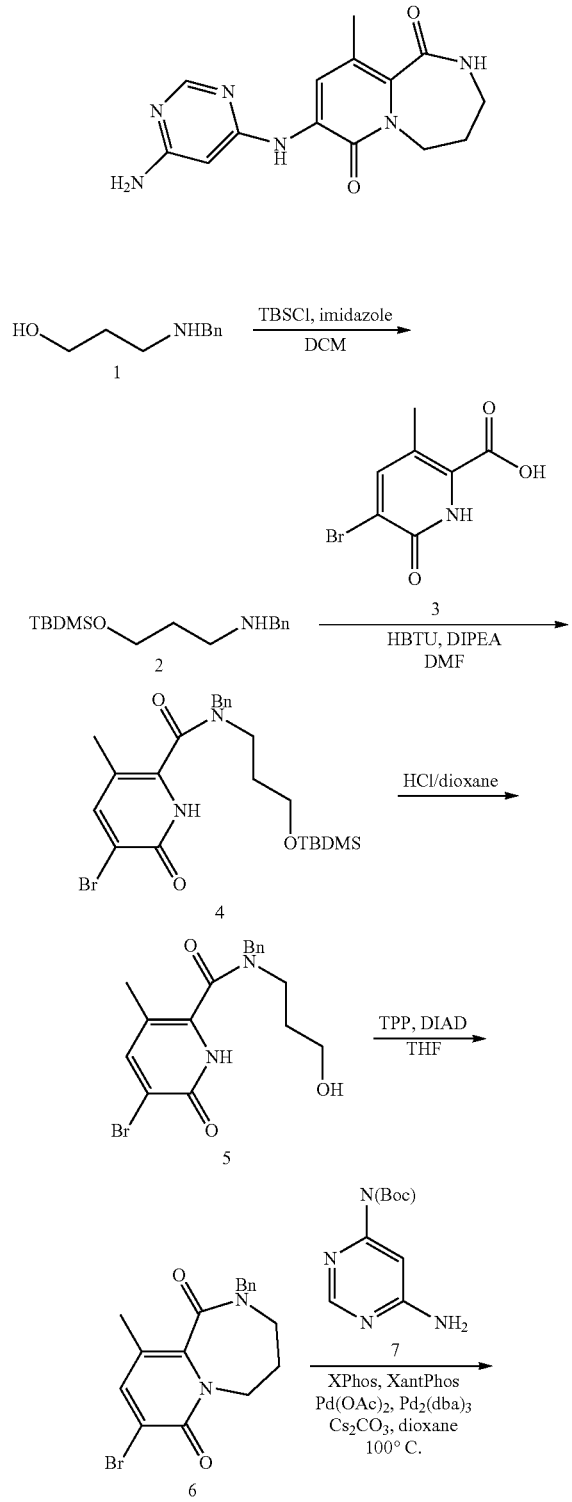

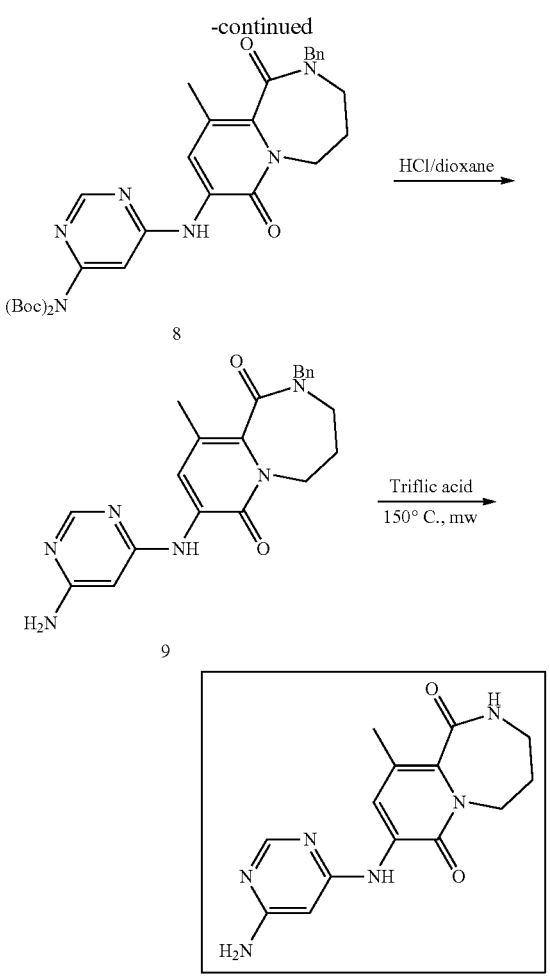

Synthesis of N-benzyl-3-((tert-butyldimethylsilyl)oxy) propan-1-amine (2)

To a stirred solution of 3-(benzylamino)propan-1-ol (1, 2.0 g, 12.1 mmol) in dichloromethane (20 mL), imidazole (2.47 g, 36.0 mmol) and tert-butyldimethylsilyl chloride (1.1 g, 13 mmol) were added at room temperature. The reaction mass was stirred at room temperature for 16 h. Water was added to the reaction mixture and layers were separated. The organic layer was dried over sodium sulfate, filtered and concentrated to afford N-benzyl-3-((tert-butyldimethylsilyl) oxy) propan-1-amine (2) as brown solid. Yield: 3.2 g, 94%; MS (ESI) m/z 280.29 [M−1]⁻.

Synthesis of N-benzyl-5-bromo-N-(3-((tert-butyldimethylsilyl) oxy) propyl)-3-methyl-6-oxo-1, 6-dihydropyridine-2-carboxamide (4)

To a stirred solution of N-benzyl-3-((tert-butyldimethylsilyl)oxy)propan-1-amine (2, 3.0 g, 12.9 mmol) in dimethylformamide (50 mL), 5-bromo-3-methyl-6-oxo-1,6-dihydropyridine-2-carboxylic acid (3, 3.6 g, 12.9 mmol), HBTU (6.4 g, 16.9 mmol) and N,N-diisopropylethylamine (2.2 g, 16.9 mmol) were added at room temperature. The mixture was stirred for 16 h. TLC showed completion of reaction. The reaction mixture was quenched with aqeous sodium bicarbonate solution and extracted with ethyl acetate (250 mL). The organic layer was dried over sodium sulfate, filtered and concentrated to afford N-benzyl-5-bromo-N-(3-((tert-butyldimethylsilyl) oxy) propyl)-3-methyl-6-oxo-1, 6-dihydropyridine-2-carboxamide (4) as yellow liquid. Yield: 3.0 g, 47%; MS (ESI) m/z 495.24 [M−1]⁻.

Synthesis of N-benzyl-5-bromo-N-(3-hydroxypropyl)-3-methyl-6-oxo-1, 6-dihydropyridine-2-carboxamide (5)

To a stirred solution of N-benzyl-5-bromo-N-(3-((tert-butyldimethylsilyl)oxy)propyl)-3-methyl-6-oxo-1,6-dihydropyridine-2-carboxamide (4, 3.0 g, 6.0 mmol) in dioxane (20 mL), hydrochloric acid in dioxane (20 mL) was added at room temperature. The mixture was stirred for 16 h. After completion, the solvent was removed. The residue was diluted with aqeous sodium bicarbonate and extracted with 5% methanol/dichloromethane (3×200 mL). The organic layer was dried over sodium sulfate, filtered and concentrated to get N-benzyl-5-bromo-N-(3-hydroxypropyl)-3-methyl-6-oxo-1, 6-dihydropyridine-2-carboxamide (5) as brown liquid. Yield: 2.2 g, 95%; MS (ESI) m/z 381.22 [M−1]⁻.

Synthesis of 2-benzyl-8-bromo-10-methyl-2, 3, 4, 5-tetrahydropyrido [1, 2-a] [1, 4]diazepine-1, 7-dione (6)

To a stirred solution of N-benzyl-5-bromo-N-(3-hydroxypropyl)-3-methyl-6-oxo-1,6-dihydropyridine-2-carboxamide (5, 1.5 g, 3.9 mmol) in tetrahydrofuran (30 mL), triphenylphosphine (1.5 g, 5.9 mmol) and diisopropyl azodicarboxylate (1.2 g, 5.9 mmol) were added at 0° C. The mixture was stirred at room temperature for 16 h. After completion, solvent was removed under reduced pressure and the crude was purified by flash chromatography eluting with 40% ethyl acetate in hexane. Appropriate fractions were concentrated under reduced pressure to afford 2-benzyl-8-bromo-10-methyl-2,3,4,5-tetrahydropyrido[1,2-a][1,4]diazepine-1,7-dione (6) as yellow solid. Yield: 0.9 g, 64%; MS (ESI) m/z 361.18 [M+1]⁺.

Synthesis of 8-((6-(di-(tert-butoxycarbonyl)-amino) pyrimidin-4-yl)amino)-2-benzyl-10-methyl-2,3,4,5-tetrahydropyrido[1,2-a][1,4]diazepine-1, 7-dione (8)

The synthesis of intermediate 8 was carried out as described above using the general protocol of Procedure H. Yellow solid; Yield: 0.9 g, 69%; MS (ESI) m/z 591.66 [M+1]⁺.

Synthesis of 8-((6-aminopyrimidin-4-yl)amino)-2-benzyl-10-methyl-2, 3,4,5-tetrahydropyrido[1,2-a] [1,4]diazepine-1, 7-dione (9)

The synthesis of intermediate 9 was carried out as described above using the general protocol of Procedure D. Yellow solid. Yield: 0.59 g, 99%; MS (ESI) m/z 391.32 [M+1]⁺.

Synthesis of 8-((6-aminopyrimidin-4-yl)amino)-10-methyl-2,3,4,5-tetrahydropyrido[1,2-a][1,4]diazepine-1, 7-dione (Cpd. No. 217)

A vial was charged with 8-((6-aminopyrimidin-4-yl) amino)-2-benzyl-10-methyl-2,3,4,5-tetrahydropyrido[1,2-a] [1,4]diazepine-1,7-dione (9, 0.3 g, 76.9 mmol) and triflic acid (7.0 mL) was added. The reaction mixture was heated under microwave at 150° C. for 20 min. TLC showed completion of the reaction and the mixture was cooled to ambient temperature. This was then basified with aqeous sodium bicarbonate solution and extracted with 5% methanol/dichloromethane (3×200 mL). The organic layer was dried over sodium sulfate and solvent was removed under reduced pressure to afford 8-((6-aminopyrimidin-4-yl) amino)-10-methyl-2,3,4,5-tetrahydropyrido[1,2-a][1,4]diazepine-1,7-dione (Cpd. No. 217) as a brown solid. Yield: 0.06 g, 26%; MS (ESI) m/z 301.15 [M+1]⁺; ¹H NMR (400 MHz, DMSO-d₆) δ 8.51 (s, 1H), 8.36-8.20 (m, 2H), 8.15 (s, 1H), 6.52 (brs, 2H), 6.13 (s, 1H), 5.05 (brs, 1H), 3.26-3.04 (m, 2H), 2.95-2.80 (m, 1H), 2.13 (s, 3H), 1.87 (brs, 2H).

Example 218

Synthesis 6-amino-4-((8'-methyl-1',5'-dioxo-1',5'-dihydro-2'H-spiro[cyclohexane-1,3'-imidazo[1,5-a] pyridin]-6'-yl)amino)pyrimidine 1-oxide (Cpd. No. 218)

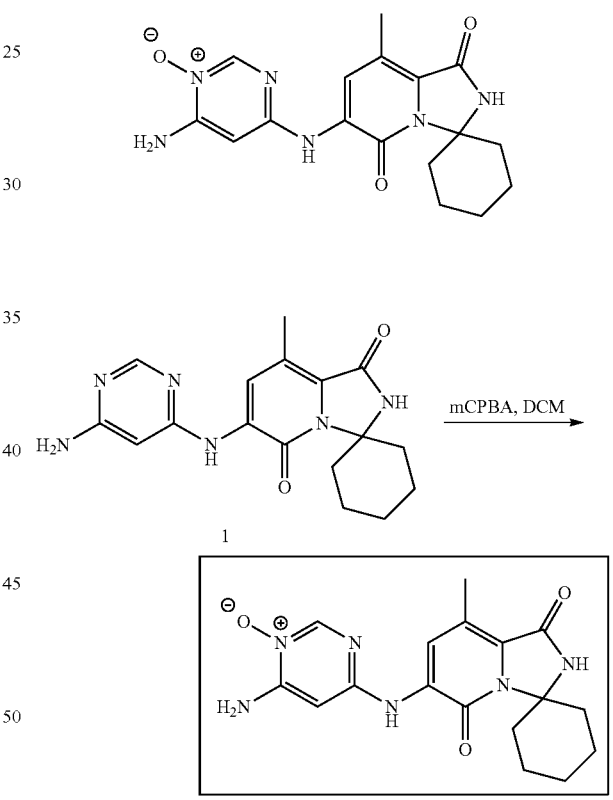

Synthesis of 6-amino-4-((8'-methyl-1',5'-dioxo-1',5'-dihydro-2'H-spiro[cyclohexane-1,3'-imidazo[1,5-a] pyridin]-6'-yl)amino)pyrimidine 1-oxide (Cpd. No. 218)

To a solution of 6'-((6-aminopyrimidin-4-yl)amino)-8'-methyl-2'H-spiro[cyclohexane-1,3'-imidazo[1,5-a]pyridine]-1',5'-dione (1, 0.1 g, 0.29 mmol) in dichloromethane (25 mL), 3-chloroperbenzoic acid (0.10 g, 0.59 mmol) was added. The reaction mixture was stirred at room temperature for 16 h. After completion the reaction mixture was diluted with saturated sodium bicarbonate solution (50 mL) and stirred for 30 m at room temperature. Yellow solid precipitated out and was filtered and dried to obtain the crude. The crude was purified by prep purification to afford 6-amino-4-((8'-methyl-1',5'-dioxo-1',5'-dihydro-2'H-spiro[cyclohexane-1,3'-imidazo[1,5-a]pyridin]-6'-yl)amino)pyrimidine 1-oxide (Cpd. No. 218) as yellow solid. Yield: 50 mg, 50%; MS (ESI) m/z 357.18 [M+1]$^+$; $^1$H NMR (400 MHz, DMSO-d$_6$) δ 10.02 (s, 1H), 9.01 (s, 1H), 8.53 (s, 1H), 8.23 (s, 1H), 7.48 (brs, 1H), 6.65 (s, 1H), 3.02-2.96 (m, 2H), 2.42 (s, 3H), 1.75-1.58 (m, 5H), 1.45-1.42 (m, 2H), 1.22-1.19 (m, 1H).

Example 219

Synthesis of 6-((6-aminopyrimidin-4-yl)amino)-1',8-dimethyl-2H-spiro[imidazo[1,5-a]pyridine-3,4'-piperidine]-1,5-dione hydrochloride (Cpd. No. 219)

Synthesis of tert-butyl N-tert-butoxycarbonyl-N-(6-((1',8-dimethyl-1,5-dioxo-1,5-dihydro-2H-spiro[imidazo[1,5-a]pyridine-3,4'-piperidin]-6-yl)amino)pyrimidin-4-yl)carbamate (3)

The synthesis of intermediate 3 was carried out as described above using the general protocol of Procedure H. Off white solid; Yield: 320 mg, 38%; MS (ESI) m/z 556.67 [M+1]$^+$.

Synthesis of 6-((6-aminopyrimidin-4-yl)amino)-1',8-dimethyl-2H-spiro[imidazo[1,5-a]pyridine-3,4'-piperidine]-1,5-dione hydrochloride (Cpd. No. 219)

The synthesis of compound 219 was carried out as described above using the general protocol of Procedure F. Light yellow solid. Yield: 274 mg, 97%; MS (ESI) m/z 356.18 [M+1]$^+$; $^1$H NMR (400 MHz, DMSO-d$_6$) δ 10.64 (brs, 1H), 10.45 (s, 1H), 9.73 (s, 1H), 8.46 (s, 1H), 8.15 (s, 1H), 7.91 (brs, 2H), 6.45 (s, 1H), 3.62-3.42 (m, 6H), 2.82 (s, 3H), 2.46 (s, 3H), 1.81-1.78 (m, 2H).

Example 220

Synthesis of 6-((6-amino-5-methylpyrimidin-4-yl)amino)-1',8-dimethyl-2H-spiro[imidazo[1,5-a]pyridine-3,4'-piperidine]-1,5-dione (Cpd. No. 220)

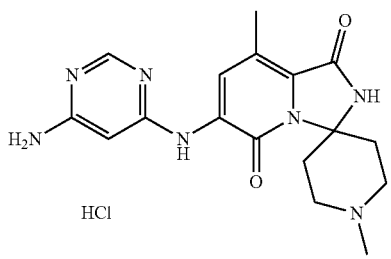 [SMILES: Cc1cc(Nc2cc(N)ncn2)c(=O)n2c1C(=O)NC21CCN(C)CC1 ; Cl]

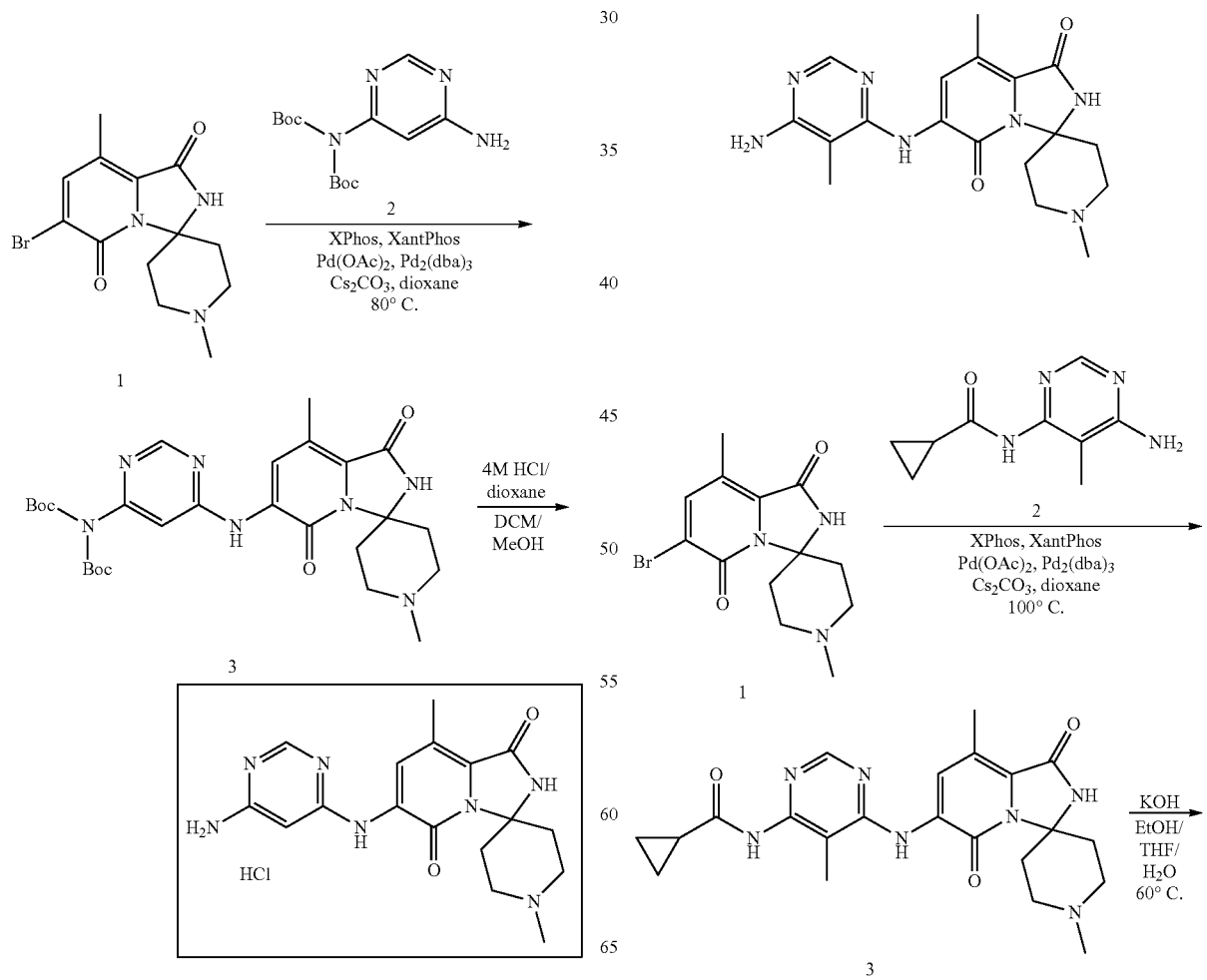

-continued

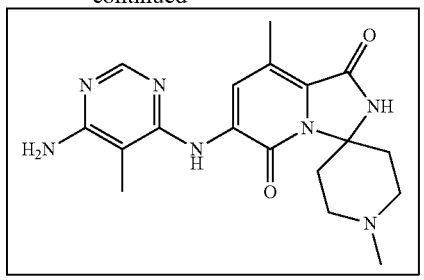

Synthesis of N-(6-((1',8-dimethyl-1,5-dioxo-1,5-dihydro-2H-spiro[imidazo[1,5-a]pyridine-3,4'-piperidin]-6-yl)amino)-5-methylpyrimidin-4-yl)cyclopropanecarboxamide (3)

The synthesis of intermediate 3 was carried out as described above using the general protocol of Procedure H. Yellow solid. Yield: 450 mg, 67%; MS (ESI) m/z 438.36 [M+1]+.

Synthesis of 6-((6-amino-5-methylpyrimidin-4-yl)amino)-1',8-dimethyl-2H-spiro[imidazo[1,5-a]pyridine-3,4'-piperidine]-1,5-dione (Cpd. No. 220)

The synthesis of compound 220 was carried out as described above using the general protocol of Procedure I. Off white solid. Yield: 150 mg, 39%; MS (ESI) m/z 370.20 [M+1]+; $^1$H NMR (400 MHz, DMSO-$d_6$) δ 10.07 (s, 1H), 8.47 (s, 1H), 8.11 (s, 1H), 8.00 (s, 1H), 6.48 (s, 2H), 3.30-3.20 (m, 2H), 2.78-2.75 (m, 2H), 2.44 (s, 3H), 2.40-2.32 (m, 2H), 2.24 (s, 3H), 1.98 (s, 3H), 1.40-1.36 (m, 2H).

Example 221

Synthesis of 6'-((2-chloropyrimidin-4-yl)thio)-8'-methyl-2'H-spiro[cyclohexane-1,3'-imidazo[1,5-a]pyridine]-1',5'-dione (Cpd. No. 221)

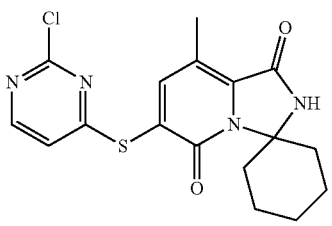 [SMILES: Cc1cc(Sc2ccnc(Cl)n2)c(=O)n2c1C(=O)NC21CCCCC1]

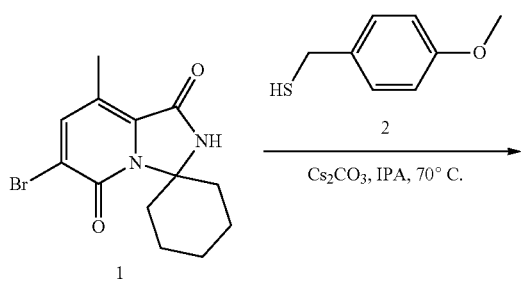

-continued

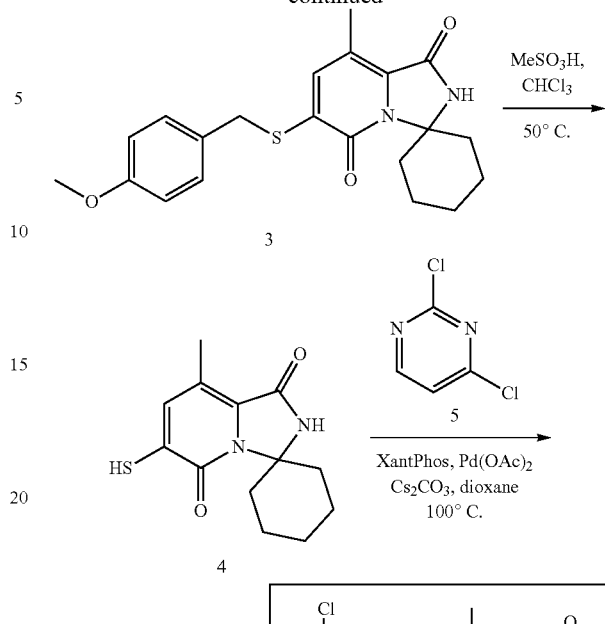

Synthesis of 6'-((4-methoxybenzyl)thio)-8'-methyl-2'H-spiro[cyclohexane-1,3'-imidazo[1,5-a]pyridine]-1',5'-dione (3)

6'-Bromo-8'-methyl-2'H-spiro[cyclohexane-1,3'-imidazo[1,5-a]pyridine]-1',5'-dione (1, 2.0 g, 6.42 mmol) was dissolved in 2-propanol (20 mL). To this mixture was added cesium carbonate (6.28 g, 19.28 mmol), followed by (4-methoxyphenyl)methanethiol (1.18 g, 7.71 mmol). The reaction mixture was stirred at 70° C. for 16 h. After completion, solvent was evaporated under reduced pressure and the crude was washed with water (50 mL) followed by diethyl ether and then dried under reduced pressure to afford 6'-((4-methoxybenzyl)thio)-8'-methyl-2'H-spiro[cyclohexane-1,3'-imidazo[1,5-a]pyridine]-1',5'-dione (3) as grey solid. Yield: 2.15 g, 87%; MS (ESI) m/z 385.5 [M+1]+.

Synthesis of 6'-mercapto-8'-methyl-2'H-spiro[cyclohexane-1,3'-imidazo[1,5-a]pyridine]-1',5'-dione (4)

6'-((4-Methoxybenzyl)thio)-8'-methyl-2'H-spiro[cyclohexane-1,3'-imidazo[1,5-a]pyridine]-1',5'-dione (3, 3.3 g, 8.59 mmol) was dissolved in chloroform (20 mL) and methanesulfonic acid (10 mL) was added. The reaction mixture was stirred at 50° C. for 16 h. After completion, solvent was evaporated under reduced pressure. Obtained crude was washed with water (50 mL) followed by ethyl acetate and then dried under reduced pressure to afford 6'-mercapto-8'-methyl-2'H-spiro[cyclohexane-1,3'-imidazo[1,5-a]pyridine]-1',5'-dione as grey solid. Yield: 1.3 g, 59%; MS (ESI) m/z 265.6 [M+1]+.

Synthesis of 6'-((2-chloropyrimidin-4-yl)thio)-8'-methyl-2'H-spiro[cyclohexane-1,3'-imidazo[1,5-a]pyridine]-1',5'-dione (Cpd. No. 221)

The synthesis of compound 221 was carried out as described above using the general protocol of Procedure B. White solid; Yield: 0.4 g, 56%; MS (ESI) m/z 377.27 [M+1]$^+$; $^1$H NMR (400 MHz, DMSO-d$_6$) δ 10.52 (s, 1H), 8.45 (d, J=5.2 Hz, 1H), 8.08 (s, 1H), 7.32 (d, J=5.6 Hz, 1H), 2.92-2.84 (m, 2H), 2.42 (s, 3H), 1.74-1.71 (m, 2H), 1.65-1.52 (m, 3H), 1.47-1.44 (m, 2H), 1.18-1.15 (m, 1H).

Example 222

Synthesis of 6'-((6-amino-5-methylpyrimidin-4-yl)amino)-8'-methyl-2'H-spiro[cyclohexane-1,3'-imidazo[1,5-a]pyridine]-1',5'-dione (Cpd. No. 222)

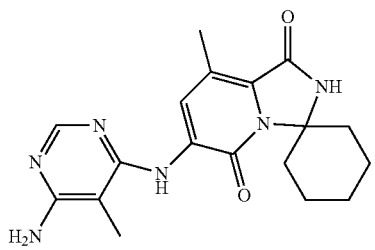 [SMILES: Cc1cc(Nc2ncnc(N)c2C)c(=O)n2c1C(=O)NC21CCCCC1]

Synthesis of N-(5-methyl-6-((8'-methyl-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (3)

The synthesis of intermediate 3 was carried out as described above using the general protocol of Procedure H. Yellow solid; Yield: 0.17 g, 31%; MS (ESI) m/z 423.21 [M+1]$^+$.

Synthesis of 6'-((6-amino-5-methylpyrimidin-4-yl)amino)-8'-methyl-2'H-spiro[cyclohexane-1,3'-imidazo[1,5-a]pyridine]-1',5'-dione (Cpd. No. 222)

The synthesis of compound 222 was carried out as described above using the general protocol of Procedure I. White solid; Yield: 0.10 g, 70%; MS (ESI) m/z 355.18 [M+1]$^+$; $^1$H NMR (400 MHz, DMSO-d$_6$) δ 10.05 (s, 1H), 8.48 (s, 1H), 8.12 (s, 1H), 8.01 (s, 1H), 6.48 (s, 2H), 2.98 (t, J=9.2 Hz, 2H), 2.45 (s, 3H), 1.98 (s, 3H), 1.73-1.58 (m, 5H), 1.48-1.42 (m, 2H), 1.30-1.23 (m, 1H).

Example 223

Synthesis of 6'-((6-amino-5-chloropyrimidin-4-yl)amino)-8'-methyl-2'H-spiro[cyclohexane-1,3'-imidazo[1,5-a]pyridine]-1',5'-dione hydrochloride (Cpd. No. 223)

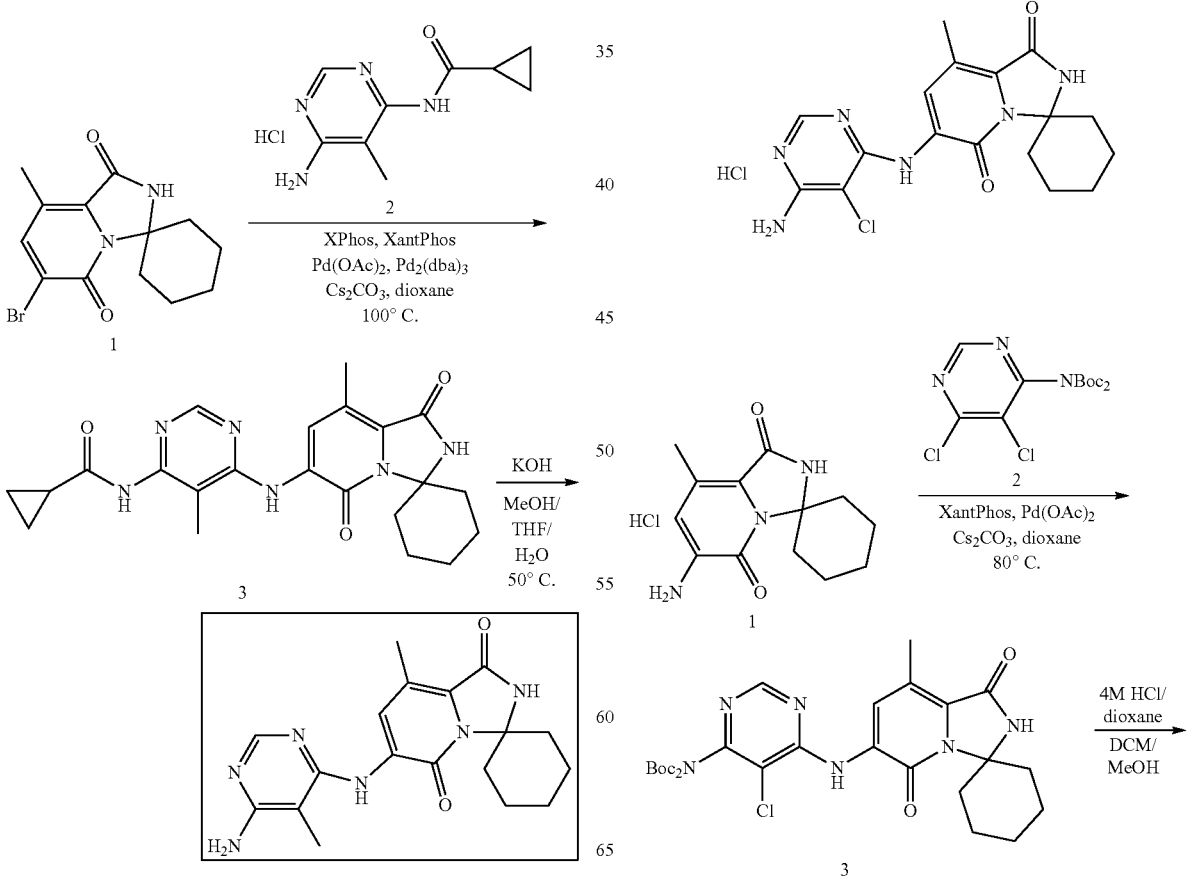

-continued

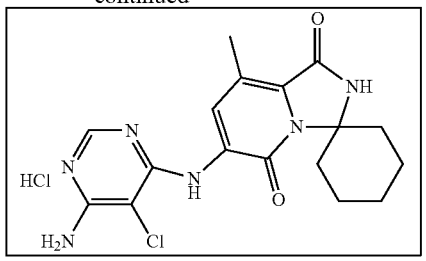

Synthesis of tert-butyl N-tert-butoxycarbonyl-N-(5-Chloro-6-((8'-methyl-1',5'-dioxo-1',5'-dihydro-2'H-spiro[cyclohexane-1,3'-imidazo[1,5-a]pyridin]-6'-yl) amino)pyrimidin-4-yl)carbamate (3)

The synthesis of intermediate 3 was carried out as described above using the general protocol of Procedure B. Off white solid; Yield: 0.32 g, 39%; MS (ESI) m/z 575.23 [M+1]$^+$; $^1$H NMR (400 MHz, DMSO-d$_6$) δ 10.26 (s, 1H), 9.03 (s, 1H), 8.79 (s, 1H), 8.55 (s, 1H), 2.96 (m, 2H), 2.5 (s, 3H), 1.76-1.58 (m, 5H), 1.49 (m, 2H), 1.39 (s, 18H), 1.25 (m, 1H).

Synthesis of 6'-((6-amino-5-chloropyrimidin-4-yl) amino)-8'-methyl-2'H-spiro[cyclohexane-1,3'-imidazo[1,5-a]pyridine]-1',5'-dione hydrochloride (Cpd. No. 223)

The synthesis of compound 223 was carried out as described above using the general protocol of Procedure F. Yellow solid. Yield: 0.20 g, 88%; MS (ESI) m/z 375.13 [M+1]$^+$; $^1$H NMR (400 MHz, DMSO-d$_6$) δ 10.15 (s, 1H), 8.60 (s, 1H), 8.47 (s, 1H), 8.21 (s, 1H), 7.23 (brs, 2H), 2.97 (t, J=9.6, Hz, 2H), 2.46 (s, 3H), 1.76-1.58 (m, 5H), 1.48-1.42 (m, 2H), 1.30-1.21 (m, 1H).

Example 224

Synthesis of 6'-((2-chloropyrimidin-4-yl)oxy)-8'-methyl-2'H-spiro[cyclohexane-1,3'-imidazo[1,5-a] pyridine]-1',5'-dione (Cpd. No. 224)

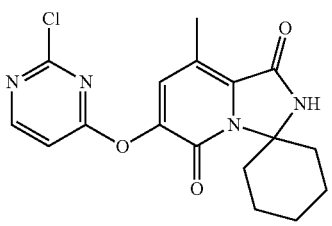 [SMILES: Cc1cc(Oc2ccnc(Cl)n2)c(=O)n2c1C(=O)NC21CCCCC1]

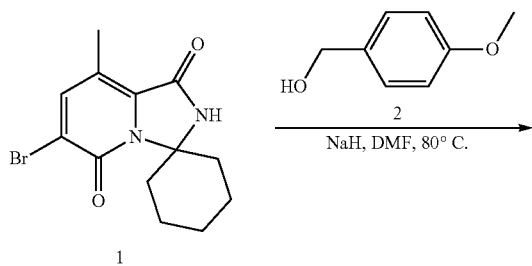

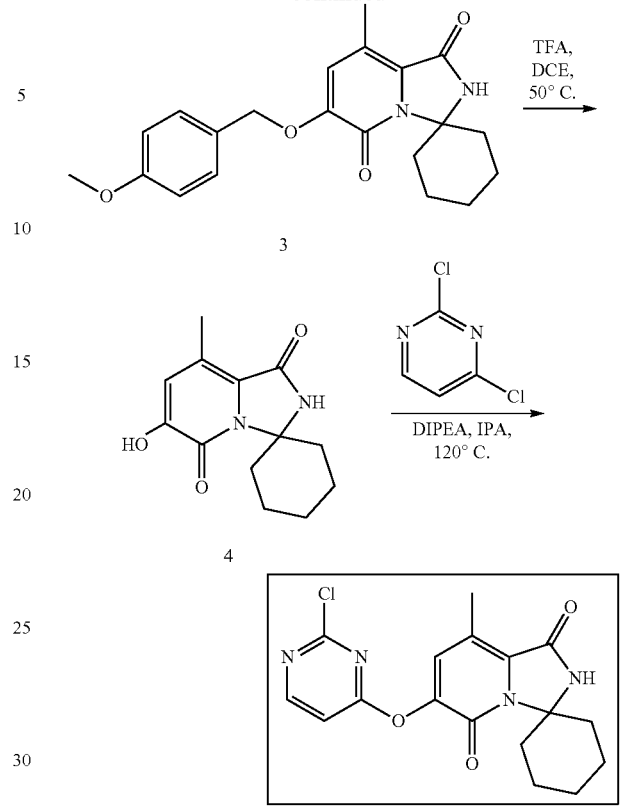

Synthesis of 6'-((4-methoxybenzyl)oxy)-8'-methyl-2'H-spiro[cyclohexane-1,3'-imidazo[1,5-a]pyridine]-1',5'-dione (3)

To a solution of 6'-bromo-8'-methyl-2'H-spiro[cyclohexane-1,3'-imidazo[1,5-a]pyridine]-1',5'-dione (1, 2.5 g, 8.03 mmol) in dimethylformamide (20 mL), sodium hydride (1.15 g, 48.23 mmol) was added portion wise. The reaction mixture was stirred at 0° C. for 30 m. To the reaction mixture was added (4-methoxyphenyl)methanol (3.34 g, 24.11 mmol) and the reaction was stirred at 80° C. for 16 h. After completion, solvent was evaporated under reduced pressure. Obtained crude was washed with water (50 mL) followed by diethyl ether and dried under reduced pressure to afford 6'-((4-methoxybenzyl)oxy)-8'-methyl-2'H-spiro[cyclohexane-1,3'-imidazo[1,5-a]pyridine]-1',5'-dione (3) as yellow solid. Yield: 1.4 g, 48%; MS (ESI) m/z 369.15 [M+1]$^+$.

Synthesis of 6'-hydroxy-8'-methyl-2'H-spiro[cyclohexane-1,3'-imidazo[1,5-a]pyridine]-1',5'-dione (4)

6'-((4-Methoxybenzyl)oxy)-8'-methyl-2'H-spiro[cyclohexane-1,3'-imidazo[1,5-a]pyridine]-1',5'-dione (3, 3.3 g, 8.59 mmol) was dissolved in 1,2-dichloroethane (25 mL) and trifluoroacetic acid (10 mL) was added. The reaction mixture was stirred at 50° C. for 2 h. After completion, solvent was evaporated under reduced pressure. Obtained crude was washed with water (50 mL) followed by n-pentane and dried under reduced pressure to afford 6'-hydroxy-8'-methyl-2'H-spiro[cyclohexane-1,3'-imidazo[1,5-a]pyridine]-1',5'-dione (4) as yellow solid. Yield: 0.85 g, 90%; MS (ESI) m/z 249.07 [M+1]$^+$.

Synthesis of 6'-((2-chloropyrimidin-4-yl)oxy)-8'-methyl-2'H-spiro[cyclohexane-1,3'-imidazo[1,5-a]pyridine]-1',5'-dione (Cpd. No. 224)

6'-Hydroxy-8'-methyl-2'H-spiro[cyclohexane-1,3'-imidazo[1,5-a]pyridine]-1',5'-dione (4, 0.5 g, 2.01 mmol) was dissolved in 2-propanol (20 mL) and N,N-diisopropylethylamine (780 mg, 6.05 mmol) and 2,4-dichloropyrimidine (0.30 g, 2.83 mmol) were added. The reaction mixture was stirred at 120° C. for 36 h. After completion, the solvent was evaporated under reduced pressure and water (100 mL) was added. The precipitated yellow solid was filtered and dried under reduced pressure. This crude was purified by silica gel (220-400 mesh) column chromatography using 2-5% methanol in dichloromethane as an eluent to afford 6'-((2-chloropyrimidin-4-yl)oxy)-8'-methyl-2'H-spiro[cyclohexane-1,3'-imidazo[1,5-a]pyridine]-1',5'-dione (Cpd. No. 224). Yield: 0.33 g, 46%; MS (ESI) m/z 361.12 [M+1]$^+$; $^1$H NMR (400 MHz, DMSO-$d_6$) δ 10.37 (s, 1H), 8.65 (d, J=5.6 Hz, 1H), 7.61 (s, 1H), 7.28 (d, J=5.6 Hz, 1H), 6.55 (s, 2H), 2.88-2.72 (m, 2H), 2.44 (s, 3H), 1.72-1.70 (m, 2H), 1.64-1.58 (m, 3H), 1.45-1.42 (m, 2H), 1.17-1.13 (m, 1H).

Example 225

Synthesis of 2-(6-(((6-aminopyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 225)

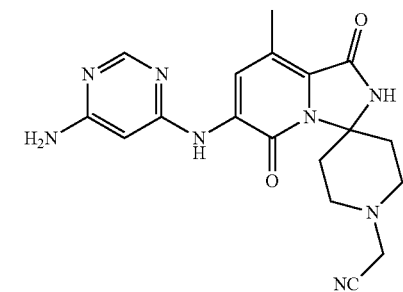 [SMILES: Cc1cc(Nc2cc(N)ncn2)c(=O)n2c1C(=O)NC21CCN(CC#N)CC1]

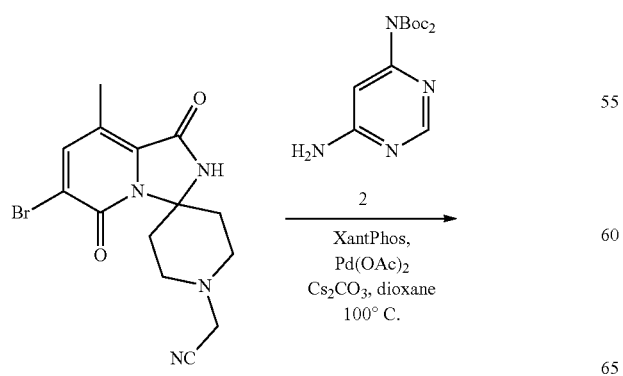

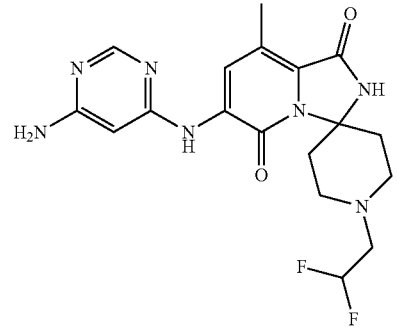

Synthesis of di-tert-butyl (6-((1'-(cyanomethyl)-8-methyl-1,5-dioxo-1,5-dihydro-2H-spiro[imidazo[1,5-a]pyridine-3,4'-piperidin]-6-yl)amino)pyrimidin-4-yl)-12-azanecarboxylate (3)

The synthesis of intermediate 3 was carried out as described above using the general protocol of Procedure B. Yellow solid; Yield: 0.25 g, 60%; MS (ESI) m/z 581.49 [M+1]$^+$.

Synthesis of 2-(6-(((6-aminopyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 225)

The synthesis of compound 225 was carried out as described above using the general protocol of Procedure F. White solid; Yield: 37 mg, 38%; MS (ESI) m/z 381.19 [M+1]$^+$; $^1$H NMR (400 MHz, DMSO-$d_6$) δ 10.40 (s, 1H), 9.47 (s, 1H), 8.38 (s, 1H), 8.18 (s, 1H), 7.54 (brs, 2H), 6.34 (s, 1H), 3.74 (s, 2H), 3.30-3.23 (m, 2H), 2.89-2.87 (m, 2H), 2.66-2.64 (s, 2H), 2.42 (s, 3H), 1.50-1.47 (m, 2H).

Example 226

Synthesis of 6-((6-aminopyrimidin-4-yl)amino)-1'-(2,2-difluoroethyl)-8-methyl-2H-spiro[imidazo[1,5-a]pyridine-3,4'-piperidine]-1,5-dione (Cpd. No. 226)

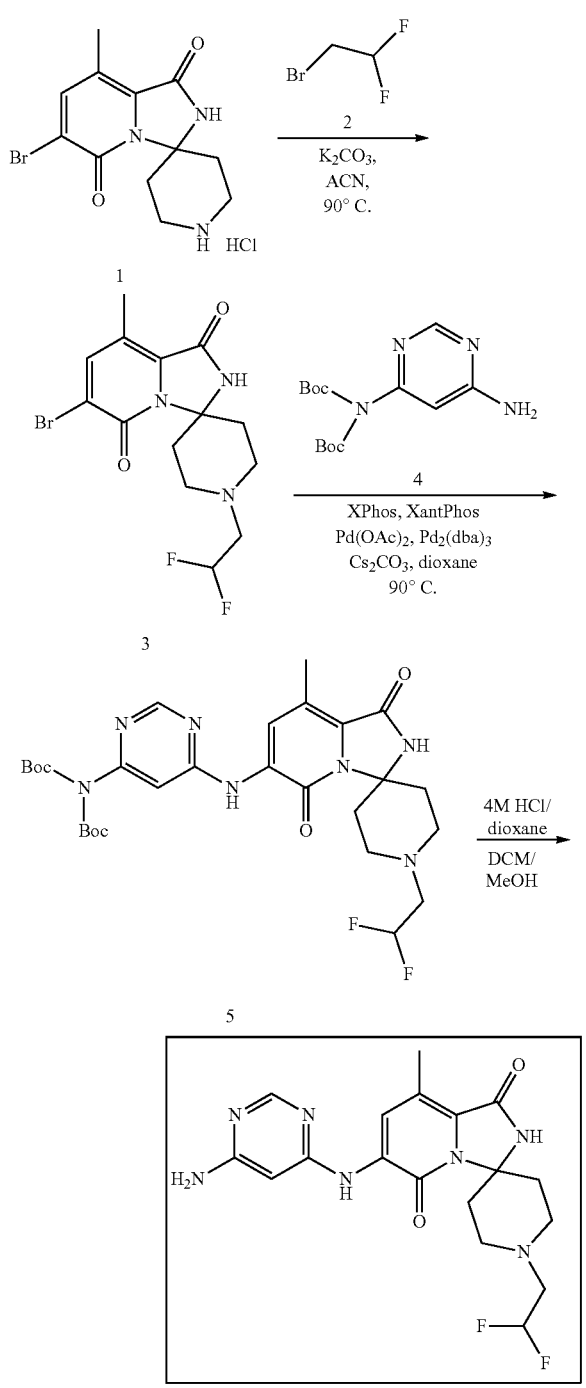

Synthesis of 6-bromo-1'-(2,2-difluoroethyl)-8-methyl-2H-spiro[imidazo[1,5-a]pyridine-3,4'-piperidine]-1,5-dione (3)

To a solution of 6-bromo-8-methyl-2H-spiro[imidazo[1,5-a]pyridine-3,4'-piperidine]-1,5-dione hydrochloride (1, 300 mg, 0.96 mmol) in acetonitrile was added 2-bromo-1,1-difluoroethane (348 mg, 2.40 mmol) and potassium carbonate (397 mg, 2.88 mmol). The reaction was heated at 90° C. for 18 h. On completion of reaction, solvent was removed and the crude was purified by silica gel (200-400 mesh) column chromatography eluting with 5-7% methanol in dichloromethane. Appropriate column fractions were concentrated under reduced pressure to afford 6-bromo-1'-(2,2-difluoroethyl)-8-methyl-2H-spiro[imidazo[1,5-a]pyridine-3,4'-piperidine]-1,5-dione (3) as light yellow solid. Yield: 180 mg, 37%; MS (ESI) m/z 378.22 [M+1]$^+$.

Synthesis of tert-butyl N-tert-butoxycarbonyl-N-(6-((1'-(2,2-difluoroethyl)-8-methyl-1,5-dioxo-1,5-dihydro-2H-spiro[imidazo[1,5-a]pyridine-3,4'-piperidin]-6-yl)amino)pyrimidin-4-yl)carbamate (5)

The synthesis of intermediate 5 was carried out as described above using the general protocol of Procedure H. Off white solid; Yield: 200 mg, 69%; MS (ESI) m/z 606.18.

Synthesis of 6-((6-aminopyrimidin-4-yl)amino)-1'-(2,2-difluoroethyl)-8-methyl-2H-spiro[imidazo[1,5-a]pyridine-3,4'-piperidine]-1,5-dione (Cpd. No. 226)

The synthesis of compound 226 was carried out as described above using the general protocol of Procedure F. White solid; Yield: 14 mg, 8%; MS (ESI) m/z 406.20 [M+1]$^+$; $^1$H NMR (400 MHz, DMSO-d$_6$) δ 10.08 (s, 1H), 8.57 (s, 1H), 8.38 (s, 1H), 8.16 (s, 1H), 6.51 (s, 2H), 6.30-6.00 (m, 2H), 3.25-3.22 (m, 2H), 2.94-2.91 (m, 2H), 2.87-2.79 (m, 2H), 2.69-2.63 (m, 2H), 2.42 (s, 3H), 1.39-1.36 (m, 2H).

Example 227

Synthesis of 6-((5-methoxypyrimidin-4-yl)amino)-1',8-dimethyl-2H-spiro[imidazo[1,5-a]pyridine-3,4'-piperidine]-1,5-dione (Cpd. No. 227)

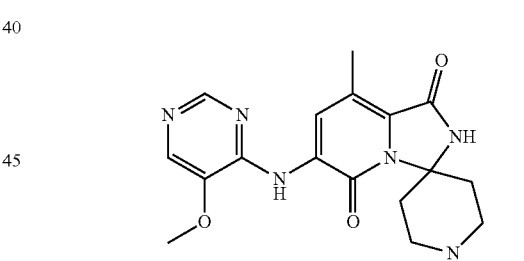

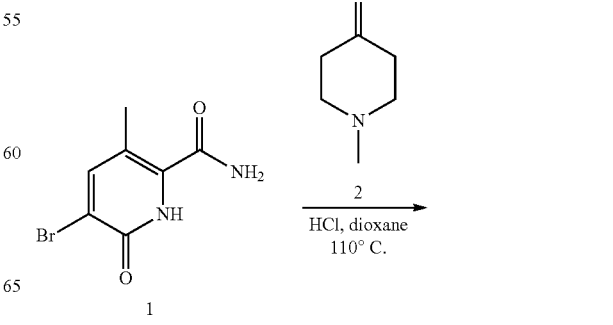

Example 228

Synthesis of 6-((6-amino-5-methoxypyrimidin-4-yl)amino)-1',8-dimethyl-2H-spiro[imidazo[1,5-a]pyridine-3,4'-piperidine]-1,5-dione (Cpd. No. 228)

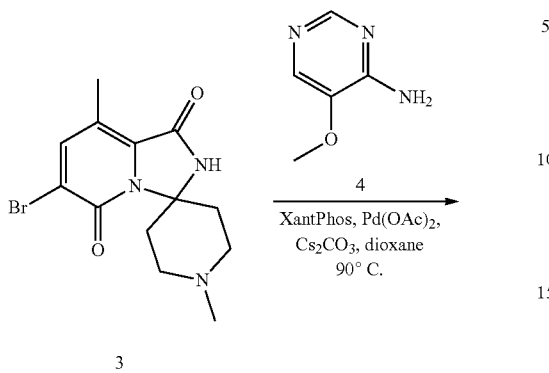

Synthesis of 6-bromo-1',8-dimethyl-2H-spiro[imidazo[1,5-a]pyridine-3, 4'-piperidine]-1,5-dione (3)

To a stirred solution of 5-bromo-3-methyl-6-oxo-1,6-dihydropyridine-2-carboxamide (1, 3 g, 12.98 mmol) in 1,4-dioxane (25 mL), 1-methylpiperidin-4-one (2.2 g, 19.47 mmol) was added at room temperature. To the mixture 4 M hydrogenchloride in dioxane (6.5 mL, 2.59 mmol) was added dropwise. The reaction was heated up to 110° C. for 16 h. After completion, solvent was removed under reduced pressure and obtained solid was washed with warm water followed by pentane and ether to afford 6-bromo-1',8-dimethyl-2H-spiro[imidazo[1,5-a]pyridine-3,4'-piperidine]-1,5-dione (3) as off white solid. Yield: 2.5 g, 59%; MS (ESI) m/z 326 [M+1]$^+$.

Synthesis of 6-((5-methoxypyrimidin-4-yl)amino)-1',8-dimethyl-2H-spiro[imidazo[1,5-a]pyridine-3,4'-piperidine]-1,5-dione (Cpd. No. 227)

The synthesis of compound 227 was carried out as described above using the general protocol of Procedure B. Off white solid; Yield: 103 mg, 18%; MS (ESI) m/z 371.16 [M+1]$^+$; $^1$H NMR (400 MHz, DMSO-$d_6$) δ 10.16 (brs, 1H), 8.62 (s, 1H), 8.58 (s, 1H), 8.48 (s, 1H), 8.24 (s, 1H), 4.00 (s, 3H), 3.25-3.21 (m, 2H), 2.84-2.81 (m, 2H), 2.45 (s, 3H), 2.48-2.42 (m, 2H), 2.28 (s, 3H), 1.44-1.41 (m, 2H).

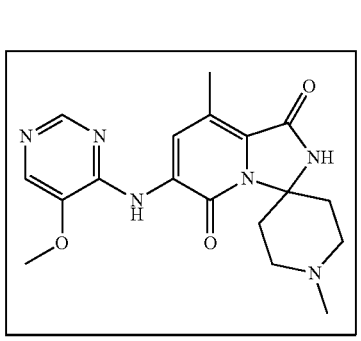

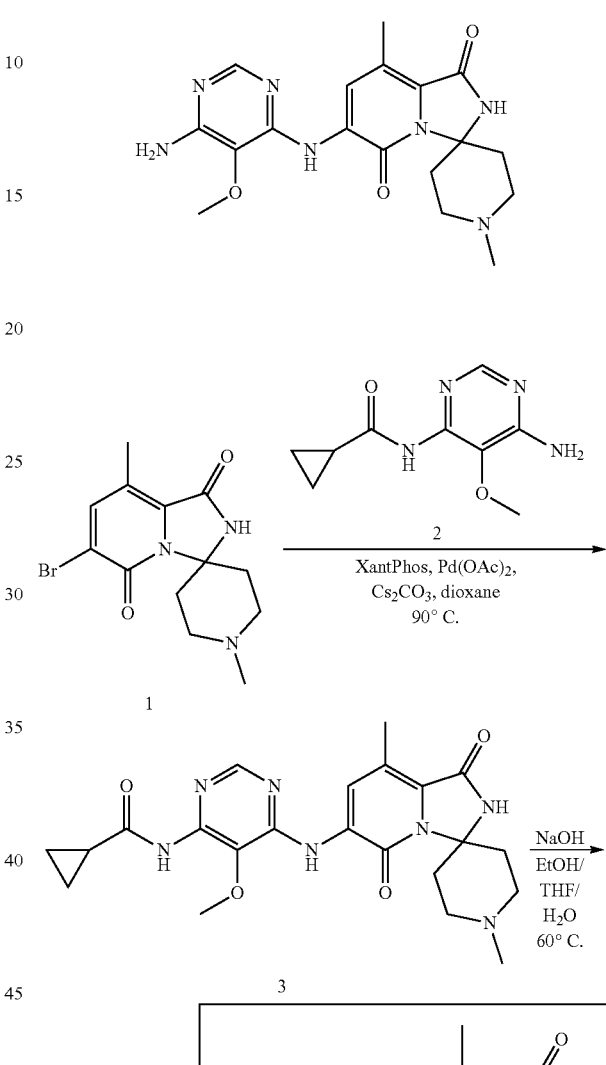

Synthesis N-(6-((1',8-dimethyl-1,5-dioxo-1,5-dihydro-2H-spiro[imidazo[1,5-a]pyridine-3,4'-piperidin]-6-yl)amino)-5-methoxypyrimidin-4-yl)cyclopropanecarboxamide (3)

The synthesis of intermediate 3 was carried out as described above using the general protocol of Procedure B. Light yellow solid; Yield: 103 mg, 31%; MS (ESI) m/z 454.15 [M+1]$^+$.

Synthesis of 6-((6-amino-5-methoxypyrimidin-4-yl)amino)-1',8-dimethyl-2H-spiro[imidazo[1,5-a]pyridine-3,4'-piperidine]-1,5-dione (Cpd. No. 228)

A flask containing tetrahydrofuran, ethanol and water (1:1:1, 5 mL each) was charged with 6-((6-amino-5-methoxypyrimidin-4-yl)amino)-1',8-dimethyl-2H-spiro[imidazo[1,5-a]pyridine-3,4'-piperidine]-1,5-dione (3, 0.2 g, 0.441 mmol) and sodium hydroxide (88 mg, 2.2 mmol). The reaction was stirred at 60° C. for 16 h. After completion, the reaction mass was extracted with 10% 2-propanol in chloroform (5×50 mL). Combined organic layer was concentrated and obtained solid was washed with methanol and dried under vacuum to afford 6-((6-amino-5-methoxypyrimidin-4-yl)amino)-1',8-dimethyl-2H-spiro[imidazo[1,5-a]pyridine-3,4'-piperidine]-1,5-dione (Cpd. No. 228) as light yellow solid. Yield: 88 mg, 52%; MS (ESI) m/z 386.19 [M+1]$^+$; $^1$H NMR (400 MHz, DMSO-d$_6$) δ 10.11 (s, 1H), 8.45 (s, 1H), 8.32 (s, 1H), 8.00 (s, 2H), 6.67 (s, 2H), 3.69 (s, 3H), 3.30-3.20 (m, 2H), 2.90 (brs, 2H), 2.50-2.46 (m, 2H), 2.45 (s, 3H), 2.33 (s, 3H), 1.47-1.45 (m, 2H).

Example 229

Synthesis of 2-(6-((5-methoxypyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 229)

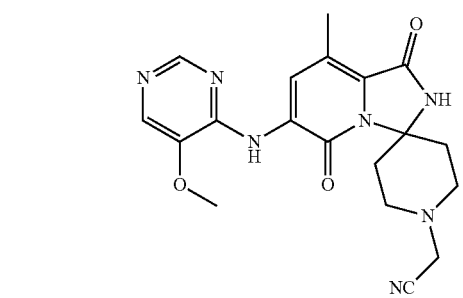 [SMILES: COc1cncnc1Nc1cc(C)c2n(c1=O)C1(CCN(CC#N)CC1)NC2=O]

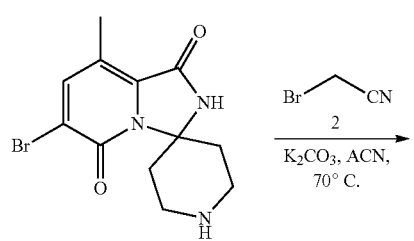

Synthesis of 2-(6-bromo-8-methyl-1,5-dioxo-1,5-dihydro-2H-spiro[imidazo[1,5-a]pyridine-3,4'-piperidin]-1'-yl)acetonitrile (3)

A flask was charged with 6-bromo-8-methyl-2H-spiro[imidazo[1,5-a]pyridine-3,4'-piperidine]-1,5-dione (1, 0.50 g, 1.6 mmol) and acetonitrile (15 mL). The reaction mass was cooled to 0° C. and potassium carbonate (664 mg, 4.8 mmol) was added followed by the addition of 2-bromoacetonitrile (288.18 mg, 2.40 mmol). The reaction mass was stirred at 70° C. for 16 h. After completion, reaction mixture was diluted with saturated ammonium chloride solution (50 mL). The precipitate was filtered and dried under reduced pressure to afford 2-(6-bromo-8-methyl-1,5-dioxo-1,5-dihydro-2H-spiro[imidazo[1,5-a]pyridine-3,4'-piperidin]-1'-yl)acetonitrile (3) as white solid. Yield: 0.32 g, 58%; MS (ESI) m/z 351.26 [M+1]$^+$.

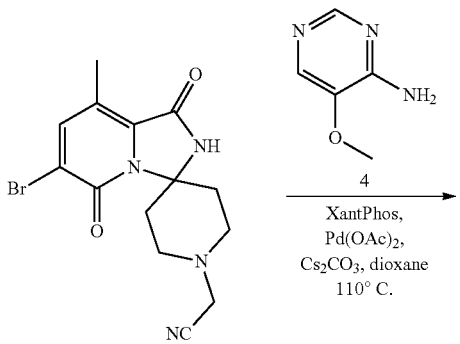

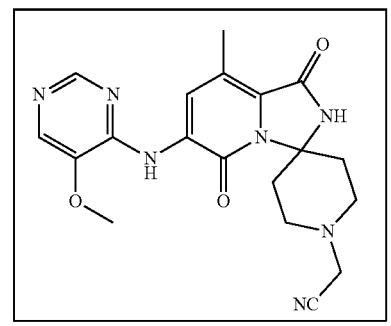

Synthesis of 2-(6-((5-methoxypyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 229)

The synthesis of compound 229 was carried out as described above using the general protocol of Procedure B. Yellow solid. Yield: 0.068 g, 20%; MS (ESI) m/z 396.5 [M+1]$^+$; $^1$H NMR (400 MHz, DMSO-d$_6$ with d$_1$-TFA) δ 8.94 (s, 1H), 8.53 (s, 1H), 8.44 (s, 1H), 4.47 (s, 2H), 4.07 (s, 3H), 3.71-3.68 (m, 2H), 3.47-3.39 (m, 4H), 2.47 (s, 3H), 1.92-1.89 (m, 2H).

Example 230

Synthesis of 1'-(2,2-difluoroethyl)-6-((5-methoxypyrimidin-4-yl)amino)-8-methyl-2H-spiro[imidazo[1,5-a]pyridine-3,4'-piperidine]-1,5-dione (Cpd. No. 230)

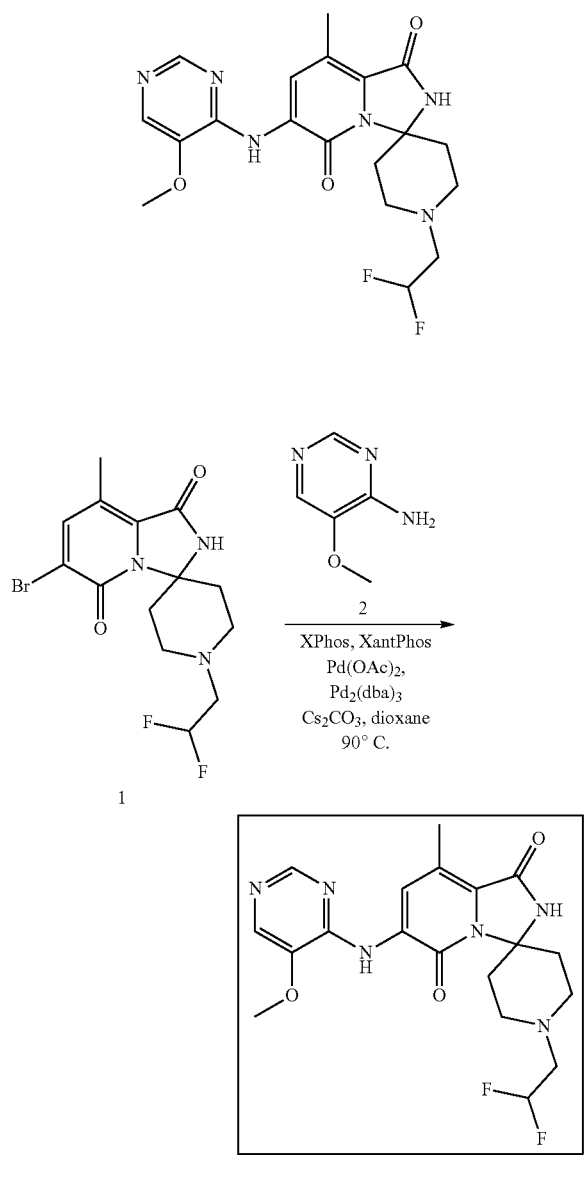

Synthesis of 1'-(2, 2-difluoroethyl)-6-((5-methoxypyrimidin-4-yl)amino)-8-methyl-2H-spiro[imidazo[1,5-a]pyridine-3,4'-piperidine]-1,5-dione (Cpd. No. 230)

The synthesis of compound 230 was carried out as described above using the general protocol of Procedure H. Off white solid; Yield: 65 mg, 45%; MS (ESI) m/z 421.13 [M+1]$^+$; $^1$H NMR (400 MHz, DMSO-d$_6$) δ 10.22 (s, 1H), 8.64 (s, 1H), 8.58 (s, 1H), 8.48 (s, 1H), 8.24 (s, 2H), 6.30-6.00 (m, 1H), 4.00 (s, 1H), 3.31-3.17 (m, 2H), 2.95-2.92 (m, 2H), 2.87-2.78 (m, 2H), 2.68-2.62 (m, 2H), 2.49 (s, 3H), 1.43-1.40 (m, 2H).

Example 231

Synthesis of 6'-((6-amino-5-methoxypyrimidin-4-yl)amino)-8'-methyl-2'H-spiro[cyclohexane-1,3'-imidazo[1,5-a]pyridine]-1',5'-dione (Cpd. No. 231)

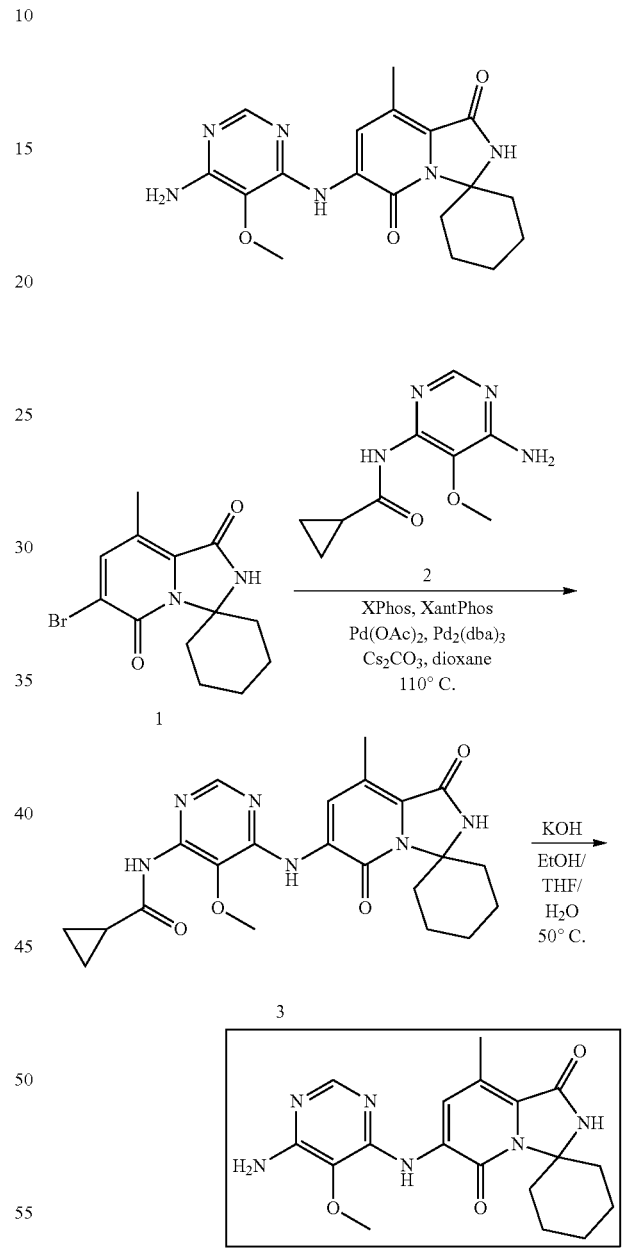

Synthesis of N-(5-methoxy-6-((8'-methyl-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (3)

The synthesis of intermediate 3 was carried out as described above using the general protocol of Procedure H. Light yellow solid; Yield: 0.3 g, 71%; MS (ESI) m/z 439.14 [M+1]$^+$.

Synthesis of 6'-((6-amino-5-methoxypyrimidin-4-yl)amino)-8'-methyl-2'H-spiro[cyclohexane-1,3'-imidazo[1,5-a]pyridine]-1',5'-dione (Cpd. No. 231)

The synthesis of compound 231 was carried out as described above using the general protocol of Procedure I. Yellow solid; Yield: 0.085 g, 27%; MS (ESI) m/z 371.16 [M+1]$^+$; $^1$H NMR (400 MHz, DMSO-d$_6$) δ 10.06 (s, 1H), 8.47 (s, 1H), 8.33 (s, 1H), 8.00 (s, 1H), 6.67 (s, 2H), 3.69 (s, 3H), 3.02-2.95 (m, 2H), 2.45 (s, 3H), 1.78-1.58 (m, 5H), 1.47-1.43 (m, 2H), 1.29-1.20 (m, 1H).

Example 232

Synthesis of 6-((6-aminopyrimidin-4-yl)amino)-8-methyl-1'-(2,2,2-trifluoroethyl)-2H-spiro[imidazo[1,5-a]pyridine-3,4'-piperidine]-1,5-dione (Cpd. No. 232)

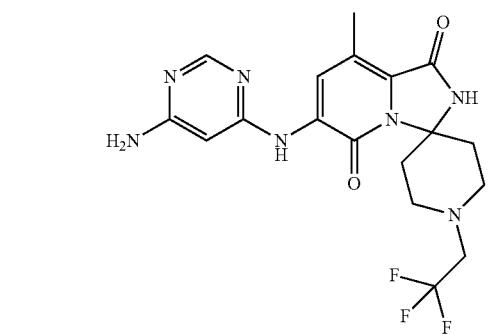 [SMILES: Cc1cc(Nc2cc(N)ncn2)c(=O)n2c1C(=O)NC21CCN(CC(F)(F)F)CC1]

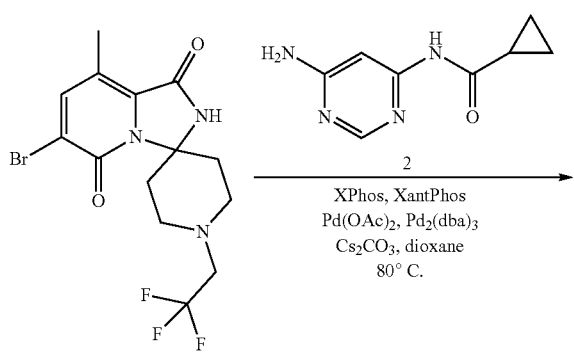

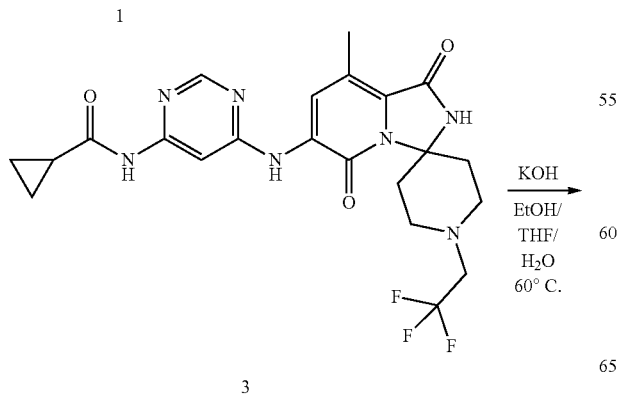

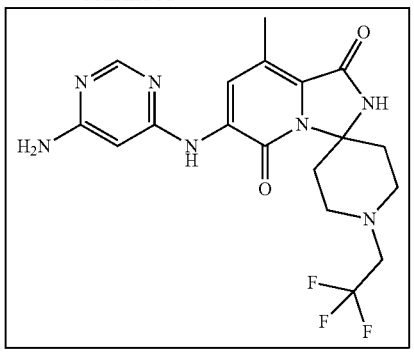

Synthesis of N-(6-((8-methyl-1,5-dioxo-1'-(2,2,2-trifluoroethyl)-1,5-dihydro-2H-spiro[imidazo[1,5-a]pyridine-3,4'-piperidin]-6-yl)amino)pyrimidin-4-yl)cyclopropanecarboxamide (3)

The synthesis of intermediate 3 was carried out as described above using the general protocol of Procedure H. Yellow solid. Yield: 300 mg, 60%; MS (ESI) m/z 492.10 [M+1]$^+$.

Synthesis of 6-((6-aminopyrimidin-4-yl)amino)-8-methyl-1'-(2,2,2-trifluoroethyl)-2H-spiro[imidazo[1,5-a]pyridine-3,4'-piperidine]-1,5-dione (Cpd. No. 232)

The synthesis of compound 232 was carried out as described above using the general protocol of Procedure I. White solid; Yield: 60 mg, 23%; MS (ESI) m/z 424.19 [M+1]$^+$; $^1$H NMR (400 MHz, DMSO-d$_6$) δ 10.14 (s, 1H), 8.65 (s, 1H), 8.37 (s, 1H), 8.18 (s, 1H), 6.60 (s, 2H), 6.18 (s, 1H), 3.27-3.22 (m, 4H), 2.95-2.90 (m, 2H), 2.85-2.76 (m, 2H), 2.42 (s, 3H), 1.41-1.36 (m, 2H).

Example 233

Synthesis of 6-((6-amino-5-methylpyrimidin-4-yl)amino)-1'-(2,2-difluoroethyl)-8-methyl-2H-spiro[imidazo[1,5-a]pyridine-3,4'-piperidine]-1,5-dione (Cpd. No. 233)

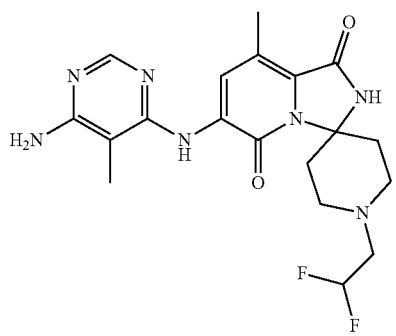 [SMILES: Cc1cc(Nc2ncnc(N)c2C)c(=O)n2c1C(=O)NC21CCN(CC(F)F)CC1]

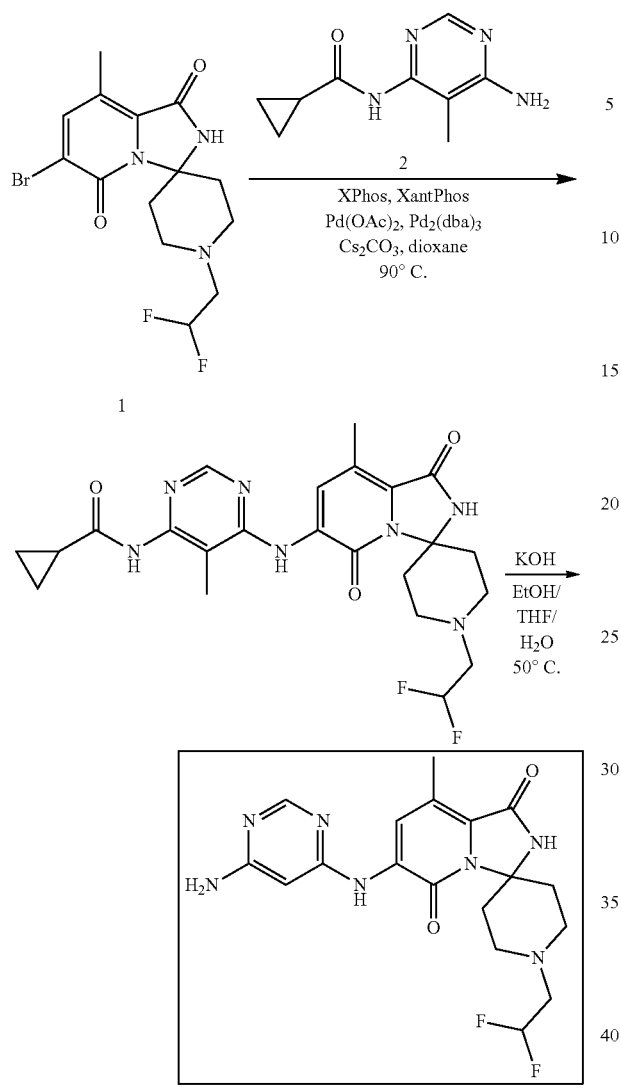

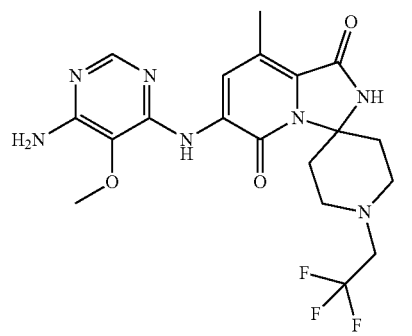 [SMILES: COc1c(N)ncnc1Nc1cc(C)c2n(c1=O)C1(CCN(CC(F)(F)F)CC1)NC2=O]

Synthesis of N-(6-(((1'-(2,2-difluoroethyl)-8-methyl-1,5-dioxo-1,5-dihydro-2H-spiro[imidazo[1,5-a]pyridine-3,4'-piperidin]-6-yl)amino)-5-methylpyrimidin-4-yl)cyclopropanecarboxamide (3)

The synthesis of intermediate 3 was carried out as described above using the general protocol of Procedure H. Light yellow solid; Yield: 0.35 g, 65%; MS (ESI) m/z 488.27 [M+1]$^+$.

Synthesis of 6-((6-amino-5-methylpyrimidin-4-yl)amino)-1'-(2,2-difluoroethyl)-8-methyl-2H-spiro[imidazo[1,5-a]pyridine-3,4'-piperidine]-1,5-dione (Cpd. No. 233)

The synthesis of compound 233 was carried out as described above using the general protocol of Procedure I. Off white solid; Yield: 80 mg, 26%; MS (ESI) m/z 420.20 [M+1]$^+$; $^1$H NMR (400 MHz, DMSO-d$_6$) δ 10.13 (s, 1H), 8.48 (s, 1H), 8.12 (s, 1H), 8.00 (s, 1H), 6.48 (s, 2H), 6.30-6.00 (m, 1H), 3.27-3.21 (m, 2H), 2.94-2.91 (m, 2H), 2.86-2.77 (m, 2H), 2.67-2.61 (m, 2H), 2.44 (s, 3H), 1.98 (s, 3H), 1.41-1.38 (m, 2H).

Example 234

Synthesis of 6-((6-amino-5-methoxypyrimidin-4-yl)amino)-8-methyl-1'-(2,2,2-trifluoroethyl)-2H-spiro[imidazo[1,5-a]pyridine-3,4'-piperidine]-1,5-dione (Cpd. No. 234)

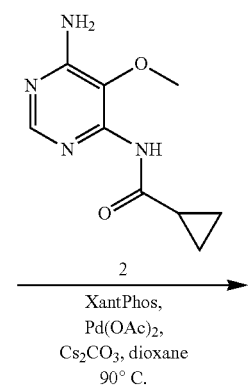

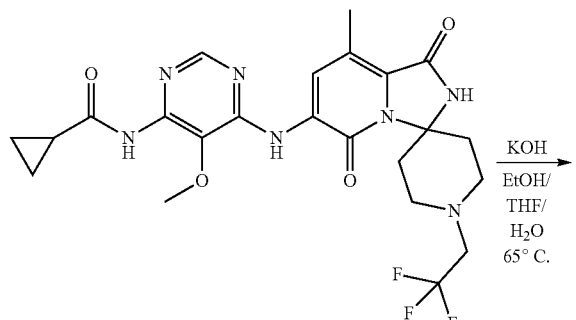

371

-continued

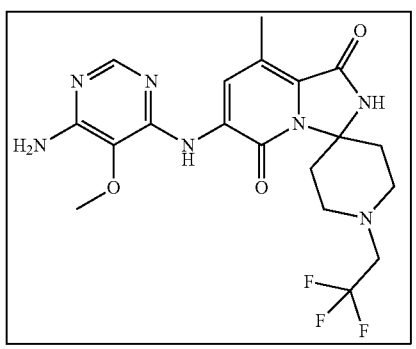

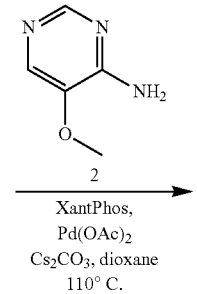

Synthesis N-(5-methoxy-6-((8-methyl-1,5-dioxo-1'-(2,2,2-trifluoroethyl)-1,5-dihydro-2H-spiro[imidazo[1,5-a]pyridine-3,4'-piperidin]-6-yl)amino)pyrimidin-4-yl)cyclopropanecarboxamide (3)

The synthesis of intermediate 3 was carried out as described above using the general protocol of Procedure B. Light yellow solid; Yield: 400 mg, 76%; MS (ESI) m/z 522.19 [M+1]$^+$.

Synthesis of 6-((6-amino-5-methoxypyrimidin-4-yl)amino)-8-methyl-1'-(2,2,2-trifluoroethyl)-2H-spiro[imidazo[1,5-a]pyridine-3,4'-piperidine]-1,5-dione (Cpd. No. 234)

The synthesis of compound 234 was carried out as described above using the general protocol of Procedure I. Light yellow solid; Yield: 100 mg, 29%; MS (ESI) m/z 354.12 [M+1]$^+$; $^1$H NMR (400 MHz, DMSO-d$_6$) δ 10.19 (s, 1H), 8.45 (s, 1H), 8.32 (s, 1H), 8.00 (s, 1H), 6.67 (s, 2H), 3.69 (s, 3H), 3.27-3.21 (m, 4H), 2.97-2.90 (m, 2H), 2.83-2.77 (m, 2H), 2.45 (s, 3H), 1.42-1.38 (m, 2H).

Example 235

Synthesis of 6-((5-methoxypyrimidin-4-yl)amino)-8-methyl-1'-(2,2,2-trifluoroethyl)-2H-spiro[imidazo[1,5-a]pyridine-3,4'-piperidine]-1,5-dione (Cpd. No. 235)

372

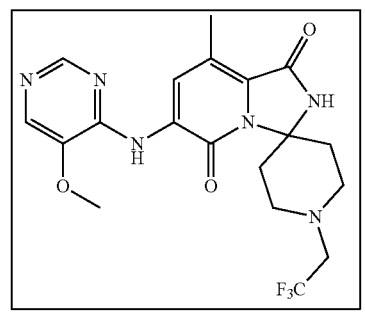

Synthesis of 6-((5-methoxypyrimidin-4-yl)amino)-8-methyl-1'-(2,2, 2-trifluoroethyl)-2H-spiro[imidazo[1,5-a]pyridine-3,4'-piperidine]-1,5-dione (Cpd. No. 235)

The synthesis of compound 235 was carried out as described above using the general protocol of Procedure B. Off white solid; Yield: 0.13 g, 39%; MS (ESI) m/z 439.21 [M+1]$^+$; $^1$H NMR (400 MHz, DMSO-d$_6$) δ 10.29 (s, 1H), 8.65 (s, 1H), 8.58 (s, 1H), 8.48 (s, 1H), 8.24 (s, 1H), 4.00 (s, 3H), 3.32-3.22 (m, 4H), 2.96-2.90 (m, 2H), 2.85-2.79 (m, 2H), 2.45 (s, 3H), 1.42-1.39 (m, 2H).

Example 236

Synthesis of 6-((6-amino-5-methylpyrimidin-4-yl)amino)-8-methyl-1'-(2,2,2-trifluoroethyl)-2H-spiro[imidazo[1,5-a]pyridine-3,4'-piperidine]-1,5-dione (Cpd. No. 236)

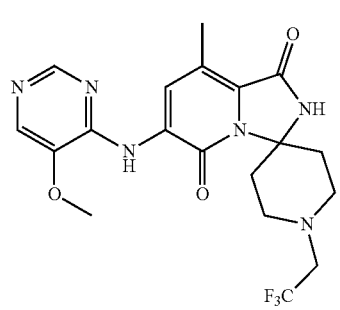 [SMILES: COc1cncnc1Nc1cc(C)c2n(c1=O)C1(CCN(CC(F)(F)F)CC1)NC2=O]

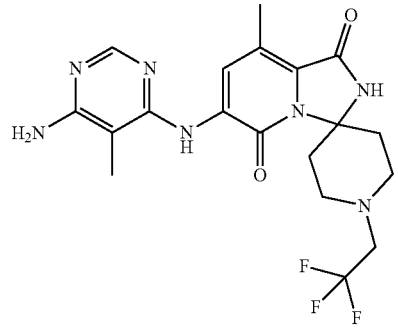 [SMILES: Cc1cc(Nc2ncnc(N)c2C)c(=O)n2c1C(=O)NC21CCN(CC(F)(F)F)CC1]

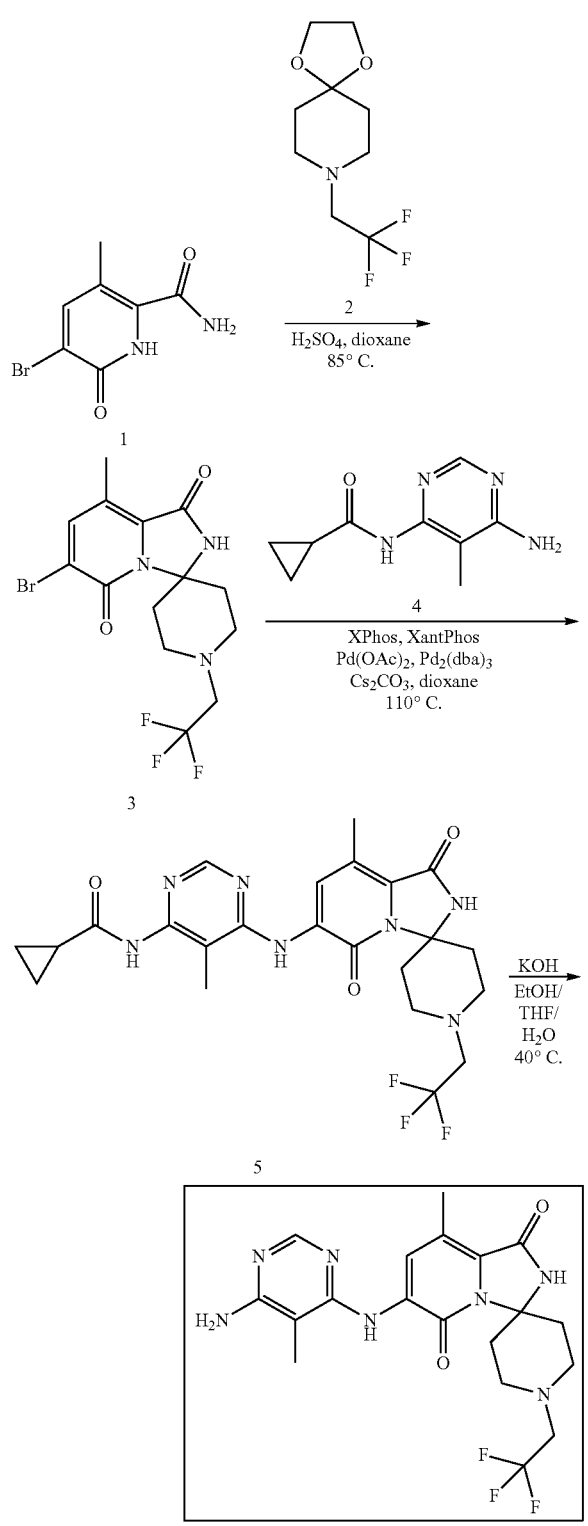

Synthesis of 6-bromo-8-methyl-1'-(2,2,2-trifluoroethyl)-2H-spiro[imidazo[1,5-a]pyridine-3,4'-piperidine]-1,5-dione (3)

The synthesis of intermediate 3 was carried out as described above using the general protocol of Procedure A. Yield: 5.0 g, 58%; MS (ESI) m/z 394.08 [M+1]+.

Synthesis of N-(5-methyl-6-((8-methyl-1,5-dioxo-1'-(2,2,2-trifluoroethyl)-1,5-dihydro-2H-spiro[imidazo[1,5-a]pyridine-3,4'-piperidin]-6-yl)amino)pyrimidin-4-yl)cyclopropanecarboxamide (5)

The synthesis of intermediate 5 was carried out as described above using the general protocol of Procedure H. Brown solid; Yield: 0.32 g, 62%; MS (ESI) m/z 506.23 [M+1]+.

Synthesis of 6-((6-amino-5-methylpyrimidin-4-yl)amino)-8-methyl-1'-(2,2,2-trifluoroethyl)-2H-spiro[imidazo[1,5-a]pyridine-3,4'-piperidine]-1,5-dione (Cpd. No. 236)

The synthesis of compound 236 was carried out as described above using the general protocol of Procedure I. Yield: 70 mg, 27%; MS (ESI) m/z 438.16 [M+1]+; $^1$H NMR (400 MHz, DMSO-$d_6$ with $d_1$-TFA) δ 10.17 (s, 1H), 8.48 (s, 1H), 8.12 (s, 1H), 8.00 (s, 1H), 6.48 (s, 2H), 3.32-3.20 (m, 4H), 2.95-2.93 (m, 2H), 2.85-2.75 (m, 2H), 2.45 (s, 3H), 1.98 (s, 3H), 1.41-1.38 (m, 2H).

Example 237

Synthesis of 6-((6-amino-5-chloropyrimidin-4-yl)amino)-1',8-dimethyl-2H-spiro[imidazo[1,5-a]pyridine-3,4'-piperidine]-1,5-dione (Cpd. No. 237)

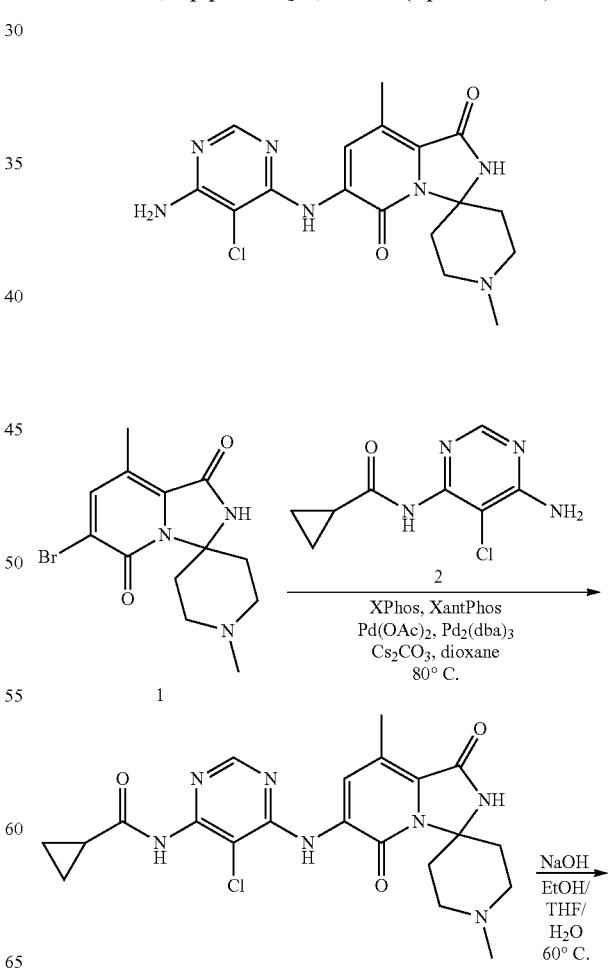

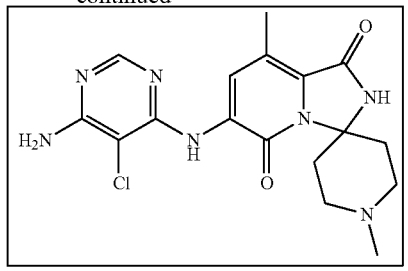

Synthesis of N-(5-chloro-6-(((1',8-dimethyl-1,5-di-oxo-1,5-dihydro-2H-spiro[imidazo[1,5-a]pyridine-3,4'-piperidin]-6-yl)amino)pyrimidin-4-yl)cyclopropanecarboxamide (3)

The synthesis of intermediate 3 was carried out as described above using the general protocol of Procedure H. Light brown solid; Yield: 210 mg, 50%; MS (ESI) m/z 458.12 [M+1]$^+$.

Synthesis of 6-((6-amino-5-chloropyrimidin-4-yl)amino)-1',8-dimethyl-2H-spiro[imidazo[1,5-a]pyridine-3,4'-piperidine]-1,5-dione (Cpd. No. 237)

A flask containing tetrahydrofuran, ethanol and water (1:1:1, 5 mL each) was charged with 6-((6-amino-5-methoxypyrimidin-4-yl)amino)-1',8-dimethyl-2H-spiro[imidazo[1,5-a]pyridine-3,4'-piperidine]-1,5-dione (3, 0.17 g, 0.371 mmol) and sodium hydroxide (75 mg, 1.85 mmol). The reaction was stirred at 50° C. for 16 h. After completion, the reaction mass was extracted with 10% methanol in dichloromethane. Combined organic layer was washed with water, brine, dried over anhydrous sodium sulfate concentrated under vacuum obtained solid was washed with ether and dried under vacuum to afford 6-((6-amino-5-chloropyrimidin-4-yl)amino)-1',8-dimethyl-2H-spiro[imidazo[1,5-a]pyridine-3,4'-piperidine]-1,5-dione as light yellow solid. Yield: 88 mg, 31%; MS (ESI) m/z 390.14 [M+1]$^+$; $^1$H NMR (400 MHz, DMSO-d$_6$) δ 10.16 (s, 1H), 8.52 (s, 1H), 8.50 (s, 1H), 8.17 (s, 1H), 7.10 (brs, 2H), 3.30-3.20 (m, 2H), 2.90-2.82 (brs, 2H), 2.49-2.40 (m, 2H), 2.46 (s, 3H), 2.30 (s, 3H), 1.46-1.40 (m, 2H).

Example 238

Synthesis of 2-(6-((6-amino-5-chloropyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 238)

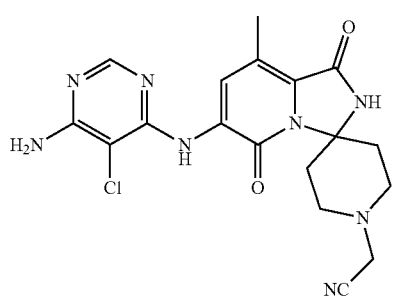 [SMILES: Cc1cc(Nc2ncnc(N)c2Cl)c(=O)n2c1C(=O)NC21CCN(CC#N)CC1]

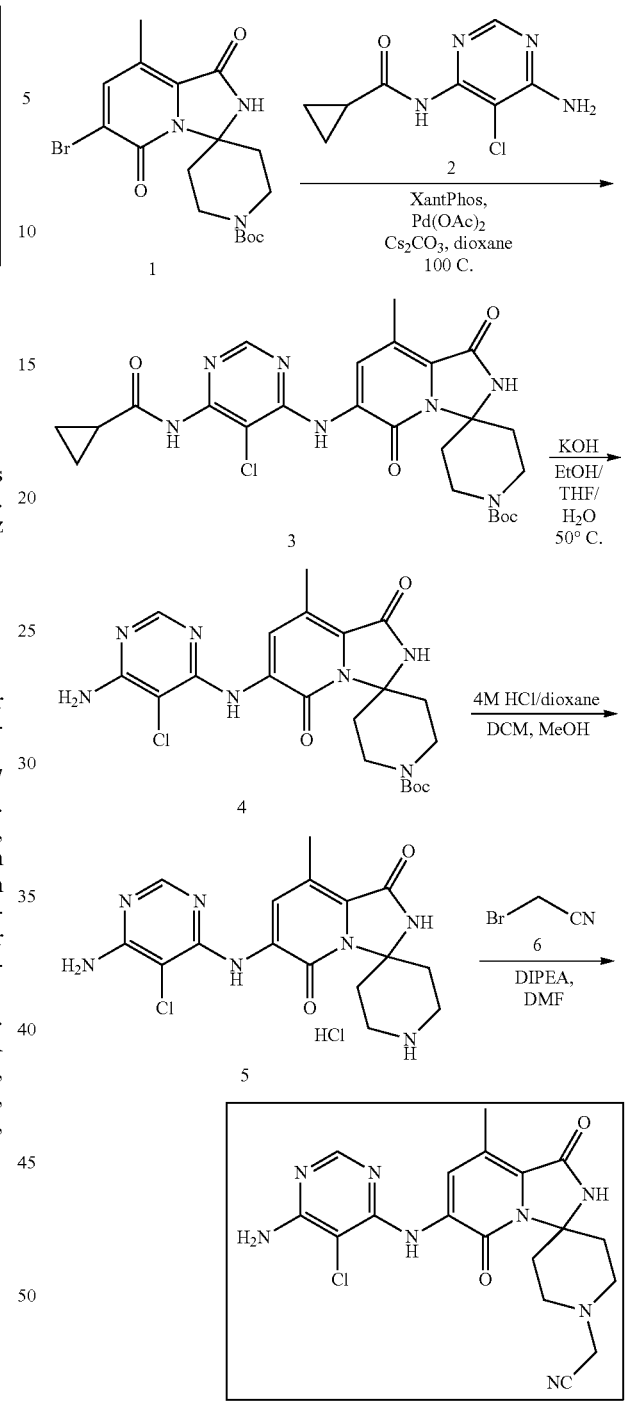

Synthesis of tert-butyl 6-((5-chloro-6-(cyclopropanecarboxamido)pyrimidin-4-yl)amino)-8-methyl-1,5-dioxo-1,5-dihydro-2H-spiro[imidazo[1,5-a]pyridine-3,4'-piperidine]-1'-carboxylate (3)

The synthesis of intermediate 3 was carried out as described above using the general protocol of Procedure B. Light yellow solid; Yield: 0.35 g, crude; MS (ESI) m/z 544.27 [M+1]$^+$.

Synthesis of tert-butyl 6-((6-amino-5-chloropyrimi-din-4-yl)amino)-8-methyl-1,5-dioxo-1,5-dihydro-2H-spiro[imidazo[1,5-a]pyridine-3,4'-piperidine]-1'-carboxylate (4)

The synthesis of intermediate 4 was carried out as described above using the general protocol of Procedure I. Yellow solid; Yield: 300 mg, crude; MS (ESI) m/z 476.23 [M+1]+.

Synthesis of 6-((6-amino-5-chloropyrimidin-4-yl)amino)-8-methyl-2H-spiro[imidazo[1,5-a]pyridine-3,4'-piperidine]-1,5-dione hydrochloride (5)

The synthesis of intermediate 5 was carried out as described above using the general protocol of Procedure F. Light yellow solid; Yield: 0.075 g, crude; MS (ESI) m/z 376.23 [M+1]+.

Synthesis of 2-(6-((6-amino-5-chloropyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 238)

6-((6-Amino-5-chloropyrimidin-4-yl)amino)-8-methyl-2H-spiro[imidazo[1,5-a]pyridine-3,4'-piperidine]-1,5-dione hydrochloride (5, 75 mg, 0.20 mmol) was dissolved in dimethylformamide (5 mL). To this mixture N,N-diisopropylethylamine (77 mg, 0.60 mmol) and bromoacetonitrile (36 mg, 0.30 mmol) were added. The reaction mixture was stirred at room temperature for 2 h. After completion reaction mixture was diluted with saturated ammonium chloride solution (50 mL). The yellow precipitate out was filtered and dried under reduced pressure. The crude was purified by prep purification to afford 2-(6-((6-amino-5-chloropyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 238) as white solid. Yield: 14 mg, 17%; MS (ESI) m/z 414.85 [M+1]+; $^1$H NMR (400 MHz, DMSO-$d_6$ with $d_1$-TFA) δ 8.49 (s, 1H), 8.33 (s, 1H), 4.49 (s, 2H), 3.76-3.71 (m, 2H), 3.58-3.41 (m, 4H), 2.42 (s, 3H), 1.90-1.87 (m, 2H).

Example 239

Synthesis of 6-((6-amino-5-methylpyrimidin-4-yl)amino)-8-methyl-2',3',5',6'-tetrahydro-2H-spiro[imidazo[1,5-a]pyridine-3,4'-pyran]-1,5-dione (Cpd. No. 239)

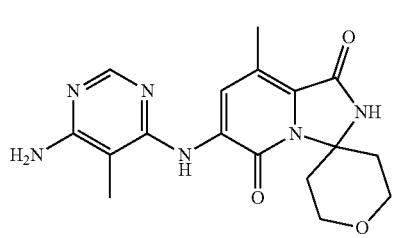 [SMILES: Cc1cc(Nc2ncnc(N)c2C)c(=O)n2c1C(=O)NC21CCOCC1]

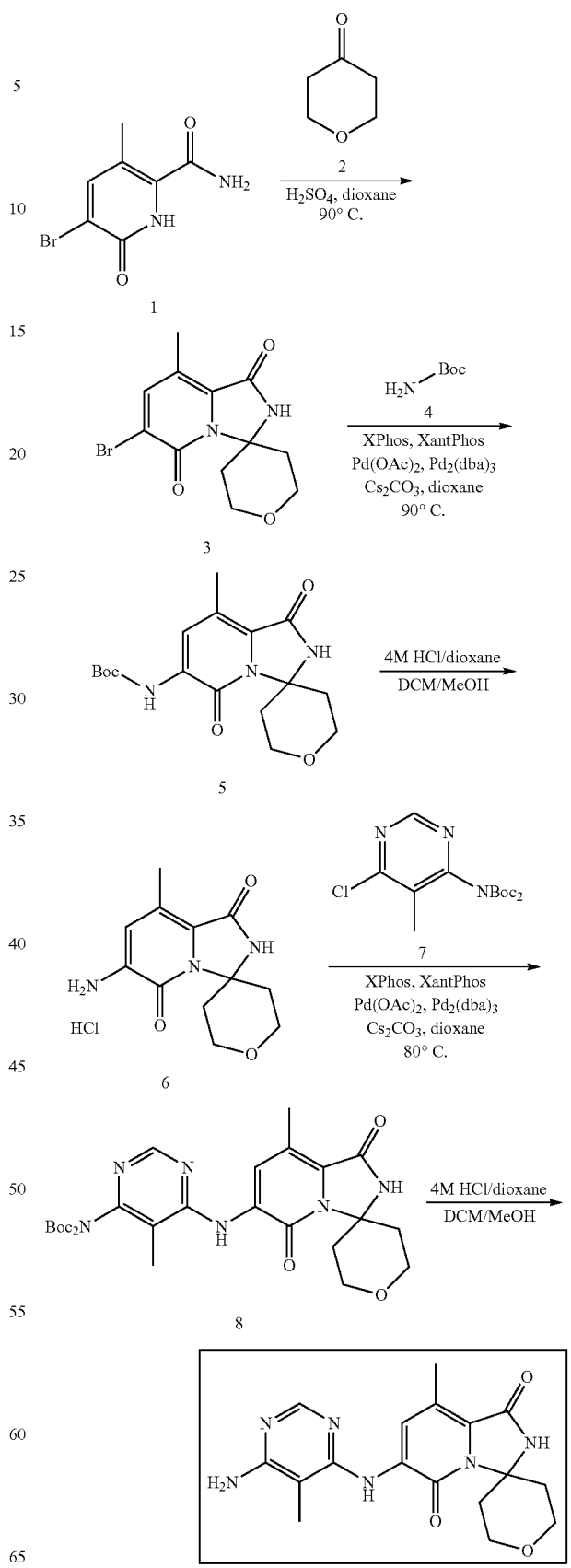

Synthesis of 6-bromo-8-methyl-2',3',5',6'-tetrahydro-2H-spiro[imidazo[1,5-a]pyridine-3,4'-pyran]-1,5-dione (3)

The synthesis of intermediate 3 was carried out as described above using the general protocol of Procedure A. Off white solid; Yield: 1.4 g, 69%; MS (ESI) m/z 313 [M+1]$^+$.

Synthesis of tert-butyl (8-methyl-1,5-dioxo-1,2',3',5,5',6'-hexahydro-2H-spiro[imidazo[1,5-a]pyridine-3,4'-pyran]-6-yl)carbamate (5)

The synthesis of intermediate 5 was carried out as described above using the general protocol of Procedure H. Off white solid; Yield: 1.2 g, crude; MS (ESI) m/z 350 [M+1]$^+$.

Synthesis of 6-amino-8-methyl-2',3',5',6'-tetrahydro-2H-spiro[imidazo[1,5-a]pyridine-3, 4'-pyran]-1,5-dione hydrochloride (6)

The synthesis of intermediate 6 was carried out as described above using the general protocol of Procedure F. Off white solid; Yield: 0.45 g, 42%; MS (ESI) m/z 285 [M+1]$^+$.

Synthesis of 6-((6-(di-(tert-butoxycarbonyl)-amino)-5-methylpyrimidin-4-yl)amino)-8-methyl-2',3',5',6'-tetrahydro-2H-spiro[imidazo[1,5-a]pyridine-3,4'-pyran]-1,5-dione (8)

The synthesis of intermediate 8 was carried out as described above using the general protocol of Procedure H. Off white solid; Yield: 0.26 g, 44%; MS (ESI) m/z 557 [M+1]$^+$.

Synthesis of 6-((6-amino-5-methylpyrimidin-4-yl)amino)-8-methyl-2',3',5',6'-tetrahydro-2H-spiro[imidazo[1,5-a]pyridine-3,4'-pyran]-1,5-dione (Cpd. No. 239)

The synthesis of compound 239 was carried out as described above using the general protocol of Procedure F. Off white solid; Yield: 0.12 g, 72%; MS (ESI) m/z 357 [M+1]+; $^1$H NMR (400 MHz, DMSO-d$_6$) δ 10.47 (s, 1H), 8.54 (s, 1H), 8.41 (s, 1H), 8.21 (s, 1H), 7.73 (brs, 2H), 3.96-3.90 (m, 2H), 3.69 (t, J=12.44 Hz, 2H), 3.25-3.15 (m, 2H), 2.46 (m, 3H), 2.07 (s, 3H), 1.46-1.41 (m, 2H).

Example 240

Synthesis of 2-(6-((6-amino-5-methylpyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 240)

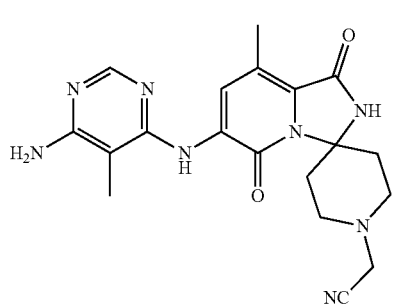 [SMILES: Cc1cc(Nc2ncnc(N)c2C)c(=O)n2c1C(=O)NC21CCN(CC#N)CC1]

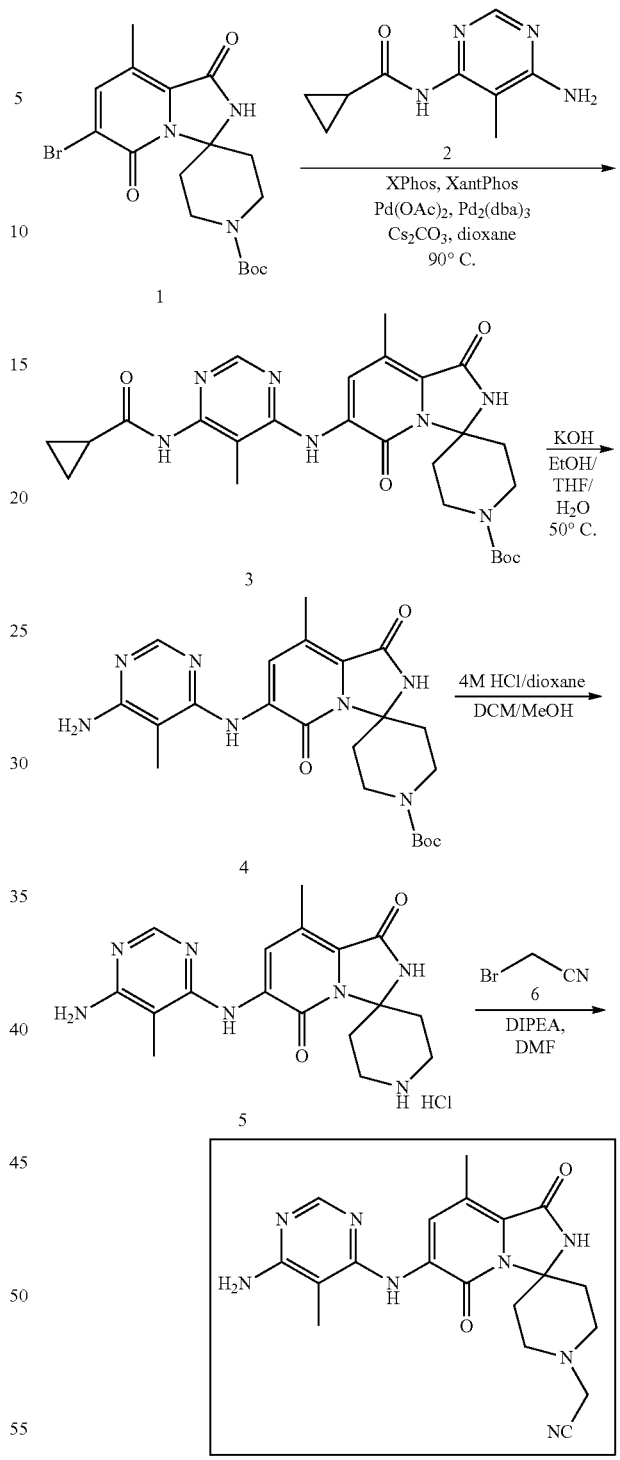

Synthesis of tert-butyl 6-((6-(cyclopropanecarboxamido)-5-methylpyrimidin-4-yl)amino)-8-methyl-1,5-dioxo-1,5-dihydro-2H-spiro[imidazo[1,5-a]pyridine-3,4'-piperidine]-1'-carboxylate (3)

The synthesis of intermediate 3 was carried out as described above using the general protocol of Procedure H. Light yellow solid; Yield: 0.75 g, 83%; MS (ESI) m/z 524.41 [M+1]$^+$.

Synthesis of tert-butyl 6-((6-amino-5-methylpyrimi-din-4-yl)amino)-8-methyl-1,5-dioxo-1,5-dihydro-2H-spiro[imidazo[1,5-a]pyridine-3,4'-piperidine]-1'-carboxylate (4)

The synthesis of intermediate 4 was carried out as described above using the general protocol of Procedure I. Yellow solid. Yield: 650 mg, 33%; MS (ESI) m/z 456.33 [M+1]+.

Synthesis of 6-((6-amino-5-methylpyrimidin-4-yl)amino)-8-methyl-2H-spiro[imidazo[1,5-a]pyridine-3,4'-piperidine]-1,5-dione hydrochloride (5)

The synthesis of intermediate 5 was carried out as described above using the general protocol of Procedure F. Light brown solid; Yield: 0.41 g, 80%; MS (ESI) m/z 356.12 [M+1]+.

Synthesis of 2-(6-((6-amino-5-methylpyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 240)

6-((6-amino-5-methylpyrimidin-4-yl)amino)-8-methyl-2H-spiro[imidazo[1,5-a]pyridine-3,4'-piperidine]-1,5-dione hydrochloride (5, 0.2 g, 0.56 mmol) was dissolved in dimethylformamide (10 mL). To it was added N,N-diisopropylethylamine (0.22 g, 1.68 mmol), followed by bromoacetonitrile (0.10 g, 0.84 mmol). The reaction mixture was stirred at room temperature for 30 min. After completion reaction mixture was diluted with 50 mL ethyl acetate, It was washed with saturated ammonium chloride solution and brine solution, solvent was removed under reduced pressure and the resulting residue was further washed with methanol ether and pentane, dried under vacuum to afford 2-(6-((6-amino-5-methylpyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 240) as light yellow solid. Yield: 95 mg, 43%; MS (ESI) m/z 395.18 [M+1]+; 1H NMR (400 MHz, DMSO-d6) δ 10.26 (s, 1H), 8.48 (s, 1H), 8.12 (s, 1H), 7.99 (s, 1H), 6.47 (s, 2H), 3.74 (s, 2H), 3.33-3.30 (m, 2H), 2.92-2.85 (m, 2H), 2.70-2.58 (m, 2H), 2.44 (s, 3H), 1.98 (s, 3H), 1.53-1.46 (m, 2H).

Example 241

Synthesis of 6-((6-amino-5-chloropyrimidin-4-yl)amino)-1'-(2,2-difluoroethyl)-8-methyl-2H-spiro[imidazo[1,5-a]pyridine-3,4'-piperidine]-1,5-dione (Cpd. No. 241)

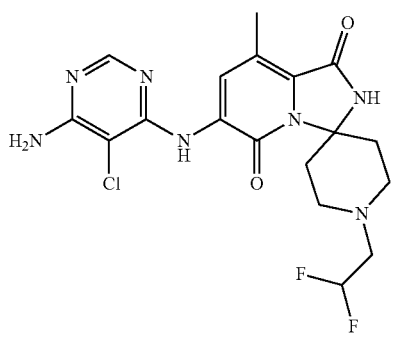 [SMILES: Cc1cc(Nc2ncnc(N)c2Cl)c(=O)n2c1C(=O)NC21CCN(CC(F)F)CC1]

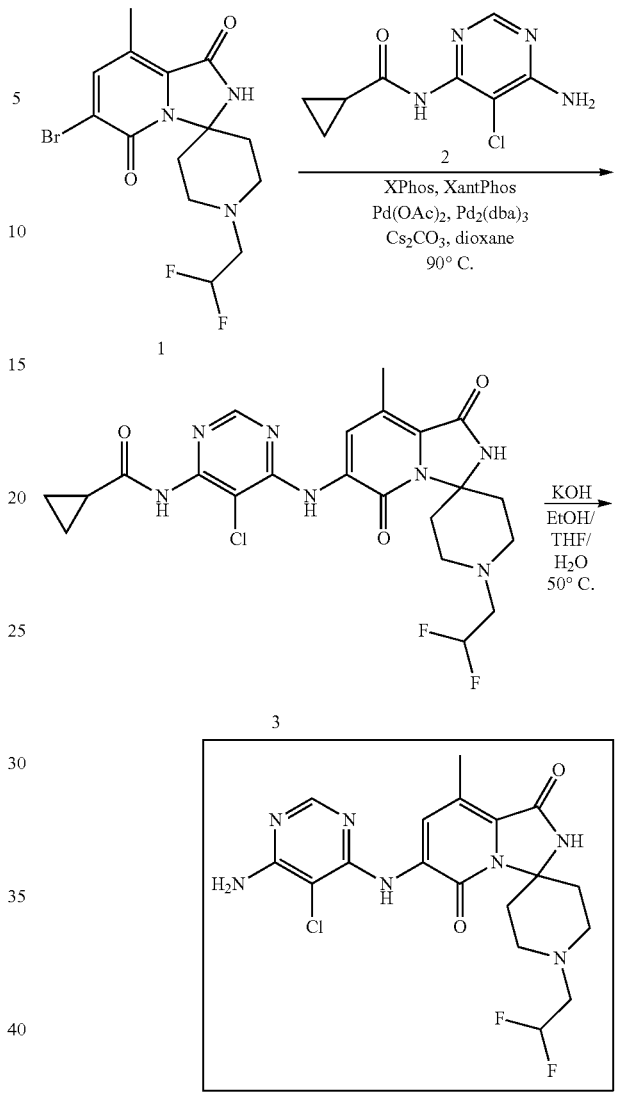

Synthesis of N-(5-chloro-6-((1'-(2,2-difluoroethyl)-8-methyl-1,5-dioxo-1,5-dihydro-2H-spiro[imidazo[1,5-a]pyridine-3,4'-piperidin]-6-yl)amino)pyrimidin-4-yl)cyclopropanecarboxamide (3)

The synthesis of intermediate 3 was carried out as described above using the general protocol of Procedure H. Light yellow solid; Yield: 0.38 g, 70%; MS (ESI) m/z 508.18 [M+1]+.

Synthesis of 6-((6-amino-5-chloropyrimidin-4-yl)amino)-1'-(2,2-difluoroethyl)-8-methyl-2H-spiro[imidazo[1,5-a]pyridine-3,4'-piperidine]-1,5-dione (Cpd. No. 241)

The synthesis of compound 241 was carried out as described above using the general protocol of Procedure I. White solid; Yield: 25 mg, 8%; MS (ESI) m/z 410.14 [M+1]+; 1H NMR (400 MHz, DMSO-d6) δ 10.26 (s, 1H), 8.53 (s, 1H), 8.51 (s, 1H), 8.18 (s, 1H), 7.21 (brs, 2H), 6.46 (t, J=56.0 Hz, 1H), 3.35-2.98 (m, 8H), 2.46 (s, 3H), 1.71-1.52 (m, 2H).

Example 242

Synthesis of 6-((6-amino-5-chloropyrimidin-4-yl)amino)-8-methyl-1'-(2,2,2-trifluoroethyl)-2H-spiro[imidazo[1,5-a]pyridine-3,4'-piperidine]-1,5-dione (Cpd. No. 242)

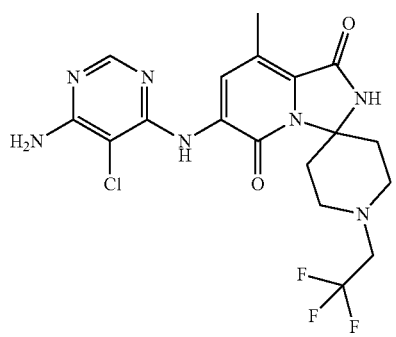 [SMILES: Cc1cc(Nc2ncnc(N)c2Cl)c(=O)n2c1C(=O)NC21CCN(CC(F)(F)F)CC1]

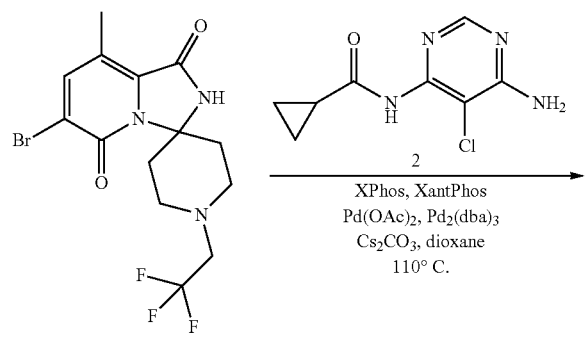

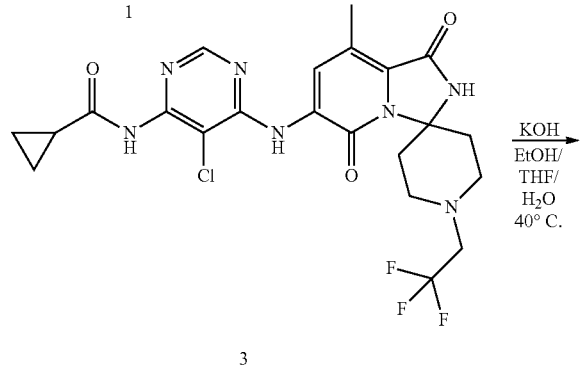

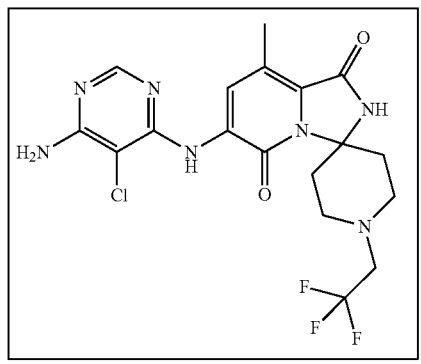

Synthesis of N-(5-chloro-6-((8-methyl-1,5-dioxo-1'-(2,2,2-trifluoroethyl)-1,5-dihydro-2H-spiro[imidazo[1,5-a]pyridine-3,4'-piperidin]-6-yl)amino)pyrimidin-4-yl)cyclopropanecarboxamide (3)

The synthesis of intermediate 3 was carried out as described above using the general protocol of Procedure H. Off white solid; Yield: 0.40 g; MS (ESI) m/z 524.1 [M−1]⁻.

Synthesis of 6-((6-amino-5-chloropyrimidin-4-yl)amino)-8-methyl-1'-(2,2,2-trifluoroethyl)-2H-spiro[imidazo[1,5-a]pyridine-3,4'-piperidine]-1,5-dione (Cpd. No. 242)

The synthesis of compound 242 was carried out as described above using the general protocol of Procedure I. Yield: 60 mg, 17%; MS (ESI) m/z 458.11 [M+1]⁺; ¹H NMR (400 MHz, DMSO-d₆) δ 10.26 (brs, 1H), 8.53 (s, 1H), 8.50 (s, 1H), 8.17 (s, 1H), 7.10 (brs, 2H), 3.40-3.22 (m, 4H), 2.96-2.93 (m, 2H), 2.84-2.78 (m, 2H), 2.46 (s, 3H), 1.42-1.39 (m, 2H).

Example 243

Synthesis of 2-(6-((6-amino-5-methoxypyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 243)

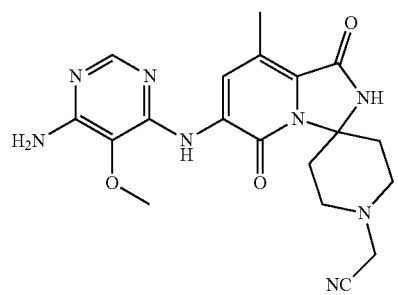 [SMILES: COc1c(N)ncnc1Nc1cc(C)c2n(c1=O)C1(CCN(CC#N)CC1)NC2=O]

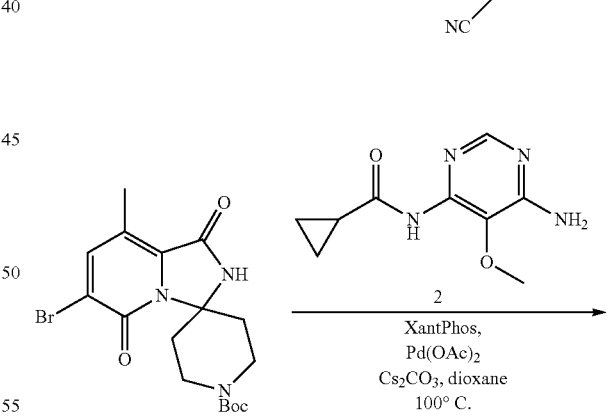

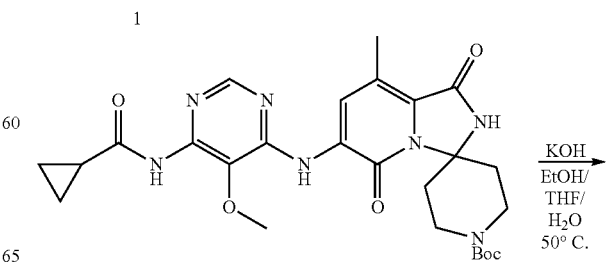

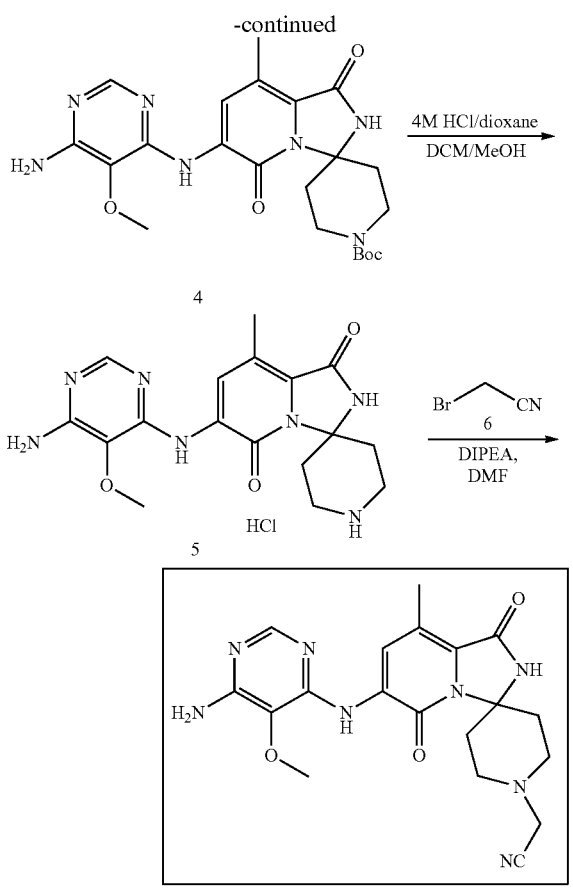

Synthesis of tert-butyl 6-((6-(cyclopropanecarbox-amido)-5-methoxypyrimidin-4-yl)amino)-8-methyl-1,5-dioxo-1,5-dihydro-2H-spiro[imidazo[,5-a]pyridine-3,4'-piperidine]-1'-carboxylate (3)

The synthesis of intermediate 3 was carried out as described above using the general protocol of Procedure B. Light yellow solid; Yield: 0.55 g; MS (ESI) m/z 540.31 [M+1]$^+$.

Synthesis of tert-butyl 6-((6-amino-5-methoxypy-rimidin-4-yl)amino)-8-methyl-1,5-dioxo-1,5-di-hydro-2H-spiro[imidazo[1,5-a]pyridine-3,4'-piperi-dine]-1'-carboxylate (4)

The synthesis of intermediate 4 was carried out as described above using the general protocol of Procedure I. Yellow solid; Yield: 250 mg; MS (ESI) m/z 472.28 [M+1]$^+$.

Synthesis of 6-((6-amino-5-methoxypyrimidin-4-yl)amino)-8-methyl-2H-spiro[imidazo[1,5-a]pyridine-3,4'-piperidine]-1,5-dione hydrochloride (5)

The synthesis of intermediate 5 was carried out as described above using the general protocol of Procedure F. Yellow solid; Yield: 0.18 g; MS (ESI) m/z 372.22 [M+1]$^+$.

Synthesis of 2-(6-(((6-amino-5-methoxypyrimidin-4-yl)amino)-8-methyl-1,5-dioxo-1,5-dihydro-2H-spiro[imidazo[1,5-a]pyridine-3,4'-piperidin]-1'-yl)acetoni-trile (Cpd. No. 243)

6-((6-Amino-5-methoxypyrimidin-4-yl)amino)-8-methyl-2H-spiro[imidazo[1,5-a]pyridine-3,4'-piperidine]-1,5-dione hydrochloride (5, 0.18 g, 0.44 mmol) was dissolved in dimethylformamide (5 mL). To this mixture N,N-diiso-propylethylamine (0.23 g, 1.76 mmol) was added followed by bromoacetonitrile (79 mg, 0.66 mmol). The reaction mixture was stirred at room temperature for 2 h. After completion the reaction mixture was diluted with saturated ammonium chloride solution (50 mL). Yellow precipitate was filtered and dried under reduced pressure. The compound was then purified by prep purification to afford 2-(6-(((6-amino-5-methoxypyrimidin-4-yl)amino)-8-methyl-1,5-dioxo-1,5-dihydro-2H-spiro[imidazo[1,5-a]pyridine-3,4'-piperidin]-1'-yl)acetonitrile (Cpd. No. 243) as white solid. Yield: 40 mg, 22%; MS (ESI) m/z 411.20 [M+1]$^+$; $^1$H NMR (400 MHz, DMSO-d$_6$ with d$_1$-TFA) δ 8.37 (s, 1H), 8.27 (s, 1H), 4.49 (s, 2H), 3.76 (s, 3H), 3.74-3.71 (m, 2H), 3.56-3.40 (m, 4H), 2.43 (s, 3H), 1.90-1.87 (m, 2H).

Example 244

Synthesis of 1'-(2,2-difluoroethyl)-6-((5-methoxypy-rimidin-4-yl)amino)-8-methyl-2H-spiro[imidazo[1,5-a]pyridine-3,4'-piperidine]-1,5-dione (Cpd. No. 244)

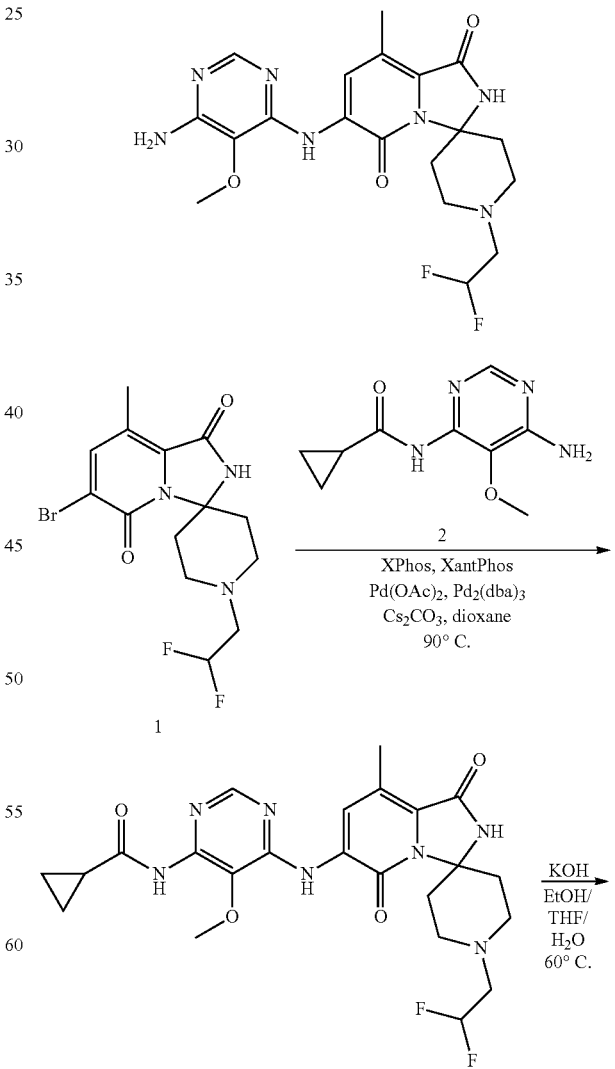

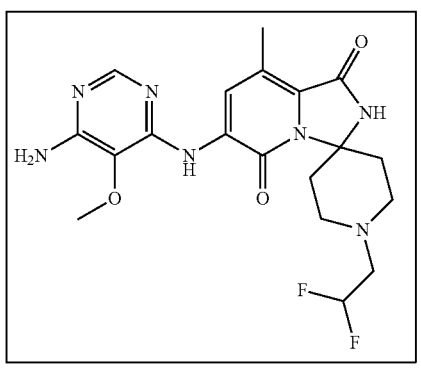

Synthesis of N-(6-((1'-(2,2-difluoroethyl)-8-methyl-1,5-dioxo-1,5-dihydro-2H-spiro[imidazo[1,5-a]pyridine-3,4'-piperidin]-6-yl)amino)-5-methoxypyrimidin-4-yl)cyclopropanecarboxamide (3)

The synthesis of intermediate 3 was carried out as described above using the general protocol of Procedure H. Light yellow solid; Yield: 0.30 g, 26%; MS (ESI) m/z 504.14 [M+1]$^+$.

Synthesis of 1'-(2, 2-difluoroethyl)-6-((5-methoxypyrimidin-4-yl)amino)-8-methyl-2H-spiro[imidazo[1,5-a]pyridine-3,4'-piperidine]-1,5-dione (Cpd. No. 244)

The synthesis of compound 244 was carried out as described above using the general protocol of Procedure I. Light brown solid; Yield: 27 mg, 10%; MS (ESI) m/z [M+1]$^+$; $^1$H NMR (400 MHz, DMSO-d$_6$ with d$_1$-TFA) δ 8.42 (s, 1H), 8.26 (s, 1H), 6.56 (t, J=56 Hz, 1H), 384-3.64 (m, 7H), 3.60-3.40 (m, 4H), 2.46 (s, 3H), 1.92-1.86 (m, 2H).

Example 245

Synthesis of 3'-((6-aminopyrimidin-4-yl)amino)-1'-methylspiro[cyclohexane-1,5'-pyrrolo[3,4-b]pyridine]-4',7'(1'H,6'H)-dione (Cpd. No. 245)

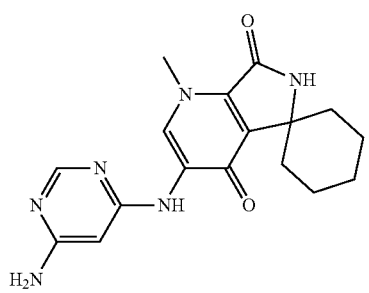 [SMILES: Cn1cc(Nc2cc(N)ncn2)c(=O)c2c1C(=O)NC21CCCCC1]

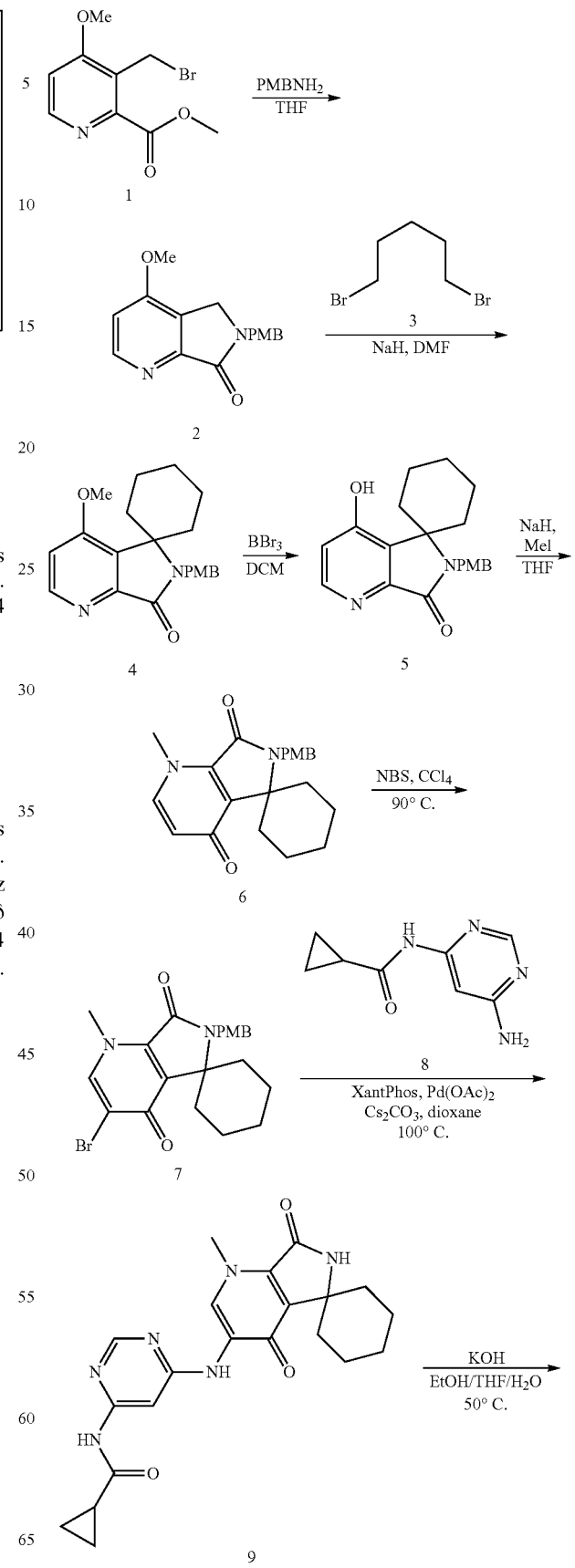

-continued

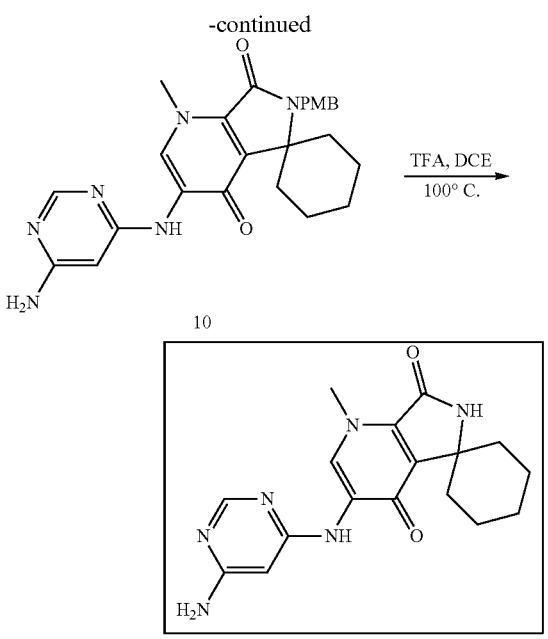

Synthesis of 4-methoxy-6-(4-methoxybenzyl)-5,6-dihydro-7H-pyrrolo[3,4-b]pyridin-7-one (2)

Treat a solution of methyl 3-(bromomethyl)-4-methoxypicolinate (1.0 mmol, 1 eq) in tetrahydrofuran with 4-methoxybenzylamine (2.0 mmol, 2 eq) and stir the reaction for 16 h. After completion dilute the mixture with ethyl acetate and water and separate the layers. Wash the organic layer with 1 M hydrochloric acid and water. Concentrate the organic layer to give crude. Purify the crude by silica gel column chromatography to afford 4-methoxy-6-(4-methoxybenzyl)-5,6-dihydro-7H-pyrrolo[3,4-b]pyridin-7-one (2).

Synthesis of 4'-methoxy-6'-(4-methoxybenzyl)spiro[cyclohexane-1,5'-pyrrolo[3,4-b]pyridin]-7'(6'H)-one (4)

To a solution of 4-methoxy-6-(4-methoxybenzyl)-5,6-dihydro-7H-pyrrolo[3,4-b]pyridin-7-one (2, 1.0 mmol, 1 eq) in tetrahydrofuran (25 mL) add sodium hydride (2.5 mmol, 2.5 eq) at 0° C. Stir the mixture for 20 min and then add 1,5-dibromo pentane (3, 1.5 mmol, 1.5 eq) and stir for 8 h. After completion quench the mixture with water at 0° C. and add ethyl acetate. Separate the layer and remove the solvent to get crude. Purify the crude by silica gel column chromatography to afford 4'-methoxy-6'-(4-methoxybenzyl)spiro[cyclohexane-1,5'-pyrrolo[3,4-b]pyridin]-7'(6'H)-one (4).

Synthesis of 4'-hydroxy-6'-(4-methoxybenzyl)spiro[cyclohexane-1,5'-pyrrolo[3,4-b]pyridin]-7'(6'H)-one (5)

Treat a solution of 4'-methoxy-6'-(4-methoxybenzyl)spiro[cyclohexane-1,5'-pyrrolo[3,4-b]pyridin]-7'(6'H)-one (4, 1.0 mmol, 1 eq) in dichloromethane (25 mL) with boron tribromide (2.0 mmol, 2 eq) at 0° C. Stir the mixture for 2 h at room temperature and quench with water at 0° C. Extract the mixture with ethyl acetate and remove the solvent under reduced pressure to get the crude. Purify the crude by silica gel column chromatography to get 4'-hydroxy-6'-(4-methoxybenzyl)spiro[cyclohexane-1,5'-pyrrolo[3,4-b]pyridin]-7'(6'H)-one (5).

Synthesis of 6'-(4-methoxybenzyl)-1'-methylspiro[cyclohexane-1,5'-pyrrolo[3,4-b]pyridine]-4',7'(1'H,6'H)-dione (6)

To a solution of 4'-hydroxy-6'-(4-methoxybenzyl)spiro[cyclohexane-1,5'-pyrrolo[3,4-b]pyridin]-7'(6'H)-one (1.0 mmol, 1 eq) in tetrahydrofuran (25 mL), add sodium hydride (2.5 mmol, 2.5 eq) at 0° C. and stir for 20 min. Add iodomethane (2.5 mmol, 2.5 eq) to the above mixture and stir for 16 h. After completion add water to the reaction and extract with ethyl acetate. Remove the solvent under reduced pressure to get the crude which is purified by column chromatography to give 6'-(4-methoxybenzyl)-1'-methylspiro[cyclohexane-1,5'-pyrrolo[3,4-b]pyridine]-4',7'(1'H, 6'H)-dione (6).

Synthesis of 3'-bromo-6'-(4-methoxybenzyl)-1'-methylspiro[cyclohexane-1,5'-pyrrolo[3,4-b]pyridine]-4',7'(1'H,6'H)-dione (7)

To a solution of 6'-(4-methoxybenzyl)-1'-methylspiro[cyclohexane-1,5'-pyrrolo[3,4-b]pyridine]-4',7'(1'H,6'H)-dione (1.0 mmol, 1 eq) in carbon tetrachloride (25 mL), add N-bromosuccinimide and heat the mixture at 90° C. for 16 h. After completion the mixture was diluted with water and extracted with ethyl acetate. Remove the solvent under reduced pressure to get the crude. Purify the crude by column chromatography to afford 3'-bromo-6'-(4-methoxybenzyl)-1'-methylspiro[cyclohexane-1,5'-pyrrolo[3,4-b]pyridine]-4',7'(1'H,6'H)-dione (7).

Synthesis of N-(6-((1'-methyl-4',7'-dioxo-1',4',6',7'-tetrahydrospiro[cyclohexane-1,5'-pyrrolo[3,4-b]pyridin]-3'-yl)amino)pyrimidin-4-yl)cyclopropanecarboxamide (9)

The synthesis of intermediate 9 is carried out as described above using the general protocol of Procedure B.

Synthesis of 3'-((6-aminopyrimidin-4-yl)amino)-6'-(4-methoxybenzyl)-1'-methylspiro[cyclohexane-1,5'-pyrrolo[3,4-b]pyridine]-4',7'(1'H,6'H)-dione (10)

The synthesis of intermediate 10 is carried out as described above using the general protocol of Procedure I.

Synthesis of 3'-((6-aminopyrimidin-4-yl)amino)-1'-methylspiro[cyclohexane-1,5'-pyrrolo[3,4-b]pyridine]-4',7'(1'H, 6'H)-dione (Cpd. No. 245)

Treat a solution of 3'-((6-aminopyrimidin-4-yl)amino)-6'-(4-methoxybenzyl)-1'-methylspiro[cyclohexane-1,5'-pyrrolo[3,4-b]pyridine]-4',7'(1'H,6'H)-dione (1.0 mmol, 1 eq) in 1,2-dichloroethane (15 mL) with trifluoroacetic acid (20 mmol, 20 eq) and heat the mixture to 100° C. for 5 h. After completion, cool the mixture and remove the solvent. Triturate the mixture with ether to get solid. The solid is again triturated with methanol to get 3'-((6-aminopyrimidin-4-yl)amino)-1'-methylspiro[cyclohexane-1,5'-pyrrolo[3,4-b]pyridine]-4',7'(1'H,6'H)-dione (Cpd. No. 245).

Example 246

Synthesis of 6'-((6-aminopyrimidin-4-yl)amino)-8'-methyl-2'H-spiro[cyclohexane-1,3'-indolizine]-1',5'-dione (Cpd. No. 246)

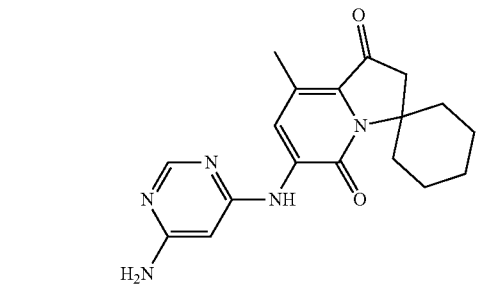 [SMILES: Cc1cc(Nc2cc(N)ncn2)c(=O)n2c1C(=O)CC21CCCCC1]

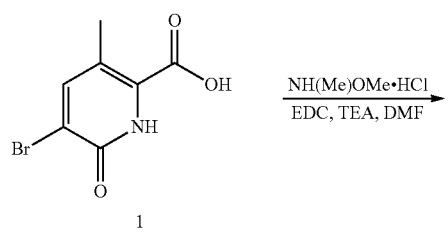

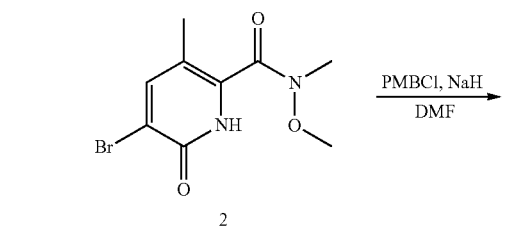

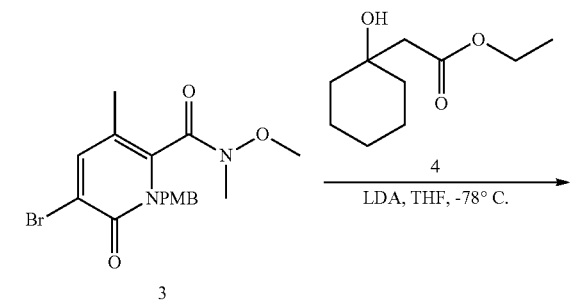

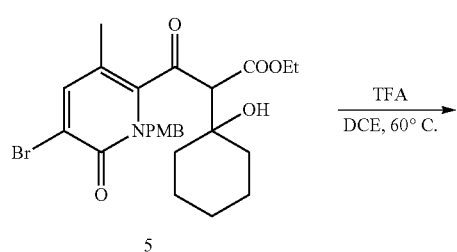

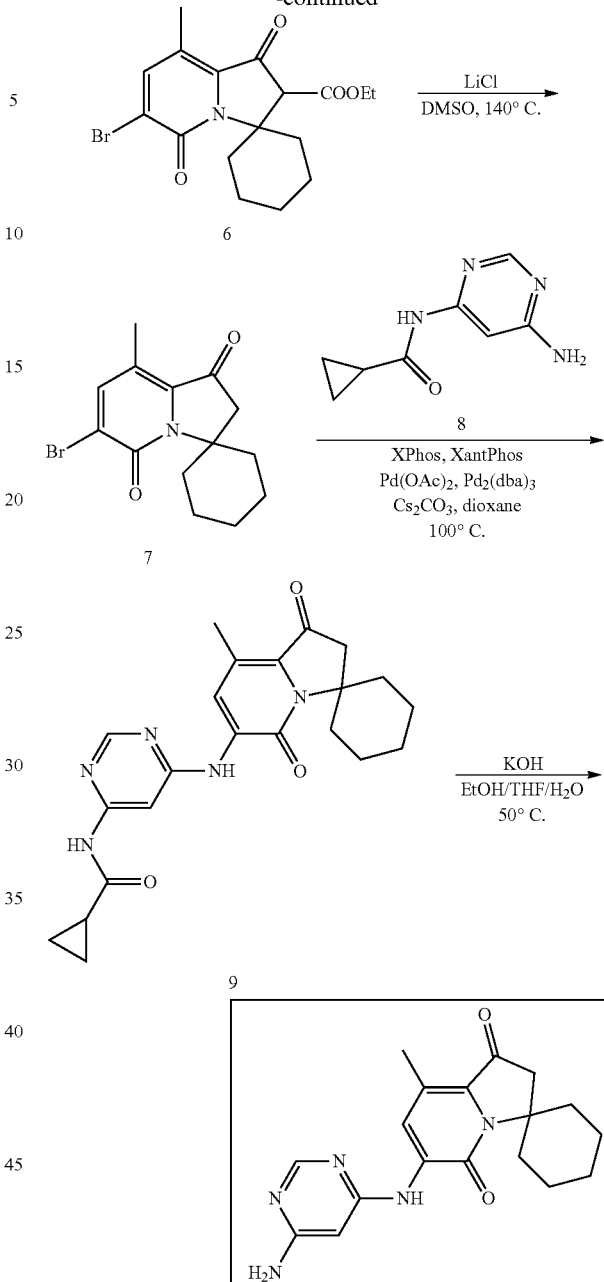

Synthesis of 5-bromo-N-methoxy-N, 3-dimethyl-6-oxo-1, 6-dihydropyridine-2-carboxamide (2)

To a solution of 5-bromo-3-methyl-6-oxo-1,6-dihydropyridine-2-carboxylic acid (1, 1.0 mmol, 1 eq) in dimethylformamide (25 mL), add N-(3-dimethylaminopropyl)-N'-ethylcarbodiimide (2 mmol, 2 eq), triethylamine (3.0 mmol, 3 eq) and N,O-dimethylhydroxylamine hydrochloride (1.5 mmol, 1.5 eq) and stir the reaction for 6 h. After completion add water to the mixture and extract with ethyl acetate. Wash the ethyl acetate layer with water and brine, remove the solvent under reduced pressure to get 5-bromo-N-methoxy-N,3-dimethyl-6-oxo-1,6-dihydropyridine-2-carboxamide (2).

393

Synthesis of 5-bromo-N-methoxy-1-(4-methoxyben-zyl)-N, 3-dimethyl-6-oxo-1,6-dihydropyridine-2-carboxamide (3)

Add sodium hydride (2.5 mmol, 2.5 eq) to a cooled solution of 5-bromo-N-methoxy-N,3-dimethyl-6-oxo-1,6-dihydropyridine-2-carboxamide (2, 1.0 mmol, 1 eq) in dimethylformamide (25 mL) and stir the reaction for 20 min. Add 4-methoxybenzyl chloride (1.2 mmol, 1.2 eq) and stir the reaction for 16 h. After completion, quench the reaction with water and extract with ethyl acetate. Remove the solvent and purify the crude by column chromatography to afford 5-bromo-N-methoxy-1-(4-methoxybenzyl)-N,3-dimethyl-6-oxo-1,6-dihydropyridine-2-carboxamide (3).

Synthesis of ethyl 3-(5-bromo-1-(4-methoxyben-zyl)-3-methyl-6-oxo-1,6-dihydropyridin-2-yl)-2-(1-hydroxycyclohexyl)-3-oxopropanoate (5)

To a solution of ethyl 2-(1-hydroxycyclohexyl)acetate (4, 1.2 mmol, 1.2 eq) in tetrahydrofuran (15 mL), add lithium diisopropylamide (2.5 mmol, 2.5 eq) at −78° C. and stir the reaction for 20 min. Add a solution of 5-bromo-N-methoxy-1-(4-methoxybenzyl)-N,3-dimethyl-6-oxo-1,6-dihydropyridine-2-carboxamide (3, 1.0 mmol, 1.0 eq) in tetrahydrofuran (10 mL) at −78° C. in 10 min and continue stirring for another 3 h. After completion, add saturate aqueous ammonium chloride solution and extract the reaction mass with ethyl acetate. Evaporate the solvent under reduced pressure and to get the crude which is passed through a silica gel bed to get ethyl 3-(5-bromo-1-(4-methoxybenzyl)-3-methyl-6-oxo-1,6-dihydropyridin-2-yl)-2-(1-hydroxycyclohexyl)-3-oxopropanoate (5).

Synthesis of ethyl 6'-bromo-8'-methyl-1',5'-dioxo-1',5'-dihydro-2'H-spiro[cyclohexane-1, 3'-indolizine]-2'-carboxylate (6)

To a solution of ethyl 3-(5-bromo-1-(4-methoxybenzyl)-3-methyl-6-oxo-1,6-dihydropyridin-2-yl)-2-(1-hydroxycyclohexyl)-3-oxopropanoate (5, 1.0 mmol, 1.0 eq) in 1,2-dichloroethane (15 mL), add trifluoroacetic acid (10 mmol, 10 eq) and heat the reaction at 60° C. for 16 h. After completion, remove the solvent and quench the reaction with ammonia and extract with dichloromethane. Remove the solvent under reduced pressure and purify the crude using silica gel column chromatography to afford ethyl 6'-bromo-8'-methyl-1',5'-dioxo-1',5'-dihydro-2'H-spiro[cyclohexane-1,3'-indolizine]-2'-carboxylate (6).

Synthesis of 6'-bromo-8'-methyl-2'H-spiro[cyclohexane-1,3'-indolizine]-1',5'-dione (7)

To a solution of ethyl 6'-bromo-8'-methyl-1',5'-dioxo-1',5'-dihydro-2'H-spiro[cyclohexane-1,3'-indolizine]-2'-carboxylate (6, 1.0 mmol, 1.0 eq) in dimethylsulfoxide (15 mL) add lithium chloride (5.0 mmol, 5 eq) and heat the reaction at 140° C. for 16 h. After completion cool the reaction, add water and extract with dichloromethane. Remove the solvent under reduced pressure and purify the crude by silica gel column chromatography to get 6'-bromo-8'-methyl-2'H-spiro[cyclohexane-1,3'-indolizine]-1',5'-dione (7).

394

Synthesis of N-(6-((8'-methyl-1',5'-dioxo-1',5'-dihydro-2'H-spiro[cyclohexane-1, 3'-indolizin]-6'-yl)amino)pyrimidin-4-yl)cyclopropanecarboxamide (9)

The synthesis of intermediate 9 is carried out as described above using the general protocol of Procedure H.

Synthesis of 6'-((6-aminopyrimidin-4-yl)amino)-8'-methyl-2'H-spiro[cyclohexane-1,3'-indolizine]-1',5'-dione (Cpd. No. 246)

The synthesis of compound 246 is carried out as described above using the general protocol of Procedure I.

Example 247

Synthesis of 6'-((6-amino-5-methylpyrimidin-4-yl)amino)-8'-methyl-2'H-spiro[cyclohexane-1,3'-indolizine]-1',5'-dione (Cpd. No. 247)

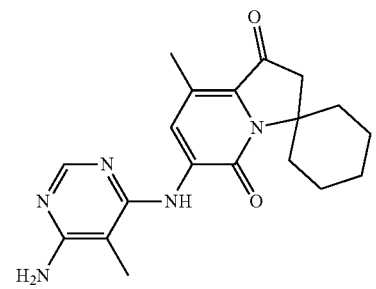 [SMILES: Cc1cc(Nc2ncnc(N)c2C)c(=O)n2c1C(=O)CC21CCCCC1]

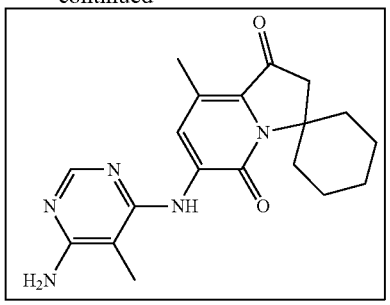

Synthesis of N-(5-methyl-6-((8'-methyl-1',5'-dioxo-1',5'-dihydro-2'H-spiro[cyclohexane-1,3'-indolizin]-6'-yl)amino)pyrimidin-4-yl)cyclopropanecarboxamide (3)

The synthesis of intermediate 3 is carried out as described above using the general protocol of Procedure B.

Synthesis of 6'-((6-amino-5-methylpyrimidin-4-yl)amino)-8'-methyl-2'H-spiro[cyclohexane-1,3'-indolizine]-1',5'-dione (Cpd. No. 247)

The synthesis of compound 247 is carried out as described above using the general protocol of Procedure I.

Example 248

Large-Scale Synthesis of Intermediates and Formula I Compounds

Compounds in accordance with the present invention are candidate therapeutics for treating Mnk related disorders, such as inflammatory disorders and cancer. To provide commercial quantities of the inventive compounds, the present invention illustrates a large-scale synthetic protocol for an exemplary Formula I compound as well as methods for the manufacture and characterization of the hydrochloride salt form (HCl-salt form) of such a compound.

Preparation of N-(6-aminopyrimidin-4-yl) cyclopropanecarboxamide

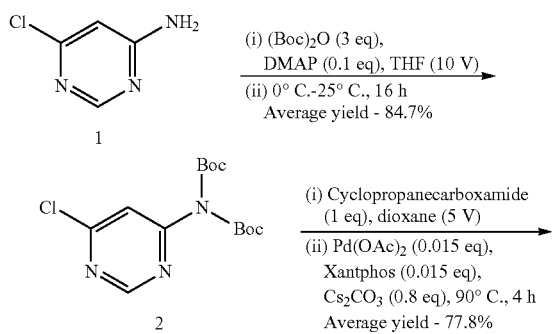

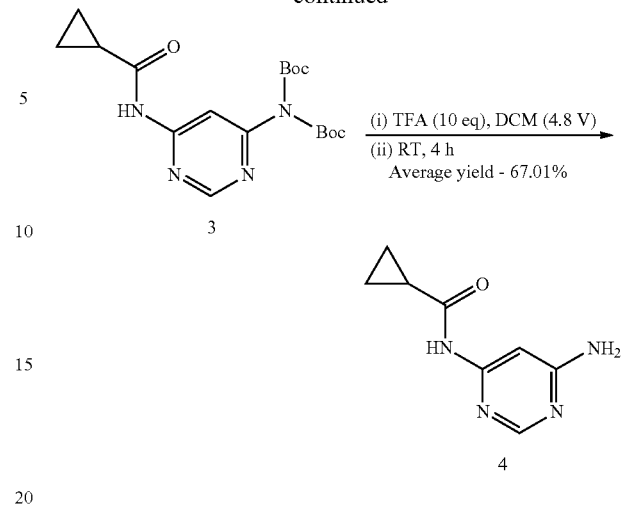

A. Preparation of Di-tert-butyl (6-chloropyrimidin-4-yl) carbamate (2)

To a stirred solution of 6-chloropyrimidin-4-amine (4900 g, 1 equiv, 37.08 moles) in tetrahydrofuran (10 V, 50 L), at 0° C. was added N, N-dimethylaminopyridine (463 g, 0.1 equiv, 3.70 moles). Di-tert-butyl dicarbonate (24.8 L, 3 equiv, 113.9 moles) was then added slowly over 1 h (gas evolution was observed) to the resultant reaction. The reaction mixture became dark brown with stirring at room temperature over a period of 16 h. Progress of the reaction was monitored by TLC and LCMS. LCMS showed the complete disappearance of SM, as well as peaks corresponding to the product, 73.89% at RT-2.55 ((M+1)–330.3); tert-butyl (6-chloropyrimidin-4-yl) carbamate side product, 4.09% at RT-1.98 ((M+1)–330.3).

After completion of reaction, the reaction mixture was poured into an ice/water mixture (30 L), and further stirred for 30 min prior to solvent extraction of the aqueous phase with ethyl acetate (10 L). The organic and aqueous phases were separated and the resultant aqueous layer was extracted twice with ethyl acetate (2×10 L). The combined organic layer was washed twice with water (2×10 L), then brine (1×10 L), and dried over anhydrous sodium sulfate. The dry organic layer was concentrated under reduced pressure at 50° C. to obtain crude product which was slurried with hexane (10 L) for 1 h, filtered and dried under reduced pressure at 50° C. to obtain brick red solid. Yield: 10.3 Kg, (82.6%). MS (ESI) m/z 329.78 [M+1]+; LCMS purity: 99.37%; 1H NMR (400 MHz, DMSO-d6) δ: 8.86 (s, 1H), 7.85 (s, 1H), 1.48 (s, 18H).

B. Preparation of di-tert-butyl (6-(cyclopropanecarboxamido) pyrimidin-4-yl) carbamate (3)

To a stirring solution of di-tert-butyl (6-chloropyrimidin-4-yl) carbamate (5000 g, 1 equiv, 15.20 moles) in dioxane (5 V, 25 L), at room temperature was added cyclopropanecarboxamide (1291 g, 1 equiv, 15.20 moles) followed by the addition of cesium carbonate (3950 g, 0.8 equiv, 12.15 moles). After purging the reaction mixture (dark brown solution) with argon for 30 minutes, xantphos (120 g, 0.015 equiv, 0.23 moles), and palladium (II) acetate (51 g, 0.015 equiv, 0.23 moles) were added. Purging of reaction mass with argon was continued for another 15 min and the reaction mixture was then heated to 90° C. and kept at that temperature for 4 h, during which time the color of the reaction mass changed to orange. Progress of reaction was monitored by TLC and LCMS. LCMS showed complete disappearance of SM, and a peak corresponding to product at RT-2.32 min., 86.92%, ((M+1)–379.15). In addition, the LCMS showed peaks corresponding to tert-butyl (6-(cyclopropanecarboxamido) pyrimidin-4-yl) carbamate 3.83%; at RT-1.94 ((M+1)-279.08) and some unknown byproducts (5.18% at RT-2.43 (M+1)–605.2, 1.48% at RT-2.83 (M+1)–589.2).

After completion of the reaction as judged by TLC and LCMS, the reaction mixture was cooled to 50° C. and was filtered through celite bed. The celite bed was washed with EtOAc (3×10 L) to ensure complete extraction of the product. Combined organic layers were washed with water (2×10 L), dried over anhydrous sodium sulphate and concentrated under reduced pressure to get crude (6.2 Kg). Diethyl ether (6.0 L) was added to the crude material and the mixture was stirred for 30 min to get free flowing solid. The solid was filtered, washed with ether (2×1 L) and then dried to afford di-tert-butyl (6-(cyclopropanecarboxamido) pyrimidin-4-yl) carbamate as an orange solid. This compound was used in the next step without further purification. Yield: 4.5 Kg, (78.2%); MS (ESI) m/z 378.43 [M+1]+; LCMS purity: 95.10%; 1H NMR (400 MHz, DMSO-d6) δ:11.30 (s, 1H), 8.66 (s, 1H), 8.25 (s, 1H), 2.02 (m, 1H), 1.46 (s, 18H), 0.85 (m, 4H).

C. Preparation of N-(6-aminopyrimidin-4-yl) cyclopropanecarboxamide (4)

Trifluoroacetic acid (16 L, 10 equiv, 212 moles) was slowly added over 1 h to a stirring solution of di-tert-butyl (6-(cyclopropanecarboxamido) pyrimidin-4-yl) ((3); 8050 g, 1 equiv, 21.20 moles) in dichloromethane (5 V, 40 L). Evolution of gas was observed during the addition of trifluoroacetic acid and the reaction became dark brown when stirred continuously for 4 h at room temperature. Progress of reaction was monitored by TLC.

After completion of reaction, the reaction mass was concentrated to dryness under reduced pressure (TFA must be distilled off as much as possible prior to addition of ammonia) and dichloromethane (25 L) was added to the residue. The mixture was cooled to 0° C. and NH4OH (25% aq. Solution, 6 L) was added slowly (pH-10) over 30 min while stirring the reaction mixture continuously. The resulting mixture was stirred at 0° C. for an additional 30 min and the solid formed was filtered and washed with water (2×10 L) followed by washing with methanol (2×2 L) and dichloromethane (15 L). The washed solid was dried under high vacuum overnight to afford N-(6-aminopyrimidin-4-yl) cyclopropanecarboxamide as creamish yellow solid. Yield: 2.32 Kg (61.02%); MS (ESI) m/z 178.19 [M+1]+; UPLC: 99.80%; 1H NMR (400 MHz, DMSO-d6) δ:10.54 (s, 1H), 8.10 (s, 1H), 7.10 (s, 1H), 6.72 (brs, 2H), 1.97 (m, 1H), 0.79 (m, 4H).

The final material from all batches were combined, slurried with dichloromethane (10 L) for 20 min, filtered and dried under vacuum for 6 h to obtain a single batch of N-(6-aminopyrimidin-4-yl) cyclopropanecarboxamide (3665.3).

Preparation of ethyl 5-bromo-3-methyl-6-oxo-1,6-dihydropyridine-2-carboxamide

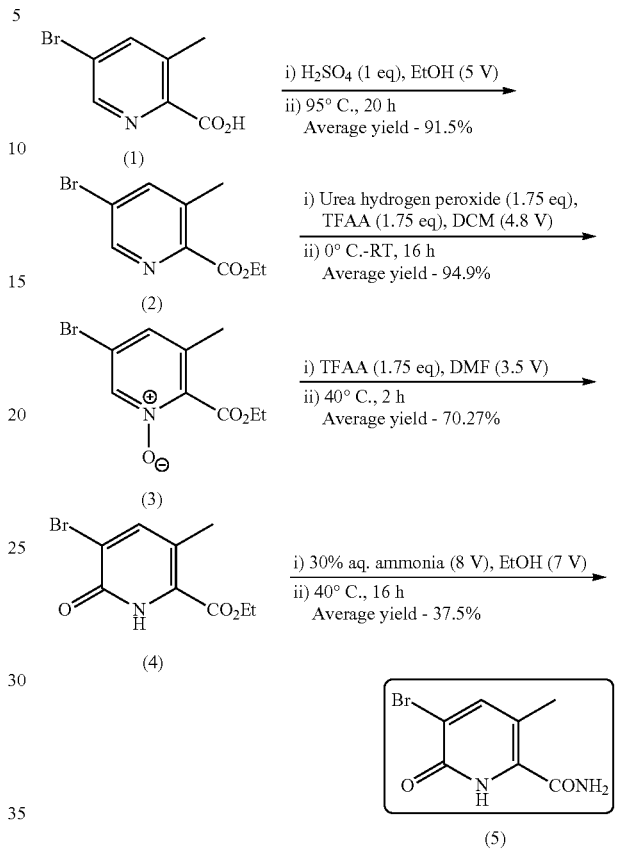

A. Preparation of ethyl 5-bromo-3-methylpicolinate (2)

To a stirring solution of 5-bromo-3-methylpicolinic acid (10000 g, 1 equiv, 46.29 moles) in ethanol (50 L) at 0° C. was added sulfuric acid (2.52 L, 1 equiv, 46.29 moles) over 1 h. Following addition of sulfuric acid, the mixture was heated at 95° C. for 20 h. Reaction progress was monitored by using TLC and LCMS. After 20 hours, LCMS showed 12.61% unreacted SM, at RT-0.67 ((M−1)−215.92) and 86.95% product at RT-2.04 ((M+1)−244.2). The reaction mass heated for additional 6 h and LCMS analysis following the additional heating showed 10.07% unreacted SM, at RT-0.7 and 89.93% product at RT-2.08 ((M+1)−244.2. The reaction was stopped by concentrating the reaction mixture under reduced pressure to remove as much solvent as possible. To the residue was added dichloromethane (DCM), (25 L) and the reaction mixture was poured into ice cold water (20 L). The organic (DCM) layer was separated from the aqueous layer and the latter was further extracted twice with DCM (10 L). The combined organic layers were washed with saturated sodium bicarbonate solution (30 L), dried over sodium sulfate, and concentrated under reduced pressure to obtain a brown oil. This brown oil was used in the next step without further purification. Yield: 10.1 Kg, (89.4%); MS (ESI) m/z 244.2 [M+1]+; LCMS purity: 99.11%; 1H NMR (400 MHz, DMSO-d6) δ: 8.61 (s, 1H), 8.13 (s, 1H), 4.29 (q, 2H), 2.44 (s, 1H), 1.28 (t, 3H).

B. Preparation of 5-bromo-2-(ethoxycarbonyl)-3-methylpyridine 1-oxide (3)

To a stirring solution of ethyl 5-bromo-3-methylpicolinate (9.49 Kg, 1 equiv, 38.88 moles) in dichloromethane (47.5 L) at 0° C. was added urea hydrogen peroxide (6.3 Kg, 1.75 equiv, 68.04 moles), followed by the addition of trifluoroacetic anhydride (9.7 L, 1.75 equiv, 68.04 moles) at 0° C. over a period of 3 h. This reaction is strongly exothermic (0-30° C.). Following addition, the reaction mixture was gently warmed to room temperature (RT) and permitted to stir at RT for 16 h. Reaction progress was monitored by using TLC and LCMS analysis. At the end of 16 hours, LCMS showed 0.74% unreacted SM at RT-2.04 ((M+1)-244.02); 91.61% product at RT-1.38 ((M+1)-260.01) and some unknown byproducts (4.67% at RT-1.28 (M+1)-188.1, 2.98% at RT-1.90 (M+1)-217.11).

The crude reaction mixture was poured into an ice/water mixture (30 L) and the organic and aqueous phases were permitted to separate. The aqueous layer was extracted with dichloromethane (10 L), separated from the aqueous layer and combined with the first organic layer. The combined organic layers were then washed with aqueous sodium bicarbonate solution (50 L), followed by water (20 L), dried over sodium sulfate and concentrated to afford 5-bromo-2-(ethoxycarbonyl)-3-methylpyridine 1-oxide as a reddish yellow oil. This compound was used for the next step without further purification. Yield: 9 Kg, (89%); MS (ESI) m/z 260.09 [M+1]+; LCMS purity: 99.34%; 1H NMR (400 MHz, DMSO-d6) δ: 8.56 (s, 1H), 7.67 (s, 1H), 4.32 (q, 2H), 2.21 (s, 3H), 1.27 (t, 3H).

C. Preparation of ethyl 5-bromo-3-methyl-6-oxo-1,6-dihydropyridine-2-carboxylate (4)

To a stirring solution of 5-bromo-2-(ethoxycarbonyl)-3-methylpyridine 1-oxide (9 Kg, 1 equiv, 34.62 moles) in N,N-dimethylformamide (35 L) at RT was added trifluoroacetic anhydride (8.65 L, 1.75 equiv, 60.58 moles), over a period of 3 h. The temperature of the reaction was maintained at 35-40° C. during the addition of trifluoroacetic anhydride. The reaction mixture was stirred at 40° C. (internal) for 2 h and reaction progress was monitored by using TLC and LCMS analysis. LCMS analysis showed 6.26% unreacted SM at RT-1.37 ((M+1)-260.01), 31.33% product at RT-1.58 ((M+1)-259.97), 25.88% DMF at RT-0.31 and some unknown byproducts (8.06% at RT-1.06 (M+1)-259.97, 22.42% at RT-2.29 (M+1)-323.86).

Following LCMS analysis, the reaction mass was stirred for additional 1 h, then poured into ice cold water (100 L), to give a white solid that was filtered and washed with water (20 L). The crude solid compound was further washed with n-hexane (20 L) and dried under high vacuum to afford ethyl 5-bromo-3-methyl-6-oxo-1, 6-dihydropyridine-2-carboxylate as off white solid. Yield: 6 Kg (66.6%); MS (ESI) m/z 260.09 [M+1]+; UPLC: 66.49% (96.85% by HPLC); 1H NMR (400 MHz, DMSO-d6) δ:11.53 (brs, 1H), 7.99 (s, 1H), 4.23 (q, 2H), 2.27 (brs, 3H), 1.28 (t, 3H).

D. Preparation of ethyl 5-bromo-3-methyl-6-oxo-1,6-dihydropyridine-2-carboxamide (5)

To a stirring solution of ethyl 5-bromo-3-methyl-6-oxo-1,6-dihydropyridine-2-carboxylate (1 Kg, 1 equiv, 3.84 moles) in ethanol (5 L) was added 30% aq. ammonia (7 L). The round bottom flask was then closed and sealed to avoid ammonia from escaping out of the reaction mass. The reaction mixture was then stirred at 40° C. for 16 h and reaction progress was monitored by using TLC and LCMS analysis. LCMS analysis of the reaction mixture showed disappearance of SM, 64.82% product at RT-1.09 ((M+1)-231.17), and some unknown byproducts 18.2% at RT-0.83 ((M+1)-232.11), 4.74% at RT-1.76 ((M+1)-262.19).

Following LCMS, the reaction mass was concentrated under reduced pressure to remove ethanol and water so as to yield a crude solid material. The crude material (wet) obtained from several synthetic batches were combined and slurried with saturated aqueous sodium bicarbonate solution (50 L) for 2 h, filtered and then washed with water (2×10 L). The white solid thus obtained was washed with dichloromethane (20 L), and then slurried with 20% methanol in dichloromethane (30 L) for 1 h. The slurry was filtered, washed with dichloromethane (15 L), and dried under vacuum for 6 h at 60° C. to yield 2.69 Kg of 5-bromo-3-methyl-6-oxo-1,6-dihydropyridine-2-carboxamide (5) as an off white solid. Yield: 2.69 Kg (50.94%); MS (ESI) m/z 231[M+1]+; UPLC: 99.80%; 1H NMR (400 MHz, DMSO-d6) δ: 11.85 (brs, 1H), 7.88 (s, 2H), 7.75 (s, 1H), 2.14 (s, 1H).

In a separate experiment, 5-bromo-3-methyl-6-oxo-1,6-dihydropyridine-2-carboxamide, 2.2 Kg, obtained by combining the solid from several synthetic batches was slurried in dichloromethane (5.0 L) for 30 min, filtered and dried under vacuum to yield 4554.1 g 5-bromo-3-methyl-6-oxo-1, 6-dihydropyridine-2-carboxamide.

Synthesis of 6'-((6-aminopyrimidin-4-yl)amino)-8'-methyl-2'H-spiro[cyclohexane-1,3'-imidazo[1,5-a]pyridine]-1',5'-dione hydrochloride (Cpd. 107)

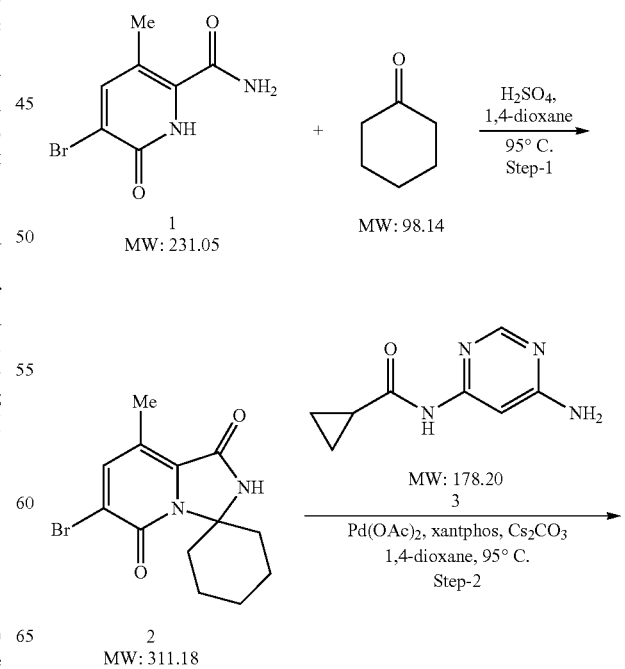

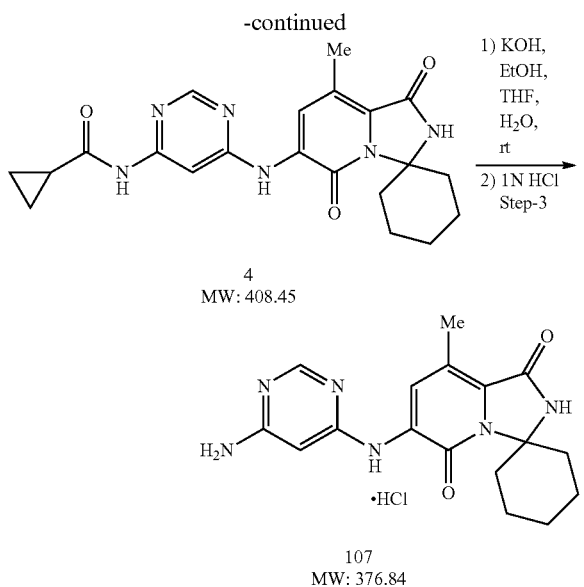

4
MW: 408.45

107
MW: 376.84

A. Procedure for the Purification of 5-bromo-3-methyl-6-oxo-1,6-dihydropyridine-2-carboxamide (1)

Solid sodium bicarbonate (3.3 kg) and water (40.0 L, DI) were charged into a 45 L carboy and stirred until the sold dissolved. 5-bromo-3-methyl-6-oxo-1,6-dihydropyridine-2-carboxamide (1; 1.5 kg) was placed in a 50-L reactor and the solution of saturated sodium bicarbonate was added while maintaining the temperature of this reaction mixture at 18° C. HPLC analysis of the reaction mixture after 16 h showed that the 5-bromo-3-methyl-6-oxo-1,6-dihydropyridine-2-carboxamide (1) had a purity of 92.8%. The solid 5-bromo-3-methyl-6-oxo-1,6-dihydropyridine-2-carboxamide was filtered through a Nutsche filter (18" polypropylene tight weave cloth). The reactor and filter cake were rinsed with water (3.0 L) and the solid was conditioned at ambient temperature until liquid no longer flowed out. The solid material was transferred to drying trays and dried under vacuum at 45-50° C. The dried material weighed 1.16 kg (yield ~77%), and had a purity of 92.8%. KF analysis showed 2.6% residual water.

B. Synthesis of 6'-bromo-8'-methyl-2'H-spiro[cyclohexane-1,3'-imidazo[1,5-a]pyridine]-1',5'-dione (2)

5-bromo-3-methyl-6-oxo-1,6-dihydropyridine-2-carboxamide (1), (1.16 kg, 1.0 equiv.); 1,4-dioxane (13.8 L); and cyclohexanone (1.96 kg) were added to a 50-L reactor and agitated at 75-125 RPM. Sulfuric acid (0.13 L) was added to the reactor using a dosing pump. The temperature of the reaction mixture was 19.5° C. at the start of addition of sulfuric acid and increased to 21.8° C. upon the complete addition of sulfuric acid. The temperature of the reaction mixture (batch temperature) was raised to 95° C. Following stirring for 3 h, HPLC analysis of the reaction mixture indicated completion of the reaction. The batch temperature was then adjusted to 20-30° C. and the solvent was distilled under vacuum (28.5"/Hg, 80° C. jacket temperature) to no less than 75% of the initial reaction volume.

Following distillation, the batch temperature was adjusted to 25° C. and held at that temperature for 13 h. The reaction mixture (batch) was filtered through Nutsche filter (18"), and the mother liquor was added back to the reactor as a rinse and then added to the filter cake. Water (12 L, DI) was then added to the reactor as a rinse and then transferred to the filter cake. The filter cake was conditioned until liquid no longer flowed out. The solid material thus obtained was transferred to drying trays and dried under vacuum at 45-50° C. The dried material weighed 1.28 kg (82% yield) and had a purity >99%. KF analysis showed 1.4% residual water. 1H NMR (500 MHz, DMSO-d6) δ 10.37 (s, 1H), 8.01 (s, 1H), 2.82-2.92 (m, 2H), 2.38 (s, 3H), 1.75-1.65 (m, 5H), 1.43 (d, J=24 Hz, 2H), 1.25-1.15 (m, 1H).

C. Synthesis of N-(6-((8'-methyl-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (4)

To a 50-L reactor was added 6'-bromo-8'-methyl-2'H-spiro[cyclohexane-1,3'-imidazo[1,5-a]pyridine]-1',5'-dione (2) (1.23 kg); 1,4-dioxane (15.4 L), N-(6-aminopyrimidin-4-yl)cyclopropanecarboxamide (3), (0.65 kg); and cesium carbonate (1.03 kg) and the reaction mixture was agitated as it was sparged with argon for 20 min. at ambient temperature. To the reactor was then added palladium (II) acetate (18.0 g) and xantphos (46.0 g) and sparging with argon was continued for an additional 20 min. The sparge tube was then removed and the batch temperature was adjusted to 95° C. The reaction mixture (batch) was stirred for 18 h, at which time, analysis by HPLC indicated the reaction was complete. Following completion of the reaction, the batch temperature was adjusted to 20° C. Water (24.6 L, DI) was added to the reactor and the batch was stirred for 1 h, followed by filtration through a Nutsche filter (18"). The mother liquor was used to rinse the reactor and then added to the filter cake. Next, acetone (6.15 L) was added as a rinse to the reactor and then transferred to the filter cake. The filter cake was conditioned until no liquid flowed from the filter. Following this, the cake was added back to the reactor, suspended using methanol (12.0 L) and agitated at 125 RPM. The batch temperature was adjusted to 20° C. and agitation continued for 10 min. The batch was again filtered through a Nutsche filter (18") and conditioned until liquid no longer flowed from the filter. The solid material thus obtained was transferred to drying trays and dried under vacuum at 45° C. The dried material weighted 1.42 kg, (98% yield) and had a purity of 97.5%. 1H NMR (500 MHz, DMSO-d6) δ 10.85 (brs, 1H), 10.07 (brs, 1H), 9.09 (s, 1H), 8.53 (s, 1H), 8.46 (s, 1H), 7.85 (s, 1H), 3.95-3.05 (m, 2H), 2.45 (s, 3H), 1.95-2.05 (m, 1H), 1.80-1.60 (m, 5H), 1.44 (d, J=24 Hz, 2H), 1.25-1.15 (m, 1H), 0.89-0.80 (m, 4H).

D. Synthesis of 6'-((6-aminopyrimidin-4-yl)amino)-8'-methyl-2'H-spiro[cyclohexane-1,3'-imidazo[1,5-a]pyridine]-1',5'-dione (107)

N-(6-((8'-methyl-1',5'-dioxo-1',5'-dihydro-2'H-spiro[cyclohexane-1,3'-imidazo[1,5-a]pyridin]-6'-yl)amino)pyrimidin-4-yl)cyclopropanecarboxamide (cpd. 4), (1.42 kg); tetrahydrofuran (5.7 L); and EtOH (5.7 L) were added to a 50-L reactor and agitated at 100 RPM. The batch temperature was adjusted to 20° C. To a 45-L carboy was added water (5.7 L, DI) and KOH (1.17 kg) and the contents of the carboy were agitated until a solution formed. The KOH solution was then added to the 50-L reactor followed by addition of ethylenediamine (2.83 L). The batch temperature increased to 33° C. upon addition of ethylenediamine and was readjusted to 20° C. After stirring for 16 h HPLC analysis indicated 18.6% of unreacted compound (4) remained. A solution of KOH (1.17 kg) and water (5.7 L), therefore, was added to the reactor and stirring continued at 20° C. for an additional 16 h. Following stirring, HPLC analysis indicated 1.3% of unreacted compound (4). The pH of the batch was adjusted to 2 by the addition of concentrated HCl (11.8 kg), over a time period of 2.5 h, and a solid begins to form when the batch (reaction mixture) is at a pH of 12.7. The batch temperature was adjusted to 20° C. and the mixture was agitated for 10 minutes following which the batch containing solid material was filtered through a Nutsche filter (18").

The reactor was then rinsed with water (14.15 L, DI) and the aqueous rinse was transferred to the filter while manually suspending the solid in the wash. A second rinse was performed using water (14.15 L, DI) and the rinse was transferred again to the filter while manually suspending the solid in the wash. Sodium bicarbonate (1.3 kg) and water (26.0 L, DI) were then added to the rinsed 50-L reactor and the filter cake was slowly introduced into the reactor over a time period of about 30 min to avoid excess gas liberation. The resulting suspension was agitated for 2 h followed by filtration through a Nutsche filter (18"). The filter cake was washed with water (15.0 L) and allowed to condition overnight. The filter cake was once again suspended in an aqueous solution of sodium bicarbonate, agitated for 2 h and filtered through a Nutsche filter (18"). Following washing with water, the filter cake was allowed to condition overnight and then transferred to drying trays and dried under vacuum at 45° C. The dried batch weighed 1.05 kg, (80% yield) and had a purity of 98.5%. IC analysis showed 0.7% chloride. 1H NMR (500 MHz, DMSO-d6) δ 10.20 (s, 1H), 9.68 (s, 1H), 8.47 (s, 1H), 8.09 (s, 1H), 7.97 (brs, 2H), 6.42 (s, 1H), 3.00-2.90 (m, 2H), 2.43 (s, 3H), 1.80-1.60 (m, 5H), 1.5 (d, J=24 Hz, 2H), 1.25-1.12 (m, 1H).

E. Synthesis of 6'-((6-aminopyrimidin-4-yl)amino)-8'-methyl-2'H-spiro[cyclohexane-1,3'-imidazo[1,5-a]pyridine]-1',5'-dione hydrochloride (107 HCl)

6'-((6-aminopyrimidin-4-yl)amino)-8'-methyl-2'H-spiro[cyclohexane-1,3'-imidazo[1,5-a]pyridine]-1',5'-dione ((107), (0.99 kg)) was added to a 50-L vessel. To a separate 45-L carboy were added tetrahydrofuran (8.22 L), ethanol (8.22 L), and water (8.22 L, DI). This solution was then transferred to the 50-L vessel containing compound 9107) and the temperature of the reaction mixture was adjusted to 5° C. To the cold reaction mixture was added KOH (0.45 kg) and the entire mixture was agitated until a solution formed. The solution was then transferred to the 45-L carboy and then passed, under vacuum, through a polish filter (0.3 u Hepa Cap polish filter) back to the 50-L vessel.

The temperature of the solution (batch) was adjusted to 5° C. and the pH was adjusted to pH 1 by the addition of concentrated HCl (37%, 1.17 L). The temperature of the acidic batch was adjusted to 20° C. following which the batch was agitated for 16 h. Seed crystals (9.2 g) were added to the batch and the agitation was continued for 16 h. After agitation, the batch was filtered through a Nutsche filter (18") and the reactor rinsed once with the mother liquor. The rinse was added to the filter cake, followed rinsing of the filter cake with a solution of THF, ethanol and water (1:1:1). After conditioning the filter cake overnight, it was transferred to drying trays and dried under vacuum at 45° C. The dried batch weighed 1.12 kg, 102% yield, with 4.0% water (KF oven). 1H NMR (500 MHz, DMSO-d6) δ 10.20 (s, 1H), 9.68 (s, 1H), 8.47 (s, 1H), 8.09 (s, 1H), 7.97 (brs, 2H), 6.42 (s, 1H), 3.00-2.90 (m, 2H), 2.43 (s, 3H), 1.80-1.60 (m, 5H), 1.5 (d, J=24 Hz, 2H), 1.25-1.12 (m, 1H). XRPD (Cu, ° 02 (Theta) values): 3.5 (s), 8.5 (1), 10.5 (m), 14 (s), 17 (s), 19.5 (s), 27 (m).

Biological Studies

Example 249: Mnk Biochemical Enzymatic Assay

Compounds are screened for Mnk inhibition using the ADP-Glo kinase assay kit (Promega, catalogue No. V9101). All kinase reactions are performed in Reaction Buffer E (15 mM HEPES pH7.4, 20 mM NaCl, 1 mM EGTA, 10 mM $MgCl_2$, 0.1 mg/ml BGG, and 0.02% Tween-20). Final Mnk1 reactions contained 10 nM recombinant Mnk1 (Life Technologies, PR9138A), 100 μM Mnk substrate peptide Ac-TATKSGSTTKNR-NH2 (American Peptide Company), 300 μM ATP, and varying concentrations of the inhibitory compound of interest. Final Mnk2 reactions contained 3 nM recombinant Mnk2 (Life Technologies, PV5607), 50 μM Mnk substrate peptide Ac-TATKSGSTTKNR-NH2 (American Peptide Company), 10 μM ATP, and varying concentrations of the inhibitory compound of interest. Final DMSO concentration in each reaction is 1%.

Kinase reactions are carried out in 96-well half-area white flat-bottom polystyrene plates in a final volume of 25 al. Mnk1/2 enzymes are pre-incubated with compound and peptide substrate for 5 minutes prior to the addition of ATP. After the addition of ATP, kinase reactions are incubated at room temperature for 40 minutes. Reactions are subsequently stopped by the addition of 25 μl of ADP-Glo Reagent and incubating for an additional 40 minutes. The final luminescent signal used for kinase activity readout is produced by the addition of 45 μl of Kinase Detection Reagent (ADP-Glo kit, Promega) and incubating for 40 minutes. The luminescent signal is detected using a Victor 2 multilabel counter (Perkin Elmer) and the concentration of compound necessary to achieve inhibition of enzyme activity by 50% ($IC_{50}$) is calculated using signals from an 8-point compound dilution series.

The results of these assays are set forth in Table 1 below. To this end, $IC_{50}$ values of less than 0.01 μM are labelled as "+++", from 0.01 to 0.1 μM are labelled as "++", and greater than 0.1 to 10.0 μM are labelled as "+" (NA means "not available").

TABLE 1

Mnk Biochemical Enzymatic Assay ($IC_{50}$)

| Cpd. No. | $IC_{50}$ Mnk1 | Mnk2 |
|---|---|---|
| 1 | NA | + |
| 2 | ++ | ++ |
| 3 | NA | + |
| 4 | NA | + |
| 5 | NA | + |
| 6 | +++ | ++ |
| 7 | ++ | +++ |
| 8 | ++ | ++ |
| 9 | ++ | ++ |
| 10 | +++ | +++ |
| 11 | ++ | ++ |
| 12 | ++ | ++ |
| 13 | ++ | ++ |
| 14 | ++ | +++ |
| 15 | NA | + |

TABLE 1-continued

Mnk Biochemical Enzymatic Assay (IC$_{50}$)

| Cpd. No. | IC$_{50}$ Mnk1 | Mnk2 |
|---|---|---|
| 16 | +++ | ++ |
| 17 | NA | + |
| 18 | +++ | ++ |
| 19 | NA | + |
| 20 | ++ | +++ |
| 21 | +++ | +++ |
| 22 | +++ | +++ |
| 23 | +++ | +++ |
| 24 | +++ | +++ |
| 25 | NA | + |
| 26 | ++ | + |
| 27 | ++ | ++ |
| 28 | ++ | ++ |
| 29 | +++ | +++ |
| 30 | +++ | +++ |
| 31 | ++ | ++ |
| 32 | NA | + |
| 33 | ++ | ++ |
| 34 | ++ | ++ |
| 35 | +++ | +++ |
| 36 | +++ | +++ |
| 37 | ++ | ++ |
| 38 | +++ | +++ |
| 39 | +++ | +++ |
| 40 | NA | + |
| 41 | + | ++ |
| 42 | +++ | +++ |
| 43 | +++ | +++ |
| 44 | +++ | +++ |
| 45 | +++ | +++ |
| 46 | +++ | +++ |
| 47 | +++ | +++ |
| 48 | +++ | +++ |
| 49 | +++ | +++ |
| 50 | +++ | +++ |
| 51 | +++ | +++ |
| 52 | +++ | +++ |
| 53 | ++ | ++ |
| 54 | ++ | +++ |
| 55 | +++ | +++ |
| 56 | +++ | +++ |
| 57 | +++ | +++ |
| 58 | +++ | +++ |
| 59 | + | ++ |
| 60 | +++ | +++ |
| 61 | +++ | +++ |
| 62 | +++ | +++ |
| 63 | +++ | +++ |
| 64 | ++ | ++ |
| 65 | +++ | +++ |
| 66 | +++ | +++ |
| 67 | ++ | +++ |
| 68 | + | + |
| 69 | +++ | +++ |
| 70 | +++ | +++ |
| 71 | + | + |
| 72 | +++ | +++ |
| 73 | +++ | +++ |
| 74 | +++ | +++ |
| 75 | ++ | ++ |
| 76 | +++ | +++ |
| 77 | +++ | +++ |
| 78 | +++ | +++ |
| 79 | ++ | +++ |
| 80 | +++ | +++ |
| 81 | + | + |
| 82 | ++ | ++ |
| 83 | +++ | +++ |
| 84 | +++ | +++ |
| 85 | +++ | +++ |
| 86 | +++ | +++ |
| 87 | +++ | +++ |
| 88 | +++ | +++ |
| 89 | +++ | +++ |
| 90 | +++ | +++ |
| 91 | +++ | +++ |
| 92 | +++ | +++ |
| 93 | +++ | +++ |
| 94 | +++ | +++ |
| 95 | +++ | +++ |
| 96 | +++ | +++ |
| 97 | +++ | +++ |
| 98 | +++ | +++ |
| 99 | +++ | +++ |
| 100 | +++ | +++ |
| 101 | +++ | +++ |
| 102 | +++ | +++ |
| 103 | +++ | +++ |
| 104 | +++ | +++ |
| 105 | +++ | +++ |
| 106 | +++ | +++ |
| 107 | +++ | +++ |
| 108 | +++ | +++ |
| 109 | +++ | +++ |
| 110 | +++ | +++ |
| 111 | +++ | +++ |
| 112 | +++ | +++ |
| 113 | +++ | +++ |
| 114 | +++ | +++ |
| 115 | +++ | +++ |
| 116 | +++ | +++ |
| 117 | +++ | +++ |
| 118 | NA | +++ |
| 119 | NA | +++ |
| 120 | NA | +++ |
| 121 | NA | +++ |
| 122 | NA | +++ |
| 123 | NA | +++ |
| 124 | NA | +++ |
| 125 | NA | +++ |
| 126 | +++ | +++ |
| 127 | +++ | +++ |
| 128 | +++ | +++ |
| 129 | +++ | +++ |
| 130 | +++ | ++ |
| 131 | ++ | +++ |
| 132 | NA | NA |
| 133 | NA | +++ |
| 134 | NA | NA |
| 135 | NA | NA |
| 136 | NA | NA |
| 137 | NA | NA |
| 138 | NA | + |
| 139 | NA | NA |
| 140 | NA | NA |
| 141 | NA | NA |
| 142 | +++ | +++ |
| 143 | +++ | +++ |
| 144 | NA | NA |
| 145 | +++ | +++ |
| 146 | +++ | +++ |
| 147 | NA | NA |
| 148 | NA | NA |
| 149 | NA | NA |
| 150 | NA | NA |
| 151 | NA | + |
| 152 | NA | NA |
| 153 | NA | + |
| 154 | NA | NA |
| 155 | NA | +++ |
| 156 | NA | ++ |
| 157 | NA | +++ |
| 158 | NA | ++ |
| 159 | NA | NA |
| 160 | NA | +++ |
| 161 | NA | + |
| 162 | NA | ++ |
| 163 | NA | ++ |

TABLE 1-continued

Mnk Biochemical Enzymatic Assay (IC$_{50}$)

| Cpd. No. | Mnk1 | Mnk2 |
|---|---|---|
| 164 | NA | +++ |
| 165 | ++ | ++ |
| 166 | NA | NA |
| 167 | NA | NA |
| 168 | NA | NA |
| 169 | NA | +++ |
| 170 | +++ | +++ |
| 171 | NA | NA |
| 172 | NA | NA |
| 173 | NA | NA |
| 174 | NA | NA |
| 175 | NA | NA |
| 176 | NA | NA |
| 177 | NA | NA |
| 178 | NA | NA |
| 179 | NA | NA |
| 180 | NA | NA |
| 181 | ++ | ++ |
| 182 | NA | NA |
| 183 | NA | NA |
| 184 | NA | NA |
| 185 | NA | NA |
| 186 | NA | NA |
| 187 | +++ | +++ |
| 188 | NA | +++ |
| 189 | NA | +++ |
| 190 | NA | + |
| 191 | NA | +++ |
| 192 | NA | +++ |
| 193 | NA | +++ |
| 194 | NA | +++ |
| 195 | NA | +++ |
| 196 | NA | +++ |
| 197 | NA | +++ |
| 198 | NA | + |
| 199 | NA | NA |
| 200 | NA | + |
| 201 | NA | + |
| 202 | NA | ++ |
| 203 | NA | + |
| 204 | NA | ++ |
| 205 | NA | NA |
| 206 | NA | +++ |
| 207 | NA | +++ |
| 208 | NA | +++ |
| 209 | NA | NA |
| 210 | NA | NA |
| 211 | NA | + |
| 212 | NA | NA |
| 213 | NA | ++ |
| 214 | NA | ++ |
| 215 | NA | ++ |
| 216 | NA | ++ |
| 217 | NA | + |
| 218 | NA | + |
| 219 | NA | +++ |
| 220 | NA | +++ |
| 221 | NA | Inactive |
| 222 | NA | +++ |
| 223 | NA | +++ |
| 224 | NA | Inactive |
| 225 | NA | +++ |
| 226 | NA | +++ |
| 227 | NA | NA |
| 228 | NA | NA |
| 229 | NA | NA |
| 230 | NA | +++ |
| 231 | NA | +++ |
| 232 | NA | +++ |
| 233 | NA | +++ |
| 234 | NA | +++ |
| 235 | NA | +++ |
| 236 | NA | +++ |
| 237 | NA | NA |
| 238 | NA | NA |
| 239 | NA | NA |
| 240 | NA | NA |
| 241 | NA | NA |
| 242 | NA | NA |
| 243 | NA | NA |
| 244 | NA | NA |
| 245 | NA | NA |
| 246 | NA | NA |
| 247 | NA | NA |

Example 250: peIF4E Signaling Cellular Assay

Phosphorylated eIF4E is assayed using the CisBio peIF4E HTRF® assay kit (CisBio, catalogue No. 64EF4PEG). Cells are plated in 96-well tissue-culture treated plate in appropriate growth medium (90 μL). Compounds (10×) are diluted using 3-fold serial dilutions in cell culture medium and added to cells. Plates are incubated for 2 hrs at 37° C. The cell supernatant is carefully removed either by aspirating supernatant or by flicking the plate. Immediately 50 μL of supplemented lysis buffer (1×) is added and incubated for at least 30 minutes at room temperature under shaking. After homogenization by pipeting up and down, 16 μL of cell lysate is transferred from the 96-well cell-culture plate to a 384-well small volume white plate. 4 μL of premixed antibody solutions (vol/vol) is prepared in the detection buffer and added. The plate is covered with a plate sealer and incubated overnight at room temperature. The fluorescence emissions at two different wavelengths are read (665 nm and 620 nm) on a Wallac Victor2. Emission ratios are converted into percent inhibitions and imported into GraphPad Prism software. The concentration of compound necessary to achieve inhibition of enzyme activity by 50% (IC$_{50}$) is calculated using concentrations ranging from 20 μM to 0.1 nM (12-point curve). IC$_{50}$ values are determined using a nonlinear regression model available in GraphPad Prism 5.

The results of these assays are set forth in Table 2 below. To this end, IC$_{50}$ values of less than 0.05 μM are labelled as "+++", from 0.05 to 1.0 μM are labelled as "++", greater than 1.0 to 100 μM are labelled as "+", and NA means "not available".

TABLE 2 peIF4E Signaling Cellular Assay (IC$_{50}$)

| Cpd. No. | IC$_{50}$ | Cpd. No. | IC$_{50}$ | Cpd. No. | IC$_{50}$ |
|---|---|---|---|---|---|
| 1 | NA | 26 | NA | 51 | +++ |
| 2 | + | 27 | ++ | 52 | +++ |
| 3 | NA | 28 | NA | 53 | ++ |
| 4 | NA | 29 | +++ | 54 | ++ |
| 5 | NA | 30 | +++ | 55 | +++ |
| 6 | ++ | 31 | ++ | 56 | +++ |
| 7 | ++ | 32 | NA | 57 | ++ |
| 8 | + | 33 | ++ | 58 | +++ |
| 9 | ++ | 34 | + | 59 | + |
| 10 | +++ | 35 | +++ | 60 | +++ |
| 11 | + | 36 | +++ | 61 | +++ |
| 12 | ++ | 37 | ++ | 62 | +++ |
| 13 | + | 38 | +++ | 63 | +++ |
| 14 | ++ | 39 | +++ | 64 | ++ |
| 15 | NA | 40 | NA | 65 | +++ |

TABLE 2-continued peIF4E Signaling Cellular Assay (IC$_{50}$)

| Cpd. No. | IC$_{50}$ | Cpd. No. | IC$_{50}$ | Cpd. No. | IC$_{50}$ |
|---|---|---|---|---|---|
| 16 | ++ | 41 | + | 66 | +++ |
| 17 | NA | 42 | +++ | 67 | ++ |
| 18 | ++ | 43 | +++ | 68 | NA |
| 19 | NA | 44 | +++ | 69 | ++ |
| 20 | ++ | 45 | +++ | 70 | +++ |
| 21 | +++ | 46 | +++ | 71 | ++ |
| 22 | +++ | 47 | ++ | 72 | + |
| 23 | +++ | 48 | +++ | 73 | +++ |
| 24 | +++ | 49 | +++ | 74 | ++ |
| 25 | NA | 50 | +++ | 75 | + |
| 76 | +++ | 102 | ++ | 128 | +++ |
| 77 | +++ | 103 | +++ | 129 | ++ |
| 78 | +++ | 104 | ++ | 130 | + |
| 79 | + | 105 | +++ | 131 | + |
| 80 | +++ | 106 | ++ | 132 | NA |
| 81 | + | 107 | +++ | 133 | ++ |
| 82 | + | 108 | +++ | 134 | NA |
| 83 | +++ | 109 | +++ | 135 | NA |
| 84 | +++ | 110 | +++ | 136 | NA |
| 85 | +++ | 111 | +++ | 137 | NA |
| 86 | +++ | 112 | ++ | 138 | + |
| 87 | +++ | 113 | + | 139 | NA |
| 88 | +++ | 114 | +++ | 140 | NA |
| 89 | +++ | 115 | +++ | 141 | NA |
| 90 | ++ | 116 | ++ | 142 | ++ |
| 91 | +++ | 117 | +++ | 143 | +++ |
| 92 | ++ | 118 | + | 144 | NA |
| 93 | +++ | 119 | +++ | 145 | +++ |
| 94 | +++ | 120 | +++ | 146 | + |
| 95 | +++ | 121 | +++ | 147 | NA |
| 96 | +++ | 122 | +++ | 148 | NA |
| 97 | +++ | 123 | +++ | 149 | NA |
| 98 | +++ | 124 | ++ | 150 | NA |
| 99 | +++ | 125 | + | 151 | + |
| 100 | +++ | 126 | + | 152 | NA |
| 101 | ++ | 127 | +++ | 153 | NA |
| 154 | NA | 180 | NA | 206 | NA |
| 155 | + | 181 | + | 207 | NA |
| 156 | ++ | 182 | NA | 208 | ++ |
| 157 | ++ | 183 | NA | 209 | NA |
| 158 | ++ | 184 | NA | 210 | NA |
| 159 | NA | 185 | NA | 211 | NA |
| 160 | ++ | 186 | NA | 212 | NA |
| 161 | + | 187 | +++ | 213 | + |
| 162 | + | 188 | +++ | 214 | + |
| 163 | + | 189 | ++ | 215 | + |
| 164 | ++ | 190 | NA | 216 | + |
| 165 | + | 191 | ++ | 217 | + |
| 166 | NA | 192 | ++ | 218 | NA |
| 167 | NA | 193 | +++ | 219 | ++ |
| 168 | NA | 194 | +++ | 220 | ++ |
| 169 | +++ | 195 | +++ | 221 | NA |
| 170 | ++ | 196 | +++ | 222 | +++ |
| 171 | NA | 197 | +++ | 223 | +++ |
| 172 | NA | 198 | NA | 224 | NA |
| 173 | NA | 199 | NA | 225 | + |
| 174 | NA | 200 | + | 226 | + |
| 175 | NA | 201 | NA | 227 | + |
| 176 | NA | 202 | NA | 228 | ++ |
| 177 | NA | 203 | NA | 229 | + |
| 178 | NA | 204 | NA | 230 | + |
| 179 | NA | 205 | NA | 231 | +++ |
| 232 | ++ | 238 | ++ | 244 | ++ |
| 233 | ++ | 239 | +++ | 245 | NA |
| 234 | +++ | 240 | ++ | 246 | NA |
| 235 | + | 241 | +++ | 247 | NA |
| 236 | ++ | 242 | ++ | | |
| 237 | +++ | 243 | ++ | | |

Example 251: Pharmacokinetic Studies

Groups of Balb/c mice or Sprague-Dawley rats (n≥3 per dose group) are administered single doses of test compound. Compounds are formulated either as solutions in 10% N-methylpyrrolidone, 90% polyethyleneglycol 400 or as suspensions in 0.5% methylcellulose in water for oral gavage administration at a nominal dose level of 10 mg/kg. Compounds are formulated in 10% dimethylisosorbide, 15% ethanol, 35% propylene glycol, and 40% saline (or 40% D5W) for intravenous administration at a nominal dose level of 1 mg/kg. For intravenously dosed animals, blood samples are collected at 0.083, 0.25, 0.5, 1, 2, 4, 8, and 24 h post dose. For orally dosed animals, blood samples are collected at 0.25, 0.5, 1, 2, 4, 8, and 24 h post dose. Blood samples are collected from mice either serially via submandibular vein (approximately 0.1 mL each) or terminally via cardiac puncture (approximately 0.5 mL each). Blood samples are collected serially from rats via jugular vein catheter (approximately 0.2 mL each). Each blood sample is collected into a tube that is chilled and contains potassium EDTA as the anticoagulant. Plasma is separated and stored at approximately −80 C until analysis. Following protein precipitation with acetonitrile containing an internal standard, plasma samples are analyzed using a liquid chromatography/high-resolution mass spectrometry (LC-HRMS) method to determine plasma concentrations. Plasma concentration versus time data are subjected to noncompartmental pharmacokinetic analysis using Phoenix™ Winnonlin® (Certara LP) to determine pharmacokinetic parameters, including Area Under the Curve (AUC), Clearance (Cl), Volume of Distribution at Steady-State (Vss), and terminal half-life (T½). Data from orally and intravenously dose are highlighted in Tables 3 and 4, respectively.

TABLE 3

Pharmacokinetics Parameters in Balb/c Mice Following a Single Oral Gavage Administration at 10 mg/kg

| Cpd. No. | Formulation | T½ (h) | Tmax (h) | Cmax (ug/mL) | Tlast (h) | AUClast (h * ug/mL) | Gender |
|---|---|---|---|---|---|---|---|
| 9 | 0.5MC | 0.831 | 0.50 | 5.05 | 8 | 4.83 | M |
| 10 | 10NMP/90PEG400 | 1.87 | 0.50 | 1.72 | 8 | 6.42 | F |
| 10 | 0.5MC | 4.22 | 1.00 | 2.16 | 24 | 8.75 | M |
| 14 | 0.5MC | ND | 0.50 | 0.405 | 8 | 0.255 | M |
| 20 | 0.5MC | 0.643 | 0.50 | 2.24 | 4 | 2.09 | F |
| 21 | 0.5MC | 2.66 | 0.50 | 0.0502 | 4 | 0.109 | F |
| 22 | 0.5MC | 1.93 | 2.00 | 0.371 | 8 | 1.62 | F |
| 23 | 0.5MC | 3.49 | 1.00 | 0.0175 | 8 | 0.0757 | F |
| 24 | 0.5MC | 1.91 | 2.00 | 0.192 | 8 | 0.921 | F |
| 35 | 10NMP/90PEG400 | 3.46 | 2.00 | 6.93 | 24 | 71.29 | F |

TABLE 3-continued

Pharmacokinetics Parameters in Balb/c Mice
Following a Single Oral Gavage Administration at 10 mg/kg

| Cpd. No. | Formulation | T½ (h) | Tmax (h) | Cmax (ug/mL) | Tlast (h) | AUClast (h * ug/mL) | Gender |
|---|---|---|---|---|---|---|---|
| 43 | 0.5MC | 6.75 | 2.00 | 0.0218 | 8 | 0.132 | F |
| 45 | 0.5MC | 7.55 | 2.00 | 0.00916 | 8 | 0.0429 | F |
| 50 | 0.5MC | 8.43 | 4.00 | 0.0472 | 24 | 0.464 | F |
| 50 | 5NMP/95PEG400 | 2.82 | 8.00 | 0.55 | 24 | 7.15 | F |
| 51 | 0.5MC | 7.38 | 2.00 | 3.16 | 24 | 31.3 | F |
| 51 | 5NMP/95PEG400 | 8.36 | 8.00 | 2.44 | 24 | 35.8 | F |
| 52 | 0.5MC | 5.41 | 4.00 | 3.37 | 24 | 38.1 | F |
| 52 | 10NMP/90PEG400 | 3.56 | 0.25 | 1.7 | 24 | 22.3 | F |
| 54 | 0.5MC | 0.743 | 0.50 | 1.05 | 4 | 1.23 | F |
| 54 | 10NMP/90PEG400 | 3.22 | 0.25 | 1.9 | 24 | 3.64 | F |
| 55 | 5NMP/95PEG400 | 2.61 | 1.00 | 6.17 | 24 | 56.9 | F |
| 56 | 10NMP/90PEG400 | ND | BQL | BQL | ND | ND | F |
| 58 | 0.5MC | 5.32 | 2.00 | 0.69 | 24 | 5.43 | F |
| 60 | 10NMP/90PEG400 | 2.21 | 1.00 | 0.036 | 4 | 0.0782 | F |
| 70 | 10NMP/90PEG400 | 2.00 | 0.25 | 0.983 | 8 | 1.47 | F |
| 70 | 10NMP/90PEG400 | 3.74 | 0.50 | 1.65 | 8 | 2.01 | F |
| 88 | 0.5MC | 2.97 | 0.50 | 0.81 | 8 | 2.04 | F |
| 94 | 10NMP/90PEG400 | 2 | 0.50 | 1.8 | 8 | 6.07 | F |
| 98 | 10NMP/90PEG400 | 3.1 | 0.30 | 1.2 | 8 | 4.18 | F |
| 99 | 10NMP/90PEG400 | 1.6 | 0.30 | 0.4 | 8 | 1.38 | F |
| 102 | 10NMP/90PEG400 | 1.4 | 0.30 | 1.8 | | | F |
| 103 | 10NMP/90PEG400 | 2.1 | 0.30 | 2.5 | 8 | 4.65 | F |
| 107 | 10NMP/90PEG400 | 5.3 | 1 | 0.95 | 8 | 2.76 | F |
| 108 | 10NMP/90PEG400 | 0.3 | 0.30 | 0.044 | | | F |
| 109 | 10NMP/90PEG400 | 2.5 | 0.30 | 0.63 | | | F |
| 110 | 10NMP/90PEG400 | 2.6 | 0.30 | 1.7 | | | F |

Abbreviations:
NMP—N-methylpyrrolidone;
PEG400—polyethyleneglycol 400;
MC—methylcellulose

TABLE 4

Pharmacokinetic Pparameters in Balb/c
Following a Single Intravenous Bolus Administration at 1 mg/kg

| Cpd. No. | Formulation | Cl_obs (mL/min/kg) | T½ (h) | Vss (L/kg) | AUCINF_obs (h * ug/mL) | Gender |
|---|---|---|---|---|---|---|
| 10 | 10DMI/15EtOH/35PG/40Saline | 42.1 | 2.80 | 5.45 | 0.396 | F |
| 50 | 10DMI/15EtOH/35PG/40Saline | 18.8 | 2.47 | 3.18 | 0.887 | F |
| 51 | 10DMI/15EtOH/35PG/40Saline | 6.66 | 5.78 | 2.79 | 2.50 | F |
| 70 | 10DMI/15EtOH/35PG/40D5W | 50.1 | 0.561 | 1.80 | 0.333 | F |
| 88 | 10DMA/15EtOH/35PEG300/40D5W | 61 | 1.3 | 3.03 | 0.273 | F |
| 94 | 10DMA/15EtOH/35PEG300/40D5W | 20.5 | 5.81 | 12.2 | 0.812 | F |
| 98 | 10DMA/15EtOH/35PEG300/40D5W | 46.6 | 1.79 | 3.56 | 0.358 | F |
| 103 | 10DMA/15EtOH/35PEG300/40D5W | 27.8 | 1.51 | 2.49 | 0.6 | F |
| 107 | 10DMA/15EtOH/35PEG300/40D5W | 33.2 | 2.91 | 3.21 | 0.502 | F |

Abbreviations:
DMI—dimethylisosorbide;
EtOH—ethanol;
PG—propylenglycol;
D5W—5% dextrose in water The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A process for preparing a compound according to 5a

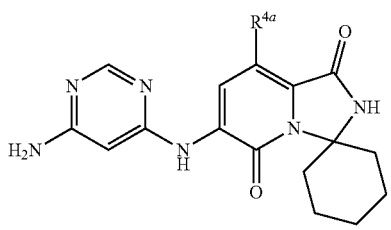

comprising:

(a) contacting a compound of 1a

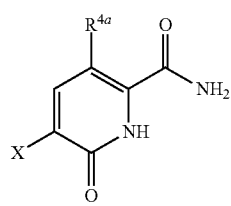

with a cyclohexanone to obtain a compound of 2a

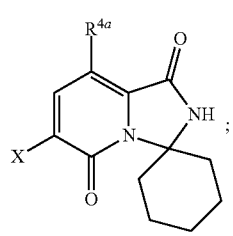

(b) coupling a compound of 2a with a compound of 3a

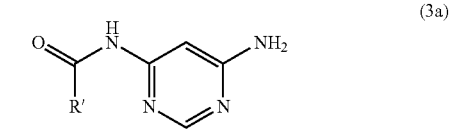

in the presence of a metal catalyst, an inorganic base, and a phosphine ligand in a non-polar aprotic solvent to obtain compound (4a)

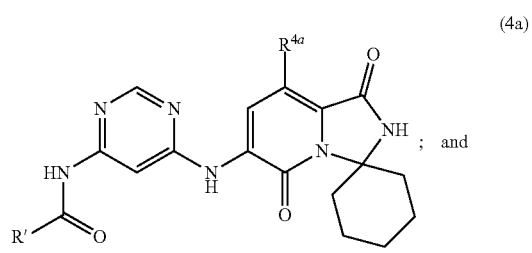

(c) reacting a compound of 4a in an aqueous base and organic solvent to obtain a compound of 5a

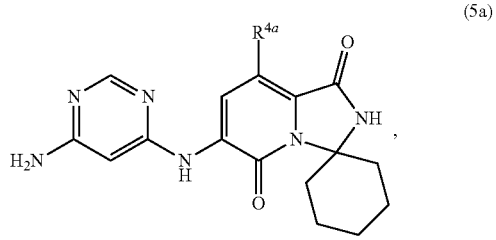

wherein:
X is halogen, -OTf, —B(OH)$_2$ or —B(OR')$_2$,
R$^{4a}$ is —H, halogen, —OH, —SH, hydroxyalkylene, —CN, alkyl, alkoxy, acyl, thioalkyl, alkenyl, alkynyl, cycloalkyl, aryl or heterocyclyl; and
R' is alkyl, cycloalkyl, aryl, heterocyclyl or heteroaryl.

2. The process according to claim 1, further comprising reacting a compound of 5a with an acid to afford a pharmaceutically acceptable salt.

3. The process according to claim 2, wherein the acid is HCl, sulfuric or methanesulfonic acid.

4. The process according to claim 1, step a, wherein compound 1a is contacted with cyclohexanone in a non-polar organic solvent and an acid to obtain compound 2a.

5. The process according to claim 4, wherein the acid is sulfuric or hydrochloric acid in an amount ranging from about 0.1 to 0.9 molar equivalents with respect to compound 1a.

6. The process according to claim 4, wherein the non-polar organic solvent is 1,4-dioxane.

7. The process according to claim 4, wherein the reaction temperature is between 90° C. and 105° C.

8. The process according to claim 1, step b, wherein the metal catalyst is a palladium catalyst, the inorganic base is Cs$_2$CO$_3$, and the phosphine ligand is xantphos.

9. The process according to claim 8, wherein the palladium catalyst is Pd$_2$(dba)$_3$ or Pd(OAc)$_2$.

10. The process according to claim 8, wherein the non-polar aprotic solvent is 1,4-dioxane.

11. The process according to claim 8, wherein the reaction temperature is between 90° C. and 105° C.

12. The process according to claim 1, step c, wherein the aqueous base is KOH and the organic solvent is a mixture of ethanol, tetrahydrofuran and water.

13. The process according to claim 1, wherein $R^{4a}$ is alkyl.

14. The process according to claim 1, wherein X is bromine.

15. The process according to claim 1, wherein R' is cycloalkyl.

16. Compound 1a or a stereoisomer or tautomer thereof:

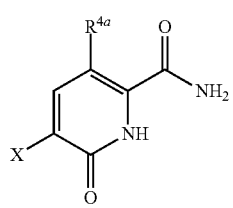

1a wherein,

X is halogen, -OTf, —B(OH)$_2$ or —B(OR')$_2$, and $R^{4a}$ is —H, halogen, —OH, —SH, hydroxyalkylene, —CN, alkyl, alkoxy, acyl, thioalkyl, alkenyl, alkynyl, cycloalkyl, aryl or heterocyclyl.

17. The compound according to claim 16, wherein $R^{4a}$ is alkyl and X is Br.

18. Compound 2a or a stereoisomer or tautomer thereof:

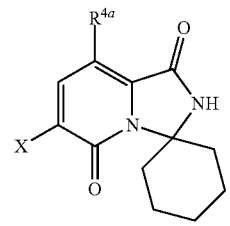

2a wherein:

X is halogen, -OTf, —B(OH)$_2$ or —B(OR')$_2$, and $R^{4a}$ is —H, halogen, —OH, —SH, hydroxyalkylene, —CN, alkyl, alkoxy, acyl, thioalkyl, alkenyl, alkynyl, cycloalkyl, aryl or heterocyclyl.

19. The compound according to claim 18, wherein $R^{4a}$ is alkyl and X is Br.

20. The compound according to claim 19, wherein $R^{4a}$ is methyl.

* * * * *